United States Patent
Cosford et al.

(10) Patent No.: US 10,597,367 B2
(45) Date of Patent: Mar. 24, 2020

(54) METABOTROPIC GLUTAMATE RECEPTOR NEGATIVE ALLOSTERIC MODULATORS (NAMS) AND USES THEREOF

(71) Applicant: Sanford Burnham Prebys Medical Discovery Institute, La Jolla, CA (US)

(72) Inventors: Nicholas David Peter Cosford, La Jolla, CA (US); Dhanya Raveendra-Panickar, La Jolla, CA (US); Douglas J. Sheffler, La Jolla, CA (US); John Howard Hutchinson, La Jolla, CA (US); Reto Andreas Gadient, La Jolla, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 0 days.

(21) Appl. No.: 15/950,683

(22) Filed: Apr. 11, 2018

(65) Prior Publication Data
US 2019/0016715 A1    Jan. 17, 2019

Related U.S. Application Data

(62) Division of application No. 15/315,363, filed as application No. PCT/US2015/034964 on Jun. 9, 2015, now Pat. No. 9,969,726.

(Continued)

(51) Int. Cl.
| | | |
|---|---|---|
| C07D 243/12 | (2006.01) | |
| A61K 31/551 | (2006.01) | |
| A61P 25/00 | (2006.01) | |
| C07D 243/14 | (2006.01) | |
| A61K 31/4196 | (2006.01) | |
| A61K 31/426 | (2006.01) | |
| A61K 31/427 | (2006.01) | |
| A61K 31/433 | (2006.01) | |
| C07D 217/06 | (2006.01) | |
| C07D 417/04 | (2006.01) | |
| C07D 249/08 | (2006.01) | |
| C07D 277/20 | (2006.01) | |
| C07D 285/08 | (2006.01) | |
| C07D 403/12 | (2006.01) | |
| C07D 233/54 | (2006.01) | |
| C07D 401/04 | (2006.01) | |
| C07D 401/10 | (2006.01) | |
| C07D 401/12 | (2006.01) | |
| C07D 403/10 | (2006.01) | |
| C07D 405/04 | (2006.01) | |

(Continued)

(52) U.S. Cl.
CPC ........ *C07D 243/14* (2013.01); *A61K 31/4196* (2013.01); *A61K 31/426* (2013.01); *A61K 31/427* (2013.01); *A61K 31/433* (2013.01); *A61K 31/505* (2013.01); *A61K 31/506* (2013.01); *A61P 25/00* (2018.01); *C07D 217/06* (2013.01); *C07D 231/12* (2013.01); *C07D 233/54* (2013.01); *C07D 233/64* (2013.01); *C07D 239/26* (2013.01); *C07D 243/12* (2013.01); *C07D 249/08* (2013.01); *C07D 261/08* (2013.01); *C07D 263/32* (2013.01); *C07D 271/06* (2013.01); *C07D 275/02* (2013.01); *C07D 277/20* (2013.01); *C07D 277/26* (2013.01); *C07D 277/30* (2013.01); *C07D 285/08* (2013.01); *C07D 307/38* (2013.01); *C07D 333/24* (2013.01); *C07D 401/04* (2013.01); *C07D 401/10* (2013.01); *C07D 401/12* (2013.01); *C07D 401/14* (2013.01); *C07D 403/10* (2013.01); *C07D 403/12* (2013.01); *C07D 405/04* (2013.01); *C07D 405/10* (2013.01); *C07D 409/02* (2013.01); *C07D 409/04* (2013.01); *C07D 409/14* (2013.01); *C07D 413/04* (2013.01); *C07D 413/14* (2013.01); *C07D 417/04* (2013.01); *C07D 417/10* (2013.01); *C07D 417/14* (2013.01)

(58) Field of Classification Search
CPC .......................... C07D 243/14; C07D 243/12; A61K 31/4196; A61K 31/551; A61P 25/00
See application file for complete search history.

(56) References Cited

U.S. PATENT DOCUMENTS

| | | |
|---|---|---|
| 6,407,094 B1 | 6/2002 | Adam et al. |
| 6,509,328 B1 | 1/2003 | Adam et al. |

(Continued)

FOREIGN PATENT DOCUMENTS

| | | |
|---|---|---|
| JP | 2004536037 A | 12/2004 |
| JP | 2006516110 A | 6/2006 |

(Continued)

OTHER PUBLICATIONS

Woltering et al., "Synthesis and characterization of 8-ethynyl-1,3-dihydro-benzo[b][1,4]diazepin-2-one derivatives: new potent non-competitive metabotropic glutamate receptor 2/3 antagonists. Part 1," Bioorg. Med. Chem. Lett. Dec. 15, 2007; 17(24): 6811-15. PMID: 17964783. (Year: 2007).*

(Continued)

*Primary Examiner* — Theodore R. West
(74) *Attorney, Agent, or Firm* — Wilson Sonsini Goodrich & Rosati

(57) ABSTRACT

Provided herein are small molecule active metabotropic glutamate subtype-2 and -3 receptor negative allosteric modulators (NAMs), compositions comprising the compounds, and methods of using the compounds and compositions.

20 Claims, 1 Drawing Sheet

Related U.S. Application Data

(60) Provisional application No. 62/009,910, filed on Jun. 10, 2014.

(51) Int. Cl.

| | | |
|---|---|---|
| *C07D 239/26* | (2006.01) | |
| *C07D 409/04* | (2006.01) | |
| *C07D 271/06* | (2006.01) | |
| *C07D 275/02* | (2006.01) | |
| *C07D 277/30* | (2006.01) | |
| *A61K 31/505* | (2006.01) | |
| *A61K 31/506* | (2006.01) | |
| *C07D 231/12* | (2006.01) | |
| *C07D 233/64* | (2006.01) | |
| *C07D 261/08* | (2006.01) | |
| *C07D 263/32* | (2006.01) | |
| *C07D 277/26* | (2006.01) | |
| *C07D 307/38* | (2006.01) | |
| *C07D 333/24* | (2006.01) | |
| *C07D 401/14* | (2006.01) | |
| *C07D 405/10* | (2006.01) | |
| *C07D 409/02* | (2006.01) | |
| *C07D 409/14* | (2006.01) | |
| *C07D 413/04* | (2006.01) | |
| *C07D 413/14* | (2006.01) | |
| *C07D 417/10* | (2006.01) | |
| *C07D 417/14* | (2006.01) | |

(56) References Cited

U.S. PATENT DOCUMENTS

| | | | |
|---|---|---|---|
| 6,544,985 B2 | 4/2003 | Adam et al. | |
| 6,548,495 B2 | 4/2003 | Adam et al. | |
| 6,949,542 B2 | 9/2005 | Adam et al. | |
| 6,960,578 B2 | 11/2005 | Adam et al. | |
| 7,018,998 B2 | 3/2006 | Adam et al. | |
| 7,151,098 B2 | 12/2006 | Adam et al. | |
| 9,193,710 B2 | 11/2015 | Hutchinson et al. | |
| 2002/0193367 A1* | 12/2002 | Adam | C07D 401/04 514/221 |
| 2007/0232583 A1 | 10/2007 | McArthur et al. | |
| 2007/0249645 A1 | 10/2007 | Cochran et al. | |
| 2011/0201601 A1* | 8/2011 | Gillet | A61K 31/167 514/221 |
| 2011/0263615 A1 | 10/2011 | Gatti et al. | |
| 2017/0217951 A1 | 8/2017 | Cosford et al. | |

FOREIGN PATENT DOCUMENTS

| | | |
|---|---|---|
| JP | 2006522128 A | 9/2006 |
| WO | WO-02083665 A1 | 10/2002 |
| WO | WO-03066623 A1 | 8/2003 |
| WO | WO-03077918 A1 | 9/2003 |
| WO | WO-2004058762 A1 | 7/2004 |
| WO | WO-2005012263 A1 | 2/2005 |
| WO | WO-2007002563 A1 | 1/2007 |
| WO | WO-2009153665 A2 | 12/2009 |
| WO | WO-2011073119 A1 | 6/2011 |
| WO | WO-2011116356 A2 | 9/2011 |
| WO | WO-2013033246 A2 | 3/2013 |
| WO | WO-2015191630 A1 | 12/2015 |

OTHER PUBLICATIONS

Megens et al., "mGlu2 receptor-mediated modulation of conditioned avoidance behavior in rats," Eur. J. Pharmacol. (2014), 727, 130-39. (Year: 2014).*

Dandegaonker et al., "Tetrahydrodiazepines," Indian J. Chem. (1963), 1(7), 298-300. (Year: 1963).*

Chen et al. Enantioselective synthesis of 4-substituted 4,5-dihydro-1H-[1,5]benzodiazepin-2(3H)-ones by the Lewis base-catalyzed hydrosilylation. J Org Chem 76:9109-9115 (2011).

Cho. Recent Advances in Oral Prodrug Discovery. Annual Reports in Medicinal Chemistry 41:395-407 (2006).

Gonzalez-Maeso et al. Identification of a serotonin/glutamate receptor complex implicated in psychosis. Nature 452(7183):93-97 (2008).

Lee et al. Solid-Phase Synthesis of 3,4,5-Substituted 1,5-Benzodiazepin-2-ones. J Org Chem 64:3060-3065 (1999).

Milligan. G-protein-coupled receptor heterodimers: pharmacology, function and relevance to drug discovery. Drug Discov Today 11(11-12):541-549 (2006).

Murray et al. Evaluation of the mGluR 2/3 agonist LY379268 in rodent models of Parkinson's disease. Pharmacol Biochem Behav 73:455-466 (2002).

Nogrady. Medicinal Chemistry a Biochemical Approach, Oxford University Press, New York, pp. 388-392 (1985).

PCT/US2015/034964 International Preliminary Report on Patentability dated Dec. 22, 2016.

PCT/US2015/034964 International Search Report and Written Opinion dated Sep. 1, 2015.

Reddy et al. One-Pot, Three-Component Synthesis of Novel 4-Phenyl-2-[3-(alkynyl/alkenyl/aryl)phenyl]pyrimidine Libraries via Michael Addition, Cyclization, and C-C Coupling Reactions: A New MCR Strategy. Synthesis 45(1):75-84 (2013).

Romano et al. Metabotropic glutamate receptor 5 is a disulfide-linked dimer. J Biol Chem 271(45):28612-28616 (1996).

Rooseboom et al. Enzyme-catalyzed activation of anticancer prodrugs. Pharmacological Reviews 56(1):53-102 (2004).

Rueping et al. First Highly Enantioselective Synthesis of Benzodiazepinones by Catalytic Hydrogenation. Adv. Synth. Catal. 352:2629-2634 (2010).

Sheffler et al. Recent progress in the synthesis and characterization of group II metabotropic glutamate receptor allosteric modulators. ACS Chem Neurosci 2:382-393 (2011).

Silverman et al. Chapter 8: Prodrugs and drug delivery systems. In: The Organic Chemistry of Drug Design and Drug Action. San Diego: Academic Press, Inc. p. 352-401 (1992).

Wang et al. Efficient Syntheses of β-Amino-N-acylbenzotriazoles and Cinnamides through Regioselective 1,4- or 1,2-Addition of Amines to N-Cinnamoylbenzotriazoles. Synlett 20:3042-3046 (2005).

Woltering et al. Synthesis and characterization of 8-ethynyl-1,3-dihydro-benzo[b][1,4]diazepin-2-one derivatives: part 2. New potent non-competitive metabotropic glutamate receptor 2/3 antagonists. Bioorg Med Chem Letts. 18:1091-1095 (2008).

Zhao et al. Solution-phase parallel synthesis of diverse 1,5-benzodiazepin-2-ones. J Comb Chem 9:1164-1176 (2007).

* cited by examiner

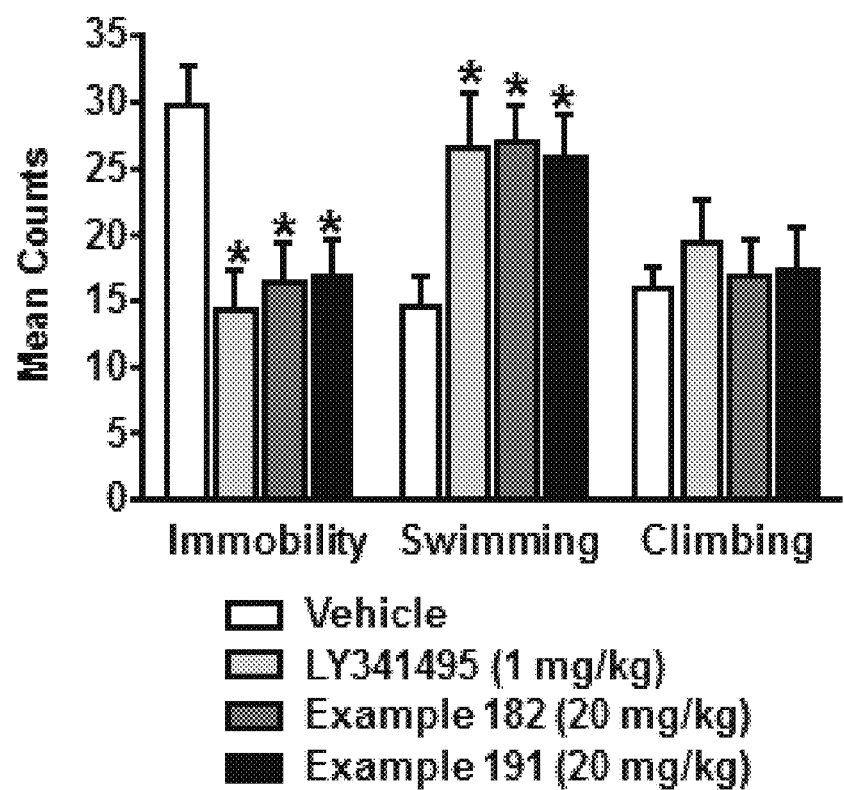

METABOTROPIC GLUTAMATE RECEPTOR NEGATIVE ALLOSTERIC MODULATORS (NAMS) AND USES THEREOF

CROSS-REFERENCE

This is a divisional application of U.S. National Phase Patent application Ser. No. 15/315,363, filed Apr. 20, 2017, which claims priority to U.S. International Application No. PCT/US2015/034964, filed Jun. 9, 2015, and claims benefit of U.S. Provisional Application No. 62/009,910, filed on Jun. 10, 2014, all of which are herein incorporated by reference in their entirety.

STATEMENT OF GOVERNMENT SUPPORT

This invention was made with government support under R01 MH087989 awarded by the National Institutes of Health. The government has certain rights in the invention.

FIELD OF THE INVENTION

Described herein are metabotropic glutamate subtype-2 and -3 (mGlu2/3) (collectively Group II mGlus) receptor negative allosteric modulators (NAMs), methods of making such compounds, pharmaceutical compositions and medicaments comprising such compounds, and methods of using such compounds in the treatment of conditions, diseases, or disorders in which metabotropic glutamate receptors are involved.

SUMMARY OF THE INVENTION

Described herein are compounds and compositions, and methods of using these compounds and compositions, as negative allosteric modulators of the metabotropic glutamate receptor subtype 2 receptor (mGlu2), and of the metabotropic glutamate receptor subtype 3 receptor (mGlu3) (collectively Group II mGlus), and for treating CNS disorders associated with Group II mGlus.

In one aspect, described herein is a method for treating or preventing a disease or condition in a mammal that would benefit from the modulation of the metabotropic glutamate receptor subtype 2 receptor (mGlu2), and/or of the metabotropic glutamate receptor subtype 3 receptor (mGlu3) activities comprising administering a modulator of mGlu2 and/or mGlu3 to the mammal in need thereof. In some embodiments, the modulator of mGlu2 and mGlu3 is a small molecule. In some embodiments, the modulator of mGlu2 and mGlu3 is a negative allosteric modulator. In some embodiments, the negative allosteric modulator of mGlu2 and mGlu3 is a compound having the structure of Formula (I), Formula (Ia), Formula (Ib), Formula (Ic), Formula (II), Formula (IIa), Formula (IIb), Formula (IIc), Formula (III), Formula (IIIa), or Formula (IIIb), Formula (IV), Formula (IVa), or Formula (IVb), or a pharmaceutically acceptable salt thereof.

In one aspect, described herein is a compound, or a pharmaceutically acceptable salt thereof, having the structure of Formula (I):

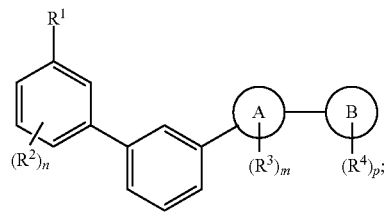

Formula (I)

wherein:

ring Ⓐ is a heteroaryl ring;

ring Ⓐ is an aryl ring or heteroaryl ring;

$R^1$ is —$CO_2H$, —CN, —C(O)NHOH, —C(O)NHOMe, —C(O)NHSO$_2$Me, —NHC(O)Me, —C(O)NHMe,

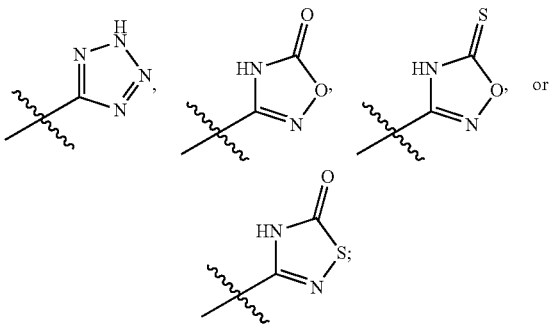

each $R^2$ is independently halogen, —$OR^5$, substituted or unsubstituted $C_1$-$C_6$alkyl, or substituted or unsubstituted $C_1$-$C_6$fluoroalkyl;

each $R^3$ is independently substituted or unsubstituted $C_1$-$C_6$alkyl, substituted or unsubstituted $C_1$-$C_6$fluoroalkyl, substituted or unsubstituted $C_3$-$C_6$cycloalkyl, or substituted or unsubstituted aryl;

each $R^4$ is independently halogen, —$OR^5$, substituted or unsubstituted $C_1$-$C_6$alkyl, substituted or unsubstituted $C_1$-$C_6$fluoroalkyl, substituted or unsubstituted $C_3$-$C_6$cycloalkyl, or substituted or unsubstituted aryl;

or two $R^4$ taken together with the carbon atoms to which they are attached to form a substituted or unsubstituted $C_2$-$C_8$heterocycloalkyl;

each $R^5$ is independently hydrogen, or substituted or unsubstituted $C_1$-$C_6$alkyl;

n is 0, 1, 2, or 3;

m is 0 or 1; and p is 0, 1, 2, or 3n is 0, 1, 2, or 3;

m is 0 or 1; and p is 0, 1, 2, or 3.

In some embodiments is a compound of Formula (I), or a pharmaceutically acceptable salt thereof, wherein ring Ⓐ is thiazolyl, oxadiazolyl, thiadiazolyl, triazolyl, imidazolyl, or isothiazolyl.

In some embodiments is a compound of Formula (I), or a pharmaceutically acceptable salt thereof, having the structure of Formula (Ia):

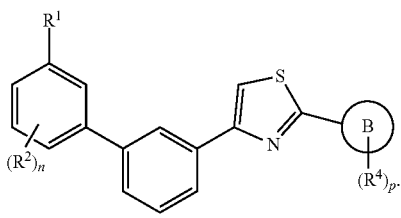

Formula (Ia)

In some embodiments is a compound of Formula (I), or a pharmaceutically acceptable salt thereof, having the structure of Formula (Ib):

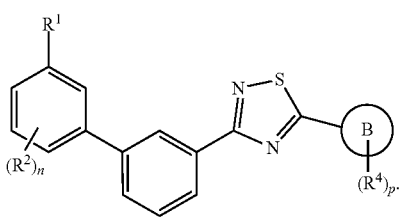

Formula (Ib)

In some embodiments is a compound of Formula (I), or a pharmaceutically acceptable salt thereof, having the structure of Formula (Ic):

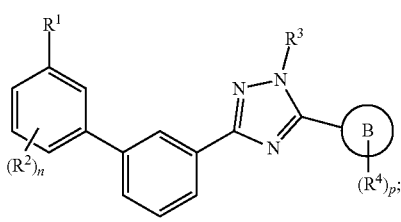

Formula (Ic)

wherein $R^3$ is substituted or unsubstituted $C_1$-$C_6$alkyl or substituted or unsubstituted aryl. In some embodiments is a compound of Formula (Ic), or a pharmaceutically acceptable salt thereof, wherein $R^3$ is unsubstituted phenyl.

In some embodiments is a compound of Formula (I), (Ia), (Ib), or (Ic), or a pharmaceutically acceptable salt thereof, wherein ring Ⓐ is a phenyl ring. In some embodiments is a compound of Formula (I), (Ia), (Ib), or (Ic), or a pharmaceutically acceptable salt thereof, wherein ring Ⓐ is a heteroaryl ring. In some embodiments is a compound of Formula (I), (Ia), (Ib), or (Ic), or a pharmaceutically acceptable salt thereof, wherein ring Ⓐ is furanyl, thiophenyl, benzofuranyl, benzothiophenyl, or pyridinyl. In some embodiments is a compound of Formula (I), (Ia), (Ib), or (Ic), or a pharmaceutically acceptable salt thereof, wherein p is 1 and $R^4$ is halogen, —$CF_3$, or —$OCH_3$. In some embodiments is a compound of Formula (I), (Ia), (Ib), or (Ic), or a pharmaceutically acceptable salt thereof, wherein p is 0. In some embodiments is a compound of Formula (I), (Ia), (Ib), or (Ic), or a pharmaceutically acceptable salt thereof, wherein n is 1 and $R^2$ is halogen, —$CF_3$, or —$OCH_3$. In some embodiments is a compound of Formula (I), (Ia), (Ib), or (Ic), or a pharmaceutically acceptable salt thereof, wherein n is 1 and $R^2$ is F. In some embodiments is a compound of Formula (I), (Ia), (Ib), or (Ic), or a pharmaceutically acceptable salt thereof, wherein n is 0. In some embodiments is a compound of Formula (I), (Ia), (Ib), or (Ic), or a pharmaceutically acceptable salt thereof, wherein $R^1$ is —$CO_2H$.

In some embodiments is a compound of Formula (I), or a pharmaceutically acceptable salt thereof, having the structure:

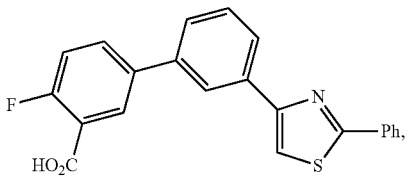

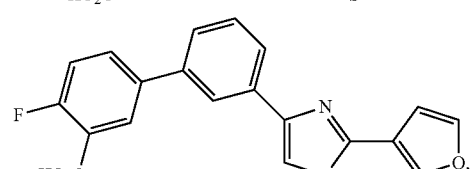

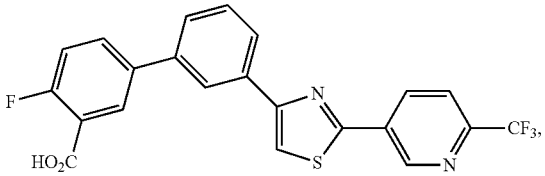

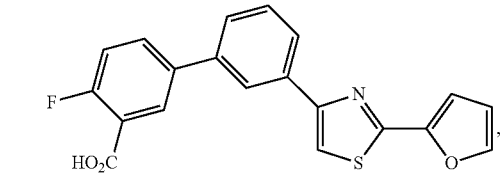

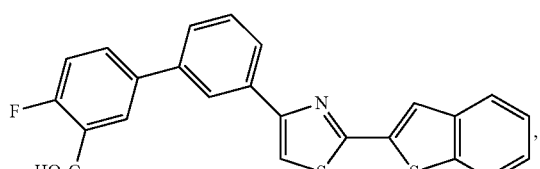

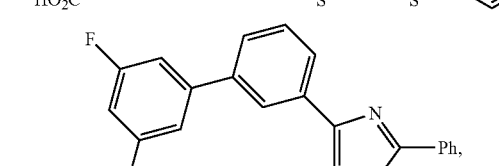

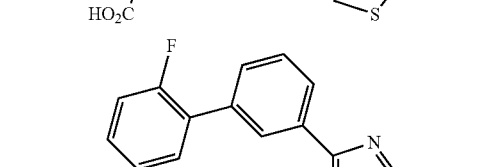

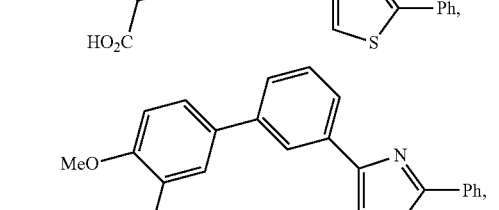

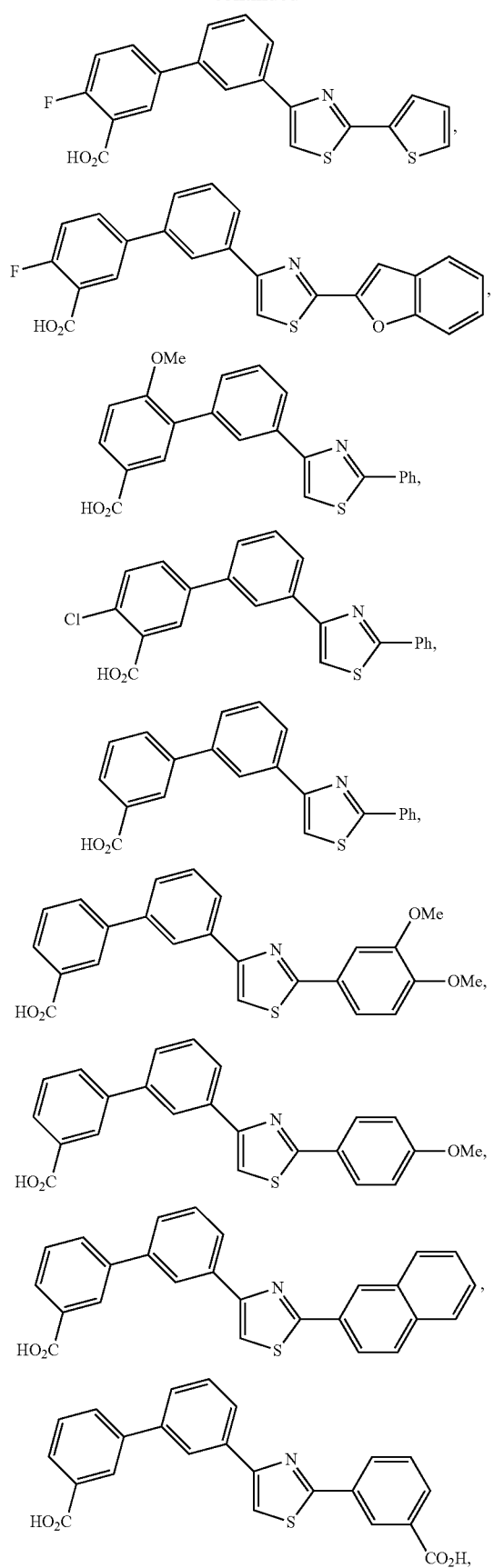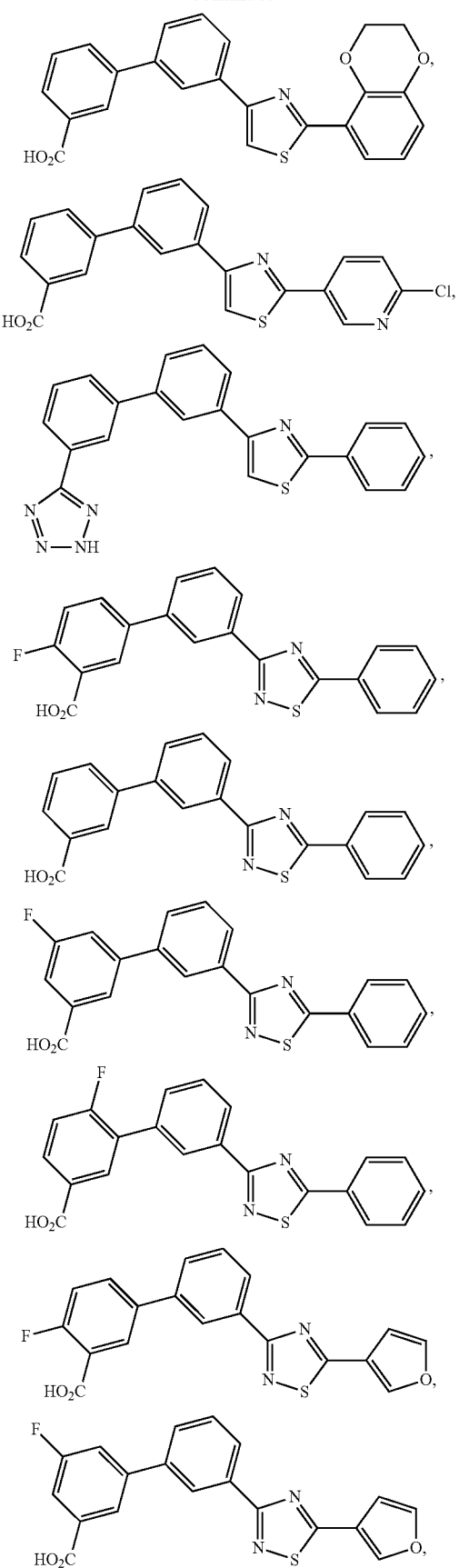

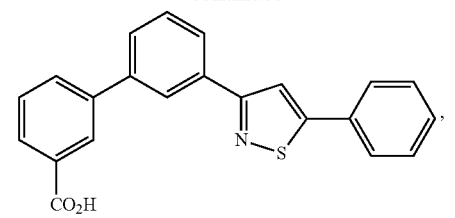
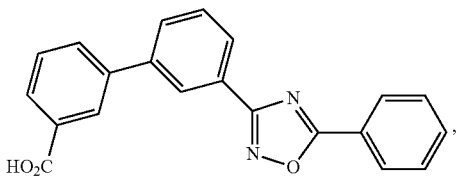
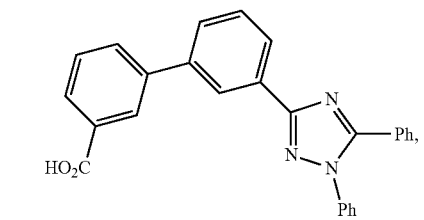
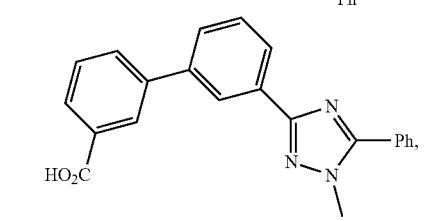
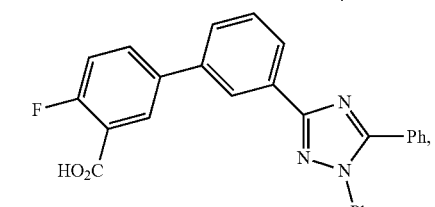
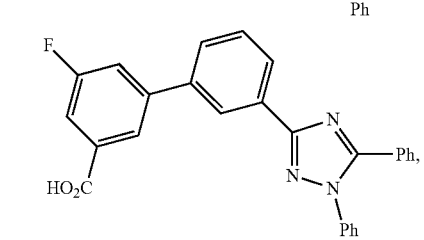
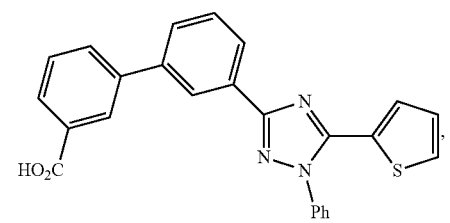
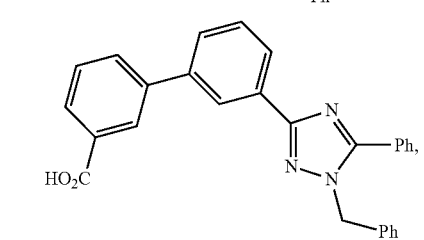
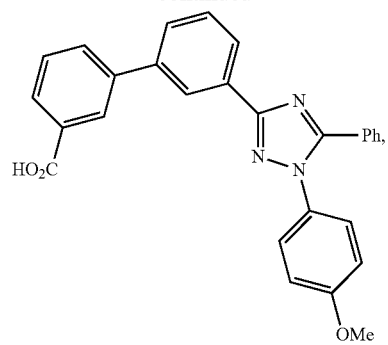
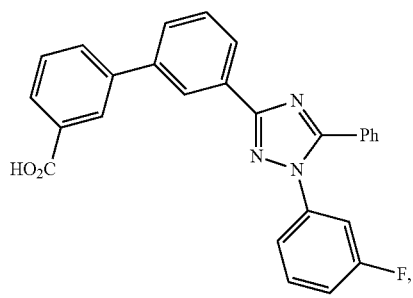
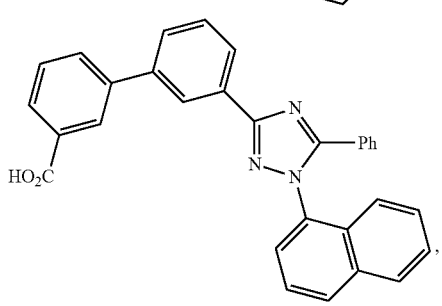
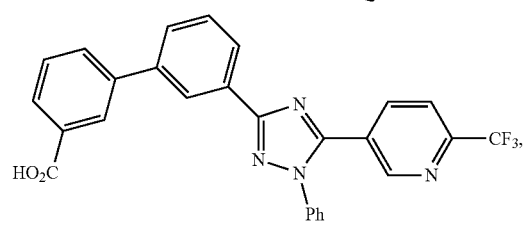
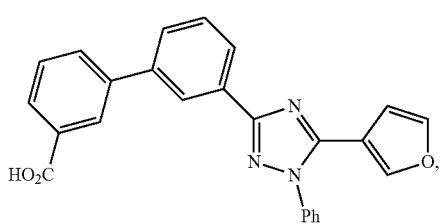
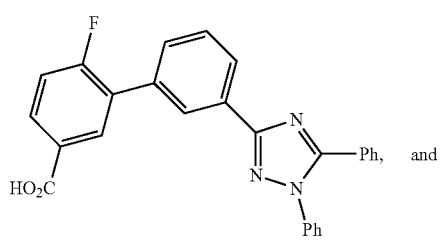

-continued

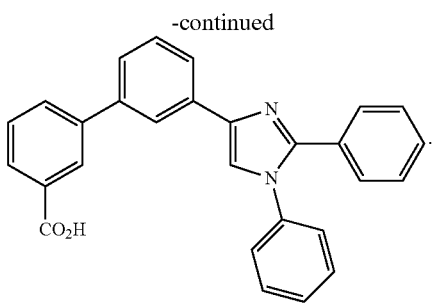

In another aspect, described herein is a compound that has the structure of Formula (II), or a pharmaceutically acceptable salt thereof:

Formula (II)

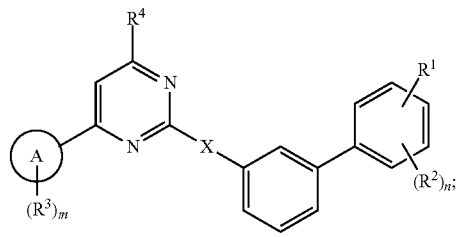

wherein:
ring Ⓐ is an aryl ring or heteroaryl ring;
X is a bond, —O—, —S—, or —N(R⁶)—;
R¹ is —CO₂H, —CN, —C(O)NHOH, —C(O)NHOMe, —C(O)NHSO₂Me, —NHC(O)Me, —C(O)NHMe,

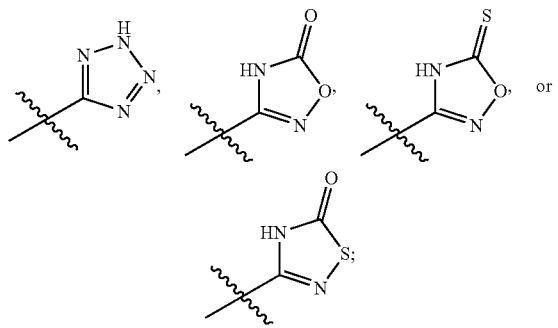

each R² is independently halogen, —OR⁵, NO₂, substituted or unsubstituted $C_1$-$C_6$alkyl, or substituted or unsubstituted $C_1$-$C_6$fluoroalkyl;
each R³ is independently halogen, —OR⁵, —SR⁵, substituted or unsubstituted $C_1$-$C_6$alkyl, substituted or unsubstituted $C_1$-$C_6$fluoroalkyl, substituted or unsubstituted $C_3$-$C_6$cycloalkyl, or substituted or unsubstituted aryl;
R⁴ is H, —CF₃, —CH₃, or substituted or unsubstituted phenyl;
each R⁵ is independently hydrogen, or substituted or unsubstituted $C_1$-$C_6$alkyl;
R⁶ is hydrogen, or substituted or unsubstituted $C_1$-$C_6$alkyl;
n is 0, 1, 2, or 3; and
m is 0, 1 or 2.

In some embodiments is a compound of Formula (II), or a pharmaceutically acceptable salt thereof, wherein ring Ⓐ is a heteroaryl ring selected from furanyl, thiophenyl, benzofuranyl, benzothiophenyl, thiazolyl, pyrrolyl, and pyridinyl.

In some embodiments is a compound of Formula (II), or a pharmaceutically acceptable salt thereof, having the structure of Formula (IIa):

Formula (IIa)

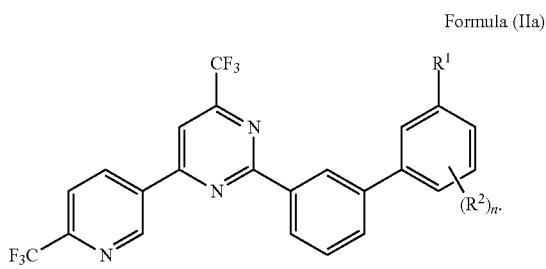

In some embodiments is a compound of Formula (II), or a pharmaceutically acceptable salt thereof, having the structure of Formula (IIb):

Formula (IIb)

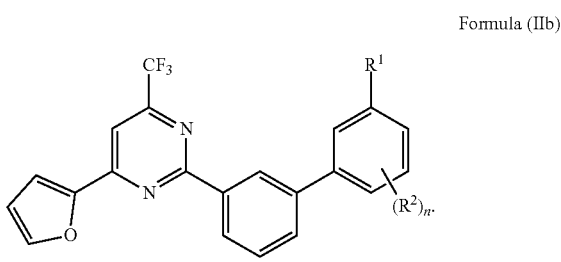

In some embodiments is a compound of Formula (II), or a pharmaceutically acceptable salt thereof, having the structure of Formula (IIc):

Formula (IIc)

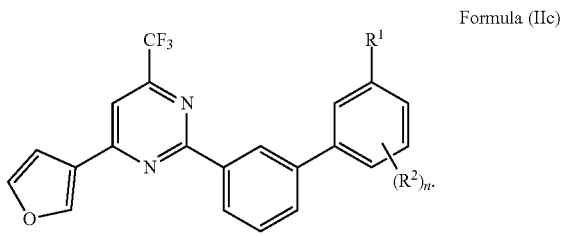

In some embodiments is a compound of Formula (II), (IIa), (IIb), or (IIc), or a pharmaceutically acceptable salt thereof, wherein n is 1 and R² is halogen or —OCH₃. In some embodiments is a compound of Formula (II), (IIa), (IIb), or (IIc), or a pharmaceutically acceptable salt thereof, wherein n is 1 and R² is F. In some embodiments is a compound of Formula (II), (IIa), (IIb), or (IIc), or a pharmaceutically acceptable salt thereof, wherein n is 0. In some embodiments is a compound of Formula (II), (IIa), (IIb), or (IIc), or a pharmaceutically acceptable salt thereof, wherein R¹ is —CO₂H.

In some embodiments is a compound of Formula (II), or a pharmaceutically acceptable salt thereof, having the structure:

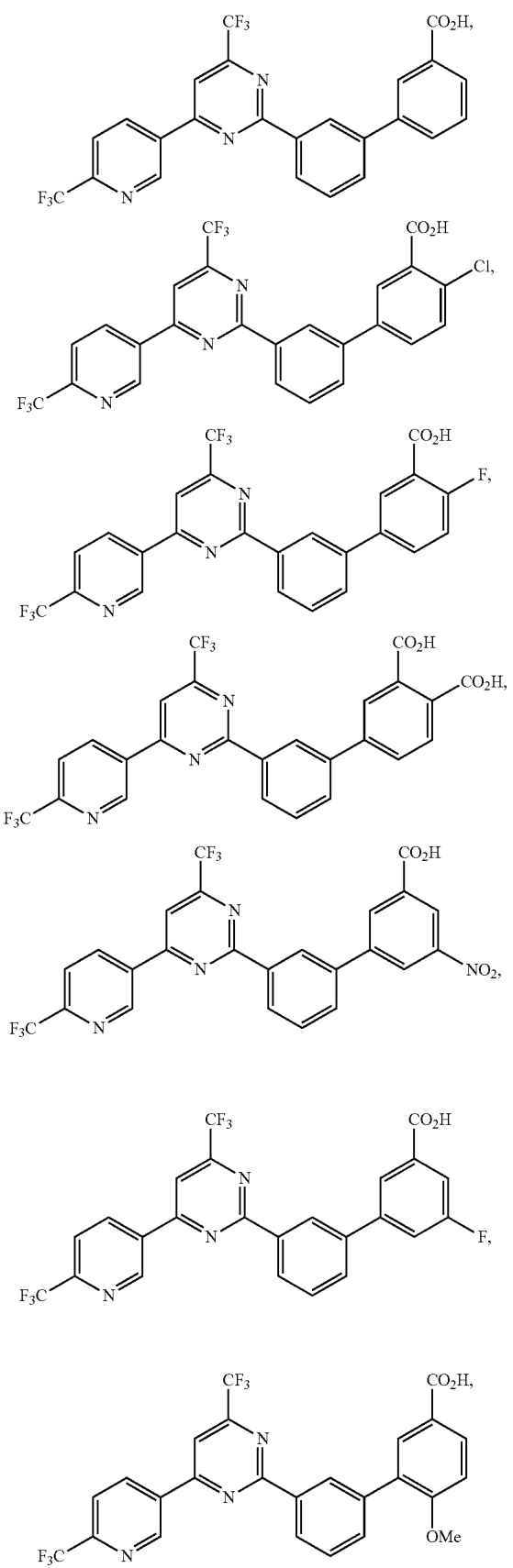
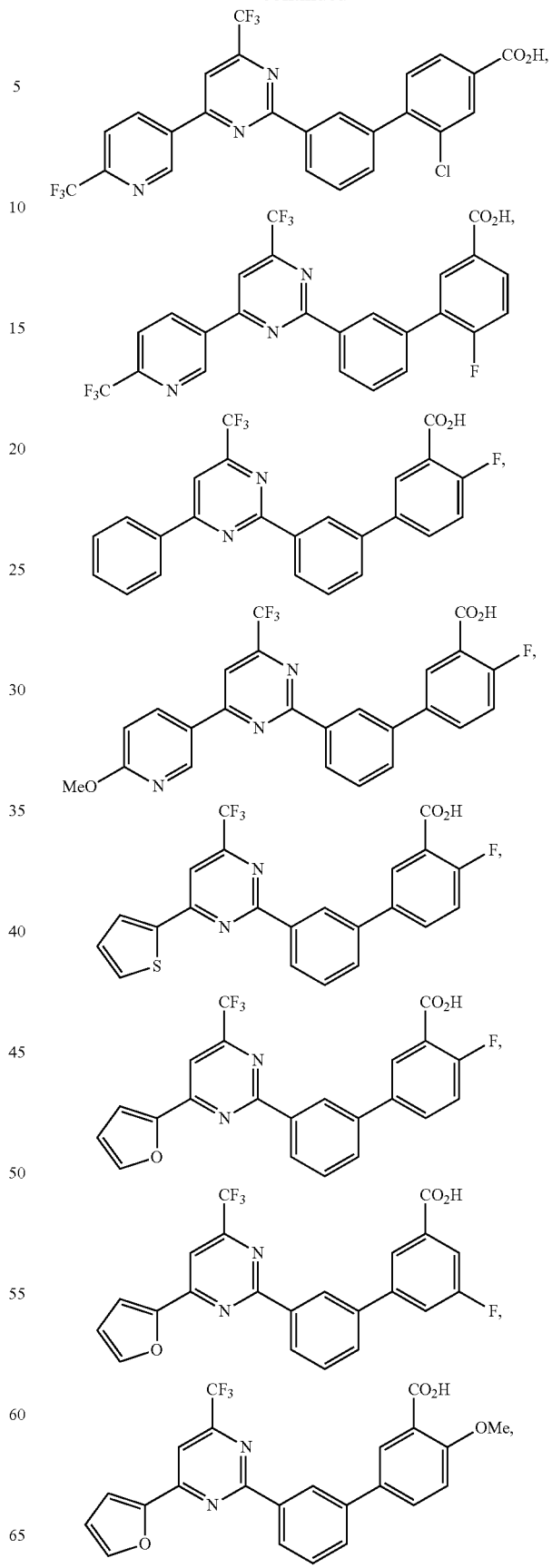

-continued
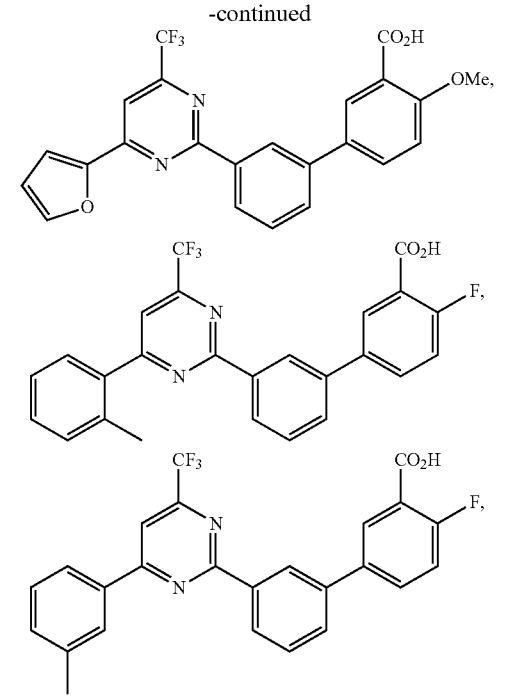
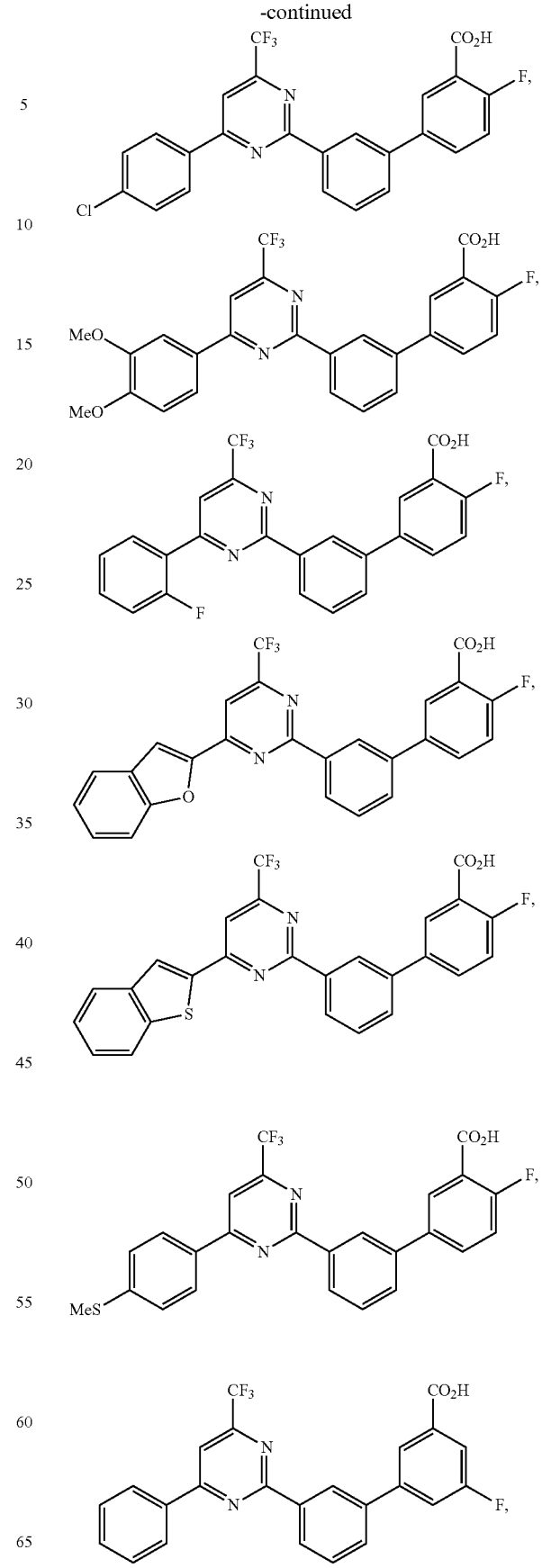

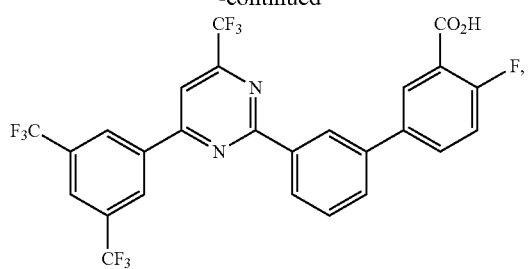
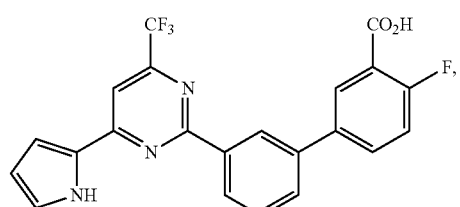
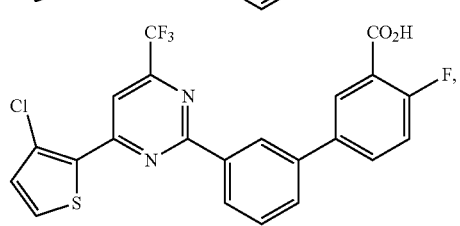
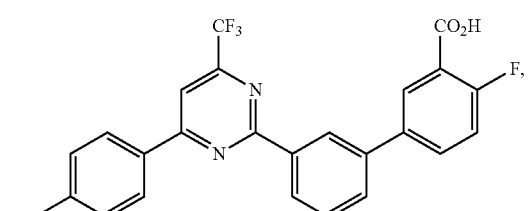
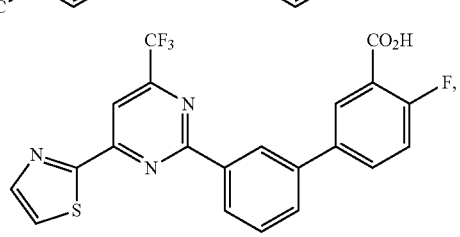
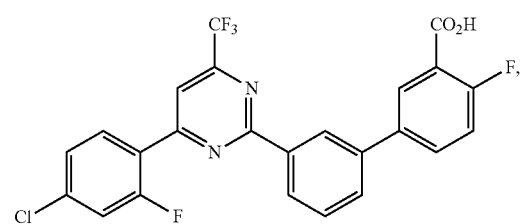
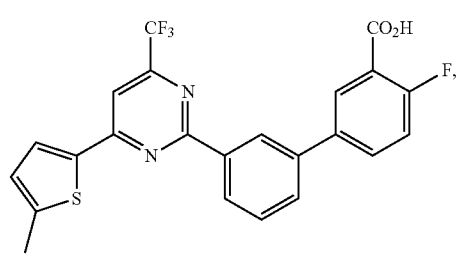
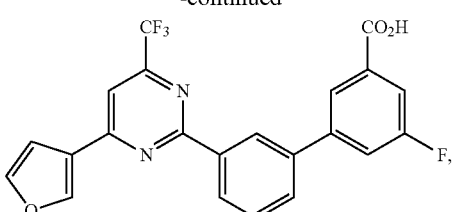
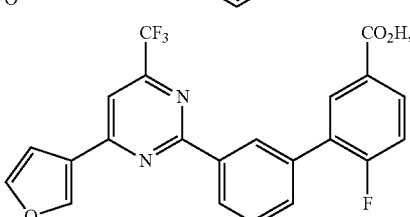
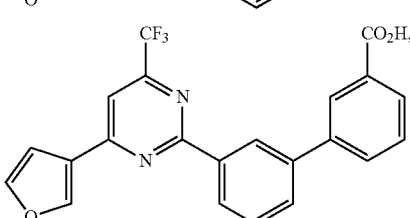
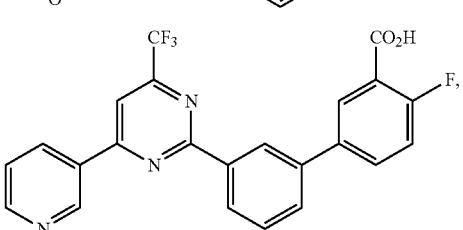
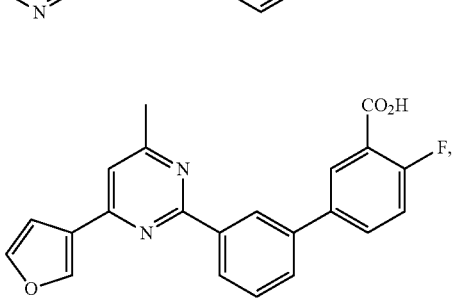
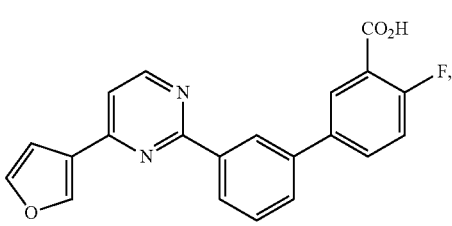
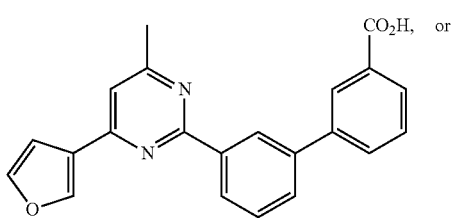

-continued

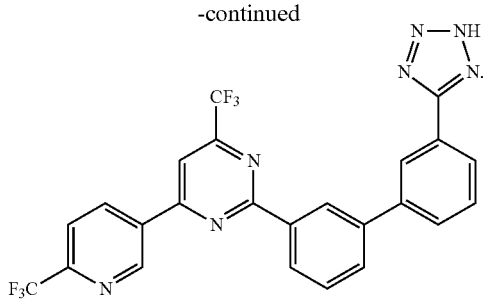

In another aspect, described herein is a compound that has the structure of Formula (III), or a pharmaceutically acceptable salt thereof:

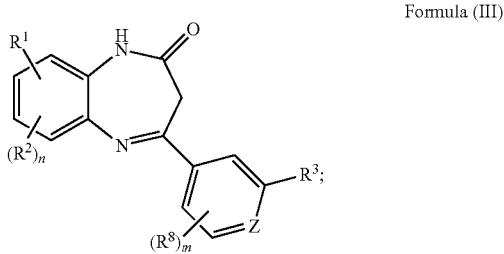

Formula (III)

wherein:
Z is =N— or =C(H)—;
R¹ is halogen, —OR⁵, —NO₂, —CN, substituted or unsubstituted $C_1$-$C_6$alkyl, substituted or unsubstituted $C_1$-$C_6$fluoroalkyl, substituted or unsubstituted aryl, substituted or unsubstituted heteroaryl, or —CO₂R⁶;
each R² is independently halogen, —OR⁵, NO₂, substituted or unsubstituted $C_1$-$C_6$alkyl, or substituted or unsubstituted $C_1$-$C_6$fluoroalkyl;
R³ is hydrogen, halogen, —CN, substituted or unsubstituted $C_1$-$C_6$alkyl, substituted or unsubstituted $C_1$-$C_6$fluoroalkyl, substituted or unsubstituted $C_3$-$C_6$cycloalkyl, substituted or unsubstituted $C_2$-$C_7$heterocycloalkyl, substituted or unsubstituted aryl, unsubstituted heteroaryl, —C(O)NR⁹R¹⁰, or —X—R⁴;
X is —O—, —S—, —S(O)₂—, —N(R⁷)—, or —C≡C—;
R⁴ is substituted or unsubstituted $C_1$-$C_6$alkyl, substituted or unsubstituted $C_3$-$C_6$cycloalkyl, substituted or unsubstituted aryl, or substituted or unsubstituted heteroaryl;
each R⁵ is independently hydrogen, or substituted or unsubstituted $C_1$-$C_6$alkyl;
R⁶ is hydrogen, or substituted or unsubstituted $C_1$-$C_6$alkyl;
R⁷ is hydrogen, or substituted or unsubstituted $C_1$-$C_6$alkyl;
each R⁸ is independently halogen, or substituted or unsubstituted $C_1$-$C_6$alkyl;
R⁹ and R¹⁰ are independently hydrogen, or substituted or unsubstituted $C_1$-$C_6$alkyl;
n is 0, 1, 2, or 3; and
m is 0, 1, or 2.

In some embodiments is a compound of Formula (III), or a pharmaceutically acceptable salt thereof, wherein Z is =N—.

In some embodiments is a compound of Formula (III), or a pharmaceutically acceptable salt thereof, having the structure of Formula (IIIa):

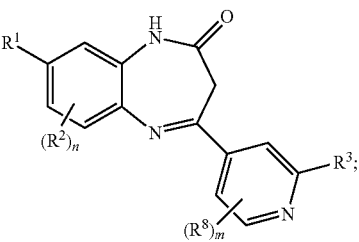

Formula (IIIa)

wherein R³ is halogen, —CN, unsubstituted heteroaryl, or —X—R⁴; and R⁴ is substituted or unsubstituted aryl, or substituted or unsubstituted heteroaryl.

In some embodiments is a compound of Formula (III), or a pharmaceutically acceptable salt thereof, having the structure of Formula (IIIb):

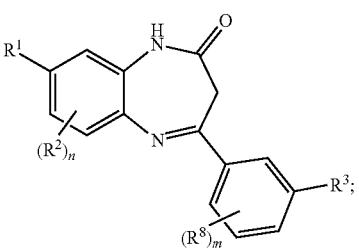

Formula (IIIb)

wherein R³ is —CN, unsubstituted heteroaryl, or —X—R⁴; and R⁴ is substituted or unsubstituted $C_1$-$C_6$alkyl, substituted or unsubstituted aryl, or substituted or unsubstituted heteroaryl.

In some embodiments is a compound of Formula (III), (IIIa), or (IIIb), or a pharmaceutically acceptable salt thereof, wherein n is 1 and R² is halogen or —CH₃. In some embodiments is a compound of Formula (III), (IIIa), or (IIIb), or a pharmaceutically acceptable salt thereof, wherein n is 1 and R² is —CH₃. In some embodiments is a compound of Formula (III), (IIIa), or (IIIb), or a pharmaceutically acceptable salt thereof, wherein n is 0. In some embodiments is a compound of Formula (III), (IIIa), or (IIIb), or a pharmaceutically acceptable salt thereof, wherein R¹ is —CF₃. In some embodiments is a compound of Formula (III), (IIIa), or (IIIb), or a pharmaceutically acceptable salt thereof, wherein m is 0.

In another aspect, described herein is a compound that has the structure of Formula (IV), or a pharmaceutically acceptable salt thereof:

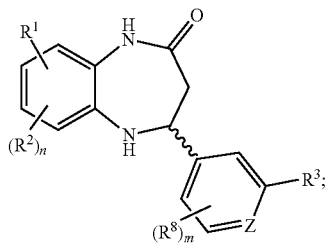

Formula (IV)

wherein:

Z is =N— or =C(H)—;

R$^1$ is halogen, —OR$^5$, —NO$_2$, —CN, substituted or unsubstituted C$_1$-C$_6$alkyl, substituted or unsubstituted C$_1$-C$_6$fluoroalkyl, substituted or unsubstituted aryl, substituted or unsubstituted heteroaryl, or —CO$_2$R$^6$;

R$^2$ is halogen, —OR$^5$, NO$_2$, substituted or unsubstituted C$_1$-C$_6$alkyl, or substituted or unsubstituted C$_1$-C$_6$fluoroalkyl;

R$^3$ is hydrogen, halogen, —CN, substituted or unsubstituted C$_1$-C$_6$alkyl, substituted or unsubstituted C$_1$-C$_6$fluoroalkyl, substituted or unsubstituted C$_3$-C$_6$cycloalkyl, substituted or unsubstituted C$_2$-C$_7$heterocycloalkyl, substituted or unsubstituted aryl, unsubstituted heteroaryl, —C(O)NR$^9$R$^{10}$, or —X—R$^4$;

X is —O—, —S—, —S(O)$_2$—, —N(R$^7$)—, or —C≡C—;

R$^4$ is substituted or unsubstituted C$_1$-C$_6$alkyl, substituted or unsubstituted C$_3$-C$_6$cycloalkyl, substituted or unsubstituted aryl, or substituted or unsubstituted heteroaryl;

each R$^5$ is independently hydrogen, or substituted or unsubstituted C$_1$-C$_6$alkyl;

R$^6$ is hydrogen, or substituted or unsubstituted C$_1$-C$_6$alkyl;

R$^7$ is hydrogen, or substituted or unsubstituted C$_1$-C$_6$alkyl;

R$^8$ is halogen, or substituted or unsubstituted C$_1$-C$_6$alkyl;

R$^9$ and R$^{10}$ are independently hydrogen, or substituted or unsubstituted C$_1$-C$_6$alkyl;

n is 0, 1, 2, or 3; and m is 0, 1, or 2.

In some embodiments is a compound of Formula (IV), or a pharmaceutically acceptable salt thereof, wherein Z is =N—.

In some embodiments is a compound of Formula (IV), or a pharmaceutically acceptable salt thereof, having the structure of Formula (IVa):

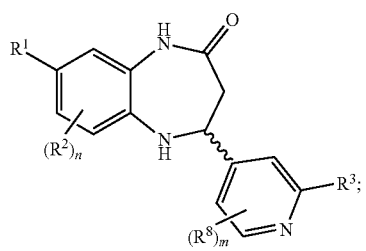

Formula (IVa)

wherein R$^3$ is halogen, —CN, unsubstituted heteroaryl, or —X—R$^4$; and R$^4$ is substituted or unsubstituted aryl, or substituted or unsubstituted heteroaryl.

In some embodiments is a compound of Formula (IV), or a pharmaceutically acceptable salt thereof, having the structure of Formula (IVb):

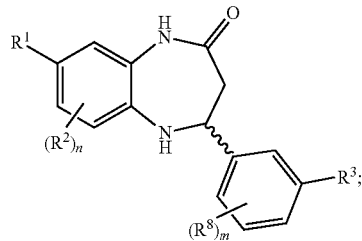

Formula (IVb)

wherein R$^3$ is —CN, unsubstituted heteroaryl, or —X—R$^4$; and R$^4$ is substituted or unsubstituted C$_1$-C$_6$alkyl, substituted or unsubstituted aryl, or substituted or unsubstituted heteroaryl.

In some embodiments is a compound of Formula (IV), (IVa), or (IVb), or a pharmaceutically acceptable salt thereof, wherein n is 1 and R$^2$ is halogen or —CH$_3$. In some embodiments is a compound of Formula (IV), (IVa), or (IVb), or a pharmaceutically acceptable salt thereof, wherein n is 1 and R$^2$ is —CH$_3$. In some embodiments is a compound of Formula (IV), (IVa), or (IVb), or a pharmaceutically acceptable salt thereof, wherein n is 0. In some embodiments is a compound of Formula (IV), (IVa), or (IVb), or a pharmaceutically acceptable salt thereof, wherein R$^1$ is —CF$_3$. In some embodiments is a compound of Formula (IV), (IVa), or (IVb), or a pharmaceutically acceptable salt thereof, wherein m is 0.

In some embodiments is a compound, or a pharmaceutically acceptable salt thereof, having the structure:

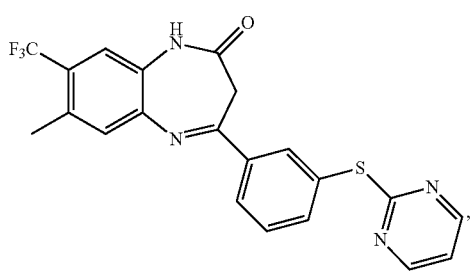

,

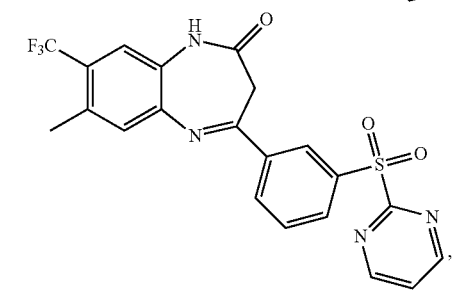

,

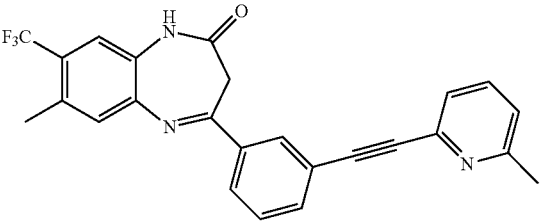

,

-continued
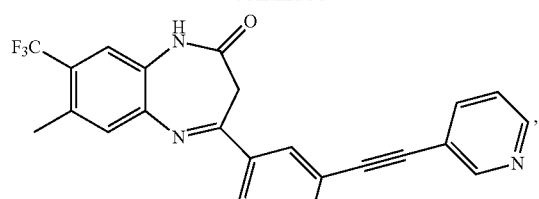
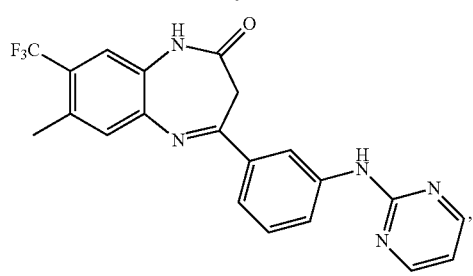
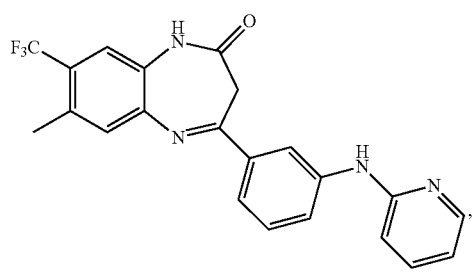
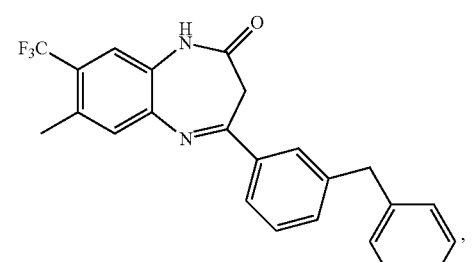
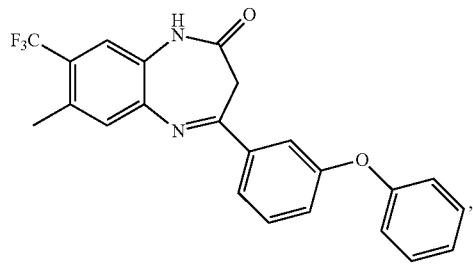
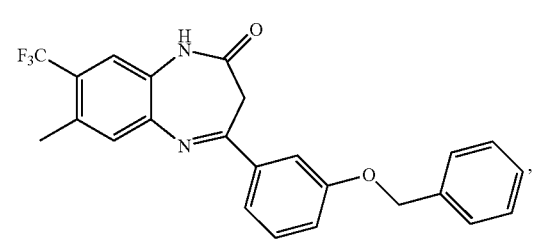
-continued
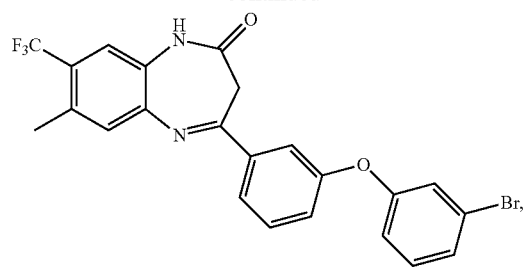
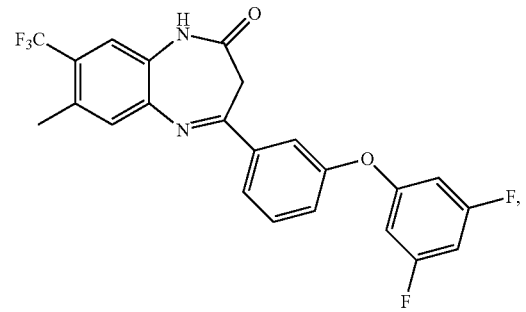
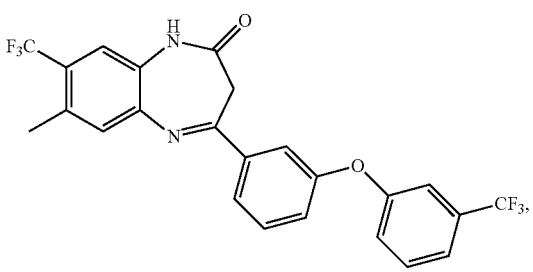
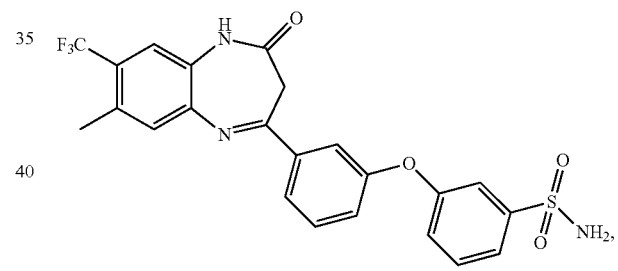
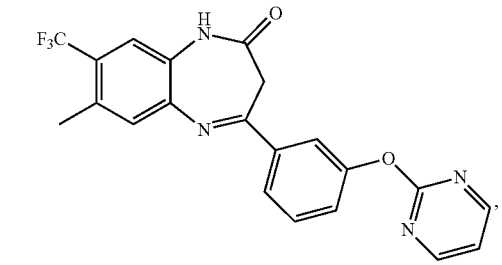
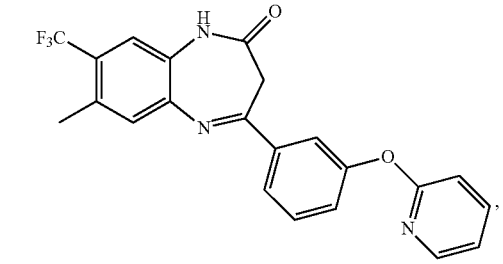

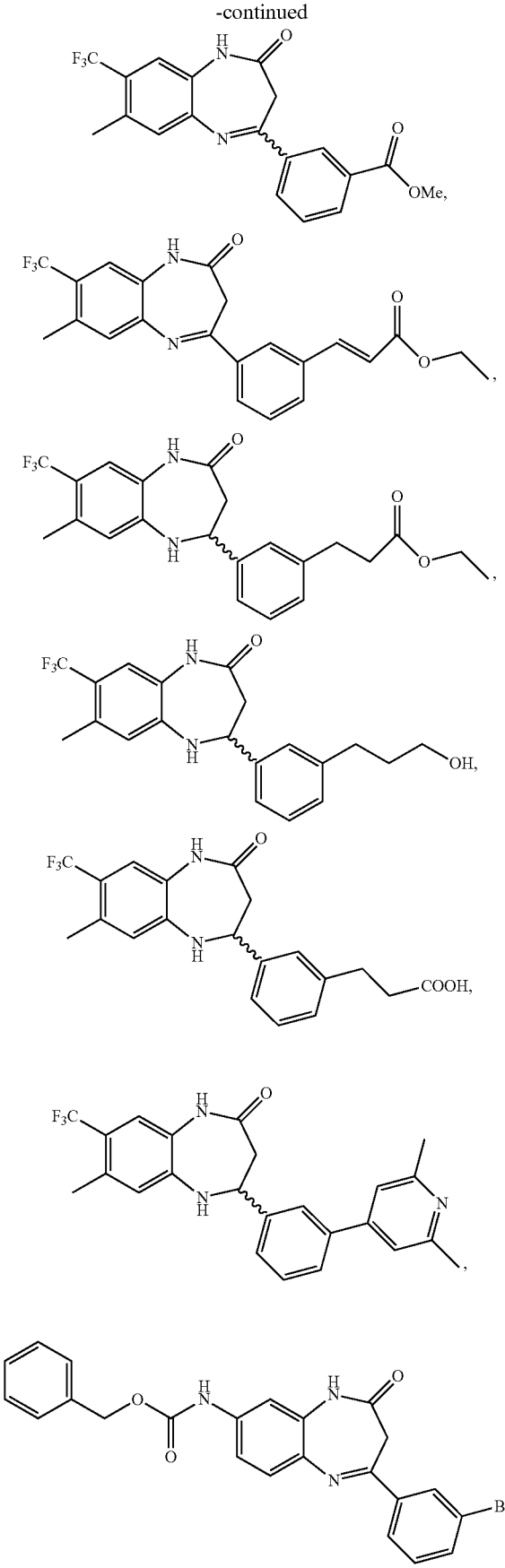
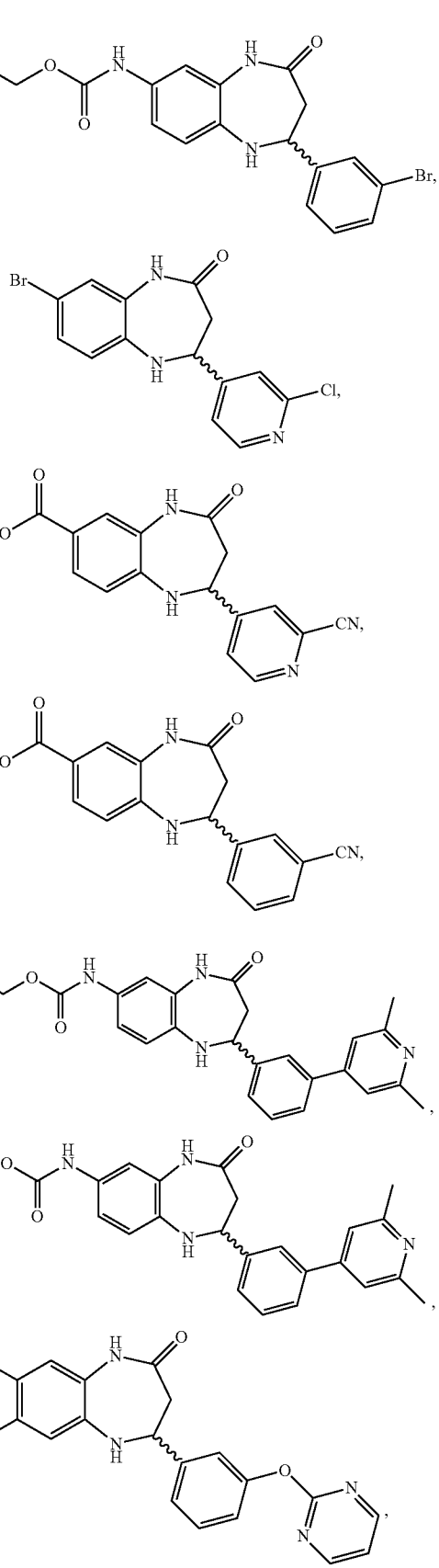

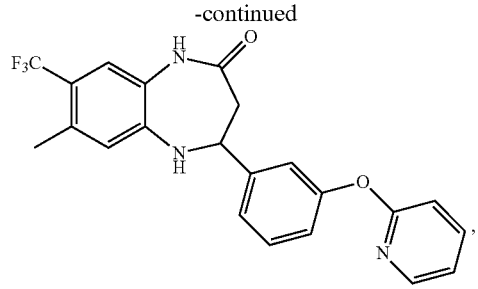,
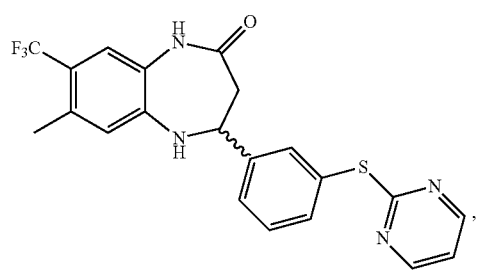,
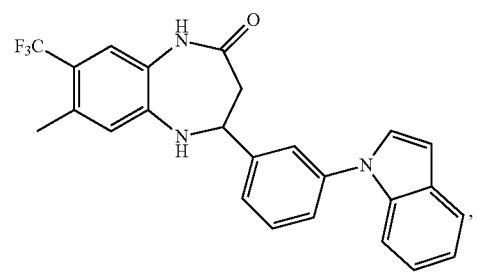,
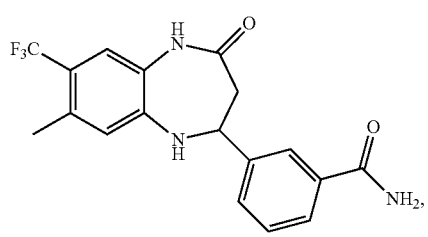,
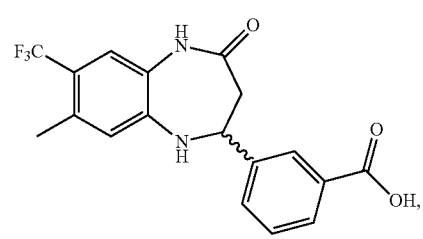,
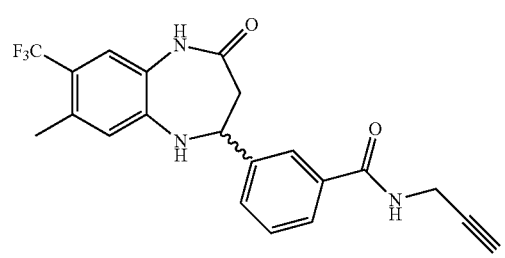,
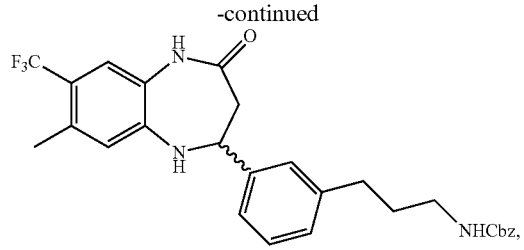,
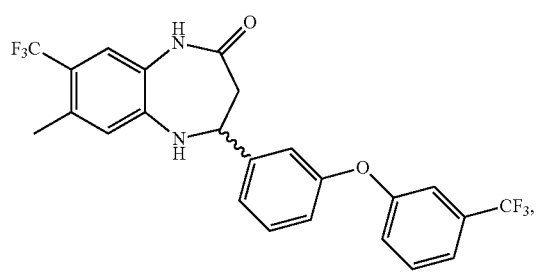,
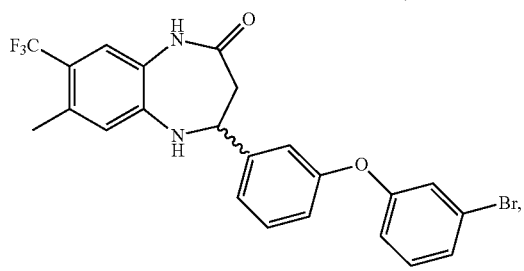,
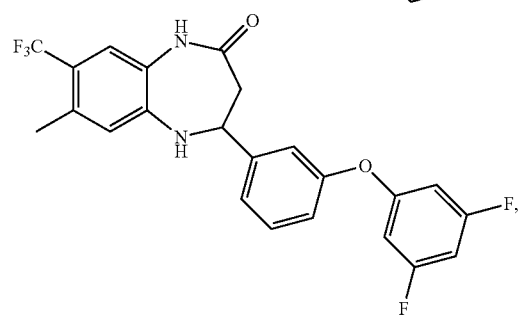,
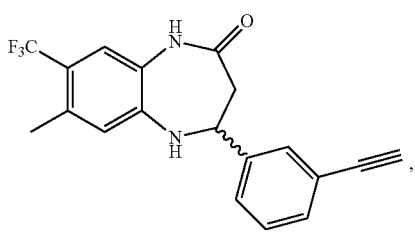,
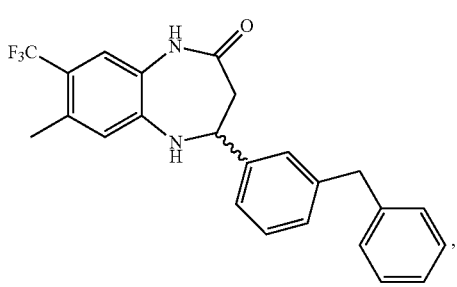,

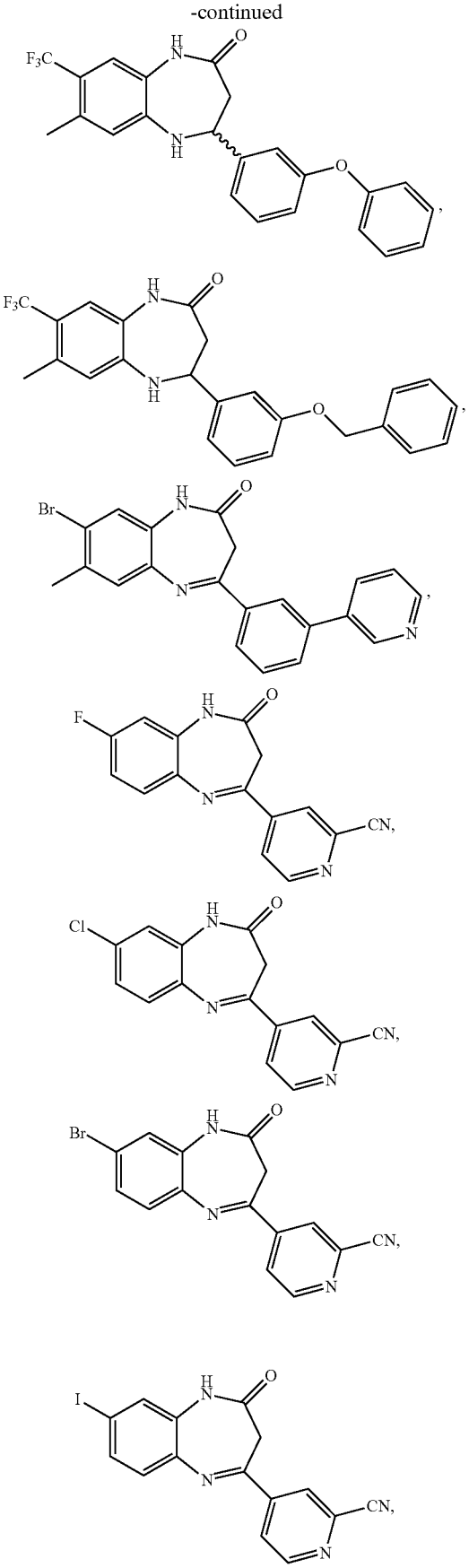
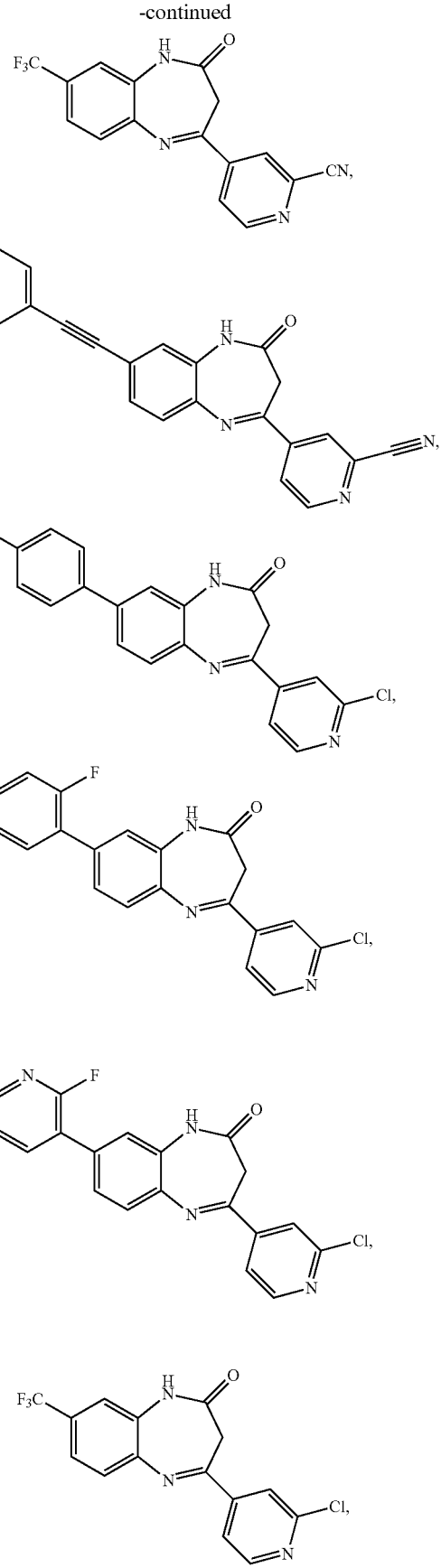

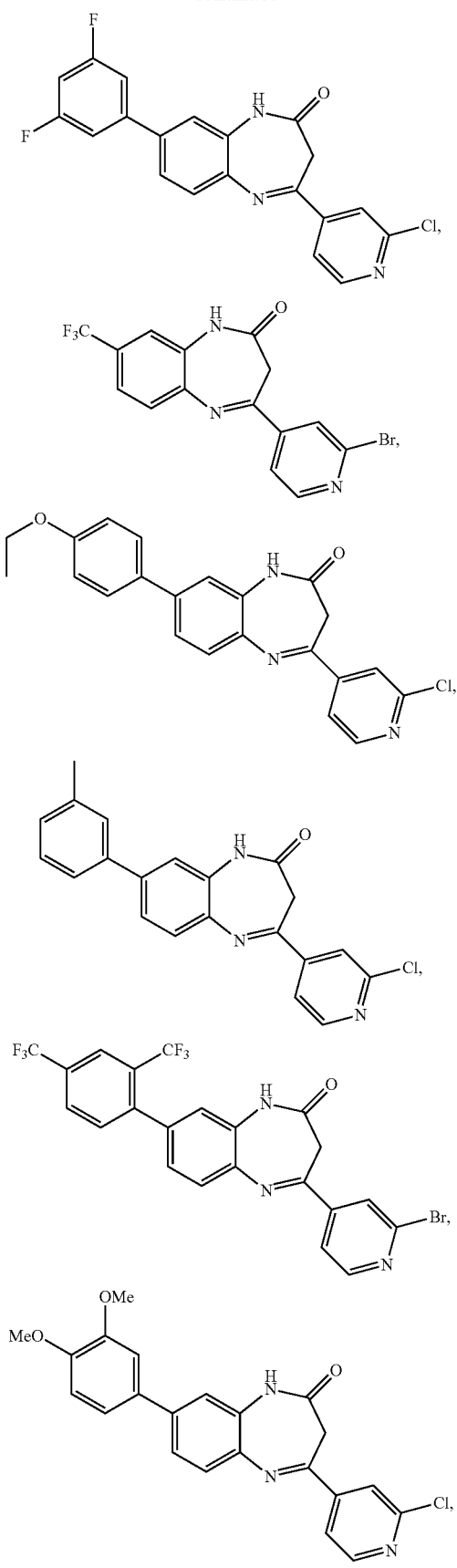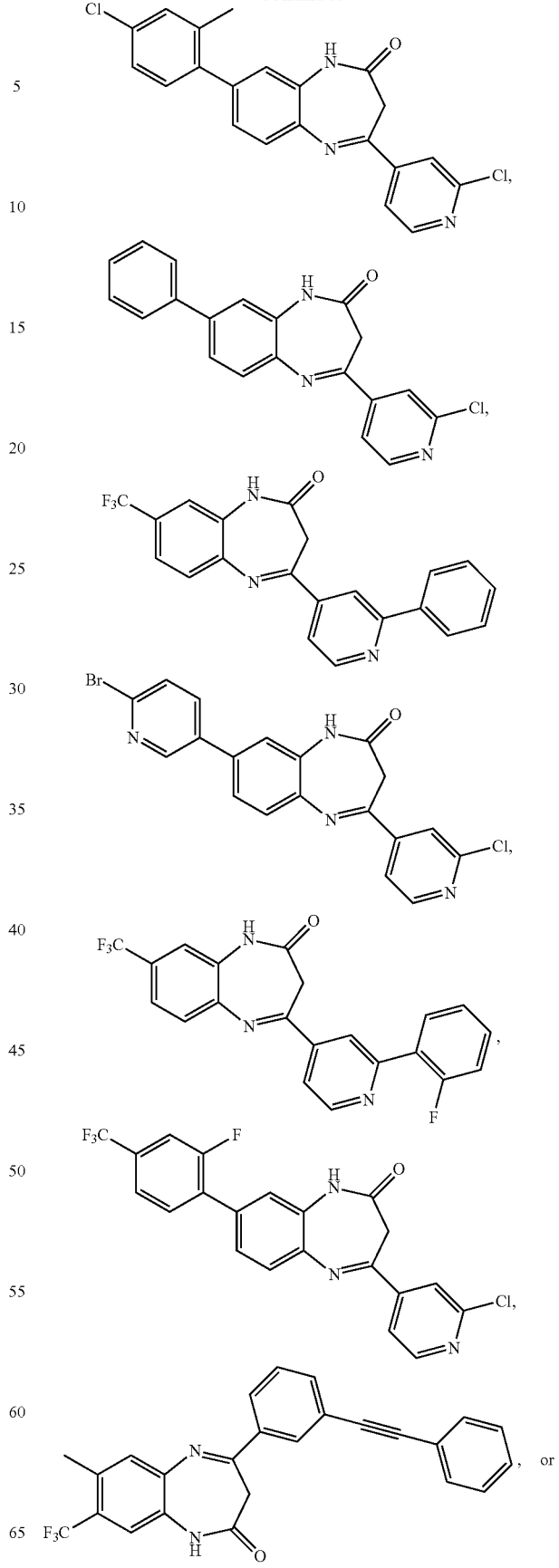

-continued

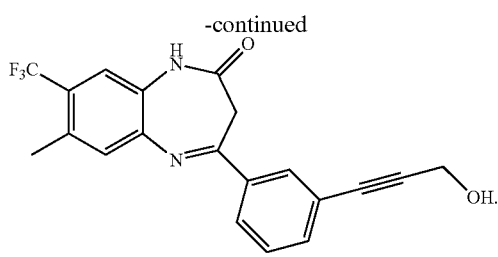

Any combination of the groups described above or below for the various variables is contemplated herein. Throughout the specification, groups and substituents thereof are chosen by one skilled in the field to provide stable moieties and compounds.

In one aspect, provided herein is a pharmaceutical composition comprising a compound of Formula (I), (Ia), (Ib), (Ic), (II), (IIa), (IIb), (IIc), (III), (IIIa), (IIIb), (IV), (IVa), or (IVb), or a pharmaceutically acceptable salt thereof, and at least one pharmaceutically acceptable excipient.

In some embodiments, the compound of Formula (I), (Ia), (Ib), (Ic), (II), (IIa), (IIb), (IIc), (III), (IIIa), (IIIb), (IV), (IVa), or (IVb), or a pharmaceutically acceptable salt thereof, is formulated for administration to a mammal by intravenous administration, subcutaneous administration, oral administration, inhalation, nasal administration, dermal administration, or ophthalmic administration. In some embodiments, the compound of Formula (I), (Ia), (Ib), (Ic), (II), (IIa), (IIb), (IIc), (III), (IIIa), (IIIb), (IV), (IVa), or (IVb), or a pharmaceutically acceptable salt thereof, is in the form of a tablet, a pill, a capsule, a liquid, a suspension, a gel, a dispersion, a solution, an emulsion, an ointment, or a lotion.

In another aspect, described herein is a method of treating a central nervous disorder (CNS) disorder, the method comprising the step of administering to a subject in need thereof, an effective amount of the compound of Formula (I), (Ia), (Ib), (Ic), (II), (IIa), (IIb), (IIc), (III), (IIIa), (IIIb), (IV), (IVa), or (IVb), thereby treating the disorder.

In some embodiments, the CNS disorder is schizophrenia.
In some embodiments, the CNS disorder is depression.
In some embodiments, the CNS disorder is treatment resistant depression (TRD).
In some embodiments, the CNS disorder is anxiety.
In some embodiments, the CNS disorder is insomnia.
In some embodiments, the CNS disorder is psychosis.
In some embodiments, the CNS disorder is epilepsy.
In some embodiments, the CNS disorder is traumatic brain injury (TBI).
In some embodiments, the CNS disorder is bipolar disorder.
In some embodiments, the CNS disorder is post traumatic stress disorder (PTSD).
In some embodiments, the CNS disorder is associated with a reduction in neurogenesis.
In some embodiments, the disorder is an addictive disorder.
In some embodiments, the CNS disorder is a neurodegenerative disease.
In some embodiments, the neurodegenerative disease is Alzheimer's disease, Parkinson's disease, Huntington's disease, or Lou Gehrig's disease (Amyotrophic Lateral Sclerosis or ALS).

In another aspect, described herein is a method of treating cancer, the method comprising the step of administering to a subject in need thereof, an effective amount of the compound of Formula (I), (Ia), (Ib), (Ic), (II), (IIa), (IIb), (IIc), (III), (IIIa), (IIIb), (IV), (IVa), or (IVb), thereby treating the cancer. In some embodiments, the cancer is glioblastoma. In some embodiments, the cancer is melanoma.

In another aspect, described herein is a method of treating pain, the method comprising the step of administering to a subject in need thereof, an effective amount of the compound of Formula (I), (Ia), (Ib), (Ic), (II), (IIa), (IIb), (IIc), (III), (IIIa), (IIIb), (IV), (IVa), or (IVb), thereby treating the pain.

In another aspect, described herein is a method of treating depression, the method comprising the step of administering to a subject in need thereof, an effective amount of the compound of Formula (I), (Ia), (Ib), (Ic), (II), (IIa), (IIb), (IIc), (III), (IIIa), (IIIb), (IV), (IVa), or (IVb). In another aspect, described herein is a method of treating treatment resistant depression (TRD), the method comprising the step of administering to a subject in need thereof, an effective amount of the compound of Formula (I), (Ia), (Ib), (Ic), (II), (IIa), (IIb), (IIc), (III), (IIIa), (IIIb), (IV), (IVa), or (IVb).

In another aspect, described herein is a method of treating schizophrenia, the method comprising the step of administering to a subject in need thereof, an effective amount of the compound of Formula (I), (Ia), (Ib), (Ic), (II), (IIa), (IIb), (IIc), (III), (IIIa), (IIIb), (IV), (IVa), or (IVb).

In another aspect, described herein is a method of treating a neurodegenerative disease, the method comprising the step of administering to a subject in need thereof, an effective amount of the compound of Formula (I), (Ia), (Ib), (Ic), (II), (IIa), (IIb), (IIc), (III), (IIIa), (IIIb), (IV), (IVa), or (IVb). In another aspect, described herein is a method of treating a neurodegenerative disease, wherein the neurodegenerative disease is Alzheimer's disease, Parkinson's disease, Huntington's disease, or Lou Gehrig's disease (Amyotrophic Lateral Sclerosis or ALS), the method comprising the step of administering to a subject in need thereof, an effective amount of the compound of Formula (I), (Ia), (Ib), (Ic), (II), (IIa), (IIb), (IIc), (III), (IIIa), (IIIb), (IV), (IVa), or (IVb).

In another aspect, described herein is a method of treating substance abuse, the method comprising the step of administering to a subject in need thereof, an effective amount of the compound of Formula (I), (Ia), (Ib), (Ic), (II), (IIa), (IIb), (IIc), (III), (IIIa), (IIIb), (IV), (IVa), or (IVb), wherein the effective amount is sufficient to diminish, inhibit or eliminate desire for and/or consumption of the substance in the subject.

In one aspect, described herein is a method of treating a disease or condition by modulation of the mGlu2 receptor in a subject in need thereof, which method comprises administering to the subject a therapeutically effective amount of a compound of Formula (I), (Ia), (Ib), (Ic), (II), (IIa), (IIb), (IIc), (III), (IIIa), (IIIb), (IV), (IVa), or (IVb), or a pharmaceutically acceptable salt thereof. In some embodiments, the disease or condition is a CNS disorder.

In another aspect, described herein is a method of treating a disease or condition by modulation of the mGlu3 receptor in a subject in need thereof, which method comprises administering to the subject a therapeutically effective amount of a compound of Formula (I), (Ia), (Ib), (Ic), (II), (IIa), (IIb), (IIc), (III), (IIIa), (IIIb), (IV), (IVa), or (IVb), or a pharmaceutically acceptable salt thereof. In some embodiments, the disease or condition is a CNS disorder.

In one aspect, described herein is a method of treating a disease or condition by dual modulation of the mGlu2/3 receptors in a subject in need thereof, which method comprises administering to the subject a therapeutically effective amount of a compound of Formula (I), (Ia), (Ib), (Ic), (II), (IIa), (IIb), (IIc), (III), (IIIa), (IIIb), (IV), (IVa), or (IVb), or a pharmaceutically acceptable salt thereof. In some embodiments, the disease or condition is a CNS disorder.

In any of the aforementioned aspects are further embodiments in which: (a) the effective amount of the compound of Formula (I), (Ia), (Ib), (Ic), (II), (IIa), (IIb), (IIc), (III), (IIIa), (IIIb), (IV), (IVa), or (IVb), is systemically administered to the mammal; and/or (b) the effective amount of the compound of Formula (I), (Ia), (Ib), (Ic), (II), (IIa), (IIb), (IIc), (III), (IIIa), (IIIb), (IV), (IVa), or (IVb) is administered orally to the mammal; and/or (c) the effective amount of the compound of Formula (I), (Ia), (Ib), (Ic), (II), (IIa), (IIb), (IIc), (III), (IIIa), (IIIb), (IV), (IVa), or (IVb) is intravenously administered to the mammal; and/or (d) the effective amount of the compound of Formula (I), (Ia), (Ib), (Ic), (II), (IIa), (IIb), (IIc), (III), (IIIa), (IIIb), (IV), (IVa), or (IVb) is administered by inhalation; and/or (e) the effective amount of the compound of Formula (I), (Ia), (Ib), (Ic), (II), (IIa), (IIb), (IIc), (III), (IIIa), (IIIb), (IV), (IVa), or (IVb) is administered by nasal administration; or and/or (f) the effective amount of the compound of Formula (I), (Ia), (Ib), (Ic), (II), (IIa), (IIb), (IIc), (III), (IIIa), (IIIb), (IV), (IVa), or (IVb) is administered by injection to the mammal; and/or (g) the effective amount of the compound of Formula (I), (Ia), (Ib), (Ic), (II), (IIa), (IIb), (IIc), (III), (IIIa), (IIIb), (IV), (IVa), or (IVb) is administered topically to the mammal; and/or (h) the effective amount of the compound of Formula (I), (Ia), (Ib), (Ic), (II), (IIa), (IIb), (IIc), (III), (IIIa), (IIIb), (IV), (IVa), or (IVb) is administered by ophthalmic administration; and/or (i) the effective amount of the compound of Formula (I), (Ia), (Ib), (Ic), (II), (IIa), (IIb), (IIc), (III), (IIIa), (IIIb), (IV), (IVa), or (IVb) is administered rectally to the mammal; and/or (j) the effective amount is administered non-systemically or locally to the mammal.

In any of the aforementioned aspects are further embodiments comprising single administrations of the effective amount of the compound of Formula (I), (Ia), (Ib), (Ic), (II), (IIa), (IIb), (IIc), (III), (IIIa), (IIIb), (IV), (IVa), or (IVb), including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound of Formula (I), (Ia), (Ib), (Ic), (II), (IIa), (IIb), (IIc), (III), (IIIa), (IIIb), (IV), (IVa), or (IVb), including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In any of the aforementioned aspects involving the administration of a compound of Formula (I), (Ia), (Ib), (Ic), (II), (IIa), (IIb), (IIc), (III), (IIIa), (IIIb), (IV), (IVa), or (IVb), or a pharmaceutically acceptable salt thereof, to a subject are further embodiments comprising administering at least one additional agent in addition to the administration of a compound having the structure of Formula (I), (Ia), (Ib), (Ic), (II), (IIa), (IIb), (IIc), (III), (IIIa), (IIIb), (IV), (IVa), or (IVb), or a pharmaceutically acceptable salt thereof. In various embodiments, the compound of Formula (I), (Ia), (Ib), (Ic), (II), (IIa), (IIb), (IIc), (III), (IIIa), (IIIb), (IV), (IVa), or (IVb) and the additional agent are administered in any order, including simultaneously. In some embodiments, the compound of Formula (I), (Ia), (Ib), (Ic), (II), (IIa), (IIb), (IIc), (III), (IIIa), (IIIb), (IV), (IVa), or (IVb) and the additional agent are administered to the subject in the same pharmaceutical composition or in separate pharmaceutical compositions.

In any of the embodiments disclosed herein, the subject is a human.

In some embodiments, compounds and compositions provided herein are administered to a human.

In some embodiments, compounds and compositions provided herein are orally administered.

In other embodiments, compounds of Formula (I), (Ia), (Ib), (Ic), (II), (IIa), (IIb), (IIc), (III), (IIIa), (IIIb), (IV), (IVa), or (IVb) provided herein are used in the manufacture of a medicament for the modulation of the mGlu2 receptor. In other embodiments, compounds of Formula (I), (Ia), (Ib), (Ic), (II), (IIa), (IIb), (IIc), (III), (IIIa), (IIIb), (IV), (IVa), or (IVb) provided herein are used in the manufacture of a medicament for the modulation of the mGlu3 receptor. In other embodiments, compounds of Formula (I), (Ia), (Ib), (Ic), (II), (IIa), (IIb), (IIc), (III), (IIIa), (IIIb), (IV), (IVa), or (IVb) provided herein are used in the manufacture of a medicament for the dual modulation of the mGlu2/3 receptors.

Articles of manufacture, which include packaging material, a compound of Formula (I), (Ia), (Ib), (Ic), (II), (IIa), (IIb), (IIc), (III), (IIIa), (IIIb), (IV), (IVa), or (IVb), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for the treatment of diseases or conditions that would benefit from the modulation of the mGlu2 receptor, are provided.

Articles of manufacture, which include packaging material, a compound of Formula (I), (Ia), (Ib), (Ic), (II), (IIa), (IIb), (IIc), (III), (IIIa), (IIIb), (IV), (IVa), or (IVb), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for the treatment of diseases or conditions that would benefit from the modulation of the mGlu3 receptor, are provided.

Articles of manufacture, which include packaging material, a compound of Formula (I), (Ia), (Ib), (Ic), (II), (IIa), (IIb), (IIc), (III), (IIIa), (IIIb), (IV), (IVa), or (IVb), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for the treatment of diseases or conditions that would benefit from the dual modulation of the mGlu2/3 receptors, are provided Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

BRIEF DESCRIPTION OF THE DRAWINGS

FIG. 1 shows the antidepressant activity of Compounds 182 and 191 by decreasing immobility and increasing swimming in the Forced Swim Test (FST).

DETAILED DESCRIPTION OF THE INVENTION

Glutamate is the major excitatory neurotransmitter in the central and peripheral nervous system and exerts its effects mainly through ionotropic (iGlus) and metabotropic glutamate receptors (mGlus). The mGlus are seven-transmembrane G protein-coupled receptors (GPCRs) and the eight known members of the mGlu family are divided into three sub-groups based on sequence homology, signal transduction and pharmacology: mGlu1 and mGlu5 belong to Group I, mGlu2 and mGlu3 belong to Group II and mGlu4, mGlu6, mGlu7 and mGlu8 belong to Group III.

The orthosteric binding site of the mGlus, which consists of a large bi-lobed extracellular amino terminal domain, is highly conserved, particularly within each group. For this reason it has been difficult to develop subtype-specific ligands (agonists and antagonists) for these receptors. Recently, advances have been made to develop highly selective compounds which modulate the activity of these receptors by binding within the receptors transmembrane heptahelical domain. These allosteric modulators are compounds that bind receptors at a non-active or non-orthosteric site and thereby can modulate receptor function even if the endogenous ligand is also bound to the receptor (orthosteric site). As a result, an allosteric modulator does not have to compete with the ligand to impact the receptor's function and permits a different approach to designing receptor modulators, such as a more selective agent able to distinguish between the various mGlus and affect only the receptor(s) of interest. As an example, the binding of an allosteric modulator may have a lower affinity to the site and still be effective unlike most conventional antagonists that must block ligand-receptor interactions. Moreover, the modulation of the allosteric site permits the natural processes of the endogenous ligand and associated receptor to continue. One type of allosteric modulator is a negative allosteric modulator (NAM) in which the modulator acts to decrease the signal sent by the endogenous ligand via the receptor. Another type of modulator is the positive allosteric modulator (PAM) which does not exhibit intrinsic agonism of the receptor but facilitates or potentiates agonist-mediated receptor activity. In some instances the modulator may be classified as an allosteric agonist in that it alone, without the effects of the natural ligand, induces receptor activity.

The GPCR contains two distinct domains; a large extracellular domain which binds glutamate at the orthosteric binding site and a heptahelical transmembrane domain, which has been found to bind a variety of ligands at one or more allosteric binding sites. Recent experimental findings show that GPCRs form homodimers, heterodimers and in some cases hetero-oligomers with members of their own class as well as with other unrelated GPCRs and impacts their trafficking, signaling, and pharmacology (Milligan *Drug Discov Today* 2006, 11(11-12): 541-549). Although a GPCR monomer is sufficient to activate a G protein, it is believed that dimerization leads to stabilization of the active conformation and enhancement of G protein activation. It has been clearly established that mGlus exist as constitutive dimers with the two subunits being linked by a disulfide bridge (Romano et al. *J Biol Chem* 1996, 271(45):28612-28616). Recent studies have found that activation or inhibition of either monomer of the dimer complex facilitates a change in the activity or function of the adjoining monomer. As an example, it was found that $G_{i/o}$ protein regulation, which is necessary for the effects of hallucinogens, is enhanced by the formation of the $5HT_{2A}$/mGlu2 dimer complex and that activation of the mGlu2 monomer suppresses hallucinogen-specific signaling, while by contrast, the affinity of $mGlu_{2/3}$ agonists was reduced in the presence of an hallucinogen (Gonzalez-Maeso et al. *Nature* 2008, 452(7183):93-97).

In some embodiments, the compounds described herein are mGlu2/3 receptor NAMs.

In some embodiments, the compounds described herein are used to treat a CNS disorder. In some embodiments, the CNS disorder is depression. In some embodiments, the CNS disorder is treatment resistant depression. In some embodiments, the CNS disorder is psychosis. In some embodiments, the CNS disorder is anxiety. In some embodiments, the CNS disorder is schizophrenia. In some embodiments, the CNS disorder is anxiety. In some embodiments, the CNS disorder is insomnia. In some embodiments, the CNS disorder is epilepsy. In some embodiments, the CNS disorder is traumatic brain injury (TBI). In some embodiments, the CNS disorder is bipolar disorder. In some embodiments, the CNS disorder is post traumatic stress disorder. (PTSD). In some embodiments, the CNS disorder is associated with a reduction in neurogenesis. In another embodiment, the CNS disorder is an addictive disorder.

In some embodiments, the addictive disorder is nicotine addiction, alcohol addiction, opiate addiction, amphetamine addiction, methamphetamine addiction, or cocaine addiction.

In some embodiments, the addictive disorder is nicotine addiction. In some embodiments, the addictive disorder is cocaine addiction.

In another aspect the disclosure provides methods for treating substance abuse, by administering to a subject in need thereof, an effective amount of a compound having Formula I, wherein the effective amount is sufficient to diminish, inhibit or eliminate desire for and/or consumption of the substance in the subject.

In another aspect the disclosure provides methods for treating substance abuse, wherein the substance is nicotine, alcohol, opiates, amphetamines, methamphetamines, or cocaine.

In another aspect the disclosure provides a method for treating an addictive disorder, by a) administering to a subject in need thereof, an effective amount of a compound having Formula I, during a first time period, wherein the first time period is a time period wherein the subject expects to be in an environment wherein, or exposed to stimuli in the presence of which, the subject habitually uses an addictive substance; and b) administering an effective amount of a compound having Formula I during a second time period, wherein the second time period is a time period wherein the subject is suffering from withdrawal.

In some embodiments, the CNS disorder is a neurodegenerative disease.

In some embodiments, the neurodegenerative disease is Alzheimer's disease. In some embodiments, the neurodegenerative disease is Parkinson's disease. In some embodiments, the neurodegenerative disease is Huntington's disease. In some embodiments, the neurodegenerative disease is Lou Gehrig's disease (Amyotrophic Lateral Sclerosis or ALS).

In some embodiments, the compounds described herein are used to treat cancer. In some embodiments, the cancer is glioblastoma. In some embodiments, the cancer is melanoma.

In some embodiments, the compounds described herein are used to treat pain.

In some embodiments, the compounds described herein provide neuroprotection.

Anxiety

Anxiety is an unpleasant state of inner turmoil, often accompanied by nervous behavior, such as pacing back and forth, somatic complaints and rumination. It is the subjectively unpleasant feelings of dread over anticipated events, such as the feeling of imminent death. Anxiety is a feeling of fear, worry, and uneasiness, usually generalized and unfocused as an overreaction to a situation that is only subjectively seen as menacing. It is often accompanied by muscular tension, restlessness, fatigue and problems in concentration. Anxiety can be appropriate, but when experienced regularly the individual may suffer from an anxiety disorder.

In some embodiments, the compounds described herein are mGlu2/3 receptor NAMs used for treating anxiety symptoms. The method includes administering to a subject in need thereof, an effective amount of at least one mGlu2/3 receptor NAM, thereby treating the anxiety symptoms.

Nicotine Addiction

Nicotine dependence is an addiction to tobacco products caused by the drug nicotine. Nicotine dependence means a person can't stop using the substance, even though it's causing harm. Nicotine produces physical and mood-altering effects in the human brain that are temporarily pleasing. These effects increase the desire to use tobacco and lead to dependence. At the same time, stopping tobacco use causes withdrawal symptoms, including irritability and anxiety.

In certain aspects, the effective amount of at least one negative allosteric modulator is administered to decrease nicotine consumption. For example, in one aspect an effective amount of a negative allosteric modulator of mGlu2 and/or mGlu3, can be administered to decrease nicotine consumption. In certain aspects of the disclosure, a negative allosteric modulator of mGlu2 and/or mGlu3 is administered while a subject is experiencing withdrawal. In another aspect of the disclosure, a negative allosteric modulator of mGlu2 and/or mGlu3 is administered during a time period when a subject is actively using an addictive substance.

Cocaine Addiction

Cocaine addiction remains a major public health problem in the United States. There are several sources of motivation that contribute to the continuance of cocaine abuse, including: the positive reinforcing effects of cocaine; and the alleviation of the negative affective aspects of cocaine withdrawal. Conditioned stimuli previously associated with cocaine administration may also elicit conditioned "cravings" leading to the reinstatement of cocaine-seeking behavior even after a prolonged period of abstinence. Recent studies indicate that the neuronal mechanisms underlying various aspects of drug abuse may differ necessitating the use of different treatments for specific aspects of drug dependence. To date, a safe and effective pharmacological treatment for cocaine dependence has yet to be identified. Thus, there remains a need for the design of new chemical entities that can be used as novel medications for cocaine addiction.

It has been found that repeated cocaine exposure may alter the function of Group II metabotropic glutamate receptors (mGlu2 and mGlu3 receptors), pointing to a possible role of these mGlu subtypes in the development of cocaine dependence. The mGlu2/3 receptor negative modulators may decrease the reinforcing effects of self-administered cocaine in rats that had extended access to cocaine, a putative model of cocaine dependence while having no effect in rats with limited access to cocaine. Negative mGlu2/3 receptor modulators may attenuate discriminatory cue-induced reinstatement of cocaine self-administration. In addition, mGlu2/3 receptor negative modulators may reverse the reward deficits associated with early cocaine abstinence.

Cocaine addiction is a chronic relapsing disorder and remains a major public health problem in the United States. The number of cases of cocaine abuse has steadily risen in the past decade. To date, a safe and effective pharmacological treatment for cocaine dependence has yet to be identified, which highlights the need to design new chemical entities that may become future novel medications for cocaine addiction. Recent evidence suggests that mGlus play a significant role in the abuse-related effects of cocaine. For example, repeated administration of cocaine has been shown to alter the function of mGlus, as well as their regulation by cysteine/glutamate exchange in the nucleus accumbens. These findings suggest that mGlu2/3 may be involved in the development of cocaine dependence and may represent a possible target for drug discovery against different aspects of cocaine abuse and dependence. There are several sources of motivation that contribute to the maintenance of cocaine abuse. These include the positive reinforcing effects of cocaine and alleviation of the negative affective aspects of cocaine withdrawal. Further, conditioned stimuli previously associated with cocaine administration may elicit conditioned "cravings" leading to the reinstatement of cocaine-seeking behavior even after a prolonged period of abstinence. Recent studies suggest that the neuronal mechanisms underlying drug self-administration are different from those mediating relapse vulnerability during abstinence, and different from those mediating the negative effects of early drug withdrawal. Therefore, it is important to explore concurrently the neurochemical mechanisms that contribute to the different aspects of cocaine dependence using animal models assessing the positive reinforcing effects of cocaine, the negative affective symptoms of early withdrawal, and cue-induced reinstatement of cocaine-seeking behavior after prolonged abstinence from drug intake. The discovery and preclinical testing of highly selective mGlu2/3 receptor modulators with good brain penetration may significantly contribute to the discovery of novel therapeutic treatments for different aspects cocaine dependence.

The intravenous drug self-administration procedure provides a reliable and robust model of human drug consumption. This procedure in animals provides a valid model of human drug abuse as studied in a controlled laboratory situation. Self-administration of drugs of abuse is thought to provide an operational measure of the rewarding effects of the drug. Increases in excitatory glutamatergic transmission are likely to contribute to the positive reinforcing properties of addictive drugs. Neurochemical studies indicate that systemic cocaine administration increase glutamate levels in the ventral tegmental area (VTA) and the nucleus accumbens, brain structures that are integral components of the extended amygdala, a brain circuit mediating the reward effects of all major drugs of abuse. The administration of a negative modulator of mGlu2/3 receptors may decrease cocaine self-administration in rats with extended access to cocaine by decreasing glutamate neurotransmission in limbic structures similar to the effects of mGlu2/3 agonists. In contrast, a negative modulator of mGlu2/3 receptors will most likely have no effect on cocaine self-administration, or possibly will shift the dose-response curve to the left, potentiating the reinforcing effects of cocaine.

Another challenge for the treatment of drug addiction is chronic vulnerability to relapse. One of the factors that precipitates drug craving and relapse to drug taking behavior in humans is environmental stimuli previously associated with drug-taking. These drug-associated stimuli can be divided into two categories: discrete drug cues (e.g., drug paraphernalia) that are associated with the rewarding effects of the drug, and discriminatory and contextual drug cues (e.g., specific environmental stimuli or specific environments) that predict drug availability. In animals, discrete, discriminative and contextual conditioned cues can reinstate drug-seeking behavior, measured by variables derived from the reinstatement procedure. Recent data showed that reinstatement of cocaine-seeking was attenuated by systemic injections of N-acetylcysteine that leads to a tonic increase in nucleus accumbens glutamate levels in rats. Preliminary results in humans suggest that N-acetylcysteine attenuated cocaine craving in addicted humans. Further, exposure to environmental cues previously paired with cocaine injections increased glutamate in the nucleus accumbens. A potential use for mGlu2/3 agonists as pharmacotherapeutic agents to inhibit relapse was recently shown using different rodent models of reinstatement. In some embodiments, mGlu2/3 agonists attenuate cocaine-seeking behavior induced by discriminative cocaine-associated cues or by cocaine priming. In addition, mGlu2/3 agonists have been shown to inhibit cue-induced reinstatement of heroin-seeking, alcohol-seeking, nicotine-seeking, and also inhibited food-seeking behavior. The decreases in cue-induced food responding suggest that the administration of mGlu2/3 agonist decreased motivation for a natural reinforcer also. Further, it has been hypothesized that susceptibility to relapse due to cue reactivity increases gradually over periods of weeks or months. Thus, the administration of a negative modulator of mGlu2/3 receptors during prolonged abstinence from cocaine self-administration will decrease, while a negative modulator of mGlu2/3 receptors will have no effect on cocaine-seeking behavior induced by discriminative stimuli associated with cocaine availability.

Avoidance and alleviation of the negative affective state of early drug withdrawal with further drug abuse is hypothesized to be an important source of motivation that contributes significantly to the development of compulsive drug use and relapse during early abstinence. It has been hypothesized that susceptibility to relapse due to affective withdrawal symptoms peaks within days of cessation reflecting early rise in withdrawal symptoms. Thus, pharmacological treatments that reverse aspects of cocaine early withdrawal would remove an important source of motivation that contributes to relapse to drug abuse shortly after the initial cessation of drug administration. Abrupt abstinence following chronic exposure to drugs of abuse, including cocaine results in a negative affective state reflected in significant elevations in intracranial self-stimulation (ICSS) thresholds. ICSS thresholds are thought to provide an operational measure of brain reward function; thus elevations in ICSS thresholds reflect deficits in brain reward function. This threshold elevation is opposite to the lowering of ICSS thresholds observed after cocaine administration that reflects an increase in brain reward function that most likely underlies, or at least relates to, cocaine's euphorigenic effects. This increase in brain reward function associated with cocaine consumption is considered essential for the establishment and maintenance of cocaine self-administration behavior. The mechanisms that contribute to withdrawal-induced reward deficits or reward facilitation remain unclear. Group II mGlus have been implicated in the synaptic adaptations that occur in response to chronic drug exposure and contribute to the aversive behavioral withdrawal syndrome. The role of glutamate transmission in the early phase of cocaine withdrawal has not been studied extensively. However, based on the nicotine dependence findings and the hypothesis of overlapping mechanisms of withdrawal from different drugs of abuse, one may hypothesize that decreased glutamatergic neurotransmission will also partly mediate cocaine withdrawal in cocaine-dependent subjects.

In some embodiments, the compounds described herein are mGlu2/3 receptor NAM used for treating cocaine addiction.

Schizophrenia

Schizophrenia is a devastating psychiatric illness that afflicts approximately 1% of the worldwide population. The core symptoms observed in schizophrenic patients include positive symptoms (thought disorder, delusions, hallucinations, and paranoia), negative symptoms (social withdrawal, anhedonia, apathy, and paucity of speech) and cognitive impairments such as deficits in perception, attention, learning, short- and long-term memory and executive function. The cognitive deficits in schizophrenia are one of the major disabilities associated with the illness and are considered a reliable predictor of long-term disability and treatment outcome. Currently available antipsychotics effectively treat the positive symptoms, but provide modest effects on the negative symptoms and cognitive impairments. Furthermore, some patients are unresponsive to current antipsychotic treatments and several of these agents are associated with adverse side effects, including disturbances in motor function, weight gain, and sexual dysfunction. Thus, there is a need for new treatment strategies for schizophrenia that provide major improvements in efficacy across multiple symptom clusters and have fewer adverse effects.

Although the underlying pathophysiology of schizophrenia remains unknown, accumulating evidence points to disruptions in multiple neurotransmitter systems that modulate neural circuits important for normal affect, sensory processing, and cognition. In particular, early clinical findings demonstrated that changes in glutamatergic transmission produced by antagonists of the N-methyl-D-aspartate (NMDA) subtype of ionotropic glutamate receptors, including phencyclidine (PCP), result in a state of psychosis in humans that is similar to that observed in schizophrenic patients. These studies suggest that agents that increase NMDA receptor function have potential as therapeutics for the treatment of all major symptom clusters (positive, negative, cognitive) of the disease. More recently, studies indicate that reduced NMDA receptor function induces complex changes in transmission through cortical and subcortical circuits that involve both glutamatergic and GABAergic synapses and include downstream increases in transmission at glutamatergic synapses in the prefrontal cortex. Importantly, these circuit changes might share common features with changes in brain circuit activities that occur in schizophrenia patients. One hypothesis is that NMDA receptors involved in these symptoms might reside at glutamatergic synapses on GABAergic projection neurons in midbrain regions as well as GABAergic interneurons and glutamatergic projection neurons in key cortical and limbic regions For example, under normal conditions the activation of NMDA receptors localized on GABAergic projection neurons in subcortical regions, such as the nucleus accumbens, provides inhibitory control on excitatory glutamatergic thalamocortical neurons that project to pyramidal neurons in the prefrontal cortex (PFC). Hypofunction or blockade of these NMDA receptors on midbrain inhibitory GABAergic neurons could result in a disinhibition of glutamatergic thalamocortical inputs to pyramidal neurons in the PFC. This disinhibition would lead to a subsequent increased activity of glutamatergic thalamic neurons and increased activity mediated by the DL-a-amino-3-hydroxy-5-methylisoxasole-4-propionate (AMPA) subtype of glutamate receptors at thalamocortical synapses in the PFC. Based on this model, manipulations that enhance NMDA receptor function, such as activation of metabotropic glutamate receptor subtype 5 (mGlu5) located on GABAergic neurons, have potential as a novel approach to the treatment of schizophrenia. An alternative approach might be to reduce excitatory glutamatergic transmission at key synapses, such as thalamocortical synapses in the PFC, by activation of metabotropic glutamate receptor subtypes 2 and 3 (mGlu2 and mGlu3) presynaptically located in these synapses. Although other viable models of circuit changes associated with schizophrenia exist, this hypothesis provides one possible framework within which to consider effects of ligands at mGlu receptors that might be relevant to schizophrenia.

A large number of preclinical and clinical studies provide strong evidence that agonists of mGlu2 and mGlu3 also have potential as a novel approach to the treatment of schizophrenia. Consistent with the animal studies, clinical studies reveal that a highly selective agonist of group II mGlu receptors has robust efficacy in improving ratings for positive and negative symptoms in patients with schizophrenia. Unlike currently marketed antipsychotic agents, there were no major adverse events reported for the mGlu2/3 agonist in the clinical studies to date. However, further clinical studies will be required to fully establish safety of these compounds after long-term dosing in schizophrenic patients, as well as assess possible efficacy on the cognitive impairments in these patients. Taken together, these findings represent an important breakthrough and could ultimately lead to introduction of group II mGlu receptor activators as a fundamentally novel approach to the treatment of schizophrenia. As mentioned above, animal studies reveal that the psychotomimetic agents increase activity of glutamatergic synapses in the PFC, and hyperactivity of glutamate neurotransmission in the PFC and limbic structures has been postulated to play a critical role in the pathophysiology of schizophrenia. Interestingly, effects of psychotomimetic agents on glutamatergic transmission in the PFC are blocked by group II mGlu receptor agonists. Although it is not yet clear whether this action of group II mGlu receptor agonists is mechanistically related to the antipsychotic actions of these compounds, these actions fit well with current models of disruptions in subcortical and cortical circuits that might be involved in the psychotomimetic effects of NMDA receptor antagonists and the range of symptoms observed in schizophrenia patients. Despite advances in development of group II mGlu receptor agonists, it is not yet clear whether orthosteric agonists of these receptors will reach the market for broad clinical use. Long-term administration of group II mGlu receptor agonists induces robust tolerance in at least one rodent model that has been used to predict antipsychotic efficacy. These orthosteric agonists also activate both mGlu2 and mGlu3 and do not provide insights into which of these group II mGlu receptor subtypes is most important for clinical efficacy. Although, recent findings demonstrate that the antipsychotic-like effects of mGlu2/3 receptor agonists are absent in mGlu2-knockout, but not mGlu3-knockout, mice. Thus, it is possible that negative allosteric modulators of mGlu2/3 might be an alternative approach that could provide greater selectivity and other potential advantages to orthosteric agonists.

In some embodiments, group II mGlu receptor agonists are useful in the treatment of schizophrenia. In some embodiments, selective mGlu2/3 NAMs represent a novel approach to the treatment of these disorders that is devoid of the adverse effects associated with currently available drugs.

In some embodiments, the compounds described herein are mGlu2/3 receptor NAM used for treating schizophrenia. The method includes administering to a subject in need thereof, an effective amount of at least one mGlu2/3 receptor NAM, thereby treating schizophrenia.

Alzheimer's Disease

Alzheimer's disease (AD), also known as Alzheimer disease, or just Alzheimer's, accounts for 60% to 70% of cases of dementia. It is a chronic neurodegenerative disease that usually starts slowly and gets worse over time. The most common early symptom is difficulty in remembering recent events (short term memory loss). As the disease advances, symptoms can include: problems with language, disorientation (including easily getting lost), mood swings, loss of motivation, not managing self-care, and behavioral issues. As a person's condition declines, she or he often withdraws from family and society. Gradually, bodily functions are lost, ultimately leading to death. Although the speed of progression can vary, the average life expectancy following diagnosis is three to nine years.

Various brain regions, including the cerebral cortex, hippocampus, striatum, amygdala, frontal cortex and nucleus accumbens, display high levels of mGlu2 and mGlu3 receptor binding. This distribution pattern suggests a role for the mGlu2/3 receptor subtypes in the pathology of neuropsychiatric disorders such as Alzheimer's disease.

In some embodiments, the compounds described herein are mGlu2/3 receptor NAM used for treating Alzheimer's disease. The method includes administering to a subject in need thereof, an effective amount of at least one mGlu2/3 receptor NAM, thereby treating Alzheimer's disease.

Huntington's Disease

Huntington's disease (HD) is a neurodegenerative genetic disorder that affects muscle coordination and leads to mental decline and behavioral symptoms. Symptoms of the disease can vary between individuals and affected members of the same family, but usually progress predictably. The earliest symptoms are often subtle problems with mood or cognition. A general lack of coordination and an unsteady gait often follows. As the disease advances, uncoordinated, jerky body movements become more apparent, along with a decline in mental abilities and behavioral symptoms. Physical abilities gradually worsen until coordinated movement becomes difficult. Mental abilities generally decline into dementia. Complications such as pneumonia, heart disease, and physical injury from falls reduce life expectancy to around twenty years from the point at which symptoms begin. Physical symptoms can begin at any age from infancy to old age, but usually begin between 35 and 44 years of age.

Excitotoxic injury to striatum by dysfunctional cortical input or aberrant glutamate uptake may contribute to Huntington's disease (HD) pathogenesis. Daily subcutaneous injection with a maximum tolerated dose (MTD) of the mGlu2/3 agonist LY379268 (20 mg/kg) beginning at 4 weeks has been found to dramatically improves the phenotype in R6/2 mice (the most commonly used animal model of Huntington's disease) (Reiner et al. Brain Research 1473 (2012) 161-172). For example, normalization of motor function in distance traveled, speed, the infrequency of pauses, and the ability to locomote in a straight line, and a rescue of a 15-20% striatal neuron loss at 10 weeks were observed.

In some embodiments, the compounds described herein are mGlu2/3 receptor NAM used for treating Huntington's disease. The method includes administering to a subject in need thereof, an effective amount of at least one mGlu2/3 receptor NAM, thereby treating Huntington's disease.

Lou Gehrig's Disease (ALS)

Amyotrophic lateral sclerosis (ALS) is a debilitating disorder characterized by rapidly progressive motor neuron degeneration, which results into weakness, muscle atrophy and spasticity. Riluzole is the only drug that improves survival of ALS patients, only to a modest extent. Thus, there is an urgent need for treatments that slow the progression of ALS. Familial ALS (FALS) is caused by mutations of several genes including SOD1 (type-1 superoxide dismutase). Although SOD1 mutations account for only 20% of FALS and about 2% of sporadic ALS, SOD1 mutant mice recapitulate several features of human ALS, and are widely employed as model for ALS. The validity of this model is strengthened by the evidence that SOD1 aggregates are detected in the spinal cord of people with sporadic ALS or with ALS caused by mutations of genes other than SOD1. The mechanisms by which SOD1 misfolding damages motor neurons are only partially elucidated and involve glutamate excitotoxicity, mitochondrial dysfunction, disruption of axonal transport, and abnormalities in astrocytes and microglia. One of the potential mechanisms of excitotoxicity in ALS is a reduced expression of the glutamate transporter, GLT-1, which clears glutamate from the synapses.

Enhancement of glial-derived neurotrophic factor (GDNF) is an established therapeutic target for amyotrophic lateral sclerosis (ALS). Activation of group II metabotropic glutamate (mGlu) receptors with the orthosteric agonist, LY379268, enhanced GDNF levels in cultured spinal cord astrocytes from wild-type mice and mGlu2 knockout mice, but not in astrocytes from mGlu3 knockout mice. LY379268 protected Sternberger monoclonal incorporated antibody-32 $(SMI-32)^+$ motor neurons against excitotoxic death in mixed cultures of spinal cord cells, and its action was abrogated by anti-GDNF antibodies. Acute systemic injection of LY379268 (0.5, 1 or 5 mg/kg, i.p.) enhanced spinal cord GDNF levels in wild-type and mGlu2 knockout mice, but not in mGlu3 knockout mice. No tolerance developed to the GDNF-enhancing effect of LY379268 when the drug was continuously delivered for 28 days by means of s.c. osmotic minipumps (0.5-5 mg/day). Continuous infusion of LY379268 also enhanced the expression of the glutamate transporter GLT-1, in the spinal cord. Continuous treatment with 1 or 5 mg/kg/day with LY379268 had a beneficial effect on neurological disability in SOD1G93A mice. At day 40 of treatment, LY379268 enhanced spinal cord levels of GDNF and GLT-1, and rescued spinal cordmotor neurons, as assessed by stereologic counting of $SMI-32^+$ cells.

In some embodiments, the compounds described herein are mGlu2/3 receptor NAM used for treating ALS. The method includes administering to a subject in need thereof, an effective amount of at least one mGlu2/3 receptor NAM, thereby treating ALS.

Parkinson's Disease

Parkinson's disease (PD) is a chronic movement disorder resulting from a disturbance in the normal functioning of the basal ganglia, a collection of subcortical nuclei that are essential for the initiation and control of motor activity. The underlying pathology of the disease is a progressive degeneration of the dopaminergic nigrostriatal tract that manifests as a range of motor deficits including akinesia or bradykinesia, tremor, rigidity and postural instability. Current therapies for PD are essentially based on dopamine replacement and include levodapa (L-DOPA), a precursor of dopamine, and dopamine receptor agonists. These agents are effective in treating the symptoms of the disease in the early stages, but are less effective as the disease progresses when debilitating side-effects such as "on-off" fluctuations in efficacy and uncontrollable dyskinesias (involuntary muscle movements) ensue. More importantly, dopaminergic treatments do not halt the disease progression. For these reasons, several investigators have started to focus on nondopaminergic interventions as symptomatic and neuroprotecive strategies in PD.

Studies have shown that Group II mGlu receptors play some role in alleviating akinesia in the rat. In functional studies (Murray et al. Pharmacology, Biochemistry and Behavior 73 (2002) 455-466), intracerebroventricular administration of LY379268 (1, 5, 10, 20 nmol/2 μl) produced a dose-dependent increase in locomotor activity in the reserpine (5 mg/kg ip)-treated rat. In contrast, systemic administration of LY379268 (0.1, 1, 10 mg/kg ip) did not reverse reserpine-induced akinesia and failed to effect rotational behaviour 1 month after unilateral lesioning of the nigrostriatal tract by 6-hydroxydopamine (6-OHDA; 4 mg infused into the substantia nigra (SN)). These results suggest that mGlus may offer a nondopaminergic approach to the treatment of PD.

In some embodiments, the compounds described herein are mGlu2/3 receptor NAM used for treating Parkinson's disease. The method includes administering to a subject in need thereof, an effective amount of at least one mGlu2/3 receptor NAM, thereby treating Parkinson's disease.

Depression

Major depressive disorder (MDD) is one of the most common psychiatric illnesses worldwide having a profound impact on public health. MDD is the most common cause of disease burden in North America and the fourth leading cause in the world as determined by the World Health Organization. Existing treatments for MDD, such as selective serotonin reuptake inhibitors (SSRIs), serotonin-norepinephrine reuptake inhibitors (SNRIs) and tricyclic antidepressants (TCAs), have serious limitations in that they usually take weeks to months to achieve their antidepressant effects. It is during this latency period, that high rates of mortality and morbidity are noted. Despite the widespread availability of these effective treatments it is estimated that between 30-70% of patients with MDD fail to fully respond to these therapies. Treatment resistant depression (TRD) is a severely disabling disorder and those suffering from TRD have very limited treatment options. There is accumulating evidence that the glutamatergic system plays an important role in the etiology, neurobiology and treatment of MDD. It has been shown that chronic administration of SSRIs cause up regulation of several glutamate receptor subunits implicating glutamate neurotransmission as an action of standard antidepressants. There are many regulatory sites of the glutamatergic system that have shown potential for modulating MDD. Regulation of the metabotropic glutamate receptors has been the focus of significant research over the past several years. Antagonists of mGlu2/3 have been shown to have dose dependent antidepressant activity in several animal models for depression (i.e. forced-swim test, novelty suppressed feeding, and mouse tail-suspension test). Also, these compounds when chronically administered stimulate hippocampal neurogenesis similar to the neurogenic effects observed for SSRIs. It has been shown that mGlu2/3 antagonists increase extracellular levels of serotonin in the medial prefrontal cortex which is attenuated by the AMPA receptor antagonist NBQX indicating that AMPA receptor stimulation is responsible for the serotonin release. In rodents, antidepressant activity of mGlu2/3 antagonists is rapid and sustained for 24 hours following acute administration. This activity was block by the AMPA receptor antagonist NBQX or the mTOR inhibitor rapamycine. This finding is very similar to the recent human studies showing ketamine, an N-methyl-D-aspartate (NMDA) antagonist, that has an antidepressant effect two hours after a sub-anaesthetic dose (intravenous administration) with effects lasting for up to two weeks. In rodents, this effect can be replicated and also blocked by NBQX and rapamycin.

Cancer

Grade IV glioma (glioblastoma, GBM), is the most frequent malignant brain cancer in adults, accounting for up to 45% of all malignant tumors in the central nervous system (CNS). GBMs arise from astrocytes, are usually highly malignant, and in 90% of the cases occur spontaneously as primary tumors. The National Institute of Health classifies GBM as a rare disorder with a prevalence of approximately 4 cases per 100,000. In the US, there are approximately 100,000 patients, with 10,000 new cases being diagnosed every year. The prognosis of patients diagnosed with GBM is very poor, with a median survival of 12-15 months, only 10% of patients surviving 5 years, and approximately 12,000 GBM patients dying every year. The standard therapeutic approach involves surgical resection of the tumor followed by radiation therapy combined with temozolomide (TMZ), a DNA alkylating agent. Although, TMZ is well tolerated, it has limited efficacy in improving disease-free survival. There are a few additional treatments including bevacizumab (Avastin), a humanized monoclonal antibody to the vascular endothelial growth factor (VEGF) which blocks angiogenesis, and carmustine, also a DNA alkylating agent. Unfortunately, in many cases within 7 months of treatment, tumors reoccur, after which patient survival is less than 1 year. Thus, there is a significant unmet need for new, effective treatments for GBM. Hence, there are a large number of new approaches that are currently being studied in the clinic, including monoclonal antibodies, vaccines and gene therapies. Recent evidence has emerged suggesting that mGlu2/3 receptor inhibitors may represent an additional treatment option for GBM patients.

Moreover, there are data indicating that inhibition of $mGlu_3$ could be useful to treat other types of cancers, such as melanoma. Mutations in the mGlu3 receptor have been identified in melanoma. The mGlu3 mutations identified in melanoma caused a gain-of-function, increasing anchor-independent growth and migration. Therefore, it is reasonable to suggest a rationale for treating melanoma using mGlu2/3 antagonists or NAMs.

Compounds

In one aspect, described herein is a compound that has the structure of Formula (I), or a pharmaceutically acceptable salt thereof:

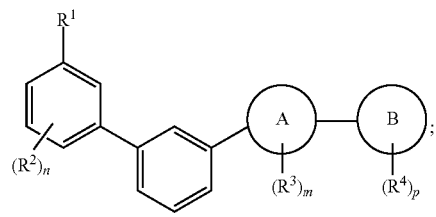

Formula (I)

wherein:

ring Ⓐ is a heteroaryl ring;

ring Ⓐ is an aryl ring or heteroaryl ring;

$R^1$ is —$CO_2H$, —CN, —C(O)NHOH, —C(O)NHOMe, —C(O)NHSO₂Me, —NHC(O)Me, —C(O)NHMe,

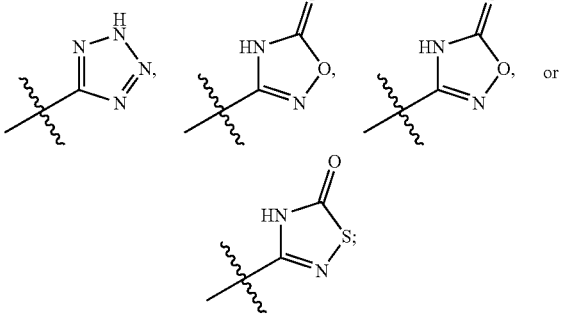

each $R^2$ is independently halogen, —$OR^5$, substituted or unsubstituted $C_1$-$C_6$alkyl, or substituted or unsubstituted $C_1$-$C_6$fluoroalkyl;

each $R^3$ is independently substituted or unsubstituted $C_1$-$C_6$alkyl, substituted or unsubstituted $C_1$-$C_6$fluoroalkyl, substituted or unsubstituted $C_3$-$C_6$cycloalkyl, or substituted or unsubstituted aryl;

each $R^4$ is independently halogen, —$OR^5$, substituted or unsubstituted $C_1$-$C_6$alkyl, substituted or unsubstituted $C_1$-$C_6$fluoroalkyl, substituted or unsubstituted $C_3$-$C_6$cycloalkyl, or substituted or unsubstituted aryl;

or two $R^4$ taken together with the carbon atoms to which they are attached to form a substituted or unsubstituted $C_2$-$C_8$heterocycloalkyl;

each $R^5$ is independently hydrogen, or substituted or unsubstituted $C_1$-$C_6$alkyl;

n is 0, 1, 2, or 3;

m is 0 or 1; and p is 0, 1, 2, or 3 n is 0, 1, 2, or 3;

m is 0 or 1; and p is 0, 1, 2, or 3.

In some embodiments is a compound of Formula (I), or a pharmaceutically acceptable salt thereof, wherein ring Ⓐ is a 5-membered or a 6-membered heteroaryl ring. In some embodiments is a compound of Formula (I), or a pharmaceutically acceptable salt thereof, wherein ring Ⓐ is a 6-membered heteroaryl ring. In some embodiments is a compound of Formula (I), or a pharmaceutically acceptable salt thereof, wherein ring Ⓐ is a 5-membered heteroaryl ring. In some embodiments is a compound of Formula (I), or a pharmaceutically acceptable salt thereof, wherein ring Ⓐ is thiazolyl, oxadiazolyl, thiadiazolyl, triazolyl, imidazolyl, or isothiazolyl. In some embodiments is a compound of Formula (I), or a pharmaceutically acceptable salt thereof, wherein ring Ⓐ is thiazolyl. In some embodiments is a compound of Formula (I), or a pharmaceutically acceptable salt thereof, wherein ring Ⓐ is oxadiazolyl. In some embodiments is a compound of Formula (I), or a pharmaceutically acceptable salt thereof, wherein ring Ⓐ is thiadiazolyl. In some embodiments is a compound of Formula (I), or a pharmaceutically acceptable salt thereof, wherein ring Ⓐ is triazolyl. In some embodiments some embodiments is a compound of Formula (I), or a pharmaceutically acceptable salt thereof, wherein ring Ⓐ is imidazolyl. In some embodiments is a compound of Formula (I), or a pharmaceutically acceptable salt thereof, wherein ring Ⓐ is isothiazolyl. In some embodiments is a compound of Formula (I), or a pharmaceutically acceptable salt thereof, wherein m is 0. In some embodiments is a compound of Formula (I), or a pharmaceutically acceptable salt thereof, wherein m is 1.

In some embodiments is a compound of Formula (I), or a pharmaceutically acceptable salt thereof, wherein ring Ⓐ is an aryl ring. In some embodiments is a compound of Formula (I), or a pharmaceutically acceptable salt thereof, wherein ring Ⓐ is a phenyl ring.

In some embodiments is a compound of Formula (I), or a pharmaceutically acceptable salt thereof, wherein ring Ⓐ is a heteroaryl ring. In some embodiments is a compound of Formula (I), or a pharmaceutically acceptable salt thereof, wherein ring Ⓐ is furanyl, thiophenyl, benzofuranyl, benzothiophenyl, or pyridinyl. In some embodiments is a compound of Formula (I), or a pharmaceutically acceptable salt thereof, wherein ring Ⓐ is furanyl. In some embodiments is a compound of Formula (I), or a pharmaceutically acceptable salt thereof, wherein ring Ⓐ is thiophenyl. In some embodiments is a compound of Formula (I), or a pharmaceutically acceptable salt thereof, wherein ring Ⓐ is benzofuranyl. In some embodiments is a compound of Formula (I), or a pharmaceutically acceptable salt thereof, wherein ring Ⓐ is benzothiophenyl. In some embodiments is a compound of Formula (I), or a pharmaceutically acceptable salt thereof, wherein ring Ⓐ is pyridinyl. In some embodiments is a compound of Formula (I), or a pharmaceutically acceptable salt thereof, wherein p is 0. In some embodiments is a compound of Formula (I), or a pharmaceutically acceptable salt thereof, wherein p is 1. In some embodiments is a compound of Formula (I), or a pharmaceutically acceptable salt thereof, wherein p is 1 and $R^4$ is halogen, —$OR^5$, substituted or unsubstituted $C_1$-$C_6$alkyl, substituted or unsubstituted $C_1$-$C_6$fluoroalkyl. In some embodiments is a compound of Formula (I), or a pharmaceutically acceptable salt thereof, wherein p is 1 and $R^4$ is halogen, —$CF_3$, or —$OCH_3$. In some embodiments is a compound of Formula (I), or a pharmaceutically acceptable salt thereof, wherein p is 1 and $R^4$ is halogen. In some embodiments is a compound of Formula (I), or a pharmaceutically acceptable salt thereof, wherein p is 1 and $R^4$ is —$CF_3$. In some embodiments is a compound of Formula (I), or a pharmaceutically acceptable salt thereof, wherein p is 1 and $R^4$ is —$OCH_3$.

In some embodiments is a compound of Formula (I), or a pharmaceutically acceptable salt thereof, wherein n is 0. In some embodiments is a compound of Formula (I), or a pharmaceutically acceptable salt thereof, wherein n is 1. In some embodiments is a compound of Formula (I), or a pharmaceutically acceptable salt thereof, wherein n is 1 and $R^2$ is halogen, —$OR^5$, substituted or unsubstituted $C_1$-$C_6$alkyl, substituted or unsubstituted $C_1$-$C_6$fluoroalkyl. In some embodiments is a compound of Formula (I), or a pharmaceutically acceptable salt thereof, wherein n is 1 and $R^2$ is halogen, —$CF_3$, or —$OCH_3$. In some embodiments is a compound of Formula (I), or a pharmaceutically acceptable salt thereof, wherein n is 1 and $R^2$ is halogen. In some embodiments is a compound of Formula (I), or a pharmaceutically acceptable salt thereof, wherein n is 1 and $R^2$ is —$CF_3$. In some embodiments is a compound of Formula (I), or a pharmaceutically acceptable salt thereof, wherein n is 1 and $R^2$ is —$OCH_3$.

In some embodiments is a compound of Formula (I), or a pharmaceutically acceptable salt thereof, wherein $R^1$ is —$CO_2H$. In some embodiments is a compound of Formula (I), or a pharmaceutically acceptable salt thereof, wherein $R^1$ is —CN. In some embodiments is a compound of Formula (I), or a pharmaceutically acceptable salt thereof, wherein $R^1$ is —C(O)NHOH. In some embodiments is a compound of Formula (I), or a pharmaceutically acceptable salt thereof, wherein $R^1$ is —C(O)NHOMe. In some embodiments is a compound of Formula (I), or a pharmaceutically acceptable salt thereof, wherein $R^1$ is —C(O)NHSO$_2$Me. In some embodiments is a compound of Formula (I), or a pharmaceutically acceptable salt thereof, wherein $R^1$ is —NHC(O)Me. In some embodiments is a compound of Formula (I), or a pharmaceutically acceptable salt thereof, wherein $R^1$ is

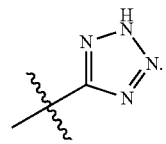 [SMILES: *c1nn[nH]n1]

In some embodiments is a compound of Formula (I), or a pharmaceutically acceptable salt thereof, wherein $R^1$ is

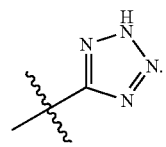 [SMILES: *c1nn[nH]n1]

In some embodiments is a compound of Formula (I), or a pharmaceutically acceptable salt thereof, wherein $R^1$ is

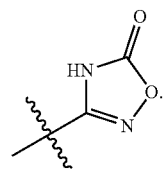 [SMILES: *c1noc(=S)[nH]1]

In some embodiments is a compound of Formula (I), or a pharmaceutically acceptable salt thereof, wherein $R^1$ is

[Structure: 1,3,4-oxadiazole-2-thione fragment]

In some embodiments is a compound of Formula (I), or a pharmaceutically acceptable salt thereof, wherein R¹ is

[Structure: 1,3,4-thiadiazol-2(3H)-one fragment]

In some embodiments, the compound of Formula (I) has the structure of Formula (Ia):

Formula (Ia)

[Structure of Formula (Ia): biphenyl-thiazole-ring B with substituents R¹, (R²)$_n$, (R⁴)$_p$]

In some embodiments is a compound of Formula (Ia), or a pharmaceutically acceptable salt thereof, wherein ring Ⓐ is an aryl ring. In some embodiments is a compound of Formula (Ia), or a pharmaceutically acceptable salt thereof, wherein ring Ⓐ is a phenyl ring.

In some embodiments is a compound of Formula (Ia), or a pharmaceutically acceptable salt thereof, wherein ring Ⓐ is a heteroaryl ring. In some embodiments is a compound of Formula (Ia), or a pharmaceutically acceptable salt thereof, wherein ring Ⓐ is furanyl, thiophenyl, benzofuranyl, benzothiophenyl, or pyridinyl. In some embodiments is a compound of Formula (Ia), or a pharmaceutically acceptable salt thereof, wherein ring Ⓐ is furanyl. In some embodiments is a compound of Formula (Ia), or a pharmaceutically acceptable salt thereof, wherein ring Ⓐ is thiophenyl. In some embodiments is a compound of Formula (Ia), or a pharmaceutically acceptable salt thereof, wherein ring Ⓐ is benzofuranyl. In some embodiments is a compound of Formula (Ia), or a pharmaceutically acceptable salt thereof, wherein ring Ⓐ is benzothiophenyl. In some embodiments is a compound of Formula (Ia), or a pharmaceutically acceptable salt thereof, wherein ring Ⓐ is pyridinyl. In some embodiments is a compound of Formula (Ia), or a pharmaceutically acceptable salt thereof, wherein p is 0. In some embodiments is a compound of Formula (Ia), or a pharmaceutically acceptable salt thereof, wherein p is 1. In some embodiments is a compound of Formula (Ia), or a pharmaceutically acceptable salt thereof, wherein p is 1 and R⁴ is halogen, —OR⁵, substituted or unsubstituted $C_1$-$C_6$alkyl, substituted or unsubstituted $C_1$-$C_6$fluoroalkyl. In some embodiments is a compound of Formula (Ia), or a pharmaceutically acceptable salt thereof, wherein p is 1 and R⁴ is halogen, —CF₃, or —OCH₃. In some embodiments is a compound of Formula (Ia), or a pharmaceutically acceptable salt thereof, wherein p is 1 and R⁴ is halogen. In some embodiments is a compound of Formula (Ia), or a pharmaceutically acceptable salt thereof, wherein p is 1 and R⁴ is —CF₃. In some embodiments is a compound of Formula (Ia), or a pharmaceutically acceptable salt thereof, wherein p is 1 and R⁴ is —OCH₃.

In some embodiments is a compound of Formula (Ia), or a pharmaceutically acceptable salt thereof, wherein n is 0. In some embodiments is a compound of Formula (Ia), or a pharmaceutically acceptable salt thereof, wherein n is 1. In some embodiments is a compound of Formula (Ia), or a pharmaceutically acceptable salt thereof, wherein n is 1 and R² is halogen, —OR⁵, substituted or unsubstituted $C_1$-$C_6$alkyl, substituted or unsubstituted $C_1$-$C_6$fluoroalkyl. In some embodiments is a compound of Formula (Ia), or a pharmaceutically acceptable salt thereof, wherein n is 1 and R² is halogen, —CF₃, or —OCH₃. In some embodiments is a compound of Formula (Ia), or a pharmaceutically acceptable salt thereof, wherein n is 1 and R² is halogen. In some embodiments is a compound of Formula (Ia), or a pharmaceutically acceptable salt thereof, wherein n is 1 and R² is —CF₃. In some embodiments is a compound of Formula (Ia), or a pharmaceutically acceptable salt thereof, wherein n is 1 and R² is —OCH₃.

In some embodiments is a compound of Formula (Ia), or a pharmaceutically acceptable salt thereof, wherein R¹ is —CO₂H.

In some embodiments, the compound of Formula (I) has the structure of Formula (Ib):

Formula (Ib)

[Structure of Formula (Ib): biphenyl-thiadiazole-ring B with substituents R¹, (R²)$_n$, (R⁴)$_p$]

In some embodiments is a compound of Formula (Ib), or a pharmaceutically acceptable salt thereof, wherein ring Ⓐ is an aryl ring. In some embodiments is a compound of Formula (Ib), or a pharmaceutically acceptable salt thereof, wherein ring Ⓐ is a phenyl ring.

In some embodiments is a compound of Formula (Ib), or a pharmaceutically acceptable salt thereof, wherein ring Ⓐ is a heteroaryl ring. In some embodiments is a compound of Formula (Ib), or a pharmaceutically acceptable salt thereof, wherein ring Ⓐ is furanyl, thiophenyl, benzofuranyl, benzothiophenyl, or pyridinyl. In some embodiments is a compound of Formula (Ib), or a pharmaceutically acceptable salt thereof, wherein ring Ⓐ is furanyl. In some embodiments is a compound of Formula (Ib), or a pharmaceutically acceptable salt thereof, wherein ring Ⓐ is thiophenyl. In some embodiments is a compound of Formula (Ib), or a pharmaceutically acceptable salt thereof, wherein ring Ⓐ is benzofuranyl. In some embodiments is a compound of Formula (Ib), or a pharmaceutically acceptable salt thereof, wherein ring Ⓐ is benzothiophenyl. In some embodiments is a compound of Formula (Ib), or a pharmaceutically acceptable salt thereof, wherein ring Ⓐ is pyridinyl. In some embodiments is a compound of Formula (Ib), or a pharmaceutically acceptable salt thereof, wherein p is 0. In some embodiments is a compound of Formula (Ib), or a pharmaceutically acceptable salt thereof, wherein p is 1. In some embodiments is a compound of Formula (Ib), or a pharmaceutically acceptable salt thereof, wherein p is 1 and $R^4$ is halogen, $-OR^5$, substituted or unsubstituted $C_1$-$C_6$alkyl, substituted or unsubstituted $C_1$-$C_6$fluoroalkyl. In some embodiments is a compound of Formula (Ib), or a pharmaceutically acceptable salt thereof, wherein p is 1 and $R^4$ is halogen, $-CF_3$, or $-OCH_3$. In some embodiments is a compound of Formula (Ib), or a pharmaceutically acceptable salt thereof, wherein p is 1 and $R^4$ is halogen. In some embodiments is a compound of Formula (Ib), or a pharmaceutically acceptable salt thereof, wherein p is 1 and $R^4$ is $-CF_3$. In some embodiments is a compound of Formula (Ib), or a pharmaceutically acceptable salt thereof, wherein p is 1 and $R^4$ is $-OCH_3$.

In some embodiments is a compound of Formula (Ib), or a pharmaceutically acceptable salt thereof, wherein n is 0. In some embodiments is a compound of Formula (Ib), or a pharmaceutically acceptable salt thereof, wherein n is 1. In some embodiments is a compound of Formula (Ib), or a pharmaceutically acceptable salt thereof, wherein n is 1 and $R^2$ is halogen, $-OR^5$, substituted or unsubstituted $C_1$-$C_6$alkyl, substituted or unsubstituted $C_1$-$C_6$fluoroalkyl. In some embodiments is a compound of Formula (Ib), or a pharmaceutically acceptable salt thereof, wherein n is 1 and $R^2$ is halogen, $-CF_3$, or $-OCH_3$. In some embodiments is a compound of Formula (Ib), or a pharmaceutically acceptable salt thereof, wherein n is 1 and $R^2$ is halogen. In some embodiments is a compound of Formula (Ib), or a pharmaceutically acceptable salt thereof, wherein n is 1 and $R^2$ is $-CF_3$. In some embodiments is a compound of Formula (Ib), or a pharmaceutically acceptable salt thereof, wherein n is 1 and $R^2$ is $-OCH_3$.

In some embodiments is a compound of Formula (Ib), or a pharmaceutically acceptable salt thereof, wherein $R^1$ is $-CO_2H$.

In some embodiments is a compound of Formula (I), or a pharmaceutically acceptable salt thereof, having the structure of Formula (Ic):

Formula (Ic)

wherein $R^3$ is substituted or unsubstituted $C_1$-$C_6$alkyl or substituted or unsubstituted aryl. In some embodiments is a compound of Formula (Ic), or a pharmaceutically acceptable salt thereof, wherein $R^3$ is unsubstituted phenyl.

In some embodiments is a compound of Formula (Ic), or a pharmaceutically acceptable salt thereof, wherein ring Ⓐ is an aryl ring. In some embodiments is a compound of Formula (Ic), or a pharmaceutically acceptable salt thereof, wherein ring Ⓐ is a phenyl ring.

In some embodiments is a compound of Formula (Ic), or a pharmaceutically acceptable salt thereof, wherein ring Ⓐ is a heteroaryl ring. In some embodiments is a compound of Formula (Ic), or a pharmaceutically acceptable salt thereof, wherein ring Ⓐ is furanyl, thiophenyl, benzofuranyl, benzothiophenyl, or pyridinyl. In some embodiments is a compound of Formula (Ic), or a pharmaceutically acceptable salt thereof, wherein ring Ⓐ is furanyl. In some embodiments is a compound of Formula (Ic), or a pharmaceutically acceptable salt thereof, wherein ring Ⓐ is thiophenyl. In some embodiments is a compound of Formula (Ic), or a pharmaceutically acceptable salt thereof, wherein ring Ⓐ is benzofuranyl. In some embodiments is a compound of Formula (Ic), or a pharmaceutically acceptable salt thereof, wherein ring Ⓐ is benzothiophenyl. In some embodiments is a compound of Formula (Ic), or a pharmaceutically acceptable salt thereof, wherein ring Ⓐ is pyridinyl. In some embodiments is a compound of Formula (Ic), or a pharmaceutically acceptable salt thereof, wherein p is 0. In some embodiments is a compound of Formula (Ic), or a pharmaceutically acceptable salt thereof, wherein p is 1. In some embodiments is a compound of Formula (Ic), or a pharmaceutically acceptable salt thereof, wherein p is 1 and $R^4$ is halogen, $-OR^5$, substituted or unsubstituted $C_1$-$C_6$alkyl, substituted or unsubstituted $C_1$-$C_6$fluoroalkyl. In some embodiments is a compound of Formula (Ic), or a pharmaceutically acceptable salt thereof, wherein p is 1 and $R^4$ is halogen, $-CF_3$, or $-OCH_3$. In some embodiments is a compound of Formula (Ic), or a pharmaceutically acceptable salt thereof, wherein p is 1 and $R^4$ is halogen. In some embodiments is a compound of Formula (Ic), or a pharmaceutically acceptable salt thereof, wherein p is 1 and $R^4$ is $-CF_3$. In some embodiments is a compound of Formula (Ic), or a pharmaceutically acceptable salt thereof, wherein p is 1 and $R^4$ is $-OCH_3$.

In some embodiments is a compound of Formula (Ic), or a pharmaceutically acceptable salt thereof, wherein n is 0. In some embodiments is a compound of Formula (Ic), or a pharmaceutically acceptable salt thereof, wherein n is 1. In some embodiments is a compound of Formula (Ic), or a pharmaceutically acceptable salt thereof, wherein n is 1 and $R^2$ is halogen, $-OR^5$, substituted or unsubstituted $C_1$-$C_6$alkyl, substituted or unsubstituted $C_1$-$C_6$fluoroalkyl. In some embodiments is a compound of Formula (Ic), or a pharmaceutically acceptable salt thereof, wherein n is 1 and $R^2$ is halogen, $-CF_3$, or $-OCH_3$. In some embodiments is a compound of Formula (Ic), or a pharmaceutically acceptable salt thereof, wherein n is 1 and $R^2$ is halogen. In some embodiments is a compound of Formula (Ic), or a pharmaceutically acceptable salt thereof, wherein n is 1 and $R^2$ is $-CF_3$. In some embodiments is a compound of Formula (Ic), or a pharmaceutically acceptable salt thereof, wherein n is 1 and $R^2$ is $-OCH_3$.

In some embodiments is a compound of Formula (Ic), or a pharmaceutically acceptable salt thereof, wherein $R^1$ is $-CO_2H$.

In another aspect, described herein is a compound that has the structure of Formula (II), or a pharmaceutically acceptable salt thereof:

Formula (II)

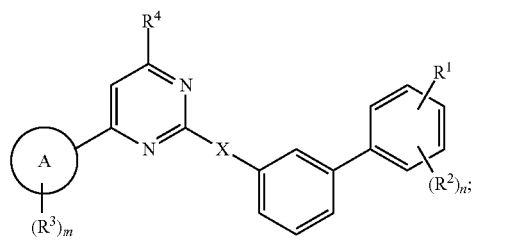

wherein:

ring Ⓐ is an aryl ring or heteroaryl ring;
X is a bond, —O—, —S—, or —N(R⁶)—;
R¹ is —CO₂H, —CN, —C(O)NHOH, —C(O)NHOMe, —C(O)NHSO₂Me, —NHC(O)Me, —C(O)NHMe,

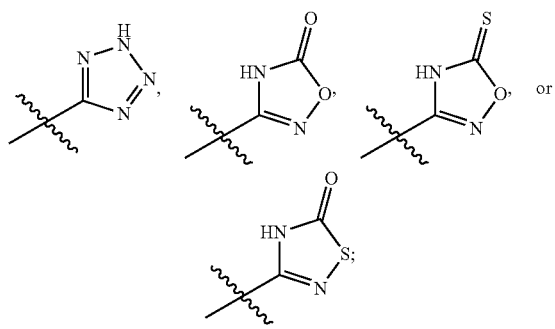

each $R^2$ is independently halogen, —OR⁵, NO₂, substituted or unsubstituted $C_1$-$C_6$alkyl, or substituted or unsubstituted $C_1$-$C_6$fluoroalkyl;
each $R^3$ is independently halogen, —OR⁵, —SR⁵, substituted or unsubstituted $C_1$-$C_6$alkyl, substituted or unsubstituted $C_1$-$C_6$fluoroalkyl, substituted or unsubstituted $C_3$-$C_6$cycloalkyl, or substituted or unsubstituted aryl;
$R^4$ is H, —CF₃, —CH₃, or substituted or unsubstituted phenyl;
each $R^5$ is independently hydrogen, or substituted or unsubstituted $C_1$-$C_6$alkyl;
$R^6$ is hydrogen, or substituted or unsubstituted $C_1$-$C_6$alkyl;
n is 0, 1, 2, or 3; and
m is 0, 1 or 2.

In some embodiments is a compound of Formula (II), or a pharmaceutically acceptable salt thereof, wherein ring Ⓐ is an aryl ring. In some embodiments is a compound of Formula (II), or a pharmaceutically acceptable salt thereof, wherein ring Ⓐ is a phenyl ring.

In some embodiments is a compound of Formula (II), or a pharmaceutically acceptable salt thereof, wherein ring Ⓐ is a heteroaryl ring. In some embodiments is a compound of Formula (II), or a pharmaceutically acceptable salt thereof, wherein ring Ⓐ is furanyl, thiophenyl, thiazolyl, pyrrolyl, or pyridinyl. In some embodiments is a compound of Formula (II), or a pharmaceutically acceptable salt thereof, wherein ring Ⓐ is furanyl. In some embodiments is a compound of Formula (II), or a pharmaceutically acceptable salt thereof, wherein ring Ⓐ is thiophenyl. In some embodiments is a compound of Formula (II), or a pharmaceutically acceptable salt thereof, wherein ring Ⓐ is thiazolyl. In some embodiments is a compound of Formula (II), or a pharmaceutically acceptable salt thereof, wherein ring Ⓐ is pyrrolyl. In some embodiments is a compound of Formula (II), or a pharmaceutically acceptable salt thereof, wherein ring Ⓐ is pyridinyl. In some embodiments is a compound of Formula (II), or a pharmaceutically acceptable salt thereof, wherein m is 0. In some embodiments is a compound of Formula (II), or a pharmaceutically acceptable salt thereof, wherein m is 1. In some embodiments is a compound of Formula (II), or a pharmaceutically acceptable salt thereof, wherein m is 1 and $R^3$ is halogen, —OR⁵, —SR⁵, substituted or unsubstituted $C_1$-$C_6$alkyl, or substituted or unsubstituted $C_1$-$C_6$fluoroalkyl. In some embodiments is a compound of Formula (II), or a pharmaceutically acceptable salt thereof, wherein m is 1 and $R^3$ is halogen, —OCH₃, —CF₃, or unsubstituted $C_1$-$C_6$alkyl. In some embodiments is a compound of Formula (II), or a pharmaceutically acceptable salt thereof, wherein m is 1 and $R^3$ is halogen. In some embodiments is a compound of Formula (II), or a pharmaceutically acceptable salt thereof, wherein m is 1 and $R^3$ is —OCH₃. In some embodiments is a compound of Formula (II), or a pharmaceutically acceptable salt thereof, wherein m is 1 and $R^3$ is —CF₃. In some embodiments is a compound of Formula (II), or a pharmaceutically acceptable salt thereof, wherein m is 1 and $R^3$ is unsubstituted $C_1$-$C_6$alkyl. In some embodiments is a compound of Formula (II), or a pharmaceutically acceptable salt thereof, wherein m is 1 and $R^3$ is —CH₃.

In some embodiments is a compound of Formula (II), or a pharmaceutically acceptable salt thereof, wherein X is a bond, —O—, —S—, or —N(H)—. In some embodiments is a compound of Formula (II), or a pharmaceutically acceptable salt thereof, wherein X is a bond. In some embodiments is a compound of Formula (II), or a pharmaceutically acceptable salt thereof, wherein X is —O—. In some embodiments is a compound of Formula (II), or a pharmaceutically acceptable salt thereof, wherein X is —S—. In some embodiments is a compound of Formula (II), or a pharmaceutically acceptable salt thereof, wherein X is —N(H)—.

In some embodiments is a compound of Formula (II), or a pharmaceutically acceptable salt thereof, wherein $R^4$ is H, —CF₃, —CH₃, or substituted or unsubstituted phenyl. In some embodiments is a compound of Formula (II), or a pharmaceutically acceptable salt thereof, wherein $R^4$ is H. In some embodiments is a compound of Formula (II), or a pharmaceutically acceptable salt thereof, wherein $R^4$ is —CF₃. In some embodiments is a compound of Formula (II), or a pharmaceutically acceptable salt thereof, wherein $R^4$ is —CH₃. In some embodiments is a compound of Formula (II), or a pharmaceutically acceptable salt thereof, wherein X is substituted phenyl. In some embodiments is a compound of Formula (II), or a pharmaceutically acceptable salt thereof, wherein X is unsubstituted phenyl.

In some embodiments is a compound of Formula (II), or a pharmaceutically acceptable salt thereof, wherein n is 0. In some embodiments is a compound of Formula (II), or a pharmaceutically acceptable salt thereof, wherein n is 1. In some embodiments is a compound of Formula (II), or a pharmaceutically acceptable salt thereof, wherein n is 1 and $R^2$ is halogen, —OR⁵, substituted or unsubstituted $C_1$-$C_6$alkyl, substituted or unsubstituted $C_1$-$C_6$fluoroalkyl. In some embodiments is a compound of Formula (II), or a pharmaceutically acceptable salt thereof, wherein n is 1 and $R^2$ is halogen, —CF₃, or —OCH₃. In some embodiments is a compound of Formula (II), or a pharmaceutically acceptable salt thereof, wherein n is 1 and R² is halogen. In some embodiments is a compound of Formula (II), or a pharmaceutically acceptable salt thereof, wherein n is 1 and R² is F. In some embodiments is a compound of Formula (II), or a pharmaceutically acceptable salt thereof, wherein n is 1 and R² is —CF₃. In some embodiments is a compound of Formula (II), or a pharmaceutically acceptable salt thereof, wherein n is 1 and R² is —OCH₃.

In some embodiments is a compound of Formula (II), or a pharmaceutically acceptable salt thereof, wherein R¹ is —CO₂H. In some embodiments is a compound of Formula (II), or a pharmaceutically acceptable salt thereof, wherein R¹ is —CN. In some embodiments is a compound of Formula (II), or a pharmaceutically acceptable salt thereof, wherein R¹ is —C(O)NHOH. In some embodiments is a compound of Formula (II), or a pharmaceutically acceptable salt thereof, wherein R¹ is —C(O)NHOMe. In some embodiments is a compound of Formula (II), or a pharmaceutically acceptable salt thereof, wherein R¹ is —C(O)NHSO₂Me. In some embodiments is a compound of Formula (II), or a pharmaceutically acceptable salt thereof, wherein R¹ is —NHC(O)Me. In some embodiments is a compound of Formula (II), or a pharmaceutically acceptable salt thereof, wherein R¹ is

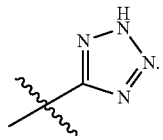 [SMILES: *c1nn[nH]n1]

In some embodiments is a compound of Formula (II), or a pharmaceutically acceptable salt thereof, wherein R¹ is

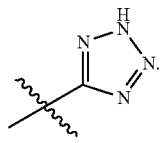 [SMILES: *c1nn[nH]n1]

In some embodiments is a compound of Formula (II), or a pharmaceutically acceptable salt thereof, wherein R¹ is

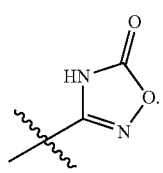 [SMILES: *c1noc(=O)[nH]1]

In some embodiments is a compound of Formula (II), or a pharmaceutically acceptable salt thereof, wherein R¹ is

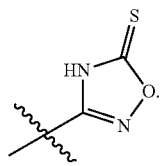

In some embodiments is a compound of Formula (II), or a pharmaceutically acceptable salt thereof, wherein R¹ is

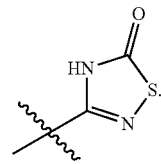 [SMILES: *c1nsc(=O)[nH]1]

In some embodiments, the compound of Formula (II) has the structure of Formula (IIa):

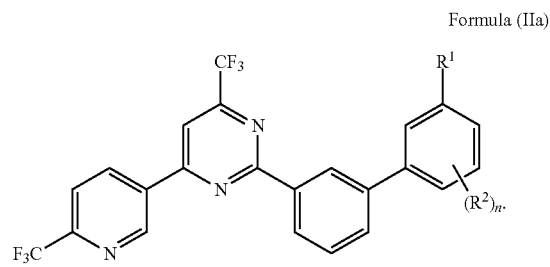

Formula (IIa)

In some embodiments is a compound of Formula (IIa), or a pharmaceutically acceptable salt thereof, wherein n is 0. In some embodiments is a compound of Formula (IIa), or a pharmaceutically acceptable salt thereof, wherein n is 1. In some embodiments is a compound of Formula (IIa), or a pharmaceutically acceptable salt thereof, wherein n is 1 and R² is halogen, —OR⁵, substituted or unsubstituted $C_1$-$C_6$alkyl, substituted or unsubstituted $C_1$-$C_6$fluoroalkyl. In some embodiments is a compound of Formula (IIa), or a pharmaceutically acceptable salt thereof, wherein n is 1 and R² is halogen, —CF₃, or —OCH₃. In some embodiments is a compound of Formula (IIa), or a pharmaceutically acceptable salt thereof, wherein n is 1 and R² is halogen. In some embodiments is a compound of Formula (IIa), or a pharmaceutically acceptable salt thereof, wherein n is 1 and R² is F. In some embodiments is a compound of Formula (IIa), or a pharmaceutically acceptable salt thereof, wherein n is 1 and R² is —CF₃. In some embodiments is a compound of Formula (IIa), or a pharmaceutically acceptable salt thereof, wherein n is 1 and R² is —OCH₃.

In some embodiments is a compound of Formula (IIa), or a pharmaceutically acceptable salt thereof, wherein R¹ is —CO₂H. In some embodiments is a compound of Formula (IIa), or a pharmaceutically acceptable salt thereof, wherein R¹ is —CO₂H and n is 0. In some embodiments is a compound of Formula (IIa), or a pharmaceutically acceptable salt thereof, wherein R¹ is —CO₂H, n is 1 and R² is halogen, —OR⁵, substituted or unsubstituted $C_1$-$C_6$alkyl, substituted or unsubstituted $C_1$-$C_6$fluoroalkyl. In some embodiments is a compound of Formula (IIa), or a pharmaceutically acceptable salt thereof, wherein R¹ is —CO₂H, n is 1 and R² is halogen, —CF₃, or —OCH₃. In some embodiments is a compound of Formula (IIa), or a pharmaceutically acceptable salt thereof, wherein R¹ is —CO₂H, n is 1 and R² is halogen. In some embodiments is a compound of Formula (IIa), or a pharmaceutically acceptable salt thereof, wherein R¹ is —CO₂H, n is 1 and R² is F. In some embodiments a compound of Formula (IIa), or a pharmaceutically acceptable salt thereof, wherein R¹ is —CO₂H, n is 1 and R² is —CF₃. In some embodiments is a compound of Formula (IIa), or a pharmaceutically acceptable salt thereof, wherein $R^1$ is —$CO_2H$, n is 1 and $R^2$ is —$OCH_3$.

In some embodiments, the compound of Formula (II) has the structure of Formula (IIb):

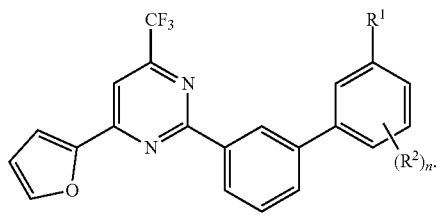

Formula (IIb)

In some embodiments is a compound of Formula (IIb), or a pharmaceutically acceptable salt thereof, wherein n is 0. In some embodiments is a compound of Formula (IIb), or a pharmaceutically acceptable salt thereof, wherein n is 1. In some embodiments is a compound of Formula (IIb), or a pharmaceutically acceptable salt thereof, wherein n is 1 and $R^2$ is halogen, —$OR^5$, substituted or unsubstituted $C_1$-$C_6$alkyl, substituted or unsubstituted $C_1$-$C_6$fluoroalkyl. In some embodiments is a compound of Formula (IIb), or a pharmaceutically acceptable salt thereof, wherein n is 1 and $R^2$ is halogen, —$CF_3$, or —$OCH_3$. In some embodiments is a compound of Formula (IIb), or a pharmaceutically acceptable salt thereof, wherein n is 1 and $R^2$ is halogen. In some embodiments is a compound of Formula (IIb), or a pharmaceutically acceptable salt thereof, wherein n is 1 and $R^2$ is F. In some embodiments is a compound of Formula (IIb), or a pharmaceutically acceptable salt thereof, wherein n is 1 and $R^2$ is —$CF_3$. In some embodiments is a compound of Formula (IIb), or a pharmaceutically acceptable salt thereof, wherein n is 1 and $R^2$ is —$OCH_3$.

In some embodiments is a compound of Formula (IIb), or a pharmaceutically acceptable salt thereof, wherein $R^1$ is —$CO_2H$. In some embodiments is a compound of Formula (IIb), or a pharmaceutically acceptable salt thereof, wherein $R^1$ is —$CO_2H$ and n is 0. In some embodiments is a compound of Formula (IIb), or a pharmaceutically acceptable salt thereof, wherein $R^1$ is —$CO_2H$, n is 1 and $R^2$ is halogen, —$OR^5$, substituted or unsubstituted $C_1$-$C_6$alkyl, substituted or unsubstituted $C_1$-$C_6$fluoroalkyl. In some embodiments is a compound of Formula (IIb), or a pharmaceutically acceptable salt thereof, wherein $R^1$ is —$CO_2H$, n is 1 and $R^2$ is halogen, —$CF_3$, or —$OCH_3$. In some embodiments is a compound of Formula (IIb), or a pharmaceutically acceptable salt thereof, wherein $R^1$ is —$CO_2H$, n is 1 and $R^2$ is halogen. In some embodiments is a compound of Formula (IIb), or a pharmaceutically acceptable salt thereof, wherein $R^1$ is —$CO_2H$, n is 1 and $R^2$ is F. In some embodiments is a compound of Formula (IIb), or a pharmaceutically acceptable salt thereof, wherein $R^1$ is —$CO_2H$, n is 1 and $R^2$ is —$CF_3$. In some embodiments is a compound of Formula (IIb), or a pharmaceutically acceptable salt thereof, wherein $R^1$ is —$CO_2H$, n is 1 and $R^2$ is —$OCH_3$.

In some embodiments, the compound of Formula (II) has the structure of Formula (IIc):

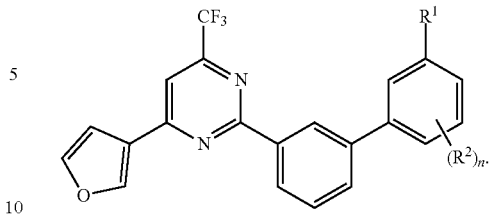

Formula (IIc)

In some embodiments is a compound of Formula (IIc), or a pharmaceutically acceptable salt thereof, wherein n is 0. In some embodiments is a compound of Formula (IIc), or a pharmaceutically acceptable salt thereof, wherein n is 1. In some embodiments is a compound of Formula (IIc), or a pharmaceutically acceptable salt thereof, wherein n is 1 and $R^2$ is halogen, —$OR^5$, substituted or unsubstituted $C_1$-$C_6$alkyl, substituted or unsubstituted $C_1$-$C_6$fluoroalkyl. In some embodiments is a compound of Formula (IIc), or a pharmaceutically acceptable salt thereof, wherein n is 1 and $R^2$ is halogen, —$CF_3$, or —$OCH_3$. In some embodiments is a compound of Formula (IIc), or a pharmaceutically acceptable salt thereof, wherein n is 1 and $R^2$ is halogen. In some embodiments is a compound of Formula (IIc), or a pharmaceutically acceptable salt thereof, wherein n is 1 and $R^2$ is F. In some embodiments is a compound of Formula (IIc), or a pharmaceutically acceptable salt thereof, wherein n is 1 and $R^2$ is —$CF_3$. In some embodiments is a compound of Formula (IIc), or a pharmaceutically acceptable salt thereof, wherein n is 1 and $R^2$ is —$OCH_3$.

In some embodiments is a compound of Formula (IIc), or a pharmaceutically acceptable salt thereof, wherein $R^1$ is —$CO_2H$. In some embodiments is a compound of Formula (IIc), or a pharmaceutically acceptable salt thereof, wherein $R^1$ is —$CO_2H$ and n is 0. In some embodiments is a compound of Formula (IIc), or a pharmaceutically acceptable salt thereof, wherein $R^1$ is —$CO_2H$, n is 1 and $R^2$ is halogen, —$OR^5$, substituted or unsubstituted $C_1$-$C_6$alkyl, substituted or unsubstituted $C_1$-$C_6$fluoroalkyl. In some embodiments is a compound of Formula (IIc), or a pharmaceutically acceptable salt thereof, wherein $R^1$ is —$CO_2H$, n is 1 and $R^2$ is halogen, —$CF_3$, or —$OCH_3$. In some embodiments is a compound of Formula (IIc), or a pharmaceutically acceptable salt thereof, wherein $R^1$ is —$CO_2H$, n is 1 and $R^2$ is halogen. In some embodiments is a compound of Formula (IIc), or a pharmaceutically acceptable salt thereof, wherein $R^1$ is —$CO_2H$, n is 1 and $R^2$ is F. In some embodiments is a compound of Formula (IIc), or a pharmaceutically acceptable salt thereof, wherein $R^1$ is —$CO_2H$, n is 1 and $R^2$ is —$CF_3$. In some embodiments is a compound of Formula (IIc), or a pharmaceutically acceptable salt thereof, wherein $R^1$ is —$CO_2H$, n is 1 and $R^2$ is —$OCH_3$.

In another aspect, described herein is a compound that has the structure of Formula (III), or a pharmaceutically acceptable salt thereof:

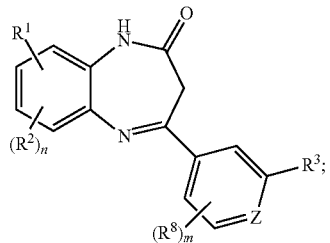

Formula (III)

wherein:

$Z$ is =N— or =C(H)—;

$R^1$ is halogen, —$OR^5$, —$NO_2$, —CN, substituted or unsubstituted $C_1$-$C_6$alkyl, substituted or unsubstituted $C_1$-$C_6$fluoroalkyl, substituted or unsubstituted aryl, substituted or unsubstituted heteroaryl, or —$CO_2R^6$;

each $R^2$ is independently halogen, —$OR^5$, $NO_2$, substituted or unsubstituted $C_1$-$C_6$alkyl, or substituted or unsubstituted $C_1$-$C_6$fluoroalkyl;

$R^3$ is hydrogen, halogen, —CN, substituted or unsubstituted $C_1$-$C_6$alkyl, substituted or unsubstituted $C_1$-$C_6$fluoroalkyl, substituted or unsubstituted $C_3$-$C_6$cycloalkyl, substituted or unsubstituted $C_2$-$C_7$heterocycloalkyl, substituted or unsubstituted aryl, unsubstituted heteroaryl, —C(O)NR$^9$R$^{10}$, or —X—R$^4$;

X is —O—, —S—, —S(O)$_2$—, —N(R$^7$)—, or —C≡C—;

$R^4$ is substituted or unsubstituted $C_1$-$C_6$alkyl, substituted or unsubstituted $C_3$-$C_6$cycloalkyl, substituted or unsubstituted aryl, or substituted or unsubstituted heteroaryl;

each $R^5$ is independently hydrogen, or substituted or unsubstituted $C_1$-$C_6$alkyl;

$R^6$ is hydrogen, or substituted or unsubstituted $C_1$-$C_6$alkyl;

$R^7$ is hydrogen, or substituted or unsubstituted $C_1$-$C_6$alkyl;

each $R^8$ is independently halogen, or substituted or unsubstituted $C_1$-$C_6$alkyl;

$R^9$ and $R^{10}$ are independently hydrogen, or substituted or unsubstituted $C_1$-$C_6$alkyl;

n is 0, 1, 2, or 3; and m is 0, 1, or 2.

In some embodiments is a compound of Formula (III), or a pharmaceutically acceptable salt thereof, wherein Z is =N—. In some embodiments is a compound of Formula (III), or a pharmaceutically acceptable salt thereof, wherein Z is =C(H)—.

In some embodiments is a compound of Formula (III), or a pharmaceutically acceptable salt thereof, wherein m is 0. In some embodiments is a compound of Formula (III), or a pharmaceutically acceptable salt thereof, wherein m is 1 and $R^8$ is halogen.

In some embodiments is a compound of Formula (III), or a pharmaceutically acceptable salt thereof, wherein m is 0 and $R^3$ is halogen, —CN, substituted or unsubstituted $C_1$-$C_6$alkyl, substituted or unsubstituted aryl, unsubstituted heteroaryl, or —X—R$^4$. In some embodiments is a compound of Formula (III), or a pharmaceutically acceptable salt thereof, wherein m is 0 and $R^3$ is halogen. In some embodiments is a compound of Formula (III), or a pharmaceutically acceptable salt thereof, wherein m is 0 and $R^3$ is —CN. In some embodiments is a compound of Formula (III), or a pharmaceutically acceptable salt thereof, wherein m is 0 and $R^3$ is substituted or unsubstituted $C_1$-$C_6$alkyl. In some embodiments is a compound of Formula (III), or a pharmaceutically acceptable salt thereof, wherein m is 0 and $R^3$ is substituted or unsubstituted aryl. In some embodiments is a compound of Formula (III), or a pharmaceutically acceptable salt thereof, wherein m is 0 and $R^3$ is unsubstituted heteroaryl. In some embodiments is a compound of Formula (III), or a pharmaceutically acceptable salt thereof, wherein m is 0 and $R^3$ is —X—R$^4$. In some embodiments is a compound of Formula (III), or a pharmaceutically acceptable salt thereof, wherein m is 0, $R^3$ is —X—R$^4$, X is —O—, and $R^4$ is substituted or unsubstituted aryl, or substituted or unsubstituted heteroaryl. In some embodiments is a compound of Formula (III), or a pharmaceutically acceptable salt thereof, wherein m is 0, $R^3$ is —X—R$^4$, X is —O—, and $R^4$ is substituted or unsubstituted phenyl. In some embodiments is a compound of Formula (III), or a pharmaceutically acceptable salt thereof, wherein m is 0, $R^3$ is —X—R$^4$, X is —O—, and $R^4$ is substituted or unsubstituted heteroaryl. In some embodiments is a compound of Formula (III), or a pharmaceutically acceptable salt thereof, wherein m is 0, $R^3$ is —X—R$^4$, X is —O—, and $R^4$ is unsubstituted pyridine. In some embodiments is a compound of Formula (III), or a pharmaceutically acceptable salt thereof, wherein m is 0, $R^3$ is —X—R$^4$, X is —O—, and $R^4$ is unsubstituted pyrimidine. In some embodiments is a compound of Formula (III), or a pharmaceutically acceptable salt thereof, wherein m is 0, $R^3$ is —X—R$^4$, X is —O—, and $R^4$ is unsubstituted pyrazine. In some embodiments is a compound of Formula (III), or a pharmaceutically acceptable salt thereof, wherein m is 0, $R^3$ is —X—R$^4$, X is —N(H)—, and $R^4$ is substituted or unsubstituted aryl, or substituted or unsubstituted heteroaryl. In some embodiments is a compound of Formula (III), or a pharmaceutically acceptable salt thereof, wherein m is 0, $R^3$ is —X—R$^4$, X is —N(H)—, and $R^4$ is substituted or unsubstituted phenyl. In some embodiments is a compound of Formula (III), or a pharmaceutically acceptable salt thereof, wherein m is 0, $R^3$ is —X—R$^4$, X is —N(H)—, and $R^4$ is substituted or unsubstituted heteroaryl. In some embodiments is a compound of Formula (III), or a pharmaceutically acceptable salt thereof, wherein m is 0, $R^3$ is —X—R$^4$, X is —N(H)—, and $R^4$ is unsubstituted pyridine. In some embodiments is a compound of Formula (III), or a pharmaceutically acceptable salt thereof, wherein m is 0, $R^3$ is —X—R$^4$, X is —N(H)—, and $R^4$ is unsubstituted pyrimidine. In some embodiments is a compound of Formula (III), or a pharmaceutically acceptable salt thereof, wherein m is 0, $R^3$ is —X—R$^4$, X is —N(H)—, and $R^4$ is unsubstituted pyrazine. In some embodiments is a compound of Formula (III), or a pharmaceutically acceptable salt thereof, wherein m is 0, $R^3$ is —X—R$^4$, X is —S—, and $R^4$ is substituted or unsubstituted aryl, or substituted or unsubstituted heteroaryl. In some embodiments is a compound of Formula (III), or a pharmaceutically acceptable salt thereof, wherein m is 0, $R^3$ is —X—R$^4$, X is —S—, and $R^4$ is substituted or unsubstituted phenyl. In some embodiments is a compound of Formula (III), or a pharmaceutically acceptable salt thereof, wherein m is 0, $R^3$ is —X—R$^4$, X is —S—, and $R^4$ is substituted or unsubstituted heteroaryl. In some embodiments is a compound of Formula (III), or a pharmaceutically acceptable salt thereof, wherein m is 0, $R^3$ is —X—R$^4$, X is —S—, and $R^4$ is unsubstituted pyridine. In some embodiments is a compound of Formula (III), or a pharmaceutically acceptable salt thereof, wherein m is 0, $R^3$ is —X—R$^4$, —S—, and $R^4$ is unsubstituted pyrimidine. In some embodiments is a compound of Formula (III), or a pharmaceutically acceptable salt thereof, wherein m is 0, $R^3$ is —X—R$^4$, X is —S—, and $R^4$ is unsubstituted pyrazine. In some embodiments is a compound of Formula (III), or a pharmaceutically acceptable salt thereof, wherein m is 0, $R^3$ is —X—R$^4$, X is —S(O)$_2$—, and $R^4$ is substituted or unsubstituted aryl, or substituted or unsubstituted heteroaryl. In some embodiments is a compound of Formula (III), or a pharmaceutically acceptable salt thereof, wherein m is 0, $R^3$ is —X—R$^4$, X is —S(O)$_2$—, and $R^4$ is substituted or unsubstituted phenyl. In some embodiments is a compound of Formula (III), or a pharmaceutically acceptable salt thereof, wherein m is 0, $R^3$ is —X—R$^4$, X is —S(O)$_2$—, and $R^4$ is substituted or unsubstituted heteroaryl. In some embodiments is a compound of Formula (III), or a pharmaceutically acceptable salt thereof, wherein m is 0, $R^3$ is —X—R⁴, X is —S(O)₂—, and R⁴ is unsubstituted pyridine. In some embodiments is a compound of Formula (III), or a pharmaceutically acceptable salt thereof, wherein m is 0, R³ is —X—R⁴, —S(O)₂—, and R⁴ is unsubstituted pyrimidine. In some embodiments is a compound of Formula (III), or a pharmaceutically acceptable salt thereof, wherein m is 0, R³ is —X—R⁴, X is —S(O)₂—, and R⁴ is unsubstituted pyrazine.

In some embodiments is a compound of Formula (III), or a pharmaceutically acceptable salt thereof, wherein R¹ is halogen, —OR⁵, substituted or unsubstituted C₁-C₆alkyl, or substituted or unsubstituted C₁-C₆fluoroalkyl. In some embodiments is a compound of Formula (III), or a pharmaceutically acceptable salt thereof, wherein R¹ is halogen, —CF₃, or —OCH₃. In some embodiments is a compound of Formula (III), or a pharmaceutically acceptable salt thereof, wherein R¹ is halogen. In some embodiments is a compound of Formula (III), or a pharmaceutically acceptable salt thereof, wherein R¹ is —CF₃. In some embodiments is a compound of Formula (III), or a pharmaceutically acceptable salt thereof, wherein R¹ is —OCH₃.

In some embodiments is a compound of Formula (III), or a pharmaceutically acceptable salt thereof, wherein n is 0. In some embodiments is a compound of Formula (III), or a pharmaceutically acceptable salt thereof, wherein n is 1. In some embodiments is a compound of Formula (III), or a pharmaceutically acceptable salt thereof, wherein n is 1 and R² is halogen, —OR⁵, substituted or unsubstituted C₁-C₆alkyl, substituted or unsubstituted C₁-C₆fluoroalkyl. In some embodiments is a compound of Formula (III), or a pharmaceutically acceptable salt thereof, wherein n is 1 and R² is halogen, —CH₃, —CF₃, or —OCH₃. In some embodiments is a compound of Formula (III), or a pharmaceutically acceptable salt thereof, wherein n is 1 and R² is halogen. In some embodiments is a compound of Formula (III), or a pharmaceutically acceptable salt thereof, wherein n is 1 and R² is —CH₃. In some embodiments is a compound of Formula (III), or a pharmaceutically acceptable salt thereof, wherein n is 1 and R² is —CF₃. In some embodiments is a compound of Formula (III), or a pharmaceutically acceptable salt thereof, wherein n is 1 and R² is —OCH₃.

In some embodiments, the compound of Formula (III) has the structure of Formula (IIIa):

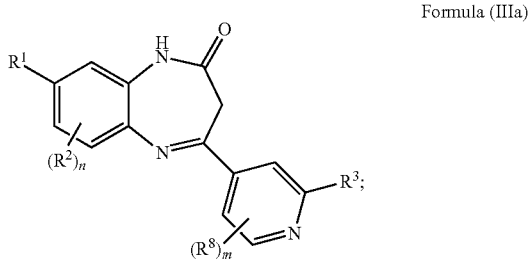

Formula (IIIa)

wherein R³ is halogen, —CN, unsubstituted heteroaryl, or —X—R⁴; and R⁴ is substituted or unsubstituted aryl, or substituted or unsubstituted heteroaryl.

In some embodiments is a compound of Formula (IIIa), or a pharmaceutically acceptable salt thereof, wherein m is 0. In some embodiments is a compound of Formula (IIIa), or a pharmaceutically acceptable salt thereof, wherein m is 1 and R⁸ is halogen.

In some embodiments is a compound of Formula (IIIa), or a pharmaceutically acceptable salt thereof, wherein m is 0 and R³ is halogen. In some embodiments is a compound of Formula (IIIa), or a pharmaceutically acceptable salt thereof, wherein m is 0 and R³ is —CN. In some embodiments is a compound of Formula (IIIa), or a pharmaceutically acceptable salt thereof, wherein m is 0 and R³ is unsubstituted heteroaryl. In some embodiments is a compound of Formula (IIIa), or a pharmaceutically acceptable salt thereof, wherein m is 0 and R³ is —X—R⁴. In some embodiments is a compound of Formula (IIIa), or a pharmaceutically acceptable salt thereof, wherein m is 0, R³ is —X—R⁴, X is —O—, and R⁴ is substituted or unsubstituted aryl, or substituted or unsubstituted heteroaryl. In some embodiments is a compound of Formula (IIIa), or a pharmaceutically acceptable salt thereof, wherein m is 0, R³ is —X—R⁴, X is —O—, and R⁴ is substituted or unsubstituted phenyl. In some embodiments is a compound of Formula (IIIa), or a pharmaceutically acceptable salt thereof, wherein m is 0, R³ is —X—R⁴, X is —O—, and R⁴ is substituted or unsubstituted heteroaryl. In some embodiments is a compound of Formula (IIIa), or a pharmaceutically acceptable salt thereof, wherein m is 0, R³ is —X—R⁴, X is —O—, and R⁴ is unsubstituted pyridine. In some embodiments is a compound of Formula (IIIa), or a pharmaceutically acceptable salt thereof, wherein m is 0, R³ is —X—R⁴, X is —O—, and R⁴ is unsubstituted pyrimidine. In some embodiments is a compound of Formula (IIIa), or a pharmaceutically acceptable salt thereof, wherein m is 0, R³ is —X—R⁴, X is —O—, and R⁴ is unsubstituted pyrazine. In some embodiments is a compound of Formula (IIIa), or a pharmaceutically acceptable salt thereof, wherein m is 0, R³ is —X—R⁴, X is —N(H)—, and R⁴ is substituted or unsubstituted aryl, or substituted or unsubstituted heteroaryl. In some embodiments is a compound of Formula (IIIa), or a pharmaceutically acceptable salt thereof, wherein m is 0, R³ is —X—R⁴, X is —N(H)—, and R⁴ is substituted or unsubstituted phenyl. In some embodiments is a compound of Formula (IIIa), or a pharmaceutically acceptable salt thereof, wherein m is 0, R³ is —X—R⁴, X is —N(H)—, and R⁴ is substituted or unsubstituted heteroaryl. In some embodiments is a compound of Formula (IIIa), or a pharmaceutically acceptable salt thereof, wherein m is 0, R³ is —X—R⁴, X is —N(H)—, and R⁴ is unsubstituted pyridine. In some embodiments is a compound of Formula (IIIa), or a pharmaceutically acceptable salt thereof, wherein m is 0, R³ is —X—R⁴, X is —N(H)—, and R⁴ is unsubstituted pyrimidine. In some embodiments is a compound of Formula (IIIa), or a pharmaceutically acceptable salt thereof, wherein m is 0, R³ is —X—R⁴, X is —N(H)—, and R⁴ is unsubstituted pyrazine. In some embodiments is a compound of Formula (IIIa), or a pharmaceutically acceptable salt thereof, wherein m is 0, R³ is —X—R⁴, X is —S—, and R⁴ is substituted or unsubstituted aryl, or substituted or unsubstituted heteroaryl. In some embodiments is a compound of Formula (IIIa), or a pharmaceutically acceptable salt thereof, wherein m is 0, R³ is —X—R⁴, X is —S—, and R⁴ is substituted or unsubstituted phenyl. In some embodiments is a compound of Formula (IIIa), or a pharmaceutically acceptable salt thereof, wherein m is 0, R³ is —X—R⁴, X is —S—, and R⁴ is substituted or unsubstituted heteroaryl. In some embodiments is a compound of Formula (IIIa), or a pharmaceutically acceptable salt thereof, wherein m is 0, R³ is —X—R⁴, X is —S—, and R⁴ is unsubstituted pyridine. In some embodiments is a compound of Formula (IIIa), or a pharmaceutically acceptable salt thereof, wherein m is 0, R³ is —X—R⁴, —S—, and R⁴ is unsubstituted pyrimidine. In some embodiments is a compound of Formula (IIIa), or a pharmaceutically acceptable salt thereof, wherein m is 0, R³ is —X—R$^4$, X is —S—, and R$^4$ is unsubstituted pyrazine. In some embodiments is a compound of Formula (IIIa), or a pharmaceutically acceptable salt thereof, wherein m is 0, R$^3$ is —X—R$^4$, X is —S(O)$_2$—, and R$^4$ is substituted or unsubstituted aryl, or substituted or unsubstituted heteroaryl. In some embodiments is a compound of Formula (IIIa), or a pharmaceutically acceptable salt thereof, wherein m is 0, R$^3$ is —X—R$^4$, X is —S(O)$_2$—, and R$^4$ is substituted or unsubstituted phenyl. In some embodiments is a compound of Formula (IIIa), or a pharmaceutically acceptable salt thereof, wherein m is 0, R$^3$ is —X—R$^4$, X is —S(O)$_2$—, and R$^4$ is substituted or unsubstituted heteroaryl. In some embodiments is a compound of Formula (IIIa), or a pharmaceutically acceptable salt thereof, wherein m is 0, R$^3$ is —X—R$^4$, X is —S(O)$_2$—, and R$^4$ is unsubstituted pyridine. In some embodiments is a compound of Formula (IIIa), or a pharmaceutically acceptable salt thereof, wherein m is 0, R$^3$ is —X—R$^4$, —S(O)$_2$—, and R$^4$ is unsubstituted pyrimidine. In some embodiments is a compound of Formula (IIIa), or a pharmaceutically acceptable salt thereof, wherein m is 0, R$^3$ is —X—R$^4$, X is —S(O)$_2$—, and R$^4$ is unsubstituted pyrazine.

In some embodiments is a compound of Formula (IIIa), or a pharmaceutically acceptable salt thereof, wherein R$^1$ is halogen, —OR$^5$, substituted or unsubstituted C$_1$-C$_6$alkyl, or substituted or unsubstituted C$_1$-C$_6$fluoroalkyl. In some embodiments is a compound of Formula (IIIa), or a pharmaceutically acceptable salt thereof, wherein R$^1$ is halogen, —CF$_3$, or —OCH$_3$. In some embodiments is a compound of Formula (IIIa), or a pharmaceutically acceptable salt thereof, wherein R$^1$ is halogen. In some embodiments is a compound of Formula (IIIa), or a pharmaceutically acceptable salt thereof, wherein R$^1$ is —CF$_3$. In some embodiments is a compound of Formula (IIIa), or a pharmaceutically acceptable salt thereof, wherein R$^1$ is —OCH$_3$.

In some embodiments is a compound of Formula (IIIa), or a pharmaceutically acceptable salt thereof, wherein n is 0. In some embodiments is a compound of Formula (IIIa), or a pharmaceutically acceptable salt thereof, wherein n is 1. In some embodiments is a compound of Formula (IIIa), or a pharmaceutically acceptable salt thereof, wherein n is 1 and R$^2$ is halogen, —OR$^5$, substituted or unsubstituted C$_1$-C$_6$alkyl, substituted or unsubstituted C$_1$-C$_6$fluoroalkyl. In some embodiments is a compound of Formula (IIIa), or a pharmaceutically acceptable salt thereof, wherein n is 1 and R$^2$ is halogen, —CH$_3$, —CF$_3$, or —OCH$_3$. In some embodiments is a compound of Formula (IIIa), or a pharmaceutically acceptable salt thereof, wherein n is 1 and R$^2$ is halogen. In some embodiments is a compound of Formula (IIIa), or a pharmaceutically acceptable salt thereof, wherein n is 1 and R$^2$ is —CH$_3$. In some embodiments is a compound of Formula (IIIa), or a pharmaceutically acceptable salt thereof, wherein n is 1 and R$^2$ is —CF$_3$. In some embodiments is a compound of Formula (IIIa), or a pharmaceutically acceptable salt thereof, wherein n is 1 and R$^2$ is —OCH$_3$.

In some embodiments, the compound of Formula (III) has the structure of Formula (IIIb):

Formula (IIIb)

wherein R$^3$ is —CN, substituted or unsubstituted heteroaryl, or —X—R$^4$; and R$^4$ is substituted or unsubstituted C$_1$-C$_6$alkyl, substituted or unsubstituted aryl, or unsubstituted heteroaryl.

In some embodiments is a compound of Formula (IIIb), or a pharmaceutically acceptable salt thereof, wherein m is 0. In some embodiments is a compound of Formula (IIIb), or a pharmaceutically acceptable salt thereof, wherein m is 1 and R$^8$ is halogen.

In some embodiments is a compound of Formula (IIIb), or a pharmaceutically acceptable salt thereof, wherein m is 0 and R$^3$ is —CN. In some embodiments is a compound of Formula (IIIb), or a pharmaceutically acceptable salt thereof, wherein m is 0 and R$^3$ is unsubstituted heteroaryl. In some embodiments is a compound of Formula (IIIb), or a pharmaceutically acceptable salt thereof, wherein m is 0 and R$^3$ is —X—R$^4$. In some embodiments is a compound of Formula (IIIb), or a pharmaceutically acceptable salt thereof, wherein m is 0, R$^3$ is —X—R$^4$, X is —O—, and R$^4$ is substituted or unsubstituted aryl, or substituted or unsubstituted heteroaryl. In some embodiments is a compound of Formula (IIIb), or a pharmaceutically acceptable salt thereof, wherein m is 0, R$^3$ is —X—R$^4$, X is —O—, and R$^4$ is substituted or unsubstituted phenyl. In some embodiments is a compound of Formula (IIIb), or a pharmaceutically acceptable salt thereof, wherein m is 0, R$^3$ is —X—R$^4$, X is —O—, and R$^4$ is substituted or unsubstituted heteroaryl. In some embodiments is a compound of Formula (IIIb), or a pharmaceutically acceptable salt thereof, wherein m is 0, R$^3$ is —X—R$^4$, X is —O—, and R$^4$ is unsubstituted pyridine. In some embodiments is a compound of Formula (IIIb), or a pharmaceutically acceptable salt thereof, wherein m is 0, R$^3$ is —X—R$^4$, X is —O—, and R$^4$ is unsubstituted pyrimidine. In some embodiments is a compound of Formula (IIIb), or a pharmaceutically acceptable salt thereof, wherein m is 0, R$^3$ is —X—R$^4$, X is —O—, and R$^4$ is unsubstituted pyrazine. In some embodiments is a compound of Formula (IIIb), or a pharmaceutically acceptable salt thereof, wherein m is 0, R$^3$ is —X—R$^4$, X is —N(H)—, and R$^4$ is substituted or unsubstituted aryl, or substituted or unsubstituted heteroaryl. In some embodiments is a compound of Formula (IIIb), or a pharmaceutically acceptable salt thereof, wherein m is 0, R$^3$ is —X—R$^4$, X is —N(H)—, and R$^4$ is substituted or unsubstituted phenyl. In some embodiments is a compound of Formula (IIIb), or a pharmaceutically acceptable salt thereof, wherein m is 0, R$^3$ is —X—R$^4$, X is —N(H)—, and R$^4$ is substituted or unsubstituted heteroaryl. In some embodiments is a compound of Formula (IIIb), or a pharmaceutically acceptable salt thereof, wherein m is 0, R$^3$ is —X—R$^4$, X is —N(H)—, and R$^4$ is unsubstituted pyridine. In some embodiments is a compound of Formula (IIIb), or a pharmaceutically acceptable salt thereof, wherein m is 0, R$^3$ is —X—R$^4$, X is —N(H)—, and R$^4$ is unsubstituted pyrimidine. In some embodiments is a compound of Formula (IIIb), or a pharmaceutically acceptable salt thereof, wherein m is 0, R$^3$ is —X—R$^4$, X is —N(H)—, and R$^4$ is unsubstituted pyrazine. In some embodiments is a compound of Formula (IIIb), or a pharmaceutically acceptable salt thereof, wherein m is 0, R$^3$ is —X—R$^4$, X is —S—, and R$^4$ is substituted or unsubstituted aryl, or substituted or unsubstituted heteroaryl. In some embodiments is a compound of Formula (IIIb), or a pharmaceutically acceptable salt thereof, wherein m is 0, R$^3$ is —X—R$^4$, X is —S—, and R$^4$ is substituted or unsubstituted phenyl. In some embodiments is a compound of Formula (IIIb), or a pharmaceutically acceptable salt thereof, wherein m is 0, R$^3$ is —X—R$^4$, X is —S—, and R$^4$ is substituted or unsubstituted heteroaryl.

In some embodiments is a compound of Formula (IIIb), or a pharmaceutically acceptable salt thereof, wherein m is 0, $R^3$ is —X—$R^4$, X is —S—, and $R^4$ is unsubstituted pyridine. In some embodiments is a compound of Formula (IIIb), or a pharmaceutically acceptable salt thereof, wherein m is 0, $R^3$ is —X—$R^4$, —S—, and $R^4$ is unsubstituted pyrimidine. In some embodiments is a compound of Formula (IIIb), or a pharmaceutically acceptable salt thereof, wherein m is 0, $R^3$ is —X—$R^4$, X is —S—, and $R^4$ is unsubstituted pyrazine. In some embodiments is a compound of Formula (IIIb), or a pharmaceutically acceptable salt thereof, wherein m is 0, $R^3$ is —X—$R^4$, X is —S(O)$_2$—, and $R^4$ is substituted or unsubstituted aryl, or substituted or unsubstituted heteroaryl. In some embodiments is a compound of Formula (IIIb), or a pharmaceutically acceptable salt thereof, wherein m is 0, $R^3$ is —X—$R^4$, X is —S(O)$_2$—, and $R^4$ is substituted or unsubstituted phenyl. In some embodiments is a compound of Formula (IIIb), or a pharmaceutically acceptable salt thereof, wherein m is 0, $R^3$ is —X—$R^4$, X is —S(O)$_2$—, and $R^4$ is substituted or unsubstituted heteroaryl. In some embodiments is a compound of Formula (IIIb), or a pharmaceutically acceptable salt thereof, wherein m is 0, $R^3$ is —X—$R^4$, X is —S(O)$_2$—, and $R^4$ is unsubstituted pyridine. In some embodiments is a compound of Formula (IIIb), or a pharmaceutically acceptable salt thereof, wherein m is 0, $R^3$ is —X—$R^4$, —S(O)$_2$—, and $R^4$ is unsubstituted pyrimidine. In some embodiments is a compound of Formula (IIIb), or a pharmaceutically acceptable salt thereof, wherein m is 0, $R^3$ is —X—$R^4$, X is —S(O)$_2$—, and $R^4$ is unsubstituted pyrazine. In some embodiments is a compound of Formula (IIIb), or a pharmaceutically acceptable salt thereof, wherein m is 0, $R^3$ is —X—$R^4$, X is —C≡C—, and $R^4$ is substituted or unsubstituted $C_1$-$C_6$alkyl.

In some embodiments is a compound of Formula (IIIb), or a pharmaceutically acceptable salt thereof, wherein $R^1$ is halogen, —$OR^5$, substituted or unsubstituted $C_1$-$C_6$alkyl, or substituted or unsubstituted $C_1$-$C_6$fluoroalkyl. In some embodiments is a compound of Formula (IIIb), or a pharmaceutically acceptable salt thereof, wherein $R^1$ is halogen, —$CF_3$, or —$OCH_3$. In some embodiments is a compound of Formula (IIIb), or a pharmaceutically acceptable salt thereof, wherein $R^1$ is halogen. In some embodiments is a compound of Formula (IIIb), or a pharmaceutically acceptable salt thereof, wherein $R^1$ is —$CF_3$. In some embodiments is a compound of Formula (IIIb), or a pharmaceutically acceptable salt thereof, wherein $R^1$ is —$OCH_3$.

In some embodiments is a compound of Formula (IIIb), or a pharmaceutically acceptable salt thereof, wherein n is 0. In some embodiments is a compound of Formula (IIIb), or a pharmaceutically acceptable salt thereof, wherein n is 1. In some embodiments is a compound of Formula (IIIb), or a pharmaceutically acceptable salt thereof, wherein n is 1 and $R^2$ is halogen, —$OR^5$, substituted or unsubstituted $C_1$-$C_6$alkyl, substituted or unsubstituted $C_1$-$C_6$fluoroalkyl. In some embodiments is a compound of Formula (IIIb), or a pharmaceutically acceptable salt thereof, wherein n is 1 and $R^2$ is halogen, —$CH_3$, —$CF_3$, or —$OCH_3$. In some embodiments is a compound of Formula (IIIb), or a pharmaceutically acceptable salt thereof, wherein n is 1 and $R^2$ is halogen. In some embodiments is a compound of Formula (IIIb), or a pharmaceutically acceptable salt thereof, wherein n is 1 and $R^2$ is —$CH_3$. In some embodiments is a compound of Formula (IIIb), or a pharmaceutically acceptable salt thereof, wherein n is 1 and $R^2$ is —$CF_3$. In some embodiments is a compound of Formula (IIIb), or a pharmaceutically acceptable salt thereof, wherein n is 1 and $R^2$ is —$OCH_3$.

In another aspect, described herein is a compound that has the structure of Formula (IV), or a pharmaceutically acceptable salt thereof:

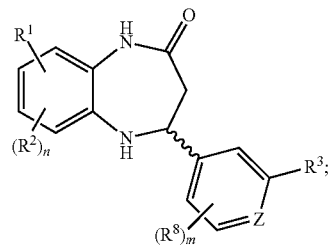

Formula (IV)

wherein:

Z is =N— or =C(H)—;

$R^1$ is halogen, —$OR^5$, —$NO_2$, —CN, substituted or unsubstituted $C_1$-$C_6$alkyl, substituted or unsubstituted $C_1$-$C_6$fluoroalkyl, substituted or unsubstituted aryl, substituted or unsubstituted heteroaryl, or —$CO_2R^6$;

each $R^2$ is independently halogen, —$OR^5$, $NO_2$, substituted or unsubstituted $C_1$-$C_6$alkyl, or substituted or unsubstituted $C_1$-$C_6$fluoroalkyl;

$R^3$ is hydrogen, halogen, —CN, substituted or unsubstituted $C_1$-$C_6$alkyl, substituted or unsubstituted $C_1$-$C_6$fluoroalkyl, substituted or unsubstituted $C_3$-$C_6$cycloalkyl, substituted or unsubstituted $C_2$-$C_7$heterocycloalkyl, substituted or unsubstituted aryl, unsubstituted heteroaryl, —C(O)$NR^9R^{10}$, or —X—$R^4$;

X is —O—, —S—, —S(O)$_2$—, —N($R^7$)—, or —C≡C—;

$R^4$ is substituted or unsubstituted $C_1$-$C_6$alkyl, substituted or unsubstituted $C_3$-$C_6$cycloalkyl, substituted or unsubstituted aryl, or substituted or unsubstituted heteroaryl;

each $R^5$ is independently hydrogen, or substituted or unsubstituted $C_1$-$C_6$alkyl;

$R^6$ is hydrogen, or substituted or unsubstituted $C_1$-$C_6$alkyl;

$R^7$ is hydrogen, or substituted or unsubstituted $C_1$-$C_6$alkyl;

each $R^8$ is independently halogen, or substituted or unsubstituted $C_1$-$C_6$alkyl;

$R^9$ and $R^{10}$ are independently hydrogen, or substituted or unsubstituted $C_1$-$C_6$alkyl;

n is 0, 1, 2, or 3; and m is 0, 1, or 2.

In some embodiments is a compound of Formula (IV), or a pharmaceutically acceptable salt thereof, wherein Z is =N—. In some embodiments is a compound of Formula (IV), or a pharmaceutically acceptable salt thereof, wherein Z is =C(H)—.

In some embodiments is a compound of Formula (IV), or a pharmaceutically acceptable salt thereof, wherein m is 0. In some embodiments is a compound of Formula (IV), or a pharmaceutically acceptable salt thereof, wherein m is 1 and $R^8$ is halogen.

In some embodiments is a compound of Formula (IV), or a pharmaceutically acceptable salt thereof, wherein m is 0 and $R^3$ is halogen, —CN, substituted or unsubstituted $C_1$-$C_6$alkyl, substituted or unsubstituted aryl, unsubstituted heteroaryl, or —X—$R^4$. In some embodiments is a compound of Formula (IV), or a pharmaceutically acceptable salt thereof, wherein m is 0 and $R^3$ is halogen. In some embodiments is a compound of Formula (IV), or a pharmaceutically acceptable salt thereof, wherein m is 0 and $R^3$ is —CN. In some embodiments is a compound of Formula (IV), or a pharmaceutically acceptable salt thereof, wherein m is 0 and $R^3$ is substituted or unsubstituted $C_1$-$C_6$alkyl. In some embodiments is a compound of Formula (IV), or a pharmaceutically acceptable salt thereof, wherein m is 0 and $R^3$ is substituted or unsubstituted aryl. In some embodiments is a compound of Formula (IV), or a pharmaceutically acceptable salt thereof, wherein m is 0 and $R^3$ is unsubstituted heteroaryl. In some embodiments is a compound of Formula (IV), or a pharmaceutically acceptable salt thereof, wherein m is 0 and $R^3$ is —X—$R^4$. In some embodiments is a compound of Formula (IV), or a pharmaceutically acceptable salt thereof, wherein m is 0, $R^3$ is —X—$R^4$, X is —O—, and $R^4$ is substituted or unsubstituted aryl, or substituted or unsubstituted heteroaryl. In some embodiments is a compound of Formula (IV), or a pharmaceutically acceptable salt thereof, wherein m is 0, $R^3$ is —X—$R^4$, X is —O—, and $R^4$ is substituted or unsubstituted phenyl. In some embodiments is a compound of Formula (IV), or a pharmaceutically acceptable salt thereof, wherein m is 0, $R^3$ is —X—$R^4$, X is —O—, and $R^4$ is substituted or unsubstituted heteroaryl. In some embodiments is a compound of Formula (IV), or a pharmaceutically acceptable salt thereof, wherein m is 0, $R^3$ is —X—$R^4$, X is —O—, and $R^4$ is unsubstituted pyridine. In some embodiments is a compound of Formula (IV), or a pharmaceutically acceptable salt thereof, wherein m is 0, $R^3$ is —X—$R^4$, X is —O—, and $R^4$ is unsubstituted pyrimidine. In some embodiments is a compound of Formula (IV), or a pharmaceutically acceptable salt thereof, wherein m is 0, $R^3$ is —X—$R^4$, X is —O—, and $R^4$ is unsubstituted pyrazine. In some embodiments is a compound of Formula (IV), or a pharmaceutically acceptable salt thereof, wherein m is 0, $R^3$ is —X—$R^4$, X is —N(H)—, and $R^4$ is substituted or unsubstituted aryl, or substituted or unsubstituted heteroaryl. In some embodiments is a compound of Formula (IV), or a pharmaceutically acceptable salt thereof, wherein m is 0, $R^3$ is —X—$R^4$, X is —N(H)—, and $R^4$ is substituted or unsubstituted phenyl. In some embodiments is a compound of Formula (IV), or a pharmaceutically acceptable salt thereof, wherein m is 0, $R^3$ is —X—$R^4$, X is —N(H)—, and $R^4$ is substituted or unsubstituted heteroaryl. In some embodiments is a compound of Formula (IV), or a pharmaceutically acceptable salt thereof, wherein m is 0, $R^3$ is —X—$R^4$, X is —N(H)—, and $R^4$ is unsubstituted pyridine. In some embodiments is a compound of Formula (IV), or a pharmaceutically acceptable salt thereof, wherein m is 0, $R^3$ is —X—$R^4$, X is —N(H)—, and $R^4$ is unsubstituted pyrimidine. In some embodiments is a compound of Formula (IV), or a pharmaceutically acceptable salt thereof, wherein m is 0, $R^3$ is —X—$R^4$, X is —N(H)—, and $R^4$ is unsubstituted pyrazine. In some embodiments is a compound of Formula (IV), or a pharmaceutically acceptable salt thereof, wherein m is 0, $R^3$ is —X—$R^4$, X is —S—, and $R^4$ is substituted or unsubstituted aryl, or substituted or unsubstituted heteroaryl. In some embodiments is a compound of Formula (IV), or a pharmaceutically acceptable salt thereof, wherein m is 0, $R^3$ is —X—$R^4$, X is —S—, and $R^4$ is substituted or unsubstituted phenyl. In some embodiments is a compound of Formula (IV), or a pharmaceutically acceptable salt thereof, wherein m is 0, $R^3$ is —X—$R^4$, X is —S—, and $R^4$ is substituted or unsubstituted heteroaryl. In some embodiments is a compound of Formula (IV), or a pharmaceutically acceptable salt thereof, wherein m is 0, $R^3$ is —X—$R^4$, X is —S—, and $R^4$ is unsubstituted pyridine. In some embodiments is a compound of Formula (IV), or a pharmaceutically acceptable salt thereof, wherein m is 0, $R^3$ is —X—$R^4$, —S—, and $R^4$ is unsubstituted pyrimidine. In some embodiments is a compound of Formula (IV), or a pharmaceutically acceptable salt thereof, wherein m is 0, $R^3$ is —X—$R^4$, X is —S—, and $R^4$ is unsubstituted pyrazine. In some embodiments is a compound of Formula (IV), or a pharmaceutically acceptable salt thereof, wherein m is 0, $R^3$ is —X—$R^4$, X is —S(O)$_2$—, and $R^4$ is substituted or unsubstituted aryl, or substituted or unsubstituted heteroaryl. In some embodiments is a compound of Formula (IV), or a pharmaceutically acceptable salt thereof, wherein m is 0, $R^3$ is —X—$R^4$, X is —S(O)$_2$—, and $R^4$ is substituted or unsubstituted phenyl. In some embodiments is a compound of Formula (IV), or a pharmaceutically acceptable salt thereof, wherein m is 0, $R^3$ is —X—$R^4$, X is —S(O)$_2$—, and $R^4$ is substituted or unsubstituted heteroaryl. In some embodiments is a compound of Formula (IV), or a pharmaceutically acceptable salt thereof, wherein m is 0, $R^3$ is —X—$R^4$, X is —S(O)$_2$—, and $R^4$ is unsubstituted pyridine. In some embodiments is a compound of Formula (IV), or a pharmaceutically acceptable salt thereof, wherein m is 0, $R^3$ is —X—$R^4$, —S(O)$_2$—, and $R^4$ is unsubstituted pyrimidine. In some embodiments is a compound of Formula (IV), or a pharmaceutically acceptable salt thereof, wherein m is 0, $R^3$ is —X—$R^4$, X is —S(O)$_2$—, and $R^4$ is unsubstituted pyrazine.

In some embodiments is a compound of Formula (IV), or a pharmaceutically acceptable salt thereof, wherein $R^1$ is halogen, —$OR^5$, substituted or unsubstituted $C_1$-$C_6$alkyl, or substituted or unsubstituted $C_1$-$C_6$fluoroalkyl. In some embodiments is a compound of Formula (IV), or a pharmaceutically acceptable salt thereof, wherein $R^1$ is halogen, —$CF_3$, or —$OCH_3$. In some embodiments is a compound of Formula (IV), or a pharmaceutically acceptable salt thereof, wherein $R^1$ is halogen. In some embodiments is a compound of Formula (IV), or a pharmaceutically acceptable salt thereof, wherein $R^1$ is —$CF_3$. In some embodiments is a compound of Formula (IV), or a pharmaceutically acceptable salt thereof, wherein $R^1$ is —$OCH_3$.

In some embodiments is a compound of Formula (IV), or a pharmaceutically acceptable salt thereof, wherein n is 0. In some embodiments is a compound of Formula (IV), or a pharmaceutically acceptable salt thereof, wherein n is 1. In some embodiments is a compound of Formula (IV), or a pharmaceutically acceptable salt thereof, wherein n is 1 and $R^2$ is halogen, —$OR^5$, substituted or unsubstituted $C_1$-$C_6$alkyl, substituted or unsubstituted $C_1$-$C_6$fluoroalkyl. In some embodiments is a compound of Formula (IV), or a pharmaceutically acceptable salt thereof, wherein n is 1 and $R^2$ is halogen, —$CH_3$, —$CF_3$, or —$OCH_3$. In some embodiments is a compound of Formula (IV), or a pharmaceutically acceptable salt thereof, wherein n is 1 and $R^2$ is halogen. In some embodiments is a compound of Formula (IV), or a pharmaceutically acceptable salt thereof, wherein n is 1 and $R^2$ is —$CH_3$. In some embodiments is a compound of Formula (IV), or a pharmaceutically acceptable salt thereof, wherein n is 1 and $R^2$ is —$CF_3$. In some embodiments is a compound of Formula (IV), or a pharmaceutically acceptable salt thereof, wherein n is 1 and $R^2$ is —$OCH_3$.

In some embodiments of the aforementioned embodiments, the compound of Formula (IV) is a single enantiomer having the structure:

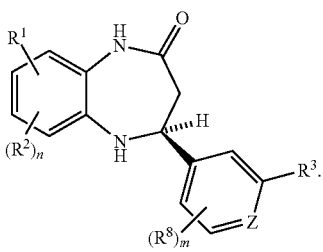

In some embodiments of the aforementioned embodiments, the compound of Formula (IV) is a single enantiomer having the structure:

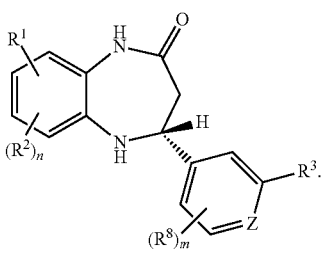

In some embodiments, the compound of Formula (IV) has the structure of Formula (IVa):

Formula (IVa)

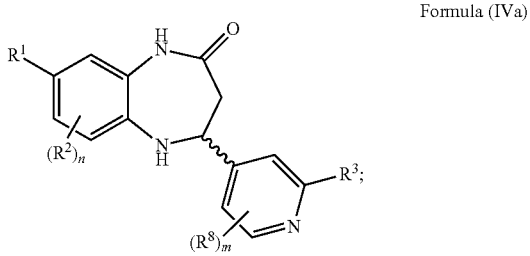

wherein $R^3$ is halogen, —CN, unsubstituted heteroaryl, or —X—$R^4$; and $R^4$ is substituted or unsubstituted aryl, or substituted or unsubstituted heteroaryl.

In some embodiments is a compound of Formula (IVa), or a pharmaceutically acceptable salt thereof, wherein m is 0. In some embodiments is a compound of Formula (IVa), or a pharmaceutically acceptable salt thereof, wherein m is 1 and $R^8$ is halogen.

In some embodiments is a compound of Formula (IVa), or a pharmaceutically acceptable salt thereof, wherein m is 0 and $R^3$ is halogen. In some embodiments is a compound of Formula (IVa), or a pharmaceutically acceptable salt thereof, wherein m is 0 and $R^3$ is —CN. In some embodiments is a compound of Formula (IVa), or a pharmaceutically acceptable salt thereof, wherein m is 0 and $R^3$ is unsubstituted heteroaryl. In some embodiments is a compound of Formula (IVa), or a pharmaceutically acceptable salt thereof, wherein m is 0 and $R^3$ is —X—$R^4$. In some embodiments is a compound of Formula (IVa), or a pharmaceutically acceptable salt thereof, wherein m is 0, $R^3$ is —X—$R^4$, X is —O—, and $R^4$ is substituted or unsubstituted aryl, or substituted or unsubstituted heteroaryl. In some embodiments is a compound of Formula (IVa), or a pharmaceutically acceptable salt thereof, wherein m is 0, $R^3$ is —X—$R^4$, X is —O—, and $R^4$ is substituted or unsubstituted phenyl. In some embodiments is a compound of Formula (IVa), or a pharmaceutically acceptable salt thereof, wherein m is 0, $R^3$ is —X—$R^4$, X is —O—, and $R^4$ is substituted or unsubstituted heteroaryl. In some embodiments is a compound of Formula (IVa), or a pharmaceutically acceptable salt thereof, wherein m is 0, $R^3$ is —X—$R^4$, X is —O—, and $R^4$ is unsubstituted pyridine. In some embodiments is a compound of Formula (IVa), or a pharmaceutically acceptable salt thereof, wherein m is 0, $R^3$ is —X—$R^4$, X is —O—, and $R^4$ is unsubstituted pyrimidine. In some embodiments is a compound of Formula (IVa), or a pharmaceutically acceptable salt thereof, wherein m is 0, $R^3$ is —X—$R^4$, X is —O—, and $R^4$ is unsubstituted pyrazine. In some embodiments is a compound of Formula (IVa), or a pharmaceutically acceptable salt thereof, wherein m is 0, $R^3$ is —X—$R^4$, X is —N(H)—, and $R^4$ is substituted or unsubstituted aryl, or substituted or unsubstituted heteroaryl. In some embodiments is a compound of Formula (IVa), or a pharmaceutically acceptable salt thereof, wherein m is 0, $R^3$ is —X—$R^4$, X is —N(H)—, and $R^4$ is substituted or unsubstituted phenyl. In some embodiments is a compound of Formula (IVa), or a pharmaceutically acceptable salt thereof, wherein m is 0, $R^3$ is —X—$R^4$, X is —N(H)—, and $R^4$ is substituted or unsubstituted heteroaryl. In some embodiments is a compound of Formula (IVa), or a pharmaceutically acceptable salt thereof, wherein m is 0, $R^3$ is —X—$R^4$, X is —N(H)—, and $R^4$ is unsubstituted pyridine. In some embodiments is a compound of Formula (IVa), or a pharmaceutically acceptable salt thereof, wherein m is 0, $R^3$ is —X—$R^4$, X is —N(H)—, and $R^4$ is unsubstituted pyrimidine. In some embodiments is a compound of Formula (IVa), or a pharmaceutically acceptable salt thereof, wherein m is 0, $R^3$ is —X—$R^4$, X is —N(H)—, and $R^4$ is unsubstituted pyrazine. In some embodiments is a compound of Formula (IVa), or a pharmaceutically acceptable salt thereof, wherein m is 0, $R^3$ is —X—$R^4$, X is —S—, and $R^4$ is substituted or unsubstituted aryl, or substituted or unsubstituted heteroaryl. In some embodiments is a compound of Formula (IVa), or a pharmaceutically acceptable salt thereof, wherein m is 0, $R^3$ is —X—$R^4$, X is —S—, and $R^4$ is substituted or unsubstituted phenyl. In some embodiments is a compound of Formula (IVa), or a pharmaceutically acceptable salt thereof, wherein m is 0, $R^3$ is —X—$R^4$, X is —S—, and $R^4$ is substituted or unsubstituted heteroaryl. In some embodiments is a compound of Formula (IVa), or a pharmaceutically acceptable salt thereof, wherein m is 0, $R^3$ is —X—$R^4$, X is —S—, and $R^4$ is unsubstituted pyridine. In some embodiments is a compound of Formula (IVa), or a pharmaceutically acceptable salt thereof, wherein m is 0, $R^3$ is —X—$R^4$, —S—, and $R^4$ is unsubstituted pyrimidine. In some embodiments is a compound of Formula (IVa), or a pharmaceutically acceptable salt thereof, wherein m is 0, $R^3$ is —X—$R^4$, X is —S—, and $R^4$ is unsubstituted pyrazine. In some embodiments is a compound of Formula (IVa), or a pharmaceutically acceptable salt thereof, wherein m is 0, $R^3$ is —X—$R^4$, X is —S(O)$_2$—, and $R^4$ is substituted or unsubstituted aryl, or substituted or unsubstituted heteroaryl. In some embodiments is a compound of Formula (IVa), or a pharmaceutically acceptable salt thereof, wherein m is 0, $R^3$ is —X—$R^4$, X is —S(O)$_2$—, and $R^4$ is substituted or unsubstituted phenyl. In some embodiments is a compound of Formula (IVa), or a pharmaceutically acceptable salt thereof, wherein m is 0, $R^3$ is —X—$R^4$, X is —S(O)$_2$—, and $R^4$ is substituted or unsubstituted heteroaryl. In some embodiments is a compound of Formula (IVa), or a pharmaceutically acceptable salt thereof, wherein m is 0, $R^3$ is —X—R⁴, X is —S(O)₂—, and R⁴ is unsubstituted pyridine. In some embodiments is a compound of Formula (IVa), or a pharmaceutically acceptable salt thereof, wherein m is 0, R³ is —X—R⁴, —S(O)₂—, and R⁴ is unsubstituted pyrimidine. In some embodiments is a compound of Formula (IVa), or a pharmaceutically acceptable salt thereof, wherein m is 0, R³ is —X—R⁴, X is —S(O)₂—, and R⁴ is unsubstituted pyrazine.

In some embodiments is a compound of Formula (IVa), or a pharmaceutically acceptable salt thereof, wherein R¹ is halogen, —OR⁵, substituted or unsubstituted C₁-C₆alkyl, or substituted or unsubstituted C₁-C₆fluoroalkyl. In some embodiments is a compound of Formula (IVa), or a pharmaceutically acceptable salt thereof, wherein R¹ is halogen, —CF₃, or —OCH₃. In some embodiments is a compound of Formula (IVa), or a pharmaceutically acceptable salt thereof, wherein R¹ is halogen. In some embodiments is a compound of Formula (IVa), or a pharmaceutically acceptable salt thereof, wherein R¹ is —CF₃. In some embodiments is a compound of Formula (IVa), or a pharmaceutically acceptable salt thereof, wherein R¹ is —OCH₃.

In some embodiments is a compound of Formula (IVa), or a pharmaceutically acceptable salt thereof, wherein n is 0. In some embodiments is a compound of Formula (IVa), or a pharmaceutically acceptable salt thereof, wherein n is 1. In some embodiments is a compound of Formula (IVa), or a pharmaceutically acceptable salt thereof, wherein n is 1 and R² is halogen, —OR⁵, substituted or unsubstituted C₁-C₆alkyl, substituted or unsubstituted C₁-C₆fluoroalkyl. In some embodiments is a compound of Formula (IVa), or a pharmaceutically acceptable salt thereof, wherein n is 1 and R² is halogen, —CH₃, —CF₃, or —OCH₃. In some embodiments is a compound of Formula (IVa), or a pharmaceutically acceptable salt thereof, wherein n is 1 and R² is halogen. In some embodiments is a compound of Formula (IVa), or a pharmaceutically acceptable salt thereof, wherein n is 1 and R² is —CH₃. In some embodiments is a compound of Formula (IVa), or a pharmaceutically acceptable salt thereof, wherein n is 1 and R² is —CF₃. In some embodiments is a compound of Formula (IVa), or a pharmaceutically acceptable salt thereof, wherein n is 1 and R² is —OCH₃.

In some embodiments of the aforementioned embodiments, the compound of Formula (IVa) is a single enantiomer having the structure:

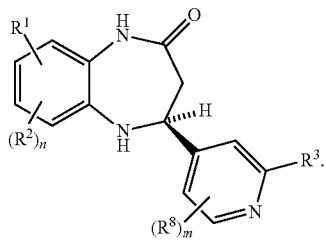

In some embodiments of the aforementioned embodiments, the compound of Formula (IVa) is a single enantiomer having the structure:

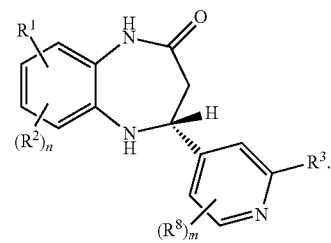

In some embodiments, the compound of Formula (IV) has the structure of Formula (IVb):

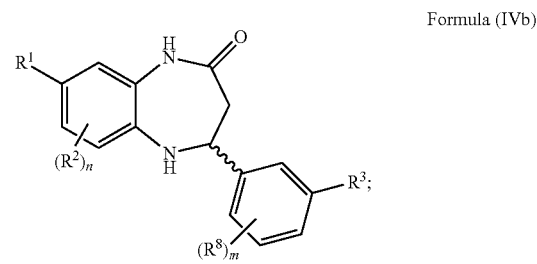

Formula (IVb)

wherein R³ is —CN, substituted or unsubstituted heteroaryl, or —X—R⁴; and R⁴ is substituted or unsubstituted C₁-C₆alkyl, substituted or unsubstituted aryl, or unsubstituted heteroaryl.

In some embodiments is a compound of Formula (IVb), or a pharmaceutically acceptable salt thereof, wherein m is 0. In some embodiments is a compound of Formula (IVb), or a pharmaceutically acceptable salt thereof, wherein m is 1 and R⁸ is halogen.

In some embodiments is a compound of Formula (IVb), or a pharmaceutically acceptable salt thereof, wherein m is 0 and R³ is —CN. In some embodiments is a compound of Formula (IVb), or a pharmaceutically acceptable salt thereof, wherein m is 0 and R³ is unsubstituted heteroaryl. In some embodiments is a compound of Formula (IVb), or a pharmaceutically acceptable salt thereof, wherein m is 0 and R³ is —X—R⁴. In some embodiments is a compound of Formula (IVb), or a pharmaceutically acceptable salt thereof, wherein m is 0, R³ is —X—R⁴, X is —O—, and R⁴ is substituted or unsubstituted aryl, or substituted or unsubstituted heteroaryl. In some embodiments is a compound of Formula (IVb), or a pharmaceutically acceptable salt thereof, wherein m is 0, R³ is —X—R⁴, X is —O—, and R⁴ is substituted or unsubstituted phenyl. In some embodiments is a compound of Formula (IVb), or a pharmaceutically acceptable salt thereof, wherein m is 0, R³ is —X—R⁴, X is —O—, and R⁴ is substituted or unsubstituted heteroaryl. In some embodiments is a compound of Formula (IVb), or a pharmaceutically acceptable salt thereof, wherein m is 0, R³ is —X—R⁴, X is —O—, and R⁴ is unsubstituted pyridine. In some embodiments is a compound of Formula (IVb), or a pharmaceutically acceptable salt thereof, wherein m is 0, R³ is —X—R⁴, X is —O—, and R⁴ is unsubstituted pyrimidine. In some embodiments is a compound of Formula (IVb), or a pharmaceutically acceptable salt thereof, wherein m is 0, R³ is —X—R⁴, X is —O—, and R⁴ is unsubstituted pyrazine. In some embodiments is a compound of Formula (IVb), or a pharmaceutically acceptable salt thereof, wherein m is 0, R³ is —X—R⁴, X is —N(H)—, and R⁴ is substituted or unsubstituted aryl, or substituted or unsubstituted heteroaryl. In some embodiments is a compound of Formula (IVb), or a pharmaceutically acceptable salt thereof, wherein m is 0, R³ is —X—R⁴, X is —N(H)—, and R⁴ is substituted or unsubstituted phenyl. In some embodiments is a compound of Formula (IVb), or a pharmaceutically acceptable salt thereof, wherein m is 0, R³ is —X—R⁴, X is —N(H)—, and R⁴ is substituted or unsubstituted heteroaryl. In some embodiments is a compound of Formula (IVb), or a pharmaceutically acceptable salt thereof, wherein m is 0, R³ is —X—R⁴, X is —N(H)—, and R⁴ is unsubstituted pyridine. In some embodiments is a compound of Formula (IVb), or a pharmaceutically acceptable salt thereof, wherein m is 0, R³ is —X—R⁴, X is —N(H)—, and R⁴ is unsubstituted pyrimidine. In some embodiments is a compound of Formula (IVb), or a pharmaceutically acceptable salt thereof, wherein m is 0, R³ is —X—R⁴, X is —N(H)—, and R⁴ is unsubstituted pyrazine. In some embodiments is a compound of Formula (IVb), or a pharmaceutically acceptable salt thereof, wherein m is 0, R³ is —X—R⁴, X is —S—, and R⁴ is substituted or unsubstituted aryl, or substituted or unsubstituted heteroaryl. In some embodiments is a compound of Formula (IVb), or a pharmaceutically acceptable salt thereof, wherein m is 0, R³ is —X—R⁴, X is —S—, and R⁴ is substituted or unsubstituted phenyl. In some embodiments is a compound of Formula (IVb), or a pharmaceutically acceptable salt thereof, wherein m is 0, R³ is —X—R⁴, X is —S—, and R⁴ is substituted or unsubstituted heteroaryl. In some embodiments is a compound of Formula (IVb), or a pharmaceutically acceptable salt thereof, wherein m is 0, R³ is —X—R⁴, X is —S—, and R⁴ is unsubstituted pyridine. In some embodiments is a compound of Formula (IVb), or a pharmaceutically acceptable salt thereof, wherein m is 0, R³ is —X—R⁴, —S—, and R⁴ is unsubstituted pyrimidine. In some embodiments is a compound of Formula (IVb), or a pharmaceutically acceptable salt thereof, wherein m is 0, R³ is —X—R⁴, X is —S—, and R⁴ is unsubstituted pyrazine. In some embodiments is a compound of Formula (IVb), or a pharmaceutically acceptable salt thereof, wherein m is 0, R³ is —X—R⁴, X is —S(O)₂—, and R⁴ is substituted or unsubstituted aryl, or substituted or unsubstituted heteroaryl. In some embodiments is a compound of Formula (IVb), or a pharmaceutically acceptable salt thereof, wherein m is 0, R³ is —X—R⁴, X is —S(O)₂—, and R⁴ is substituted or unsubstituted phenyl. In some embodiments is a compound of Formula (IVb), or a pharmaceutically acceptable salt thereof, wherein m is 0, R³ is —X—R⁴, X is —S(O)₂—, and R⁴ is substituted or unsubstituted heteroaryl. In some embodiments is a compound of Formula (IVb), or a pharmaceutically acceptable salt thereof, wherein m is 0, R³ is —X—R⁴, X is —S(O)₂—, and R⁴ is unsubstituted pyridine. In some embodiments is a compound of Formula (IVb), or a pharmaceutically acceptable salt thereof, wherein m is 0, R³ is —X—R⁴, —S(O)₂—, and R⁴ is unsubstituted pyrimidine. In some embodiments is a compound of Formula (IVb), or a pharmaceutically acceptable salt thereof, wherein m is 0, R³ is —X—R⁴, X is —S(O)₂—, and R⁴ is unsubstituted pyrazine. In some embodiments is a compound of Formula (IVb), or a pharmaceutically acceptable salt thereof, wherein m is 0, R³ is —X—R⁴, X is —C≡C—, and R⁴ is substituted or unsubstituted $C_1$-$C_6$alkyl.

In some embodiments is a compound of Formula (IVb), or a pharmaceutically acceptable salt thereof, wherein R¹ is halogen, —OR⁵, substituted or unsubstituted $C_1$-$C_6$alkyl, or substituted or unsubstituted $C_1$-$C_6$fluoroalkyl. In some embodiments is a compound of Formula (IVb), or a pharmaceutically acceptable salt thereof, wherein R¹ is halogen, —CF₃, or —OCH₃. In some embodiments is a compound of Formula (IVb), or a pharmaceutically acceptable salt thereof, wherein R¹ is halogen. In some embodiments is a compound of Formula (IVb), or a pharmaceutically acceptable salt thereof, wherein R¹ is —CF₃. In some embodiments is a compound of Formula (IVb), or a pharmaceutically acceptable salt thereof, wherein R¹ is —OCH₃.

In some embodiments is a compound of Formula (IVb), or a pharmaceutically acceptable salt thereof, wherein n is 0. In some embodiments is a compound of Formula (IVb), or a pharmaceutically acceptable salt thereof, wherein n is 1. In some embodiments is a compound of Formula (IVb), or a pharmaceutically acceptable salt thereof, wherein n is 1 and R² is halogen, —OR⁵, substituted or unsubstituted $C_1$-$C_6$alkyl, substituted or unsubstituted $C_1$-$C_6$fluoroalkyl. In some embodiments is a compound of Formula (IVb), or a pharmaceutically acceptable salt thereof, wherein n is 1 and R² is halogen, —CH₃, —CF₃, or —OCH₃. In some embodiments is a compound of Formula (IVb), or a pharmaceutically acceptable salt thereof, wherein n is 1 and R² is halogen. In some embodiments is a compound of Formula (IVb), or a pharmaceutically acceptable salt thereof, wherein n is 1 and R² is —CH₃. In some embodiments is a compound of Formula (IVb), or a pharmaceutically acceptable salt thereof, wherein n is 1 and R² is —CF₃. In some embodiments is a compound of Formula (IVb), or a pharmaceutically acceptable salt thereof, wherein n is 1 and R² is —OCH₃.

In some embodiments of the aforementioned embodiments, the compound of Formula (IVb) is a single enantiomer having the structure:

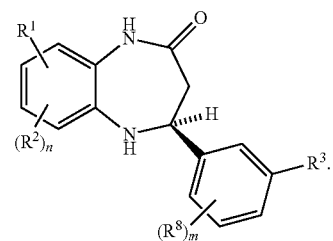

In some embodiments of the aforementioned embodiments, the compound of Formula (IVb) is a single enantiomer having the structure:

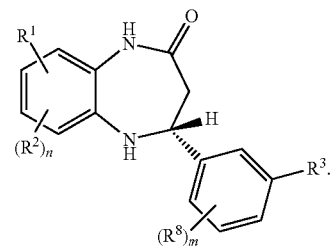

Further Forms of Compounds

In one aspect, the compound of Formula (I), (Ia), (Ib), (Ic), (II), (IIa), (IIb), (IIc), (III), (IIIa), (IIIb), (IV), (IVa), or (IVb), possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design of prodrugs of the compound is possible. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Rooseboom et al., *Pharmacological Reviews*, 56:53-102, 2004; Aesop Cho, "Recent Advances in Oral Prodrug Discovery", *Annual Reports in Medicinal Chemistry*, Vol. 41, 395-407, 2006; T. Higuchi and V. Stella, *Pro-drugs as Novel Delivery Systems*, Vol. 14 of the A.C.S. Symposium Series).

In some cases, some of the herein-described compounds may be a prodrug for another derivative or active compound.

In some embodiments, sites on the aromatic ring portion of compounds described herein are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I), (Ia), (Ib), (Ic), (II), (IIa), (IIb), (IIc), (III), (IIIa), (IIIb), (IV), (IVa), or (IVb) with acids. Pharmaceutically acceptable salts are also obtained by reacting a compound of Formula (I), (Ia), (Ib), (Ic), (II), (IIa), (IIb), (IIc), (III), (IIIa), (IIIb), (IV), (IVa), or (IVb) with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, Fisher Scientific (Fisher Chemicals), and Acros Organics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

In one aspect, compounds are synthesized as described in the Examples section.

In some embodiments, compounds described herein may be synthesized via the following general reaction procedures.

As shown in Scheme A, in some embodiments, β-ketoesters of general structure A-2 (7-methyl-4-(3-phenoxyphenyl)-8-(trifluoromethyl)-1H-benzo[b][1,4]diazepin-2(3H)-one) are prepared from the appropriately substituted benzoate (ethyl or methyl ester) A-1 (4-(3-benzylphenyl)-7-methyl-8-(trifluoromethyl)-1H-benzo[b][1,4]diazepin-2(3H)-one) [see Woltering et al *Bioorg Med Chem Letts.*, 2008, 18:1091-1095 (and references cited therein)]. Thus, treatment of ethyl acetate (or a similar ester e.g. the tert-butyl ester) with a strong base such as LDA at low temperature in an organic solvent such as THF affords the corresponding anion which, upon condensation with A-1, yields the β-ketoester A-2. The β-ketoester is then transformed into the dioxin-4-one A-3 by reaction with TFAA/TFA in acetone. In a similar fashion, starting with the appropriate heterocycle-ester, the β-ketoesters of structure A-4 are prepared. The substituent 'R$_1$' on the aryl or heteroaryl ring is transformed using standard chemical procedures to afford alternative compounds of structure A-2 and A-3.

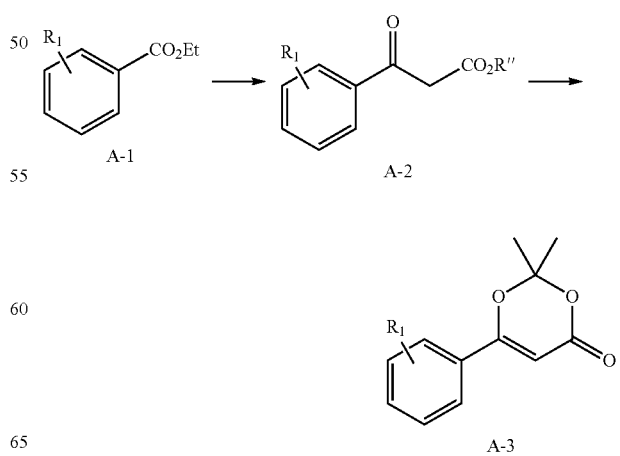

Scheme A

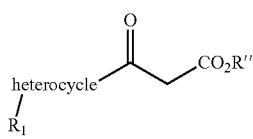

A-4

In some embodiments, the diamine B-1 is reacted with B-2 in the presence of an organic base such as Et$_3$N in a non-polar solvent such as toluene followed by heating to afford the amides B-2 (see Scheme B). Alternatively, B-1 is reacted with A-3 or A-4 to afford B-2. The amides B-2, are cyclized by heating in a high boiling solvent such as xylene to provide the benzodiazepine B-3 and regioisomer B-4 as a separable mixture. Alternatively, the diamine 2-1 is treated with A-2 in the presence of acetic acid at reflux to generate B-3 and B-4 directly as a separable mixture. The substituent 'R$_1$' on the aryl ring or the substituents 'R$_2$' or 'R$_3$' on the benzodiazepine ring is transformed using standard chemical procedures to afford alternative compounds of structure 2-3 and 2-4. Such transformations involve, for example, (a) reduction e.g. in the case of R$_1$ or R$_2$ or R$_3$=nitro group to afford an aniline which is then further modified; (b) Pd-mediated cross coupling reactions where R$_1$ or R$_2$ or R$_3$=Br or I; (c) "click-chemistry" where R$_1$ or R$_2$ or R$_3$ contains an acetylene; and the like.

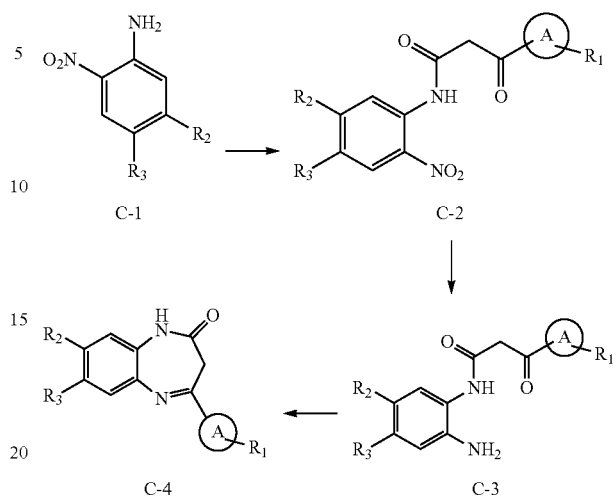

Scheme C

In some embodiments, the regioisomeric substituted nitroanilines of general structure D-1 (Scheme D) are used as starting materials for C-4. Compound D-1 is treated under standard conditions with Boc anyhdride to yield the Boc-

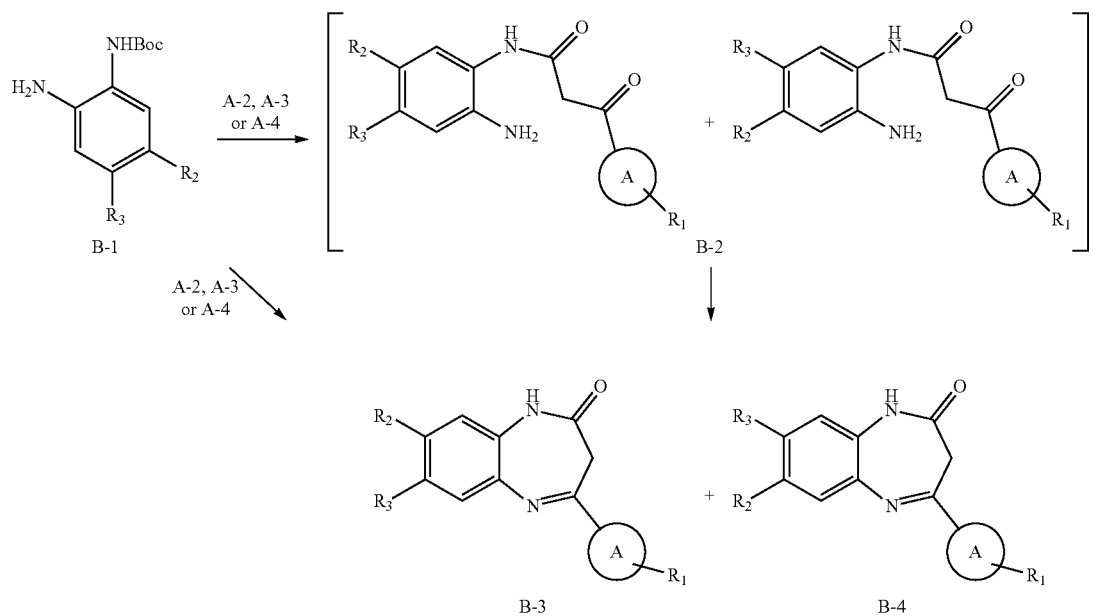

Scheme B

In some embodiments, specifically substituted benzodiazepine cores are introduced by using substituted nitroanilines of general structure C-1 (see Scheme C). Thus, the nitroaniline C-1 may be transformed to C-2 as described above. Reduction of the nitro group using standard procedures then generates the aniline C-3 which can be cyclized as described for Scheme 2 to generate the desired benzodiazepine C-4.

protected aniline D-2. Reduction of the nitro group as described above then yields D-3. Transformation of D-3 to D-4 as described above is then followed by deprotection of the Boc group using acidic conditions to afford C-3. The R$_2$ and R$_3$ substituents of D-2, D-3, D-4 and C-3 are further modified using standard chemical reactions as described in Woltering et al *Bioorg Med Chem Letts.*, 2007, 17, p 6811-6815.

Scheme D

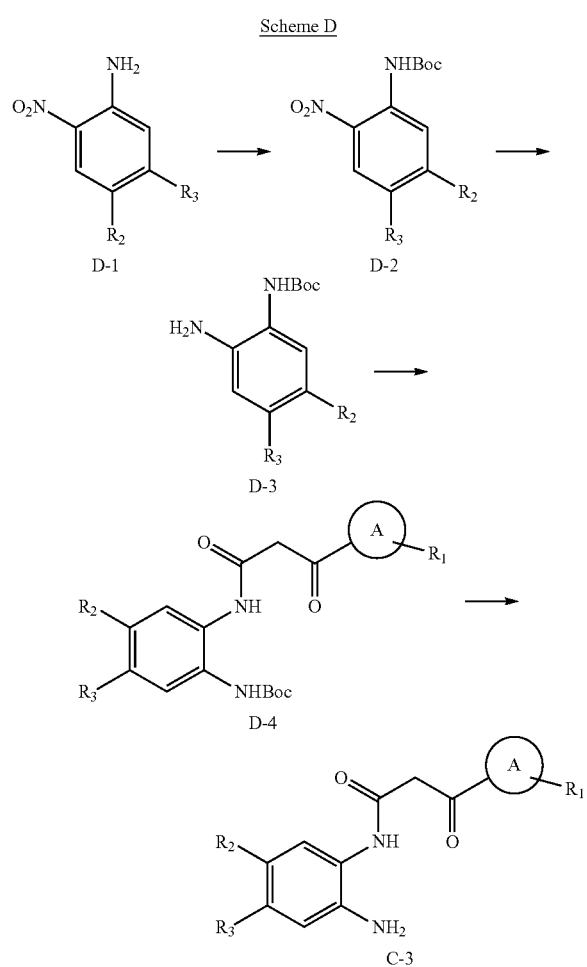

In some embodiments, hydrogenation of the N=C double bond of the benzodiazepine E-1 (Scheme E) is achieved by reduction of E-1 in the presence of hydrogen and a catalyst such as 10% Pd on carbon in an organic solvent such as ethanol. The reduction may also be carried out using borohydride based reductants such as $NaBH_4$ or $NaBH_3CN$ in protic solvents such as ethanol. Alternatively, reductants such as $HSiCl_3$ are employed in the presence of an organic Lewis Base in an organic solvent such as dichloromethane. When a chiral Lewis Base is used as a catalyst, the reduction may proceed in enantioselective fashion to generate predominantly one enantiomer (Chen et al., *J. Org. Chem.*, 2011, 76, p 9109-9115). Similarly, enantioselective reduction of E-1 may be achieved using an asymmetric hydrogenation promoted by a chiral Lewis Acid catalyst and a dihydropyridine (Rueping et al., *Adv. Synth. Catal.*, 2010, 352, p 2629-2634). In the presence of an acylating agent such as AcCl and pyridine, the reaction affords N-acylated derivatives such as E-3. The amine function of E-2 may also undergo a reductive amination reaction using standard procedures to generate E-3 in which the amine is alkylated.

Scheme E

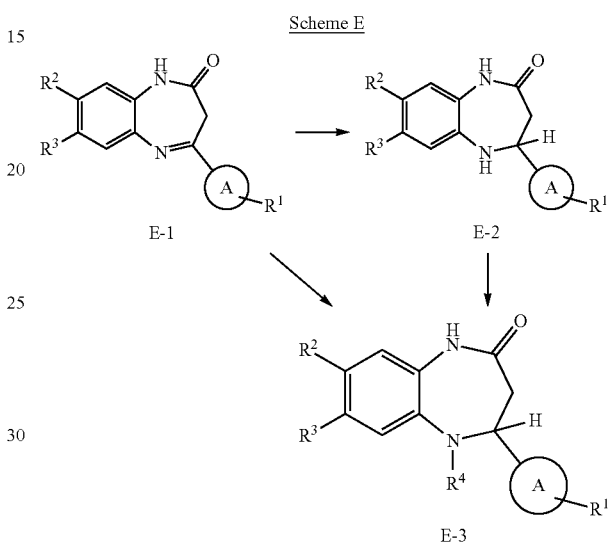

In some embodiments, dihydrobenzodiazepine compounds are prepared as shown in Scheme F (see Lee et al., *J. Org. Chem.*, 1999, 64, 3060-3065 and Zhao et al., *J. Comb. Chem.*, 2007, 9, 1164-1176). The fluoro-nitro benzoyl derivative F-1 is coupled with a β-amino acid ester F-2 to generate F-3. Reduction of the nitro group followed by ester hydrolysis and intramolecular amide bond formation then affords F-4. The benzoyl group X of F-4 is further modified using standard procedures. Further derivatization of the amine coupled with transformation of the benzoyl group X then affords targets compounds of general structure F-5.

Scheme F

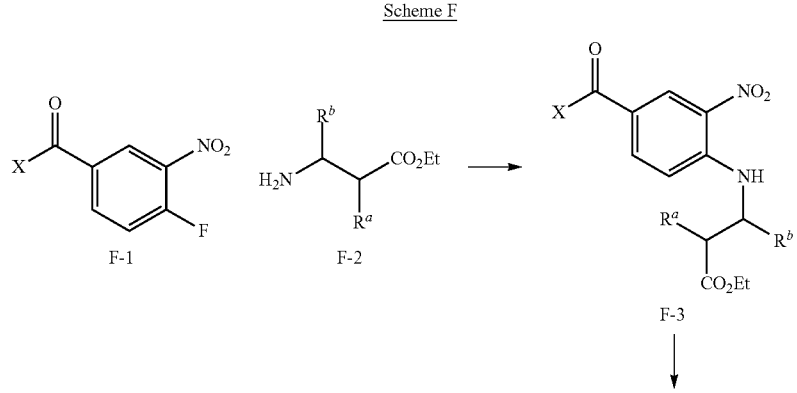

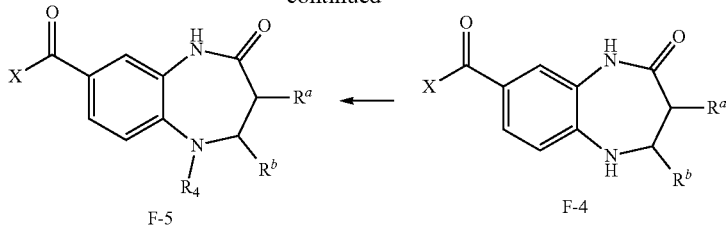

F-5          F-4

In some embodiments, dihydrobenzodiazepines of general structure G-3 are prepared according to the reaction sequence shown in Scheme G (see Wang et al., *Synlett*, 2005, 20, 3042-3046). Thus reaction of a diamine such as G-1 with N-cinnamoylbenzotriazoles G-2 via a 1,4-addition followed by ring-closure then affords the desired compounds of general structure G-3.

Scheme G

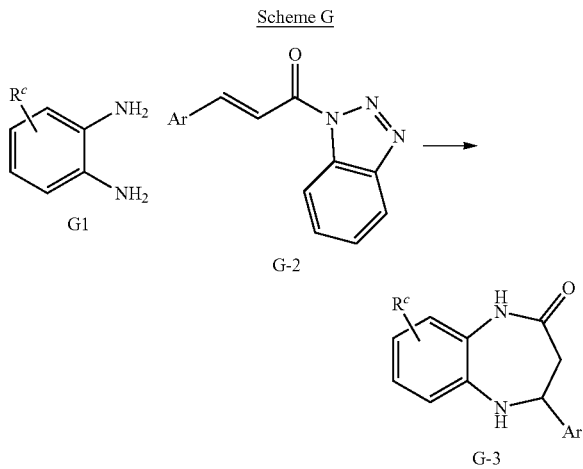

Racemic mixtures of dihydrobenzodiazepines may be resolved to provide enantiomers substantially free of the opposite enantiomer using methods well known in the art. For example, the racemates may be separated using chiral phase HPLC or, alternatively, they may be separated by formation of diastereomeric salts by crystallization in the presence of a chiral acid or base.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Oxo" refers to the =O substituent.

"Thioxo" refers to the =S substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. In some embodiments, the alkyl is —CH(CH$_3$)$_2$ or —C(CH$_3$)$_3$. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —OCH$_2$OMe, —OCH$_2$CH$_2$OMe, or —OCH$_2$CH$_2$OCH$_2$CH$_2$NH$_2$. Representative heteroalkylene groups include, but are not limited to —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthalenyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

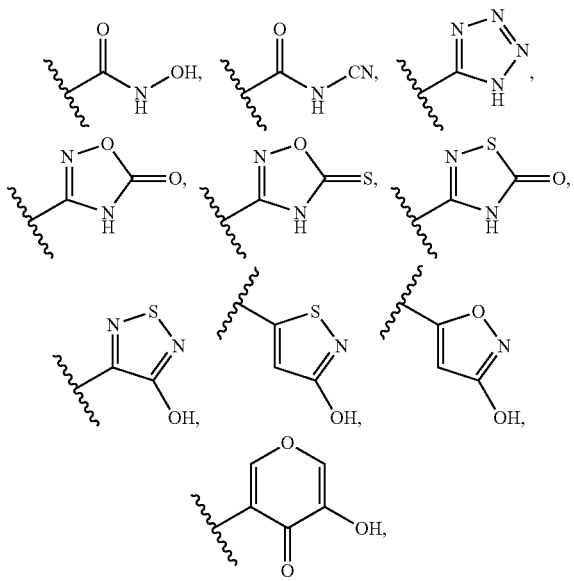

and the like.

"Cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cyclcoalkyl radicals include, for example, cyclopropyl, cyclobutyl, cyclopentyl, cyclohexyl, cycloheptyl, and cyclooctyl. In some embodiments, the monocyclic cyclcoalkyl is cyclopropyl, cyclobutyl, cyclopentyl or cyclohexyl. In some embodiments, the monocyclic cyclcoalkyl is cyclopentyl. Polycyclic radicals include, for example, adamantyl, norbornyl, decalinyl, and 3,4-dihydronaphthalen-1 (2H)-one. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 13 carbon atoms and from one to 6 heteroatoms selected from the group consisting of nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, a bicyclic heteroaryl is a $C_6$-$C_9$heteroaryl.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —$CO_2$H, —$CO_2$alkyl, nitro, and amino, including mono- and di-substituted amino groups (e.g. —$NH_2$, —NHR, —N(R)$_2$), and the protected derivatives thereof. In some embodiments, optional substituents are independently selected from alkyl, alkoxy, haloalkyl, cycloalkyl, halogen, —CN, —$NH_2$, —NH($CH_3$), —N($CH_3$)$_2$, —OH, —$CO_2$H, and —$CO_2$alkyl. In some embodiments, optional substituents are independently selected from fluoro, chloro, bromo, iodo, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), (Ia), (Ib), (Ic), (II), (IIa), (IIb), (IIc), (III), (IIIa), (IIIb), (IV), (IVa), or (IVb) and a co-agent, are both administered to a patient simultaneously in the form of a single entity or dosage. The term "non-fixed combination" means that the active ingredients, e.g. a compound of Formula (I), (Ia), (Ib), (Ic), (II), (IIa), (IIb), (IIc), (III), (IIIa), (IIIb), (IV), (IVa), or (IVb) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

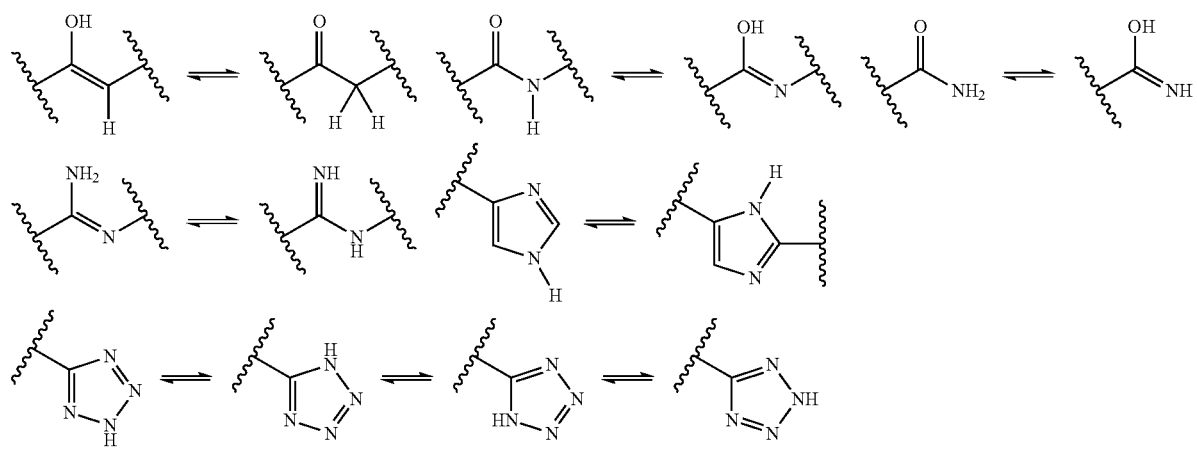

Administration and Pharmaceutical Composition

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I), (Ia), (Ib), (Ic), (II), (IIa), (IIb), (IIc), (III), (IIIa), (IIIb), (IV), (IVa), or (IVb) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds of Formula (I), (Ia), (Ib), (Ic), (II), (IIa), (IIb), (IIc), (III), (IIIa), (IIIb), (IV), (IVa), or (IVb) are administered orally.

In some embodiments, the compounds of Formula (I), (Ia), (Ib), (Ic), (II), (IIa), (IIb), (IIc), (III), (IIIa), (IIIb), (IV), (IVa), or (IVb) are administered topically. In such embodiments, the compound of Formula (I), (Ia), (Ib), (Ic), (II), (IIa), (IIb), (IIc), (III), (IIIa), (IIIb), (IV), (IVa), or (IVb) is formulated into a variety of topically administrable compositions, such as solutions, suspensions, lotions, gels, pastes, shampoos, scrubs, rubs, smears, medicated sticks, medicated bandages, balms, creams or ointments. In one aspect, the compounds of Formula (I) are administered topically to the skin.

In another aspect, the compounds of Formula (I), (Ia), (Ib), (Ic), (II), (IIa), (IIb), (IIc), (III), (IIIa), (IIIb), (IV), (IVa), or (IVb) are administered by inhalation.

In another aspect, the compounds of Formula (I), (Ia), (Ib), (Ic), (II), (IIa), (IIb), (IIc), (III), (IIIa), (IIIb), (IV), (IVa), or (IVb) are formulated for intranasal administration. Such formulations include nasal sprays, nasal mists, and the like.

In another aspect, the compounds of Formula (I), (Ia), (Ib), (Ic), (II), (IIa), (IIb), (IIc), (III), (IIIa), (IIIb), (IV), (IVa), or (IVb) are formulated as eye drops.

In any of the aforementioned aspects are further embodiments in which the effective amount of the compound of Formula (I), (Ia), (Ib), (Ic), (II), (IIa), (IIb), (IIc), (III), (IIIa), (IIIb), (IV), (IVa), or (IVb) is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound of Formula (I), (Ia), (Ib), (Ic), (II), (IIa), (IIb), (IIc), (III), (IIIa), (IIIb), (IV), (IVa), or (IVb), including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound of Formula (I), (Ia), (Ib), (Ic), (II), (IIa), (IIb), (IIc), (III), (IIIa), (IIIb), (IV), (IVa), or (IVb), including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound of Formula (I), (Ia), (Ib), (Ic), (II), (IIa), (IIb), (IIc), (III), (IIIa), (IIIb), (IV), (IVa), or (IVb) is temporarily suspended or the dose of the compound being administered is temporarily reduced; at the end of the drug holiday, dosing of the compound is resumed. In one embodiment, the length of the drug holiday varies from 2 days to 1 year.

In certain embodiments, the compound of Formula (I), (Ia), (Ib), (Ic), (II), (IIa), (IIb), (IIc), (III), (IIIa), (IIIb), (IV), (IVa), or (IVb) is administered in a local rather than systemic manner.

In some embodiments, the compound of Formula (I), (Ia), (Ib), (Ic), (II), (IIa), (IIb), (IIc), (III), (IIIa), (IIIb), (IV), (IVa), or (IVb) is administered topically. In some embodiments, the compound of Formula (I), (Ia), (Ib), (Ic), (II), (IIa), (IIb), (IIc), (III), (IIIa), (IIIb), (IV), (IVa), or (IVb) is administered systemically.

In some embodiments, the pharmaceutical formulation is in the form of a tablet. In other embodiments, pharmaceutical formulations of the compounds of Formula (I), (Ia), (Ib), (Ic), (II), (IIa), (IIb), (IIc), (III), (IIIa), (IIIb), (IV), (IVa), or (IVb) are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound of Formula (I), (Ia), (Ib), (Ic), (II), (IIa), (IIb), (IIc), (III), (IIIa), (IIIb), (IV), (IVa), or (IVb) is formulated for use as an aerosol, a mist or a powder.

For buccal or sublingual administration, the compositions may take the form of tablets, lozenges, or gels formulated in a conventional manner.

In some embodiments, compounds of Formula (I), (Ia), (Ib), (Ic), (II), (IIa), (IIb), (IIc), (III), (IIIa), (IIIb), (IV), (IVa), or (IVb) are prepared as transdermal dosage forms.

In one aspect, a compound of Formula (I), (Ia), (Ib), (Ic), (II), (IIa), (IIb), (IIc), (III), (IIIa), (IIIb), (IV), (IVa), or (IVb) is formulated into a pharmaceutical composition suitable for intramuscular, subcutaneous, or intravenous injection.

In some embodiments, the compound of Formula (I), (Ia), (Ib), (Ic), (II), (IIa), (IIb), (IIc), (III), (IIIa), (IIIb), (IV), (IVa), or (IVb) is be administered topically and can be formulated into a variety of topically administrable compositions, such as solutions, suspensions, lotions, gels, pastes, medicated sticks, balms, creams or ointments.

In some embodiments, the compounds of Formula (I), (Ia), (Ib), (Ic), (II), (IIa), (IIb), (IIc), (III), (IIIa), (IIIb), (IV), (IVa), or (IVb) are formulated in rectal compositions such as enemas, rectal gels, rectal foams, rectal aerosols, suppositories, jelly suppositories, or retention enemas.

Methods of Dosing and Treatment Regimens

In one embodiment, the compounds of Formula (I), (Ia), (Ib), (Ic), (II), (IIa), (IIb), (IIc), (III), (IIIa), (IIIb), (IV), (IVa), or (IVb) are used in the preparation of medicaments for the treatment of diseases or conditions described herein. In addition, a method for treating any of the diseases or conditions described herein in a subject in need of such treatment, involves administration of pharmaceutical compositions that include at least one compound of Formula (I), (Ia), (Ib), (Ic), (II), (IIa), (IIb), (IIc), (III), (IIIa), (IIIb), (IV), (IVa), or (IVb) or a pharmaceutically acceptable salt, active metabolite, prodrug, or solvate thereof, in therapeutically effective amounts to said subject.

In certain embodiments, the compositions containing the compounds of Formula (I), (Ia), (Ib), (Ic), (II), (IIa), (IIb), (IIc), (III), (IIIa), (IIIb), (IV), (IVa), or (IVb) are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds of Formula (I), (Ia), (Ib), (Ic), (II), (IIa), (IIb), (IIc), (III), (IIIa), (IIIb), (IV), (IVa), or (IVb) are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

Combination Treatments

In certain instances, it is appropriate to administer at least one compound of Formula (I), (Ia), (Ib), (Ic), (II), (IIa), (IIb), (IIc), (III), (IIIa), (IIIb), (IV), (IVa), or (IVb) in combination with another therapeutic agent.

In one specific embodiment, a compound of Formula (I), (Ia), (Ib), (Ic), (II), (IIa), (IIb), (IIc), (III), (IIIa), (IIIb), (IV), (IVa), or (IVb) is co-administered with a second therapeutic agent, wherein the compound of Formula (I), (Ia), (Ib), (Ic), (II), (IIa), (IIb), (IIc), (III), (IIIa), (IIIb), (IV), (IVa), or (IVb) and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

In some embodiments, compounds of Formula (I), (Ia), (Ib), (Ic), (II), (IIa), (IIb), (IIc), (III), (IIIa), (IIIb), (IV), (IVa), or (IVb) are administered to a mammal in combination with one or more additional neurodegenerative disease or disorder therapeutic agent. In some embodiments, the neurodegenerative disease or disorder is Alzheimer's disease, Parkinson's disease, Huntington's disease, or Lou Gehrig's Disease (Amyotrophic Lateral Sclerosis or ALS). In some embodiments, compounds of Formula (I), (Ia), (Ib), (Ic), (II), (IIa), (IIb), (IIc), (III), (IIIa), (IIIb), (IV), (IVa), or (IVb) are administered to a mammal in combination with one or more additional therapeutic agent that alleviate the symptoms or side effects of a neurodegenerative disease or disorder. In some embodiments the symptoms or side effects a neurodegenerative disease or disorder are dementia, memory loss, dyskinesias, cognitive impairment, tremors, rigidity, slowness of movement, postural instability, involuntary jerking or writhing movements (chorea), slow or abnormal eye movements, difficulty with the physical production of speech or swallowing, psychiatric disorders, muscle cramps and spasms, spasticity, constipation, fatigue, excessive salivation, excessive phlegm, pain, sleep problems, uncontrolled outbursts of laughing or crying.

In some embodiments, the additional therapeutic agent is an Alzheimer's disease therapeutic agent. In some embodiments, the additional therapeutic agent is a cholinesterase inhibitor. In some embodiments, the cholinesterase inhibitor is donepezil, galantamine, or rivastigmine. In some embodiments, the additional therapeutic agent is memantine. In some embodiments, the additional therapeutic agent is latrepirdine, idalopridine, or cerlapirdine.

In some embodiments, the additional therapeutic agent is a Parkinson's disease therapeutic agent. In some embodiments, the additional therapeutic agent is levodopa. In some embodiments, the additional therapeutic agent is carbidopa-levodopa. In some embodiments, the additional therapeutic agent is a Dopamine agonist. In some embodiments, the dopamine agonist is ropinirole, pramipexole, or rotigotine. In some embodiments, the additional therapeutic agent is a MAO-B inhibitor. In some embodiments, the MAO-B inhibitor is selegiline or rasagiline. In some embodiments, the additional therapeutic agent is a catechol O-methyltransferase (COMT) inhibitor. In some embodiments, the COMT inhibitor is entacapone or tolcapone. In some embodiments, the additional therapeutic agent is an Anticholinergic. In some embodiments, the anticholinergic is benztropine or trihexyphenidyl. In some embodiments, the additional therapeutic agent is amantadine.

In some embodiments, compounds of Formula (I), (Ia), (Ib), (Ic), (II), (IIa), (IIb), (IIc), (III), (IIIa), (IIIb), (IV), (IVa), or (IVb) are administered to a mammal in combination with deep brain stimulation.

In some embodiments, the additional therapeutic agent is a Huntington's disease therapeutic agent. In some embodiments, the additional therapeutic agent is tetrabenazine. In some embodiments, the additional therapeutic agent is an antipsychotic drug. In some embodiments, the antipsychotic drug is haloperidol, chlorpromazine, risperidone, olanzapine or quetiapine. In some embodiments, the additional therapeutic agent is amantadine, levetiracetam, or clonazepam. In some embodiments, the additional therapeutic agent is an antidepressant. In some embodiments, the antidepressant is citalopram, fluoxetine, or sertraline. In some embodiments, the additional therapeutic agent is a mood-stabilizing drug. In some embodiments, the mood-stabilizing drug is valproate, carbamazepine, or lamotrigine.

In some embodiments, compounds of Formula (I), (Ia), (Ib), (Ic), (II), (IIa), (IIb), (IIc), (III), (IIIa), (IIIb), (IV), (IVa), or (IVb) are administered to a mammal in combination with psychotherapy, speech therapy, physical therapy or occupational therapy.

In some embodiments, the additional therapeutic agent is a Lou Gehrig's Disease (Amyotrophic Lateral Sclerosis or ALS) therapeutic agent. In some embodiments, the additional therapeutic agent is riluzole. In some embodiments, the additional therapeutic agent is baclofen, diazepam, trihexyphenidyl or amitriptyline.

In some embodiments, compounds of Formula (I), (Ia), (Ib), (Ic), (II), (IIa), (IIb), (IIc), (III), (IIIa), (IIIb), (IV), (IVa), or (IVb) are administered to a mammal in combination with one or more additional neuropsychiatric disease or disorder therapeutic agent. In some embodiments, the neuropsychiatric disease or disorder is schizophrenia, anxiety, sleep disorder, eating disorder, psychosis, or addictions.

In some embodiments, the additional therapeutic agent is an antipsychotic. In some embodiments, the antipsychotic is aripiprazole, asenapine, clozapine, iloperidone, lurasidone, olanzapine, paliperidone, quetiapine, risperidone, ziprasidone, chlorpromazine, fluphenazine, haloperidol, or perphenazine. In some embodiments, the additional therapeutic agent is an antidepressant. In some embodiments, the antidepressant is a selective serotonin reuptake inhibitor (SSRI) or a serotonin norepinephrine reuptake inhibitor (SNRI). In some embodiments, the antidepressant is escitalopram, duloxetine, venlafaxine, or paroxetine. In some embodiments, the additional therapeutic agent is an anti-anxiety medication. In some embodiments, the anti-anxiety medication is buspirone. In some embodiments, the additional therapeutic agent is a benzodiazepine. In some embodiments the benzodiazepine is alprazolam, chlordiazepoxide, diazepam, or lorazepam.

In some embodiments, the additional therapeutic agent is a medication used to treat dependence. In some embodiments, the medication used to treat dependence is subozone, methadone, naloxone, or acamprosate.

In some embodiments, the additional therapeutic agent is a medication used to treat cancer. In some embodiments, compounds of Formula (I), (Ia), (Ib), (Ic), (II), (IIa), (IIb), (IIc), (III), (IIIa), (IIIb), (IV), (IVa), or (IVb) are administered to a mammal in combination with conventional chemotherapy, radiotherapy, hormonal therapy, and/or immunotherapy. In some embodiments, the compounds of Formula (I), (Ia), (Ib), (Ic), (II), (IIa), (IIb), (IIc), (III), (IIIa), (IIIb), (IV), (IVa), or (IVb) described herein can be co-administered with conventional chemotherapeutic agents including alkylating agents (e.g., temozolomide, cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, etc.), EGFR inhibitors (e.g., gefitinib, erlotinib, etc.), and the like.

EXAMPLES

The following examples are intended to illustrate but not limit the disclosed embodiments.

All reactions were performed in oven-dried glassware under an atmosphere of argon with magnetic stirring. All solvents and chemicals used were purchased from Sigma-Aldrich or Acros, and were used as received without further purification. Purity and characterization of compounds were established by a combination of liquid chromatography-mass spectroscopy (LC-MS) and NMR analytical techniques and was >95% for all tested compounds. Silica gel column chromatography was carried out using pre-packed silica cartridges from RediSep (ISCO Ltd.) and eluted using an Isco Companion system. $^1$H- and $^{13}$C-NMR spectra were obtained on a Joel 400 spectrometer at 400 MHz. Chemical shifts are reported in δ (ppm) relative to residual solvent peaks or TMS as internal standards. Coupling constants are reported in Hz. HPLC-MS analyses were performed on a Shimadzu 2010EV LCMS using the following conditions: Kromisil C18 column (acetonitrile and 5% water over 4.5 min; flow rate of 1 mL/min; UV photodiode array detection from 200 to 300 nm reverse phase, 4.6 mm-50 mm); a linear gradient from 10% acetonitrile and 90% water to 95%.

General Synthetic Scheme for the Preparation of (2-arylthiazol-4-yl)biphenyl Carboxylic Acid Derivatives

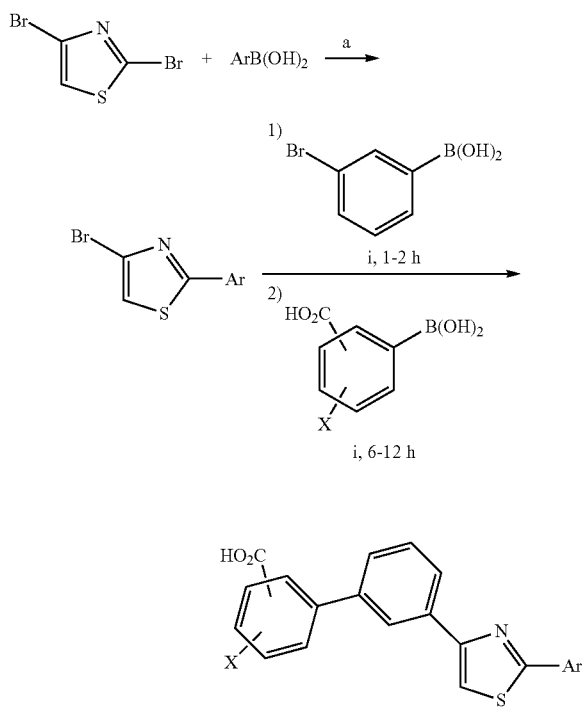

a) Pd(OAc)$_2$, Xantphos, K$_3$PO$_4$, THF, 60° C., 18 h
i) Pd(PPh$_3$)$_4$, 2M Na$_2$CO$_3$, DME, 80° C.

Example 1: 4-Fluoro-3'-(2-phenylthiazol-4-yl)biphenyl-3-carboxylic Acid

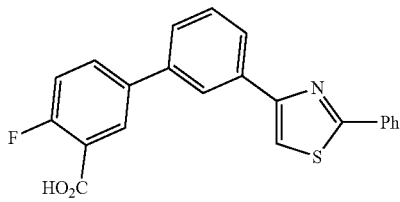 [SMILES: O=C(O)c1cc(-c2cccc(-c3csc(-c4ccccc4)n3)c2)ccc1F]

Step 1: 4-Bromo-2-phenylthiazole

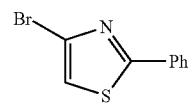

Under N$_2$ atmosphere Pd(OAc)$_2$ (0.084 g, 0.38 mmol) was combined with xantphos (0.220 g, 0.38 mmol) in 25 mL THF. After stirring for 5 min., the resulting solution was transferred to a round bottom flask containing 2,4 dibromothiazole (3.64 g, 15 mmol), phenylboronic acid (1.96 g, 16 mmol) and K$_3$PO$_4$ (9.55 g, 45 mmol). The resulting reaction mixture was heated at 60° C. for 18 h and then cooled to room temperature and filtered and washed with dichloromethane. Removal of the solvents under vacuum afforded the crude product which was purified by silica gel column chromatography using hexanes:ethyl acetate to afford 4-bromo-2-phenylthiazole as a white solid (3 g, 84%). $^1$H NMR (400 MHz, CDCl$_3$): δ 7.95 (dd, J=3.4 Hz, 8.2 Hz, 2H), 7.47-7.46 (m, 3H), 7.23 (s, 1H). LRMS (ESI) calcd. for C$_9$H$_6$BrNS [M+H]$^+$: 241.12. Found: 241.00.

Step 2: 4-(3-Bromophenyl)-2-phenylthiazole

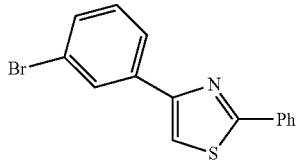 [SMILES: Brc1cccc(-c2csc(-c3ccccc3)n2)c1]

To a mixture of 4-bromo-2-phenylthiazole (3.0 g, 12.5 mmol), 3-bromophenylboronic acid (3.0 g, 15 mmol) and tetrakistriphenylphosphinepalladium(0) (1.44 g, 1.25 mmol) were in DME (40 mL) was added a 2M Na$_2$CO$_3$ solution (25 mL, 50 mmol). The resulting solution was heated at reflux in an atmosphere of N$_2$ for 2 h. The reaction mixture was cooled to room temperature and the solvent was removed under vacuum and the residue was dissolved in dichloromethane and washed with water. The organic layer was dried over anhydrous Na$_2$SO$_4$. The solvent was evaporated in vacuum to obtain the crude product as a pale yellow solid. Column chromatography using hexanes/ethyl acetate solvent system afforded 4-(3-bromophenyl)-2-phenylthiazole as a colorless solid (3.4 g, 86%). $^1$H NMR (400 MHz, CDCl$_3$): δ 8.16 (d, J=1.8 Hz, 1H), 8.03-8.01 (m, 2H), 7.90-7.87 (m, 1H), 7.48-7.44 (m, 5H), 7.31-7.38 (m, 1H). LRMS (ESI) calcd. for $C_{15}H_{10}BrNS[M+H]^+$: 315.97. Found: 316.00.

Step 3: 4-Fluoro-3'-(2-phenylthiazol-4-yl)biphenyl-3-carboxylic Acid

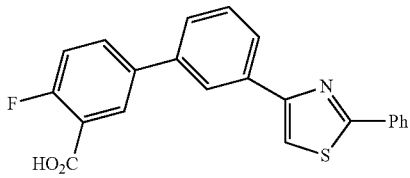 [SMILES: O=C(O)c1cc(-c2cccc(-c3csc(-c4ccccc4)n3)c2)ccc1F]

To a mixture of 4-(3-bromophenyl)-2-phenylthiazole (0.224 g, 0.71 mmol), 5-borono-2-fluorobenzoic acid (0.197 g, 1.07 mmol) and tetrakistriphenylphosphinepalladium(0) (0.081 g, 0.071 mmol) in DME (6 mL) was added a 2M $Na_2CO_3$ solution (1.4 mL). The resulting solution was heated at reflux in an atmosphere of $N_2$ for 6-12 h. The reaction mixture was cooled to room temperature and diluted with water and then acidified using 1N HCl. The aqueous phase was extracted with ethyl acetate (3×10 mL) and the combined organic layer was washed with brine, followed by drying over anhydrous $Na_2SO_4$. Filtration and removal of the solvent afforded crude product that was further purified by automated prep-HPLC to yield the desired compound as a white solid (0.083 g, 32%). $^1$H NMR (400 MHz, DMSOd$_6$): δ8.34 (s, 1H), 8.27 (s, 1H), 8.05 (dd, J=2.3 Hz, 6.9 Hz, 1H), 8.06 (d, J=7.8 Hz, 1H), 8.02-7.98 (m, 3H), 7.64 (d, J=7.3 Hz, 1H), 7.56 (t, J=7.8 Hz, 1H), 7.52-7.48 (m, 3H), 7.43 (t, J=8.2 Hz, 1H). HRMS (ESI) calcd. for $C_{22}H_{14}FNO_2S$ [M+H]$^+$: 376.0802. Found: 376.0811.

Example 2: 3'-(2-Phenylthiazol-4-yl)biphenyl-3-sulfonamide

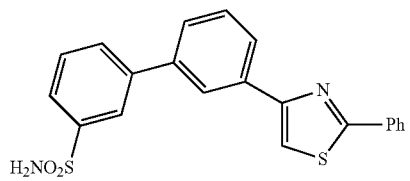 [SMILES: NS(=O)(=O)c1cccc(-c2cccc(-c3csc(-c4ccccc4)n3)c2)c1]

4-(3-Bromophenyl)-2-phenylthiazole (0.100 g, 0.32 mmol), 3-sulfamoylphenylboronic acid (0.096 g, 0.48 mmol), tetrakistriphenylphosphinepalladium(0) (0.037 g, 0.032 mmol) and 2M $Na_2CO_3$ (0.64 mL) were dissolved in DME. The reaction mixture was then processed according to the general procedure described in Example 1, step 2, to afford the title compound as a white solid (0.043 g, 34%). $^1$H NMR (400 MHz, DMSOd$_6$): δ 8.31 (s, 2H), 8.15 (d, J=1.4 Hz, 1H), 8.07 (dd, J=1.4 Hz, =8.7 Hz, 1H), 8.07-7.99 (m, 2H), 7.96 (d, J=7.8 Hz, 1H), 7.82 (d, J=7.8 Hz, 1H), 7.69-7.64 (m, 2H), 7.61 (t, J=7.8 Hz, 1H), 7.53-7.48 (m, 3H), 7.41 (s, 2H). HRMS (ESI) calcd. for $C_{21}H_{16}N_2O_2S_2$ [M+H]$^+$: 393.0726. Found: 393.0731.

Example 3: 4-Fluoro-3'-(2-phenylthiazol-5-yl)biphenyl-3-carboxylic Acid

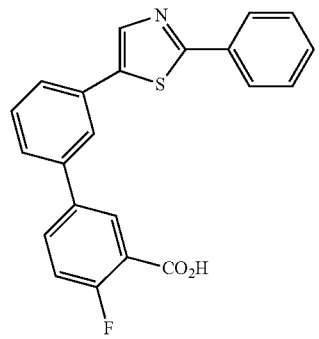 [SMILES: O=C(O)c1cc(-c2cccc(-c3cnc(-c4ccccc4)s3)c2)ccc1F]

5-(3-Bromophenyl)-2-phenylthiazole (0.325 g, 0.83 mmol), 5-borono-2-fluorobenzoic acid (0.230 g, 1.25 mmol), tetrakistriphenylphosphinepalladium(0) (0.096 g, 0.083 mmol) and 2M $Na_2CO_3$ (1.66 mL) were dissolved in DME. The reaction mixture was then processed according to the general procedure described in Example 1, step 3, to afford the title compound as a yellow solid (0.102 g, 33%). $^1$H NMR (400 MHz, DMSOd$_6$): δ 8.43 (s, 1H), 8.12 (dd, J=3.4 Hz, 6.8 Hz, 1H), 7.98-7.95 (m, 3H), 7.70 (d, J=8.2 Hz, 1H), 7.66 (d, J=8.2 Hz, 1H), 7.55 (d, J=7.8 Hz, 1H), 7.48-7.42 (m, 5H). HRMS (ESI) calcd. for $C_{22}H_{14}FNO_2S$ [M+H]$^+$: 376.0802. Found: 376.0809.

Example 4: 4-Fluoro-3'-(2-(furan-3-yl)thiazol-4-yl)biphenyl-3-carboxylic Acid

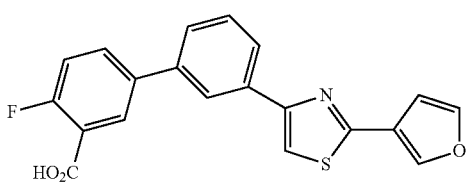

4-(3-Bromophenyl)-2-(furan-3-yl)thiazole (0.152 g, 0.5 mmol), 5-borono-2-fluorobenzoic acid (0.138 g, 0.75 mmol) tetrakistriphenylphosphinepalladium(0) (0.058 g, 0.05 mmol) and 2M $Na_2CO_3$ (1 mL) were dissolved in DME. The reaction mixture was then processed according to the general procedure described in Example 1, step 3, to afford the title compound as a yellow solid (0.053 g, 29%). $^1$H NMR (400 MHz, DMSOd$_6$): δ 8.43 (s, 1H), 8.23 (overlapping singlet and doublet, 2H), 8.11 (dd, J=2.8 Hz, 6.9 Hz, 1H), 8.02-7.97 (m, 2H), 7.82 (t, J=3.2 Hz, 1H), 7.63 (d, J=7.8 Hz, 1H), 7.54 (t, J=7.3 Hz, 1H), 7.44-7.41 (m, 1H), 7.00 (d, J=1.4 Hz, 1H). HRMS (ESI) calcd. for $C_{20}H_{12}FNO_3S$ [M+H]$^+$: 366.0595. Found: 366.0600.

Example 5: 4-Fluoro-3'-(2-(6-(trifluoromethyl)pyridin-3-yl)thiazol-4-yl)biphenyl-3-carboxylic Acid

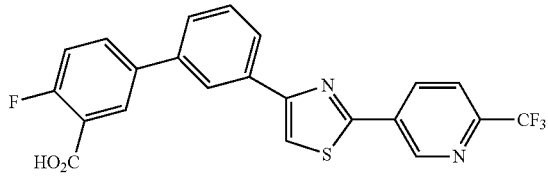 [SMILES: O=C(O)c1cc(-c2cccc(-c3csc(-c4ccc(C(F)(F)F)nc4)n3)c2)ccc1F]

4-(3-Bromophenyl)-2-(6-(trifluoromethyl)pyridin-3-yl)thiazole (0.154 g, 0.4 mmol), 5-borono-2-fluorobenzoic acid (0.110 g, 0.6 mmol), tetrakistriphenylphosphinepalladium(0) (0.046 g, 0.04 mmol) and 2M $Na_2CO_3$ (0.8 mL) were dissolved in DME. The reaction mixture was then processed according to the general procedure described in Example 1, step 3, to afford the desired compound as a white solid (0.052 g, 29%). $^1$H NMR (400 MHz, $DMSOd_6$): δ 9.42 (d, J=1.8 Hz, 1H), 8.70 (dd, J=2.3 Hz, 8.2 Hz, 1H), 8.56 (s, 1H), 8.35 (s, 1H), 8.17-8.11 (m, 2H), 8.07 (d, J=8.2 Hz, 1H), 8.03-7.99 (m, 2H), 7.72-7.69 (d, J=7.8 Hz, 1H), 7.63-7.58 (m, 1H). HRMS (ESI) calcd. for $C_{22}H_{12}F_4N_2O_2S$ [M+H]$^+$: 445.0628. Found: 445.0623.

Example 6: 4-Fluoro-3'-(2-methylthiazol-4-yl)biphenyl-3-carboxylic Acid

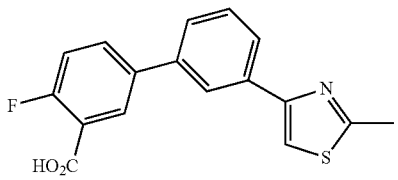

4-(3-Bromophenyl)-2-methylthiazole (0.101 g, 0.4 mmol), 5-borono-2-fluorobenzoic acid (0.110 g, 0.6 mmol), tetrakistriphenylphosphinepalladium(0) (0.046 g, 0.04 mmol) and 2M $Na_2CO_3$ (0.8 mL) were dissolved in DME. The reaction mixture was then processed according to the general procedure described in Example 1, step 3, to afford the desired compound as a white solid (0.022 g, 17%). $^1$H NMR (400 MHz, $DMSOd_6$): δ8.17 (s, 1H), 8.09-8.07 (overlapping singlet and doublet, 2H), 7.93 (d, J=7.8 Hz, 2H), 7.83 (d, J=7.3 Hz, 1H), 7.59 (d, J=7.8 Hz, 1H), 7.50 (t, J=7.3 Hz, 1H), 2.70 (s, 3H). HRMS (ESI) calcd. for $C_{17}H_{12}FNO_2S$ [M+H]$^+$: 314.0646. Found: 314.0707.

Example 7: 4-Fluoro-3'-(2-(furan-2-yl)thiazol-4-yl)biphenyl-3-carboxylic Acid

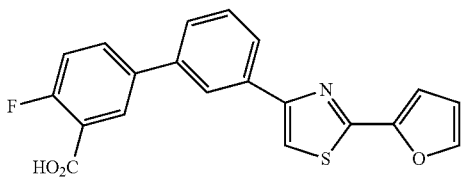

4-(3-Bromophenyl)-2-(furan-2-yl)thiazole (0.152 g, 0.5 mmol), 5-borono-2-fluorobenzoic acid (0.138 g, 0.75 mmol) tetrakistriphenylphosphinepalladium(0) (0.058 g, 0.05 mmol) and 2M $Na_2CO_3$ (1 mL) were dissolved in DME. The reaction mixture was then processed according to the general procedure described in Example 1, step 3, to afford the title compound as a yellow solid (0.020 g, 11%). $^1$H NMR (400 MHz, $DMSOd_6$): δ 8.39 (s, 1H), 8.24 (s, 1H), 8.12-8.10 (m, 2H), 8.03-7.91 (m, 2H), 7.65 (d, J=7.8 Hz, 1H), 7.57 (t, J=7.8 Hz, 1H), 7.44-7.40 (m, 3H). HRMS (ESI) calcd. for $C_{20}H_{12}FNO_3S$ [M+H]$^+$: 366.0595. Found: 366.0599.

Example 8: 3'-(2-(Benzo[b]thiophen-2-yl)thiazol-4-yl)-4-fluorobiphenyl-3-carboxylic Acid

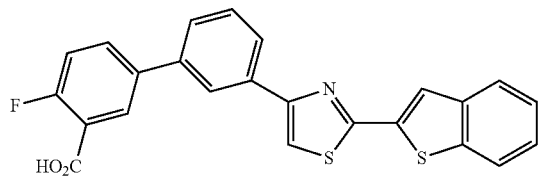 [SMILES: O=C(O)c1cc(-c2cccc(-c3csc(-c4cc5ccccc5s4)n3)c2)ccc1F]

2-(benzo[b]thiophen-2-yl)-4-(3-bromophenyl)thiazole (0.149 g, 0.4 mmol), 5-borono-2-fluorobenzoic acid (0.110 g, 0.6 mmol) tetrakistriphenylphosphinepalladium(0) (0.046 g, 0.04 mmol) and 2M $Na_2CO_3$ (1 mL) were dissolved in DME. The reaction mixture was then processed according to the general procedure described in Example 1, step 3, to afford the title compound as a yellow solid (0.063 g, 34%). $^1$H NMR (400 MHz, $DMSOd_6$): δ 8.38 (s, 1H), 8.24 (s, 1H), 8.12-8.10 (m, 2H), 8.03-7.91 (m, 4H), 7.67 (d, J=7.8 Hz, 1H), 7.58 (t, J=7.8 Hz, 1H), 7.43-7.39 (m, 4H). HRMS (ESI) calcd. for $C_{24}H_{14}FNO_2S_2$[M+H]$^+$: 432.0523. Found: 432.0515.

Example 9: 5-Fluoro-3'-(2-phenylthiazol-4-yl)biphenyl-3-carboxylic Acid

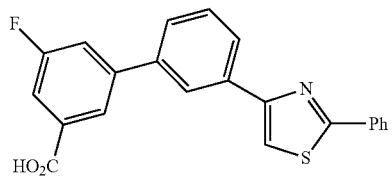 [SMILES: O=C(O)c1cc(F)cc(-c2cccc(-c3csc(-c4ccccc4)n3)c2)c1]

4-(3-Bromophenyl)-2-phenylthiazole (0.109 g, 0.35 mmol), 5-borono-3-fluorobenzoic acid (0.097 g, 0.525 mmol) tetrakistriphenylphosphinepalladium(0) (0.040 g, 0.035 mmol) and 2M $Na_2CO_3$ (0.7 mL) were dissolved in DME. The reaction mixture was then processed according to the general procedure described in Example 1, step 3, to afford the title compound as a colorless solid (0.043 g, 33%). $^1$H NMR (400 MHz, $DMSOd_6$): δ 8.37 (s, 1H), 8.32 (s, 1H), 8.11 (d, J=8.2 Hz, 1H), 8.09 (s, 1H), 8.02 (d, J=7.8 Hz, 2H), 7.89 (d, J=10.0 Hz, 1H), 7.71 (d, J=7.3 Hz, 1H), 7.65 (d, J=8.2 Hz, 1H), 7.59 (t, J=7.8 Hz, 1H), 7.53-7.49 (m, 3H). LRMS (ESI) calcd. for $C_{22}H_{14}FNO_2S$ [M+H]$^+$: 376.0802. Found: 376.0824.

Example 10: 2-Fluoro-5-(5-(2-phenylthiazol-4-yl)thiophen-2-yl)benzoic Acid

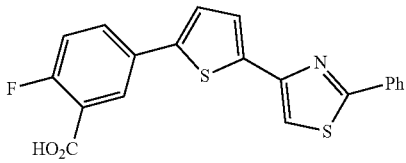 [SMILES: O=C(O)c1cc(-c2ccc(-c3csc(-c4ccccc4)n3)s2)ccc1F]

4-(5-Bromothiophen-2-yl)-2-phenylthiazole (0.113 g, 0.35 mmol), 3-borono-5-fluorobenzoic acid (0.097 g, 0.525 mmol) tetrakistriphenylphosphinepalladium(0) (0.040 g, 0.035 mmol) and 2M $Na_2CO_3$ (0.7 mL) were dissolved in DME. The reaction mixture was then processed according to the general procedure described in Example 1, step 3, to afford the title compound as a yellow solid (0.013 g, 10%). $^1$H NMR (400 MHz, $DMSOd_6$): δ 8.12 (s, 1H), 8.10 (d, J=2.8 Hz, 1H), 8.03-8.01 (m, 3H), 7.68 (d, J=3.7 Hz, 1H), 7.61 (d, J=3.7 Hz, 1H), 7.57-7.54 (m, 3H), 7.42-7.37 (m, 1H). HRMS (ESI) calcd. for $C_{20}H_{12}FNO_2S_2[M+H]^+$: 382.0366. Found: 382.0348.

Example 11: 6-Fluoro-3'-(2-phenylthiazol-4-yl)biphenyl-3-carboxylic Acid

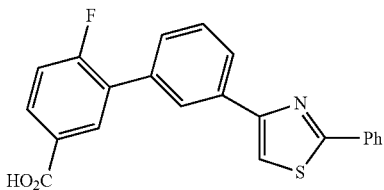 [SMILES: O=C(O)c1ccc(F)c(-c2cccc(-c3csc(-c4ccccc4)n3)c2)c1]

4-(3-Bromophenyl)-2-phenylthiazole (0.125 g, 0.4 mmol), 3-borono-4-fluorobenzoic acid (0.110 g, 0.6 mmol) tetrakistriphenylphosphinepalladium(0) (0.046 g, 0.04 mmol) and 2M $Na_2CO_3$ (0.8 mL) were dissolved in DME. The reaction mixture was then processed according to the general procedure described in Example 1, step 3, to afford the title compound as a colorless solid (0.047 g, 31%). $^1$H NMR (400 MHz, $DMSOd_6$): δ 8.29 (s, 1H), 8.20 (s, 1H), 8.11-8.09 (m, 2H), 8.01-7.98 (m, 3H), 7.59 (t, J=7.3 Hz, 1H), 7.57-7.48 (m, 4H), 7.42 (d, J=8.7 Hz, 1H). HRMS (ESI) calcd. for $C_{22}H_{14}FNO_2S$ [M+H]$^+$: 376.0802. Found: 376.0817.

Example 12: 4-Methoxy-3'-(2-phenylthiazol-4-yl)-[1,1'-biphenyl]-3-carboxylic Acid

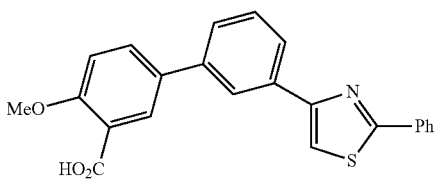 [SMILES: COc1ccc(-c2cccc(-c3csc(-c4ccccc4)n3)c2)cc1C(=O)O]

4-(3-Bromophenyl)-2-phenylthiazole (0.125 g, 0.4 mmol), 5-borono-2-methoxybenzoic acid (0.118 g, 0.6 mmol) tetrakistriphenylphosphinepalladium(0) (0.046 g, 0.04 mmol) and 2M $Na_2CO_3$ (0.8 mL) were dissolved in DME. The reaction mixture was then processed according to the general procedure described in Example 1, step 3, to afford the title compound as a pale yellow solid (0.030 g, 19%). $^1$H NMR (400 MHz, $DMSOd_6$): δ 8.32 (s, 1H), 8.24 (s, 1H), 8.30-7.99 (m, 3H), 7.93 (d, J=2.8 Hz, 1H), 7.87 (dd, J=2.3 Hz, 8.7 Hz, 1H), 7.60 (d, J=8.2 Hz, 1H), 7.54-7.48 (m, 4H), 7.21 (d, J=8.2 Hz, 1H), 3.84 (s, 3H). HRMS (ESI) calcd. for $C_{23}H_{17}NO_3S$ [M+H]$^+$: 388.1002. Found: 388.1020.

Example 13: 5-Nitro-3'-(2-phenylthiazol-4-yl)biphenyl-3-carboxylic Acid

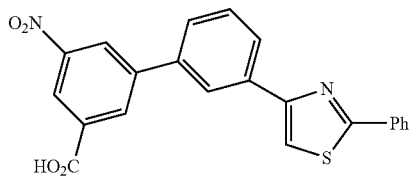 [SMILES: O=C(O)c1cc(-c2cccc(-c3csc(-c4ccccc4)n3)c2)cc([N+](=O)[O-])c1]

4-(3-Bromophenyl)-2-phenylthiazole (0.125 g, 0.4 mmol), 3-borono-5-nitrobenzoic acid (0.127 g, 0.6 mmol) tetrakistriphenylphosphinepalladium(0) (0.046 g, 0.04 mmol) and 2M $Na_2CO_3$ (0.8 mL) were dissolved in DME. The reaction mixture was then processed according to the general procedure described in Example 1, step 3, to afford the title compound as a pale yellow solid (0.038 g, 24%). $^1$H NMR (400 MHz, $DMSOd_6$): δ 8.69 (s, 1H), 8.59-8.57 (m, 2H), 8.40-7.98 (m, 2H), 8.17 (d, J=7.8 Hz, 1H), 8.03-8.01 (m, 2H), 7.80 (d, J=7.8 Hz, 1H), 7.67 (t, J=7.8 Hz, 1H), 7.52-7.50 (m, 3H). HRMS (ESI) calcd. for $C_{22}H_{14}N_2O_4S$ [M+H]$^+$: 403.0747. Found: 403.0751.

Example 14: 3'-(2-Phenylthiazol-4-yl)biphenyl-3-carbonitrile

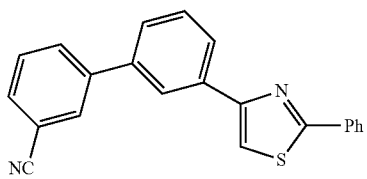 [SMILES: N#Cc1cccc(-c2cccc(-c3csc(-c4ccccc4)n3)c2)c1]

4-(3-Bromophenyl)-2-phenylthiazole (0.125 g, 0.4 mmol), 3-cyanophenylboronic acid (0.088 g, 0.6 mmol) tetrakistriphenylphosphinepalladium(0) (0.046 g, 0.05 mmol) and 2M $Na_2CO_3$ (0.8 mL) were dissolved in DME. The reaction mixture was then processed according to the general procedure described in Example 1, step 3, to afford the title compound as a white solid (0.088 g, 65%). $^1$H NMR (400 MHz, $DMSOd_6$): δ8.36 (s, 1H), 8.35 (s, 1H), 8.25 (s, 1H), 8.10 (d, J=7.3 Hz, 2H), 8.03 (dd, J=1.8 Hz, 9.2 Hz, 2H), 8.02 (d, J=7.8 Hz, 1H), 7.29 (d, J=7.8 Hz, 2H), 7.69 (t, J=7.8 Hz, 1H), 7.59 (t, J=7.8 Hz, 1H), 7.51-7.49 (m, 2H). HRMS (ESI) calcd. for $C_{22}H_{14}N_2S$ [M+H]$^+$: 339.0950. Found: 339.0963.

Example 15: 4-Fluoro-3'-(2-(thiophen-2-yl)thiazol-4-yl)biphenyl-3-carboxylic Acid

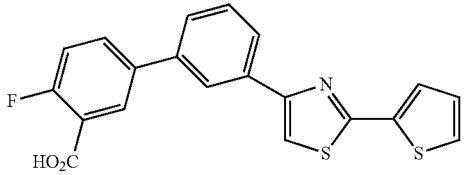

4-(3-Bromophenyl)-2-(thiophen-2-yl)thiazole (0.096 g, 0.3 mmol), 5-borono-2-fluorobenzoic acid (0.083 g, 0.45 mmol) tetrakistriphenylphosphinepalladium(0) (0.035 g, 0.03 mmol) and 2M $Na_2CO_3$ (0.6 mL) were dissolved in DME. The reaction mixture was then processed according to the general procedure described in Example 1, step 3, to afford the title compound as a yellow solid (0.015 g, 13%). $^1$H NMR (400 MHz, $DMSOd_6$): δ 8.30 (s, 1H), 8.24 (s, 1H), 8.17-8.00 (m, 3H), 7.76-7.73 (m, 1H), 7.68-7.57 (m, 2H), 7.45-7.43 (m, 2H), 7.20 (t, J=4.6 Hz, 1H). HRMS (ESI) calcd. for $C_{20}H_{12}FO_2NS_2$ $[M+H]^+$: 382.0366. Found: 382.0387.

Example 16: 3'-(2-(Benzofuran-2-yl)thiazol-4-yl)-4-fluorobiphenyl-3-carboxylic Acid

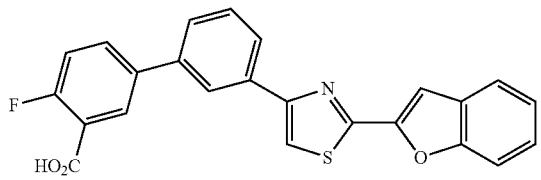

2-(Benzofuran-2-yl)-4-(3-bromophenyl)thiazole (0.142 g, 0.4 mmol), 3-borono-2-fluorobenzoic acid (0.110 g, 0.6 mmol) tetrakistriphenylphosphinepalladium(0) (0.046 g, 0.04 mmol) and 2M $Na_2CO_3$ (0.8 mL) were dissolved in DME. The reaction mixture was then processed according to the general procedure described in Example 1, step 3, to afford the title compound as a white solid (0.048 g, 29%). $^1$H NMR (400 MHz, $DMSOd_6$): δ8.46 (s, 1H), 8.27 (s, 1H), 8.12 (d, J=6.8 Hz, 1H), 8.06 (d, J=7.8 Hz, 1H), 8.23-7.98 (m, 1H), 7.72 (t, J=7.8 Hz, 2H), 7.69-7.67 (m, 2H), 7.58 (t, J=7.8 Hz, 1H), 7.45-7.39 (m, 2H), 7.32 (t, J=7.8 Hz, 1H). HRMS (ESI) calcd. for $C_{24}H_{14}FNO_3S$ $[M+H]^+$: 416.0751. Found: 416.0757.

Example 17: 4-Fluoro-4'-(2-phenylthiazol-4-yl)biphenyl-3-carboxylic Acid

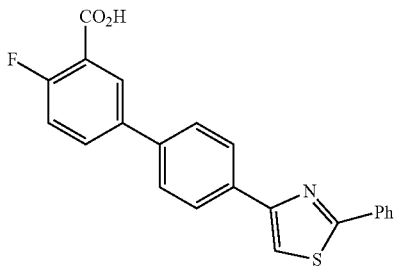 [SMILES: O=C(O)c1cc(-c2ccc(-c3csc(-c4ccccc4)n3)cc2)ccc1F]

4-(4-Bromophenyl)-2-phenyl-thiazole (0.126 g, 0.4 mmol), 3-borono-2-fluorobenzoic acid (0.110 g, 0.6 mmol) tetrakistriphenylphosphinepalladium(0) (0.046 g, 0.05 mmol) and 2M $Na_2CO_3$ (0.8 mL) were dissolved in DME. The reaction mixture was then processed according to the general procedure described in Example 1, step 3, to afford the title compound as a white solid (0.091 g, 64%). $^1$H NMR (400 MHz, $DMSOd_6$): δ 8.33 (s, 1H), 8.24 (s, 1H), 8.06 (d, J=7.8 Hz, 1H), 8.02-7.99 (m, 4H), 7.83 (d, J=8.2 Hz, 2H), 7.66 (d, J=7.8 Hz, 1H), 7.54 (t, J=7.8 Hz, 1H), 7.50-7.45 (m, 3H). HRMS (ESI) calcd. for $C_{22}H_{15}NO_2S$ $[M+H]^+$: 376.0802. Found: 376.0806.

Example 18: 4-Fluoro-2'-(2-phenylthiazol-4-yl)biphenyl-3-carboxylic Acid

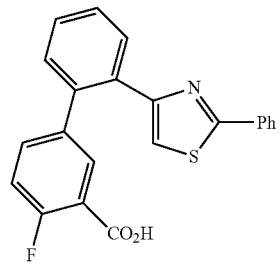 [SMILES: O=C(O)c1cc(-c2ccccc2-c2csc(-c3ccccc3)n2)ccc1F]

4-(2-Bromophenyl)-2-phenyl-thiazole (0.126 g, 0.4 mmol), 3-borono-2-fluorobenzoic acid (0.110 g, 0.6 mmol) tetrakistriphenylphosphinepalladium(0) (0.046 g, 0.05 mmol) and 2M $Na_2CO_3$ (0.8 mL) were dissolved in DME. The reaction mixture was then processed according to the general procedure described in Example 1, step 3, to afford the title compound as a white solid (0.021 g, 14%). $^1$H NMR (400 MHz, $DMSOd_6$): δ 7.83-7.78 (m, 1H), 7.76-7.70 (m, 2H), 7.67-7.65 (m, 1H), 7.52-7.47 (m, 2H), 7.47-7.38 (m, 5H), 7.28-7.20 (m, 2H). HRMS (ESI) calcd. for $C_{22}H_{14}FNO_2S$ $[M+H]^+$: 376.0802. Found: 376.0809.

Example 19: 4-Fluoro-3'-(2-phenylthiazol-4-yl)biphenyl-3-carbaldehyde

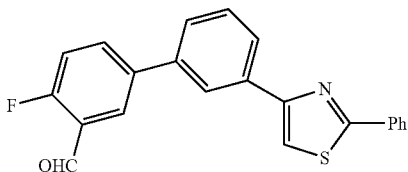 [SMILES: O=Cc1cc(-c2cccc(-c3csc(-c4ccccc4)n3)c2)ccc1F]

4-(3-Bromophenyl)-2-(furan-3-yl)thiazole (0.314 g, 1 mmol), 4-fluoro-3-formylphenylboronic acid (0.252 g, 1.5 mmol) tetrakistriphenylphosphinepalladium(0) (0.115 g, 0.01 mmol) and 2M $Na_2CO_3$ (2 mL) were dissolved in DME. The reaction mixture was then processed according to the general procedure described in Example 1, step 3, to afford the title compound as a white solid (0.121 g, 34%). $^1$H NMR (400 MHz, $DMSOd_6$): δ 10.26 (s, 1H), 8.34 (s, 1H), 8.33 (s, 1H), 8.19-8.19 (m, 2H), 8.07 (d, J=7.8 Hz, 1H), 8.02-8.00 (m, 2H), 7.66 (d, J=7.8 Hz, 1H), 7.58 (t, J=7.8 Hz, 1H), 7.53-7.48 (m, 4H). HRMS (ESI) calcd. for $C_{22}H_{14}FNOS$ $[M+H]^+$: 360.0896. Found: 360.0904.

Example 20: 4-Fluoro-3'-(2-phenylthiazol-4-yl)biphenyl-3-carbaldehyde oxime

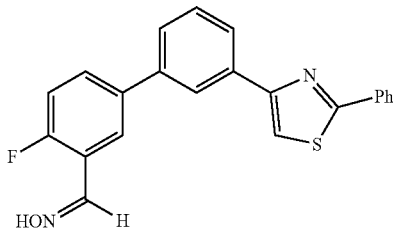

4-Fluoro-3'-(2-phenylthiazol-4-yl)biphenyl-3-carbaldehyde (0.020 g, 0.056 mmol), hydroxylamine hydrochloride (0.008 g, 0.112 mmol) and Et₃N (0.02 mL, 0.112 mmol) were taken in ethanol (2 mL) and heated at reflux for 1 h. The reaction mixture was cooled and passed through a short pad of celite. Volatile materials were removed under vacuum to afford the crude oxime which was purified by automated prep-HPLC to give the desired product as a light yellow viscous liquid (0.008 g, 40%). $^1$H NMR (400 MHz, DMSOd$_6$): δ11.68 (s, 1H), 8.36 (s, 1H), 8.32 (s, 1H), 8.31 (s, 1H), 8.06-8.05 (m, 4H), 8.02-8.00 (m, 1H), 7.68-7.48 (m, 6H). HRMS (ESI) calcd. for $C_{22}H_{15}FN_2OS$ [M+H]$^+$: 375.0962. Found: 375.0963.

Example 21: 3-Chloro-3'-(2-phenylthiazol-4-yl)biphenyl-4-carboxylic Acid

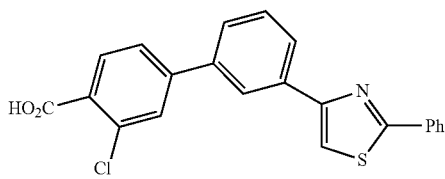 [SMILES: O=C(O)c1ccc(-c2cccc(-c3csc(-c4ccccc4)n3)c2)cc1Cl]

4-(3-Bromophenyl)-2-phenylthiazole (0.138 g, 0.44 mmol), 4-borono-2-chlorobenzoic acid (0.132 g, 0.66 mmol) tetrakistriphenylphosphinepalladium(0) (0.051 g, 0.044 mmol) and 2M Na₂CO₃ (0.88 mL) were dissolved in DME. The reaction mixture was then processed according to the general procedure described in Example 1, step 3, to afford the title compound as an off-white solid (0.063 g, 37%). $^1$H NMR (400 MHz, DMSOd$_6$): δ 8.37 (s, 1H), 8.34 (s, 1H), 8.11 (d, J=7.8 Hz, 1H), 8.02 (d, J=7.8 Hz, 2H), 7.99-7.98 (m, 2H), 7.81 (d, J=7.8 Hz, 1H), 7.31 (d, J=7.8 Hz, 1H), 7.59 (d, J=7.8 Hz, 1H), 7.53-7.48 (m, 3H). HRMS (ESI) calcd. for $C_{22}H_{14}ClNO_2S$ [M+H]$^+$: 392.0507. Found: 392.0537.

Example 22: 3'-(2-Phenylthiazol-4-yl)biphenyl-4-carboxylic Acid

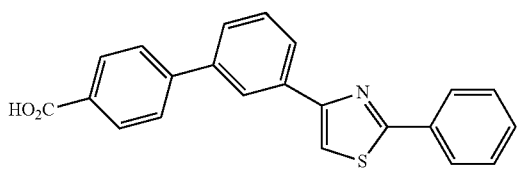 [SMILES: O=C(O)c1ccc(-c2cccc(-c3csc(-c4ccccc4)n3)c2)cc1]

4-(3-Bromophenyl)-2-phenylthiazole (0.138 g, 0.44 mmol), 4-boronobenzoic acid (0.109 g, 0.66 mmol) tetrakistriphenylphosphinepalladium(0) (0.051 g, 0.044 mmol) and 2M Na₂CO₃ (0.88 mL) were dissolved in DME. The reaction mixture was then processed according to the general procedure described in Example 1, step 3, to afford the title compound as an off-white solid (0.060 g, 42%). $^1$H NMR (400 MHz, DMSOd$_6$): δ8.33 (s, 1H), 8.24 (s, 1H), 8.07-8.00 (m, 4H), 7.83 (d, J=8.2 Hz, 2H), 7.66 (d, J=7.8 Hz, 1H), 7.53 (t, J=7.8 Hz, 1H), 7.50-7.45 (m, 4H). HRMS (ESI) calcd. for $C_{22}H_{15}NO_2S$ [M+H]$^+$: 358.0896. Found: 358.0906.

Example 23: 6-Methoxy-3'-(2-phenylthiazol-4-yl)biphenyl-3-carboxylic Acid

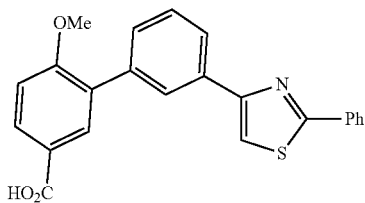 [SMILES: COc1ccc(C(=O)O)cc1-c1cccc(-c2csc(-c3ccccc3)n2)c1]

4-(3-Bromophenyl)-2-phenylthiazole (0.138 g, 0.44 mmol), 3-borono-4-methoxybenzoic acid (0.129 g, 0.66 mmol) tetrakistriphenylphosphinepalladium(0) (0.051 g, 0.044 mmol) and 2M Na₂CO₃ (0.88 mL) were dissolved in DME. The reaction mixture was then processed according to the general procedure described in Example 1, step 3, to afford the title compound as an off-white solid (0.056 g, 33%). $^1$H NMR (400 MHz, DMSOd$_6$): δ 8.22 (s, 1H), 8.08 (s, 1H), 8.02-7.98 (m, 3H), 7.95 (dd, J=2.3 Hz, 8.7 Hz, 1H), 7.84 (d, J=1.8 Hz, 1H), 7.52-7.43 (m, 5H), 7.21 (d, J=8.7 Hz, 1H), 3.84 (s, 3H). HRMS (ESI) calcd. for $C_{23}H_{17}NO_3S$ [M+H]$^+$: 388.1002. Found: 388.1009.

Example 24: 4-Chloro-3'-(2-phenylthiazol-4-yl)biphenyl-3-carboxylic Acid

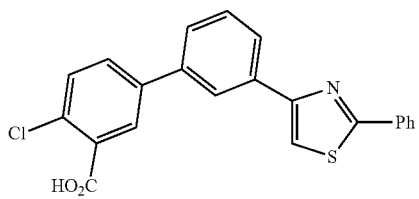 [SMILES: O=C(O)c1cc(-c2cccc(-c3csc(-c4ccccc4)n3)c2)ccc1Cl]

4-(3-Bromophenyl)-2-phenylthiazole (0.063 g, 0.2 mmol), 5-borono-2-chlorobenzoic acid (0.067 g, 0.3 mmol) tetrakistriphenylphosphinepalladium(0) (0.023 g, 0.02 mmol) and 2M Na₂CO₃ (0.4 mL) were dissolved in DME. The reaction mixture was then processed according to the general procedure described in Example 1, step 3, to afford the title compound as a white solid (0.020 g, 26%). $^1$H NMR (400 MHz, DMSOd$_6$): δ 8.35 (s, 1H), 8.30 (s, 1H), 8.07 (d, J=8.2 Hz, 2H), 8.02 (d, J=8.2 Hz, 2H), 7.88 (d, J=8.2 Hz, 1H), 7.67 (d, J=7.8 Hz, 1H), 7.61 (d, J=8.2 Hz, 1H), 7.56 (t, J=7.8 Hz, 1H), 7.51-7.49 (m, 3H). HRMS (ESI) calcd. for $C_{22}H_{14}ClNO_2S$ [M+H]$^+$: 392.0507. Found: 392.0518.

Example 25: 3'-(2-Phenylthiazol-4-yl)biphenyl-2-carboxylic Acid

4-(3-Bromophenyl)-2-phenylthiazole (0.138 g, 0.44 mmol), 2-boronobenzoic acid (0.109 g, 0.66 mmol) tetrakistriphenylphosphinepalladium(0) (0.051 g, 0.044 mmol) and 2M $Na_2CO_3$ (0.88 mL) were dissolved in DME. The reaction mixture was then processed according to the general procedure described in Example 1, step 3, to afford the title compound as a pale yellow solid (0.020 g, 13%). $^1$H NMR (400 MHz, $DMSOd_6$): δ 8.02-7.93 (m, 3H), 7.56-7.42 (m, 8H), 7.30-7.24 (m, 3H). HRMS (ESI) calcd. for $C_{22}H_{15}NO_2S$ $[M+H]^+$: 358.0896. Found: 358.0940.

Example 26: 2-Chloro-3'-(2-phenylthiazol-4-yl)biphenyl-4-carboxylic Acid

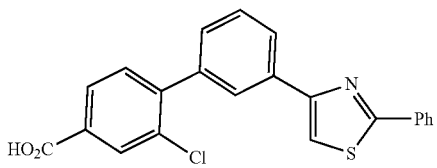 [SMILES: O=C(O)c1ccc(-c2cccc(-c3csc(-c4ccccc4)n3)c2)c(Cl)c1]

4-(3-Bromophenyl)-2-phenylthiazole (0.138 g, 0.44 mmol), 4-borono-3-chlorobenzoic acid (0.132 g, 0.66 mmol) tetrakistriphenylphosphinepalladium(0) (0.051 g, 0.044 mmol) and 2M $Na_2CO_3$ (0.88 mL) were dissolved in DME. The reaction mixture was then processed according to the general procedure described in Example 1, step 3, to afford the title compound as a white solid (0.053 g, 31%). $^1$H NMR (400 MHz, $DMSOd_6$): δ8.27 (s, 1H), 8.11-8.09 (overlapping singlet and doublet, 2H), 8.02 (s, 1H), 7.99 (d, J=7.4 Hz, 2H), 7.95 (d, J=8.2 Hz, 1H), 7.61 (d, J=7.8 Hz, 1H), 7.59 (t, J=7.8 Hz, 1H), 7.49-7.45 (m, 3H), 7.42 (d, J=7.3 Hz, 1H). HRMS (ESI) calcd. for $C_{22}H_{14}ClNO_2S$ $[M+H]^+$: 392.0507. Found: 392.0523.

Example 27: 2-Fluoro-5-(2-phenylthiazol-4-yl)benzoic Acid

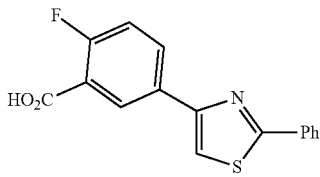 [SMILES: O=C(O)c1cc(-c2csc(-c3ccccc3)n2)ccc1F]

4-(3-Bromophenyl)-2-phenylthiazole (0.121 g, 0.5 mmol), 5-borono-2-fluorobenzoic acid (0.138 g, 0.75 mmol) tetrakistriphenylphosphinepalladium(0) (0.058 g, 0.05 mmol) and 2M $Na_2CO_3$ (1 mL) were dissolved in DME. The reaction mixture was then processed according to the general procedure described in Example 1, step 3, to afford the title compound as a tan solid (0.068 g, 45%). $^1$H NMR (400 MHz, $DMSOd_6$): δ8.48 (dd, J=2.3 Hz, 7.3 Hz, 1H), 8.26 (s, 1H), 8.25-8.24 (m, 1H), 7.99 (dd, J=5.0 Hz, 9.6 Hz, 2H), 7.52-7.48 (m, 3H), 7.40 (t, J=9.2 Hz, 1H). HRMS (ESI) calcd. for $C_{16}H_{10}FNO_2S$ $[M+H]^+$: 300.0489. Found: 300.0506.

Example 28: 3'-(2-Phenylthiazol-4-yl)biphenyl-3-carboxylic Acid

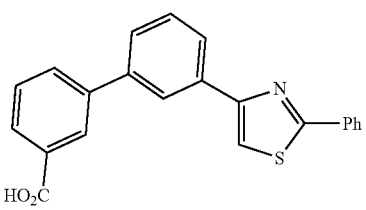 [SMILES: O=C(O)c1cccc(-c2cccc(-c3csc(-c4ccccc4)n3)c2)c1]

4-(3-Bromophenyl)-2-phenylthiazole (0.138 g, 0.44 mmol), 3-boronobenzoic acid (0.109 g, 0.66 mmol) tetrakistriphenylphosphinepalladium(0) (0.051 g, 0.044 mmol) and 2M $Na_2CO_3$ (0.88 mL) were dissolved in DME. The reaction mixture was then processed according to the general procedure described in Example 1, step 3, to afford the title compound as a white solid (0.065 g, 46%). $^1$H NMR (400 MHz, $DMSOd_6$): δ 8.34 (s, 1H), 8.30 (s, 1H), 8.22 (s, 1H), 8.07 (d, J=7.8 Hz, 1H), 8.03-7.98 (m, 2H), 7.94 (d, J=7.3 Hz, 1H), 7.67 (d, J=7.3 Hz, 1H), 7.66-7.55 (m, 3H), 7.52-7.48 (m, 3H). Found: 358.00. HRMS (ESI) calcd. for $C_{22}H_{15}NO_2S$ $[M+H]^+$: 358.0896. Found: 358.0900.

General Synthetic Scheme for the Preparation of (2-arylthiazol-4-yl)biphenyl Carboxylic Acid Derivatives

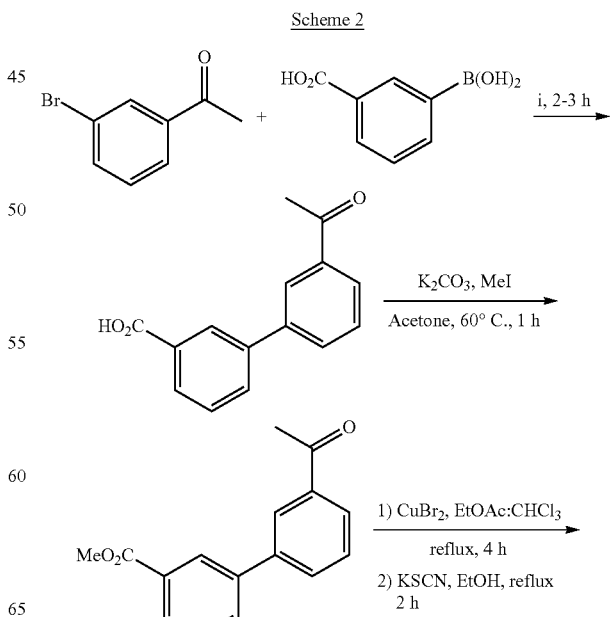

Scheme 2

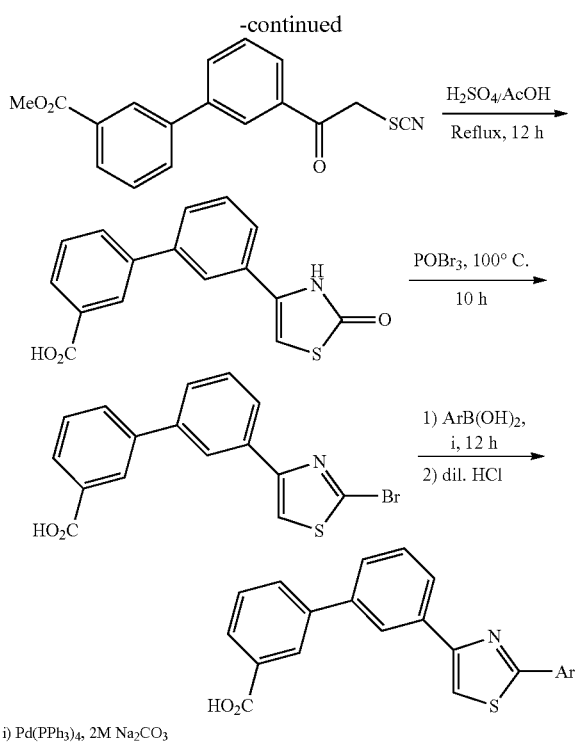

Example 29: 3-{3-[2-(3,4-Dimethoxyphenyl)-1,3-thiazol-4-yl]phenyl}benzoic Acid

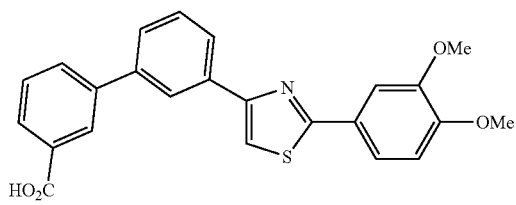 [SMILES: COc1ccc(-c2nc(-c3cccc(-c4cccc(C(=O)O)c4)c3)cs2)cc1OC]

Step 1: 3'-Acetylbiphenyl-3-carboxylic Acid

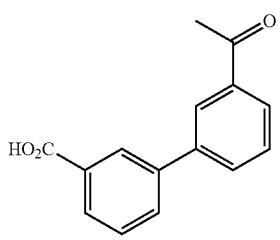 [SMILES: CC(=O)c1cccc(-c2cccc(C(=O)O)c2)c1]

1-(3-Bromophenyl)ethanone (10 g, 50 mmol) and 3-boronobenzoic acid (12.5 g, 75 mmol) were dissolved in DME (100 mL). To this solution was added palladium tetrakis triphenylphosphine (2.9 g, 2.5 mmol) and 2M Na₂CO₃ solution (50 mL, 100 mmol). The resulting mixture was heated to reflux for 2-3 h and cooled to room temperature. The mixture was diluted with water and then acidified with 2N HCl. The crude acid was collected by filtration washed with water and diethyl ether and dried and used without any further purification in the next step. Pale yellow solid (7.5 g, 62%). ¹H NMR (400 MHz, DMSOd₆): δ8.24 (t, J=1.8 Hz, 1H), 8.22 (t, J=1.8 Hz, 1H), 8.00-7.98 (m, 4H), 7.66-7.64 (m, 2H), 2.67 (s, 3H). LRMS (ESI) calcd. for $C_{15}H_{12}O_3$ [M+H]⁺: 241.07. Found: 241.00.

Step 2: Acetylbiphenyl-3-methyl carboxylate

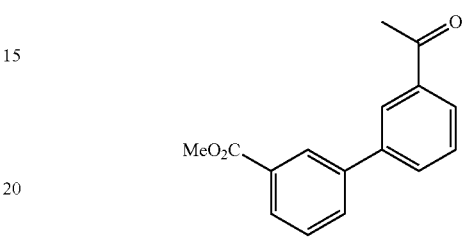

To a mixture of 3'-acetylbiphenyl-3-carboxylic acid (5 g, 20.83 mmol) in acetone (100 mL) was added MeI (2.6 mL, 42 mmol) and K₂CO₃ (5.7 g, 42 mmol). The reaction mixture was heated at reflux for 1 h, cooled to room temperature, and then filtered through a short pad of celite and washed with acetone. Removal of the solvent under reduced pressure afforded 3'-acetylbiphenyl-3-methyl carboxylate as a reddish brown viscous liquid (4 g, 80%). ¹H NMR (400 MHz, CDCl₃): δ8.28 (t, J=1.8 Hz, 1H), 8.18 (t, J=1.8 Hz, 1H), 8.00-7.98 (m, 1H), 7.82 (m, 1H), 7.79-7.78 (m, 2H), 7.57-7.53 (m, 2H), 3.92 (s, 3H), 2.65 (s, 3H). LRMS (ESI) calcd. for $C_{16}H_{14}O_3$[M+H]⁺: 255.09. Found: 255.00.

Step 3: Methyl 3'-(2-bromoacetyl)biphenyl-3-carboxylate

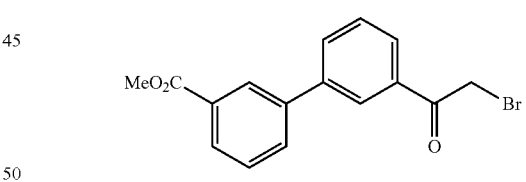

Cupric bromide (5.27 g, 23.62 mmol) was dissolved in ethyl acetate and brought to reflux. 3'-Acetylbiphenyl-3-methyl carboxylate (4 g, 15.7 mmol) was dissolved in chloroform and rapidly added to the cupric bromide mixture and heated at reflux for 4 h. The solution was cooled and the precipitated Cu(I) bromide was filtered off. The organic layer was washed with water and brine solution, and dried over anhydrous Na₂SO₄ solution. Removal of the solvent under reduced pressure followed by chromatographic separation using hexane:ethyl acetate afforded the title compound as a yellow solid (5.12 g, 98%). ¹H NMR (400 MHz, CDCl₃): δ8.27 (t, J=1.8 Hz, 1H), 8.20 (t, J=1.8 Hz, 1H), 8.08-7.95 (m, 2H), 7.85-7.78 (m, 2H), 7.59-7.52 (m, 2H), 4.50 (s, 2H), 3.94 (s, 3H). LRMS (ESI) calcd. for $C_{16}H_{13}BrO_3$ [M+H]⁺: 333.00. Found: 333.00.

Step 4: Methyl 3'-(2-thiocyanatoacetyl)biphenyl-3-carboxylate

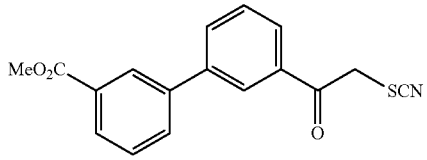

A solution of ethyl 3'-(2-bromoacetyl)biphenyl-3-carboxylate (5.12 g, 15.42 mmol) and potassium thiocyanate (5.23 g, 53.98 mmol) in ethanol was heated at reflux for 2 h. The reaction mixture was filtered hot and washed with hot ethanol. Upon cooling the filtrate, a solid was collected by filtration. The solid was washed with cold ethanol and dried under vacuum to afford the title compound as a yellow solid (4.2 g, 94%). $^1$H NMR (400 MHz, DMSOd$_6$): δ 8.23 (t, J=1.8 Hz, 1H), 8.19 (t, J=1.8 Hz, 1H), 7.97-7.94 (m, 4H), 7.62-7.60 (m, 2H), 5.15 (s, 2H), 3.82 (s, 3H). LRMS (ESI) calcd. for $C_{17}H_{13}NO_3S$ [M+H]$^+$: 312.06. Found: 312.00.

Step 5: 3'-(2-Oxo-2,3-dihydrothiazol-4-yl)biphenyl-3-carboxylic Acid

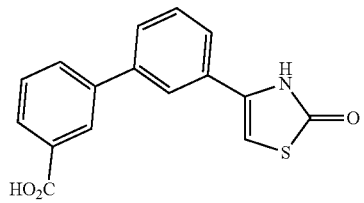 [SMILES: O=C(O)c1cccc(-c2cccc(-c3csc(=O)[nH]3)c2)c1]

50% aqueous $H_2SO_4$ (100 mL) was added to a solution of methyl 3'-(2-thiocyanatoacetyl)biphenyl-3-carboxylate (4.5 g, 14.46 mmol) in acetic acid (20 mL). The resulting mixture was heated at reflux for 12 h. The reaction mixture was cooled to room temperature and then poured into ice water. The precipitated compound was collected by filtration, washed with water, and dried under vacuum to afford 3'-(2-oxo-2,3-dihydrothiazol-4-yl)biphenyl-3-carboxylic acid as a yellow solid (4.3 g, quantitative yield). $^1$H NMR (400 MHz, DMSOd$_6$): δ 11.89 (s, 1H), 8.25 (s, 1H), 8.10 (d, J=8.2 Hz, 1H), 7.93-7.91 (m, 2H), 7.66-7.58 (m, 4H), 6.90 (s, 1H), LRMS (ESI) calcd. for $C_{16}H_{11}NO_3S$ [M+H]$^+$: 298.05. Found: 298.00.

Step 6: 3'-(2-Bromothiazol-4-yl)-[1,1'-biphenyl]-3-carboxylic Acid

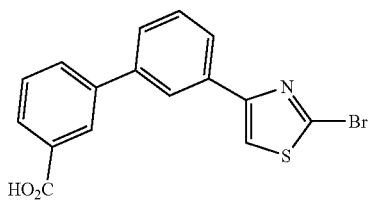 [SMILES: O=C(O)c1cccc(-c2cccc(-c3csc(Br)n3)c2)c1]

3'-(2-Oxo-2,3-dihydrothiazol-4-yl)biphenyl-3-carboxylic acid (4.3 g, 14.47 mmol) and POBr$_3$ (45 g, 156.70 mmol) were heated at 100° C. for 10 h. The reaction mixture was then cooled to room temperature and poured into ice water. The mixture was extracted with ethyl acetate (3×50 mL), washed with brine and dried over Na$_2$SO$_4$ to 3'-(2-bromothiazol-4-yl)-[1,1'-biphenyl]-3-carboxylic acid as a tan solid (3.4 g, 68%). $^1$H NMR (400 MHz, DMSOd$_6$): δ8.36 (s, 1H), 8.24 (s, 1H), 8.21 (s, 1H), 7.97 (q, J=7.33 Hz, 3H), 7.73 (d, J=7.8 Hz, 1H), 7.65-7.57 (m, 2H). LRMS (ESI) calcd. for $C_{16}H_{10}BrNO_2$ [M+H]$^+$: 359.96. Found: 360.00.

Step 7: 3-{3-[2-(3,4-Dimethoxyphenyl)-1,3-thiazol-4-yl]phenyl}benzoic Acid

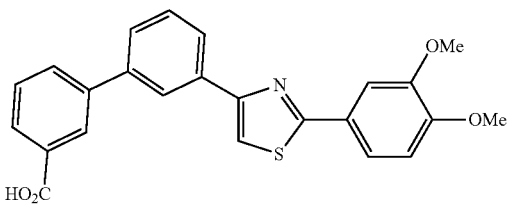 [SMILES: COc1ccc(-c2nc(-c3cccc(-c4cccc(C(=O)O)c4)c3)cs2)cc1OC]

3'-(2-Bromothiazol-4-yl)-[1,1'-biphenyl]-3-carboxylic acid (0.178 g, 0.5 mmol), 3,4-dimethoxyphenylboronic acid (0.136 g, 0.75 mmol), tetrakistriphenylphosphinepalladium (0) (0.058 g, 0.05 mmol) and 2M Na$_2$CO$_3$ (1 mL) were dissolved in DME. The reaction mixture was then processed according to the general procedure described in Example 1, step 3, to afford the title compound as a pale yellow solid (0.116 g, 56%). $^1$H NMR (400 MHz, DMSOd$_6$): δ 8.29 (t, J=1.6 Hz, 1H), 8.24-8.23 (m, 2H), 8.06 (d, J=7.8 Hz, 1H), 8.00-7.93 (m, 2H), 7.64-7.53 (m, 5H), 7.06 (d, J=8.7 Hz, 1H), 3.84 (s, 3H), 3.80 (s, 3H). HRMS (ESI) calcd. for $C_{24}H_{19}NO_4S$ [M+H]$^+$: 418.1108. Found: 418.1121.

Example 30: 3-[3-(2-Naphthyl-1,3-thiazol-4-yl)phenyl]benzoic Acid

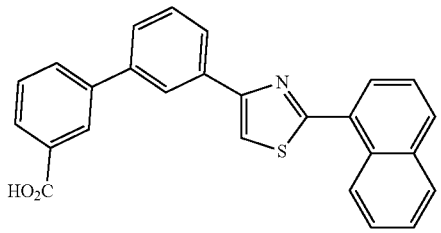 [SMILES: O=C(O)c1cccc(-c2cccc(-c3csc(-c4cccc5ccccc45)n3)c2)c1]

3'-(2-Bromothiazol-4-yl)-[1,1'-biphenyl]-3-carboxylic acid (0.178 g, 0.5 mmol), 1-naphthylboronic acid (0.129 g, 0.75 mmol), tetrakistriphenylphosphinepalladium(0) (0.058 g, 0.05 mmol) and 2M Na$_2$CO$_3$ (1 mL) were dissolved in DME. The reaction mixture was then processed according to the general procedure described in Example 1, step 3, to afford the title compound as a white solid (0.047 g, 23%). $^1$H NMR (400 MHz, DMSOd$_6$): δ 8.99 (d, J=8.7 Hz, 1H), 8.51 (s, 1H), 8.40 (s, 1H), 8.31 (s, 1H), 8.14-7.99 (m, 6H), 7.68-7.50 (m, 5H), 7.52-7.50 (m, 1H). Found: 408.00. HRMS (ESI) calcd. for $C_{26}H_{17}NO_2S$ [M+H]$^+$: 408.1053. Found: 408.1061.

Example 31: 3-{3-[2-(4-Methoxyphenyl)-1,3-thiazol-4-yl]phenyl}benzoic Acid

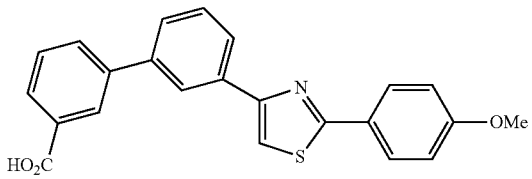 [SMILES: COc1ccc(-c2nc(-c3cccc(-c4cccc(C(=O)O)c4)c3)cs2)cc1]

3'-(2-Bromothiazol-4-yl)-[1,1'-biphenyl]-3-carboxylic acid (0.107 g, 0.3 mmol), 4-methoxyphenylboronic acid (0.068 g, 0.45 mmol), tetrakistriphenylphosphinepalladium (0) (0.035 g, 0.03 mmol) and 2M $Na_2CO_3$ (0.6 mL) were dissolved in DME. The reaction mixture was then processed according to the general procedure described in Example 1, step 3, to afford the title compound as a pale yellow solid (0.022 g, 19%). $^1$H NMR (400 MHz, $DMSOd_6$): δ 8.28 (t, J=1.8 Hz, 1H), 8.24 (s, 1H), 8.22 (t, J=1.8 Hz, 1H), 8.05 (d, J=7.8 Hz, 1H), 7.97-7.94 (m, 4H), 7.67-7.56 (m, 3H), 7.06 (d, J=8.7 Hz, 2H), 3.81 (s, 3H). HRMS (ESI) calcd. for $C_{23}H_{17}NO_3S$ $[M+H]^+$: 388.1002. Found: 388.1006.

Example 32: 3-[3-(2-(2-Naphthyl)-1,3-thiazol-4-yl)phenyl]benzoic Acid

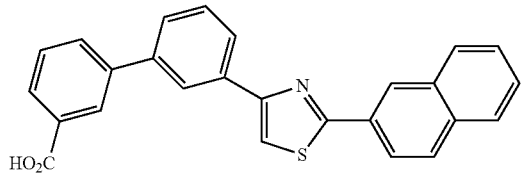 [SMILES: O=C(O)c1cccc(-c2cccc(-c3csc(-c4ccc5ccccc5c4)n3)c2)c1]

3'-(2-Bromothiazol-4-yl)-[1,1'-biphenyl]-3-carboxylic acid (0.108 g, 0.3 mmol), 2-naphthylboronic acid (0.077 g, 0.45 mmol), tetrakistriphenylphosphinepalladium(0) (0.035 g, 0.03 mmol) and 2M $Na_2CO_3$ (0.6 mL) were dissolved in DME. The reaction mixture was then processed according to the general procedure described in Example 1, step 3, to afford the title compound as a pale yellow solid (0.057 g, 46%). $^1$H NMR (400 MHz, $DMSOd_6$): δ 8.64 (s, 1H), 8.43 (s, 1H), 8.38 (s, 1H), 8.23 (s, 1H), 8.20-7.99 (m, 7H), 7.72-7.60 (m, 5H). HRMS (ESI) calcd. for $C_{26}H_{17}NO_2S$ $[M+H]^+$: 408.09. Found: 408.1054.

Example 33: 3-{4-[3-(3-Carboxyphenyl)phenyl]-1,3-thiazol-2-yl}benzoic Acid

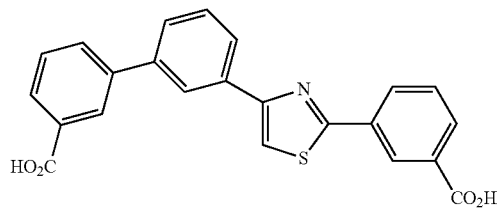 [SMILES: O=C(O)c1cccc(-c2cccc(-c3csc(-c4cccc(C(=O)O)c4)n3)c2)c1]

3'-(2-Bromothiazol-4-yl)-[1,1'-biphenyl]-3-carboxylic acid (0.100 g, 0.28 mmol), 3-boronobenzoic acid (0.070 g, 0.42 mmol), tetrakistriphenylphosphinepalladium(0) (0.032 g, 0.028 mmol) and 2M $Na_2CO_3$ (0.56 mL) were dissolved in DME. The reaction mixture was then processed according to the general procedure described in Example 1, step 3, to afford the title compound as a pale yellow solid (0.045 g, 40%). $^1$H NMR (400 MHz, $DMSOd_6$): δ 8.55 (s, 1H), 8.44 (s, 1H), 8.34 (s, 1H), 8.27 (s, 1H), 8.13 (d, J=7.8 Hz, 1H), 8.07 (d, J=7.8 Hz, 1H), 8.03-7.98 (m, 2H), 7.73-7.60 (m, 5H). HRMS (ESI) calcd. for $C_{23}H_{15}NO_4S$ $[M+H]^+$: 402.0795. Found: 402.0801.

Example 34: 3-[3-(2-(2H,3H-benzo[e]1,4-dioxin-6-yl)-1,3-thiazol-4-yl)phenyl]benzoic Acid

3'-(2-Bromothiazol-4-yl)-[1,1'-biphenyl]-3-carboxylic acid (0.107 g, 0.3 mmol), 2,3-dihydrobenzo[b][1,4]dioxin-6-ylboronic acid (0.081 g, 0.45 mmol), tetrakistriphenylphosphinepalladium(0) (0.035 g, 0.03 mmol) and 2M $Na_2CO_3$ (0.6 mL) were dissolved in DME. The reaction mixture was then processed according to the general procedure described in Example 1, step 3, to afford the title compound as a yellow solid (0.040 g, 32%). $^1$H NMR (400 MHz, $DMSOd_6$): δ 8.32 (d, J=1.8 Hz, 1H), 8.27-8.26 (m, 2H), 8.09-7.98 (m, 3H), 7.71-7.50 (m, 5H), 7.02 (dd, J=1.3 Hz, 8.7 Hz, 1H), 4.32 (s, 4H). HRMS (ESI) calcd. for $C_{24}H_{17}NO_4S$ $[M+H]^+$: 416.0951. Found: 416.0960.

Example 35: 3'-(2-(6-Chloropyridin-3-yl)thiazol-4-yl)biphenyl-3-carboxylic Acid

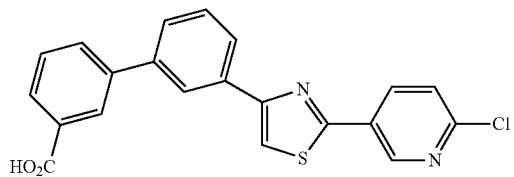 [SMILES: O=C(O)c1cccc(-c2cccc(-c3csc(-c4ccc(Cl)nc4)n3)c2)c1]

3'-(2-Bromothiazol-4-yl)-[1,1'-biphenyl]-3-carboxylic acid (0.107 g, 0.3 mmol), 6-chloropyridin-3-ylboronic acid (0.071 g, 0.45 mmol), tetrakistriphenylphosphinepalladium (0) (0.035 g, 0.03 mmol) and 2M $Na_2CO_3$ (0.6 mL) were dissolved in DME. The reaction mixture was then processed according to the general procedure described in Example 1, step 3, to afford the title compound as a pale yellow solid (0.078 g, 66%). $^1$H NMR (400 MHz, $DMSOd_6$): δ 9.07 (d, J=2.3 Hz, 1H), 8.48 (s, 1H), 8.46 (d, J=2.3 Hz, 1H), 8.34 (s, 1H), 8.27 (s, 1H), 8.11 (d, J=7.8 Hz, 1H), 8.02-7.98 (m, 2H), 7.73-7.60 (m, 4H). HRMS (ESI) calcd. for $C_{21}H_{13}ClN_2O_2S$ $[M+H]^+$: 393.0459. Found: 393.0466.

Example 36: (E)-3'-(2-Styrylthiazol-4-yl)biphenyl-3-carboxylic Acid

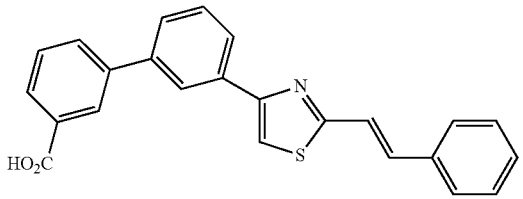 [SMILES: O=C(O)c1cccc(-c2cccc(-c3csc(/C=C/c4ccccc4)n3)c2)c1]

3'-(2-Bromothiazol-4-yl)-[1,1'-biphenyl]-3-carboxylic acid (0.107 g, 0.3 mmol), (E)-styrylboronic acid (0.067 g, 0.45 mmol), tetrakistriphenylphosphinepalladium(0) (0.035 g, 0.03 mmol) and 2M $Na_2CO_3$ (0.6 mL) were dissolved in DME. The reaction mixture was then processed according to the general procedure described in Example 1, step 3, to afford the title compound as a pale yellow solid (0.053 g, 46%). $^1$H NMR (400 MHz, DMSOd$_6$): δ 8.31 (s, 1H), 8.28 (s, 1H), 8.26 (s, 1H), 8.06 (d, J=7.8 Hz, 1H), 8.02-7.99 (m, 2H), 7.76 (d, J=7.3 Hz, 2H), 7.67-7.58 (m, 5H), 7.44-7.37 (m, 3H). HRMS (ESI) calcd. for $C_{24}H_{17}NO_2S$ [M+H]$^+$: 384.1053. Found: 384.1081.

Example 37: 4-(3'-(2H-Tetrazol-5-yl)biphenyl-3-yl)-2-phenylthiazole

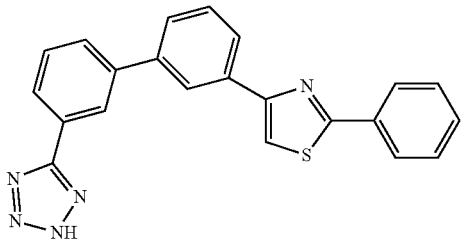 [SMILES: c1ccc(-c2nc(-c3cccc(-c4cccc(-c5nn[nH]n5)c4)c3)cs2)cc1]

3'-(2-Phenylthiazol-4-yl)biphenyl-3-carbonitrile (0.169 g, 0.5 mmol), sodium azide (0.390 g, 6 mmol), and ammonium chloride (0.324 g, 6 mmol) were taken in DMF (6 mL) and the resulting mixture was heated at 100° C. for 1 h. The reaction mixture cooled to room temperature and diluted with water and followed a usual work up with ethyl acetate. The crude residue was purified by prep-HPLC to yield the desired compound as a white solid (0.104 g, 55%). $^1$H NMR (400 MHz, DMSOd$_6$): δ 8.42 (s, 2H), 8.37 (s, 1H), 8.15-8.06 (m, 4H), 8.00 (d, J=7.8 Hz, 1H), 7.78-7.74 (m, 2H), 7.66 (t, J=7.8 Hz, 1H), 7.58-7.53 (m, 3H). HRMS (ESI) calcd. for $C_{22}H_{15}N_5S$ [M+H]$^+$: 382.1121. Found: 382.1133.

General Synthetic Scheme for the Preparation of Thiadiazole Analogues

Scheme 3

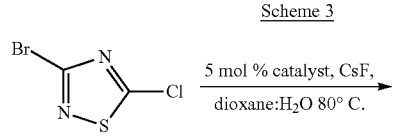

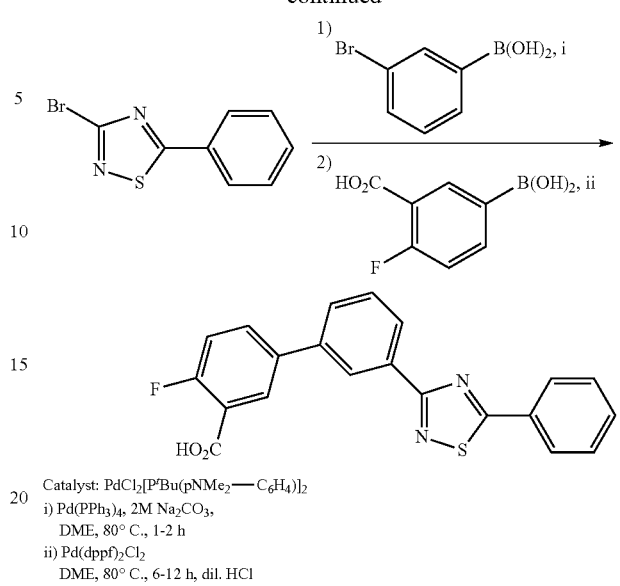

Catalyst: PdCl$_2$[P$^t$Bu(pNMe$_2$—C$_6$H$_4$)]$_2$
i) Pd(PPh$_3$)$_4$, 2M Na$_2$CO$_3$, DME, 80° C., 1-2 h
ii) Pd(dppf)$_2$Cl$_2$ DME, 80° C., 6-12 h, dil. HCl

Example 38: 4-Fluoro-3'-(5-phenyl-1,2,4-thiadiazol-3-yl)biphenyl-3-carboxylic Acid

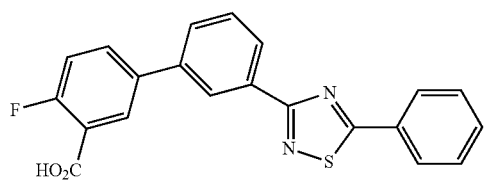 [SMILES: O=C(O)c1cc(-c2cccc(-c3nsc(-c4ccccc4)n3)c2)ccc1F]

Step 1: 3-Bromo-5-phenyl-1,2,4-thiadiazole

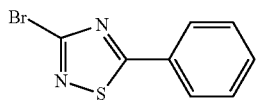

To a mixture of 3-bromo-5-chloro-1,2,4-thiadiazole (2 g, 10 mmol), cesium fluoride (3 g, 20 mmol), and phenylboronic acid (1.46 g, 12 mmol) in 1,4-dioxane w/10% H$_2$O (100 mL) was added PdCl$_2${PtBu$_2$(p-NMe$_2$-C$_6$H$_4$)} (0.354, 0.5 mmol). The resulting mixture was 80° C. for 16 h under nitrogen atmosphere. Volatile materials were removed under vacuum. The crude residue was portioned between water and ethyl acetate. The organic phase was separated and the aqueous phase was extracted further with ethyl acetate. The combined organic extracts were dried over anhydrous Na$_2$SO4, filtered, and concentrated. Purification by flash column chromatography on silica gel using hexanes:ethyl acetate gave the desired product as a colorless solid (2.03 g, 84%). $^1$H NMR (400 MHz, CDCl$_3$): δ 7.96 (d, J=7.3 Hz, 2H), 7.56-7.62 (m, 1H), 7.50-7.56 (m, 2H). LRMS (ESI) calcd. for $C_8H_5BrN_2S$: 240.93. Found: 240.00.

Step 2:
3-(3-Bromophenyl)-5-phenyl-1,2,4-thiadiazole

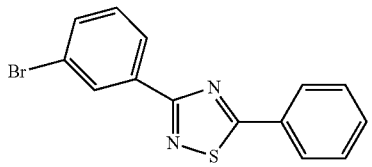 [SMILES: Brc1cccc(-c2nsc(-c3ccccc3)n2)c1]

A mixture of 3-bromo-5-phenyl-1,2,4-thiadiazole (0.770 g, 3.2 mmol), 3-bromophenylboronic acid (0.767 g, 3.83 mmol) and tetrakistriphenylphosphinepalladium(0) (0.369 g, 0.32 mmol) were taken in 25 mL DME. To this 2M Na$_2$CO$_3$ (3.2 mL, 6.4 mmol) solution was added and the resulting solution was heated at reflux in an atmosphere of N$_2$ for 2 h. It was then processed according to the general procedure in Example 1, step 2, to afford the desired product as a colorless solid (0.657 g, 65%). $^1$H NMR (400 MHz, CDCl$_3$): δ 8.54 (t, J=3.7 Hz, 1H), 8.31 (d, J=7.5 Hz, 1H), 8.04 (dd, J=1.8 Hz, 9.6 Hz, 2H), 7.59 (d, J=8.2 Hz, 1H), 7.54-7.49 (m, 4H), 7.37 (t, J=7.8 Hz, 1H). LRMS (ESI) calcd. for C$_{14}$H$_9$BrN$_2$S: 316.97. Found: 317.00.

Step 3: 4-Fluoro-3'-(5-phenyl-1,2,4-thiadiazol-3-yl)biphenyl-3-carboxylic Acid

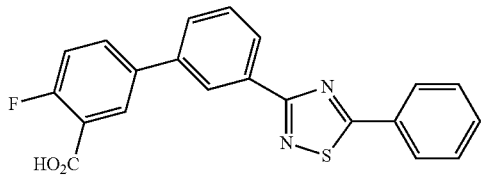 [SMILES: O=C(O)c1cc(-c2cccc(-c3nsc(-c4ccccc4)n3)c2)ccc1F]

3-(3-Bromophenyl)-5-phenyl-1,2,4-thiadiazole (0.075 g, 0.24 mmol), 5-borono-2-fluorobenzoic acid (0.064 g, 0.35 mmol), Pd(dppf)$_2$Cl$_2$ (0.018 g, 0.024 mmol) and 2M Na$_2$CO$_3$ (0.48 mL) were dissolved in DME. The reaction mixture was then processed according to the general procedure described in Example 1, step 3, to afford the desired product as a white solid (0.059 g, 66%). $^1$H NMR (400 MHz, DMSOd$_6$): δ 8.51 (s, 1H), 8.30 (d, J=6.9 Hz, 2H), 8.22-7.96 (m, 2H), 7.86 (d, J=7.8 Hz, 1H), 7.68-7.55 (m, 5H). 7.42 (t, J=7.3 Hz, 1H). HRMS (ESI) calcd. for C$_{21}$H$_{13}$FN$_2$O$_2$S [M+H]$^+$: 377.0755. Found: 377.0770.

The following compounds were synthesized according to the procedure described for 4-fluoro-3'-(5-phenyl-1,2,4-thiadiazol-3-yl)biphenyl-3-carboxylic acid (Example 38) using appropriate starting materials. Yields refer to the final coupling reaction.

Example 39: 3'-(5-Phenyl-1,2,4-thiadiazol-3-yl)biphenyl-3-carboxylic Acid

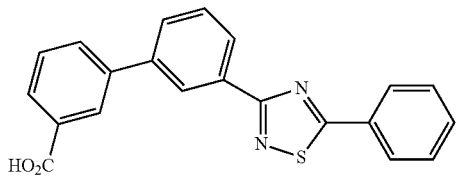 [SMILES: O=C(O)c1cccc(-c2cccc(-c3nsc(-c4ccccc4)n3)c2)c1]

White solid (0.054 g, 63%). $^1$H NMR (400 MHz, DMSOd$_6$): δ 8.53 (s, 1H), 8.30 (d, J=7.8 Hz, 1H), 8.23 (s, 1H), 8.10 (d, J=6.9 Hz, 2H), 7.98 (t, J=8.2 Hz, 2H), 7.86 (d, J=7.8 Hz, 1H), 7.68-7.57 (m, 5H). HRMS (ESI) calcd. for C$_{21}$H$_{14}$FN$_2$O$_2$S [M+H]$^+$: 359.0849. Found: 359.0856.

Example 40: 5-Fluoro-3'-(5-phenyl-1,2,4-thiadiazol-3-yl)biphenyl-3-carboxylic Acid

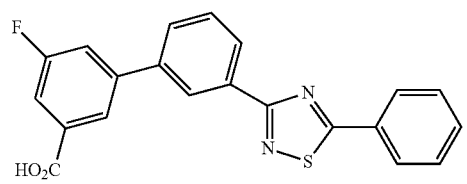 [SMILES: O=C(O)c1cc(F)cc(-c2cccc(-c3nsc(-c4ccccc4)n3)c2)c1]

White solid (0.032 g, 36%). $^1$H NMR (400 MHz, DMSOd$_6$): δ 8.59 (d, J=1.4 Hz, 1H), 8.34 (dd, J=0.9 Hz, 8.2 Hz, 1H), 8.15-8.09 (m, 3H), 7.92 (t, J=7.8 Hz, 2H), 7.72-7.59 (m, 5H). HRMS (ESI) calcd. for C$_{21}$H$_{13}$FN$_2$O$_2$S [M+H]$^+$: 377.755. Found: 377.0760.

Example 41: 6-Fluoro-3'-(5-phenyl-1,2,4-thiadiazol-3-yl)biphenyl-3-carboxylic Acid

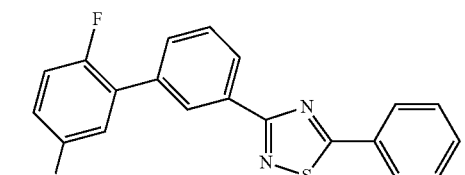

White solid (0.025 g, 28%). $^1$H NMR (400 MHz, DMSOd$_6$): δ 8.45 (s, 1H), 8.19 (s, 1H), 8.35 (d, J=7.3 Hz, 1H), 8.11-8.09 (m, 3H), 8.02-7.99 (m, 1H), 7.75 (d, J=7.8 Hz, 1H), 7.70 (t, J=7.8 Hz, 1H), 7.64-7.60 (m, 2H), 7.50-7.40 (m, 1H). LRMS (ESI) calcd. for C$_{21}$H$_{13}$FN$_2$O$_2$S [M+H]$^+$: 377.0755. Found: 377.0759.

Example 42: 4-Fluoro-3'-(5-(furan-3-yl)-1,2,4-thiadiazol-3-yl)biphenyl-3-carboxylic Acid

White solid (0.023 g, 26%). $^1$H NMR (400 MHz, DMSOd$_6$): δ8.75 (t, J=0.9 Hz, 1H), 8.47 (s, 1H), 8.26 (d, J=7.8 Hz, 1H), 8.02-8.00 (m, 1H), 7.95 (t, J=1.8 Hz, 1H), 7.86-7.82 (m, 2H), 7.66 (t, J=7.8 Hz, 1H), 7.36 (t, J=8.2 Hz, 1H), 7.14 (d, J=1.8 Hz, 1H). LRMS (ESI) calcd. for C$_{19}$H$_{11}$FN$_2$O$_3$S [M+H]$^+$: 367.05. Found: 376.00.

119

Example 43: 5-Fluoro-3'-(5-(furan-3-yl)-1,2,4-thiadiazol-3-yl)biphenyl-3-carboxylic Acid

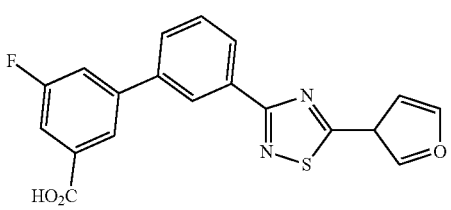

White solid (0.019 g, 21%). $^1$H NMR (400 MHz, DMSO-d$_6$): δ 8.77 (s, 1H), 8.54 (s, 1H), 8.33 (d, J=7.8 Hz, 1H), 8.10 (s, 1H), 7.97 (t, J=1.4 Hz, 1H), 7.7-7.92 (m, 2H), 7.70 (t, J=7.8 Hz, 2H), 7.16 (d, J=1.8 Hz, 1H). HRMS (ESI) calcd. for $C_{19}H_{11}FN_2O_3S$ [M+H]$^+$: 367.0547. Found: 367.0552.

General Synthetic Scheme for the Preparation of 3'-(5-Phenylisothiazol-3-yl)-[1,1'-biphenyl]-3-carboxylic Acid Scheme 4

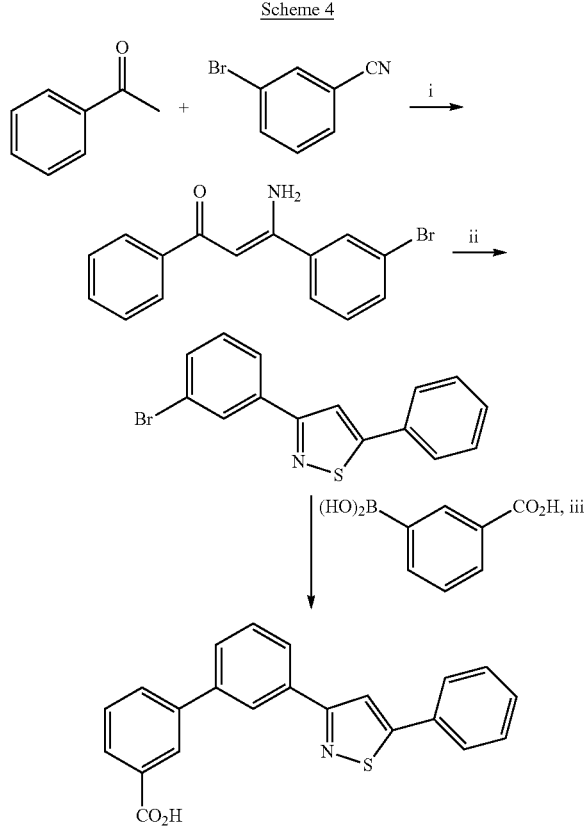

i) CuI, 2,2'-bipyridine, NaO$^t$Bu, DMF, 80° C., 12 h
ii) P$_4$S$_{10}$, NaHCO$_3$, THF, rt, 15 h
  Chloranil, 12 h
iii) Pd(PPh$_3$)$_4$, 2M Na$_2$CO$_3$, DME, reflux, 1-2 h
  dil. HCl

120

Example 44: 3'-(5-Phenylisothiazol-3-yl)-[1,1'-biphenyl]-3-carboxylic Acid

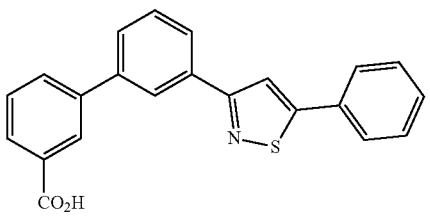

Steps 1 and 2:
3-(3-Bromophenyl)-5-phenylisothiazole

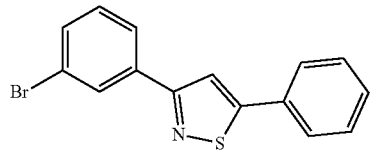

A mixture of acetophenone (0.7 mL, 6 mmol), 3-bromobenzonitrile (0.91 g, 5 mmol), Cu(I)I (0.095 g, 0.05 mmol), 2,2'bipyridine (0.0.086 g, 0.055 mmol) and NaO$^t$Bu (0.96 g, 10 mmol) in DMF (10 mL) was heated at 80° C. for 24 h. After completion of the reaction, the solvent was evaporated, and the residue was extracted with ethyl acetate (3×25 mL). The combined extracts were washed with water, brine and dried over anhydrous Na$_2$SO$_4$. After evaporation of the solvent, the residue was purified by column chromatography to give 0.302 g (20%) of the 3-amino-3-(3-bromophenyl)-1-phenylprop-2-en-1-one as a reddish brown solid. LRMS (ESI) calcd. for $C_{15}H_{12}BrNO$ [M+H]$^+$: 300.13. Found: 300.00. To a mixture of enaminone (0.302 g, 1 mmol) and P$_4$S$_{10}$ (0.134 g, 0.3 mmol) in THF (10 mL) was added NaHCO$_3$ (0.084 g, 1 mmol) and the resulting mixture was stirred at room temperature for 15 h. Chloranil (0.142 g, 0.58 mmol) was added to the mixture and the stirring was continued for another 12 h. The reaction mixture was diluted with ether and filtered and the filtrate was washed with saturated NaHCO$_3$ solution. Evaporation off the organic layer under reduced pressure afforded the crude product which was purified by column chromatography using hexanes:ethyl acetate to obtain the desired product as a yellow solid (0.180 g, 57%). $^1$H NMR (400 MHz, CDCl$_3$): δ 8.14 (t, J=1.8 Hz, 1H), 7.90 (dd, J=1.4 Hz, 9.2 Hz, 1H), 7.70 (s, 1H), 7.65 (dd, J=1.4 Hz, 9.2 Hz, 2H), 7.54-7.52 (m, 1H), 7.48-7.42 (m, 3H), 7.34 (t, J=7.8 Hz, 1H). LRMS (ESI) calcd. for $C_{15}H_{10}BrNS$ [M+H]$^+$: 317.22. Found: 317.00.

Step 3: 3'-(5-Phenylisothiazol-3-yl)-[1,1'-biphenyl]-3-carboxylic Acid

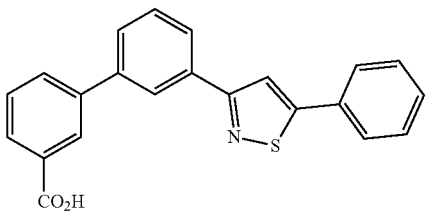

3-(3-Bromophenyl)-5-phenylisothiazole (0.180 g, 0.57 mmol) and 3-boronobenzene boronic acid (0.141 g, 0.86 mmol), tetrakistriphenylphosphinepalladium(0) (0.065 g, 0.057 mmol) and 2M Na$_2$CO$_3$ (1.14 mL) were dissolved in DME. The reaction mixture was then processed according to the general procedure described in Example 1, step 3, to afford the desired product as a colorless solid (0.035 g, 17%). $^1$H NMR (400 MHz, DMSOd$_6$): δ8.53 (s, 1H), 8.36 (s, 1H), 8.24 (s, 1H), 8.11 (d, J=7.8 Hz, 1H), 8.01 (d, J=7.8 Hz, 1H), 7.95 (d, J=7.8 Hz, 1H), 7.82 (dd, J=1.4 Hz, 8.2 Hz, 2H), 7.76 (d, J=7.8 Hz, 1H), 7.63-7.59 (m, 2H), 7.52-7.45 (m, 3H). HRMS (ESI) calcd. for C$_{22}$H$_{15}$NO$_2$S [M+H]$^+$: 358.0896. Found: 358.0904.

Example 45: 4-Fluoro-3'-(5-phenylthiophen-3-yl)-[1,1'-biphenyl]-3-carboxylic Acid Scheme 5

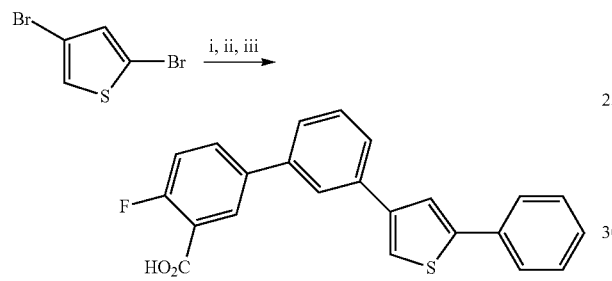

i) PhB(OH)$_2$ Pd(PPh$_3$)$_4$, 2M Na$_2$CO$_3$, toluene:water, 100° C., 4 h
ii) 3-bromo-phenylboronicacid, Pd(PPh$_3$)$_4$, 2M Na$_2$CO$_3$, DME, reflux, 1-2 h
iii) 3-borono-benzenecarboxylic acid, Pd(PPh$_3$)$_4$, 2M Na$_2$CO$_3$, DME, reflux, 12 h A mixture of 2,4-dibromo thiophene (0.500 g, 2.07 mmol), benzene boronic acid (0.253 g, 2.07 mmol), Na$_2$CO$_3$ (0.438 g, 4.13 mmol), and tetrakis(triphenylphosphine) palladium (0.012 g, 0.01) in an oxygen free toluene/water (1:1) solution was stirred at 100° C. for 4 h under nitrogen. The reaction mixture was cooled to room temperature. The aqueous layer was extracted with ethyl acetate. The combined organic layer was washed with brine, dried over Na$_2$SO$_4$, filtered, and concentrated to dryness. The product was purified by column chromatography using hexanes/ethyl acetate to afford 4-bromo-2-phenylthiophene as a pale yellow solid (0.200 g, 42%), LRMS (ESI) calcd. for C$_{10}$H$_7$BrS [M+H]$^+$: 238.94. Found: 239.00. 4-Bromo-2-phenylthiophene (0.200 g, 0.84 mmol) and 3-bromophenyl-boronic acid (0.200 g, 1 mmol) and tetrakistriphenylphos-phinepalladium(0) (0.097 g, 0.084 mmol) were dissolved in DME. The reaction mixture was then processed according to the general procedure described in Example 1, step 2, to afford 4-(3-bromophenyl)-2-phenylthiophene as a colorless solid (0.187 g, 65%). LRMS (ESI) calcd. for C$_{16}$H$_{11}$BrS [M+H]$^+$: 314.98. Found: 315.00. 4-(3-Bromophenyl)-2-phenylthiophene (0.157 g, 0.5 mmol) and 3-borono-4-fluorobenzoic acid (0.143 g, 0.75 mmol) tetrakistriphenylphos-phinepalladium(0) (0.058 g, 0.05 mmol) and 2M Na$_2$CO$_3$ (1 mL) were dissolved in DME. The reaction mixture was then processed according to the general procedure described in Example 1, step 3, to afford the title compound as a yellow solid (0.080 g, 43%). $^1$H NMR (400 MHz, DMSOd$_6$): δ8.19-8.15 (m, 2H), 8.09-8.04 (m, 3H), 7.85 (d, J=7.8 Hz, 1H), 7.80 (d, J=8.2 Hz, 2H), 7.60 (d, J=7.8 Hz, 1H), 7.57-7.55 (m, 1H), 7.46-7.33 (m, 4H). HRMS (ESI) calcd. for C$_{23}$H$_{15}$FO$_2$S [M+H]$^+$: 375.0850. Found: 375.0892.

General Synthetic Scheme for the Preparation of 3'-(5-phenylfuran-3-yl)biphenyl-3-carboxylic Acid Scheme 6

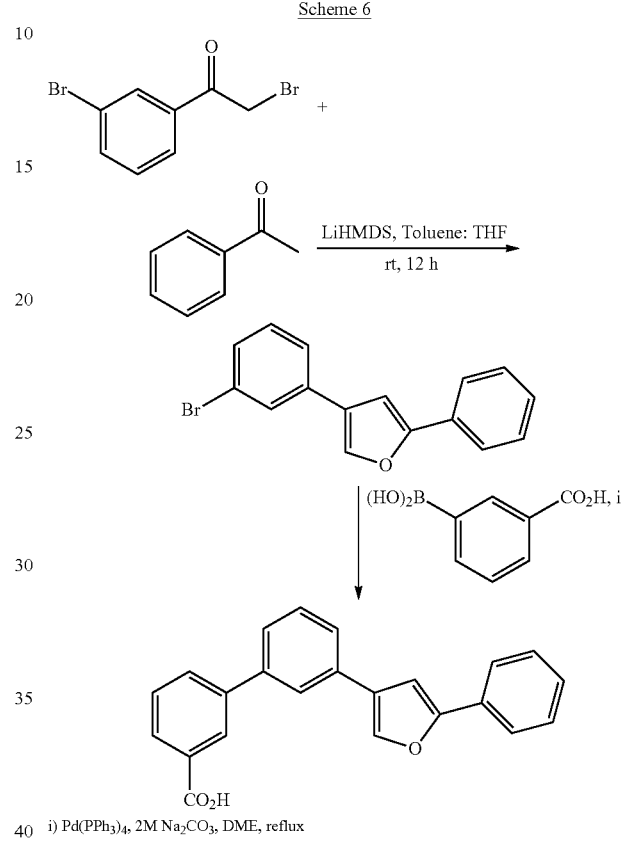

i) Pd(PPh$_3$)$_4$, 2M Na$_2$CO$_3$, DME, reflux

Example 46: 3'-(5-phenylfuran-3-yl)biphenyl-3-carboxylic Acid

Step 1: 4-(3-Bromophenyl)-2-phenylfuran

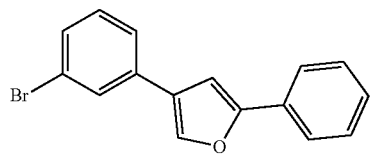 [SMILES: Brc1cccc(-c2coc(-c3ccccc3)c2)c1]

To a solution of acetophenone (1.03 g, 11 mmol) in toluene (5 mL) was added LiHMDS (7.1 mL, 1.5 M in THF) at 0° C. The resulting mixture was stirred at the same temperature for 30 min. To this a solution of 3'-bromo-phenacylbromide (2.77 g, 10 mml) in THF (10 mL) was added and the resulting solution was stirred at room temperature for 12 h. The reaction mixture was diluted with water and extracted with ethyl acetate. The organic layer washed with brine and dried over anhydrous sodium sulfate. Removal of solvent under reduced pressure afforded the crude product which was purified by column chromatography using hexanes:ethyl acetate solvent system to obtain the desired product as a yellow solid (2 g, 67%). $^1$H NMR (400 MHz, CDCl$_3$): δ 7.74 (d, J=0.9 Hz, 1H), 7.71-7.66 (m, 3H), 7.45-7.39 (m, 4H), 7.31-7.23 (m, 2H), 6.92 (d, J=0.9 Hz, 1H). LRMS (ESI) calcd. for C$_{16}$H$_{11}$BrO [M+H]$^+$: 300.16. Found: 300.00.

Step 2:
3'-(5-Phenylfuran-3-yl)biphenyl-3-carboxylic Acid

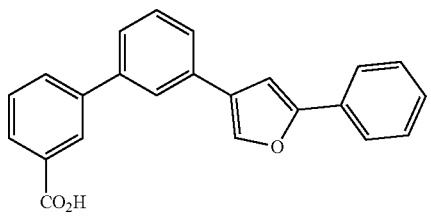 [SMILES: O=C(O)c1cccc(-c2cccc(-c3coc(-c4ccccc4)c3)c2)c1]

4-(3-Bromophenyl)-2-phenylfuran (0.100 g, 0.33 mmol) and 3-boronobenzene boronic acid (0.082 g, 0.49 mmol, tetrakistriphenylphosphinepalladium(0) (0.038 g, 0.033 mmol) and 2M Na$_2$CO$_3$ (0.66 mL) were dissolved in DME. The reaction mixture was then processed according to the general procedure described in Example 1, step 3, to afford the title compound as a yellow solid (0.053 g, 47%). $^1$H NMR (400 MHz, DMSOd$_6$): δ8.41 (s, 1H), 8.27 (t, J=1.4 Hz, 1H), 8.02-7.98 (m, 3H), 7.79 (d, J=7.3 Hz, 2H), 7.72 (d, J=7.8 Hz, 1H), 7.66-7.60 (m, 3H), 7.59 (t, J=7.3 Hz, 1H), 7.46 (t, J=7.8 Hz, 2H), 7.33 (t, J=7.3 Hz, 1H). LRMS (ESI) calcd. for C$_{23}$H$_{16}$O$_3$[M+H]$^+$: 341.37. Found: 341.00.

General Synthetic Scheme for the Preparation of 3'-(2-phenyloxazol-4-yl)-[1,1'-biphenyl]-3-carboxylic Acid Scheme 7

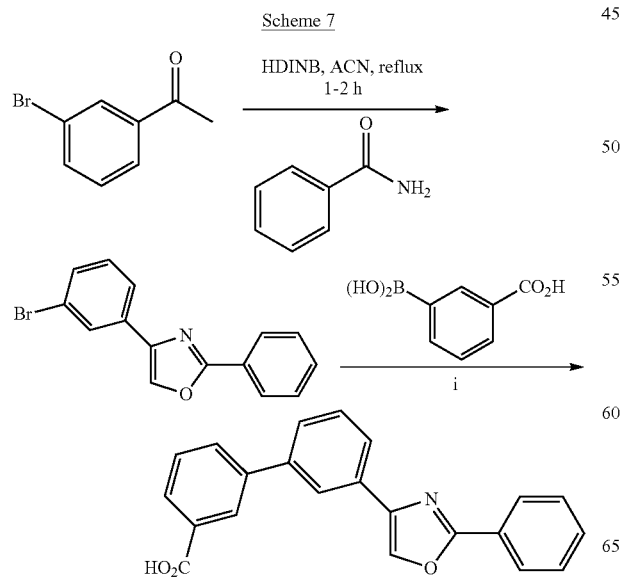

HDINB =
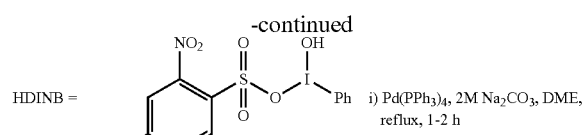
i) Pd(PPh$_3$)$_4$, 2M Na$_2$CO$_3$, DME, reflux, 1-2 h

Example 47: 3'-(2-Phenyloxazol-4-yl)-[1,1'-biphenyl]-3-carboxylic Acid

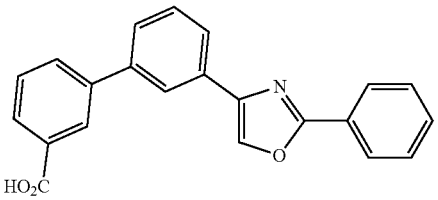 [SMILES: O=C(O)c1cccc(-c2cccc(-c3coc(-c4ccccc4)n3)c2)c1]

Step 1: 4-(3-Bromophenyl)-2-phenyloxazole

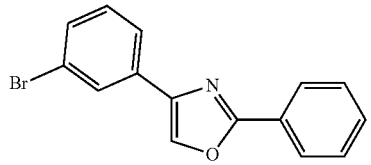 [SMILES: Brc1cccc(-c2coc(-c3ccccc3)n2)c1]

To a solution of 3-bromo-acetophenone (1.99 g, 10 mmol) in ACN (100 mL) was added HDINB (5.56 g, 12 mmol) and stirred for 2 h with reflux. After cooling to room temperature, 3-bromo-benzamide (3.63 g, 30 mmol) was added in one portion and the reaction mixture was refluxed for additional 12 h. Solvent was removed under vacuum and the crude reaction mixture was diluted with dichloromethane and water. The organic layer washed with sodium bicarbonate, water and dried over anhydrous sodium sulfate. After evaporation of the solvent, the residue was purified by column chromatography using hexanes:ethyl acetate to afford 4-(3-bromophenyl)-2-phenyloxazole as a pale yellow solid (2.2 g, 73%). $^1$H NMR (400 MHz, CDCl$_3$): δ 8.12-8.09 (m, 2H), 7.99 (t, J=1.4 Hz, 1H), 7.95 (s, 1H), 7.72 (d, J=7.8 Hz, 1H), 7.48-7.43 (m, 4H), 7.29 (t, J=7.8 Hz, 1H). LRMS (ESI) calcd. for C$_{15}$H$_{10}$BrON [M+H]$^+$: 301.15. Found: 301.13.

Step 2: 3'-(2-Phenyloxazol-4-yl)-[1,1'-biphenyl]-3-carboxylic Acid

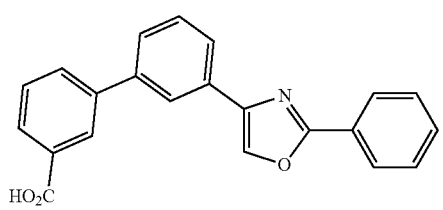 [SMILES: O=C(O)c1cccc(-c2cccc(-c3coc(-c4ccccc4)n3)c2)c1]

4-(3-Bromophenyl)-2-phenyloxazole (0.150 g, 0.5 mmol) and 3-boronobenzene boronic acid (0.124 g, 0.75 mmol), tetrakistriphenylphosphinepalladium(0) (0.058 g, 0.05 mmol) and 2M Na$_2$CO$_3$ (1 mL) were dissolved in DME. The reaction mixture was then processed according to the general procedure described in Example 1, step 3, to afford the title compound as a white solid (0.065 g, 38%). $^1$H NMR (400 MHz, DMSOd$_6$): δ 8.84 (s, 1H), 8.21 (s, 1H), 8.13 (s, 1H), 8.05-8.03 (m, 2H), 7.95-7.93 (m, 2H), 7.88 (d, J=7.8 Hz, 1H), 7.64-7.52 (m, 6H). HRMS (ESI) calcd. for C$_{22}$H$_{15}$NO$_3$ [M+H]$^+$: 342.1125. Found: 342.1131.

General Synthetic Scheme for the Preparation of 3'-(5-phenyl-1,2,4-oxadiazol-3-yl)-[1,1'-biphenyl]-3-carboxylic Acid Scheme 8

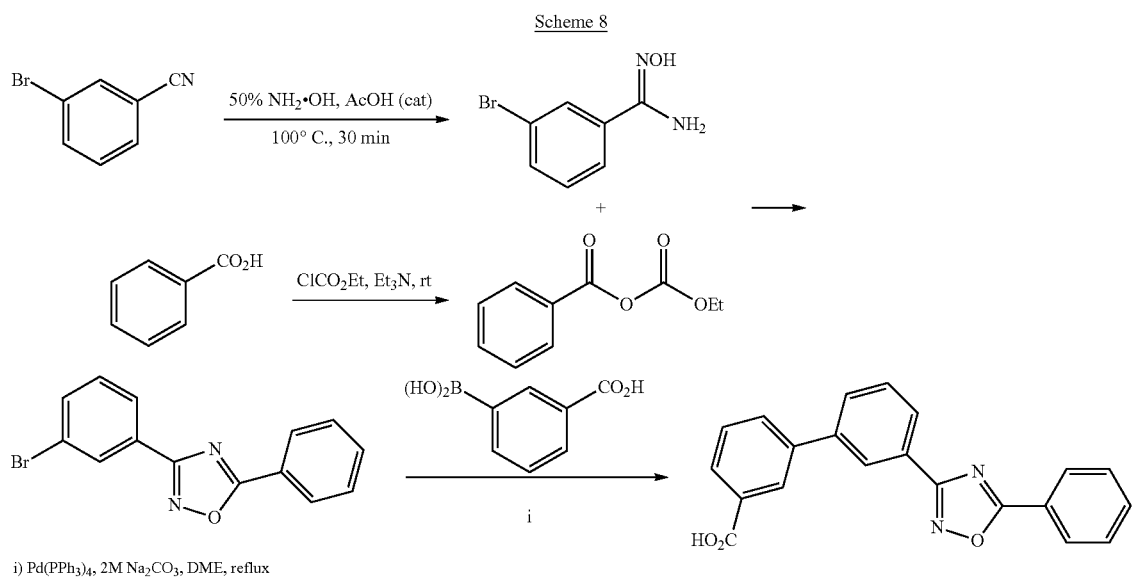

i) Pd(PPh$_3$)$_4$, 2M Na$_2$CO$_3$, DME, reflux

Example 48: 3'-(5-Phenyl-1,2,4-oxadiazol-3-yl)-[1,1'-biphenyl]-3-carboxylic Acid

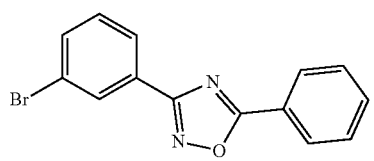 [SMILES: Brc1cccc(-c2noc(-c3ccccc3)n2)c1]

Step 1: 3-(3-Bromophenyl)-5-phenyl-1,2,4-oxadiazole

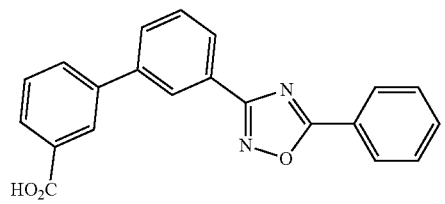

To a mixture of benzoic acid (0.610 g, 5 mmol) and Et$_3$N (1.4 mL, 10 mmol) in dichloromethane at 0° C., was added methyl chloroformate (0.46 mL, 6 mmol) drop wise. The resulting mixture as gradually warmed to room temperature and stirred for additional 30 min. To this, 3-bromo-N'-hydroxybenzimide (1.05 g, 5 mmol) was added and stirred at 35-40° C. for 12 h. The reaction mixture was cooled to room temperature and washed with saturated sodium bicarbonate solution (20 mL). The organic layer was washed with brine, dried over Na$_2$SO$_4$ followed by removal of the solvent under vacuum to afford the crude product. The crude product was purified by silica gel column chromatography using hexane:ethyl acetate solvent system to give the title compound as a white solid (1.4 g, 93%). $^1$H NMR (400 MHz, CDCl$_3$): δ 8.33 (s, 1H), 8.19 (d, J=8.2 Hz, 2H), 8.10 (dd, J=1.4 Hz, 7.8 Hz, 1H), 7.63-7.50 (m, 4H), 7.35 (t, J=8.2 Hz, 1H). LRMS (ESI) calcd. for C$_{14}$H$_9$BrN$_2$O [M+H]$^+$: 302.14. Found: 302.00.

Step 2: 3'-(5-Phenyl-1,2,4-oxadiazol-3-yl)-[1,1'-biphenyl]-3-carboxylic Acid

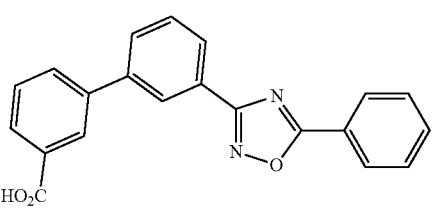

3-(3-Bromophenyl)-5-phenyl-1,2,4-oxadiazole (0.283 g, 0.93 mmol) and 3-boronobenzoic acid (0.230 g, 1.4 mmol), tetrakistriphenylphosphinepalladium(0) (0.107 g, 0.05 mmol) and 2M Na$_2$CO$_3$ (1.86 mL) were dissolved in DME. The reaction mixture was then processed according to the general procedure described in Example 1, step 3, to afford the title compound as a white solid (0.053 g, 17%). $^1$H NMR (400 MHz, DMSOd$_6$): δ8.29 (s, 1H), 8.21-8.17 (m, 3H), 8.09 (d, J=7.8 Hz, 1H), 7.99-7.97 (m, 2H), 7.93 (d, J=7.8 Hz, 1H), 7.72-7.76 (m, 5H). LRMS (ESI) calcd. for C$_{21}$H$_{14}$N$_2$O$_3$ [M+H]$^+$: 343.35. Found: 343.00.

General Synthetic Scheme for the Preparation of 3'-(5-phenylisoxazol-3-yl)-[1,1'-biphenyl]-3-carboxylic Acid Scheme 9

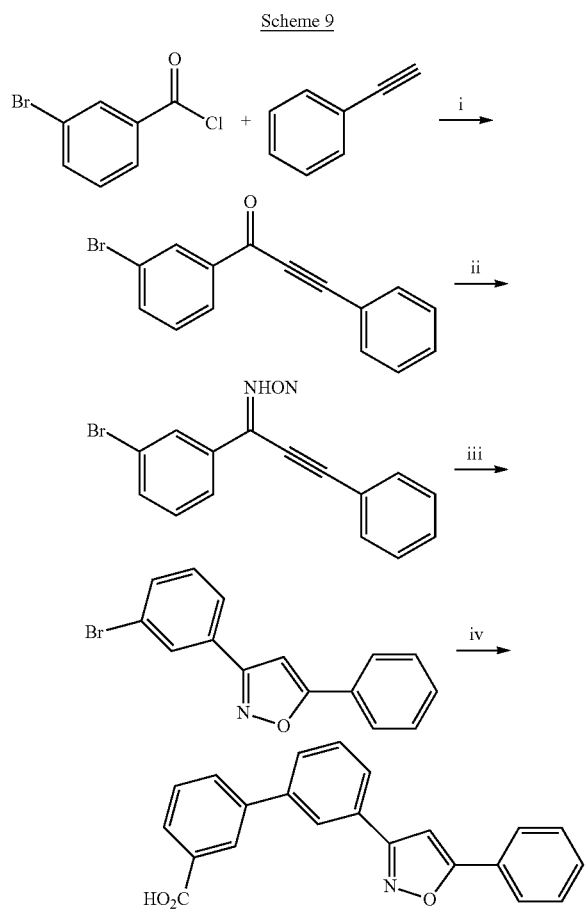

i) Cat PdCl$_2$, (PPh$_3$)$_2$, Cat. CuI, Et$_3$N, rt, 12 h
ii) NH$_2$OH•HCl, Py, MeOH, rt
iii) AuCl$_3$ (1 mol %), DCM, reflux, 30 min
iv) Pd(PPh$_3$)$_4$, 2M Na$_2$CO$_3$, DME, reflux Example 49: 3'-(5-Phenylisoxazol-3-yl)-[1,1'-biphenyl]-3-carboxylic Acid

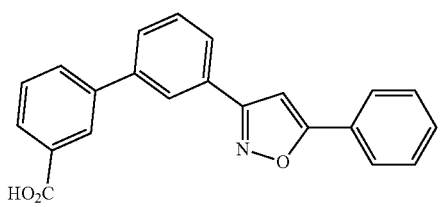 [SMILES: O=C(O)c1cccc(-c2cccc(-c3cc(-c4ccccc4)on3)c2)c1]

Step 1: 3-(3-Bromophenyl)-5-phenylisoxazole

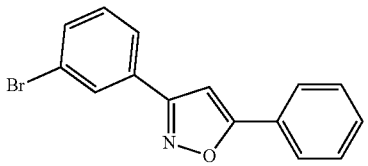 [SMILES: Brc1cccc(-c2cc(-c3ccccc3)on2)c1]

To a solution of 1-(3-bromophenyl)-3-phenylprop-2-yn-1-one oxime (0.966 g, 3.22 mmol) in dichloromethane was added AuCl$_3$ (0.01 g). The mixture was then heated at reflux under an atmosphere of N$_2$ for 30 min. The solvent was evaporated and the crude residue was purified by column chromatography using hexanes:ethyl acetate to obtain 3-(3-bromophenyl)-5-phenylisoxazole as a pale yellow solid (0.958 g, 99%). $^1$H NMR (400 MHz, CDCl$_3$): δ 8.01 (s, 1H), 7.81-7.80 (m, 3H), 7.57 (d, J=8.2 Hz, 1H), 7.56-7.47 (m, 3H), 7.33 (t, J=7.8 Hz, 1H), 6.79 (s, 1H). LRMS (ESI) calcd. for C$_{15}$H$_{10}$BrNO[M+H]$^+$: 301.15. Found: 301.13.

Step 2: 3'-(5-Phenylisoxazol-3-yl)-[1,1'-biphenyl]-3-carboxylic Acid

3-(3-Bromophenyl)-5-phenylisoxazole (0.300 g, 1 mmol)-3-boronobenzoic acid (0.247 g, 1.5 mmol), tetrakis-triphenylphosphinepalladium(0) (0.115 g, 0.1 mmol) and 2M Na$_2$CO$_3$ (2 mL) were dissolved in DME. The reaction mixture was then processed according to the general procedure described in Example 1, step 3, to afford the title compound as a yellow solid (0.247 g, 72%). $^1$H NMR (400 MHz, DMSOd$_6$): δ8.25 (s, 1H), 8.18 (s, 1H), 7.98-7.88 (m, 5H), 7.81 (d, J=7.8 Hz, 1H), 7.72 (s, 1H), 7.66-7.58 (m, 2H), 7.56-7.47 (m, 3H). LRMS (ESI) calcd. for C$_{22}$H$_{15}$NO$_3$ [M+H]$^+$: 342.11. Found: 342.00. HRMS (ESI) calcd. for C$_{22}$H$_{15}$NO$_3$ [M+H]$^+$: 342.1125. Found: 342.1156.

General Synthetic Scheme for the Preparation of 3'-(1,5-diphenyl-1H-1,2,4-triazol-3-yl)-[1,1'-biphenyl]-3-carboxylic Acid Scheme 10

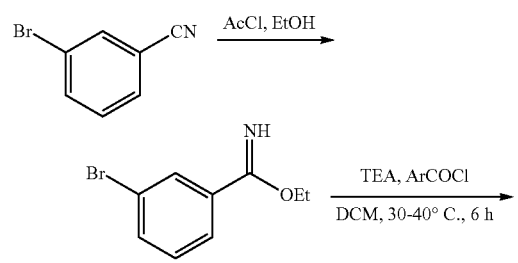

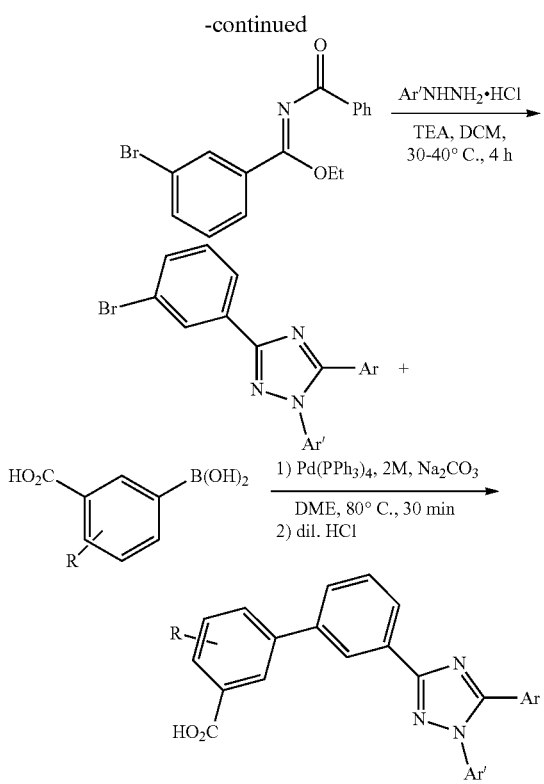

Example 49A: 3'-(1,5-Diphenyl-1H-1,2,4-triazol-3-yl)-[1,1'-biphenyl]-3-carboxylic Acid

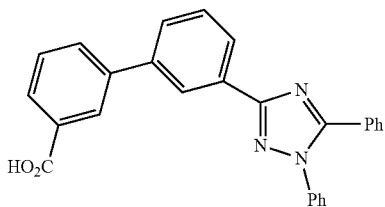

Steps 1-3:
3-(3-Bromophenyl)-1,5-diphenyl-1H-1,2,4-triazole

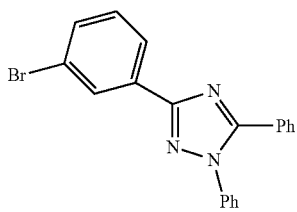 [SMILES: Brc1cccc(-c2nc(-c3ccccc3)n(-c3ccccc3)n2)c1]

Acetyl chloride (16 mL, 160 mmol) was added to a solution of 3-bromo-benzonitrile (3.64 g, 20 mmol) in ethanol (14 mL, 240 mmol). The resulting mixture was stirred at room temperature for 16 h. Volatile materials were removed under vacuum to give ethyl 3-bromobenzimidate hydrochloride as a white solid (3.5 g, 78%). $^1$H NMR (400 MHz, CDCl$_3$): δ 12.06 (brs, 1H), 8.53 (d, J=7.8 Hz, 1H), 8.33 (s, 1H), 7.79 (d, J=8.2 Hz, 1H), 7.45 (t, J=7.8 Hz, 1H), 4.91 (t, q, J=6.9 Hz, 2H), 1.61 (t, J=6.9 Hz, 3H). LRMS (ESI) calcd. for C$_9$H$_{10}$BrNO[M+H]$^+$: 227.99. Found: 228.00. Benzoyl chloride (0.76 mL, 6.58 mmol) was added in dropwise to a solution of 3-bromobenzimidate hydrochloride (1.5 g, 6.58 mmol) and Et$_3$N (0.91 mL, 6.58 mmol) in dichloromethane (50 mL). The resulting mixture was stirred at 30-40° C. for 6 h. After cooling to room temperature, the reaction mixture was poured into saturated sodium bicarbonate solution. The organic layer was washed with water, brine and dried over Na$_2$SO$_4$ to obtain ethyl (Z)—N-benzoyl-3-bromobenzimidate as a colorless solid (2.2 g, quantitative yield) which was used for next step without further purification. LRMS (ESI) calcd. for C$_{16}$H$_{14}$BrNO$_2$[M+H]$^+$: 332.02. Found: 332.00. Ethyl (Z)—N-benzoyl-3-bromobenzimidate (2.2 g, 6.58 mmol), phenyl hydrazine hydrochloride (1.9 g, 13.16 mmol), Et$_3$N (1.8 mL, 13.16 mmol) were taken in dichloromethane (50 mL) and heated at 30-40° C. for 4 h. Cooled to room temperature and diluted with water and followed by a usual work up with dichloromethane. Evaporation of the solvent followed by silica gel column chromatography using hexanes:ethyl acetate afforded 3-(3-bromophenyl)-1,5-diphenyl-1H-1,2,4-triazole as a white solid (1.8 g, 73%). $^1$H NMR (400 MHz, CDCl$_3$): δ8.40 (t, J=1.8 Hz, 1H), 8.14 (dd, J=1.3 Hz, 8.2 Hz, 1H), 7.54-7.52 (m, 3H), 7.43-7.41 (m, 9H). LRMS (ESI) calcd. for C$_{20}$H$_{14}$BrN$_3$ [M+H]$^+$: 376.25. Found: 376.00.

Step 4: 3'-(1,5-Diphenyl-1H-1,2,4-triazol-3-yl)-[1,1'-biphenyl]-3-carboxylic Acid

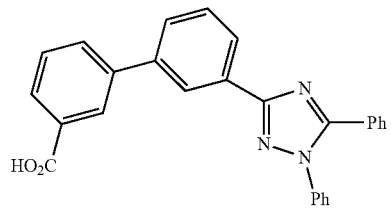

3-(3-Bromophenyl)-1,5-diphenyl-1H-1,2,4-triazole (0.188 g, 0.5 mmol) and 3-boronobenzene boronic acid (0.124 g, 0.75 mmol), tetrakistriphenylphosphinepalladium (0) (0.058 g, 0.05 mmol) and 2M Na$_2$CO$_3$ (1 mL) were dissolved in DME. The reaction mixture was then processed according to the general procedure described in Example 1, step 3, to afford the title compound as an off-white solid (0.121 g, 58%). $^1$H NMR (400 MHz, DMSOd$_6$): δ8.35 (s, 1H), 8.22 (s, 1H), 8.13 (d, J=7.8 Hz), 7.97 (t, J=8.2 Hz, 2H), 7.79 (d, J=7.8 Hz, 1H), 7.60 (q, J=7.8 Hz, 2H), 7.51-7.39 (m, 10H). HRMS (ESI) calcd. for C$_{27}$H$_{19}$N$_3$O$_2$ [M+H]$^+$: 418.1550. Found: 418.1598.

Example 50: 3'-(1-Methyl-5-phenyl-1H-1,2,4-triazol-3-yl)-[1,1'-biphenyl]-3-carboxylic Acid

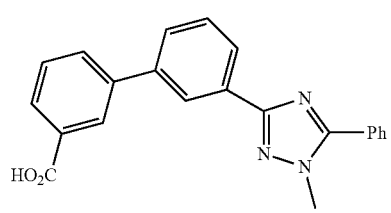 [SMILES: Cn1nc(-c2cccc(-c3cccc(C(=O)O)c3)c2)nc1-c1ccccc1]

3-(3-bromophenyl)-1-methyl-5-phenyl-1H-1,2,4-triazole (0.157 g, 0.5 mmol) and 3-boronobenzene boronic acid (0.124 g, 0.75 mmol), tetrakistriphenylphosphinepalladium (0) (0.058 g, 0.05 mmol) and 2M $Na_2CO_3$ (1 mL) were dissolved in DME. The reaction mixture was then processed according to the general procedure described in Example 1, step 3, to afford the title compound as an off-white solid (0.040 g, 23%). $^1$H NMR (400 MHz, DMSOd$_6$): δ8.28 (s, 1H), 8.20 (s, 1H), 8.08-8.02 (m, 2H), 7.94 (t, J=7.3 Hz, 2H), 7.84 (dd, J=4.2 Hz, 7.3 Hz, 2H), 7.75 (d, J=8.2 Hz, 1H), 7.60-7.55 (m, 4H). 4.01 (s, 3H). HRMS (ESI) calcd. for $C_{22}H_{17}N_3O_2$ [M+H]$^+$: 356.1394. Found: 356.1432.

Example 51: 3'-(1,5-Diphenyl-1H-1,2,4-triazol-3-yl)-4-fluoro-[1,1'-biphenyl]-3-carboxylic Acid

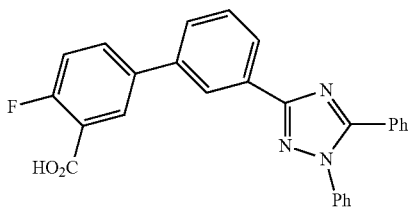 [SMILES: O=C(O)c1cc(-c2cccc(-c3nc(-c4ccccc4)n(-c4ccccc4)n3)c2)ccc1F]

3-(3-Bromophenyl)-1,5-diphenyl-1H-1,2,4-triazole (0.100 g, 0.27 mmol) and 5-borono-2-fluorobenzoic acid (0.073 g, 0.398 mmol), tetrakistriphenylphosphinepalladium (0) (0.031 g, 0.027 mmol) and 2M $Na_2CO_3$ (0.54 mL) were dissolved in DME. The reaction mixture was then processed according to the general procedure described in Example 1, step 3, to afford the title compound as an off-white solid (0.070 g, 59%), $^1$H NMR (400 MHz, DMSOd$_6$): δ8.31 (s, 1H), 8.12-8.08 (m, 2H), 7.99-7.94 (m, 2H), 7.76 (d, J=7.3 Hz, 1H), 7.62 (t, J=7.8 Hz, 1H), 7.51-7.36 (m, 10H). HRMS (ESI) calcd. for $C_{27}H_{18}N_3O_2$ [M+H]$^+$: 436.1456. Found: 436.1464.

Example 52: 3'-(1,5-Diphenyl-1H-1,2,4-triazol-3-yl)-5-fluorobiphenyl-3-carboxylic Acid

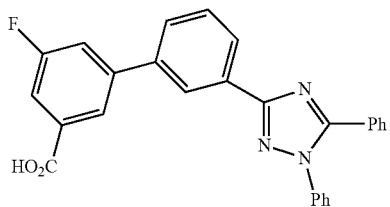 [SMILES: O=C(O)c1cc(F)cc(-c2cccc(-c3nc(-c4ccccc4)n(-c4ccccc4)n3)c2)c1]

3-(3-Bromophenyl)-1,5-diphenyl-1H-1,2,4-triazole (0.100 g, 0.27 mmol) and 3-borono-5-fluorobenzoic acid (0.073 g, 0.4 mmol), tetrakistriphenylphosphinepalladium (0) (0.031 g, 0.027 mmol) and 2M $Na_2CO_3$ (0.54 mL) were dissolved in DME. The reaction mixture was then processed according to the general procedure described in Example 1, step 3, to afford the title compound as a brown solid (0.059 g, 50%). $^1$H NMR (400 MHz, DMSOd$_6$): δ8.36 (s, 1H), 8.15 (d, J=7.3 Hz, 1H), 8.05 (s, 1H), 7.88-7.82 (m, 2H), 7.65 (q, J=7.8 Hz, 2H), 7.51-7.40 (m, 10H). HRMS (ESI) calcd. for $C_{27}H_{18}N_3O_2$ [M+H]$^+$: 436.1456. Found: 436.1471.

Example 53: 3'-(1-Phenyl-5-(thiophen-2-yl)-1H-1,2,4-triazol-3-yl)-[1,1'-biphenyl]-3-carboxylic Acid

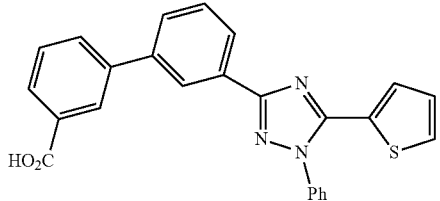 [SMILES: O=C(O)c1cccc(-c2cccc(-c3nc(-c4cccs4)n(-c4ccccc4)n3)c2)c1]

3-(3-Bromophenyl)-1-phenyl-5-(thiophen-2-yl)-1H-1,2,4-triazole (0.100 g, 0.26 mmol) and 3-boronobenzene boronic acid (0.066 g, 0.40 mmol), tetrakistriphenylphosphinepalladium(0) (0.031 g, 0.027 mmol) and 2M $Na_2CO_3$ (0.54 mL) were dissolved in DME. The reaction mixture was then processed according to the general procedure described in Example 1, step 3, to afford the title compound as an off-white solid (0.045 g, 41%). $^1$H NMR (400 MHz, DMSOd$_6$): δ 8.31 (s, 1H), 8.21 (s, 1H), 8.09 (d, J=7.8 Hz, 1H), 7.96-7.95 (m, 1H), 7.87 (d, J=7.8 Hz, 1H), 7.72 (d, J=4.1 Hz, 1H), 7.63-7.58 (m, 8H), 7.04 (t, J=4.1 Hz, 1H), 6.99 (d, J=2.8 Hz, 1H). HRMS (ESI) calcd. for $C_{25}H_{17}FN_3O_2S$ [M+H]$^+$: 424.1114. Found: 424.1131.

Example 54: 3'-(1-Benzyl-5-phenyl-1H-1,2,4-triazol-3-yl)-[1,1'-biphenyl]-3-carboxylic Acid

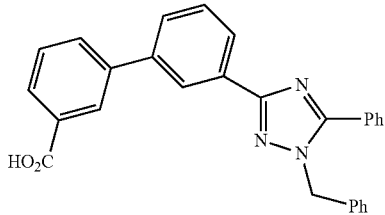 [SMILES: O=C(O)c1cccc(-c2cccc(-c3nc(-c4ccccc4)n(Cc4ccccc4)n3)c2)c1]

1-Benzyl-3-(3-bromophenyl)-5-phenyl-1H-1,2,4-triazole (0.100 g, 0.26 mmol) and 3-boronobenzene boronic acid (0.066 g, 0.40 mmol), tetrakistriphenylphosphinepalladium (0) (0.030 g, 0.026 mmol) and 2M $Na_2CO_3$ (0.54 mL) were dissolved in DME. The reaction mixture was then processed according to the general procedure described in Example 1, step 3, to afford the title compound as an off-white solid (0.025 g, 22%). $^1$H NMR (400 MHz, DMSOd$_6$): δ8.29 (s, 1H), 8.19 (s, 1H), 8.06 (d, J=7.8 Hz, 1H), 7.94-7.90 (m, 2H), 7.76 (d, J=7.8 Hz, 1H), 7.72-7.68 (m, 2H), 7.58-7.52 (m, 5H), 7.31-7.23 (m, 3H), 7.12 (d, J=6.9 Hz, 2H), 5.58 (s, 2H). HRMS (ESI) calcd. for $C_{28}H_{21}FN_3O_2$[M+H]$^+$: 432.1707. Found: 432.1731.

Example 55: 3'-(1-(4-Methoxyphenyl)-5-phenyl-1H-1,2,4-triazol-3-yl)-[1,1'-biphenyl]-3-carboxylic Acid

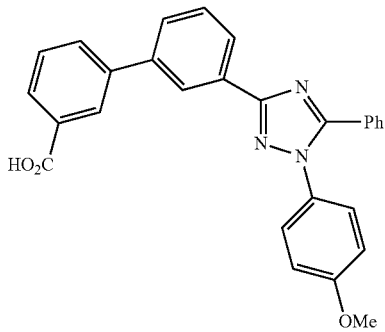 [SMILES: COc1ccc(-n2nc(-c3cccc(-c4cccc(C(=O)O)c4)c3)nc2-c2ccccc2)cc1]

3-(3-Bromophenyl)-1-(4-methoxyphenyl)-5-phenyl-1H-1,2,4-triazole (0.105 g, 0.26 mmol) and 3-boronobenzene boronic acid (0.066 g, 0.40 mmol), tetrakistriphenylphosphinepalladium(0) (0.030 g, 0.026 mmol) and 2M Na$_2$CO$_3$ (0.54 mL) were dissolved in DME. The reaction mixture was then processed according to the general procedure described in Example 1, step 3, to afford the title compound as an off-white solid (0.089 g, 76%). $^1$H NMR (400 MHz, DMSOd$_6$): δ8.34 (s, 1H), 8.21 (s, 1H), 8.12 (d J=7.8 Hz, 1H), 7.93 (t, J=9.6 Hz, 2H), 7.78 (d, J=8.2 Hz, 1H), 7.63-7.60 (m, 2H), 7.53 (d, J=7.8 Hz, 2H), 7.50-7.40 (m, 5H), 7.04 (d, J=8.7 Hz, 2H), 3.79 (s, 3H). HRMS (ESI) calcd. for C$_{28}$H$_{21}$N$_3$O$_3$ [M+H]$^+$: 448.1656. Found: 448.1667.

Example 56: 3'-(1-(3-Fluorophenyl)-5-phenyl-1H-1,2,4-triazol-3-yl)-[1,1'-biphenyl]-3-carboxylic Acid

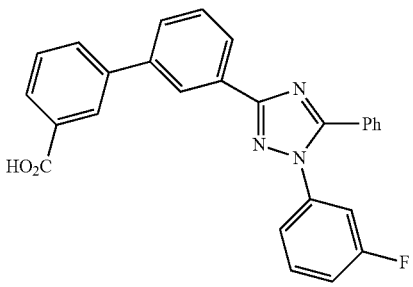 [SMILES: O=C(O)c1cccc(-c2cccc(-c3nc(-c4ccccc4)n(-c4cccc(F)c4)n3)c2)c1]

3-(3-Bromophenyl)-1-(3-fluorophenyl)-5-phenyl-1H-1,2,4-triazole (0.102 g, 0.26 mmol) and 3-boronobenzene boronic acid (0.066 g, 0.40 mmol), tetrakistriphenylphosphinepalladium(0) (0.030 g, 0.026 mmol) and 2M Na$_2$CO$_3$ (0.54 mL) were dissolved in DME. The reaction mixture was then processed according to the general procedure described in Example 1, step 3, to afford the title compound as a yellow solid (0.076 g, 67%), $^1$H NMR (400 MHz, DMSOd$_6$): δ 8.40 (t, J=1.8 Hz, 1H), 8.26 (t, J=1.4 Hz, 1H), 8.17 (d, J=7.8 Hz, 1H), 8.02-7.98 (m, 2H), 7.84 (d, J=8.2 Hz, 1H), 7.66 (q, J=7.8 Hz, 2H), 7.60-7.46 (m, 9H). HRMS (ESI) calcd. for C$_{27}$H$_8$N$_3$O$_2$[M+H]$^+$: 436.1456. Found: 436.1473.

Example 57: 3'-(1-(Naphthalen-1-yl)-5-phenyl-1H-1,2,4-triazol-3-yl)-[1,1'-biphenyl]-3-carboxylic Acid

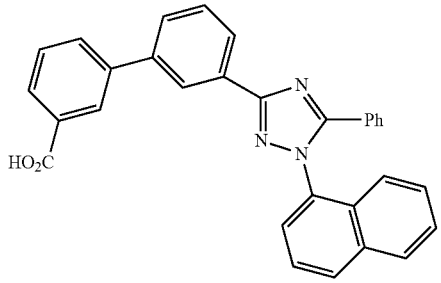 [SMILES: O=C(O)c1cccc(-c2cccc(-c3nc(-c4ccccc4)n(-c4cccc5ccccc45)n3)c2)c1]

3-(3-Bromophenyl)-1-(naphthalen-1-yl)-5-phenyl-1H-1,2,4-triazole (0.130 g, 0.3 mmol) and 3-boronobenzene boronic acid (0.076 g, 0.45 mmol) tetrakistriphenylphosphinepalladium(0) (0.035 g, 0.03 mmol) and 2M Na$_2$CO$_3$ (0.6 mL) were dissolved in DME. The reaction mixture was then processed according to the general procedure described in Example 1, step 3, to afford the title compound as a yellow solid (0.043 g, 31%). $^1$H NMR (400 MHz, DMSOd$_6$): δ8.39 (s, 1H), 8.21 (s, 1H), 8.19 (t, J=8.2 Hz, 1H), 8.09 (d, J=7.8 Hz, 1H), 7.97-7.93 (m, 2H), 7.81 (d, J=8.2 Hz, 1H), 7.76 (dd, J=1.0 Hz, 7.3 Hz, 1H), 7.63-7.53 (m, 6H), 7.44-7.27 (m, 6H). HRMS (ESI) calcd. for C$_{31}$H$_{21}$N$_3$O$_2$ [M+H]$^+$: 468.1707. Found: 468.1710.

Example 58: 3'-(1-Phenyl-5-(6-(trifluoromethyl)pyridin-3-yl)-1H-1,2,4-triazol-3-yl)-[1,1'-biphenyl]-3-carboxylic Acid

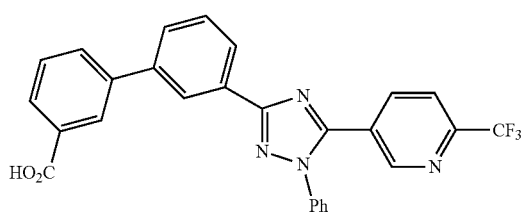 [SMILES: O=C(O)c1cccc(-c2cccc(-c3nc(-c4ccc(C(F)(F)F)nc4)n(-c4ccccc4)n3)c2)c1]

5-(3-(3-Bromophenyl)-1-phenyl-1H-1,2,4-triazol-5-yl)-2-(trifluoromethyl)pyridine (0.120 g, 0.30 mmol) and 3-boronobenzene boronic acid (0.076 g, 0.45 mmol) tetrakistriphenylphosphinepalladium(0) (0.035 g, 0.03 mmol) and 2M Na$_2$CO$_3$ (0.8 mL) were dissolved in DME. The reaction mixture was then processed according to the general procedure described in Example 1, step 3, to afford the title compound as an off-white solid (0.087 g, 60%). $^1$H NMR (400 MHz, DMSOd$_6$): δ8.85 (d, J=1.8 Hz, 1H), 8.37 (t, J=1.8 Hz, 1H), 8.21 (t, J=1.8 Hz, 1H), 8.16-8.14 (m, 2H), 7.99-7.96 (m, 3H), 7.82 (d, J=8.2 Hz, 1H), 7.64-7.54 (m, 7H). HRMS (ESI) calcd. for C$_{27}$H$_{17}$F$_3$N$_4$O$_2$[M+H]$^+$: 487.1376. Found: 487.1403.

Example 59: 3'-(5-(Furan-3-yl)-1-phenyl-1H-1,2,4-triazol-3-yl)-[1,1'-biphenyl]-3-carboxylic Acid

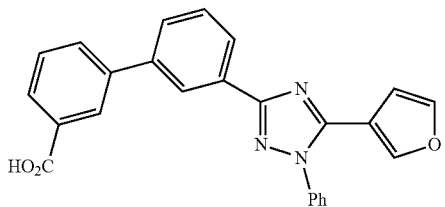 [SMILES: O=C(O)c1cccc(-c2cccc(-c3nc(-c4ccoc4)n(-c4ccccc4)n3)c2)c1]

3-(3-Bromophenyl)-5-(furan-3-yl)-1-phenyl-1H-1,2,4-triazole (0.146 g, 0.40 mmol) and 3-boronobenzene boronic acid (0.1 g, 0.6 mmol), tetrakistriphenylphosphinepalladium (0) (0.046 g, 0.04 mmol) and 2M Na$_2$CO$_3$ (0.8 mL) were dissolved in DME. The reaction mixture was then processed according to the general procedure described in Example 1, step 3, to afford the title compound as an off-white solid (0.073 g, 45%)$^1$H NMR (400 MHz, DMSOd$_6$): δ8.32 (s, 1H), 8.20 (s, 1H), 8.09 (d, J=7.8 Hz, 1H), 7.95 (t, J=6.9 Hz, 2H), 7.83 (s, 1H), 7.78 (d, J=7.8 Hz, 1H), 7.74 (t, J=3.2 Hz, 1H), 7.63-7.60 (m, 7H), 6.38 (d, J=1.4 Hz, 1H). HRMS (ESI) calcd. for C$_{25}$H$_{17}$N$_3$O$_3$ [M+H]$^+$: 408.1343. Found: 408.1355.

Example 60: 3'-(1,5-Diphenyl-1H-1,2,4-triazol-3-yl)-[1,1'-biphenyl]-4-carboxylic Acid

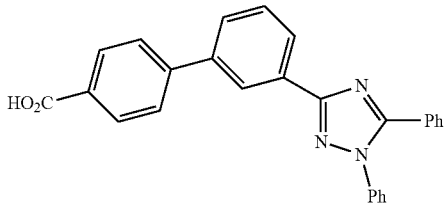 [SMILES: O=C(O)c1ccc(-c2cccc(-c3nc(-c4ccccc4)n(-c4ccccc4)n3)c2)cc1]

3-(3-Bromophenyl)-1,5-diphenyl-1H-1,2,4-triazole (0.100 g, 0.27 mmol) and 4-boronobenzene boronic acid (0.1 g, 0.40 mmol), tetrakistriphenylphosphinepalladium(0) (0.031 g, 0.027 mmol) and 2M $Na_2CO_3$ (0.54 mL) were dissolved in DME. The reaction mixture was then processed according to the general procedure described in Example 1, step 3, to afford the title compound as a yellow solid (0.058 g, 52%). $^1$H NMR (400 MHz, DMSOd$_6$): δ8.23 (s, 1H), 8.18 (s, 1H), 8.02 (d, J=8.2 Hz, 2H), 7.92 (d, J=8.7 Hz, 1H), 7.86 (d, J=8.2 Hz, 2H), 7.45 (d, J=8.2 Hz, 1H), 7.45-7.0 (m, 10H). HRMS (ESI) calcd. for $C_{27}H_{19}N_3O_2$ [M+H]$^+$: 418.1550. Found: 418.1636.

Example 61: 3'-(1,5-Diphenyl-1H-1,2,4-triazol-3-yl)-[1,1'-biphenyl]-2-carboxylic Acid

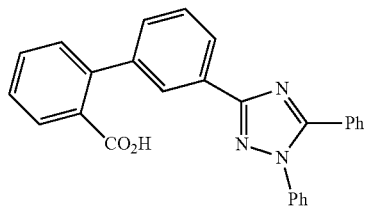 [SMILES: O=C(O)c1ccccc1-c1cccc(-c2nc(-c3ccccc3)n(-c3ccccc3)n2)c1]

3-(3-Bromophenyl)-1,5-diphenyl-1H-1,2,4-triazole (0.100 g, 0.27 mmol) and 2-boronobenzene boronic acid (0.1 g, 0.40 mmol), tetrakistriphenylphosphinepalladium(0) (0.031 g, 0.027 mmol) and 2M $Na_2CO_3$ (0.54 mL) were dissolved in DME. The reaction mixture was then processed according to the general procedure described in Example 1, step 3, to afford the title compound as an off-white solid (0.025 g, 22%), $^1$H NMR (400 MHz, DMSOd$_6$): δ8.09 (d, J=9.2 Hz, 1H), 8.06 (s, 1H), 7.77 (d, J=7.3 Hz, 1H), 7.52-7.42 (m, 15H). HRMS (ESI) calcd. for $C_{27}H_{19}N_3O_2$ [M+H]$^+$: 418.1550. Found: 418.1583.

Example 62: 2-(3-(1,5-Diphenyl-1H-1,2,4-triazol-3-yl)phenyl)furan-3-carboxylic Acid

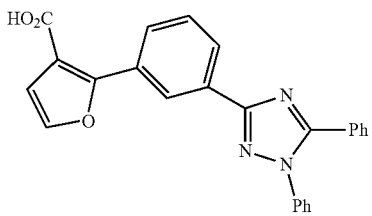 [SMILES: O=C(O)c1ccoc1-c1cccc(-c2nc(-c3ccccc3)n(-c3ccccc3)n2)c1]

3-(3-Bromophenyl)-1,5-diphenyl-1H-1,2,4-triazole (0.100 g, 0.27 mmol) and 2-boronofuran-3-carboxylic acid (0.061 g, 0.40 mmol), tetrakistriphenylphosphinepalladium (0) (0.031 g, 0.027 mmol) and 2M $Na_2CO_3$ (0.54 mL) were dissolved in DME. The reaction mixture was then processed according to the general procedure described in Example 1, step 3, to afford the title compound as an off-white solid (0.035 g, 32%), $^1$H NMR (400 MHz, DMSOd$_6$): δ8.65 (s, 1H), 8.13 (d, J=7.8 Hz, 1H), 8.06 (d, J=8.2 Hz, 1H), 7.83 (d, J=1.8 Hz, 1H), 7.59 (t, J=7.8 Hz, 1H), 7.50-7.40 (m, 10H), 6.85 (d, J=1.8 Hz, 1H). HRMS (ESI) calcd. for $C_{25}H_{17}N_3O_3$ [M+H]$^+$: 408.1343. Found: 408.1357.

Example 63: 3'-(1,5-Diphenyl-1H-1,2,4-triazol-3-yl)-6-fluoro-[1,1'-biphenyl]-3-carboxylic Acid

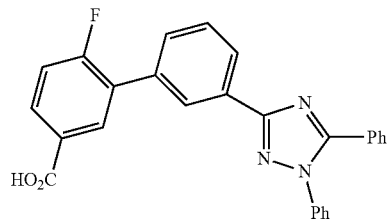 [SMILES: O=C(O)c1ccc(F)c(-c2cccc(-c3nc(-c4ccccc4)n(-c4ccccc4)n3)c2)c1]

3-(3-Bromophenyl)-1,5-diphenyl-1H-1,2,4-triazole (0.100 g, 0.27 mmol) and 3-borono-4-fluorobenzoic acid (0.072 g, 0.40 mmol), tetrakistriphenylphosphinepalladium (0) (0.031 g, 0.027 mmol) and 2M $Na_2CO_3$ (0.54 mL) were dissolved in DME. The reaction mixture was then processed according to the general procedure described in Example 1, step 3, to afford the title compound as an off-white solid (0.025 g, 22%). $^1$H NMR (400 MHz, DMSOd$_6$): δ8.25 (d, J=1.4 Hz, 1H), 8.16-8.14 (m, 1H), 8.08 (dd, J=2.3 Hz, 7.8 Hz, 1H), 8.02-7.97 (m, 1H), 7.67-7.62 (m, 2H), 7.50-7.41 (m, 11H). HRMS (ESI) calcd. for $C_{27}H_{18}N_3O_2$ [M+H]$^+$: 436.1456. Found: 436.1463.

Example 64: 3'-(1-Isopropyl-5-phenyl-1H-1,2,4-triazol-3-yl)-[1,1'-biphenyl]-3-carboxylic Acid

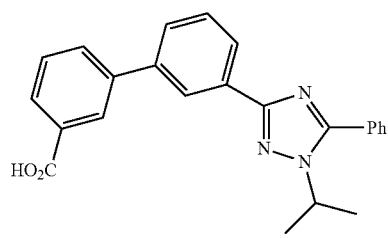 [SMILES: CC(C)n1nc(-c2cccc(-c3cccc(C(=O)O)c3)c2)nc1-c1ccccc1]

3-(3-Bromophenyl)-1-isopropyl-5-phenyl-1H-1,2,4-triazole (0.092 g, 0.27 mmol) and 3-boronobenzene boronic acid (0.066 g, 0.40 mmol), tetrakistriphenylphosphinepalladium (0) (0.031 g, 0.027 mmol) and 2M $Na_2CO_3$ (0.54 mL) were dissolved in DME. The reaction mixture was then processed according to the general procedure described in Example 1, step 3, to afford the title compound as an off-white solid (0.07 g, 67%). $^1$H NMR (400 MHz, DMSOd$_6$): δ 8.27 (s, 1H), 8.19 (s, 1H), 8.06 (d, J=7.8 Hz, 1H), 7.95 (dd, J=1.4 Hz, 7.8 Hz, 2H), 7.75 (d, J=7.8 Hz, 1H), 7.69-7.67 (m, 2H), 7.62-7.55 (m, 5H), 4.68-4.65 (m, 1H), 1.46 (d, J=6.9 Hz, 6H).). HRMS (ESI) calcd. for $C_{24}H_{21}N_3O_2$ [M+H]$^+$: 384.1707. Found: 384.1754.

Example 65: 3'-(5-Phenyl-1H-1,2,4-triazol-3-yl-[1,1'-biphenyl]-3-carboxylic Acid

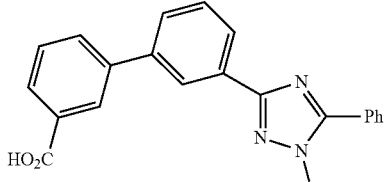

3-(3-Bromophenyl)-5-phenyl-1-tosyl-1H-1,2,4-triazole (0.122 g, 0.27 mmol) and 3-boronobenzene boronic acid (0.066 g, 0.40 mmol), tetrakistriphenylphosphinepalladium (0) (0.031 g, 0.027 mmol) and 2M $Na_2CO_3$ (0.54 mL) were dissolved in DME. The reaction mixture was then processed according to the general procedure described in Example 1, step 3, to afford the title compound as a yellow solid (0.03 g, 31%). $^1$H NMR (400 MHz, DMSOd$_6$): δ 8.39 (s, 1H), 8.29 (s, 1H), 8.14-8.10 (m, 3H), 8.02 (t, J=7.3 Hz, 2H), 7.75 (d, J=8.2 Hz, 1H), 7.67 (t, J=7.8 Hz, 1H), 7.75-7.46 (m, 5H). HRMS (ESI) calcd. for $C_{21}H_{15}N_3O_2$ [M+H]$^+$: 342.1237. Found: 342.1247.

Example 66: 3'-(1,3-Diphenyl-1H-1,2,4-triazol-5-yl)-[1,1'-biphenyl]-3-carboxylic Acid

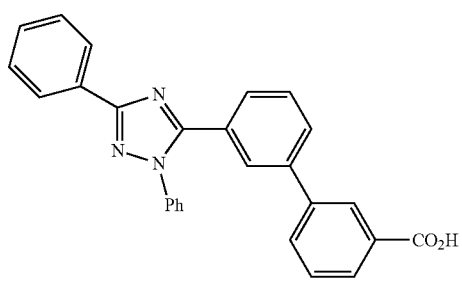 [SMILES: O=C(O)c1cccc(-c2cccc(-c3nc(-c4ccccc4)nn3-c3ccccc3)c2)c1]

5-(3-bromophenyl)-1,3-diphenyl-1H-1,2,4-triazole and (0.100 g, 0.27 mmol) and 3-boronobenzene boronic acid (0.066 g, 0.40 mmol), tetrakistriphenylphosphinepalladium (0) (0.031 g, 0.027 mmol) and 2M $Na_2CO_3$ (0.54 mL) were dissolved in DME. The reaction mixture was then processed according to the general procedure described in Example 1, step 3, to afford the title compound as an off-white solid (0.046 g, 41%). $^1$H NMR (400 MHz, DMSOd$_6$): δ8.12 (dd, J=1.4 Hz, 8.2 Hz, 1H), 7.95 (s, 1H), 7.90 (d, J=7.8 Hz, 1H), 7.78-7.71 (m, 3H), 7.75-7.49 (m, 11H). HRMS (ESI) calcd. for $C_{27}H_{19}N_3O_2$ [M+H]$^+$: 418.1550. Found: 418.1561.

Example 67: 3'-(1,2-Diphenyl-1H-imidazol-4-yl)-[1,1'-biphenyl]-3-carboxylic Acid Scheme 11

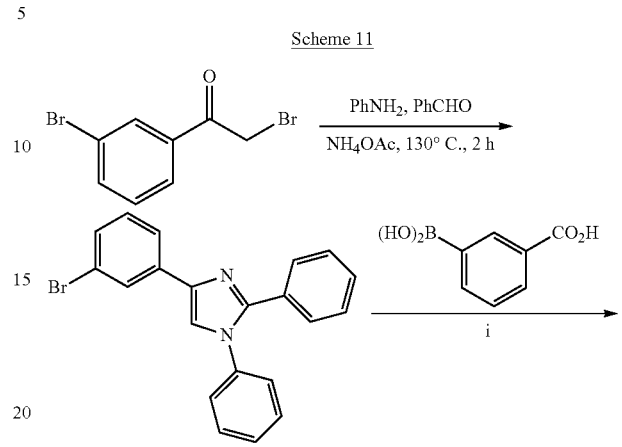

i) Pd(PPh$_3$)$_4$, 2M Na$_2$CO$_3$, DME, reflux

Step 1: 4-(3-Bromophenyl)-1,2-diphenyl-1H-imidazole

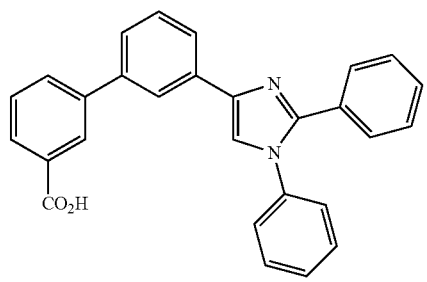

A mixture of benzaldehyde (1.06 g, 10 mmol), aniline (0.95 mL, 10 mmol), 3-bromo-phenacyl bromide (2.77 g, 10 mmol) and ammonium acetate (1.54 g, 20 mmol) were heated at 130° C. for 2 h. The reaction mixture was cooled to room temperature. The product precipitated by the addition of 1:1 acetone:water was collected by filtration and dried to afford the desired compound as a yellow solid (2.7 g, 72%). $^1$H NMR (400 MHz, CDCl$_3$): δ8.06 (t, J=1.8 Hz, 1H), 7.80 (d, J=9.1 Hz, 1H), 7.44 (s, 1H), 7.42-7.39 (m, 6H), 7.28-7.24 (m, 6H). LRMS (ESI) calcd. for $C_{21}H_{15}BrN_2$ [M+H]$^+$: 375.26. Found: 375.00.

139

Step 2: 3'-(1,2-Diphenyl-1H-imidazol-4-yl)-[1,1'-biphenyl]-3-carboxylic Acid

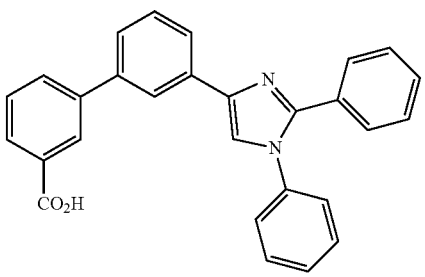 [SMILES: O=C(O)c1cccc(-c2cccc(-c3cn(-c4ccccc4)c(-c4ccccc4)n3)c2)c1]

Prepared from 4-(3-bromophenyl)-1,2-diphenyl-1H-imidazole (0.097 g, 0.26 mmol) and 3-boronobenzene boronic acid (0.064 g, 0.39 mmol), tetrakistriphenylphosphinepalladium(0) (0.030 g, 0.026 mmol) and 2M $Na_2CO_3$ (0.52 mL) were dissolved in DME. The reaction mixture was then processed according to the general procedure described in Example 1, step 3, to afford the title compound as a yellow solid (0.046 g, 24%). $^1$H NMR (400 MHz, DMSOd$_6$): δ8.28 (s, 1H), 8.24 (s, 1H), 8.21 (s, 1H), 7.97 (q, J=7.3 Hz, 3H), 7.64-7.31 (m, 13H). HRMS (ESI) calcd. for $C_{28}H_{20}N_2O_2$ [M+H]$^+$: 417.1598. Found: 417.1650.

General Synthetic Scheme for the Preparation of 3'-(5-Phenyl-1H-pyrazol-3-yl)-[1,1'-biphenyl]-3-carboxylic Acid

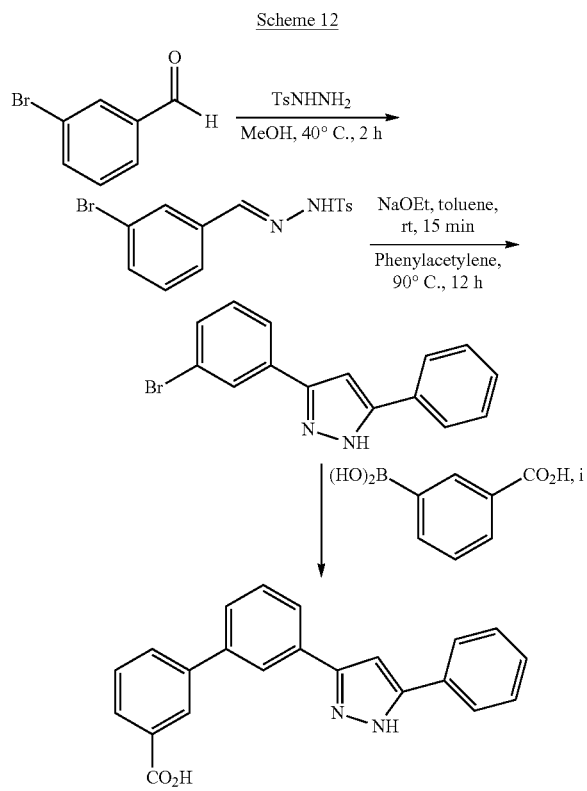

i) Pd(PPh$_3$)$_4$, 2M Na$_2$CO$_3$, DME, reflux

140

Example 68: 3'-(5-Phenyl-1H-pyrazol-3-yl)-[1,1'-biphenyl]-3-carboxylic Acid

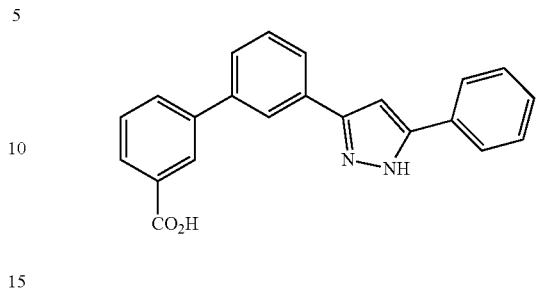

Steps 1-2:
3-(3-Bromophenyl)-5-phenyl-1H-pyrazole

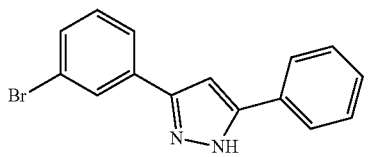 [SMILES: Brc1cccc(-c2cc(-c3ccccc3)[nH]n2)c1]

3-Bromobenzaldehyde (1.85 g, 10 mmol) was added slowly to a solution of tosyl hydrazine (2 g, 11 mmol) in MeOH (10 mL) at 40° C. The resulting mixture was stirred at the same temperature for 2 h, then cooled to room temperature and diluted with water. The precipitated tosyl hydrazide was collected by filtration, washed with water and dried under vacuum (colorless solid, 2.8 g). $^1$H NMR (400 MHz, CDCl$_3$): δ 8.72 (s, 1H), 7.87 (d, J=8.2 Hz, 2H), 7.71 (s, 1H), 7.67 (s, 1H), 745-7.43 (m, 2H), 7.29 (d, J=8.2 Hz, 2H), 7.16 (t, J=7.8 Hz, 1H), 2.34 (s, 3H). LRMS (ESI) calcd. for $C_{14}H_{13}BrN_2O_2S$ [M+H]$^+$: 352.98. Found: 353.00. To a solution of hydrazide (0.706 g, 2 mmol) in toluene (3 mL) at room temperature was added NaOEt (0.68 g, 12 mmol). The resulting mixture was stirred at room temperature for 15 min. Phenyl acetylene (1.22 g, 12 mmol) was injected to the reaction mixture and heated at 90° C. for 12 h. Upon cooling and trituration with hexanes afforded 3-(3-bromophenyl)-5-phenyl-1H-pyrazole as a colorless solid (0.450 g, 75%). $^1$H NMR (CDCl$_3$): δ 7.86 (s, 1H), 7.65-7.63 (m, 3H), 7.40-7.33 (m, 4H), 7.25 (s, 1H), 7.22 (t, J=7.8 Hz, 1H), 6.78 (s (1H). LRMS (ESI) calcd. for $C_{15}H_{11}BrN_2$ [M+H]$^+$: 300.17. Found: 300.00.

Step 3: 3'-(5-Phenyl-1H-pyrazol-3-yl)-[1,1'-biphenyl]-3-carboxylic Acid

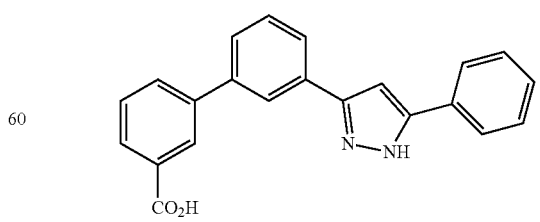

Prepared from 3-(3-bromophenyl)-5-phenyl-1H-pyrazole (0.150 g, 0.5 mmol) and 3-boronobenzene boronic acid (0.124 g, 0.75 mmol), tetrakistriphenylphosphinepalladium (0) (0.058 g, 0.05 mmol) and 2M $Na_2CO_3$ (1 mL) were dissolved in DME. The reaction mixture was then processed according to the general procedure described in Example 1, step 3, to afford the title compound as a yellow solid (0.042 g, 25%). $^1$H NMR (400 MHz, $DMSOd_6$): δ 8.30 (s, 1H), 8.19 (s, 1H), 8.10 (t, J=8.2 Hz, 2H), 7.90-7.87 (m, 3H), 7.69-7.63 (m, 2H), 7.58 (t, J=7.8 Hz, 1H), 7.47 (t, J=7.3 Hz, 2H), 7.36-7.34 (m, 2H). HRMS (ESI) calcd. for $C_{22}H_{16}N_2O_2$ [M+H]$^+$: 341.1285. Found: 341.1324.

General Synthetic Scheme for the Preparation of 3'-(4-(Trifluoromethyl)-6-(6-(trifluoromethyl)pyridin-3-yl)pyrimidin-2-yl)biphenyl Derivatives (Method 1)

Example 69: 3'-(4-(Trifluoromethyl)-6-(6-(trifluoromethyl)pyridin-3-yl)pyrimidin-2-yl)biphenyl-3-carboxylic Acid

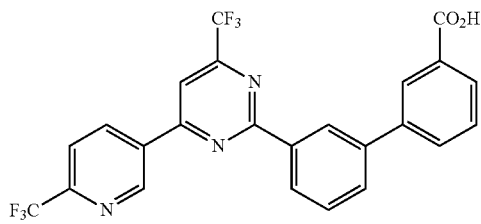 [SMILES: O=C(O)c1cccc(-c2cccc(-c3nc(-c4ccc(C(F)(F)F)nc4)cc(C(F)(F)F)n3)c2)c1]

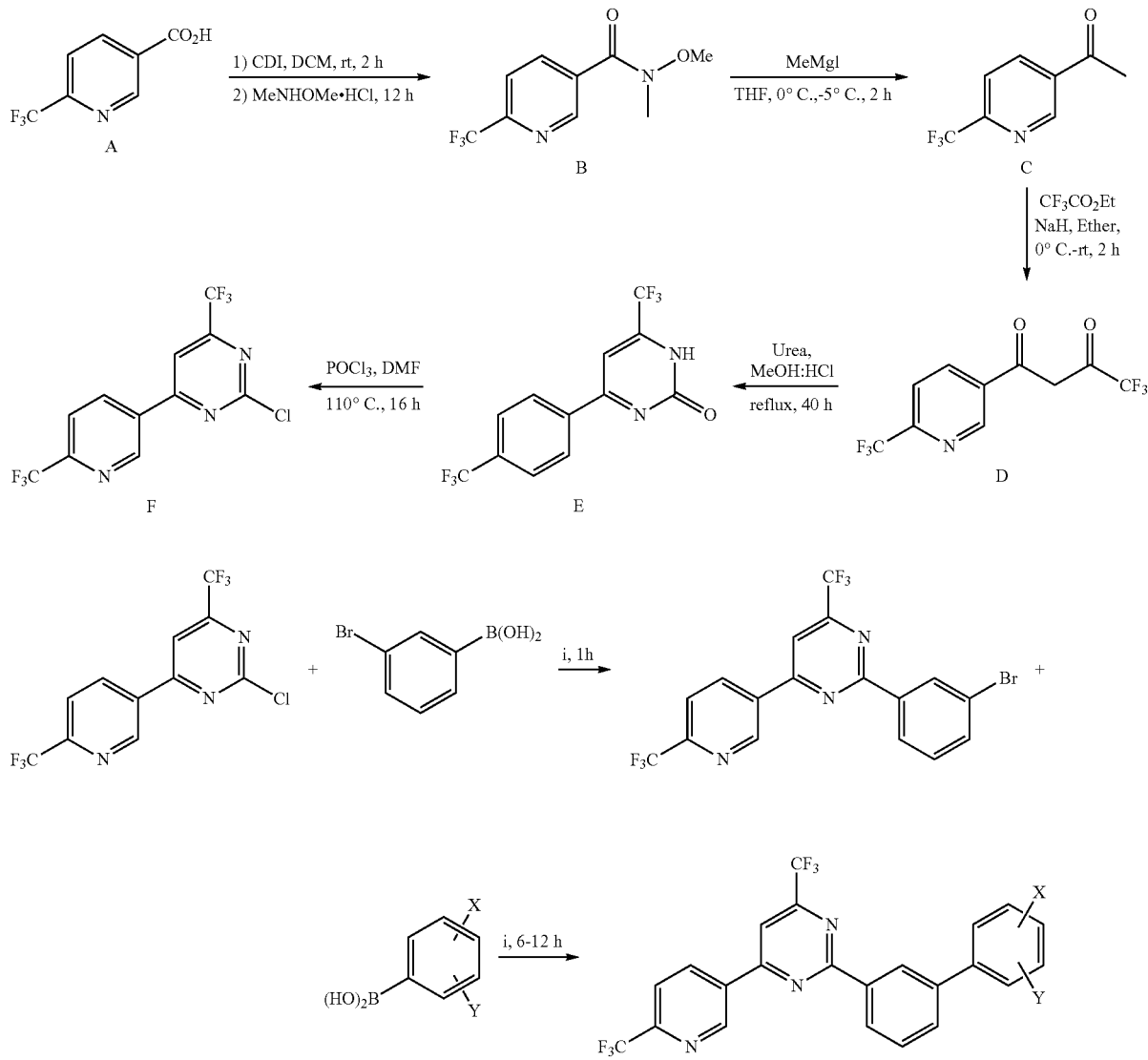

i) Pd(PPh$_3$)$_4$, 2M Na$_2$CO$_3$, DME, 80° C.
X = CO$_2$H, SO$_2$NH$_2$, NHCOR, CN, CONH$_2$
Y = H, Cl, F, OMe, NO$_2$

Step 1: N-Methoxy-N-methyl-6-(trifluoromethyl)nicotinamide (Intermediate B)

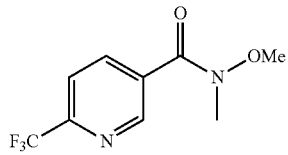

CDI (12.7 g, 78.5 mmol) was added to a solution of 6-(trifluoromethyl)nicotinic acid (15 g, 78.5 mmol) in CH$_2$Cl$_2$ (1 L). The resulting mixture was stirred for 2 h. N,O-Dimethylhydroxylamine hydrochloride (11.54 g, 117.7 mmol) was added to this mixture in one portion. After stirring for 12 h at room temperature, the reaction mixture was quenched by the addition of 0.1N NaOH solution. The dichloromethane layer was washed with water and brine. The organic phase was dried using Na$_2$SO$_4$ and evaporated to give N-methoxy-N-methyl-6-(trifluoromethyl)nicotinamide as a viscous liquid (12 g, 66%). LRMS (ESI) calcd. for C$_9$H$_9$F$_3$N$_2$O$_2$[M+H]$^+$: 235.18, 449.98. Found: 235.00. The crude product was used for the next step without further purification.

Step 2: 1-(6-(Trifluoromethyl)pyridin-3-yl)ethan-1-one (Intermediate C)

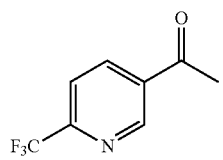

N-Methoxy-N-methyl-6-(trifluoromethyl)nicotinamide (12 g, 51 mmol) in dry THF (500 mL) was cooled to 0° C. and kept for 10 min. To this cooled solution methylmagnesium iodide (18.8 mL, 3M solution in THF) was added and stirred at the same temperature for 2 h. The reaction mixture was then quenched with the addition of saturated NH$_4$Cl solution and extracted with EtOAc (3×100 mL). The combined organic layer was washed with brine. The organic phase was dried using Na$_2$SO$_4$ and evaporated to give 1-(6-(trifluoromethyl)pyridin-3-yl)ethan-1-one as a pale yellow solid (9.61 g, 99%). $^1$H NMR (400 MHz, CDCl$_3$): δ9.23 (s, 1H), 8.40 (d, J=8.6 Hz, 1H), 7.79 (d, J=7.3 Hz, 1H), 2.68 (s, 3H). The crude product was used for the next step without further purification.

Step 3: 4,4,4-Trifluoro-1-(6-(trifluoromethyl)pyridin-3-yl)butane-1,3-dione (Intermediate D)

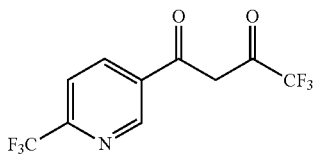 [SMILES: O=C(CC(=O)C(F)(F)F)c1ccc(C(F)(F)F)nc1]

To a stirred solution of 1-(6-(trifluoromethyl)pyridin-3-yl)ethan-1-one (7.5 g, 39.68 mmol) in diethyl ether (500 mL), was added NaH (1.19 g, 49.60 mmol) while the temperature was kept between 0-5° C. After stirring at that temperature for 30 min, ethyl trifluoroacetate (5.89 mL, 49.60 mmol) was added to the reaction mixture. The reaction mixture was poured into ice water and acidified with 2N HCl. The organic layer was separated and aqueous layer extracted with ethyl acetate (3×20 mL). The combined organic layer was washed with water and brine. The organic phase was dried using Na$_2$SO$_4$ and evaporated to give 4,4,4-trifluoro-1-(6-(trifluoromethyl)pyridin-3-yl)butane-1,3-dione as a pale yellow liquid (as enol form, 9.3 g, 82%). $^1$H NMR (400 MHz, CDCl$_3$): δ9.62 (s, 1H), 8.45 (d, J=8.6 Hz, 1H), 7.89 (d, J=7.3 Hz, 1H), 6.61 (s, 1H).

Step 4: 6-(Trifluoromethyl)-4-(6-(trifluoromethyl)pyridin-3-yl)pyrimidin-2(1H)-one (Intermediate E)

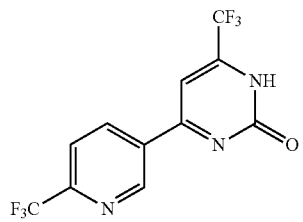 [SMILES: O=c1nc(-c2ccc(C(F)(F)F)nc2)cc(C(F)(F)F)[nH]1]

To a stirred solution of 4,4,4-trifluoro-1-(6-(trifluoromethyl)pyridin-3-yl)butane-1,3-dione (9.3 g, 32 mmol) and urea (3.92 g, 60.06 mmol) in MeOH (500 mL) was added conc. HCl (50 mL). The reaction mixture was heated under reflux conditions for 40 h. The mixture was cooled and water was added. The mixture was stirred at 0° C. for 1 h. The precipitated 6-(trifluoromethyl)-4-(4-(trifluoromethyl)phenyl)pyrimidin-2(1H)-one was collected by filtration, washed with water and dried to afford a brown solid (6.3 g, 64%). LRMS (ESI) calcd. for C$_{11}$H$_5$F$_6$N$_3$O [M+H]$^+$: 310.17, Found: 310.00.

Step 5: 2-Chloro-4-(trifluoromethyl)-6-(6-(trifluoromethyl)pyridin-3-yl)pyrimidine (Intermediate F)

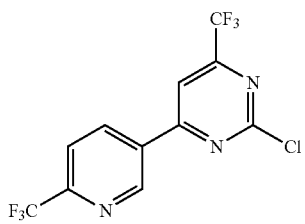

To a stirred solution of 6-(trifluoromethyl)-4-(4-(trifluoromethyl)phenyl)pyrimidin-2(1H)-one (6.3 g, 20 mmol) in phosphoroxychloride (20 mL) was added DMF (5-10 drops) and the reaction mixture was stirred at 110° C. for 16 h. The reaction mixture was cooled and excess solvent was removed under reduced pressure. Ice-water was added and the water layer was extracted three times with diethyl ether. The combined organic layer washed with water and brine. The organic layer was dried over Na$_2$SO$_4$ and evaporated to give 2-chloro-4-(trifluoromethyl)-6-(6-(trifluoromethyl)

pyridin-3-yl)pyrimidine as a pale yellow solid (5.98 g, 89%). LRMS (ESI) calcd. for $C_{11}H_{54}ClF_6N_3[M+H]^+$: 328.61, Found: 328.00.

Step 6: 2-(3-Bromophenyl)-4-(trifluoromethyl)-6-(6-(trifluoromethyl)pyridin-3-yl)pyrimidine

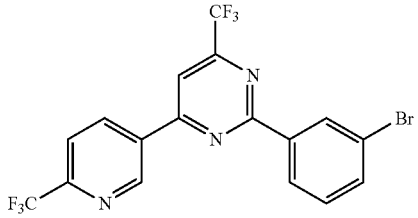 [SMILES: FC(F)(F)c1ccc(-c2cc(C(F)(F)F)nc(-c3cccc(Br)c3)n2)cn1]

A mixture of 2-chloro-4-(trifluoromethyl)-6-(6-(trifluoromethyl)pyridin-3-yl)pyrimidine (3.27 g, 10 mmol), 3-bromophenylboronic acid (3.0 g, 15 mmol) and tetrakistriphenylphosphine palladium(0) (1.15 g, 1 mmol) were dissolved in 40 mL of DME. To this mixture was added 2M $Na_2CO_3$ (20 mL, 40 mmol) solution and the resulting solution was heated at reflux in an atmosphere of $N_2$ for 1 h. The reaction mixture cooled to room temperature and the solvent was removed under vacuum and the residue was dissolved dichloromethane and washed with water and the organic layer was dried over anhydrous $Na_2SO_4$. The solvent was evaporated in vacuum to obtain the crude product as a yellow solid. Column chromatography using 4:1 Hexanes/ethyl acetate solvent system afforded 2-(3-bromophenyl)-4-(trifluoromethyl)-6-(6-(trifluoromethyl)pyridin-3-yl)pyrimidine as a white solid (3.2 g, 74%). $^1$H NMR (400 MHz, CDCl$_3$): δ9.50 (s, 1H), 8.72-8.70 (m, 2H), 8.53 (d, J=7.8 Hz, 1H), 7.96 (s, 1H), 7.90 (d, J=8.2 Hz, 1H), 7.67 (d, J=7.8 Hz, 1H), 7.40 (t, J=7.8 Hz, 1H). LRMS (ESI) calcd. for $C_{17}H_8BrF_6N_3$ [M+H]$^+$: 447.98, 449.98. Found: 448.0, 450.0.

Step 7: 3'-(4-(Trifluoromethyl)-6-(6-(trifluoromethyl)pyridin-3-yl)pyrimidin-2-yl)biphenyl-3-carboxylic Acid

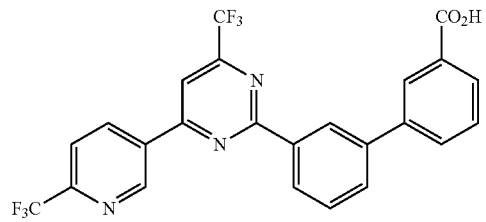 [SMILES: O=C(O)c1cccc(-c2cccc(-c3nc(-c4ccc(C(F)(F)F)nc4)cc(C(F)(F)F)n3)c2)c1]

A mixture of 2-(3-bromophenyl)-4-(trifluoromethyl)-6-(6-(trifluoromethyl)pyridin-3-yl)pyrimidine (0.129 g, 0.3 mmol), 3-borono benzoic acid (0.075 g, 0.45 mmol) and tetrakistriphenylphosphinepalladium(0) (0.034 g, 0.03 mmol) were taken 4 mL of DME. To this 2M $Na_2CO_3$ (0.6 mL, 1.2 mmol) solution was added and the resulting solution was refluxed in an atmosphere of $N_2$ for 6-12 h. The reaction mixture cooled to room temperature and diluted with water and then acidified using 1N HCl. The product was extracted with ethyl acetate and washed with brine and the organic layer was dried over anhydrous $Na_2SO_4$. The solvent was evaporated in vacuum to obtain the crude product. The crude product was purified using automated prep-HPLC to yield the desired compound as a white solid (0.082 g, 56%). $^1$H NMR (400 MHz, DMSOd$_6$): δ9.65 (s, 1H), 8.96 (d, J=7.8 Hz, 1H), 8.61 (s, 2H), 8.42 (d, J=7.3 Hz, 1H), 8.16 (s, 1H), 8.03 (d, J=7.8 Hz, 1H), 8.01 (d, J=7.3 Hz, 1H), 7.92 (d, J=7.8 Hz, 1H), 7.88 (d, J=7.3 Hz, 1H), 7.60-7.57 (m, 2H). LRMS (ESI) calcd. for $C_{24}H_{13}F_6N_3O_2[M+H]^+$: 490.09. Found: 489.95.

Example 70: 4-Chloro-3'-(4-(trifluoromethyl)-6-(6-(trifluoromethyl)pyridin-3-yl)pyrimidin-2-yl)biphenyl-3-carboxylic Acid

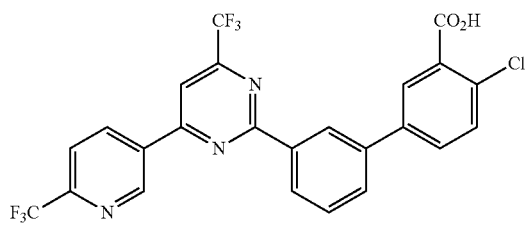 [SMILES: O=C(O)c1cc(-c2cccc(-c3nc(-c4ccc(C(F)(F)F)nc4)cc(C(F)(F)F)n3)c2)ccc1Cl]

2-(3-Bromophenyl)-4-(trifluoromethyl)-6-(6-(trifluoromethyl)pyridin-3-yl)pyrimidine (0.086 g, 0.2 mmol), 5-borono-2-chlorobenzoic acid (0.060 g, 0.3 mmol), tetrakistriphenylphosphinepalladium(0) (0.023, 0.02 mmol), 2M $Na_2CO_3$ (0.4 mL, 0.8 mmol) were dissolved in DME. The reaction mixture was then processed according to the general procedure described in Example 69, step 7, to afford the desired compound as a white solid (0.056 g, 54%). $^1$H NMR (400 MHz, DMSOd$_6$): δ9.77 (s, 1H), 9.08 (d, J=8.2 Hz, 1H), 8.73 (s, 1H), 8.72 (s, 1H), 8.54 (d, J=7.8 Hz, 1H), 8.14 (d, J=8.2 Hz, 1H), 8.06 (s, 1H), 7.92 (d, J=7.8 Hz, 1H), 7.87 (d, J=8.3 Hz, 1H), 7.72 (t, J=7.8 Hz, 1H), 7.65 (d, J=8.7 Hz, 1H). LRMS (ESI) calcd. for $C_{24}H_{12}ClF_6N_3O_2$ [M+H]$^+$: 524.05. Found: 523.90.

Example 71: 3'-(4-(Trifluoromethyl)-6-(6-(trifluoromethyl)pyridin-3-yl)pyrimidin-2-yl)biphenyl-4-carboxylic Acid

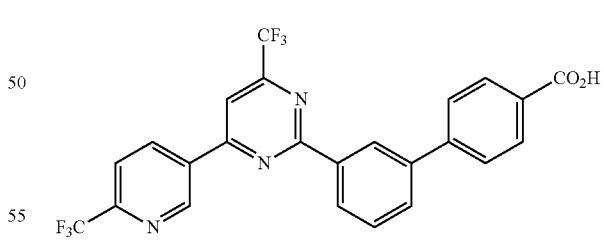

2-(3-Bromophenyl)-4-(trifluoromethyl)-6-(6-(trifluoromethyl)pyridin-3-yl)pyrimidine (0.129 g, 0.3 mmol), 4-boronobenzoic acid (0.075 g, 0.45 mmol), tetrakistriphenylphosphinepalladium(0) (0.034, 0.03 mmol), 2M $Na_2CO_3$ (0.6 mL, 1.2 mmol) were dissolved in DME. The reaction mixture was then processed according to the general procedure described in Example 69, step 7, to afford the desired compound as a white solid (0.092 g, 63%). $^1$H NMR (400 MHz, DMSOd$_6$): δ9.73 (s, 1H), 9.06 (d, J=8.2 Hz, 1H), 8.69 (s, 1H), 8.59 (d, J=8.8 Hz, 2H), 8.13 (d, J=8.2 Hz, 1H), 8.03

(d, J=8.7 Hz, 2H), 7.93 (d, J=8.7 Hz. 2H), 7.86 (d, J=8.2 Hz, 2H). LRMS (ESI) calcd. for $C_{24}H_{13}F_6N_3O_2[M+H]^+$: 490.09. Found: 489.95.

Example 72: 3'-(4-(Trifluoromethyl)-6-(6-(trifluoromethyl)pyridin-3-yl)pyrimidin-2-yl)biphenyl-2-carboxylic Acid

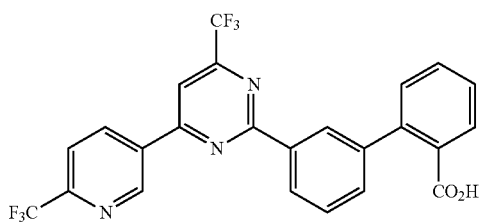 [SMILES: O=C(O)c1ccccc1-c1cccc(-c2nc(-c3ccc(C(F)(F)F)nc3)cc(C(F)(F)F)n2)c1]

2-(3-Bromophenyl)-4-(trifluoromethyl)-6-(6-(trifluoromethyl)pyridin-3-yl)pyrimidine (0.129 g, 0.3 mmol), 2-boronobenzoic acid (0.075 g, 0.45 mmol), tetrakistriphenylphosphinepalladium(0) (0.034, 0.03 mmol), 2M $Na_2CO_3$ (0.6 mL, 1.2 mmol) were dissolved in DME. The reaction mixture was then processed according to the general procedure described in Example 69, step 7, to afford the desired compound as a white solid (0.052 g, 35%). $^1$H NMR (400 MHz, DMSOd$_6$): δ9.72 (s, 1H), 9.05 (d, J=8.2 Hz, 1H), 8.70 (s, 1H), 8.49 (s, 1H), 8.11 (d, J=8.2 Hz, 1H), 7.71 (d, J=7.8 Hz, 1H), 7.62-7.50 (m, 4H), 7.46-7.42 (m, 2H). LRMS (ESI) calcd. for $C_{24}H_{13}F_6N_3O_2[M+H]^+$: 490.09. Found: 489.90.

Example 73: 4-Fluoro-3'-(4-(trifluoromethyl)-6-(6-(trifluoromethyl)pyridin-3-yl)pyrimidin-2-yl)biphenyl-3-carboxylic Acid

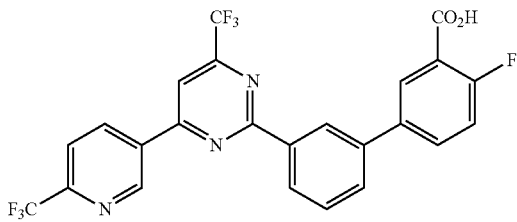 [SMILES: O=C(O)c1cc(-c2cccc(-c3nc(-c4ccc(C(F)(F)F)nc4)cc(C(F)(F)F)n3)c2)ccc1F]

2-(3-Bromophenyl)-4-(trifluoromethyl)-6-(6-(trifluoromethyl)pyridin-3-yl)pyrimidine (0.065 g, 0.15 mmol), 5-borono-2-fluorobenzoic acid (0.042 g, 0.22 mmol), tetrakistriphenylphosphinepalladium(0) (0.017, 0.015 mmol), 2M $Na_2CO_3$ (0.30 mL, 0.6 mmol) were dissolved in DME. The reaction mixture was then processed according to the general procedure described in Example 69, step 7, to afford the desired compound as a white solid (0.042 g, 55%). $^1$H NMR (400 MHz, DMSOd$_6$): δ9.70 (s, 1H), 9.00 (d, J=8.2 Hz, 1H), 8.65 (s, 1H), 8.61 (s, 1H), 8.45 (d, J=7.8 Hz, 1H), 8.09-8.07 (m, 2H), 7.94-7.88 (m, 1H), 7.83 (d, J=7.8 Hz, 1H), 7.63 (t, J=7.8 Hz, 1H), 7.39 (t, J=8.7 Hz, 1H). LRMS (ESI) calcd. for $C_{24}H_{12}F_7N_3O_2$ [M+H]$^+$: 508.08. Found: 508.00.

Example 74: 3-Chloro-3'-(4-(trifluoromethyl)-6-(6-(trifluoromethyl)pyridin-3-yl)pyrimidin-2-yl)biphenyl-4-carboxylic Acid

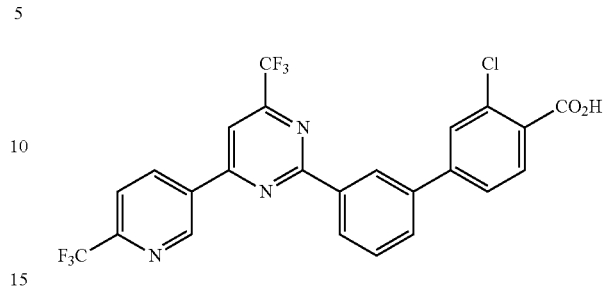

2-(3-Bromophenyl)-4-(trifluoromethyl)-6-(6-(trifluoromethyl)pyridin-3-yl)pyrimidine (0.1 g, 0.23 mmol), 4-borono-2-chlorobenzoic acid (0.069 g, 0.35 mmol), tetrakistriphenylphosphinepalladium(0) (0.027, 0.023 mmol), 2M $Na_2CO_3$ (0.46 mL, 0.92 mmol) were dissolved in DME. The reaction mixture was then processed according to the general procedure described in Example 69, step 7, to afford the desired compound as a white solid (0.072 g, 60%). $^1$H NMR (400 MHz, CDCl$_3$): δ9.75 (s, 1H), 9.06 (d, J=7.8 Hz, 1H), 8.70 (s, 1H), 8.52 (d, J=8.2 Hz, 1H), 8.11 (d, J=8.2 Hz, 1H), 7.93 (d, J=8.2 Hz, 1H), 7.92 (d, J=8.2 Hz, 1H), 7.88 (d, J=1.3 Hz, 1H), 7.78 (dd, J=1.8 Hz, 9.0 Hz, 1H), 7.70 (t, J=7.8 Hz, 1H), 7.65 (d, J=8.7 Hz, 1H). LRMS (ESI) calcd. for $C_{24}H_{12}ClF_6N_3O_2[M+H]^+$: 524.05. Found: 523.95.

Example 75: 5-Nitro-3'-(4-(trifluoromethyl)-6-(6-(trifluoromethyl)pyridin-3-yl)pyrimidin-2-yl)biphenyl-3-carboxylic Acid

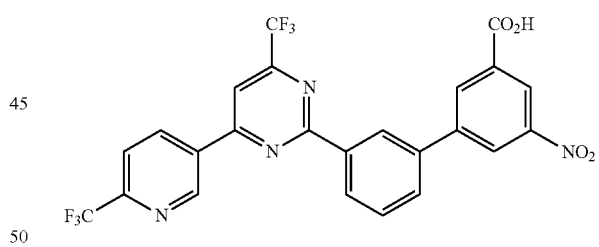

2-(3-Bromophenyl)-4-(trifluoromethyl)-6-(6-(trifluoromethyl)pyridin-3-yl)pyrimidine (0.1 g, 0.23 mmol), 3-borono-5-nitrobenzoic acid (0.073 g, 0.35 mmol), tetrakistriphenylphosphinepalladium(0) (0.027, 0.023 mmol), 2M $Na_2CO_3$ (0.46 mL, 0.92 mmol) were dissolved in DME. The reaction mixture was then processed according to the general procedure described in Example 69, step 7, to afford the desired compound as an off-white solid (0.080 g, 65%). $^1$H NMR (400 MHz, DMSOd$_6$): δ9.71 (s, 1H), 9.02 (d, J=7.2 Hz, 1H), 8.68 (s, 1H), 8.59-4.49 (m, 5H), 8.08 (d, J=8.2 Hz, 1H), 7.96 (d, J=7.8 Hz, 1H), (t, J=7.8 Hz, 1H). LRMS (ESI) calcd. for $C_{24}H_{12}F_6N_4O_4[M+H]^+$: 535.07. Found: 535.25.

Example 76: 5-Fluoro-3'-(4-(trifluoromethyl)-6-(6-(trifluoromethyl)pyridin-3-yl)pyrimidin-2-yl)biphenyl-3-carboxylic Acid

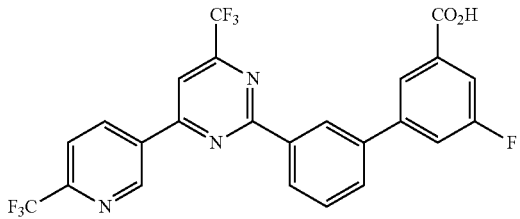 [SMILES: O=C(O)c1cc(F)cc(-c2cccc(-c3nc(-c4ccc(C(F)(F)F)nc4)cc(C(F)(F)F)n3)c2)c1]

2-(3-Bromophenyl)-4-(trifluoromethyl)-6-(6-(trifluoromethyl)pyridin-3-yl)pyrimidine (0.086 g, 0.2 mmol), 3-borono-5-fluorobenzoic acid (0.055 g, 0.3 mmol), tetrakistriphenylphosphinepalladium(0) (0.023, 0.02 mmol), 2M $Na_2CO_3$ (0.4 mL, 0.8 mmol) were dissolved in DME. The reaction mixture was then processed according to the general procedure described in Example 69, step 7, to afford the desired compound as a white solid (0.043 g, 43%). $^1H$ NMR (400 MHz, DMSOd$_6$): δ9.64 (s, 1H), 8.95 (d, J=8.2 Hz, 1H), 8.59 (s, 1H), 8.58 (s, 1H), 8.37 (d, J=7.8 Hz, 1H), 8.05-8.10 (m, 2H), 7.85-7.78 (m, 1H), 7.76 (d, J=7.8 Hz, 1H), 7.57 (t, J=7.7 Hz, 1H), 7.35 (t, J=8.2 Hz, 1H). LRMS (ESI) calcd. for $C_{24}H_{12}F_7N_3O_2$ [M+H]$^+$: 508.08. Found: 508.0.

Example 77: 6-Methoxy-3'-(4-(trifluoromethyl)-6-(6-(trifluoromethyl)pyridin-3-yl)pyrimidin-2-yl)biphenyl-3-carboxylic Acid

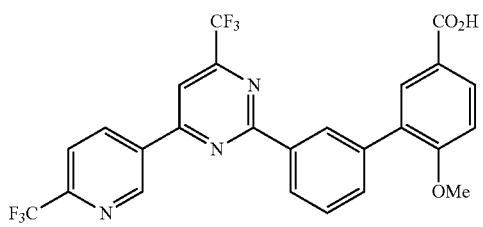 [SMILES: COc1ccc(C(=O)O)cc1-c1cccc(-c2nc(-c3ccc(C(F)(F)F)nc3)cc(C(F)(F)F)n2)c1]

2-(3-Bromophenyl)-4-(trifluoromethyl)-6-(6-(trifluoromethyl)pyridin-3-yl)pyrimidine (0.086 g, 0.2 mmol), 3-borono-4-methoxybenzoic acid (0.059 g, 0.3 mmol), tetrakistriphenylphosphinepalladium(0) (0.023, 0.02 mmol), 2M $Na_2CO_3$ (0.4 mL, 0.8 mmol) were dissolved in DME. The reaction mixture was then processed according to the general procedure described in Example 69, step 7, to afford the desired compound as a white solid (0.068 g, 65%). $^1H$ NMR (400 MHz, DMSOd$_6$): δ9.71 (s, 1H), 9.02 (d, J=8.2 Hz, 1H), 8.68 (s, 1H), 8.56 (s, 1H), 8.49 (d, J=7.8 Hz, 1H), 8.11 (d, J=8.3 Hz, 1H), 7.86 (d, J=7.8 Hz, 1H), 7.86 (s, 1H), 7.68-7.62 (m, 2H), 7.22 (d, J=8.7 Hz, 1H), 3.83 (s, 3H). LRMS (ESI) calcd. for $C_{25}H_{15}F_6N_3O_3$[M+H]$^+$: 520.10. Found: 520.0.

Example 78: 2-Chloro-3'-(4-(trifluoromethyl)-6-(6-(trifluoromethyl)pyridin-3-yl)pyrimidin-2-yl)biphenyl-4-carboxylic Acid

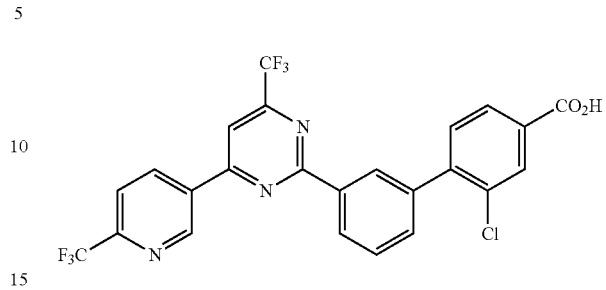

2-(3-Bromophenyl)-4-(trifluoromethyl)-6-(6-(trifluoromethyl)pyridin-3-yl)pyrimidine (0.1 g, 0.23 mmol), 4-borono-3-chlorobenzoic acid (0.069 g, 0.35 mmol), tetrakistriphenylphosphinepalladium(0) (0.027, 0.023 mmol), 2M $Na_2CO_3$ (0.46 mL, 0.92 mmol) were dissolved in DME. The reaction mixture was then processed according to the general procedure described in Example 69, step 7, to afford the desired compound as a white solid (0.050 g, 41%). $^1H$ NMR (400 MHz, DMSOd$_6$): δ9.46 (s, 1H), 8.65 (d, J=8.2 Hz, 1H), 8.59 (s, 1H), 8.75 (d, J=7.8 Hz, 1H), 8.11 (s, 1H), 7.96-7.95 (m, 2H), 7.83 (d, J=7.8 Hz, 1H), 7.57 (m, 2H), 7.42 (d, J=8.7 Hz, 1H). LRMS (ESI) calcd. for $C_{24}H_{12}ClF_6N_3O_2$[M+H]$^+$: 524.05. Found: 523.95.

Example 79: 6-Fluoro-3'-(4-(trifluoromethyl)-6-(6-(trifluoromethyl)pyridin-3-yl)pyrimidin-2-yl)biphenyl-3-carboxylic Acid

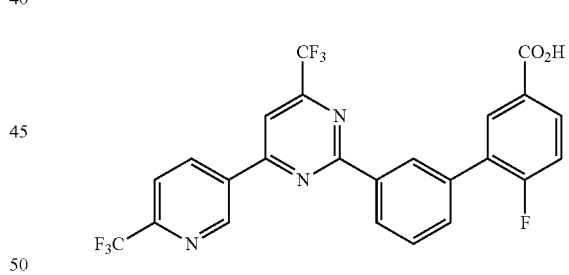

2-(3-Bromophenyl)-4-(trifluoromethyl)-6-(6-(trifluoromethyl)pyridin-3-yl)pyrimidine (0.086 g, 0.2 mmol), 3-borono-4-fluorobenzoic acid (0.055 g, 0.3 mmol), tetrakistriphenylphosphinepalladium(0) (0.046, 0.03 mmol), 2M $Na_2CO_3$ (0.4 mL, 0.8 mmol) were dissolved in DME. The reaction mixture was then processed according to the general procedure described in Example 69, step 7, to afford the desired compound as a white solid (0.044 g, 44%). $^1H$ NMR (400 MHz, DMSOd$_6$): δ9.67 (s, 1H), 9.00 (d, J=7.8 Hz, 1H), 8.65-8.64 (m, 2H), 8.62 (d, J=6.9 Hz, 1H), 8.06 (d, J=7.8 Hz, 2H), 7.99 (d, J=1.3 Hz, 1H), 7.85 (dd, J=3.3 Hz, 6.8 Hz, 1H), 7.75-7.62 (m, 1H), 7.61-7.60 (m, 1H). LRMS (ESI) calcd. for $C_{24}H_{12}F_7N_3O_2$[M+H]$^+$: 508.08. Found: 507.95.

Example 80: 5-(3-(4-(Trifluoromethyl)-6-(6-(trifluoromethyl)pyridin-3-yl)pyrimidin-2-yl)phenyl)thiophene-2-carboxylic Acid

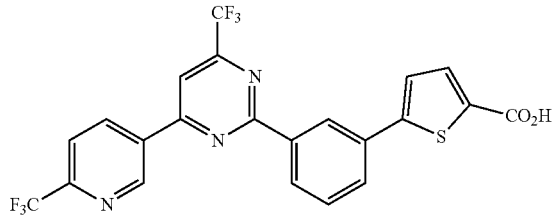 [SMILES: O=C(O)c1ccc(-c2cccc(-c3nc(-c4ccc(C(F)(F)F)nc4)cc(C(F)(F)F)n3)c2)s1]

2-(3-Bromophenyl)-4-(trifluoromethyl)-6-(6-(trifluoromethyl)pyridin-3-yl)pyrimidine (0.112 g, 0.25 mmol), 5-borono-2-chlorobenzoic acid (0.065 g, 0.375 mmol), tetrakistriphenylphosphinepalladium(0) (0.029, 0.025 mmol), 2M Na$_2$CO$_3$ (0.5 mL, 1 mmol) were dissolved in DME. The reaction mixture was then processed according to the general procedure described in Example 69, step 7, to afford the desired compound as an off-white solid (0.060 g, 48%). $^1$H NMR (400 MHz, DMSOd$_6$): δ9.71 (s, 1H), 9.02 (d, J=8.2 Hz, 1H), 8.67 (s, 1H), 8.66 (s, 1H), 8.42 (d, J=7.8 Hz, 1H), 8.10 (d, 1H, J=8.3 Hz), 7.90 (d, J=8.2 Hz, 1H), 7.69-7.61 (m, 3H). LRMS (ESI) calcd. for C$_{24}$H$_{11}$F$_6$N$_3$O$_2$S[M+H]$^+$: 496.05. Found: 496.0.

Example 81: 4'-(4-(Trifluoromethyl)-6-(6-(trifluoromethyl)pyridin-3-yl)pyrimidin-2-yl)biphenyl-4-carboxylic Acid

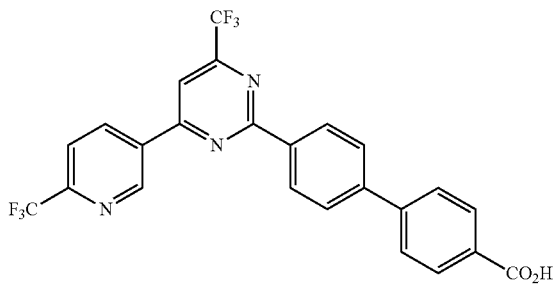 [SMILES: O=C(O)c1ccc(-c2ccc(-c3nc(-c4ccc(C(F)(F)F)nc4)cc(C(F)(F)F)n3)cc2)cc1]

2-(4-Bromophenyl)-4-(trifluoromethyl)-6-(6-(trifluoromethyl)pyridin-3-yl)pyrimidine (0.075 g, 0.17 mmol), 4-boronobenzoic acid (0.042 g, 0.255 mmol), tetrakistriphenylphosphinepalladium(0) (0.019, 0.017 mmol), 2M Na$_2$CO$_3$ (0.34 mL, 0.68 mmol) were dissolved in DME. The reaction mixture was then processed according to the general procedure described in Example 69, step 7, to afford the desired compound as a white solid (0.049 g, 59%). $^1$H NMR (400 MHz, DMSOd$_6$): δ9.73 (s, 1H), 9.06 (d, J=8.2 Hz, 1H), 8.69 (s, 1H), 8.59 (d, J=8.7 Hz, 2H), 8.13 (d, J=8.2 Hz, 1H), 8.02 (d, J=8.7 Hz, 2H), 7.92 (d, J=8.7 Hz, 2H), 7.86 (d, J=8.2 Hz, 2H). LRMS (ESI) calcd. for C$_{24}$H$_{13}$F$_6$N$_3$O$_2$[M+H]$^+$: 490.09. Found: 489.95.

Example 82: 4-Fluoro-4'-(4-(trifluoromethyl)-6-(6-(trifluoromethyl)pyridin-3-yl)pyrimidin-2-yl)biphenyl-3-carboxylic Acid

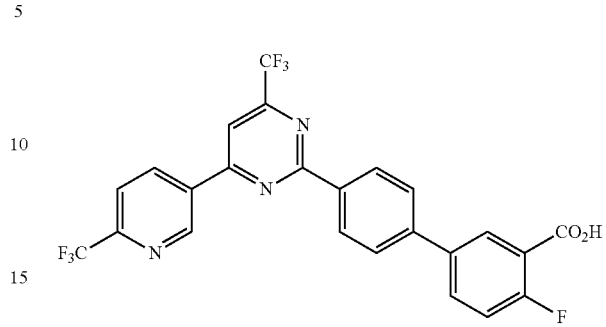

2-(4-Bromophenyl)-4-(trifluoromethyl)-6-(6-(trifluoromethyl)pyridin-3-yl)pyrimidine (0.100 g, 0.23 mmol), 5-borono-2-fluorobenzoic acid (0.064 g, 0.35 mmol), tetrakistriphenylphosphinepalladium(0) (0.027, 0.023 mmol), 2M Na$_2$CO$_3$ (0.46 mL, 0.92 mmol) were dissolved in DME. The reaction mixture was then processed according to the general procedure described in Example 69, step 7, to afford the desired compound as a white solid (0.072 g, 62%). $^1$H NMR (400 MHz, DMSOd$_6$): δ9.56 (s, 1H), 8.89 (d, J=8.3 Hz, 1H), 8.54 (s, 1H), 8.37 (d, J=8.2 Hz, 2H), 8.06 (d, J=8.2 Hz, 1H), 8.03 (d, J=8.2 Hz, 1H), 8.00-7.97 (m, 1H), 7.70 (d, J=8.2 Hz, 2H), 7.31 (t, J=8.7 Hz, 1H).

Example 83: 4-Chloro-4'-(4-(trifluoromethyl)-6-(6-(trifluoromethyl)pyridin-3-yl)pyrimidin-2-yl)biphenyl-3-carboxylic Acid

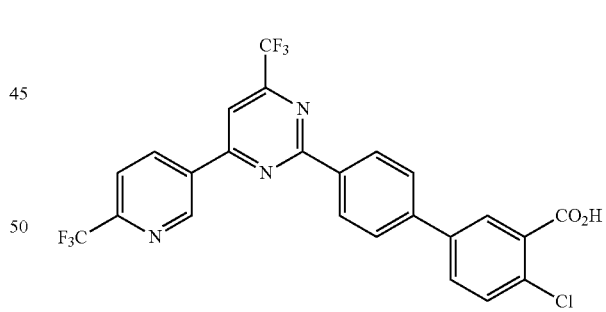

2-(4-Bromophenyl)-4-(trifluoromethyl)-6-(6-(trifluoromethyl)pyridin-3-yl)pyrimidine (0.100 g, 0.23 mmol), 5-borono-2-chlorobenzoic acid (0.069 g, 0.35 mmol), tetrakistriphenylphosphinepalladium(0) (0.027, 0.023 mmol), 2M Na$_2$CO$_3$ (0.46 mL, 0.92 mmol) were dissolved in DME. The reaction mixture was then processed according to the general procedure described in Example 69, step 7, to afford the desired compound as a white solid (0.056 g, 46%). $^1$H NMR (400 MHz, DMSOd$_6$): δ9.71 (d, J=8.8 Hz, 1H), 9.06-9.01 (m, 1H), 8.69-8.53 (m, 3H), 8.12-8.06 (m, 2H), 7.89-7.87 (m, 3H), 7.64-7.61 (m, 1H). LRMS (ESI) calcd. for C$_{24}$H$_{12}$ClF$_6$N$_3$O$_2$[M+H]$^+$: 524.05. Found: 524.0.

Example 84: 5-Fluoro-4'-(4-(trifluoromethyl)-6-(6-(trifluoromethyl)pyridin-3-yl)pyrimidin-2-yl)biphenyl-3-carboxylic Acid

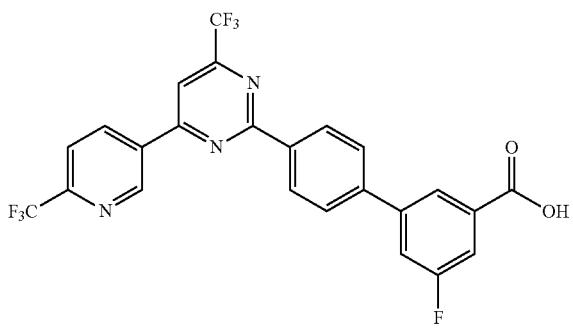 [SMILES: O=C(O)c1cc(F)cc(-c2ccc(-c3nc(-c4ccc(C(F)(F)F)nc4)cc(C(F)(F)F)n3)cc2)c1]

2-(4-Bromophenyl)-4-(trifluoromethyl)-6-(6-(trifluoromethyl)pyridin-3-yl)pyrimidine (0.197 g, 0.44 mmol), 3-borono-5-fluorobenzoic acid (0.120 g, 0.66 mmol), tetrakistriphenylphosphinepalladium(0) (0.050, 0.044 mmol), 2M $Na_2CO_3$ (0.88 mL, 1.6 mmol) were dissolved in DME. The reaction mixture was then processed according to the general procedure described in Example 69, step 7, to afford the desired compound as a white solid (0.115 g, 52%). $^1H$ NMR (400 MHz, $DMSOd_6$): δ9.71 (s, 1H), 9.03 (d, J=8.2 Hz, 1H), 8.67 (s, 1H), 8.56 (d, J=8.2 Hz, 2H), 8.12 (d, J=8.2 Hz, 1H), 8.07 (s, 1H), 7.93 (s, 1H), 7.91 (s, 1H), 7.87 (d, J=8.7 Hz, 1H), 7.65 (d, J=8.7 Hz, 1H). LRMS (ESI) calcd. for $C_{24}H_{12}F_7N_3O_2$ $[M+H]^+$: 508.08. Found: 508.0.

Example 85: 4-Chloro-N-methyl-3'-(4-(trifluoromethyl)-6-(6-(trifluoromethyl)pyridin-3-yl)pyrimidin-2-yl)biphenyl-3-carboxamide

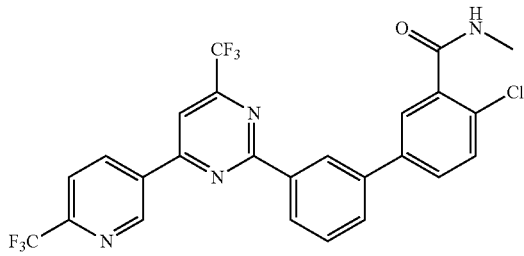 [SMILES: CNC(=O)c1cc(-c2cccc(-c3nc(-c4ccc(C(F)(F)F)nc4)cc(C(F)(F)F)n3)c2)ccc1Cl]

4-Chloro-3'-(4-(trifluoromethyl)-6-(6-(trifluoromethyl)pyridin-3-yl)pyrimidin-2-yl)biphenyl-3-carboxylic acid (0.025, 0.047 mmol) was dissolved in DMF (2 mL) at room temperature. HOBt (0.008 g, 0.06 mmol) was added in one portion followed by EDC (0.010 g, 0.06 mmol). The resulting mixture was stirred at room temperature for 30 min. To this solution methylamine hydrochloride (0.005 g, 0.071 mmol) and triethylamine (0.009 mL, 0.07 mmol) were added and stirred for 2 h, and the organic phase was evaporated under reduced pressure. The crude product was purified using automated prep-HPLC to afford the amide as a white solid (0.02, 80%). $^1H$ NMR (400 MHz, $DMSOd_6$): δ9.78 (s, 1H), 9.11 (s, 1H), 9.08 (s, 1H), 8.54 (d, J=8.7 Hz, 1H), 8.46-8.45 (m, 1H), 8.16 (d, J=8.2 Hz, 1H), 7.82 (d, J=6.9 Hz, 1H), 7.76 (d, J=8.2 Hz, 1H), 7.73 (s, 1H), 7.71 (t, J=8.2 Hz, 1H), 7.62 (d, J=8.2 Hz, 1H), 2.76 (d, J=4.1 Hz, 3H). LRMS (ESI) calcd. for $C_{25}H_{15}ClF_6N_4O$ $[M+H]^+$: 537.08. Found: 536.95.

General Synthetic Scheme for the Preparation of 4-aryl/heteroaryl pyrimidin-2-yl-biphenyl carboxylic Acid Derivatives (Method 2)

Scheme 14

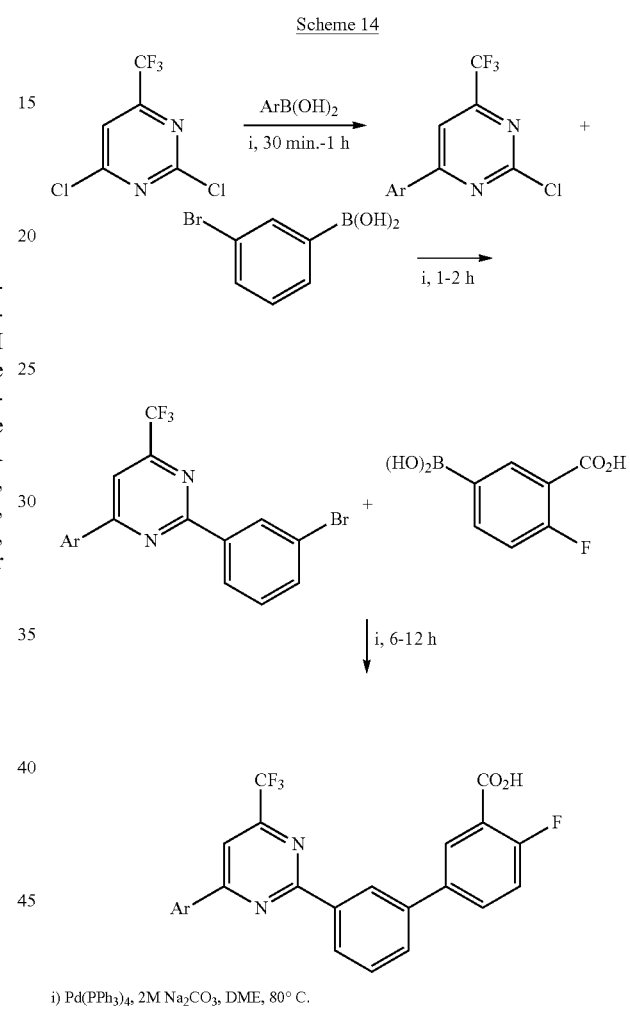

i) $Pd(PPh_3)_4$, 2M $Na_2CO_3$, DME, 80° C.

Example 86: 4-Fluoro-3'-(4-phenyl-6-(trifluoromethyl)pyrimidin-2-yl)biphenyl-3-carboxylic Acid

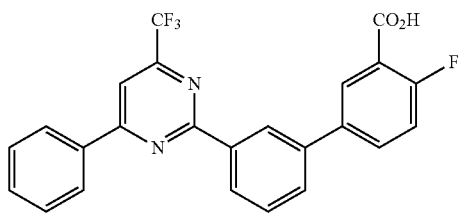 [SMILES: O=C(O)c1cc(-c2cccc(-c3nc(-c4ccccc4)cc(C(F)(F)F)n3)c2)ccc1F]

Step 1: 2,4-Dichloro-6-(trifluoromethyl)pyrimidine

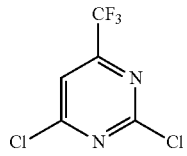 [SMILES: FC(F)(F)c1cc(Cl)nc(Cl)n1]

6-Trifluromethyl uracil (3 g, 16.66 mmol) was taken in dry CH₃CN (15 mL). To this was added N,N-dimethylaniline (1.96 mL, 15.37 mmol) and POCl₃ (5.74 mL, 61.48 mmol). The resulting mixture was heated to reflux for 6 h. The reaction mixture was cooled to room temperature and the volatile materials were removed in vacuum. The residue was dissolved in diethyl ether and washed with water. The organic layer was dried over Na₂SO₄, and the solvent was evaporated to afford the title compound as a yellow liquid (2.72 g, 74%) which was used for next step without further purification. $^1$H NMR (400 MHz, CDCl₃): δ7.63 (s, 1H).

Step 2: 2-Chloro-4-phenyl-6-(trifluoromethyl)pyrimidine

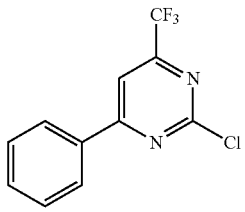 [SMILES: FC(F)(F)c1cc(-c2ccccc2)nc(Cl)n1]

To a mixture of phenylboronic acid (0.134 g, 1.1 mmol), 2,4-dichloro-6-(trifluoromethyl)pyrimidine (0.226 g, 1 mmol) and tetrakistriphenylphosphinepalladium(0) (0.115 mg, 0.1 mmol) in 4 mL of DME was added a 2M Na₂CO₃ (2 mL, 4 mmol) solution. The reaction mixture was then processed according to the general procedure described in Example 69, step 6, to afford the desired compound as a colorless solid (0.178 g, 69%). $^1$H NMR (400 MHz, CDCl₃): δ8.11 (d, J=8.3 Hz, 2H), 7.94 (s, 1H), 7.63-7.54 (m, 3H). LRMS (ESI) calcd. for C₁₁H₆ClF₃N₂[M+H]⁺: 259.01. Found: 259.0.

Step 3: 2-(3-Bromophenyl)-4-phenyl-6-(trifluoromethyl)pyrimidine

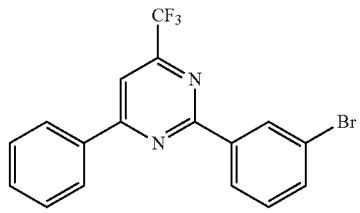 [SMILES: FC(F)(F)c1cc(-c2ccccc2)nc(-c2cccc(Br)c2)n1]

To a mixture of 3-bromophenylboronic acid (0.166 g, 0.83 mmol), 2-chloro-4-phenyl-6-(trifluoromethyl)pyrimidine (0.178 g, 0.69 mmol) and tetrakistriphenylphosphinepalladium(0) (0.079 g, 0.069 mmol) in 6 mL of DME was added a 2M Na₂CO₃ (1.7 mL, 3.4 mmol) solution. The reaction mixture was then processed according to the general procedure described in Example 69, step 6, to afford the desired compound as a colorless solid (0.298 g, 79%). $^1$H NMR (400 MHz, CDCl₃): δ8.75 (s, 1H), 8.55 (d, J=7.8 Hz, 1H), 8.25-8.23 (m, 2H), 7.91 (s, 1H), 7.65 (d, J=8.2 Hz, 1H), 7.64-7.57 (m, 3H), 7.41 (t, J=7.8 Hz, 1H). LRMS (ESI) calcd. for C₁₇H₁₀BrF₃N₂[M+H]⁺: 378.99, 380.99. Found: 379.0, 381.0.

Step 4: 4-Fluoro-3'-(4-phenyl-6-(trifluoromethyl)pyrimidin-2-yl)biphenyl-3-carboxylic Acid

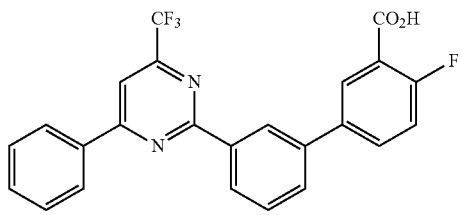 [SMILES: O=C(O)c1cc(-c2cccc(-c3nc(-c4ccccc4)cc(C(F)(F)F)n3)c2)ccc1F]

A mixture of 5-borono-2-fluorobenzoic acid (0.108 g, 0.6 mmol), 2-(3-bromophenyl)-4-phenyl-6-(trifluoromethyl)pyrimidine (0.151 g, 0.4 mmol) and tetrakistriphenylphosphinepalladium(0) (0.046 g, 0.04 mmol) in 6 mL of DME was added a 2M Na₂CO₃ (0.8 mL, 1.6 mmol) solution was added. The reaction mixture was then processed according to the general procedure described in Example 69, step 7, to afford the desired compound as a colorless solid (0.100 g, 58%). $^1$H NMR (400 MHz, DMSOd₆): δ8.52 (s, 1H), 8.36 (d, J=7.8 Hz, 1H), 8.33 (d, J=7.3 Hz, 2H), 8.28 (s, 1H), 8.05 (dd, J=2.8 Hz, 6.8 Hz, 1H), 7.84-7.82 (m, 1H), 7.43 (d, J=7.8 Hz, 1H), 7.55-7.51 (m, 4H), 7.34 (t, J=10.0 Hz, 1H). LRMS (ESI) calcd. for C₂₄H₁₄F₄N₂O₂[M+H]⁺: 439.09. Found: 438.90.

The following compounds (Examples 87-122) were synthesized from 2,4-dichloro-6-(trifluoromethyl)pyrimidine (0.4 mmol, 1 equiv.), boronic acid (1.1 equiv), 3-bromophenylboronic acid (0.44 mmol, 1.1 equiv), and appropriate borono benzoic acid derivatives (0.6 mmol, 1.5 equiv.) according to the method described in Example 86.

Example 87: 4-Fluoro-3'-(4-(4-methoxyphenyl)-6-(trifluoromethyl)pyrimidin-2-yl)biphenyl-3-carboxylic Acid

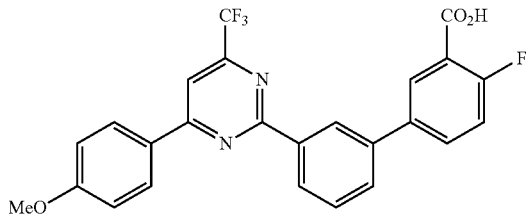

Off-white solid (0.09 g, 48%). $^1$H NMR (400 MHz, DMSOd₆): δ9.09 (s, 1H), 8.50 (dd, J=2.3 Hz, 8.7 Hz, 1H), 4.46 (s, 1H), 8.31 (d, J=6.9 Hz, 1H), 8.25 (s, 1H), 8.04 (dd, J=2.3 Hz, 8.7 Hz, 1H), 7.84-7.82 (m, 1H), 7.21 (d, J=7.8 Hz, 1H), 7.52 (t, J=7.8 Hz, 1H), 7.35 (t, J=8.7 Hz, 1H), 6.85 (d, J=8.9 Hz, 1H), 3.87 (s, 3H). LRMS (ESI) calcd. $C_{25}H_{16}F_4N_2O_3[M+H]^+$: 469.10. Found: 468.90.

Example 87A: 4-Fluoro-3'-(4-(thiophen-2-yl)-6-(trifluoromethyl)pyrimidin-2-yl)biphenyl-3-carboxylic Acid

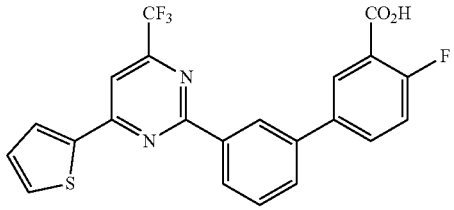 [SMILES: O=C(O)c1cc(-c2cccc(-c3nc(-c4cccs4)cc(C(F)(F)F)n3)c2)ccc1F]

Off-white solid (0.07 g, 39%). $^1$H NMR (400 MHz, DMSOd$_6$): δ8.58 (s, 1H), 8.41-8.38 (m, 3H), 8.12 (d, J=6.9 Hz, 1H), 7.96-7.95 (m, 2H), 7.88 (t, J=8.7 Hz, 1H), 7.70-7.67 (m, 1H), 7.44 (t, J=8.7 Hz, 1H), 7.31-7.30 (m, 1H). LRMS (ESI) calcd. for $C_{22}H_{12}F_4N_2O_2S$ [M+H]$^+$: 445.04. Found: 444.80.

Example 88: 4-Fluoro-3'-(4-(furan-2-yl)-6-(trifluoromethyl)pyrimidin-2-yl)biphenyl-3-carboxylic Acid

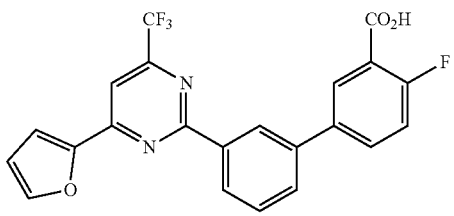 [SMILES: O=C(O)c1cc(-c2cccc(-c3nc(-c4ccco4)cc(C(F)(F)F)n3)c2)ccc1F]

White solid (0.075 g, 44%). $^1$H NMR (400 MHz, DMSOd$_6$): δ8.55 (s, 1H), 8.40 (d, J=7.8 Hz, 1H), 8.07 (dd, J$_1$=2.3 Hz, J$_2$=8.7 Hz 1H), 8.06 (s, 1H), 8.00 (s, 1H), 7.92-7.90 (m, 1H), 7.82 (d, J=7.8 Hz, 1H), 7.75 (d, J=3.2 Hz, 1H), 7.64 (t, J=8.7 Hz, 1H), 7.40 (t, J=8.7 Hz, 1H), 6.80-6.79 (m, 1H). LRMS (ESI) calcd. for $C_{22}H_{12}F_4N_2O_3[M+H]^+$: 429.07. Found: 428.85.

Example 89: 5-Fluoro-3'-(4-(furan-2-yl)-6-(trifluoromethyl)pyrimidin-2-yl)biphenyl-3-carboxylic Acid

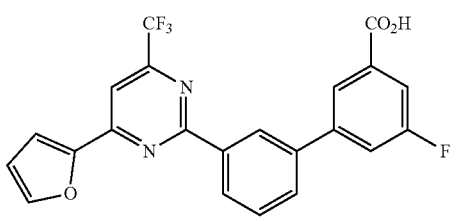 [SMILES: O=C(O)c1cc(F)cc(-c2cccc(-c3nc(-c4ccco4)cc(C(F)(F)F)n3)c2)c1]

Off-white solid (0.069 g, 40%). $^1$H NMR (400 MHz, DMSOd$_6$): δ8.53 (s, 1H), 8.38 (d, J=7.8 Hz, 1H), 8.04 (s, 1H), 7.98 (s, 1H), 7.94 (s, 1H), 7.82 (d, J=8.2 Hz, 1H), 7.74-7.73 (m, 1H), 7.72 (d, J=3.2 Hz, 1H), 7.61 (q, J=7.8 Hz, 2H), 6.80-6.79 (m, 1H). LRMS (ESI) calcd. for $C_{22}H_{12}F_4N_2O_3[M+H]^+$: 429.07. Found: 429.0.

Example 90: 3'-(4-(Furan-2-yl)-6-(trifluoromethyl)pyrimidin-2-yl)-4-methoxybiphenyl-3-carboxylic Acid

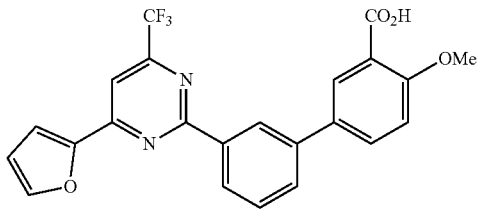 [SMILES: COc1ccc(-c2cccc(-c3nc(-c4ccco4)cc(C(F)(F)F)n3)c2)cc1C(=O)O]

Off-white solid (0.08 g, 45%). $^1$H NMR (400 MHz, DMSOd$_6$): δ 8.56 (s, 1H), 8.37 (d, J=7.8 Hz, 1H), 8.08 (s, 1H), 8.04 (s, 1H), 7.92 (d, J=1.8 Hz, 1H), 7.84-7.80 (m, 2H), 7.77 (d, J=3.2 Hz, 1H), 7.63-7.59 (m, 1H), 7.23 (d, J=8.7 Hz, 1H), 6.81-6.80 (m, 1H), 3.88 (s, 3H). LRMS (ESI) calcd. for $C_{23}H_{15}F_3N_2O_4[M+H]^+$: 441.09. Found: 441.0.

Example 91: 4-Fluoro-3'-(4-o-tolyl-6-(trifluoromethyl)pyrimidin-2-yl)biphenyl-3-carboxylic Acid

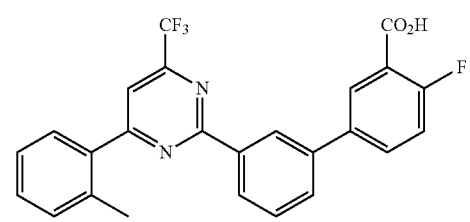 [SMILES: Cc1ccccc1-c1cc(C(F)(F)F)nc(-c2cccc(-c3ccc(F)c(C(=O)O)c3)c2)n1]

White solid (0.04 g, 22%). $^1$H NMR (400 MHz, DMSOd$_6$): δ8.59 (s, 1H), 8.39 (d, J=7.8 Hz, 1H), 8.90-8.07 (m, 2H), 7.85-7.68 (m, 4H), 7.64-7.26 (m, 4H), 2.48 (s, 3H). LRMS (ESI) calcd. for $C_{25}H_{16}F_4N_2O_2[M+H]^+$: 453.11. Found: 453.0.

Example 92: 4-Fluoro-3'-(4-m-tolyl-6-(trifluoromethyl)pyrimidin-2-yl)biphenyl-3-carboxylic Acid

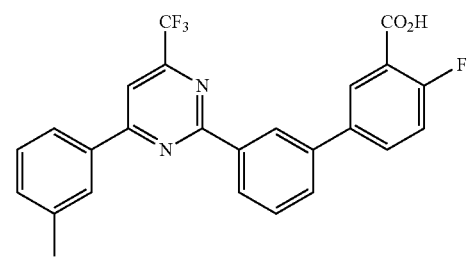 [SMILES: Cc1cccc(-c2cc(C(F)(F)F)nc(-c3cccc(-c4ccc(F)c(C(=O)O)c4)c3)n2)c1]

White solid (0.60 g, 33%). $^1$H NMR (400 MHz, DMSOd$_6$): δ8.68 (s, 1H), 8.53 (d, J=7.8 Hz, 1H), 8.29 (s, 1H), 8.26 (d, J=7.3 Hz, 1H), 8.14 (dd, J=3.4 Hz, 6.8 Hz, 1H), 7.99-7.93 (m, 1H), 7.89 (d, J=7.8 Hz, 1H), 7.70 (t, J=7.8 Hz, 1H), 7.50-7.41 (m, 3H), 7.16 (d, J=6.8 Hz, 1H), 2.36 (s, 3H). LRMS (ESI) calcd. for $C_{25}H_{16}F_4N_2O_2[M+H]^+$: 453.11. Found: 453.0.

Example 93: 3'-(4-(3,5-Dimethylphenyl)-6-(trifluoromethyl)pyrimidin-2-yl)-4-fluorobiphenyl-3-carboxylic Acid

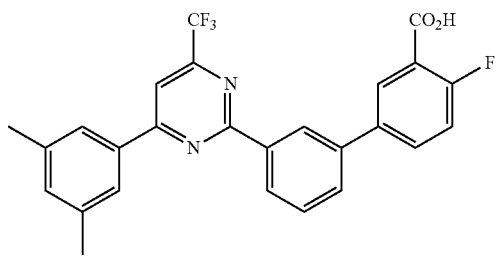 [SMILES: Cc1cc(C)cc(-c2cc(C(F)(F)F)nc(-c3cccc(-c4ccc(F)c(C(=O)O)c4)c3)n2)c1]

White solid (0.072 g, 38%). $^1$H NMR (400 MHz, DMSOd$_6$): δ 8.68 (s, 1H), 8.51 (d, J=7.3 Hz, 1H), 8.45 (s, 1H), 8.08 (s, 2H), 7.90 (d, J=7.8 Hz, 2H), 7.69 (t, J=7.8 Hz, 1H), 7.43-7.41 (m, 2H), 7.26 (s, 1H), 2.38 (s, 6H). LRMS (ESI) calcd. for $C_{26}H_{18}F_4N_2O_2[M+H]^+$: 467.13. Found: 467.0.

Example 94: 4-Fluoro-3'-(4-(furan-3-yl)-6-(trifluoromethyl)pyrimidin-2-yl)biphenyl-3-carboxylic Acid

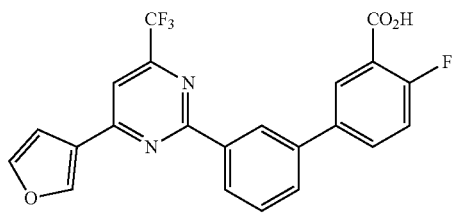 [SMILES: O=C(O)c1cc(-c2cccc(-c3nc(-c4ccoc4)cc(C(F)(F)F)n3)c2)ccc1F]

Off-white solid (0.085 g, 49%). $^1$H NMR (400 MHz, DMSOd$_6$): δ 8.57 (s, 1H), 8.37 (d, J=7.8 Hz, 1H), 8.06 (s, 1H), 8.00 (s, 1H), 7.93 (d, J=2.3 Hz, 1H), 7.85 (d, t=8.2 Hz, 1H), 7.78 (d, J=3.7 Hz, 1H), 7.63-7.23 (m, 2H), 6.81-6.80 (m, 1H). LRMS (ESI) calcd. for $C_{22}H_{12}F_4N_2O_3 [M+H]^+$: 429.07. Found: 428.85.

Example 95: (E)-4-Fluoro-3'-(4-styryl-6-(trifluoromethyl)pyrimidin-2-yl)biphenyl-3-carboxylic Acid

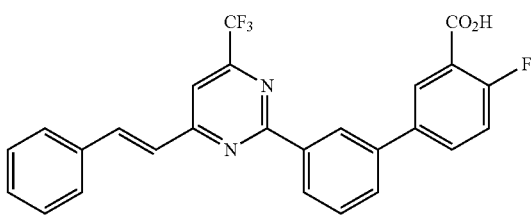 [SMILES: O=C(O)c1cc(-c2cccc(-c3nc(/C=C/c4ccccc4)cc(C(F)(F)F)n3)c2)ccc1F]

White solid (0.098 g, 53%). $^1$H NMR (400 MHz, DMSOd$_6$): δ 8.68 (s, 1H), 8.43 (d, J=7.8 Hz, 1H), 8.20-8.14 (m, 2H), 8.01-7.90 (m, 2H), 7.22-7.63 (m, 5H), 7.56 (t, J=7.8 Hz, 1H), 7.41-7.38 (m, 3H). LRMS (ESI) calcd. for $C_{22}H_{16}F_4N_2O_2[M+H]^+$: 465.41. Found: 465.0.

Example 96: 3'-(4-(4-tert-Butylphenyl)-6-(trifluoromethyl)pyrimidin-2-yl)-4-fluorobiphenyl-3-carboxylic Acid

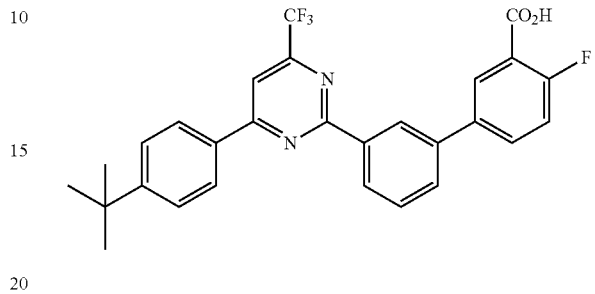

White solid (0.068 g, 34%). $^1$H NMR (400 MHz, DMSOd$_6$): δ8.63 (s, 1H), 8.46 (d, 1H, J=7.8 Hz), 8.38 (s, 1H), 8.33 (d, 2H, J=8.2 Hz), 8.10 (d, 1H, J=9.0 Hz), 7.93-7.92 (m, 1H), 7.84 (d, 1H, J=7.8 Hz), 7.63 (t, 1H, J=7.8 Hz), 7.57 (d, 2H, J=8.2 Hz), 742 (t, 1H, J=8.2 Hz), 1.32 (s, 9H). LRMS (ESI) calcd. for $C_{28}H_{22}F_4N_2O_2[M+H]^+$: 495.16. Found: 495.0.

Example 97: 4-Fluoro-3'-(4-(2-fluoropyridin-3-yl)-6-(trifluoromethyl)pyrimidin-2-yl)biphenyl-3-carboxylic Acid

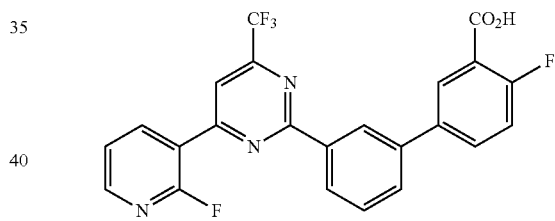

White solid (0.102 g, 56%). $^1$H NMR (400 MHz, DMSOd$_6$): δ8.82-8.81 (m, 1H), 8.57 (s, 1H), 8.43-8.42 (overlapping doublet and singlet, 2H), 8.20 (s, 1H), 8.07 (dd, J=2.8 Hz, 6.8 Hz, 1H), 7.93-7.92 (m, 1H), 7.85 (d, J=7.8 Hz, 1H), 7.63 (t, J=7.8 Hz, 1H), 7.61-7.59 (m, 1H), 7.39 (t, J=8.7 Hz, 1H). LRMS (ESI) calcd. for $C_{23}H_{12}F_5N_3O_2[M+H]^+$: 458.08. Found: 458.0.

Example 98: 3'-(4-(4-Chlorophenyl)-6-(trifluoromethyl)pyrimidin-2-yl)-4-fluorobiphenyl-3-carboxylic Acid

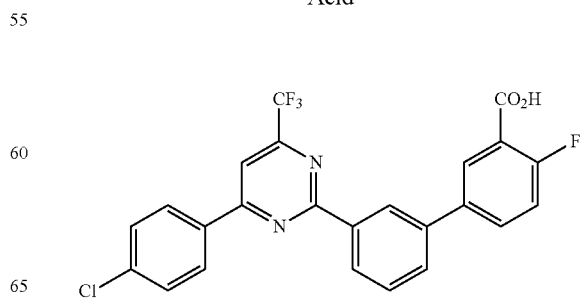

White solid (0.07 g, 32%). $^1$H NMR (400 MHz, DMSOd$_6$): δ8.53 (s, 1H), 8.40-8.39 (m, 4H), 8.07 (dd, J=2.5 Hz, 6.8 Hz, 1H), 7.89-7.88 (m, 1H), 7.80 (d, J=7.8 Hz, 1H), 7.58-7.57 (m, 3H), 7.38 (t, J=9.0 Hz, 1H). LRMS (ESI) calcd. for $C_{22}H_{13}ClF_4N_2O_2$ [M+H]$^+$: 473.06. Found: 473.0.

Example 99: 3'-(4-(3,4-Dimethoxyphenyl)-6-(trifluoromethyl)pyrimidin-2-yl)-4-fluorobiphenyl-3-carboxylic Acid

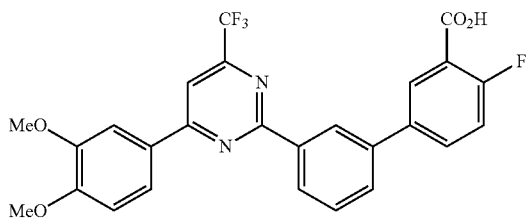 [SMILES: COc1ccc(-c2cc(C(F)(F)F)nc(-c3cccc(-c4ccc(F)c(C(=O)O)c4)c3)n2)cc1OC]

Off-white solid (0.092 g, 46%). $^1$H NMR (400 MHz, DMSOd$_6$): δ8.67 (s, 1H), 8.45 (d, J=7.8 Hz, 1H), 8.41 (s, 1H), 8.13 (d, J=6.9 Hz, 1H), 8.07 (dd, J=1.8 Hz, 9.0 Hz, 1H), 7.98-7.95 (m, 2H), 7.87 (d, J=6.9 Hz, 1H), 7.66 (t, J=7.7 Hz, 1H), 7.42 (t, J=10 Hz, 1H), 7.11 (d, J=8.7 Hz, 1H), 3.89 (s, 3H), 3.84 (s, 3H). LRMS (ESI) calcd. $C_{26}H_{18}F_4N_2O_4$[M+H]$^+$: 499.12. Found: 498.95.

Example 100: 4-Fluoro-3'-(4-(2-fluorophenyl)-6-(trifluoromethyl)pyrimidin-2-yl)biphenyl-3-carboxylic Acid

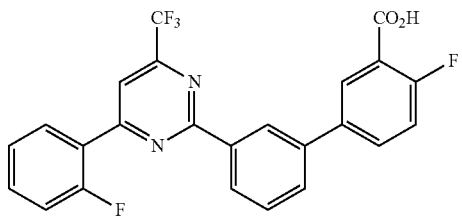 [SMILES: O=C(O)c1cc(-c2cccc(-c3nc(-c4ccccc4F)cc(C(F)(F)F)n3)c2)ccc1F]

Off-white solid (0.060 g, 33%). $^1$H NMR (400 MHz, DMSOd$_6$): δ8.58 (s, 1H), 8.44 (d, J=8.2 Hz, 1H), 8.26 (t, J=9.6 Hz, 1H), 8.13 (s, 1H), 8.08 (dd, J=2.8 Hz, 9.6 Hz, 1H), 7.92-7.85 (m, 1H), 7.84 (d, J=7.8 Hz, 1H), 7.64 (t, J=7.3 Hz, 1H), 7.43-7.10 (m, 3H). LRMS (ESI) calcd. for $C_{24}H_{13}F_5N_2O_2$[M+H]$^+$: 457.08. Found: 456.90.

Example 101: 3'-(4-(Benzofuran-2-yl)-6-(trifluoromethyl)pyrimidin-2-yl)-4-fluorobiphenyl-3-carboxylic Acid

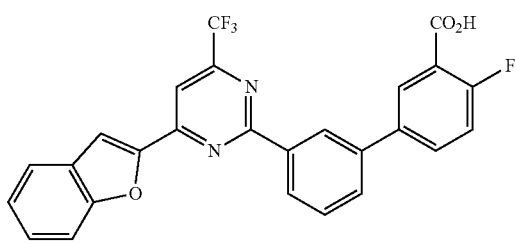 [SMILES: O=C(O)c1cc(-c2cccc(-c3nc(-c4cc5ccccc5o4)cc(C(F)(F)F)n3)c2)ccc1F]

Off-white solid (0.100 g, 52%). $^1$H NMR (400 MHz, DMSOd$_6$): δ8.60 (s, 1H), 8.43 (d, J=8.7 Hz, 1H), 8.18 (s, 1H), 8.17 (s, 1H), 8.10 (dd, J=3.3 Hz, 6.9 Hz, 1H), 7.95-7.92 (m, 1H), 7.85 (dd, J=3.3 Hz, 6.9 Hz, 1H), 7.9 (d, J=7.9 Hz, 1H), 7.71-7.76 (m, 2H), 7.48-7.32 (m, 3H). LRMS (ESI) calcd. for $C_{26}H_{14}F_4N_2O_3$[M+H]$^+$: 479.09. Found: 479.0.

Example 102: 3'-(4-(Benzo[b]thiophen-2-yl)-6-(trifluoromethyl)pyrimidin-2-yl)-4-fluorobiphenyl-3-carboxylic Acid

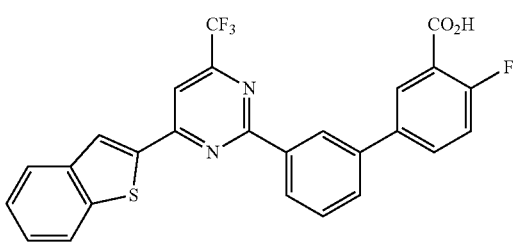

Off-white solid (0.120 g, 61%). $^1$H NMR (400 MHz, DMSOd$_6$): δ 8.71 (s, 1H), 8.56 (s, 1H), 8.53 (s, 1H), 8.40 (d, 1H, J=7.8 Hz), 8.12 (dd, 1H, J=2.8 Hz, 6.9 Hz), 8.02 (d, 1H, J=7.8 Hz), 7.92-7.85 (m, 2H), 7.84 (d, 1H, J=7.8 Hz), 7.65 (t, 1H, J=7.8 Hz), 7.45-7.41 (m, 3H). LRMS (ESI) calcd. for $C_{26}H_{14}F_4N_2O_2S$ [M+H]$^+$: 495.07. Found: 494.95.

Example 103: 4-Fluoro-3'-(4-(4-(methylthio)phenyl)-6-(trifluoromethyl)pyrimidin-2-yl)biphenyl-3-carboxylic Acid

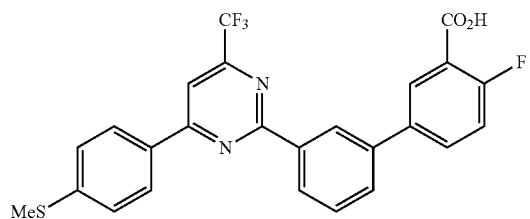 [SMILES: CSc1ccc(-c2cc(C(F)(F)F)nc(-c3cccc(-c4ccc(F)c(C(=O)O)c4)c3)n2)cc1]

White solid (0.096 g, 49%). $^1$H NMR (400 MHz, DMSOd$_6$): δ8.63 (s, 1H), 8.47 (d, 2H, J=8.2 Hz), 8.40 (t, 2H, J=7.3 Hz), 8.11 (dd, 1H, J=2.3 Hz, J=6.9 Hz), 7.95-7.94 (m, 1H), 7.86 (d, 1H, J=7.8 Hz), 7.67 (t, 1H, J=7.8 Hz), 7.43-7.38 (m, 3H), 2.53 (s, 3H). LRMS (ESI) calcd. for $C_{25}H_{16}F_4N_2O_2S$ [M+H]$^+$: 485.08. Found: 485.0.

Example 104: 5-Fluoro-3'-(4-phenyl-6-(trifluoromethyl)pyrimidin-2-yl)biphenyl-3-carboxylic Acid

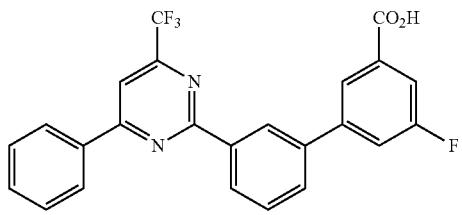 [SMILES: O=C(O)c1cc(F)cc(-c2cccc(-c3nc(-c4ccccc4)cc(C(F)(F)F)n3)c2)c1]

White solid (0.095 g, 54%). $^1$H NMR (400 MHz, DMSOd$_6$): δ8.63 (s, 1H), 8.49 (d, J=7.8 Hz, 1H), 8.41-8.39 (m, 2H), 8.00 (s, 1H), 7.89-7.80 (m, 3H), 7.66-7.57 (m, 5H). LRMS (ESI) calcd. for C$_{24}$H$_{14}$F$_4$N$_2$O$_2$[M+H]$^+$: 439.09. Found: 438.90.

Example 105: 3'-(4-(3,5-Bis(trifluoromethyl)phenyl)-6-(trifluoromethyl)pyrimidin-2-yl)-4-fluorobiphenyl-3-carboxylic Acid

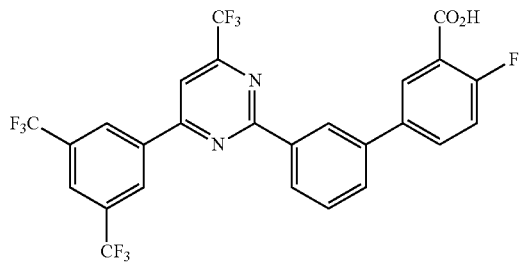 [SMILES: O=C(O)c1cc(-c2cccc(-c3nc(-c4cc(C(F)(F)F)cc(C(F)(F)F)c4)cc(C(F)(F)F)n3)c2)ccc1F]

White solid (0.07 g, 30%). $^1$H NMR (400 MHz, DMSOd$_6$): δ9.04 (s, 1H), 8.87 (s, 1H), 8.63 (s, 1H), 8.47 (d, J=7.8 Hz, 1H), 8.26 (s, 1H), 8.15 (s 1H), 7.96-7.93 (m, 1H), 7.35 (d, J=7.8 Hz, 1H), 7.90 (s, 1H), 7.68 (t, J=7.8 Hz, 1H), 7.42 (t, J=9.0 Hz, 1H). LRMS (ESI) calcd. for C$_{26}$H$_{12}$F$_{10}$N$_2$O$_2$ [M+H]$^+$: 575.07. Found: 575.0.

Example 106: 3'-(4-(1H-Pyrrol-2-yl)-6-(trifluoromethyl)pyrimidin-2-yl)-4-fluorobiphenyl-3-carboxylic Acid

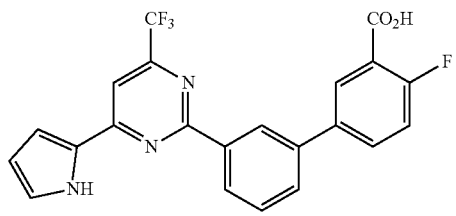 [SMILES: O=C(O)c1cc(-c2cccc(-c3nc(-c4ccc[nH]4)cc(C(F)(F)F)n3)c2)ccc1F]

Yellow solid (0.080 g, 47%). $^1$H NMR (400 MHz, DMSOd$_6$): δ12.16 (s, 1H), 8.78 (s, 1H), 8.57 (d, J=7.8 Hz, 1H), 8.14 ((dd, J=4.5 Hz, 6.9 Hz, 1H), 8.11 (s, 1H), 8.08-8.00 (m, 1H), 7.86 (d, J=7.8 Hz, 1H), 7.65 (t, J=7.8 Hz, 1H), 7.47-7.45 (m, 3H), 6.31-6.30 (m, 1H). LRMS (ESI) calcd. for C$_{22}$H$_{13}$F$_4$N$_3$O$_2$[M+H]$^+$: 428.09. Found: 428.0.

Example 107: 3'-(4-(3-Chlorothiophen-2-yl)-6-(trifluoromethyl)pyrimidin-2-yl)-4-fluorobiphenyl-3-carboxylic Acid

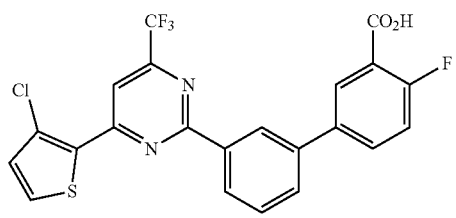 [SMILES: O=C(O)c1cc(-c2cccc(-c3nc(-c4sccc4Cl)cc(C(F)(F)F)n3)c2)ccc1F]

White solid (0.060 g, 31%). $^1$H NMR (400 MHz, DMSOd$_6$): δ8.59 (s, 1H), 8.39 (d, J=7.8 Hz, 1H), 8.36 (s, 1H), 8.12 (dd, J=4.6 Hz, 9.1 Hz, 1H), 8.06 (d, J=6.9 Hz, 1H), 7.95-9.89 (m, 2H), 7.69 (t, J=7.8 Hz, 1H), 7.34 (t, J=9.0 Hz, 1H), 7.33 (d, J=6.9 Hz, 1H). LRMS (ESI) calcd. for C$_{22}$H$_{11}$ClF$_4$N$_2$O$_2$S [M+H]$^+$: 479.01. Found: 479.0.

Example 108: 4-Fluoro-3'-(4-(trifluoromethyl)-6-(4-(trifluoromethyl)phenyl)pyrimidin-2-yl)biphenyl-3-carboxylic Acid

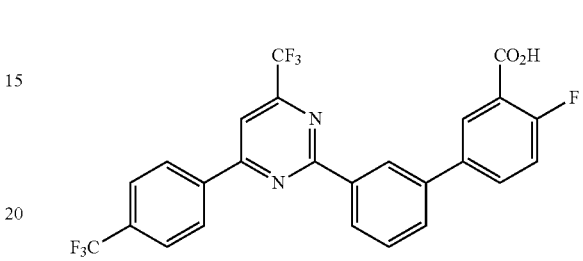

White solid (0.130 g, 64%). $^1$H NMR (400 MHz, DMSOd$_6$): δ8.64 (d, J=6.8 Hz, 3H), 8.62 (s, 1H), 8.57 (s, 1H), 8.48 (d, J=8.7 Hz, 1H), 8.10 (dd, J=3.4 Hz, 6.8 Hz, 1H), 7.96-7.93 (m, 3H), 7.87 (d, J=7.3 Hz, 1H), 7.68 (t, J=7.8 Hz, 1H), 7.41 (t, J=9.0 Hz, 1H). LRMS (ESI) calcd. for C$_{25}$H$_{13}$F$_7$N$_2$O$_2$[M+H]$^+$: 507.08. Found: 506.95.

Example 109: 4-Fluoro-3'-(4-(thiazol-2-yl)-6-(trifluoromethyl)pyrimidin-2-yl)biphenyl-3-carboxylic Acid

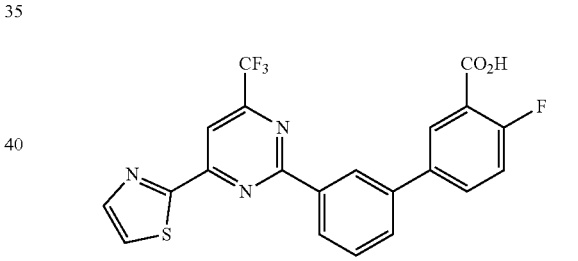

Light yellow solid (0.089 g, 50%). $^1$H NMR (400 MHz, DMSOd$_6$): δ 8.58 (s, 1H), 8.42 (d, J=7.8 Hz, 1H), 8.26 (s, 1H), 8.19-8.11 (m, 3H), 7.96-7.89 (m, 2H), 7.69 (t, J=7.8 Hz, 1H), 7.42 (t, J=9.0 Hz, 1HLRMS (ESI) calcd. for C$_{21}$H$_{11}$F$_4$N$_3$O$_2$S [M+H]$^+$: 446.05. Found: 446.0.

Example 110: 3'-(4-(4-Chloro-2-fluorophenyl)-6-(trifluoromethyl)pyrimidin-2-yl)-4-fluorobiphenyl-3-carboxylic Acid

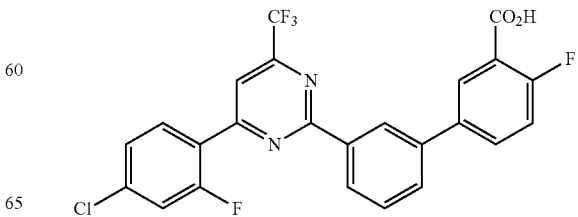

White solid (0.110 g, 56%). $^1$H NMR (400 MHz, DMSOd$_6$): δ 8.89 (s, 1H), 8.63 (s, 1H), 8.47 (d, J=7.8 Hz, 1H), 8.23 (s, 1H), 8.12 (dd, J=3.4 Hz, 6.8 Hz, 1H), 7.97-7.89 (m, 1H), 7.87 (d, J=1.4 Hz, 1H), 7.86 (d, J=7.8 Hz, 1H), 7.65 (t, J=7.8 Hz, 1H), 7.42 (t, J=8.7 Hz, 1H), 7.40 (s, 1H). LRMS (ESI) calcd. for C$_{24}$H$_{12}$ClF$_5$N$_2$O$_2$ [M+H]$^+$: 491.05. Found: 491.0.

Example 111: 3'-(4-(3,5-Dimethylisoxazol-4-yl)-6-(trifluoromethyl)pyrimidin-2-yl)-4-fluorobiphenyl-3-carboxylic Acid

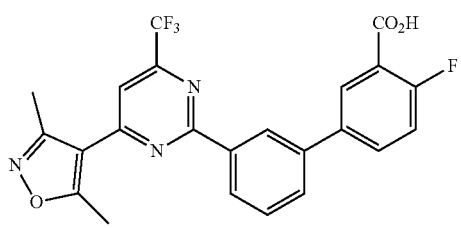 [SMILES: Cc1noc(C)c1-c1cc(C(F)(F)F)nc(-c2cccc(-c3ccc(F)c(C(=O)O)c3)c2)n1]

Yellow solid (0.130 g, 71%). $^1$H NMR (400 MHz, DMSOd$_6$): δ 8.63 (s, 1H), 8.39 (d, J=7.8 Hz, 1H), 8.14-8.13 (m, 1H), 7.97-7.95 (m, 1H), 7.91 (s, 1H), 7.90 (d, J=7.8 Hz, 1H), 7.68 (t, J=7.8 Hz, 1H), 7.42 (t, J=9.6 Hz, 1H), 2.76 (s, 3H), 2.55 (s, 3H). LRMS (ESI) calcd. for C$_{23}$H$_{15}$F$_4$N$_3$O$_3$ [M+H]$^+$: 458.10. Found: 457.90.

Example 112: 4-Fluoro-3'-(4-(5-methylthiophen-2-yl)-6-(trifluoromethyl)pyrimidin-2-yl)biphenyl-3-carboxylic Acid

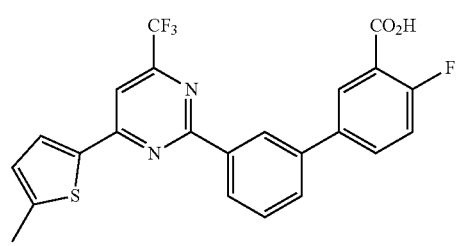 [SMILES: Cc1ccc(-c2cc(C(F)(F)F)nc(-c3cccc(-c4ccc(F)c(C(=O)O)c4)c3)n2)s1]

White solid (0.050 g, 27%). $^1$H NMR (400 MHz, DMSOd$_6$): δ 8.57 (s, 1H), 8.40 (d, J=7.8 Hz, 1H), 8.39 (s, 1H), 8.21 (d, J=3.7 Hz, 1H), 8.20-8.19 (m, 1H), 7.87 (d, J=7.8 Hz, 1H), 7.75-7.66 (m, 2H), 7.43 (t, J=8.7 Hz, 1H), 7.02-7.01 (m, 1H), 2.57 (s, 3H). LRMS (ESI) calcd. for C$_{23}$H$_{14}$F$_4$N$_2$O$_2$S [M+H]$^+$: 458.07. Found: 459.0.

Example 113: 5-Fluoro-3'-(4-(furan-3-yl)-6-(trifluoromethyl)pyrimidin-2-yl)biphenyl-3-carboxylic Acid

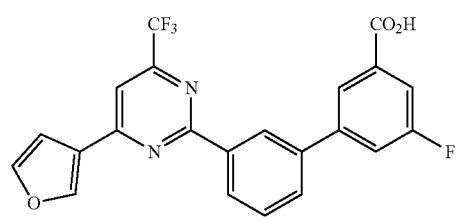 [SMILES: O=C(O)c1cc(F)cc(-c2cccc(-c3nc(-c4ccoc4)cc(C(F)(F)F)n3)c2)c1]

White solid (0.069 g, 37%). $^1$H NMR (400 MHz, DMSOd$_6$): δ 8.92 (s, 1H), 8.68 (s, 1H), 8.52 (d, J=7.8 Hz, 1H), 8.26 (s, 1H), 7.95 (s, 1H), 7.93-7.87 (m, 4H), 7.69 (t, J=7.8 Hz, 2H), 7.39 (d, J=1.8 Hz, 1H). LRMS (ESI) calcd. for C$_{22}$H$_{12}$F$_4$N$_2$O$_3$[M+H]$^+$: 429.09. Found: 429.00.

Example 114: 6-Fluoro-3'-(4-(furan-3-yl)-6-(trifluoromethyl)pyrimidin-2-yl)biphenyl-3-carboxylic Acid

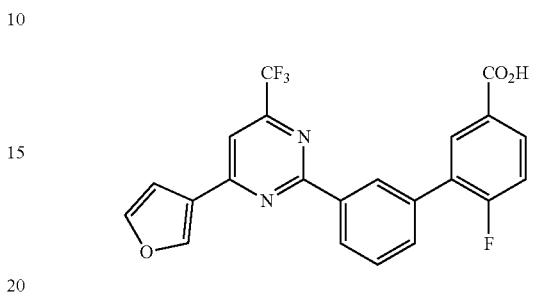

White solid (0.042 g, 22%). $^1$H NMR (400 MHz, DMSOd$_6$): δ8.89 (s, 1H), 8.60 (s, 1H), 8.54 (d, J=7.8 Hz, 1H), 8.26 (s, 1H), 8.09 (dd, J=2.3 Hz, 6.8 Hz, 1H), 8.07-8.00 (m, 1H), 7.89 (t, J=3.2 Hz, 1H), 7.79-7.77 (m, 1H), 7.69 (t, J=7.8 Hz, 1H), 7.49-7.47 (m, 1H), 7.36 (d, J=1.4 Hz, 1H). LRMS (ESI) calcd. for C$_{22}$H$_{12}$F$_4$N$_2$O$_3$[M+H]$^+$: 429.09. Found: 429.00.

Example 115: 3'-(4-(Furan-3-yl)-6-(trifluoromethyl)pyrimidin-2-yl)biphenyl-3-carboxylic Acid

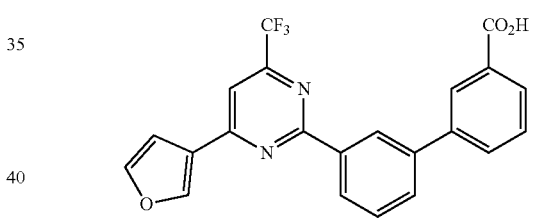

White solid (0.071 g, 39%). $^1$H NMR (400 MHz, DMSOd$_6$): δ 8.91 (s, 1H), 8.67 (s, 1H), 8.50 (d, J=7.8 Hz, 1H), 8.25 (s, 1H), 8.22 (s, 1H), 7.98-7.90 (m, 4H), 7.70-7.64 (m, 2H), 7.32 (d, J=1.8 Hz, 1H). LRMS (ESI) calcd. for C$_{22}$H$_{12}$F$_3$N$_2$O$_3$[M+H]$^+$: 411.09. Found: 411.00.

Example 116: 4-Fluoro-3'-(4-(pyridin-3-yl)-6-(trifluoromethyl)pyrimidin-2-yl)biphenyl-3-carboxylic Acid

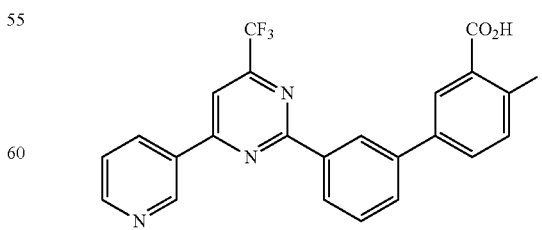

White solid (0.062 g, 32%). $^1$H NMR (400 MHz, DMSOd$_6$): δ 9.59 (s, 1H), 8.79-8.78 (m, 2H), 8.67 (s, 1H), 8.59 (s, 1H), 8.51 (d, J=8.2 Hz, 1H), 8.12 (dd, J=2.3 Hz, 6.9

Hz, 1H), 7.98-7.96 (m, 1H), 7.89 (d, J=7.8 Hz, 1H), 7.68 (t, J=7.8 Hz, 1H), 7.63-7.61 (m, 1H), 7.45-7.42 (m, 1H). LRMS (ESI) calcd. for $C_{23}H_{13}F_4N_3O_2[M+H]^+$: 440.09. Found: 440.00.

Example 117: 4-Fluoro-3'-(4-(furan-3-yl)-6-methyl-pyrimidin-2-yl)biphenyl-3-carboxylic Acid

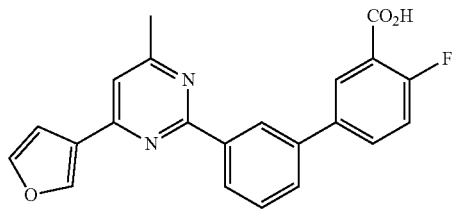 [SMILES: Cc1cc(-c2ccoc2)nc(-c2cccc(-c3ccc(F)c(C(=O)O)c3)c2)n1]

White solid (0.064 g, 39%). $^1$H NMR (400 MHz, DMSOd$_6$): δ 8.64 (d, J=8.2 Hz, 2H), 8.46 (d, J=8.0 Hz, 1H), 8.11 (dd, J=7.3 Hz, 2.7 Hz, 1H), 7.97-7.96 (m, 1H), 7.83 (t, J=1.8 Hz, 1H), 7.78 (d, J=7.8 Hz, 1H), 7.61-7.59 (m, 2H), 7.46-7.41 (m, 1H), 7.19 (d, J=1.0 Hz, 1H), 2.53 (s, 3H). LRMS (ESI) calcd. for $C_{22}H_{15}FN_2O_3[M+H]^+$: 375.11. Found: 375.00.

Example 118: 4-Fluoro-3'-(4-(furan-3-yl)pyrimidin-2-yl)biphenyl-3-carboxylic Acid

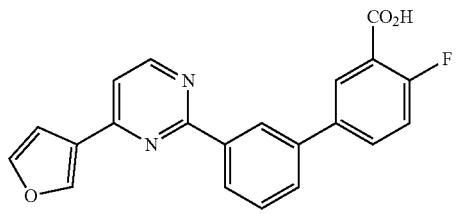 [SMILES: O=C(O)c1cc(-c2cccc(-c3nccc(-c4ccoc4)n3)c2)ccc1F]

White solid (0.055 g, 35%). $^1$H NMR (400 MHz, DMSOd$_6$): δ8.87 (d, J=5.5 Hz, 1H), 8.68 (d, J=3.7 Hz, 2H), 8.48 (d, J=7.8 Hz, 1H), 8.14 (dd, J=6.8 Hz, 2.3 Hz, 1H), 7.99-7.98 (m, 1H), 7.85-7.81 (m, 2H), 7.71 (d, J=5.5 Hz, 1H), 7.64 (t, J=7.8 Hz, 1H), 7.44-7.41 (m, 1H), 7.23 (d, J=1.4 Hz, 1H). LRMS (ESI) calcd. for $C_{21}H_{13}FN_2O_3[M+H]^+$: 361.09. Found: 361.00.

Example 119: 3'-(4-(Furan-3-yl)-6-methylpyrimidin-2-yl)biphenyl-3-carboxylic Acid

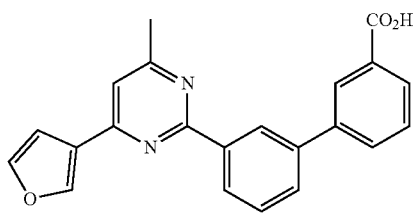 [SMILES: Cc1cc(-c2ccoc2)nc(-c2cccc(-c3cccc(C(=O)O)c3)c2)n1]

White solid (0.037 g, 24%). $^1$H NMR (400 MHz, DMSOd$_6$): δ 8.69 (s, 1H), 8.63 (s, 1H), 8.49 (d, J=7.8 Hz, 1H), 8.22 (s, 1H), 7.94 (t, J=6.9 Hz, 2H), 7.84-7.83 (m, 2H), 7.61 (t, J=8.2 Hz, 3H), 7.20 (d, J=1.8 Hz, 1H), 2.49 (s, 3H). LRMS (ESI) calcd. for $C_{22}H_{16}N_2O_3$ [M+H]$^+$: 357.12. Found: 357.00.

Example 120: 4-Fluoro-3'-(4-(6-methoxypyridin-3-yl)-6-(trifluoromethyl)pyrimidin-2-yl)-[1,1'-biphenyl]-3-carboxylic Acid

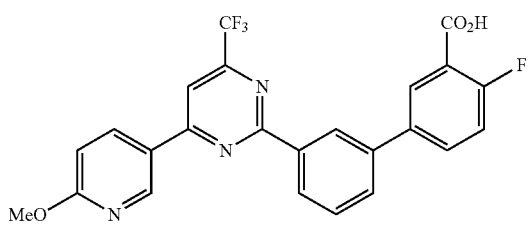

Off-white solid (0.082 g, 45%). LRMS (ESI) calcd. $C_{24}H_{15}F_4N_3O_3[M+H]^+$: 470.10. Found: 470.00.

Example 121: 5-Fluoro-3'-(4-(furan-3-yl)-6-methyl-pyrimidin-2-yl)-[1,1'-biphenyl]-3-carboxylic Acid

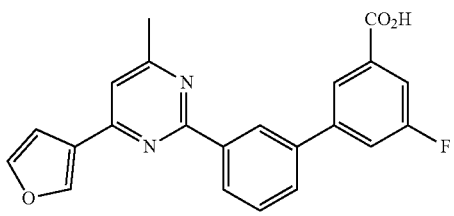 [SMILES: Cc1cc(-c2ccoc2)nc(-c2cccc(-c3cc(F)cc(C(=O)O)c3)c2)n1]

White solid (0.084 g, 56%). LRMS (ESI) calcd. $C_{22}H_{15}FN_2O_3[M+H]^+$: 375.11. Found: 375.00.

Example 122: 4-Fluoro-3'-(4-(thiophen-3-yl)-6-(trifluoromethyl)pyrimidin-2-yl)-[1,1'-biphenyl]-3-carboxylic Acid

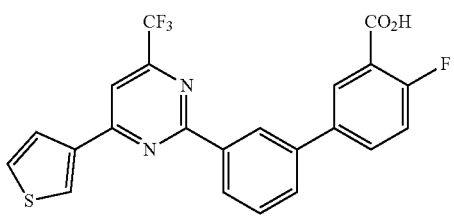

White solid (0.092 g, 52%). $^1$H NMR (400 MHz, DMSOd$_6$): δ8.89-8.88 (m, 1H), 8.66 (s, 1H), 8.50 (d, J=7.8 Hz, 1H), 8.38 (s, 1H), 8.14-8.09 (m, 2H), 8.02-7.98 (m, 1H), 7.88 (d, J=7.8 Hz, 1H), 7.78-7.76 (m, 1H), 7.68 (t, J=7.8 Hz, 1H), 7.46-7.42 (m, 1H). LRMS (ESI) calcd. $C_{22}H_{12}F_4N_2O_2S$ [M+H]$^+$: 445.05. Found: 445.00.

Example 123: 2-(3'-(2H-Tetrazol-5-yl)biphenyl-3-yl)-4-(trifluoromethyl)-6-(6-(trifluoromethyl)pyridin-3-yl)pyrimidine

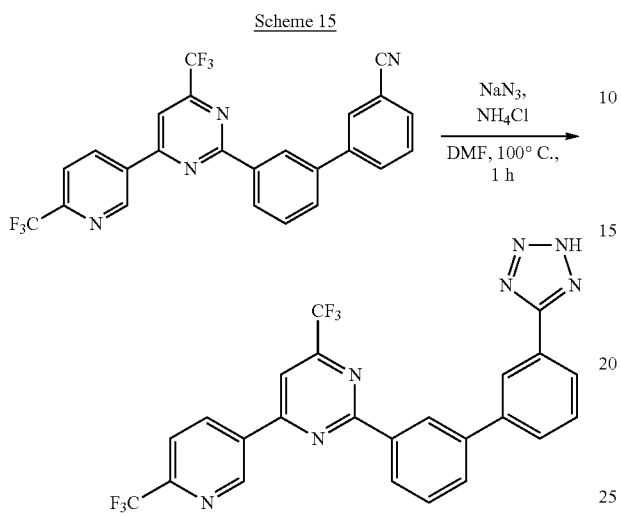

3'-(4-Trifluoromethyl)-6-(6-(trifluoromethyl)pyridin-3-yl)pyrimidin-2-yl)biphenyl-3-carbonitrile (0.047 g, 0.1 mmol), sodium azide (0.078 g, 1.2 mmol), and ammonium chloride (0.078 g, 1.2 mmol) were taken in DMF (2 mL) and the resulting mixture was heated at 100° C. for 1 h. The reaction mixture was cooled to room temperature and diluted with water and followed a usual work up with ethyl acetate. The crude residue was purified by prep-HPLC to yield the title compound as a white solid (0.034 g, 67%). $^1$H NMR (400 MHz, DMSOd$_6$): δ9.78 (s, 1H), 9.04 (dd, J=1.8 Hz, 10.0 Hz, 1H), 8.79 (s, 1H), 8.75 (s, 1H), 8.58 (d, J=7.8 Hz, 1H), 8.37 (s, 1H), 8.14 (d, J=8.2 Hz, 1H), 8.06 (d, J=7.8 Hz, 1H), 7.97 (t, J=8.7 Hz, 3H), 7.75 (d, J=7.8 Hz, 2H).). LRMS (ESI) calcd. for C$_{24}$H$_{13}$F$_6$N$_7$ [M+H]$^+$: 514.11. Found: 514.00.

Example 124: 2-(4'-Fluoro-3'-(2H-tetrazol-5-yl)-[1,1'-biphenyl]-3-yl)-4-(trifluoromethyl)-6-(6-(trifluoromethyl)pyridin-3-yl)pyrimidine

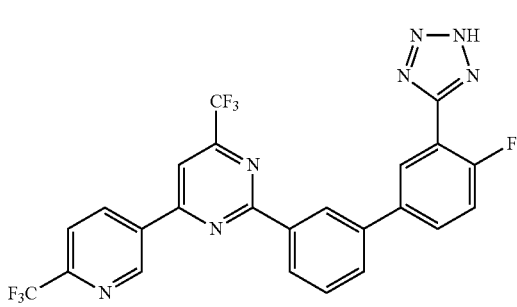 [SMILES: Fc1ccc(-c2cccc(-c3nc(-c4ccc(C(F)(F)F)nc4)cc(C(F)(F)F)n3)c2)cc1-c1nn[nH]n1]

4-Fluoro-3'-(4-(trifluoromethyl)-6-(6-(trifluoromethyl)pyridin-3-yl)pyrimidin-2-yl)-[1,1'-biphenyl]-3-carbonitrile (0.2 g, 0.489 mmol), sodium azide (0.381 g, 5.86 mmol), and ammonium chloride (0.314 g, 5.59 mmol) were taken in DMF (5 mL) and the resulting mixture was heated at 100° C. for 1 h. The reaction mixture was cooled to room temperature and diluted with water and followed a usual work up with ethyl acetate. The crude residue was purified by prep-HPLC to yield the title compound. White solid (0.150 g, 68%). $^1$H NMR (400 MHz, DMSOd$_6$): δ8.90 (s, 1H), 8.70 (s, 1H), 8.50 (d, J=7.8 Hz, 1H), 8.33 (dd, J=2.8 Hz, 9.2 Hz, 1H), 8.25 (s, 1H), 8.02-7.98 (m, 1H), 7.94-7.90 (m, 2H), 7.71 (t, J=7.8 Hz, 1H), 7.60-7.58 (m, 1H), 7.39 (d, J=1.8 Hz, 1H). LRMS (ESI) calcd. C$_{24}$H$_{12}$F$_7$N$_7$ [M+H]$^+$: 532.10. Found: 532.00.

Example 125: 3-(1-(4-(Trifluoromethyl)-6-(6-(trifluoromethyl)pyridin-3-yl)pyrimidin-2-yl)-1H-imidazol-4-yl)benzenesulfonamide

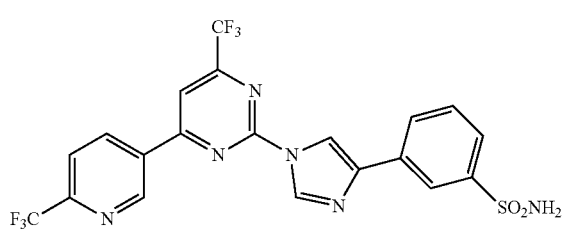 [SMILES: NS(=O)(=O)c1cccc(-c2cn(-c3nc(-c4ccc(C(F)(F)F)nc4)cc(C(F)(F)F)n3)cn2)c1]

2-(4-Iodo-1H-imidazol-1-yl)-4-(trifluoromethyl)-6-(6-(trifluoromethyl)pyridin-3-yl)pyrimidine$^1$ (0.048 g, 0.1 mmol), 3-sulfamoylphenylboronic acid (0.030 g, 0.15 mmol), tetrakistriphenylphosphinepalladium(0) (0.011, 0.01 mmol), 2M Na$_2$CO$_3$ (0.2 mL, 4 mmol) were dissolved in 4 mL of DME. The reaction mixture was then processed according to the general procedure described in Example 69, step 6, to afford the title compound as a yellow solid (0.014 g, 29%). $^1$H NMR (400 MHz, DMSOd$_6$): δ9.87 (s, 1H), 9.18 (d, J=8.2 Hz, 1H), 8.96 (s, 1H), 8.67 (d, J=8.7 Hz, 2H), 8.43 (s, 1H), 8.30-8.15 (m, 2H), 7.20 (d, J=7.8 Hz, 1H), 7.58 (t, J=9.0 Hz, 1H), 7.38 (s, 2H). LRMS (ESI) calcd. for C$_{20}$H$_{12}$F$_6$N$_6$O$_2$S [M+H]$^+$: 515.06. Found: 515.0.

Example 126: 3-(1-(4-(Trifluoromethyl)-6-(6-(trifluoromethyl)pyridin-3-yl)pyrimidin-2-yl)-1H-imidazol-4-yl)aniline

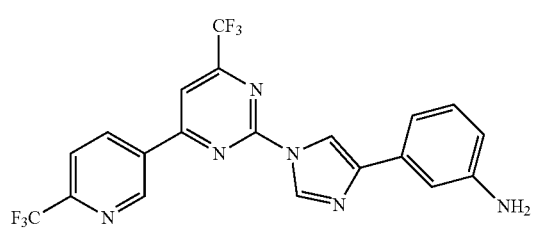 [SMILES: Nc1cccc(-c2cn(-c3nc(-c4ccc(C(F)(F)F)nc4)cc(C(F)(F)F)n3)cn2)c1]

2-(4-Iodo-1H-imidazol-1-yl)-4-(trifluoromethyl)-6-(6-(trifluoromethyl)pyridin-3-yl)pyrimidine$^1$ (0.048 g, 0.1 mmol), 3-aminophenylboronic acid (0.023 g, 0.15 mmol), tetrakistriphenylphosphinepalladium(0) (0.011, 0.01 mmol), 2M Na$_2$CO$_3$ (0.2 mL, 4 mmol) were dissolved in 4 mL of DME. The reaction mixture was then processed according to the general procedure described in Example 69, step 6, to afford the title compound as a yellow solid (0.011 g, 24%). $^1$H NMR (400 MHz, DMSOd$_6$): δ11.37 (s, 1H), 9.12 (s, 1H), 8.67 (d, J=8.7 Hz, 2H), 8.23 (s, 1H), 7.68 (d, J=8.2 Hz, 1H), 7.39 (t, J=7.8 Hz, 1H), 6.73 (s, 1H), 6.5 (s, 1H), 6.1 (s, 1H). LRMS (ESI) calcd. for C$_{20}$H$_{12}$F$_6$N$_6$ [M+H]$^+$: 451.10. Found: 451.0.

General Synthetic Scheme for the Preparation of 4-Fluoro-3'-(4-(furan-2-yl)-6-(trifluoromethyl)pyrimidin-2-yl)biphenyl Carboxylic Acid Derivatives

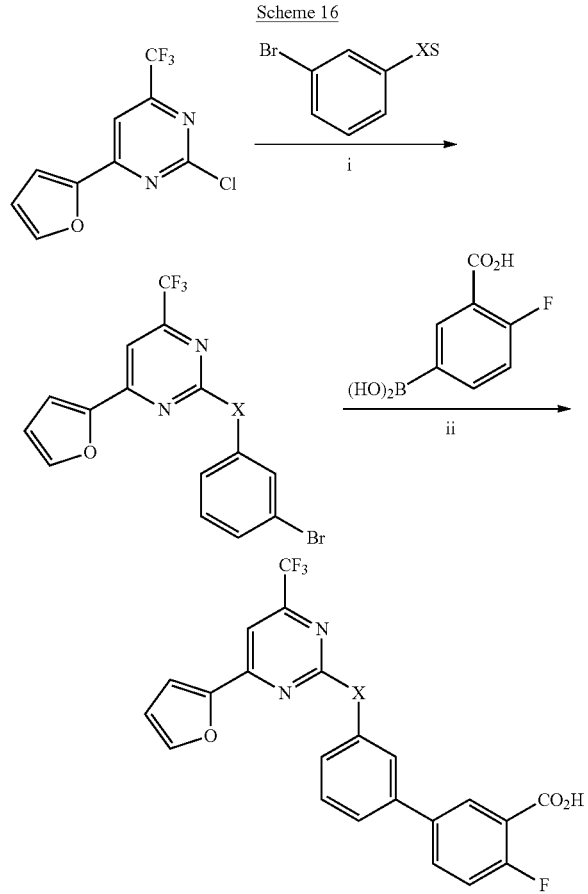

i) $K_2CO_3$, $CH_3CN$, 80° C.;
ii) $Pd(PPh_3)_4$, 2M $Na_2CO_3$, DME, 80° C., 12 h
X = NH, O, S

Example 127: 4-Fluoro-3'-(4-(furan-2-yl)-6-(trifluoromethyl)pyrimidin-2-ylamino)biphenyl-3-carboxylic Acid

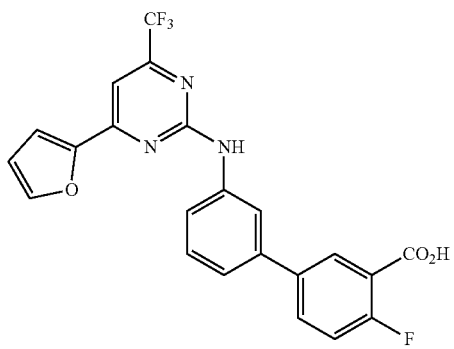 [SMILES: O=C(O)c1cc(-c2cccc(Nc3nc(-c4ccco4)cc(C(F)(F)F)n3)c2)ccc1F]

Step 1: N-(3-Bromophenyl)-4-(furan-2-yl)-6-(trifluoromethyl)pyrimidin-2-amine

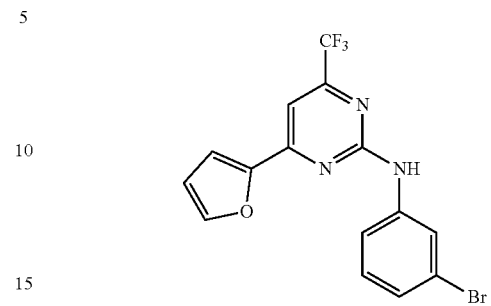

Potassium carbonate (0.103 g, 0.75 mmol) was added to a solution of 2-chloro-4-(furan-2-yl)-6-(trifluoromethyl)pyrimidine (0.124 g, 0.5 mmol) and 3-bromoaniline (0.129 g, 0.75 mmol) in $CH_3CN$ (5 mL). After stirring for 12 h at 80° C., the organic phase was evaporated under reduced pressure and the crude material was partitioned between water and $CH_2Cl_2$. The aqueous layer was extracted with $CH_2Cl_2$ (3×15 mL). The organic layer was washed with 1N HCl (5 mL) and then dried over $Na_2SO_4$ and evaporated to give N-(3-bromophenyl)-4-(furan-2-yl)-6-(trifluoromethyl)pyrimidin-2-amine (0.158 g, 82%). The crude product was used for the next step without further purification. LRMS (ESI) calcd. for $C_{15}H_9BrF_3N_3O$ [M+H]$^+$: 383.98, 385.97. Found: 384.0, 386.0.

Step 2: 4-Fluoro-3'-(4-(furan-2-yl)-6-(trifluoromethyl)pyrimidin-2-ylamino)biphenyl-3-carboxylic Acid

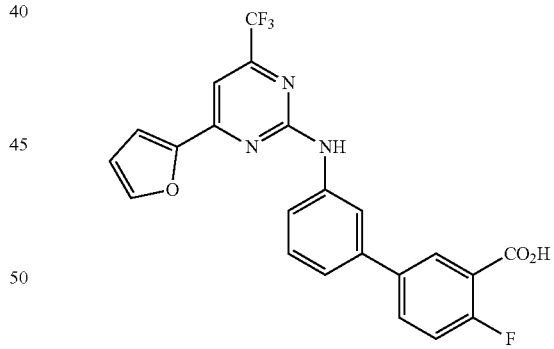

2 N-(3-Bromophenyl)-4-(furan-2-yl)-6-(trifluoromethyl)pyrimidin-2-amine (0.155 g, 0.4 mmol), 5-borono-5-fluorobenzoic acid (0.110 g, 0.6 mmol), tetrakistriphenylphosphinepalladium(0) (0.060 g, 0.04 mmol), 2M $Na_2CO_3$ (0.8 mL, 4 mmol) were dissolved in DME. The reaction mixture was then processed according to the general procedure described in Example 69, step 7, to afford the title compound as a yellow solid (0.088 g, 49%). $^1$H NMR (400 MHz, DMSOd$_6$): δ10.35 (s, 1H), 8.33 (s, 1H), 8.14 (dd, J=2.8 Hz, 6.8 Hz, 1H), 8.02 (s, 1H), 7.90-7.87 (m, 1H), 7.71 (d, J=9.0 Hz, 1H), 7.52 (d, J=3.3 Hz, 1H), 7.52 (s, 1H), 7.43 (t, J=8.2 Hz, 1H), 7.30 (s, 1H), 6.77 (m, 1H). LRMS (ESI) calcd. for $C_{22}H_{13}F_4N_3O_3$[M+H]$^+$: 444.08. Found: 444.0.

Example 128: 4-Fluoro-3'-(4-(furan-2-yl)-6-(trifluoromethyl)pyrimidin-2-yloxy)biphenyl-3-carboxylic Acid

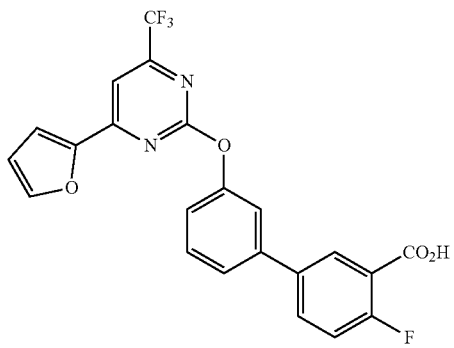 [SMILES: O=C(O)c1cc(-c2cccc(Oc3nc(-c4ccco4)cc(C(F)(F)F)n3)c2)ccc1F]

Step 1: 2-(3-Bromophenoxy)-4-(furan-2-yl)-6-(trifluoromethyl)pyrimidine

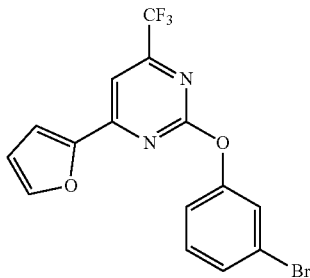 [SMILES: FC(F)(F)c1cc(-c2ccco2)nc(Oc2cccc(Br)c2)n1]

Potassium carbonate (0.103 g, 0.75 mmol) was added to a solution of 2-chloro-4-(furan-2-yl)-6-(trifluoromethyl)pyrimidine (0.124 g, 0.5 mmol) and 3-bromophenol (0.129 g, 0.75 mmol) in $CH_3CN$ (5 mL). After stirring for 2 h at 80° C., the organic phase was evaporated under reduced pressure and the crude material was partitioned between water and $CH_2Cl_2$. The aqueous layer was extracted with $CH_2Cl_2$ (3×15 mL). The organic layer was dried over $Na_2SO_4$ and evaporated to give 2-(3-bromophenoxy)-4-(furan-2-yl)-6-(trifluoromethyl)pyrimidine (0.192 g, quantitative). The crude product was used for the next step without further purification. LRMS (ESI) calcd. for $C_{15}H_8BrF_3N_2O_2$ $[M+H]^+$: 384.97, 386.99. Found: 385.0, 387.0.

Step 2: 4-Fluoro-3'-(4-(furan-2-yl)-6-(trifluoromethyl)pyrimidin-2-yloxy)biphenyl-3-carboxylic Acid

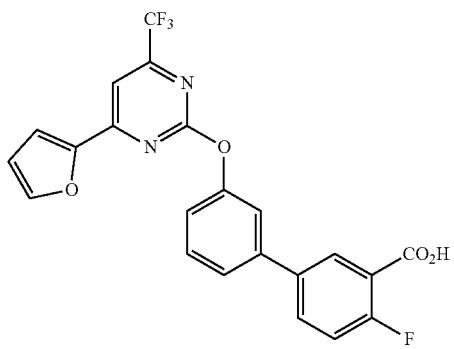 [SMILES: O=C(O)c1cc(-c2cccc(Oc3nc(-c4ccco4)cc(C(F)(F)F)n3)c2)ccc1F]

2-(3-Bromophenoxy)-4-(furan-2-yl)-6-(trifluoromethyl)pyrimidine (0.154 g, 0.4 mmol), 5-borono-5-fluorobenzoic acid (0.110 g, 0.6 mmol), tetrakistriphenylphosphinepalladium(0) (0.060 g, 0.04 mmol), 2M $Na_2CO_3$ (0.8 mL, 4 mmol) were dissolved in DME. The reaction mixture was then processed according to the general procedure described in Example 69, step 7, to afford the title compound as an off-white solid (0.09 g, 51%). $^1H$ NMR (400 MHz, $DMSOd_6$): δ8.09 (dd, J=2.3 Hz, 6.8 Hz, 1H), 8.07 (s, 1H), 8.03-7.92 (m, 2H), 7.66-7.54 (m, 4H), 7.38 (t, J=9.0 Hz, 1H), 7.31 (d, J=7.8 Hz, 1H), 6.75-6.74 (m, 1H). LRMS (ESI) calcd. for $C_{22}H_{12}F_4N_2O_4[M+H]^+$: 445.07. Found: 445.0.

Example 129: 4-Fluoro-3'-(4-(furan-2-yl)-6-(trifluoromethyl)pyrimidin-2-ylthio)biphenyl-3-carboxylic Acid

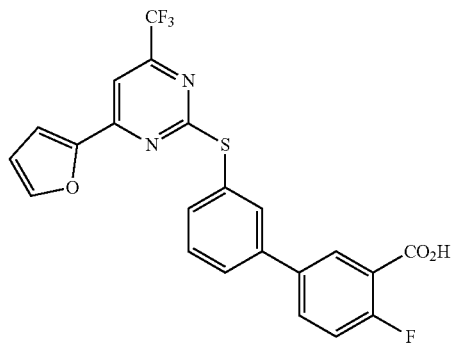 [SMILES: O=C(O)c1cc(-c2cccc(Sc3nc(-c4ccco4)cc(C(F)(F)F)n3)c2)ccc1F]

Step 1: 2-(3-Bromophenylthio)-4-(furan-2-yl)-6-(trifluoromethyl)pyrimidine

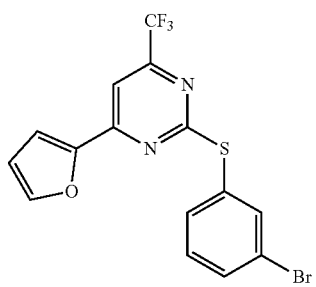 [SMILES: FC(F)(F)c1cc(-c2ccco2)nc(Sc2cccc(Br)c2)n1]

Potassium carbonate (0.103 g, 0.75 mmol) was added to a solution of 2-chloro-4-(furan-2-yl)-6-(trifluoromethyl)pyrimidine (0.124 g, 0.5 mmol) and 3-bromobenzenethiol (0.08 mL, 0.75 mmol) in $CH_3CN$ (5 mL). After stirring for 2 h at 80° C., the organic phase was evaporated under reduced pressure and the crude material was partitioned between water and $CH_2Cl_2$. The aqueous layer was extracted with $CH_2Cl_2$ (3×15 mL). The organic layer was dried over $Na_2SO_4$ and evaporated to give 2-(3-bromophenylthio)-4-(furan-2-yl)-6-(trifluoromethyl)pyrimidine (0.190 g, 94%). The crude product was used for the next step without further purification. LRMS (ESI) calcd. for $C_{15}H_8BrF_3N_2OS$ $[M+H]^+$: 400.94, 402.94. Found: 401.0, 403.0.

Step 2: Fluoro-3'-(4-(furan-2-yl)-6-(trifluoromethyl)pyrimidin-2-ylthio)biphenyl-3-carboxylic Acid

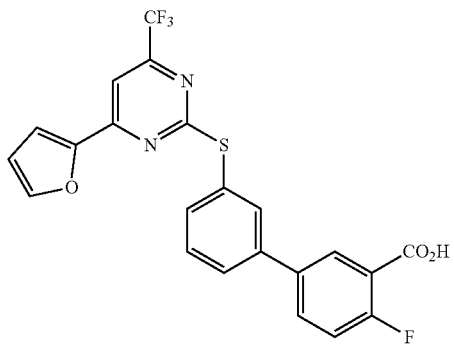 [SMILES: O=C(O)c1cc(-c2cccc(Sc3nc(-c4ccco4)cc(C(F)(F)F)n3)c2)ccc1F]

2-(3-Bromophenylthio)-4-(furan-2-yl)-6-(trifluoromethyl)pyrimidine (0.161 g, 0.4 mmol), 5-borono-5-fluorobenzoic acid (0.110 g, 0.6 mmol), tetrakistriphenylphosphinepalladium(0) (0.060 g, 0.04 mmol), 2M $Na_2CO_3$ (0.8 mL, 4 mmol) were dissolved in DME. The reaction mixture was then processed according to the general procedure described in Example 69, step 7, to afford the title compound as a yellow solid (0.120 g, 65%). $^1$H NMR (400 MHz, DMSOd$_6$): δ8.62 (s, 1H), 8.45 (d, J=7.8 Hz, 1H), 8.20 (s, 1H), 7.90 (d, J=7.8 Hz, 1H), 7.86 (s, 1H), 7.70-7.68 (m, 3H), 7.58-7.52 (m, 2H), 7.42 (t, J=9.0 Hz, 1H). LRMS (ESI) calcd. for $C_{22}H_{12}F_4N_2O_3S$ [M+H]$^+$: 461.05. Found: 460.85.

Example 130: 2-(3-((4-Fluorophenyl)ethynyl)phenyl)-4-(trifluoromethyl)-6-(6-(trifluoromethyl)pyridin-3-yl)pyrimidine Scheme 17

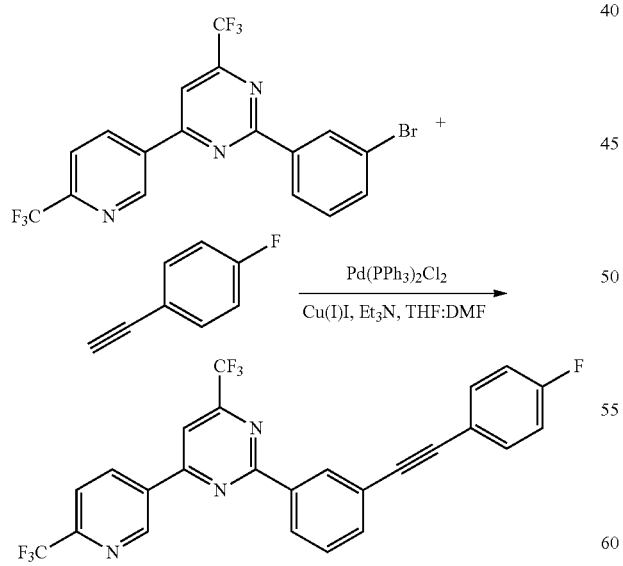

To a stirred mixture of Pd(PPh$_3$)$_2$Cl$_2$ (0.004 g, 0.006 mmol), copper iodide (0.002, 0.009 mmol) and triethylamine (0.03 mL, 0.24 mmol) in THF:DMF (1:1, 2 mL) was added 3-bromophenyl)-4-(trifluoromethyl)-6-(6-(trifluoromethyl)pyridin-3-yl)pyrimidine (0.025 g, 0.06 mmol).

The resulting reaction mixture was sparged with N$_2$ for 10 min and 4-fluoro-phenylacetylene (0.021 g, 0.18 mmol)) was added to the reaction mixture. The resulting brown solution was heated to reflux for 2 h. After cooling, the reaction mixture was diluted with EtOAc and filtered through a pad of Celite. The filtrate was concentrated under reduced pressure and the crude product was purified by HPLC to give a white solid (0.006 g, 21%). $^1$H NMR (400 MHz, DMSOd$_6$): δ9.77 (s, 1H), 9.18 (d, J=8.2 Hz, 1H), 8.76 (s, 1H), 8.64 (s, 1H), (d, J=8.2 Hz, 1H), 8.16 (d, J=7.8 Hz, 1H), 7.79 (d, J=8.2 Hz, 1H), 7.69-7.66 (m, 3H), 7.58 (t, J=9.0 Hz, 2H). LRMS (ESI) calcd. for $C_{25}H_{12}F_7N_3$ [M+H]$^+$: 488.09. Found: 488.0.

General Scheme for the Synthesis of 4-fluoro-3'-(4-(furan-3-yl)-6-(trifluoromethyl)pyrimidin-2-yl)-N-hydroxy/N-methoxy-[1,1'-biphenyl]-3-carboxamide Derivatives Scheme 18

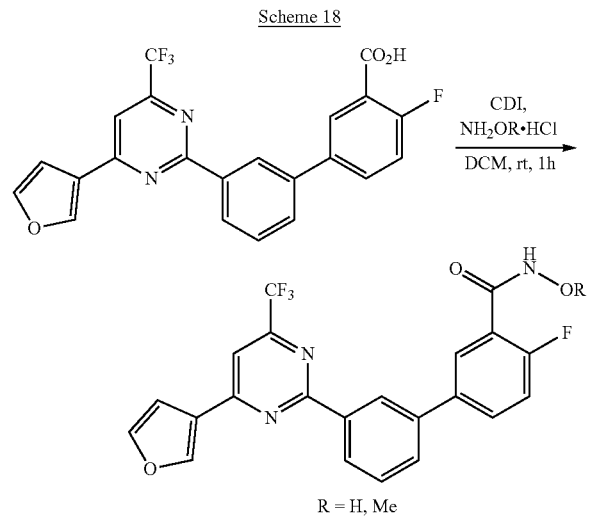

R = H, Me

Example 131: 4-Fluoro-3'-(4-(furan-3-yl)-6-(trifluoromethyl)pyrimidin-2-yl)-N-hydroxy-[1,1'-biphenyl]-3-carboxamide

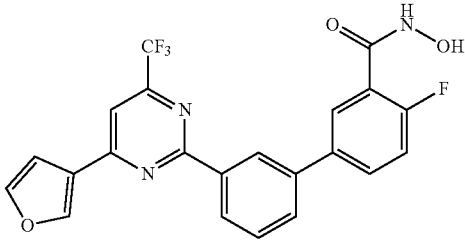 [SMILES: O=C(NO)c1cc(-c2cccc(-c3nc(-c4ccoc4)cc(C(F)(F)F)n3)c2)ccc1F]

To a solution of 4-fluoro-3'-(4-(furan-3-yl)-6-(trifluoromethyl)pyrimidin-2-yl)biphenyl-3-carboxylic acid (0.043 g, 0.1 mmol) in DCM (2 mL), was added carbonyl diimidazole (0.018 g, 0.11 mmol). The resulting mixture was stirred at room temperature for 1 h. Hydroxylamine hydrochloride (0.011 g, 0.150 mmol) was added to the same reaction mixture and stirring was continued for another 1 h after that time solvent was removed under reduced pressure. The crude product was purified by reverse phase HPLC to give the title compound as a colorless solid (0.028 g, 63.2%). $^1$H NMR (400 MHz, DMSO-d$_6$): δ 11.09 (s, 1H), 8.90 (s, 1H), 8.66 (s, 1H), 8.47 (d, J=7.8 Hz, 1H), 8.25 (s, 1H), 7.91-7.84 (m, 4H), 7.65 (t, J=7.8 Hz, 1H), 7.42-7.38 (m, 2H). LC-MS (ESI) calcd for C$_{22}$H$_{13}$F$_4$N$_3$O$_3$[M+H]$^+$: 444.36. Found: 444.0

Example 132: 4-Fluoro-3'-(4-(furan-3-yl)-6-(trifluoromethyl)pyrimidin-2-yl)-N-methoxy-[1,1'-biphenyl]-3-carboxamide

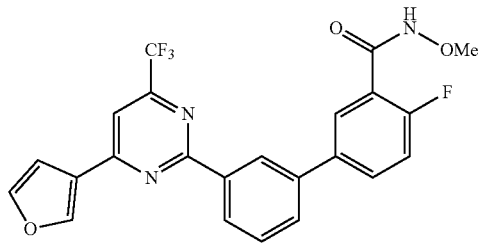 [SMILES: CONC(=O)c1cc(-c2cccc(-c3nc(-c4ccoc4)cc(C(F)(F)F)n3)c2)ccc1F]

In a similar manner described for 4-fluoro-3'-(4-(furan-3-yl)-6-(trifluoromethyl)pyrimidin-2-yl)-N-hydroxy-[1,1'-biphenyl]-3-carboxamide (Example 127) with appropriate starting materials, the title compound was prepared as a colorless solid (0.037 g, 81%). $^1$H NMR (DMSO-d$_6$): δ 11.67 (s, 1H), 8.90 (d, J=3.4 Hz, 1H), 8.65 (d, J=3.7 Hz, 1H), 8.46 (t, J=5.5 Hz, 1H), 8.24 (t, J=7.4 Hz, 1H), 7.89-7.68 (m, 4H), 7.66-7.63 (m, 1H), 7.44-7.38 (m, 2H), 3.72 (s, 3H). LC-MS (ESI) calcd for C$_{23}$H$_{15}$F$_4$N$_3$O$_3$[M+H]$^+$: 458.38. Found: 458.0

Example 133: 3-(4-Fluoro-3'-(4-(furan-3-yl)-6-(trifluoromethyl)pyrimidin-2-yl)-[1,1'-biphenyl]-3-yl)-1,2,4-oxadiazol-5(4H)-one Scheme 19

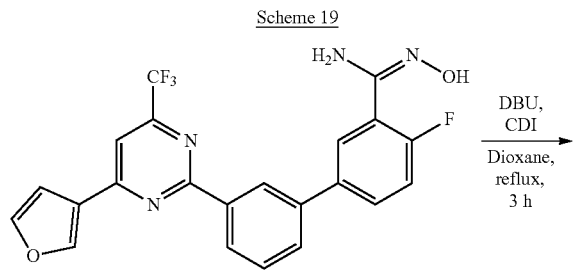

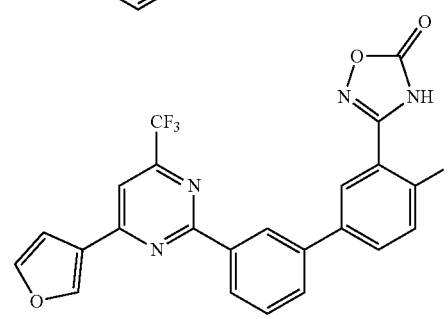

Step 1: 4-Fluoro-3'-(4-(furan-3-yl)-6-(trifluoromethyl)pyrimidin-2-yl)-N'-hydroxy-[1,1'-biphenyl]-3-carboximidamide

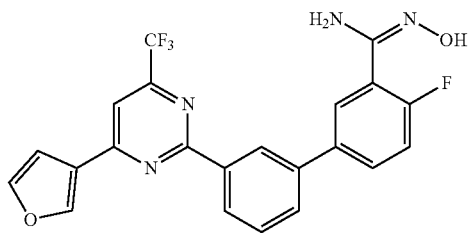 [SMILES: N/C(=N/O)c1cc(-c2cccc(-c3nc(-c4ccoc4)cc(C(F)(F)F)n3)c2)ccc1F]

4-Fluoro-3'-(4-(furan-3-yl)-6-(trifluoromethyl)pyrimidin-2-yl)biphenyl-3-carbonitrile (1 g, 2.443 mmol) and hydroxylamine (50% aqueous solution, 0.28 mL) were taken in EtOH (10 mL) and refluxed for 30 min in the presence of AcOH (few drops), cooled and diluted with water. The precipitated 4-fluoro-3'-(4-(furan-3-yl)-6-(trifluoromethyl)pyrimidin-2-yl)-N'-hydroxy-[1,1'-biphenyl]-3-carboximidamide was collected by filtration and purified by silica gel column chromatography (Hexanes:Ethyl acetate, 4:1) to afford the desired compound as a white solid (0.51 g, 47.2%). LC-MS (ESI) calcd for C$_{22}$H$_{14}$F$_4$N$_4$O$_2$[M+H]$^+$: 443.38. Found: 443.00.

Step 2: 3-(4-Fluoro-3'-(4-(furan-3-yl)-6-(trifluoromethyl)pyrimidin-2-yl)-[1,1'-biphenyl]-3-yl)-1,2,4-oxadiazol-5(4H)-one

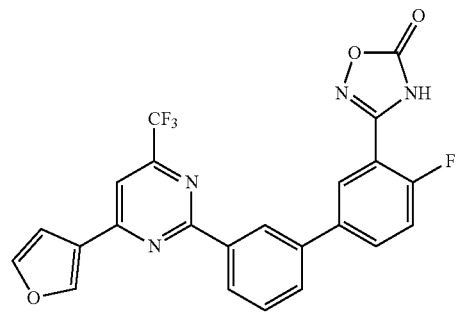 [SMILES: O=c1[nH]c(-c2cc(-c3cccc(-c4nc(-c5ccoc5)cc(C(F)(F)F)n4)c3)ccc2F)no1]

A mixture of 4-fluoro-3'-(4-(furan-3-yl)-6-(trifluoromethyl)pyrimidin-2-yl)-N'-hydroxy-[1,1'-biphenyl]-3-carboximidamide (0.150 g, 0.339 mmol), carbonyl diimidazole (0.082 g, 0.509 mmol) and DBU (0.206 g, 1.356 mmol) were taken in dioxane (5 mL) and heated at reflux for 3 h. Excess solvent was removed under vacuum and diluted with water and pH adjusted to 4-5 with dil. HCl and extracted with ethyl acetate (3×5 mL). The organic layer washed with brine, dried over Na$_2$SO$_4$, followed by removal of the solvent under reduced pressure to yield the crude product which was purified by reverse phase HPLC to give the title compound as a white solid (0.085 g, 53.5%). $^1$H NMR (DMSO-d$_6$): δ 8.91 (s, 1H), 8.69 (s, 1H), 8.49 (d, J=7.8 Hz, 1H), 8.26 (s, 1H), 8.12 (dd, J=2.2 Hz, 6.4 Hz, 1H), 8.06-8.02 (m, 1H), 7.92-7.90 (m, 2H), 7.69 (t, J=7.8 Hz, 1H), 7.60-7.56 (m, 1H), 7.40 (d, J=1.8 Hz, 1H). LC-MS (ESI) calcd for C$_{23}$H$_{12}$F$_4$N$_4$O$_3$[M+H]$^+$: 469.37. Found: 469.0

179

Example 134: 3-(4-Fluoro-3'-(4-(furan-3-yl)-6-(trifluoromethyl)pyrimidin-2-yl)-[1,1'-biphenyl]-3-yl)-1,2,4-oxadiazole-5(4H)-thione Scheme 20

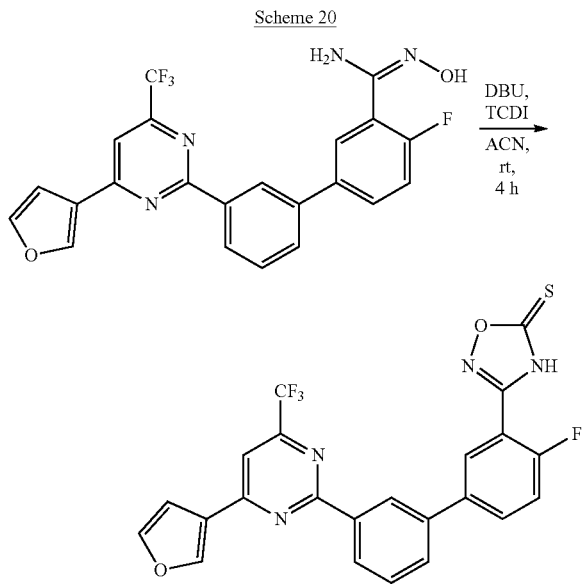

A mixture of 4-fluoro-3'-(4-(furan-3-yl)-6-(trifluoromethyl)pyrimidin-2-yl)-N'-hydroxy-[1,1'-biphenyl]-3-carboximidamide (0.100 g, 0.226 mmol), thiocarbonyl diimidazole (0.06 g, 0.339 mmol) and DBU (0.138 g, 0.904 mmol) in acetonitrile (5 mL) was stirred at rt for 4 h. Excess solvent was removed under vacuum and diluted with water and pH adjusted to 4-5 with dil. HCl and extracted with ethyl acetate (3×5 mL). The organic layer washed with brine, dried over $Na_2SO_4$, followed by removal of the solvent under reduced pressure to yield the crude product which was purified by reverse phase HPLC to give the title compound as a white solid (0.08 g, 73.1%). $^1$H NMR (DMSO-$d_6$): δ 8.91 (s, 1H), 8.69 (s, 1H), 8.49 (d, J=7.8 Hz, 1H), 8.26 (s, 1H), 8.23 (dd, J=2.8 Hz, 6.4 Hz, 1H), 8.06-8.03 (m, 1H), 7.92-7.90 (m, 2H), 7.69 (t, J=7.8 Hz, 1H), 7.60-7.56 (m, 1H), 7.40 (d, J=1.8 Hz, 1H). LC-MS (ESI) calcd for $C_{23}H_{12}F_4N_4O_2S$ [M+H]$^+$: 485.42. Found: 485.0.

Example 135: 3-(4-Fluoro-3'-(4-(furan-3-yl)-6-(trifluoromethyl)pyrimidin-2-yl)-[1,1'-biphenyl]-3-yl)-1,2,4-thiadiazol-5(4H)-one Scheme 21

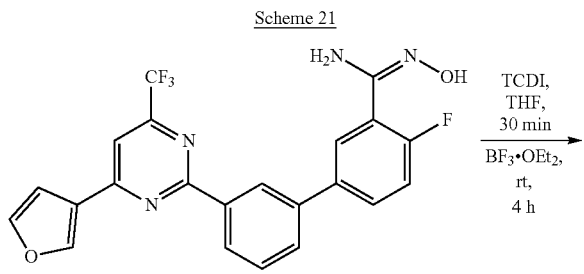

180

-continued

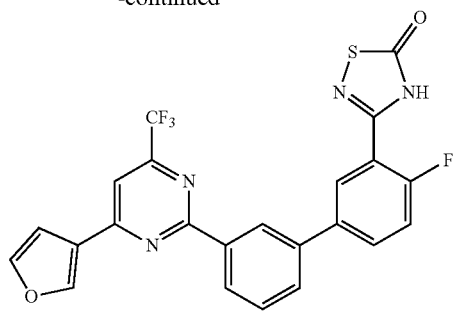

A mixture of 4-fluoro-3'-(4-(furan-3-yl)-6-(trifluoromethyl)pyrimidin-2-yl)-N'-hydroxy-[1,1'-biphenyl]-3-carboximidamide (0.15 g, 0.339 mmol) and thiocarbonyl diimidazole (0.072 g, 0.407 mmol) in THF (5 mL) was stirred at rt for 30 min. The mixture was diluted with water and extracted with ethyl acetate (3×5 mL). The organic phase was washed with water and concentrated. The residue was redissolved in THF (5 mL), $BF_3·OEt_2$ (0.241 g, 1.7 mmol) was added, and the reaction mixture was stirred at rt for 1 h. The reaction mixture was diluted with water and extracted with ethyl acetate (3×5 mL). The organic layer washed with 1N HCl and dried over anhydrous $Na_2SO_4$, removal of the solvent, followed by reverse phase HPLC yielded the title compound as a yellow solid (0.1 g, 60.9%). $^1$H NMR (DMSO-$d_6$): δ 8.91 (s, 1H), 8.68 (s, 1H), 8.49 (d, J=7.8 Hz, 1H), 8.26 (s, 1H), 8.10 (d, J=6.9 Hz, 1H), 7.96-7.90 (m, 4H), 7.69 (t, J=7.8 Hz, 1H), 7.60-7.56 (m, 1H), 7.39 (s, 1H). LC-MS (ESI) calcd for $C_{23}H_{12}F_4N_4O_2S$ [M+H]$^+$: 485.42. Found: 485.0.

Synthesis of Intermediates G-R

Ethyl 3-(3-bromophenyl)-3-oxopropanoate (G)

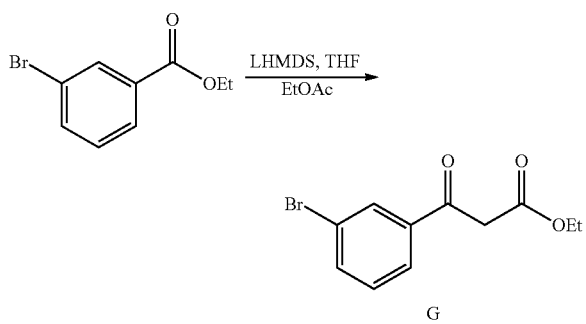

To a stirred solution of 1.3 M LHMDS (25 mL, 32.7 mmol) in THF (10 mL) was added EtOAc (1.9 g, 21.8 mmol) at −78° C. under inert atmosphere. After being stirred for 15 min, ethyl-3-bromo benzoate (5 g, 21.8 mmol) was added and stirring was continued for 2 h; progress of the reaction was monitored by TLC. The reaction was quenched with aq. $NH_4Cl$ (10 mL) and extracted with EtOAc (3×20 mL). The combined organic extracts were dried over anhydrous $Na_2SO_4$ and concentrated under reduced pressure to obtain the crude product. The crude material was purified by silica gel column chromatography eluting with 4% EtOAc/Hexane to afford compound G (4.5 g, 76.9%) as a mixture with its enolic form as a brown oil. $^1$H NMR (500 MHz, CDCl$_3$): δ 8.07 (s, 1H), 7.86 (d, J=7.5 Hz, 1H), 7.73-7.69 (m, 1H), 7.37 (t, J=7.0 Hz, 1H), 4.28-4.26 (m, 2H), 3.92 (s, 2H), 1.24 (t, J=6.2 Hz, 3H). MS (ESI): m/z 298.8 [M−1].

Methyl 3-(3-cyanophenyl)-3-oxopropanoate (H)

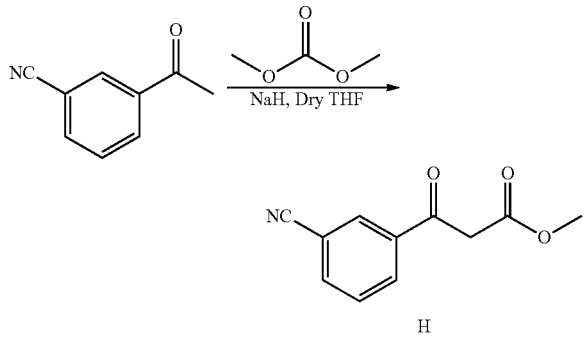

To a stirred solution of 3-acetylbenzonitrile (1 g, 6.89 mmol) in dry THF (30 mL) under inert atmosphere was added sodium hydride (60%) (326 mg, 13.5 mmol) portion wise at 0° C. followed by dimethyl carbonate (1.24 g, 13.7 mmol). The reaction mixture was heated to 60° C. and stirred for 7 h; progress of the reaction was monitored by TLC. The reaction mixture was quenched with dil. HCl (2 mL), diluted with water (50 mL) and extracted with EtOAc (2×30 mL). The combined organic extracts were dried over anhydrous Na$_2$SO$_4$ and concentrated under reduced pressure to obtain the crude product. The crude material was purified by silica gel column chromatography eluting with 10% EtOAc/Hexane to afford compound H as a mixture of its enolic form (950 mg, 67.8%) as a pale yellow liquid. $^1$H NMR (500 MHz, DMSO-d$_6$): δ 8.40 (s, 1H), 8.31-8.22 (m, 1H), 8.19-8.12 (m, 1H), 7.77-7.75 (m, 1H), 4.29 (s, 2H), 3.64 (s, 3H). MS (ESI): m/z 204 [M+1]$^+$.

Methyl 3-(2-chloropyridin-4-yl)-3-oxopropanoate (I)

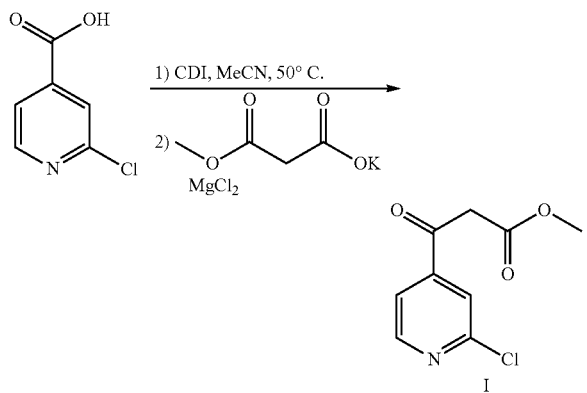

To the solution of 2-chloroisonicotinic acid (5 g, 31.7 mmol) in ACN (30 mL) was added CDI (11.6 g, 71.4 mmol) and the mixture was stirred at 25° C. for 1 h. potassium 3-methoxy-3-oxopropanoate (5.4 g, 31.7 mmol) and MgCl$_2$ (2.9 g, 31.7 mmol) were added then the mixture was stirred at 25° C. for 12 hrs. After removal of the solvent, the residue was extracted with EtOAc (20 mL×3). The organic layer was dried over Na$_2$SO$_4$, concentrated and purified by column chromatography to give compound I. (4.2 g, yield: 58.3%). $^1$H NMR (400 MHz, DMSO-d$_6$): δ 12.32 (s, 1H), 8.63 (d, J=4.8 Hz, 2H), 8.52 (d, J=5.2 Hz, 1H), 7.93 (s, 2H), 7.87 (s, 1H), 7.79-7.84 (m, 1H), 6.22 (s, 1H), 4.22-4.28 (m, 4H), 4.10-4.15 (m, 4H), 4.01-4.08 (m, 2H), 1.98 (s, 3H), 1.25-1.29 (m, 3H), 1.20-1.23 (m, 6H).

Methyl 3-(2-cyanopyridin-4-yl)-3-oxopropanoate (J)

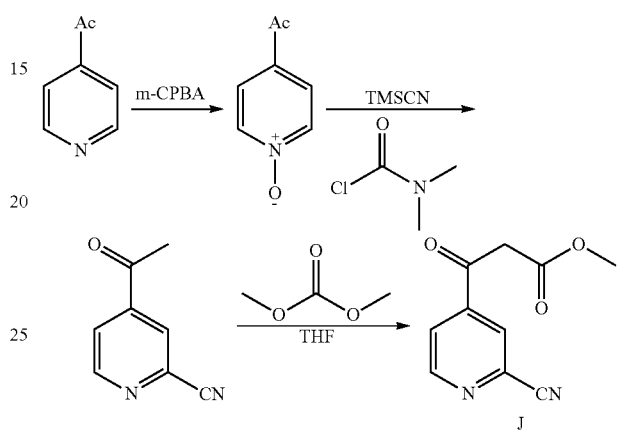

To the solution of 1-(pyridin-4-yl)ethanone (10 g, 82.5 mmol) in DCM (150 mL) was added m-CPBA (19 g, 90.8 mmol). The reaction mixture was stirred under reflux for 16 hrs. After removal of the solvent, the residue was washed with MTBE to give 1-(pyridin-4-yl)ethanone N-oxide (10 g, yield: 88%).

To a solution of 1-(pyridin-4-yl)ethanone N-oxide (0.5 g, 3.65 mmol) in DCM (8 mL) was added TMSCN (398 mg, 4.01 mmol). After stirring for 5 mins, dimethylcarbamoyl chloride (431 mg, 4.01 mmol) was added and the reaction mixture was stirred at room temperature for 16 hrs. 10% of aq. K$_2$CO$_3$ (10 mL) was added, the aqueous layer was extracted with DCM (8 mL×3). The organic layer was dried over Na$_2$SO$_4$ and concentrated to give 4-acetylpicolinonitrile (200 mg, 38%). LC/MS: 147.1 (M+1)

To the solution of t-BuOK (615 mg, 5.48 mmol) in THF (20 mL) was added a solution of 4-acetylpicolinonitrile (400 mg, 2.74 mmol) in THF (20 mL). Carbonic acid dimethyl ester (493 mg, 5.48 mmol) was added and the reaction was stirred at room temperature for 1 h and then with heating to 60° C. for 3 hrs. The reaction was diluted with ethyl acetate (30 mL) and aq.NH$_4$Cl (30 mL). The aqueous layer was extracted with ethyl acetate (30 mL×2). The organic layer was dried over Na$_2$SO$_4$ and concentrated and purified by flash chromatography (PE:EA=100:1-5:1) to give compound J (170 mg, 30%). LC/MS: 204.6 (M+1).

Ethyl 3-(3-hydroxyphenyl)-3-oxopropanoate (K)

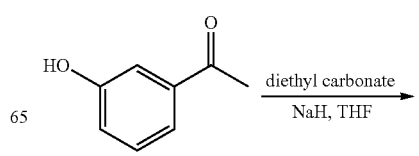

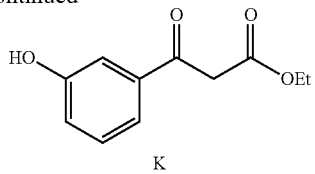

K

To a stirred solution of 3-hydroxy acetophenone (3 g, 22.03 mmol) in dry THF (50 mL) under inert atmosphere was added sodium hydride (60%) (3.17 g, 0.13 mmol) portion wise at 0° C. After being stirred for 10 min, the reaction mixture was warmed to RT and diethyl carbonate (3.9 g, 33.05 mmol) was added; heated to 70° C. and stirred for 12 h. The progress of the reaction was monitored by TLC. After completion of the reaction, the reaction mixture was diluted with water (30 mL) and extracted with ethyl acetate (3×25 mL). The combined organic extracts were washed with water (30 mL), dried over sodium sulfate, filtered and concentrated under reduced pressure to obtain the crude product. The crude product was purified by silica gel column chromatography [Eluent: 15% EtOAc/Hexanes] to afford compound K (2.4 g, 52%) as a colorless liquid. $^1$H NMR (400 MHz, DMSO-$d_6$): δ 9.84 (s, 1H), 7.40-7.28 (m, 3H), 7.07-7.04 (m, 1H), 4.11-4.08 (m, 4H), 1.19-1.15 (m, 3H).

Ethyl 3-oxo-3-(3-(pyridin-2-yloxy) phenyl) propanoate (L)

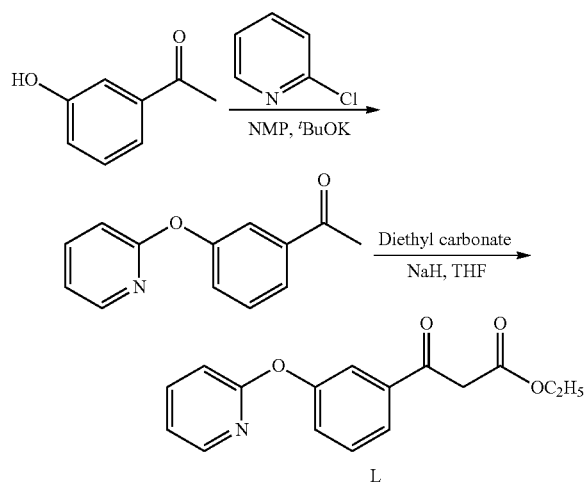

Step 1: 1-(3-(Pyridin-2-yloxy)phenyl)ethanone

To a stirred solution of 3-hydroxy acetophenone (3 g, 22.03 mmol) in N-methyl pyrrolidinone under inert atmosphere were added 2-chloropyridine (10 mL), and potassium tertiary butoxide (4.94 g, 44.06 mmol) at RT. The reaction mixture was heated to 150° C. and stirred for 24 h. The progress of the reaction was monitored by TLC. After completion of the reaction, the reaction mixture was quenched with 10% NaOH solution (20 mL) and extracted with CH$_2$Cl$_2$ (3×30 mL). The combined organic extracts were washed with water (30 mL), dried over sodium sulfate, filtered and concentrated under reduced pressure to obtain the crude product. The crude product was purified by silica gel column chromatography [Eluent: 20% EtOAc/Hexanes] to afford 1-(3-(pyridin-2-yloxy)phenyl)ethanone (1.9 g, 41%) as colorless liquid. $^1$H NMR (400 MHz, DMSO-$d_6$): δ 8.15-8.14 (m, 1H), 7.89-7.88 (m, 1H), 7.81-7.80 (m, 1H), 7.64-7.63 (m, 1H), 7.57 (t, J=8.0 Hz, 1H), 7.40-7.39 (m, 1H), 7.17-7.14 (m, 1H), 7.09-7.08 (m, 1H), 2.58 (s, 3H).

Step 2: Ethyl 3-oxo-3-(3-(pyridin-2-yloxy) phenyl) propanoate (F)

To a stirred solution of 1-(3-(pyridin-2-yloxy)phenyl) ethanone (100 mg, 0.46 mmol) in dry THF (7 mL) under inert atmosphere was added NaH (60%) (33.8 mg, 1.40 mmol) portion wise at 0° C. After being stirred for 10 min, the reaction mixture was warmed to RT and was added diethyl carbonate (83.1 mg, 0.70 mmol); heated to 60-70° C. and stirred for 6 h. The progress of the reaction was monitored by TLC. After completion of the reaction, the reaction mixture was diluted with water (30 mL) and extracted with ethyl acetate (2×20 mL). The combined organic extracts were washed with water (20 mL), dried over sodium sulfate, filtered and concentrated under reduced pressure to obtain the crude product. The crude product was purified by silica gel column chromatography [Eluent: 12% EtOAc/Hexanes] to afford intermediate F (50 mg, 38%) as a colorless liquid. $^1$H NMR (500 MHz, DMSO-$d_6$): δ 8.14-8.13 (m, 1H), 7.90-7.86 (m, 1H), 7.80-7.79 (m, 1H), 7.65 (s, 1H), 7.59 (t, J=7.5 Hz, 1H), 7.44 (d, J=7.5 Hz, 1H), 7.17-7.14 (m, 1H), 7.09 (d, J=8.0 Hz, 1H), 4.18 (s, 2H), 4.12-4.08 (m, 2H), 1.15 (s, 3H).

Ethyl 3-(3-(1H-indol-1-yl) phenyl)-3-oxopropanoate (M)

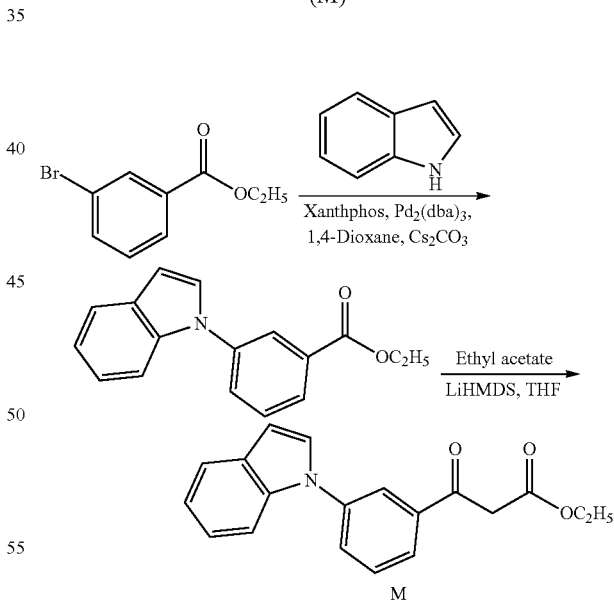

Step 1: Ethyl 3-(1H-indol-1-yl)benzoate

To a stirred solution of 1H-indole (3 g, 25.60 mmol) in 1,4-dioxane (200 mL) under inert atmosphere were added ethyl 3-bromobenzoate (5.86 g, 25.60 mmol), cesium carbonate (14.98 g, 46.09 mmol), xanthphos (663.7 mg, 1.28 mmol) at RT and purged with argon for 30 min. Then Pd$_2$(dba)$_3$ (937.9 mg, 1.02 mmol) was added and again degassed for another 30 min; heated to 60° C. and stirred for 12 h. The progress of the reaction was monitored by TLC. After completion of the reaction, the volatiles were evaporated under reduced pressure to obtain the crude product. The crude product was purified by silica gel column chromatography [Eluent: 5% EtOAc/Hexanes] to afford ethyl 3-(1H-indol-1-yl)benzoate (1.3 g, 19%) as colorless liquid. $^1$H NMR (400 MHz, DMSO-$d_6$): δ 8.06-8.04 (m, 1H), 7.98-7.96 (m, 1H), 7.89-7.87 (m, 1H), 7.76-7.67 (m, 3H), 7.56-7.52 (m, 1H), 7.25-7.15 (m, 2H), 6.75-6.73 (m, 1H), 4.39-4.32 (m, 2H), 1.34 (s, 3H).

Step 2: Ethyl 3-(3-(1H-indol-1-yl) phenyl)-3-oxo-propanoate (M)

To a stirred solution of 1.49 M LiHMDS (5.78 mL, 8.64 mmol) in THF (20 mL) under inert atmosphere was added ethyl acetate (331.6 mg, 3.76 mmol) at −78° C. After being stirred for 10 min, ethyl 3-(1H-indol-1-yl)benzoate (1 g, 3.76 mmol) was added and stirring was continued for 4 h. The progress of the reaction was monitored by TLC. After completion of the reaction, the reaction mixture was quenched with aq. NH$_4$Cl (20 mL) and extracted with ethyl acetate (3×20 mL). The combined organic extracts were washed with water (20 mL), dried over sodium sulfate, filtered and concentrated under reduced pressure to obtain the crude product. The crude product was purified by silica gel column chromatography [Eluent: 10% EtOAc/Hexanes] to afford compound M (550 mg, 48%) as a brown oil. $^1$H NMR (400 MHz, DMSO-$d_6$): δ 8.12-8.11 (m, 1H), 8.10-7.90 (m, 2H), 7.77-7.73 (m, 2H), 7.68 (d, J=7.6 Hz, 1H), 7.60 (d, J=8.4 Hz, 1H), 7.24-7.14 (m, 2H), 6.76-6.74 (m, 1H), 4.31 (s, 2H), 4.16-4.11 (m, 2H), 1.18 (s, 3H).

Methyl 3-oxo-3-(3-phenoxyphenyl) propanoate (N)

reaction mixture was filtered under vacuum and the filtrate was concentrated under reduced pressure to obtain the crude product. The crude product was purified by silica gel column chromatography [Eluent: 5% EtOAc/Hexanes] to afford 1-(3-phenoxyphenyl)ethanone (350 mg, 45%) as a colorless liquid. $^1$H NMR (400 MHz, DMSO-$d_6$): δ 7.75-7.73 (m, 1H), 7.56-7.52 (m, 1H), 7.52-7.48 (m, 1H), 7.45-7.41 (m, 2H), 7.30-7.29 (m, 1H), 7.17-7.07 (m, 1H), 7.06-7.04 (m, 2H), 2.56 (s, 3H).

Step 2: Methyl 3-oxo-3-(3-phenoxyphenyl) propanoate (N)

To a stirred solution of 1-(3-phenoxyphenyl)ethanone (500 mg, 2.35 mmol) in dry THF (20 mL) under inert atmosphere was added sodium hydride (141.5 mg, 5.89 mmol, 60%) portion wise at 0° C. After being stirred for 10 min, dimethyl carbonate (531.1 mg, 5.89 mmol) was added and warmed to RT and the resulting solution was stirred at 60-70° C. for 12 h. The progress of the reaction was monitored by TLC. After completion of the reaction, reaction mixture was quenched with 10% HCl solution (20 mL) and diluted with water (30 mL) and extracted with ethyl acetate (2×20 mL). The combined organic extracts were washed with water (25 mL), dried over sodium sulfate, filtered and concentrated under reduced pressure to obtain the crude product. The crude material was purified by silica gel column chromatography [Eluent: 7% EtOAc/Hexanes] to afford compound N (300 mg, 47%) as a colorless liquid. $^1$H NMR (400 MHz, CDCl$_3$): δ 7.65 (d, J=7.6 Hz, 1H), 7.55-7.46 (m, 1H), 7.44-7.38 (m, 1H), 7.37-7.33 (m, 1H), 7.25-7.23 (m, 1H), 7.22-7.11 (m, 2H), 7.02 (d, J=8.4 Hz, 2H), 3.96 (s, 2H), 3.74 (s, 3H).

Methyl 3-(3-(benzyloxy) phenyl)-3-oxopropanoate (O)

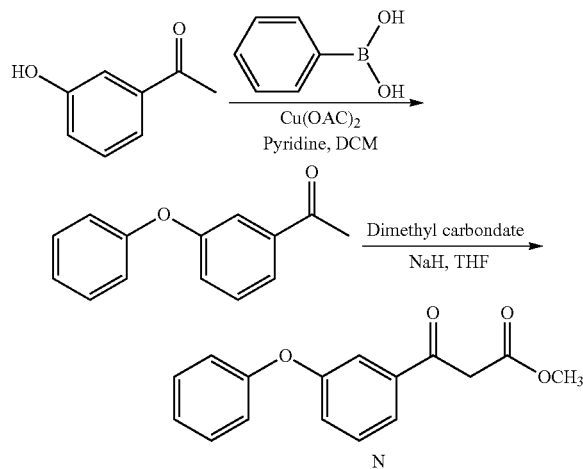

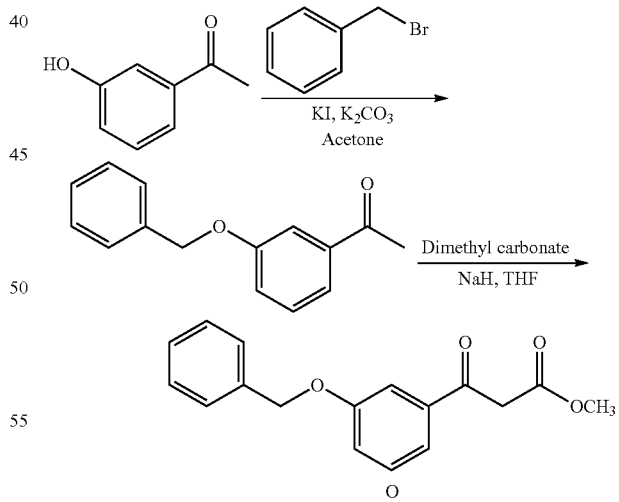

Step 1: 1-(3-Phenoxyphenyl)ethanone

To a stirred mixture of molecular sieves (5 g) in CH$_2$Cl$_2$ (25 mL) under inert atmosphere were added 3-hydroxy acetophenone (500 mg, 36.72 mmol), phenylboronic acid (896.0 mg, 7.34 mmol), copper acetate (1.46 g, 7.34 mmol) and pyridine (1.45 g, 18.36 mmol) at RT and stirred under N$_2$ atmosphere for 48 h. The progress of the reaction was monitored by TLC. After completion of the reaction, the

Step 1: Synthesis of 1-(3-(benzyloxy)phenyl)ethanone

To a stirred solution of 3-hydroxy acetophenone (1 g, 7.35 mmol) in acetone (25 mL) under inert atmosphere was added potassium iodide (244.1 mg, 1.47 mmol), potassium carbonate (2.02 g, 14.70 mmol) and benzyl bromide (1.5 g, 8.82 mmol) at RT. The reaction mixture was heated at 70° C. and stirred for 20 h. The progress of the reaction was monitored by TLC. After completion of the reaction, the volatiles were evaporated under reduced pressure and the residue was diluted with water (30 mL) and extracted with EtOAc (2×30 mL). The combined organic extracts were washed with water (25 mL), dried over sodium sulfate, filtered and concentrated under reduced pressure to obtain the crude product. The crude product was purified by silica gel column chromatography [Eluent: 7% EtOAc/Hexanes] to afford 1-(3-(benzyloxy)phenyl)ethanone (1.6 g, 69%) as a colorless liquid. $^1$H NMR (400 MHz, DMSO-$d_6$): δ 7.55-7.51 (m, 2H), 7.45-7.25 (m, 7H), 5.16 (s, 2H), 2.55 (s, 3H).

Step 2: Methyl 3-(3-(benzyloxy) phenyl)-3-oxopropanoate (O)

To a stirred solution of 1-(3-(benzyloxy) phenyl)ethanone (500 mg, 2.21 mmol) in dry THF (15 mL) under inert atmosphere was added sodium hydride (132.7 mg, 5.53 mmol, 60%) portion wise at 0° C. After being stirred for 10 min, dimethyl carbonate (498.2 mg, 5.53 mmol) was added, warmed to RT and the resulting solution was stirred at 60-70° C. for 12 h. The progress of the reaction was monitored by TLC. After completion of the reaction, the reaction mixture was quenched with 10% HCl solution (20 mL), diluted with water (30 mL) and extracted with ethyl acetate (2×20 mL). The combined organic extracts were washed with water (25 mL), dried over sodium sulfate, filtered and concentrated under reduced pressure to obtain the crude product. The crude material was purified by silica gel column chromatography [Eluent: 5% EtOAc/Hexanes] to afford compound 0 (500 mg, 80%) as a colorless liquid. $^1$H NMR (400 MHz, DMSO-$d_6$): δ 7.55-7.51 (m, 2H), 7.48-7.45 (m, 3H), 7.42-7.40 (m, 2H), 7.38-7.32 (m, 2H), 5.18 (s, 2H), 4.20 (s, 2H), 3.64 (s, 3H).

Ethyl 3-(3-nitrophenyl)-3-oxopropanoate (P)

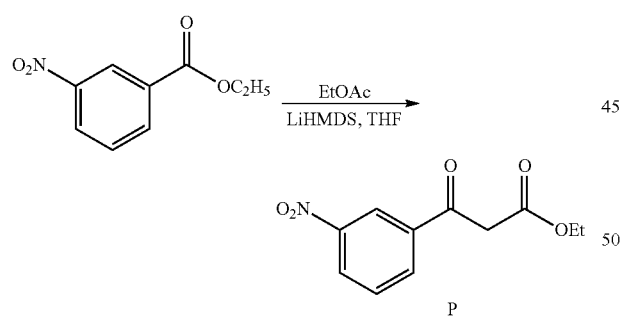

To a stirred solution of LiHMDS (9.84 g, 58.97 mmol) in dry THF (20 mL) under inert atmosphere was added ethyl acetate (2.25 g, 25.6 mmol) drop wise at −78° C. under inert atmosphere. After being stirred for 30 min, ethyl 3-nitro benzoate (5 g, 25.6 mmol) was added and stirred for 1 h at −78° C. The progress of the reaction was monitored by TLC. After completion of the reaction, the reaction mixture was quenched with aq. NH$_4$Cl solution (50 mL) and extracted with ethylacetate (2×50 mL). The combined organic extracts were washed with water (50 mL), dried over anhydrous sodium sulfate, filtered and concentrated under reduced pressure to obtain the crude product. The crude product was purified by silica gel column chromatography [Eluent: 10% EtOAc/Hexanes] to afford compound P (4 g, 67.56%) as an off-white solid. $^1$H NMR (400 MHz, CDCl$_3$): δ 8.46-8.44 (m, 1H), 8.30-8.29 (m, 1H), 8.09-8.08 (m, 1H), 7.71 (t, J=8.0 Hz, 1H), 4.31-4.04 (m, 2H), 4.24 (s, 2H), 1.35-1.25 (m, 3H).

4-(3-bromophenyl)-7-methyl-8-(trifluoromethyl)-1H-benzo[b][1,4]diazepin-2(3H)-one (Q)

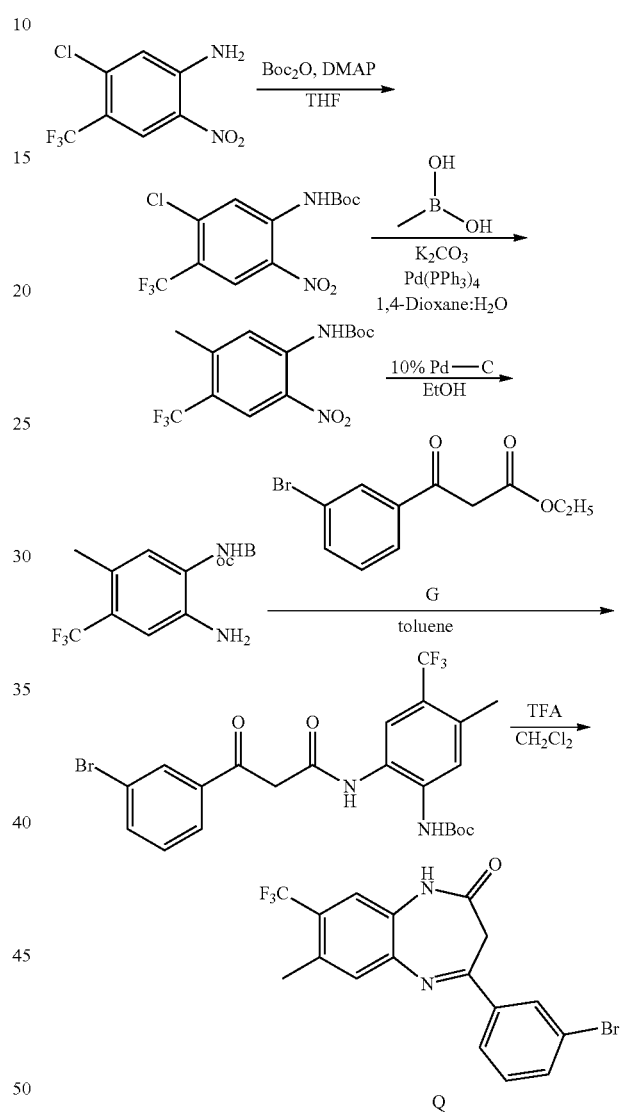

Step 1: tert-Butyl 5-chloro-2-nitro-4-(trifluoromethyl)phenylcarbamate

To a stirred solution of 5-chloro-2-nitro-4-(trifluoromethyl)aniline (1.3 g, 5.42 mmol) in THF (20 mL) was added Boc anhydride (1.77 g, 8.12 mmol) followed by DMAP (198 mg, 1.62 mmol) at 0° C. under inert atmosphere. The resulting reaction mixture was allowed to warm to RT and stirred for 2 hr. After the consumption of starting material (by TLC), the reaction mixture was concentrated under reduced pressure. The crude material was purified by silica gel column chromatography eluting with 5% EtOAc/Hexane to afford tert-butyl 5-chloro-2-nitro-4-(trifluoromethyl)phenylcarbamate (1.3 g, 70.7%) as a pale yellow solid. $^1$H NMR (500 MHz, CDCl$_3$): δ 9.88 (bs, 1H), 8.91 (s, 1H), 8.56 (s, 1H), 1.54 (d, J=9.5 Hz, 9H). MS (ESI): 339 [M−1].

Step 2: tert-Butyl 5-methyl-2-nitro-4-(trifluoromethyl)phenylcarbamate

To a stirred solution of tert-butyl 5-chloro-2-nitro-4-(trifluoromethyl)phenylcarbamate (1.3 g, 3.82 mmol) in 1,4-dioxane:H$_2$O (20 mL, 4:1) were added methylboronic acid (0.228 g, 3.82 mmol) and K$_2$CO$_3$ (1.58 g, 11.47 mmol) at RT under inert atmosphere. The reaction mixture was degassed with argon for 30 min and then Pd(PPh$_3$)$_4$ (0.44 g, 0.38 mmol) was added and again degassed for another 30 min. The resulting reaction mixture was heated to 100° C. and stirred for 16 h. The progress of the reaction was monitored by TLC. After completion of the reaction, the reaction mixture was filtered through a bed of celite to remove solids. The filtrate was then concentrated under reduced pressure to obtain the crude product. The crude material was purified by silica gel column chromatography eluting with 5% EtOAc/Hexane to afford tert-butyl 5-methyl-2-nitro-4-(trifluoromethyl)phenylcarbamate (1 g, 81.9%) as a pale yellow solid. $^1$H NMR (400 MHz, CDCl$_3$): δ 9.86 (bs, 1H), 8.60 (s, 1H), 8.47 (s, 1H), 2.55 (s, 3H), 1.54 (d, J=7.6 Hz, 9H).

Step 3: tert-Butyl 2-amino-5-methyl-4-(trifluoromethyl)phenylcarbamate

To a stirred solution of tert-butyl 5-methyl-2-nitro-4-(trifluoromethyl)phenylcarbamate (1.0 g, 2.94 mmol) in EtOH (20 mL) was added 10% Pd—C (5 mg) at RT under inert atmosphere. The resulting reaction mixture was agitated under H$_2$ atmosphere (balloon pressure) for 2 h at RT. The reaction mixture was filtered through a celite pad and the filtrate was concentrated under reduced pressure to afford tert-butyl 2-amino-5-methyl-4-(trifluoromethyl)phenylcarbamate (0.7 g, 82.4%) as a pale yellow solid. $^1$H NMR (500 MHz, CDCl$_3$): δ 7.41-7.39 (m, 1H), 7.03 (s, 1H), 6.42 (br s, 1H, Exc), 3.58 (br s, 2H, Exc), 2.35 (s, 3H), 1.52 (s, 9H). MS (ESI): m/z 291.1 [M+1]$^+$.

Step 4: tert-Butyl 2-(3-(3-bromophenyl)-3-oxopropanamido)-5-methyl-4-(trifluoromethyl)phenylcarbamate To a stirred solution of tert-butyl 2-amino-5-methyl-4-(trifluoromethyl)phenylcarbamate (0.9 g, 3.10 mmol) in toluene (20 mL) was added compound G (0.92 g, 3.10 mmol) at RT under inert atmosphere. The resulting reaction mixture was stirred for 12 h at 110° C.; progress of the reaction was monitored by TLC. The reaction mixture was concentrated under reduced pressure. The crude material was triturated with hexane (50 mL) to afford tert-butyl 2-(3-(3-bromophenyl)-3-oxopropanamido)-5-methyl-4-(trifluoromethyl)phenylcarbamate (0.9 g, 56.6%) as an off-white solid. $^1$H NMR (400 MHz, DMSO-d$_6$): δ 9.75 (bs, 1H), 8.68 (bs, 1H), 8.14 (s, 1H), 8.01 (d, J=7.6 Hz, 1H), 7.89 (d, J=8.8 Hz, 1H), 7.81 (s, 1H), 7.76-7.72 (m, 1H), 7.56-7.49 (m, 1H), 4.22 (s, 2H), 2.39 (s, 3H), 1.48 (d, J=6.0 Hz, 9H). MS (ESI): m/z 513 [M−2].

Step 5: 4-(3-Bromophenyl)-7-methyl-8-(trifluoromethyl)-1H-benzo[b][1,4]diazepin-2(3H)-one (Q)

To a stirred solution of tert-butyl 2-(3-(3-bromophenyl)-3-oxopropanamido)-5-methyl-4-(trifluoromethyl)phenylcarbamate (0.9 g, 1.74 mmol) in CH$_2$Cl$_2$ (20 mL) was added TFA (9 mL) at 0° C. under inert atmosphere. The resultant reaction mixture was allowed to warm to RT and stirred for 12 h. The progress of the reaction was monitored by TLC. The reaction mixture was quenched with aq. NaHCO$_3$ solution (10 mL) and extracted with CH$_2$Cl$_2$ (3×20 mL). The combined organic extracts were dried over anhydrous Na$_2$SO$_4$ and concentrated under reduced pressure to afford compound Q (0.6 g, 86.6%) as an off-white solid. $^1$H NMR (400 MHz, DMSO-d$_6$): δ 10.71 (bs, 1H), 8.24 (s, 1H), 8.06 (d, J=8.4 Hz, 1H), 7.79 (d, J=6.0 Hz, 1H), 7.55-7.50 (m, 3H), 3.58 (s, 2H), 2.45 (s, 3H). MS (ESI): m/z 399 [M+2]$^+$.

4-(3-Hydroxyphenyl)-7-methyl-8-(trifluoromethyl)-1H-benzo[b][1,4]diazepin-2(3H)-one (R)

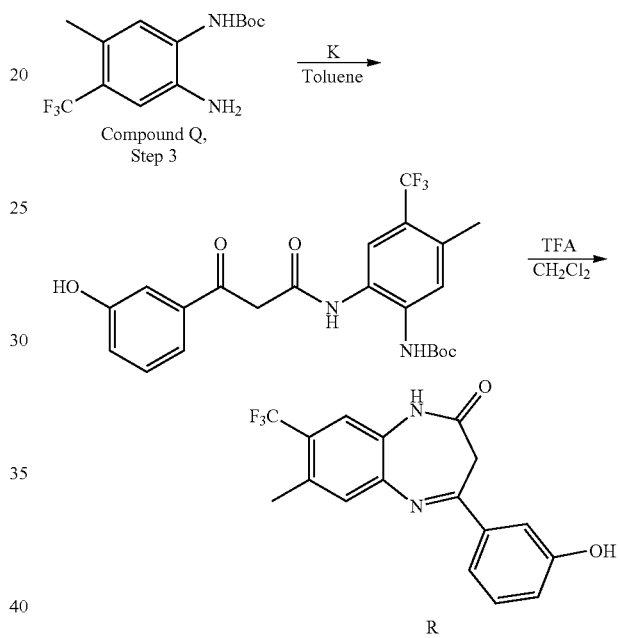

Step 1: tert-Butyl 2-(3-(3-hydroxyphenyl)-3-oxopropanamido)-5-methyl-4-(trifluoromethyl)phenylcarbamate To a stirred solution of tert-butyl 2-amino-5-methyl-4-(trifluoromethyl)phenylcarbamate (1 g, 3.44 mmol) in toluene (20 mL) under inert atmosphere was added compound K (717.24 mg, 3.44 mmol) at RT. The reaction mixture was heated to 120° C. and stirred for 15 h. The progress of the reaction was monitored by TLC. After completion of the reaction, the volatiles were evaporated under reduced pressure to obtain the crude product. The crude product was triturated with diethyl ether (2×10 mL) to afford tert-butyl 2-(3-(3-hydroxyphenyl)-3-oxopropanamido)-5-methyl-4-(trifluoromethyl)phenylcarbamate (1.3 g, 83%) as a colorless liquid. $^1$H NMR (400 MHz, DMSO-d$_6$): δ 14.02 (s, 1H), 9.85 (s, 1H), 9.73 (s, 1H), 7.88 (s, 1H), 7.83 (s, 1H), 7.73 (s, 1H), 7.47 (d, J=8.0 Hz, 1H), 7.38-7.34 (m, 1H), 6.92-6.89 (m, 1H), 4.14 (s, 2H), 2.50-2.49 (s, 3H), 1.49 (s, 9H).

Step-2: 4-(3-Hydroxyphenyl)-7-methyl-8-(trifluoromethyl)-1H-benzo[b][1,4]diazepin-2(3H)-one (R)

To a stirred solution of tert-butyl 2-(3-(3-hydroxyphenyl)-3-oxopropanamido)-5-methyl-4-(trifluoromethyl)phenylcarbamate (1.3 g, 2.87 mmol) in DCM (20 mL) under inert atmosphere was added TFA (4 mL) at 0° C. The reaction mixture was warmed to RT and stirred for 6 h. The progress of the reaction was monitored by TLC. After completion of the reaction, the reaction mixture was diluted with water (40 mL) and extracted with DCM (3×20 mL). The combined organic extracts were washed with saturated NaHCO₃ solution (2×20 mL), water (20 mL), dried over sodium sulfate, filtered and concentrated under reduced pressure to obtain the crude product. The crude product was triturated with diethyl ether (2×15 mL) to afford compound R (900 mg, 94%) as an off-white solid. ¹H NMR (500 MHz, DMSO-d₆): δ 10.64 (s, 1H), 9.74 (s, 1H), 7.50-7.49 (m, 2H), 7.48 (s, 1H), 7.33 (t, J=8.0 Hz, 1H), 6.96 (d, J=9.0 Hz, 1H), 3.49-3.38 (m, 2H), 2.44 (s, 3H). MS (ESI): m/z 335[M+1]⁺ HPLC: 98.2%.

Example 136: 7-Methyl-4-(3-(pyrimidin-2-ylthio)phenyl)-8-(trifluoromethyl)-1H-benzo[b][1,4]diazepin-2(3H)-one

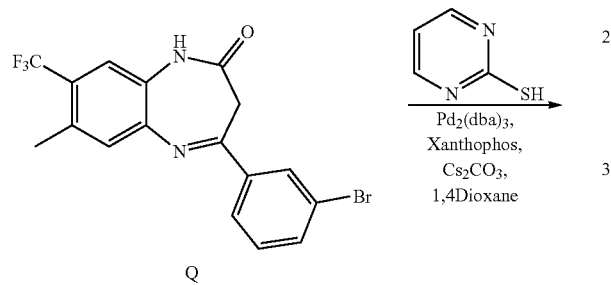

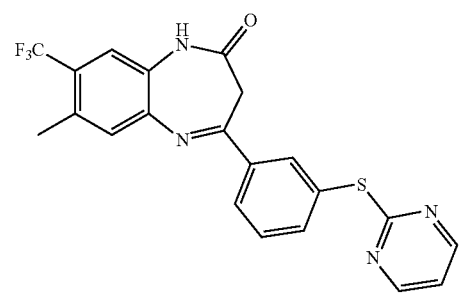

To a stirred solution of compound Q (300 mg, 0.75 mmol) in 1,4-dioxane (10 mL) under inert atmosphere were added pyrimidine-2-thiol (84 mg, 0.75 mmol), cesium carbonate (443 mg, 1.36 mmol), xanthphos (19.6 mg, 0.03 mmol) at RT and purged with argon for 45 min. Then Pd₂(dba)₃ (27.7 mg, 0.03 mmol) was added and again purged for 10 min. The reaction mixture was heated to 100° C. and stirred for 12 h. The progress of the reaction was monitored by TLC. After completion of the reaction, the reaction mixture was filtered through celite pad. The filtrate was concentrated under reduced pressure to obtain the crude product. The crude product was purified by silica gel column chromatography [Eluent: 40% EtOAc/Hexanes] to afford the title compound (250 mg, 77%) as pale yellow solid. ¹H NMR (400 MHz, DMSO-d₆): δ 10.70 (s, 1H), 8.61-8.60 (m, 2H), 8.29-8.28 (m, 1H), 8.15 (d, J=8.4 Hz, 1H), 7.81 (d, J=7.6 Hz, 1H), 7.66 (t, J=8.0 Hz, 1H), 7.49 (d, J=8.0 Hz, 2H), 7.26 (t, J=4.8 Hz, 1H), 3.61-3.59 (m, 2H), 2.49 (s, 3H).

Example 137: 7-Methyl-4-(3-(pyrimidin-2-ylsulfonyl) phenyl)-8-(trifluoromethyl)-1H-benzo[b][1,4]diazepin-2(3H)-one

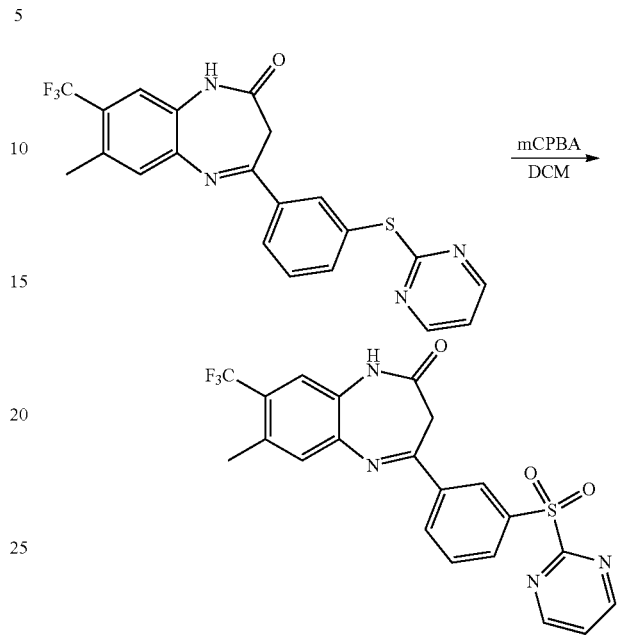

To a stirred solution of 7-methyl-4-(3-(pyrimidin-2-yl-thio)phenyl)-8-(trifluoromethyl)-1H-benzo[b][1,4]diazepin-2(3H)-one (Example 136) (50 mg, 0.11 mmol) in CH₂Cl₂ (7 mL) under inert atmosphere was added m-chloro perbenzoic acid (50 mg, 0.29 mmol) at 0° C. The reaction mixture was warmed to RT and stirred for 2 h. The progress of the reaction was monitored by TLC. After completion of the reaction, the reaction mixture was diluted with water (15 mL) and extracted with CH₂Cl₂ (3×15 mL). The combined organic extracts were washed with saturated NaHCO₃ solution (15 mL), water (15 mL), dried over sodium sulfate, filtered and concentrated under reduced pressure to obtain the crude product. The crude product was purified by silica gel column chromatography [Eluent: 80% EtOAc/Hexanes] to afford the title compound (5 mg, 9%) as pale yellow solid. ¹H NMR (400 MHz, DMSO-d₆): δ 10.75 (s, 1H), 9.05-9.04 (m, 2H), 8.62 (s, 1H), 8.44 (d, J=8.4 Hz, 1H), 8.19 (d, J=8.4 Hz, 1H), 7.89 (t, J=7.6 Hz, 1H), 7.81 (t, J=4.8 Hz, 1H), 7.53 (d, J=11.6 Hz, 2H), 3.64 (s, 2H), 2.50 (s, 3H). MS (ESI): m/z 461 [M+1]⁺ HPLC: 90.0%.

Example 138: 7-Methyl-4-(3-((6-methylpyridin-2-yl) ethynyl)phenyl)-8-(trifluoromethyl)-1H-benzo[b][1,4]diazepin-2 (3H)-one

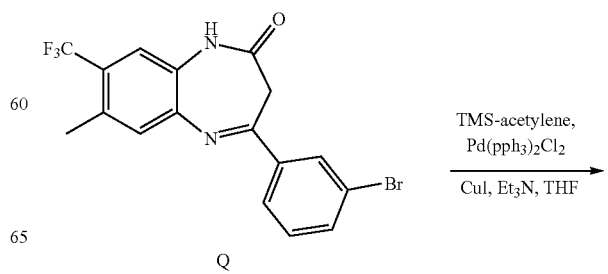

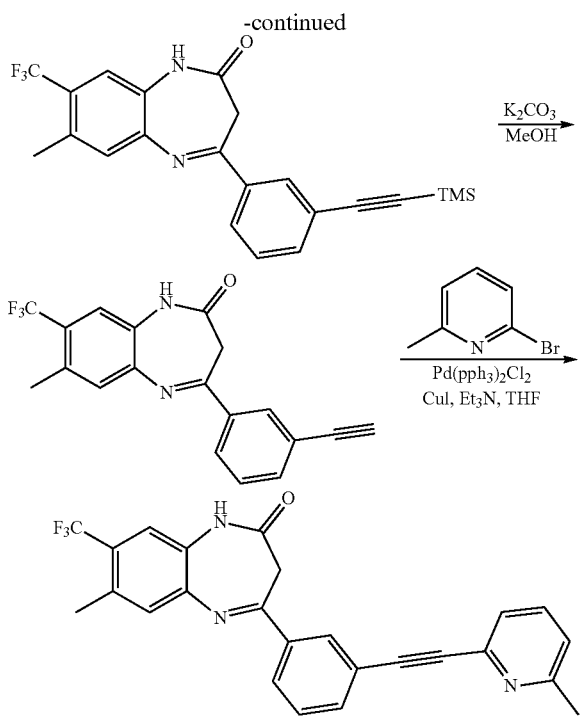

Step 1: 7-Methyl-8-(trifluoromethyl)-4-(3-((trimethylsilyl)ethynyl)phenyl)-1H-benzo[b][1,4]diazepin-2 (3H)-one To a stirred solution of compound Q (200 mg, 0.50 mmol) in THF (3 mL) under inert atmosphere were added TMS-acetylene (98 mg, 1.00 mmol), triphenyl phosphine (6.6 mg, 0.02 mmol), copper iodide (2 mg, 0.01 mmol) and triethyl amine (228 mg, 2.26 mmol) at RT and purged with argon for 20 min. Then Pd(pph$_3$)$_2$Cl$_2$ (17.6 mg, 0.02 mmol) was added to the reaction mixture and again purged for 15 min; heated to 60° C. and stirred for 25 h. The progress of the reaction was monitored by TLC. After completion of the reaction, the reaction mixture was diluted with 5% citric acid solution (5 mL) and extracted with EtOAc (2×10 mL). The combined organic extracts were washed with saturated NaHCO$_3$ solution (10 mL), brine (10 mL), dried over sodium sulfate, filtered and concentrated under reduced pressure to obtain the crude product. The crude product was purified by silica gel column chromatography [Eluent: 5% EtOAc/Hexanes] to afford 7-methyl-8-(trifluoromethyl)-4-(3-((trimethylsilyl)ethynyl)phenyl)-1H-benzo[b][1,4]diazepin-2 (3H)-one (170 mg, 82%) as an off-white solid. $^1$H NMR (400 MHz, DMSO-d$_6$): δ 10.70 (s, 1H), 8.11-8.08 (m, 2H), 7.67-7.64 (m, 1H), 7.57 (d, J=7.6 Hz, 1H), 7.54-7.49 (m, 2H), 3.60 (s, 2H), 2.50 (s, 3H). 0.26 (s, 9H).

Step 2: 4-(3-Ethynylphenyl)-7-methyl-8-(trifluoromethyl)-1H-benzo[b][1,4]diazepin-2(3H)-one To a stirred solution of 7-methyl-8-(trifluoromethyl)-4-(3-((trimethylsilyl)ethynyl)phenyl)-1H-benzo[b][1,4]diazepin-2 (3H)-one (100 mg, 0.24 mmol) in methanol (3 mL) under inert atmosphere was added potassium carbonate (66 mg, 0.48 mmol) at 0° C. The reaction mixture was warmed to RT and stirred for 45 min. The progress of the reaction was monitored by TLC. After completion of the reaction, the reaction mixture was diluted with water (20 mL) and extracted with CH$_2$Cl$_2$ (3×20 mL). The combined organic extracts were washed with water (20 mL), dried over sodium sulfate, filtered and concentrated under reduced pressure to obtain crude 4-(3-ethynylphenyl)-7-methyl-8-(trifluoromethyl)-1H-benzo[b][1,4]diazepin-2(3H)-one (78 mg) as an off-white solid. $^1$H NMR (400 MHz, DMSO-d$_6$): δ 10.80 (s, 1H), 8.25 (s, 1H), 8.21 (d, J=8.0 Hz, 1H), 7.79 (d, J=7.6 Hz, 1H), 7.68 (t, J=8.0 Hz, 1H), 7.61-7.59 (m, 2H), 4.42 (s, 1H), 3.68 (s, 2H), 2.56 (s, 3H).

Step 3: 7-Methyl-4-(3-((6-methylpyridin-2-yl) ethynyl)phenyl)-8-(trifluoromethyl)-1H-benzo[b][1,4] diazepin-2 (3H)-one To a stirred solution of 4-(3-ethynylphenyl)-7-methyl-8-(trifluoromethyl)-1H-benzo[b][1,4]diazepin-2(3H)-one (78 mg, 0.22 mmol) in THF (5 mL) under inert atmosphere were added 2-bromo-6-methylpyridine (78 mg, 0.45 mmol), triphenyl phosphine (2.9 mg, 0.01 mmol), copper iodide (0.8 mg, 0.004 mmol) and triethyl amine (103 mg, 1.02 mmol) at RT and purged with argon for 20 min. Then Pd(pph$_3$)$_2$Cl$_2$ (8 mg, 0.01 mmol) was added to the reaction mixture and again purged for 15 min; heated to 60° C. and stirred for 25 h. The progress of the reaction was monitored by TLC. After completion of the reaction, the reaction mixture was diluted with 5% citric acid solution (5 mL) and extracted with EtOAc (2×20 mL). The combined organic extracts were washed with saturated NaHCO$_3$ solution (15 mL), brine (15 mL), dried over sodium sulfate, filtered and concentrated under reduced pressure to obtain the crude product. The crude product was purified by silica gel column chromatography [Eluent: 30% EtOAc/Hexanes] to afford the title compound (6 mg, 6%) as an off-white solid. $^1$H NMR (400 MHz, DMSO-d$_6$): δ 10.72 (s, 1H), 8.29 (s, 1H), 8.16-8.14 (m, 1H), 7.80-7.74 (m, 2H), 7.64 (t, J=8.0 Hz, 1H), 7.52-7.50 (m, 3H), 7.31 (d, J=8.0 Hz, 1H), 3.62 (s, 2H), 2.52 (s, 3H), 2.49 (s, 3H). MS (ESI): m/z 434 [M+1]$^+$ HPLC: 93.9%.

Example 139: 7-Methyl-4-(3-(pyridin-3-ylethynyl)phenyl)-8-(trifluoromethyl)-1H-benzo[b][1,4]diazepin-2(3H)-one

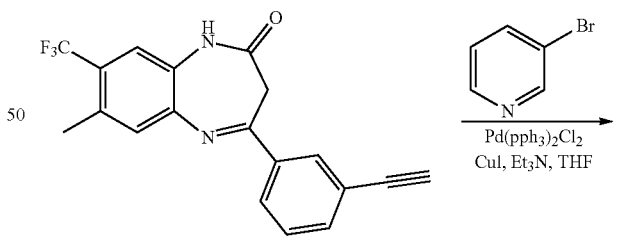

Example 138,
Step 2

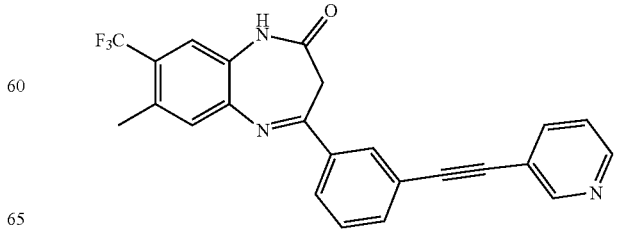

To a stirred solution of the compound from Example 138, Step 2 (56 mg, 0.16 mmol) in THF (5 mL) under inert atmosphere were added 3-bromo pyridine (51 mg, 0.32 mmol), triphenyl phosphine (2.1 mg, 0.008 mmol), copper iodide (0.6 mg, 0.003 mmol) and triethyl amine (74 mg, 0.73 mmol) at RT and purged with argon for 20 min. Then Pd(pph$_3$)$_2$Cl$_2$ (5.7 mg, 0.008 mmol) to the reaction mixture and again purged for 15 min; heated to 60° C. and stirred for 25 h. The progress of the reaction was monitored by TLC. After completion of the reaction, the reaction mixture was diluted with 5% citric acid solution (5 mL) and extracted with EtOAc (2×20 mL). The combined organic extracts were washed with saturated NaHCO$_3$ solution (15 mL), brine (15 mL), dried over sodium sulfate, filtered and concentrated under reduced pressure to obtain the crude product. The crude product was purified by silica gel column chromatography [Eluent: 30% EtOAc/Hexanes] to afford the title compound (9 mg, 13%) as an off-white solid. $^1$H NMR (400 MHz, DMSO-d$_6$): δ 10.72 (s, 1H), 8.82 (s, 1H), 8.62-8.61 (m, 1H), 8.27 (s, 1H), 8.15 (d, J=8.0 Hz, 1H), 8.04 (d, J=8.0 Hz, 1H), 7.80 (d, J=7.6 Hz, 1H), 7.64 (t, J=7.6 Hz, 1H), 7.52-7.48 (m, 3H), 3.63 (s, 2H), 2.46 (s, 3H). MS (ESI): m/z 420 [M+1]$^+$ HPLC: 96.9%.

Example 140: 7-Methyl-4-(3-(pyrimidin-2-ylamino)phenyl)-8-(trifluoromethyl)-1H-benzo[b][1,4]diazepin-2 (3H)-one

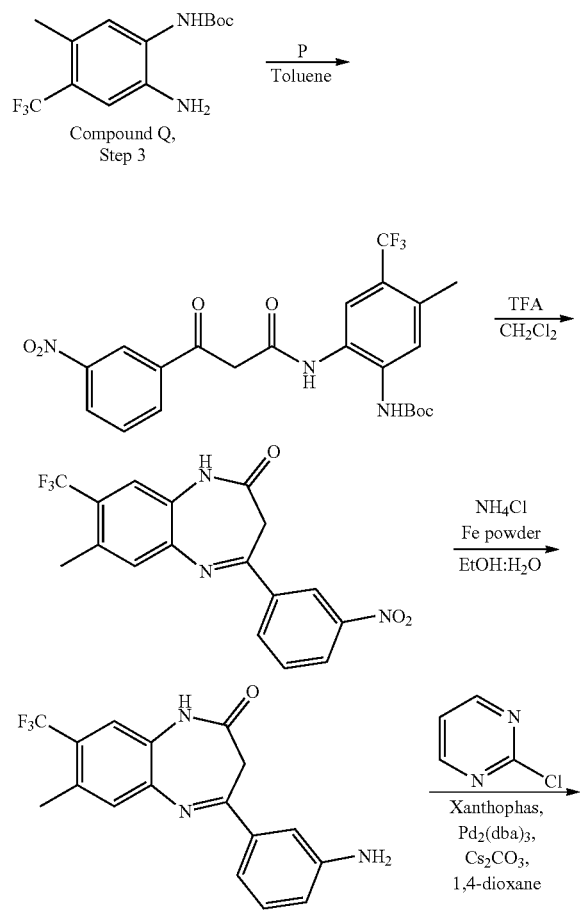

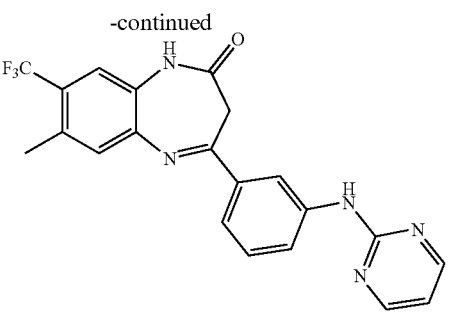

Step 1: tert-Butyl (5-methyl-2-(3-(3-nitrophenyl)-3-oxopropanamido)-4-(trifluoromethyl) phenyl)carbamate To a stirred solution of the compound from compound Q, Step 3 (500 mg, 1.72 mmol) in toluene (50 mL) under inert atmosphere was added intermediate P (408 mg, 1.72 mmol) at RT. The reaction mixture was heated to 110° C. and stirred for 12 h. The progress of the reaction was monitored by TLC. After completion of the reaction, the reaction mixture was filtered and the solid was washed with toluene (2×10 mL), dried under reduced pressure to afford crude tert-butyl (5-methyl-2-(3-(3-nitrophenyl)-3-oxopropanamido)-4-(trifluoromethyl)phenyl)carbamate (390 mg) as an off-white solid.

Step 2: 7-Methyl-4-(3-nitrophenyl)-8-(trifluoromethyl)-1H-benzo[b][1,4]diazepin-2(3H)-one To a stirred solution of tert-butyl (5-methyl-2-(3-(3-nitrophenyl)-3-oxopropanamido)-4-(trifluoromethyl)phenyl)carbamate (390 mg, 0.81 mmol) in CH$_2$Cl$_2$ (10 mL) under inert atmosphere was added TFA (2 mL) at 0° C. The reaction mixture was warmed to RT and stirred for 6 h. The progress of the reaction was monitored by TLC. After completion of the reaction, the reaction mixture was diluted with water (25 mL) and extracted with CH$_2$Cl$_2$ (2×25 mL). The combined organic extracts were washed with water (20 mL), dried over sodium sulfate, filtered and concentrated under reduced pressure to obtain the crude product. The crude product was triturated with diethyl ether (2×10 mL) to afford 7-methyl-4-(3-nitrophenyl)-8-(trifluoromethyl)-1H-benzo[b][1,4]diazepin-2(3H)-one (240 mg, 82%) as an off-white solid. $^1$H NMR (400 MHz, DMSO-d$_6$): δ 10.67 (s, 1H), 8.84-8.83 (m, 1H), 8.49 (d, J=8.0 Hz, 1H), 8.42 (d, J=7.6 Hz, 1H), 7.87 (t, J=8.0 Hz, 1H), 7.54 (d, J=9.2 Hz, 2H), 3.67 (s, 2H), 2.49 (s, 3H). MS (ESI): m/z 362 [M+1]$^+$ HPLC: 98.8%.

Step 3: 4-(3-Aminophenyl)-7-methyl-8-(trifluoromethyl)-1H-benzo[b][1,4]diazepin-2(3H)-one To a stirred solution of 7-methyl-4-(3-nitrophenyl)-8-(trifluoromethyl)-1H-benzo[b][1,4]diazepin-2(3H)-one (90 mg, 0.24 mmol) in EtOH:H$_2$O (10:1, 22 mL) were added iron powder (69.2 mg, 1.25 mmol), ammonium chloride (33 mg, 0.61 mmol) at RT. The reaction mixture was heated to 100° C. and stirred for 2 h. The progress of the reaction was monitored by TLC. After completion of the reaction, the reaction mixture was filtered through celite pad. The filtrate was concentrated under reduced pressure to obtain the crude product. The crude product was purified by silica gel column chromatography [Eluent: 60% EtOAc/Hexanes] to afford 4-(3-aminophenyl)-7-methyl-8-(trifluoromethyl)-1H-benzo

[b][1,4]diazepin-2(3H)-one (80 mg, 97%) as pale yellow solid. $^1$H NMR (500 MHz, DMSO-$d_6$): δ 10.61 (s, 1H), 7.48 (s, 1H), 7.44 (s, 1H), 7.30 (s, 1H), 7.20-7.16 (m, 2H), 6.76-6.74 (m, 1H), 5.35-5.33 (m, 2H), 3.48 (s, 2H), 2.45 (s, 3H). MS (ESI): m/z 334 [M+1]$^+$ HPLC: 98.6%.

Step 4: 7-Methyl-4-(3-(pyrimidin-2-ylamino) phenyl)-8-(trifluoromethyl)-1H-benzo[b][1,4]diazepin-2(3H)-one To a stirred solution of 4-(3-aminophenyl)-7-methyl-8-(trifluoromethyl)-1H-benzo[b][1,4]diazepin-2(3H)-one (50 mg, 0.15 mmol) in 1,4-dioxane (10 mL) under inert atmosphere were added 2-chloro pyrimidine (17 mg, 0.15 mmol), xanthphos (3 mg, 0.007 mmol), cesium carbonate (87 mg, 0.27 mmol) at RT in a sealed tube and purged with argon for 30 min. Then Pd$_2$(dba)$_3$ (5 mg, 0.006 mmol) was added to the reaction mixture and again purged for 15 min; heated to 110° C. and stirred for 12 h. The progress of the reaction was monitored by TLC. After completion of the reaction, the reaction mixture was filtered through celite pad. The filtrate was concentrated under reduced pressure to obtain the crude product. The crude product was purified by silica gel column chromatography [Eluent: 30% EtOAc/Hexanes] to afford the title compound (10 mg, 16%) as a pale yellow solid. $^1$H NMR (500 MHz, DMSO-$d_6$): δ 10.45 (s, 1H), 9.80 (s, 1H), 8.51-8.48 (m, 3H), 7.99 (d, J=10 Hz, 1H), 7.65 (d, J=7.5 Hz, 1H), 7.50 (s, 1H), 7.49 (s, 2H), 6.88-6.86 (m, 1H), 3.57-3.55 (m, 2H), 2.45 (s, 3H). MS (ESI): m/z 412 [M+1]$^+$ and HPLC: 90.8%.

Example 141: 7-Methyl-4-(3-(pyridin-2-ylamino)phenyl)-8-(trifluoromethyl)-1H-benzo[b][1,4]diazepin-2(3H)-one

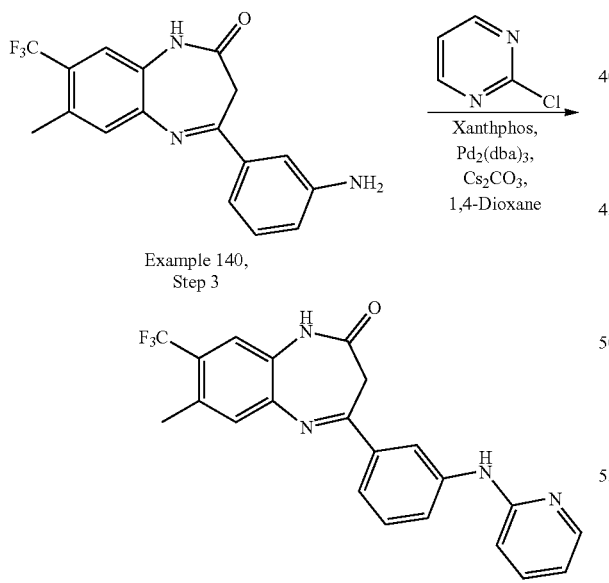

To a stirred solution of the compound from Example 140, Step 3 (50 mg, 0.15 mmol) in 1,4-dioxane (10 mL) under inert atmosphere were added 2-bromo pyridine (23 mg, 0.15 mmol), xanthphos (3 mg, 0.007 mmol), cesium carbonate (87 mg, 0.27 mmol) at RT in a sealed tube and purged with argon for 30 min. Then Pd$_2$(dba)$_3$ (5 mg, 0.006 mmol) was added to the reaction mixture and again purged for 15 min; heated to 100° C. and stirred for 16 h. The progress of the reaction was monitored by TLC. After completion of the reaction, the reaction mixture was filtered through celite pad. The filtrate was concentrated under reduced pressure to obtain the crude product. The crude product was purified by silica gel column chromatography [Eluent: 15% EtOAc/Hexanes] to afford the title compound (18 mg, 30%) as an off-white solid. $^1$H NMR (400 MHz, DMSO-$d_6$): δ 10.66 (s, 1H), 9.28 (s, 1H), 8.30 (s, 1H), 8.19-8.18 (m, 1H), 8.05 (d, J=8.4 Hz, 1H), 7.61-7.57 (m, 2H), 7.51 (s, 1H), 7.44-7.41 (m, 2H), 6.86 (d, J=8.4 Hz, 1H), 6.79-6.76 (m, 1H), 3.55 (s, 2H), 2.49 (s, 3H). MS (ESI): m/z 411 [M+1]$^+$ HPLC: 92.6%.

Example 142: 4-(3-Benzylphenyl)-7-methyl-8-(trifluoromethyl)-4,5-dihydro-1H-benzo[b][1,4]diazepin-2(3H)-one

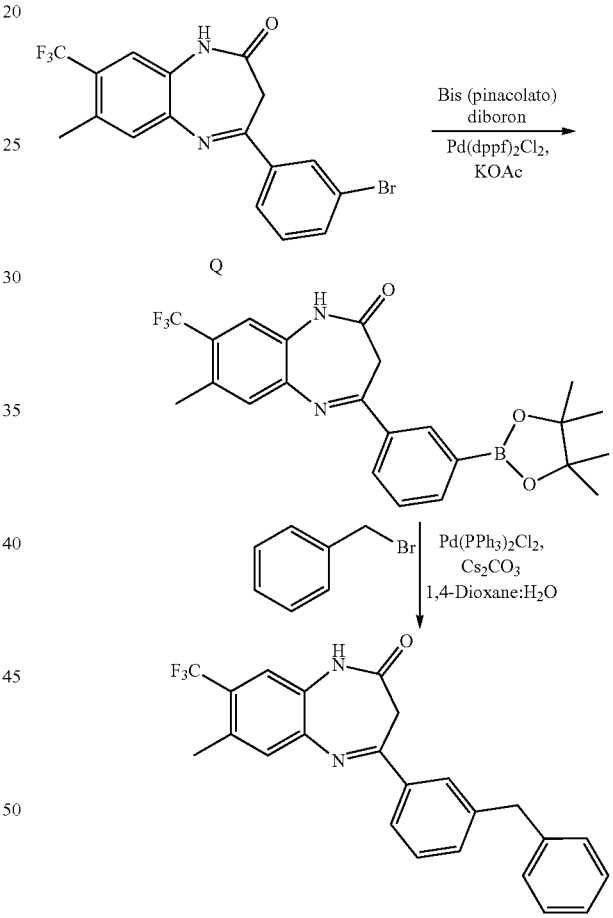

Step 1: 7-Methyl-4-(3-(4,4,5,5-tetramethyl-1,3,2-dioxaborolan-2-yl)phenyl)-8-(trifluoromethyl)-1H-benzo[b][1,4]diazepin-2(3H)-one Compound Q was converted to 7-methyl-4-(3-(4,4,5,5-tetramethyl-1,3,2-dioxaborolan-2-yl)phenyl)-8-(trifluoromethyl)-1H-benzo[b][1,4]diazepin-2(3H)-one by treatment in 1,4-dioxane (25 mL) under inert atmosphere with fused potassium acetate and bis(pinacolato)diboron then purged with argon for 10 min. Then Pd(dppf)$_2$Cl$_2$ was added and again degassed for another 15 min; heated to 100° C. and stirred for 3 h. The progress of the reaction was monitored by TLC. After completion of the reaction, the reaction mixture was diluted with water (20 mL) and extracted with EtOAc (2×25 mL). The combined organic extracts were washed with water (20 mL), dried over sodium sulfate, filtered and concentrated under reduced pressure to obtain the crude product. The crude product was purified by silica gel column chromatography.

Step 2: 4-(3-Benzylphenyl)-7-methyl-8-(trifluoromethyl)-4,5-dihydro-1H-benzo[b][1,4]diazepin-2(3H)-one To a stirred solution of 7-methyl-4-(3-(4,4,5,5-tetramethyl-1,3,2-dioxaborolan-2-yl)phenyl)-8-(trifluoromethyl)-1H-benzo[b][1,4]diazepin-2(3H)-one (100 mg, 0.22 mmol) in 1,4-dioxane:H$_2$O (11 mL, 4:1) were added benzyl bromide (38.5 mg, 0.22 mmol) and cesium carbonate (219.5 mg, 0.66 mmol) at RT and purged with argon for 30 min. Then Pd (PPh$_3$)$_2$Cl$_2$ (31.6 mg, 0.04 mmol) was added to the reaction mass and again purged for another 30 min. The reaction mixture was heated to 100° C. and stirred for 12 h. The progress of the reaction was monitored by TLC. After completion of the reaction, the reaction mixture was diluted with water (20 mL) and extracted with EtOAc (2×20 mL). The combined organic extracts were washed with water (20 mL), dried over sodium sulfate, filtered and concentrated under reduced pressure to obtain the crude product. The crude product was purified by silica gel column chromatography [Eluent: 5% EtOAc/Hexanes] to afford the title compound (10 mg, 11%) as a pale yellow solid. $^1$H NMR (500 MHz, DMSO-d$_6$): δ 10.63 (s, 1H), 7.97 (s, 1H), 7.88 (d, J=7.5 Hz, 1H), 7.48-7.44 (m, 4H), 7.30-7.26 (m, 4H), 7.20-7.17 (m, 1H), 4.04 (s, 2H), 3.56-3.54 (m, 2H), 2.43 (s, 3H). MS (ESI): m/z 409 [M+1]$^+$ HPLC: 93.2%.

Example 142A: 4-(3-Benzylphenyl)-7-methyl-8-(trifluoromethyl)-4,5-dihydro-1H-benzo[b][1,4]diazepin-2(3H)-one Enantiomer A; and Example 142B: 4-(3-Benzylphenyl)-7-methyl-8-(trifluoromethyl)-4,5-dihydro-1H-benzo[b][1,4]diazepin-2(3H)-one Enantiomer B Chiral preparative HPLC of Enantiomers: The enantiomers of Example 142 (40 mg, 0.09 mmol) were separated by normal-phase preparative high performance liquid chromatography (Chiralpak IA, 250×4.6 mm, 5 μm); (A) 0.1% DEA in n-hexane (B) DCM:MeOH (80:20) (A:B: 75:25; Flow rate: 1.0 mL/min) to obtain enantiomer A (5 mg) and enantiomer B (15 mg) as off-white solids.

Analytical data for enantiomer A: $^1$H NMR (400 MHz, DMSO-d$_6$): δ 9.56 (s, 1H), 7.36-7.10 (m, 9H), 6.81 (s, 1H), 6.55-6.54 (m, 1H), 4.91-4.89 (m, 1H), 4.14-4.12 (m, 1H), 3.92 (s, 2H), 2.81-2.76 (m, 1H), 2.68-2.64 (m, 1H), 2.26 (s, 3H). Chiral HPLC: 100% R$_t$=8.13 min (Chiralpak IA, 250×4.6 mm, 5μ); mobile phase (A) 0.1% DEA in n-Hexane (B) DCM:Methanol (80:20) (A:B: 75:25); flow Rate: 1.0 mL/min) MS (ESI): m/z 411 [M+1]$^+$ HPLC: 91.8%

Analytical data for enantiomer B: $^1$H NMR (400 MHz, DMSO-d$_6$): δ 9.56 (s, 1H), 7.28-7.10 (m, 9H), 6.81 (s, 1H), 6.55-6.54 (m, 1H), 4.91-4.89 (m, 1H), 4.14-4.12 (m, 1H), 3.92 (s, 2H), 2.81-2.76 (m, 1H), 2.68-2.64 (m, 1H), 2.26 (s, 3H). Chiral HPLC: 99.9% R$_t$=12.30 min (Chiralpak IA, 250×4.6 mm, 5μ); mobile phase (A) 0.1% DEA in n-Hexane (B) DCM:Methanol (80:20) (A:B: 75:25); flow Rate: 1.0 mL/min) MS (ESI): m/z 411 [M+1]$^+$ HPLC: 93.6%.

Example 143: 7-Methyl-4-(3-phenoxyphenyl)-8-(trifluoromethyl)-1H-benzo [b][1,4]diazepin-2 (3H)-one

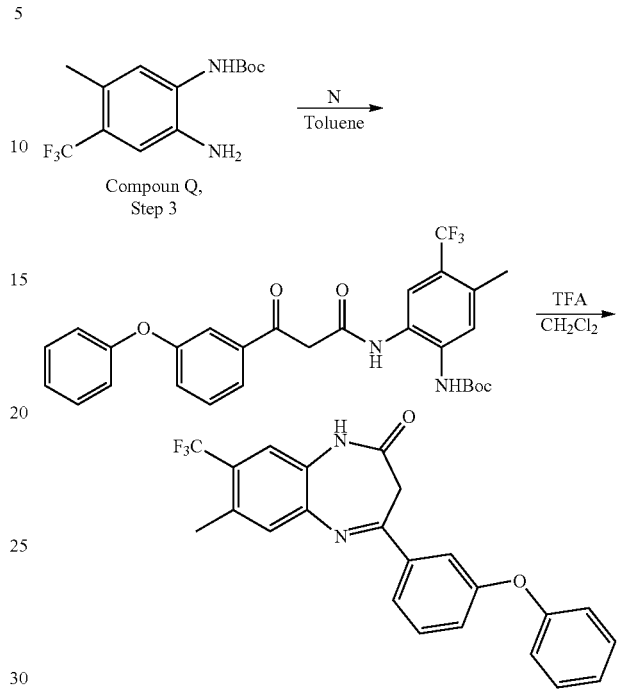

Step 1: tert-Butyl (5-methyl-2-(3-oxo-3-(3-phenoxyphenyl)propanamido)-4-(trifluoromethyl)phenyl) carbamate To a stirred solution of the compound from compound Q, Step 3 (200 mg, 0.68 mmol) in toluene (20 mL) under inert atmosphere was added compound N (186.2 mg, 0.68 mmol) at RT. The reaction mixture was heated to 120° C. and stirred for 12 h. The progress of the reaction was monitored by TLC. After completion of the reaction, the reaction mixture was diluted with water (30 mL) and extracted with ethyl acetate (2×25 mL). The combined organic extracts were washed with water (25 mL), dried over sodium sulfate, filtered and concentrated under reduced pressure to obtain the crude tert-butyl (5-methyl-2-(3-oxo-3-(3-phenoxyphenyl)propanamido)-4-(trifluoromethyl)phenyl)carbamate (500 mg) as a pale yellow solid.

Step 2: 7-Methyl-4-(3-phenoxyphenyl)-8-(trifluoromethyl)-1H-benzo [b][1,4]diazepin-2 (3H)-one To a stirred solution of tert-butyl (5-methyl-2-(3-oxo-3-(3-phenoxyphenyl) propanamido)-4-(trifluoromethyl) phenyl) carbamate (500 mg, crude) in CH$_2$Cl$_2$ (20 mL) under inert atmosphere was added TFA (1 mL) at 0° C. The reaction mixture was warmed to RT and stirred for 12 h. The progress of the reaction was monitored by TLC. After completion of the reaction, the reaction mixture was quenched with water (30 mL) and extracted with CH$_2$Cl$_2$ (3×25 mL). The combined organic extracts were washed with water (25 mL), dried over sodium sulfate, filtered and concentrated under reduced pressure to obtain the crude product. The crude product was purified by silica gel column chromatography [Eluent: 10-15% EtOAc/Hexanes] to afford the title compound (100 mg, 26%) as a pale yellow solid. $^1$H NMR (500 MHz, DMSO-$d_6$): δ 10.67 (s, 1H), 7.85-7.83 (m, 2H), 7.70 (s, 1H), 7.57 (t, J=8.0 Hz, 1H), 7.50 (s, 1H), 7.44-7.41 (m, 1H), 7.24-7.15 (m, 3H), 7.08-7.07 (m, 2H), 3.56-3.54 (m, 2H), 2.43 (s, 3H). MS (ESI): m/z 411 [M+1]$^+$ HPLC: 98.5%.

Example 144: 4-(3-(Benzyloxy)phenyl)-7-methyl-8-(trifluoromethyl)-1H-benzo[b][1,4]diazepin-2(3H)-one

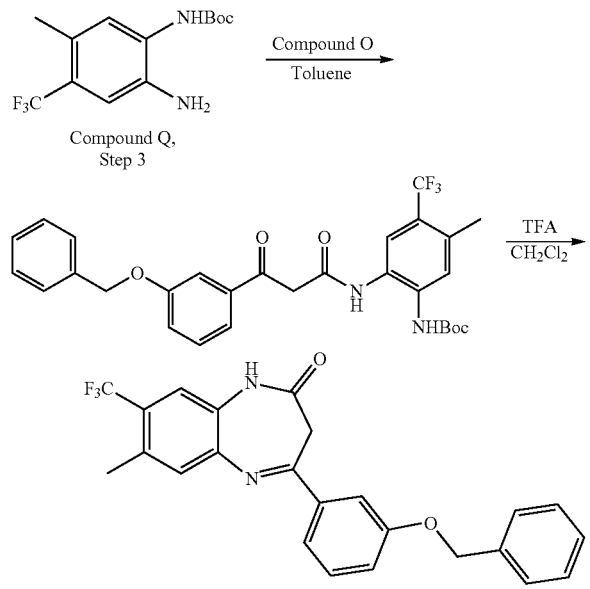

Step 1: tert-Butyl (2-(3-(3-(benzyloxy)phenyl)-3-oxopropanamido)-5-methyl-4-(trifluoromethyl)phenyl)carbamate To a stirred solution of the compound from compound Q, Step 3 (150 mg, 0.51 mmol) in toluene (10 mL) under inert atmosphere was added compound O (146.8 mg, 0.51 mmol) at RT. The reaction mixture was heated to 120° C. and stirred for 12 h. The progress of the reaction was monitored by TLC. After completion of the reaction, the volatiles were evaporated under reduced pressure to obtain the crude tert-butyl (2-(3-(3-(benzyloxy)phenyl)-3-oxopropanamido)-5-methyl-4-(trifluoromethyl)phenyl)carbamate (250 mg) as an off-white solid.

Step 2: 4-(3-(Benzyloxy)phenyl)-7-methyl-8-(trifluoromethyl)-1H-benzo[b][1,4]diazepin-2(3H)-one To a stirred solution of tert-butyl (2-(3-(3-(benzyloxy)phenyl)-3-oxopropanamido)-5-methyl-4-(trifluoromethyl)phenyl)carbamate (250 mg, crude) in CH$_2$Cl$_2$ (10 mL) under inert atmosphere was added TFA (2 mL) at 0° C. The reaction mixture was warmed to RT and stirred for 12 h. The progress of the reaction was monitored by TLC. After completion of the reaction, the reaction mixture was quenched with water (20 mL) and extracted with CH$_2$Cl$_2$ (3×20 mL). The combined organic extracts were washed with water (20 mL), dried over sodium sulfate, filtered and concentrated under reduced pressure to obtain the crude product. The crude product was purified by silica gel column chromatography [Eluent: 10% EtOAc/Hexanes] to afford the title compound (40 mg, 21%) as an off-white solid. $^1$H NMR (500 MHz, DMSO-$d_6$): δ 10.66 (s, 1H), 7.70 (s, 1H), 7.64 (d, J=7.5 Hz, 1H), 7.49-7.45 (m, 4H), 7.44-7.38 (m, 1H), 7.34-7.31 (m, 2H), 7.24-7.22 (m, 1H), 5.18 (s, 2H), 3.55 (s, 2H), 2.44 (s, 3H). MS (ESI): m/z 425 [M+1]$^+$ HPLC: 99.1%.

Example 145: 4-(3-(3-Bromophenoxy)phenyl)-7-methyl-8-(trifluoromethyl)-1H-benzo[b][1,4]diazepin-2(3H)-one

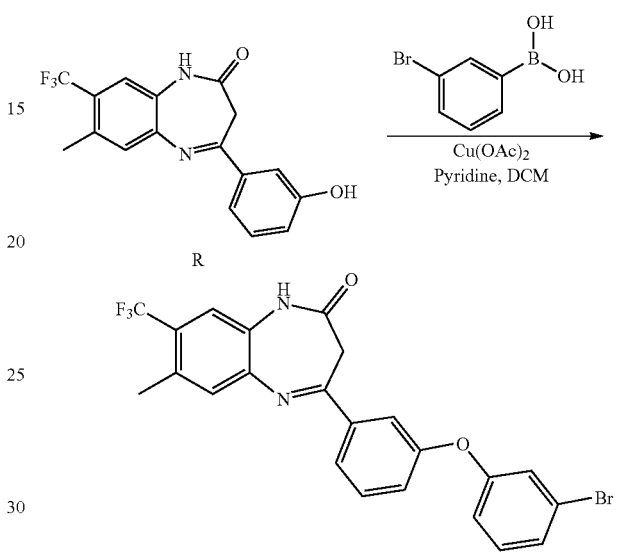

To a stirred solution of molecular sieves (1.5 g) in CH$_2$Cl$_2$ (20 mL) under inert atmosphere were added compound R (150 mg, 0.44 mmol), (3-bromophenyl) boronic acid (135.2 mg, 0.67 mmol), copper acetate (134.4 mg, 0.67 mmol) and pyridine (177.3 mg 2.24 mmol) at RT and stirred under O$_2$ atmosphere for 12 h. The progress of the reaction was monitored by TLC. After completion of the reaction, the reaction mixture was filtered under vacuum and the filtrate was concentrated under reduced pressure to obtain the crude product. The crude product was purified by silica gel column chromatography [Eluent: 8% EtOAc/Hexanes] to afford the title compound (100 mg, 46%) as a pale yellow solid. $^1$H NMR (400 MHz, DMSO-$d_6$): δ 10.69 (s, 1H), 7.89 (d, J=8.8 Hz, 1H), 7.75-7.55 (m, 1H), 7.61 (t, J=8.0 Hz, 1H), 7.50 (s, 1H), 7.45 (s, 1H), 7.38-7.36 (m, 2H), 7.30-7.28 (m, 2H), 7.08-7.05 (m, 1H), 3.58-3.56 (m, 2H), 2.50 (s, 3H). MS (ESI): m/z 490 [M+2]$^+$ HPLC: 98.6%.

Example 146: 4-(3-(3,5-difluorophenoxy)phenyl)-7-methyl-8-(trifluoromethyl)-1H-benzol[b][1,4]diazepin-2(3H)-one

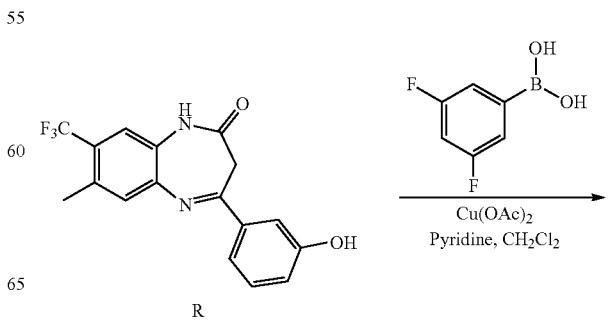

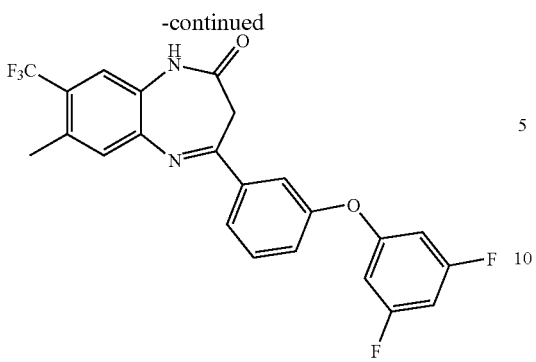

To a stirred solution of molecular sieves (2 g) in DCM (20 mL) under inert atmosphere were added compound R (200 mg, 0.59 mmol), (3,5-difluorophenyl)boronic acid (141.9 mg, 0.89 mmol), copper acetate (179.2 mg, 0.89 mmol) and pyridine (236.5 mg, 2.99 mmol) at RT and stirred under $O_2$ atmosphere for 15 h. The progress of the reaction was monitored by TLC. After completion of the reaction, the reaction mixture was filtered under vacuum and the filtrate was concentrated under reduced pressure to obtain the crude product. The crude product was purified by silica gel column chromatography [Eluent: 7% EtOAc/Hexanes] to afford the title compound (125 mg, 45%) as a pale yellow solid. $^1$H NMR (400 MHz, DMSO-$d_6$): δ 10.70 (s, 1H), 7.94 (d, J=8.0 Hz, 1H), 7.80 (s, 1H), 7.62 (t, J=8.4 Hz, 1H), 7.51-7.49 (m, 2H), 7.36 (d, J=8.0 Hz, 1H), 7.06-7.04 (m, 1H), 6.80 (d, J=7.5 Hz, 2H), 3.60 (s, 2H), 2.50 (s, 3H). MS (ESI): m/z 447 [M+1]$^+$ HPLC: 90.0%.

Example 147: 7-Methyl-8-(trifluoromethyl)-4-(3-(3-(trifluoromethyl)phenoxy)phenyl)-1H-benzo[b][1,4]diazepin-2(3H)-one

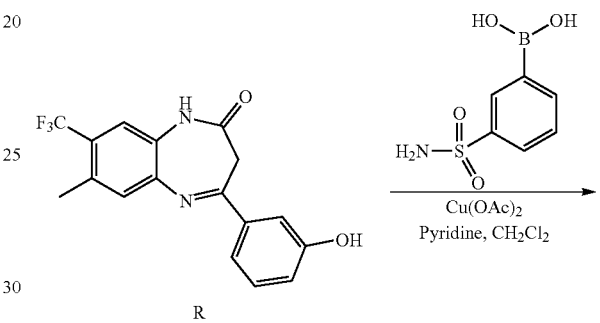

To a stirred solution of molecular sieves (1.5 g) in CH$_2$Cl$_2$ (20 mL) under inert atmosphere were added compound R (150 mg, 0.44 mmol), (3-(trifluoromethyl)phenyl)boronic acid (127.9 mg, 0.67 mmol), copper acetate (134.4 mg, 0.67 mmol) and pyridine (177.3 mg 2.24 mmol) at RT and stirred for 12 h under O$_2$ atmosphere. The progress of the reaction was monitored by TLC. After completion of the reaction, the reaction mixture was filtered under vacuum and the filtrate was concentrated under reduced pressure to obtain the crude product. The crude product was purified by silica gel column chromatography [Eluent: 8% EtOAc/Hexanes] to afford the title compound (100 mg, 47%) as a pale yellow solid. $^1$H NMR (400 MHz, DMSO-$d_6$): δ 10.69 (s, 1H), 7.92 (d, J=7.6 Hz, 1H), 7.79-7.78 (m, 1H), 7.67-7.60 (m, 2H), 7.54-7.50 (m, 2H), 7.42 (d, J=14.0 Hz, 2H), 7.36-7.31 (m, 2H), 3.58-3.56 (m, 2H), 2.50 (s, 3H). MS (ESI): m/z 479.4 [M+1]$^+$ HPLC: 97.7%.

Example 148: 4-(3-(7-Methyl-2-oxo-8-(trifluoromethyl)-2,3-dihydro-1H-benzo[b][1,4]diazepin-4-yl)phenoxy)benzenesulfonamide

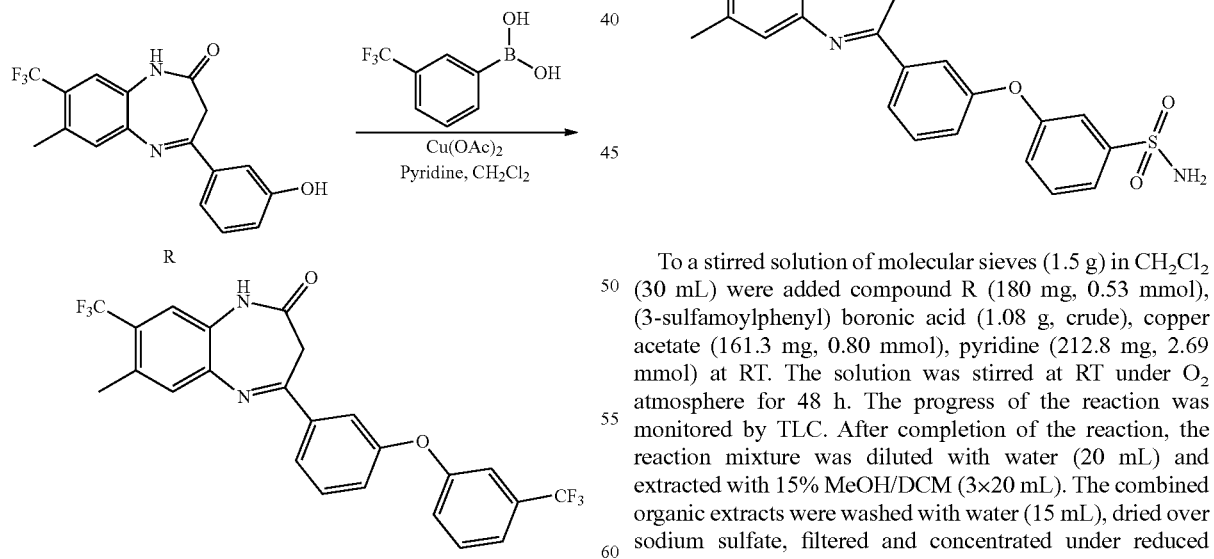

To a stirred solution of molecular sieves (1.5 g) in CH$_2$Cl$_2$ (30 mL) were added compound R (180 mg, 0.53 mmol), (3-sulfamoylphenyl) boronic acid (1.08 g, crude), copper acetate (161.3 mg, 0.80 mmol), pyridine (212.8 mg, 2.69 mmol) at RT. The solution was stirred at RT under O$_2$ atmosphere for 48 h. The progress of the reaction was monitored by TLC. After completion of the reaction, the reaction mixture was diluted with water (20 mL) and extracted with 15% MeOH/DCM (3×20 mL). The combined organic extracts were washed with water (15 mL), dried over sodium sulfate, filtered and concentrated under reduced pressure to obtain the crude product. The crude product was purified by silica gel column chromatography [Eluent: 3% MeOH/DCM] to afford the title compound (3.5 mg, 2%) as a brown color liquid. $^1$H NMR (400 MHz, CDCl$_3$): δ 7.98-7.96 (m, 2H), 7.75-7.67 (m, 2H), 7.56-7.50 (m, 3H), 7.39 (s, 1H), 7.33-7.28 (m, 2H), 7.21 (br s, 2H), 3.47 (s, 2H), 2.51 (s, 3H). MS (ESI): m/z 490 [M+1]$^+$ HPLC: 92.6%.

Example 149: 7-Methyl-4-(3-((2-(methylsulfonyl)pyrimidin-5-yl) oxy)phenyl)-8-(trifluoromethyl)-1H-benzo[b][1,4]diazepin-2(3H)-one

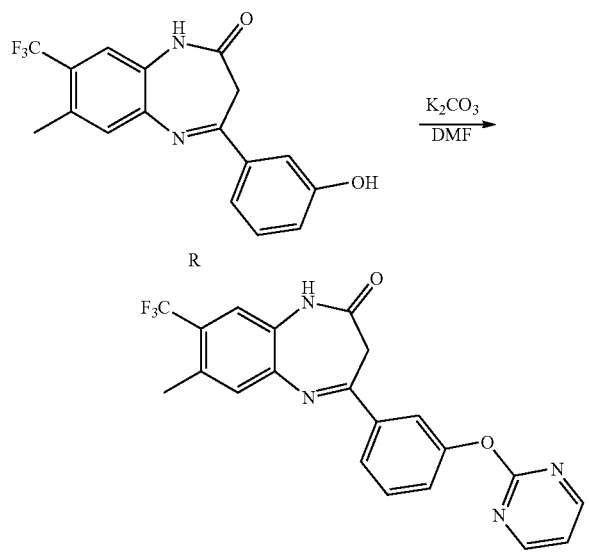

To a stirred solution of compound R (100 mg, 0.29 mmol) in DMF (10 mL) under inert atmosphere were added potassium carbonate (82.6 mg, 0.59 mmol) and 2-(methylsulfonyl) pyrimidine at 0° C. The reaction mixture was warmed to RT and stirred for 12 h. The progress of the reaction was monitored by TLC. After completion of the reaction, the reaction mixture was diluted with water (20 mL) and extracted with EtOAc (2×20 mL). The combined organic extracts were washed with water (15 mL), dried over sodium sulfate, filtered and concentrated under reduced pressure to obtain the crude product. The crude product was purified by silica gel column chromatography [Eluent: 50% EtOAc/Hexanes] to afford the title compound (75 mg, 61%) as a pale yellow solid. $^1$H NMR (500 MHz, DMSO-$d_6$): δ 10.68 (s, 1H), 8.66-8.65 (m, 2H), 7.96 (d, J=8.0 Hz, 1H), 7.87 (s, 1H), 7.60 (t, J=9.0 Hz, 1H), 7.49 (s, 1H), 7.45-7.43 (m, 2H), 7.30-7.28 (m, 1H), 3.58 (s, 1H), 2.43 (s, 3H). MS (ESI): m/z 413 [M+1]$^+$ HPLC: 90.3%.

Example 150: 7-Methyl-4-(3-(pyridin-2-yloxy)phenyl)-8-(trifluoromethyl)-1H-benzo [b][1,4]diazepin-2(3H)-one

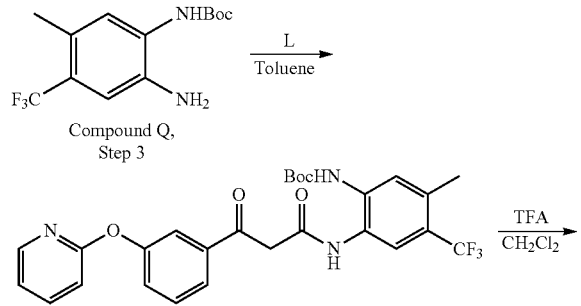

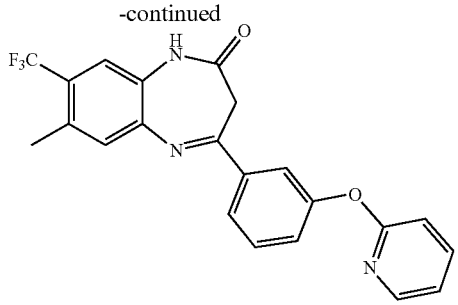

Step 1: tert-Butyl (5-methyl-2-(3-oxo-3-(3-(pyridin-2-yloxy)phenyl)propanamido)-4-(trifluoro methyl)phenyl)carbamate To a stirred solution of the compound from compound Q, Step 3 (315 mg, 1.08 mmol) in toluene (10 mL) under inert atmosphere was added compound L (310 mg, 1.08 mmol) at RT; heated to 120° C. and stirred for 12 h. The progress of the reaction was monitored by TLC. After completion of the reaction, the volatiles were evaporated under reduced pressure to obtain the crude product. The crude product was triturated with diethyl ether (2×10 mL) to afford tert-butyl (5-methyl-2-(3-oxo-3-(3-(pyridin-2-yloxy)phenyl)propanamido)-4-(trifluoro methyl)phenyl)carbamate (290 mg, 50%) as a colorless liquid. $^1$H NMR (500 MHz, DMSO-$d_6$): δ 9.84 (s, 1H), 9.73 (s, 1H), 8.67-8.66 (m, 1H), 8.13-8.12 (m, 1H), 7.88-7.86 (m, 2H), 7.81-7.80 (m, 1H), 7.61 (d, J=8.5 Hz, 1H), 7.46 (d, J=8.0 Hz, 1H), 7.37-7.27 (m, 1H), 7.16-7.09 (m, 1H), 7.06 (d, J=8.0 Hz, 1H), 4.20-4.13 (m, 2H), 2.38 (s, 3H), 1.48 (s, 9H).

Step 2: 7-Methyl-4-(3-(pyridin-2-yloxy) phenyl)-8-(trifluoromethyl)-1H-benzo [b][1,4]diazepin-2(3H)-one To a stirred solution of tert-butyl (5-methyl-2-(3-oxo-3-(3-(pyridin-2-yloxy)phenyl)propanamido)-4-(trifluoro methyl)phenyl)carbamate (26 mg, 0.049 mmol) in $CH_2Cl_2$ (2 mL) under inert atmosphere was added TFA (0.1 mL) at 0° C.; warmed to RT and stirred for 6 h. The progress of the reaction was monitored by TLC. After completion of the reaction, the reaction mixture was quenched with water (10 mL) and extracted with $CH_2Cl_2$ (3×10 mL). The combined organic extracts were washed with water (10 mL), dried over sodium sulfate, filtered and concentrated under reduced pressure to obtain the crude product. The crude product was triturated with diethyl ether (2×4 mL) to afford the title compound (13 mg, 65%) as an off-white solid. $^1$H NMR (500 MHz, DMSO-$d_6$): δ 10.68 (s, 1H), 8.15-8.14 (m, 1H), 7.92-7.87 (m, 2H), 7.80 (s, 1H), 7.59 (t, J=8.0 Hz, 1H), 7.49 (s, 1H), 7.44 (s, 1H), 7.34 (t, J=10.0 Hz, 1H), 7.16-7.10 (m, 2H), 3.56 (s, 2H), 2.43 (s, 3H). MS (ESI): m/z 412 [M+1]$^+$ HPLC: 96.1%.

Example 151: (±)-Methyl 3-(8-methyl-4-oxo-7-(trifluoromethyl)-2,3,4,5-tetrahydro-1H-benzo[b][1,4]diazepin-2-yl)benzoate (Racemate)

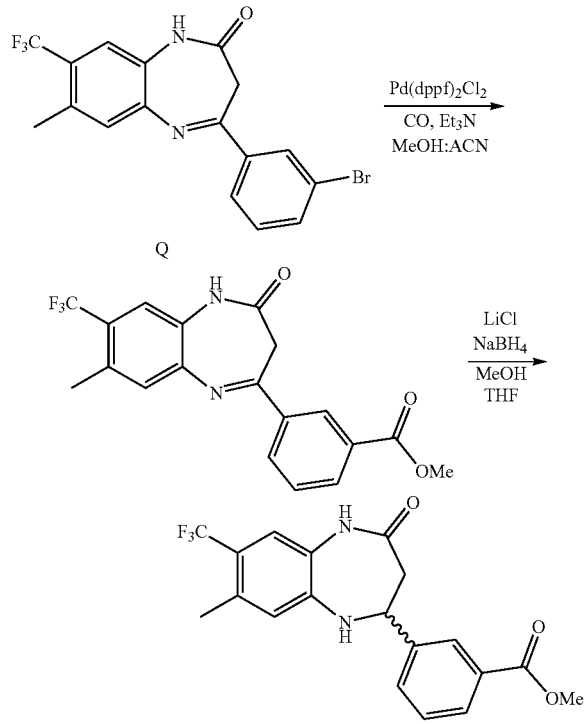

Step 1: Methyl 3-(7-methyl-2-oxo-8-(trifluoromethyl)-2,3-dihydro-1H-benzo[b][1,4]diazepin-4-yl)benzoate Compound Q (0.5 g, 1.26 mmol), MeOH:ACN (4:1, 20 mL), Et$_3$N (0.318 g, 3.14 mmol) and Pd(dppf)$_2$Cl$_2$ (0.184 g, 0.25 mmol) were mixed in a nitrogen-inerted pressure vessel steel bomb at RT. The reaction mixture was repeatedly purged with argon to remove residual air or oxygen. The steel bomb then vented and re-pressurized with carbon monoxide to 7 Bar absolute pressure and the mixture stirred at 80° C. for 48 h, maintaining the carbon monoxide pressure within the vessel at 7 Bar. After completion of reaction, the reaction mixture was cooled to ambient temperature, vented to atmospheric pressure and then filtered through a bed of celite to remove solids. The filtrate was then concentrated under reduced pressure and the obtained crude product was purified by silica gel column chromatography [eluent: 15% EtOAc/Hexane] to afford methyl 3-(7-methyl-2-oxo-8-(trifluoromethyl)-2,3-dihydro-1H-benzo[b][1,4]diazepin-4-yl)benzoate (0.25 g, 53%) as an off-white solid. $^1$H NMR (500 MHz, DMSO-d$_6$): δ 10.72 (bs, 1H), 8.65 (s, 1H), 8.34 (d, J=7.5 Hz, 1H), 8.15 (d, J=8.0 Hz, 1H), 7.72 (t, J=7.5 Hz, 1H), 7.52 (s, 2H), 3.91 (s, 3H), 3.62 (s, 2H), 2.46 (s, 3H). MS (ESI): m/z 377 [M+1]$^+$.

Step 2: (±)-Methyl 3-(8-methyl-4-oxo-7-(trifluoromethyl)-2,3,4,5-tetrahydro-1H-benzo[b][1,4]diazepin-2-yl)benzoate (Racemate)

To a stirred solution of LiCl (394 mg, 0.93 mmol) in MeOH (10 mL) was added NaBH$_4$ (30 mg, 0.79 mmol) at 0° C. under inert atmosphere. After being stirred for 15 min; a solution of compound methyl 3-(7-methyl-2-oxo-8-(trifluoromethyl)-2,3-dihydro-1H-benzo[b][1,4]diazepin-4-yl)benzoate (100 mg, 0.27 mmol) in THF (20 mL) was added drop wise to the reaction mixture and stirring was continued for another 5 min. After consumption of the starting material (by TLC), the reaction mixture was quenched with water (10 mL) and extracted with CH$_2$Cl$_2$ (2×100 mL). The combined organic extracts were dried over anhydrous Na$_2$SO$_4$ and concentrated under reduced pressure. The obtained crude material was purified by silica gel column chromatography [eluent: 25% EtOAc/Hexane] to afford the ester as a racemate (30 mg, 30%) as an off-white solid. $^1$H NMR (400 MHz, DMSO-d$_6$): δ 9.56 (bs, 1H), 8.00 (s, 1H), 7.86 (d, J=8.0 Hz, 1H), 7.66 (d, J=7.6 Hz, 1H), 7.50 (t, J=8.0 Hz, 1H), 7.16 (s, 1H), 6.85 (s, 1H), 6.72-6.71 (m, 1H), 5.10-5.09 (m, 1H), 3.84 (s, 3H), 2.81-2.78 (m, 2H), 2.28 (s, 3H).

Example 151A: (±)-Methyl 3-(8-methyl-4-oxo-7-(trifluoromethyl)-2,3,4,5-tetrahydro-1H-benzo[b][1,4]diazepin-2-yl)benzoate Enantiomer A; and
Example 151B: (−)-Methyl 3-(8-methyl-4-oxo-7-(trifluoromethyl)-2,3,4,5-tetrahydro-1H-benzo[b][1,4]diazepin-2-yl)benzoate Enantiomer B Chiral preparative HPLC of enantiomers: The enantiomers of Example 151 (30 mg, 0.079 mmol) were separated by normal-phase preparative high performance liquid chromatography (Chiralpak IA, 250×20 mm, 5µ; using (A) 0.1% TEA in n-hexane—(B) ethanol A:B: (85:15) as a mobile phase; Flow rate: 1.0 mL/min) to obtain (+) enantiomer (10.2 mg) and (−) enantiomer (8.4 mg).

Analytical data for (+) enantiomer: $^1$H NMR (400 MHz, DMSO-d$_6$): δ 9.56 (bs, 1H), 8.00 (s, 1H), 7.86 (d, J=8.0 Hz, 1H), 7.66 (d, J=7.6 Hz, 1H), 7.50 (t, J=8.0 Hz, 1H), 7.16 (s, 1H), 6.85 (s, 1H), 6.72-6.71 (m, 1H), 5.10-5.09 (m, 1H), 3.84 (s, 3H), 2.81-2.78 (m, 2H), 2.28 (s, 3H). Chiral HPLC: 100% R$_f$=14.89 min (Chiralpak IA, 250×4.6 mm, 5µ; mobile phase (A) 0.1% TEA in n-Hexane (B) ethanol A:B: (85:15); flow Rate: 1.00 mL/min). MS (ESI): m/z 379 [M+1]$^+$. HPLC: 99.2%. Optical rotation [α]$_D^{25}$: +24.56° (c 0.25, CHCl$_3$).

Analytical data for (−) enantiomer: $^1$H NMR (400 MHz, DMSO-d$_6$): δ 9.56 (bs, 1H), 8.00 (s, 1H), 7.86 (d, J=8.0 Hz, 1H), 7.66 (d, J=7.6 Hz, 1H), 7.50 (t, J=8.0 Hz, 1H), 7.16 (s, 1H), 6.85 (s, 1H), 6.72-6.71 (m, 1H), 5.10-5.09 (m, 1H), 3.84 (s, 3H), 2.81-2.78 (m, 2H), 2.28 (s, 3H). Chiral HPLC: 100% R$_f$=26.79 min (Chiralpak IA, 250×4.6 mm, 5µ; mobile phase (A) 0.1% TEA in n-Hexane (B) ethanol A:B: (85:15); flow Rate: 1.00 mL/min). MS (ESI): m/z 379 [M+1]$^+$. HPLC: 98.3%. Optical rotation [α]$_D^{25}$: −26.65° (c 0.25, CHCl$_3$).

Example 152: Ethyl 3-(3-((E)-7-methyl-2-oxo-8-(trifluoromethyl)-2,3-dihydro-1H-benzo[b][1,4]diazepin-4-yl)phenyl)acrylate

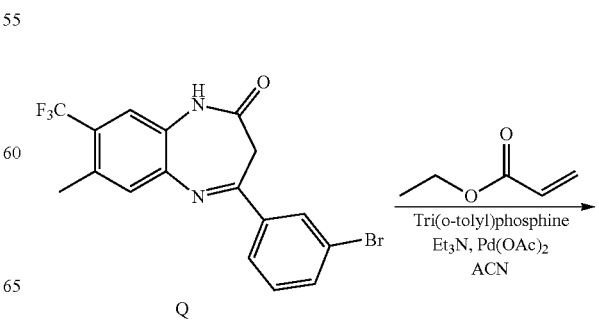

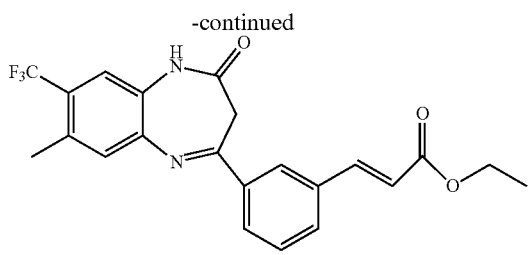

Compound Q (0.3 g, 0.75 mmol), ACN (15 mL), tri(o-tolyl)phosphine (0.045 g, 0.15 mmol), ethyl acrylate (0.252 g, 2.54 mmol) and Et$_3$N (0.303 g, 3.02 mmol) were mixed in a microwave vessel at RT. The reaction mixture was degassed with argon for 15 min, Pd(OAc)$_2$ (0.017 g, 0.07 mmol) was added at RT and again degassed for another 15 min. The resulting reaction mixture was heated in a microwave at 90° C. for 1 h. After consumption of starting material (by TLC), the volatiles were evaporated under reduced pressure. The obtained crude material was purified by silica gel column chromatography [eluent: 15% EtOAc/Hexane] to afford the title compound (0.2 g, 63.4%) as a white solid. $^1$H NMR (500 MHz, DMSO-d$_6$): δ 10.69 (bs, 1H), 8.38 (s, 1H), 8.12 (d, J=7.5 Hz, 1H), 7.95 (d, J=7.0 Hz, 1H), 7.77-7.74 (m, 1H), 7.60 (t, J=7.5 Hz, 1H), 7.50 (d, J=9.0 Hz, 2H), 6.79 (d, J=16.0 Hz, 1H), 4.22 (q, 2H), 3.66 (s, 2H), 2.46 (s, 3H), 1.28 (t, J=6.5 Hz, 3H). MS (ESI): 418 [M+1]$^+$.

Example 153: Ethyl 3-(3-(8-methyl-4-oxo-7-(trifluoromethyl)-2,3,4,5-tetrahydro-1H-benzo[b][1,4]diazepin-2-yl)phenyl)propanoate (Racemate)

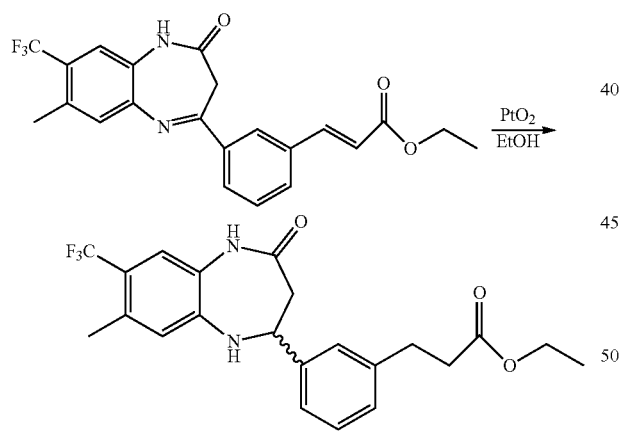

To a stirred solution of ethyl 3-(3-((E)-7-methyl-2-oxo-8-(trifluoromethyl)-2,3-dihydro-1H-benzo[b][1,4]diazepin-4-yl)phenyl)acrylate (Example 152) (30 mg, 0.07 mmol) in EtOH (5 mL) was added catalytic amount of platinum oxide at RT under inert atmosphere. The resulting reaction mixture was agitated for 3 h under H$_2$ atmosphere (balloon pressure) at RT; progress of the reaction was monitored by TLC. The reaction mixture was then filtered through a celite pad and the filtrate was concentrated under reduced pressure. The crude material was purified by silica gel column chromatography [eluent: 25% EtOAc/Hexane] to afford the title compound (15 mg, 49.6%) as a white solid. $^1$H NMR (400 MHz, DMSO-d$_6$): δ 9.56 (bs, 1H), 7.25-7.11 (m, 5H), 6.85 (s, 1H), 6.55-6.54 (m, 1H), 4.91-4.89 (m, 1H), 4.03 (q, 2H), 2.85-2.81 (m, 3H), 2.78-2.76 (m, 1H), 2.68-2.67 (m, 2H), 2.27 (s, 3H), 1.14 (t, J=7.0 Hz, 3H). Mass: m/z 421 [M+1]$^+$.

Example 153A: Ethyl 3-(3-(8-methyl-4-oxo-7-(trifluoromethyl)-2,3,4,5-tetrahydro-1H-benzo[b][1,4]diazepin-2-yl)phenyl)propanoate Enantiomer A; and Example 153B: Ethyl 3-(3-(8-methyl-4-oxo-7-(trifluoromethyl)-2,3,4,5-tetrahydro-1H-benzo[b][1,4]diazepin-2-yl)phenyl)propanoate Enantiomer B Chiral preparative HPLC of Enantiomers: The enantiomers of Example 153 (15 mg, 0.34 mmol) were separated by normal-phase preparative high performance liquid chromatography (Chiralpak IA, 250×4.6 mm, 5µ; using (A) 0.1% DEA in n-hexane (B) EtOH (A:B: 70:30) as a mobile phase; Flow rate: 1.0 mL/min) to obtain enantiomer A (5.48 min RT) (4.7 mg) and enantiomer B (7.72 min RT) (5.1 mg).

Analytical data for enantiomer A: $^1$H NMR (400 MHz, DMSO-d$_6$): δ 9.56 (bs, 1H), 7.25-7.11 (m, 5H), 6.85 (s, 1H), 6.55-6.54 (m, 1H), 4.91-4.89 (m, 1H), 4.03 (q, 2H), 2.85-2.81 (m, 3H), 2.78-2.76 (m, 1H), 2.68-2.67 (m, 2H), 2.27 (s, 3H), 1.14 (t, J=7.0 Hz, 3H). Mass: m/z 421 [M+1]$^+$. HPLC purity: 90.9%. Chiral HPLC: 100% at R$_t$=5.48 min (Chiralpak IA, 250×4.6 mm, 5µ; mobile phase (A) 0.1% DEA in n-Hexane (B) Ethanol (A:B: 70:30); flow Rate: 1.00 mL/min).

Analytical data for enantiomer B: $^1$H NMR (400 MHz, DMSO-d$_6$): δ 9.55 (bs, 1H), 7.24-7.10 (m, 5H), 6.84 (s, 1H), 6.54-6.53 (m, 1H), 4.90-4.88 (m, 1H), 4.02 (q, 2H), 2.82-2.80 (m, 3H), 2.59-2.57 (m, 3H), 2.26 (s, 3H), 1.14 (t, J=7.0 Hz, 3H). Mass: m/z 421 [M+1]$^+$. HPLC purity: 98.6%. Chiral HPLC: 100% at R$_t$=7.72 min (Chiralpak IA, 250×4.6 mm, 5µ; mobile phase (A) 0.1% DEA in n-Hexane (B) Ethanol (A:B: 70:30); flow Rate: 1.00 mL/min).

Example 154: 4-(3-(3-Hydroxypropyl)phenyl)-7-methyl-8-(trifluoromethyl)-4,5-dihydro-1H-benzo[b][1,4]diazepin-2(3H)-one (Racemate)

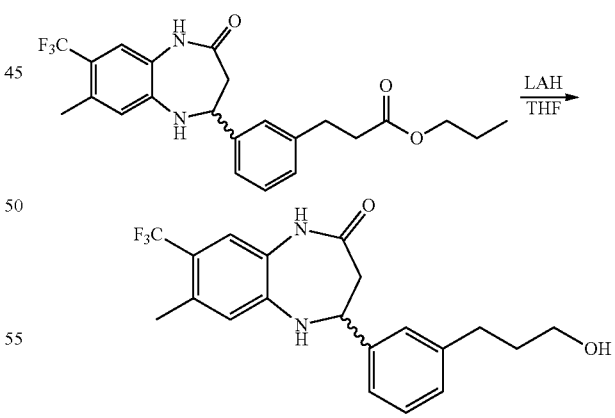

To a stirred solution of LAH (10.8 mg, 0.28 mmol) in THF (1.0 mL) was added ethyl 3-(3-(8-methyl-4-oxo-7-(trifluoromethyl)-2,3,4,5-tetrahydro-1H-benzo[b][1,4]diazepin-2-yl)phenyl)propanoate (Example 153) (50 mg, 0.12 mmol) at 0° C. under inert atmosphere. The resulting reaction mixture was stirred for 2 h at RT; progress of the reaction was monitored by TLC. The reaction mixture was then quenched with saturated NH$_4$Cl (20 mL) and extracted with EtOAc (2×15 mL). The combined organic extracts were dried over anhydrous Na$_2$SO$_4$ and concentrated under reduced pressure to obtain the crude product. The crude material was purified by silica gel column chromatography (eluent: 50% EtOAc/Hexane) to obtain the title compound (35 mg, 78%) as an off-white solid. $^1$H NMR (500 MHz, DMSO-d$_6$): δ 9.56 (bs, 1H), 7.50-7.16 (m, 4H), 7.10 (d, J=7.0 Hz, 1H), 6.84 (s, 1H), 6.56 (s, 1H), 4.91-4.90 (m, 1H), 4.44 (bs, 1H), 3.41 (t, J=6.0 Hz, 2H), 2.81-2.77 (m, 1H), 2.72-2.63 (m, 1H), 2.60-2.57 (m, 2H), 2.27 (s, 3H), 1.72-1.66 (m, 2H). LCMS: m/z 379 [M+1]$^+$ at 3.40 RT (96.8% purity). HPLC: 97.1%.

Example 154A: 4-(3-(3-Hydroxypropyl)phenyl)-7-methyl-8-(trifluoromethyl)-4,5-dihydro-1H-benzo[b][1,4]diazepin-2(3H)-one Enantiomer A; and Example 154B: 4-(3-(3-Hydroxypropyl)phenyl)-7-methyl-8-(trifluoromethyl)-4,5-dihydro-1H-benzo[b][1,4]diazepin-2(3H)-one Enantiomer B Chiral preparative HPLC of enantiomers: The enantiomers of Example 154 (35 mg, 0.092 mmol) were separated by normal-phase preparative high performance liquid chromatography (Chiralpak IA, 250×4.6 mm, 5μ; mobile phase (A) n-Hexane (B) DCM:MeOH:THF: A:B:C (60:20:20) A:B: (70:30); flow Rate: 1.0 mL/min) to obtain enantiomer A (10 mg) and enantiomer B (10 mg).

Analytical data for enantiomer A: $^1$H NMR (500 MHz, DMSO-d$_6$): δ 9.56 (bs, 1H), 7.50-7.16 (m, 4H), 7.10 (d, J=7.0 Hz, 1H), 6.84 (s, 1H), 6.56 (s, 1H), 4.91-4.90 (m, 1H), 4.44-4.43 (m, 1H), 3.41 (t, J=6.0 Hz, 2H), 2.81-2.77 (m, 1H), 2.72-2.63 (m, 1H), 2.60-2.57 (m, 2H), 2.27 (s, 3H), 1.72-1.66 (m, 2H). Mass: m/z 379.3 [M+1]$^+$. HPLC: 90%. Chiral HPLC: 99.5% at R$_t$=7.87 min (Chiralpak IA, 250×4.6 mm, 5μ; mobile phase (A) n-Hexane (B) DCM:MeOH:THF: A:B:C (60:20:20) (A:B: 70:30); flow Rate: 1.00 mL/min).

Analytical data for enantiomer B: $^1$H NMR (500 MHz, DMSO-d$_6$): δ 9.56 (bs, 1H), 7.50-7.16 (m, 4H), 7.10 (d, J=7.0 Hz, 1H), 6.84 (s, 1H), 6.56 (s, 1H), 4.91-4.90 (m, 1H), 4.44-4.43 (m, 1H), 3.41 (t, J=6.0 Hz, 2H), 2.81-2.77 (m, 1H), 2.72-2.63 (m, 1H), 2.60-2.57 (m, 2H), 2.27 (s, 3H), 1.72-1.66 (m, 2H). Mass: m/z 379.4 [M+1]$^+$. HPLC: 82.4%. Chiral HPLC: 100% at R$_t$=10.10 min (Chiralpak IA, 250×4.6 mm, 5μ; mobile phase (A) n-Hexane (B) DCM:MeOH:THF: A:B:C (60:20:20) (A:B: 70:30); flow Rate: 1.00 mL/min).

Example 155: 3-(3-(8-methyl-4-oxo-7-(trifluoromethyl)-2,3,4,5-tetrahydro-1H-benzo[b][1,4]diazepin-2-yl)phenyl)propanoic Acid (Racemate)

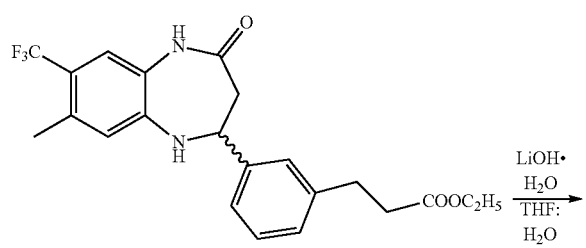

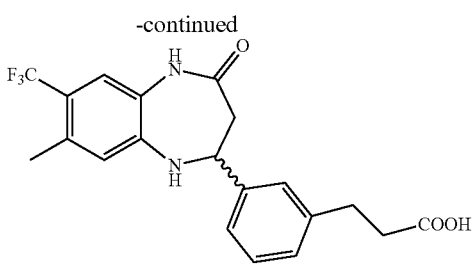

To a stirred solution of ethyl 3-(3-(8-methyl-4-oxo-7-(trifluoromethyl)-2,3,4,5-tetrahydro-1H-benzo[b][1,4]diazepin-2-yl)phenyl)propanoate (Example 153) (75 mg, 0.17 mmol) in THF (10 mL) was added a solution of LiOH.H$_2$O (37.5 mg, 0.89 mmol) in H$_2$O (2 mL) at RT and stirred for 12 h. The progress of the reaction was monitored by TLC. The reaction mixture was diluted with water (20 mL), acidified to pH~6 using saturated citric acid solution and extracted with EtOAc (3×25 mL). The combined organic extracts were dried over anhydrous Na$_2$SO$_4$ and concentrated under reduced pressure to obtain the crude product. The crude material was triturated with diethyl ether (5 mL) to afford the title compound (55 mg, 78.6%) as an off-white solid. $^1$H NMR (500 MHz, DMSO-d$_6$): δ 12.10 (bs, 1H), 9.57 (bs, 1H), 7.25-7.12 (m, 5H), 6.85 (s, 1H), 6.54 (s, 1H), 4.90 (d, J=7.0 Hz, 1H), 2.82-2.77 (m, 3H), 2.67-2.64 (m, 1H), 2.53-2.50 (m, 2H), 2.27 (s, 3H). LCMS: m/z 393.2 [M+1]$^+$ at 3.23 RT (97.6% purity). HPLC: 99.5%.

Example 155A: 3-(3-(8-methyl-4-oxo-7-(trifluoromethyl)-2,3,4,5-tetrahydro-1H-benzo[b][1,4]diazepin-2-yl)phenyl)propanoic acid (Enantiomer A); and Example 155B: 3-(3-(8-methyl-4-oxo-7-(trifluoromethyl)-2,3,4,5-tetrahydro-1H-benzo[b][1,4]diazepin-2-yl)phenyl)propanoic acid (Enantiomer B)

Chiral preparative HPLC of Enantiomers: The enantiomers of Example 155 (55 mg, 0.14 mmol) were separated by normal-phase preparative high performance liquid chromatography (Chiralpak IA, 250×4.6 mm, 5μ; using (A) 0.1% TFA in n-hexane—(B) DCM:MeOH:THF (60:20:20) (A:B: 80:20) as a mobile phase; Flow rate: 1.0 mL/min) to obtain enantiomer A (15 mg) and enantiomer B (15 mg).

Analytical data for enantiomer A: $^1$H NMR (500 MHz, DMSO-d$_6$): δ 12.10 (bs, 1H), 9.57 (bs, 1H), 7.25-7.12 (m, 5H), 6.85 (s, 1H), 6.54 (s, 1H), 4.90 (d, J=7.0 Hz, 1H), 2.82-2.77 (m, 3H), 2.67-2.64 (m, 1H), 2.53-2.50 (m, 2H), 2.27 (s, 3H). Mass: m/z 393.4 [M+1]$^+$. HPLC: 92.3%. Chiral HPLC: 96.9% at R$_t$=7.77 min (Chiralpak IA, 250×4.6 mm, 5μ; mobile phase (A) n-Hexane (B) DCM:MeOH:THF: A:B:C (60:20:20) (A:B: 70:30); flow Rate: 1.00 mL/min).

Analytical data for enantiomer B: $^1$H NMR (500 MHz, DMSO-d$_6$): δ 12.10 (bs, 1H), 9.57 (bs, 1H), 7.25-7.12 (m, 5H), 6.85 (s, 1H), 6.54 (s, 1H), 4.90 (d, J=7.0 Hz, 1H), 2.82-2.77 (m, 3H), 2.67-2.64 (m, 1H), 2.53-2.50 (m, 2H), 2.27 (s, 3H). Mass: m/z 393.4 [M+1]$^+$. HPLC: 82.3%. Chiral HPLC: 99.8% at R$_t$=9.86 min (Chiralpak IA, 250×4.6 mm, 5μ; mobile phase (A) n-Hexane (B) DCM:MeOH:THF: A:B:C (60:20:20) (A:B: 70:30); flow Rate: 1.00 mL/min).

Example 156: 4-(3-(2,6-Dimethylpyridin-4-yl)phenyl)-7-methyl-8-(trifluoromethyl)-4,5-dihydro-1H-benzo[b][1,4]diazepin-2(3H)-one (Racemate)

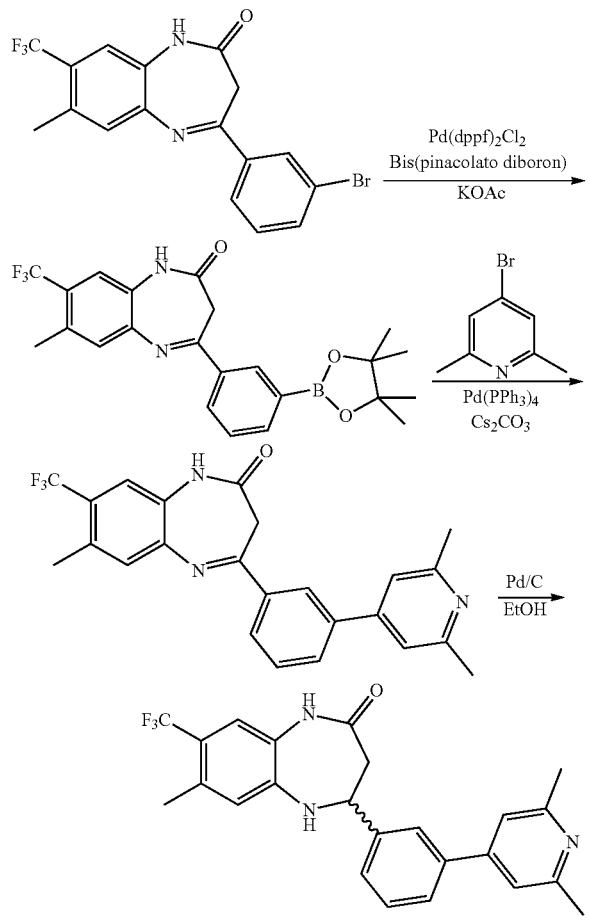

Step 1: 7-Methyl-4-(3-(4,4,5,5-tetramethyl-1,3,2-dioxaborolan-2-yl)phenyl)-8-(trifluoromethyl)-1H-benzo[b][1,4]diazepin-2(3H)-one To a stirred solution of compound Q (0.5 g, 1.25 mmol) in 1,4-dioxane (25 mL) were added bis (pinacolato diboron) (0.38 g, 1.51 mmol) and KOAc (0.37 g, 3.77 mmol). The reaction mixture was degassed with argon for 15 min and was added Pd(dppf)$_2$Cl$_2$ (0.092 g, 0.012 mmol) and again degassed for another 15 min at RT. The resulting reaction mixture was heated to 110° C. and stirred for 12 h. After consumption of the starting material (by TLC), the reaction mixture was filtered through celite bed and the obtained filtrate was dried over anhydrous Na$_2$SO$_4$ and concentrated under reduced pressure. The crude material was purified by silica gel column chromatography eluting with 5% EtOAc/Hexane to afford 7-methyl-4-(3-(4,4,5,5-tetramethyl-1,3,2-dioxaborolan-2-yl)phenyl)-8-(trifluoromethyl)-1H-benzo[b][1,4]diazepin-2(3H)-one (450 mg, 80.5%) as an off-white solid. $^1$H NMR (400 MHz, DMSO-d$_6$): δ 10.70 (bs, 1H), 8.38 (s, 1H), 8.19 (d, J=7.5 Hz, 1H), 7.85 (d, J=7.2 Hz, 1H), 7.57 (t, J=7.0 Hz, 1H), 7.51 (s, 2H), 3.58 (2, 2H), 2.46 (s, 3H), 1.34 (s, 12H). MS (ESI): m/z 445 [M+1]$^+$. HPLC: 85.2%.

Step 2: 4-(3-(2,6-Dimethylpyridin-4-yl)phenyl)-7-methyl-8-(trifluoromethyl)-1H-benzo[b][1,4]diazepin-2(3H)-one To a stirred solution of 7-methyl-4-(3-(4,4,5,5-tetramethyl-1,3,2-dioxaborolan-2-yl)phenyl)-8-(trifluoromethyl)-1H-benzo[b][1,4]diazepin-2(3H)-one (0.23 g, 0.52 mmol) in 1,4-dioxane:EtOH:H$_2$O (10 mL, 4:2:1) were added 4-bromo-2,6-dimethylpyridine (0.096 g, 0.52 mmol) and Cs$_2$CO$_3$ (0.50 g, 1.55 mmol). The reaction mixture was degassed with argon for 15 min and was added Pd(PPh$_3$)$_4$ (0.059 g, 0.05 mmol) and again degassed for another 15 min at RT. The resulting reaction mixture was heated to 100° C. and stirred for 12 h. After consumption of the starting material (by TLC), the reaction mixture was filtered through celite bed and the obtained filtrate was dried over anhydrous Na$_2$SO$_4$ and concentrated under reduced pressure. The crude material was triturated with EtOAc (5 mL) to afford 4-(3-(2,6-dimethylpyridin-4-yl)phenyl)-7-methyl-8-(trifluoromethyl)-1H-benzo[b][1,4]diazepin-2(3H)-one (62 mg, 28.4%) as a brown solid. $^1$H NMR (500 MHz, DMSO-d$_6$): δ 10.70 (bs, 1H), 8.39 (s, 1H), 8.15 (d, J=7.5 Hz, 1H), 7.96 (d, J=7.5 Hz, 1H), 7.70-7.62 (m, 2H), 7.52-7.49 (m, 2H), 7.45 (s, 1H), 3.68 (s, 2H), 2.51 (s, 6H), 2.46 (s, 3H). MS (ESI): m/z 424 [M+1]$^+$.

Step 3: 4-(3-(2,6-Dimethylpyridin-4-yl)phenyl)-7-methyl-8-(trifluoromethyl)-4,5-dihydro-1H-benzo[b][1,4]diazepin-2(3H)-one (Racemate)

To a solution of 4-(3-(2,6-dimethylpyridin-4-yl)phenyl)-7-methyl-8-(trifluoromethyl)-1H-benzo[b][1,4]diazepin-2(3H)-one (32 mg, 0.075 mmol) in ethanol (10 mL) was added 10% Pd/C (5 mg) at RT under N$_2$ atmosphere. The resulting reaction mixture was agitated for 4 h under H$_2$ atmosphere (balloon pressure) at RT; progress of the reaction was monitored by TLC. The reaction mixture was filtered through a pad of celite and then the filtrate was concentrated under vacuum. The crude material was purified by column chromatography to afford the title compound (15 mg, 46.8%) as an off-white solid. $^1$H NMR (400 MHz, DMSO-d$_6$): δ 9.60 (bs, 1H), 7.76 (s, 1H), 7.65 (d, J=7.2 Hz, 1H), 7.50-7.46 (m, 2H), 7.33 (s, 2H), 7.18 (s, 1H), 6.89 (s, 1H), 6.65-6.64 (m, 1H), 5.06-5.04 (m, 1H), 2.92-2.87 (m, 1H), 2.79-2.74 (m, 1H), 2.50 (s, 6H), 2.28 (s, 3H). HPLC: 91.8%. MS (ESI): m/z 426.4 [M+1]$^+$.

Example 156A: 4-(3-(2,6-Dimethylpyridin-4-yl)phenyl)-7-methyl-8-(trifluoromethyl)-4,5-dihydro-1H-benzo[b][1,4]diazepin-2(3H)-one (Enantiomer A); and Example 156B: 4-(3-(2,6-Dimethylpyridin-4-yl)phenyl)-7-methyl-8-(trifluoromethyl)-4,5-dihydro-1H-benzo[b][1,4]diazepin-2(3H)-one (Enantiomer B)

Chiral preparative HPLC of Enantiomers: The enantiomers of Example 156 (15 mg, 0.035 mmol) were separated by normal-phase preparative high performance liquid chromatography (Chiralpak IA, 250×4.6 mm, 5µ; mobile phase (A) 0.1% DEA in n-Hexane (B) ethanol A:B (85:15); flow Rate: 1.00 mL/min) to obtain enantiomer A (4.7 mg) and enantiomer B (5.1 mg).

Analytical data for enantiomer A: $^1$H NMR (400 MHz, DMSO-d$_6$): δ 9.60 (bs, 1H), 7.76 (s, 1H), 7.65 (d, J=7.2 Hz, 1H), 7.50-7.46 (m, 2H), 7.33 (s, 2H), 7.18 (s, 1H), 6.89 (s, 1H), 6.65-6.64 (m, 1H), 5.06-5.04 (m, 1H), 2.92-2.87 (m, 1H), 2.79-2.74 (m, 1H), 2.50 (s, 6H), 2.28 (s, 3H). Chiral HPLC: 100% R$_f$=12.17 min (Chiralpak IA, 250×4.6 mm, 5µ; mobile phase (A) 0.1% DEA in n-Hexane (B) ethanol A:B (85:15); flow Rate: 1.00 mL/min). MS (ESI): m/z 426.4 [M+1]$^+$. HPLC: 85.4%

Analytical data for enantiomer B: $^1$H NMR (400 MHz, DMSO-d$_6$): δ 9.60 (bs, 1H), 7.76 (s, 1H), 7.65 (d, J=7.2 Hz, 1H), 7.50-7.46 (m, 2H), 7.33 (s, 2H), 7.18 (s, 1H), 6.89 (s, 1H), 6.65-6.64 (m, 1H), 5.06-5.04 (m, 1H), 2.92-2.87 (m, 1H), 2.79-2.74 (m, 1H), 2.50 (s, 6H), 2.28 (s, 3H). Chiral HPLC: 99.9% R$_f$=16.70 min (Chiralpak IA, 250×4.6 mm, 5µ; mobile phase (A) 0.1% DEA in n-Hexane (B) ethanol A:B (85:15); flow Rate: 1.00 mL/min). MS (ESI): m/z 426.5 [M+1]$^+$. HPLC: 98.5%.

Example 157: Benzyl (4-(3-bromophenyl)-2-oxo-2,3-dihydro-1H-benzo[b][1,4]diazepin-8-yl)carbamate

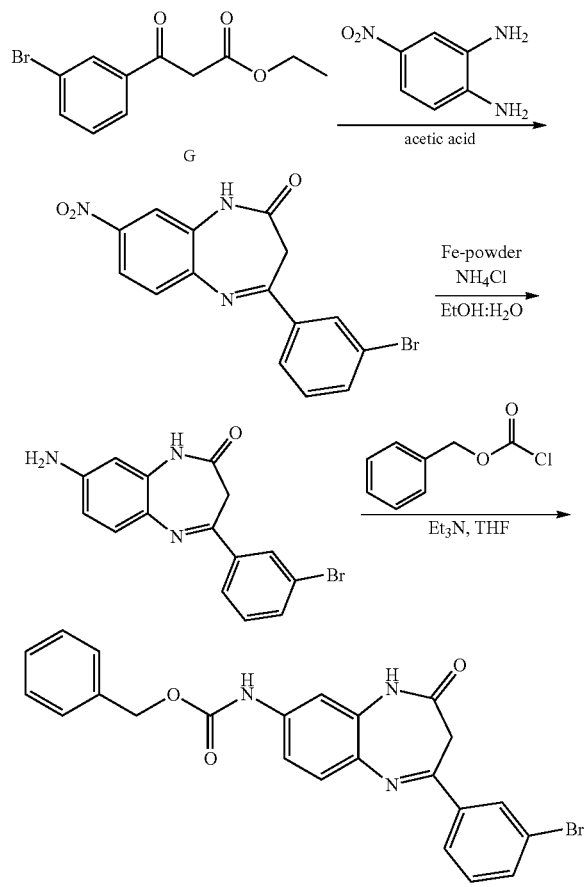

Step 1: 4-(3-bromophenyl)-8-nitro-1H-benzo[b][1,4]diazepin-2(3H)-one

To a stirred solution of 4-nitrobenzene-1,2-diamine (1) (1.0 g, 6.53 mmol) in acetic acid (20 mL) was added ethyl 3-(3-bromophenyl)-3-oxopropanoate (A) (1.75 g, 6.53 mmol) at RT under inert atmosphere. The resulting reaction mixture was heated to 110° C. and stirred for 12 h. After complete consumption of the starting material (by TLC), the reaction mixture was cooled to RT and diluted with water (100 mL) and extracted with EtOAc (3×50 mL). The combined organic extracts were dried over anhydrous Na$_2$SO$_4$ and concentrated under reduced pressure and the obtained crude product was purified by silica gel column chromatography (eluent: 25% EtOAc/Hexane) to afford 4-(3-bromophenyl)-8-nitro-1H-benzo[b][1,4]diazepin-2(3H)-one (0.91 g, 39.5%) as a yellow solid. $^1$H NMR (500 MHz, DMSO-d$_6$): δ 10.91 (bs, 1H), 8.25 (s, 1H), 8.09-8.01 (m, 3H), 7.82 (d, J=6.4 Hz, 1H), 7.68 (d, J=7.6 Hz, 1H), 7.57-7.48 (m, 1H), 3.67 (s, 2H). MS (ESI): 361 [M+1]$^+$.

Step 2: 8-Amino-4-(3-bromophenyl)-1H-benzo[b][1,4]diazepin-2(3H)-one

To a stirred solution of 4-(3-bromophenyl)-8-nitro-1H-benzo[b][1,4]diazepin-2(3H)-one (0.1 g, 0.27 mmol) in EtOH:H$_2$O (10 mL, 6:3) was added Fe-powder (0.076 g, 1.39 mmol) followed by NH$_4$Cl (0.037 g, 0.70 mmol) at RT. The resulting reaction mixture was heated to 90° C. and stirred for 1 h; progress of the reaction was monitored by TLC. The reaction mixture was then cooled to RT; the reaction mixture was filtered and the obtained filtrate was concentrated under reduced pressure. The residue was diluted with water (10 mL) and then extracted with EtOAc (2×10 mL). The combined organic extracts were dried over anhydrous Na$_2$SO$_4$ and concentrated under reduced pressure to afford 8-amino-4-(3-bromophenyl)-1H-benzo[b][1,4]diazepin-2(3H)-one (35 mg, 38%) as a yellow solid. $^1$H NMR (400 MHz, DMSO-d$_6$): δ 10.32 (bs, 1H), 8.15-8.13 (m, 1H), 7.97 (d, J=7.6 Hz, 1H), 7.69 (d, J=7.2 Hz, 1H), 7.48 (d, J=7.6 Hz, 1H), 7.12 (d, J=8.8 Hz, 1H), 6.52 (d, J=8.4 Hz, 1H), 6.32 (s, 1H), 5.48 (bs, 2H), 3.42 (s, 2H). Mass: m/z 331 [M+1]$^+$.

Step 3: Benzyl (4-(3-bromophenyl)-2-oxo-2,3-dihydro-1H-benzo[b][1,4]diazepin-8-yl)carbamate To a stirred solution of 8-amino-4-(3-bromophenyl)-1H-benzo[b][1,4]diazepin-2(3H)-one (50 mg, 0.15 mmol) in THF (5 mL) was added Et$_3$N (0.031 mL, 0.22 mmol) followed by benzyl chloroformate (1.06 mL, 0.18 mmol) at 0° C. under inert atmosphere. The resulting reaction mixture was allowed to warm to RT and stirred for 12 h. After complete consumption of the starting material (by TLC), the reaction mixture was diluted with water and extracted with EtOAc. The combined organic extracts were washed with water, dried over anhydrous Na$_2$SO$_4$ and concentrated under reduced pressure. The obtained crude material was purified by silica gel column chromatography [eluent: 35% EtOAc/hexane] to afford the title compound (15 mg, 21.4%) as an off-white solid. $^1$H NMR (400 MHz, DMSO-d$_6$): δ 10.60 (bs, 1H), 10.00 (bs, 1H), 8.18 (s, 1H), 8.02 (d, J=7.6 Hz, 1H), 7.74 (d, J=7.6 Hz, 1H), 7.51-7.28 (m, 9H), 5.18 (s, 2H), 3.49 (s, 2H). MS (ESI): 466 [M+1]$^+$. HPLC: 87.6%.

Example 158: Benzyl (2-(3-bromophenyl)-4-oxo-2,3,4,5-tetrahydro-1H-benzo[b][1,4]diazepin-7-yl) carbamate (Racemate))

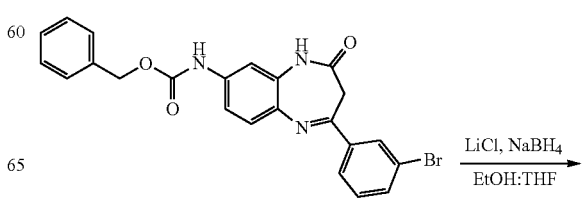

-continued

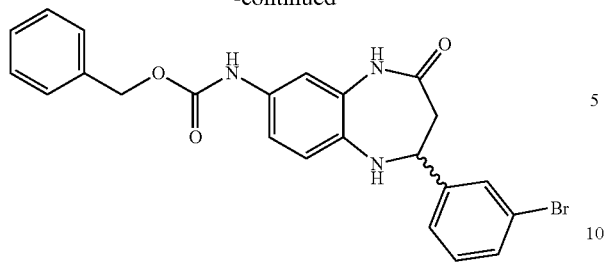

To a stirred solution of LiCl (19 mg, 0.45 mmol) in EtOH (3 mL) was added NaBH$_4$ (17 mg, 0.45 mmol) at 0° C. under inert atmosphere. After being stirred for 45 min at RT; a solution of benzyl (4-(3-bromophenyl)-2-oxo-2,3-dihydro-1H-benzo[b][1,4]diazepin-8-yl)carbamate (Example 157) (70 mg, 0.15 mmol) in THF (10 mL) at 0° C. was added dropwise to the reaction mixture and stirring was continued for another 5 min. The resulting reaction mixture was allowed to warm to RT and stirred for 48 h. After consumption of the starting material (by TLC), the reaction mixture was diluted with water and extracted with EtOAc. The combined organic extracts were washed with water, dried over anhydrous Na$_2$SO$_4$ and concentrated under reduced pressure. The crude material was purified by silica gel column chromatography [eluent: 35% EtOAc/hexane] to afford the title compound (15 mg, 21%) as a pale brown solid. $^1$H NMR (400 MHz, DMSO-d$_6$): δ 9.57 (bs, 2H), 7.62 (s, 1H), 7.46-7.28 (m, 8H), 7.12 (s, 1H), 7.03 (d, J=6.8 Hz, 1H), 6.87 (d, J=8.4 Hz, 1H), 5.54 (bs, 1H), 5.12 (s, 2H), 4.92-4.90 (m, 1H), 2.65-2.62 (m, 1H), 2.45-2.41 (m, 1H). HPLC: 90.7%. MS (ESI): m/z 466.3 [M+1]$^+$.

Example 159: 8-Bromo-4-(2-chloropyridin-4-yl)-4,5-dihydro-1H-benzo[b][1,4]diazepin-2(3H)-one (Racemate)

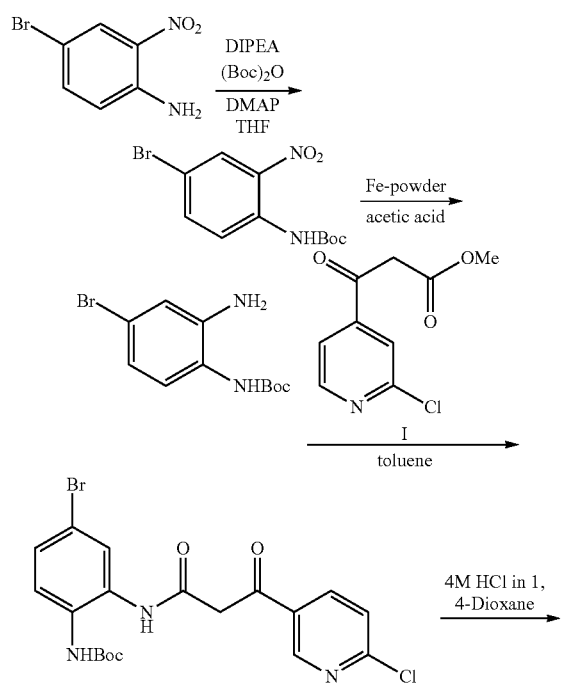

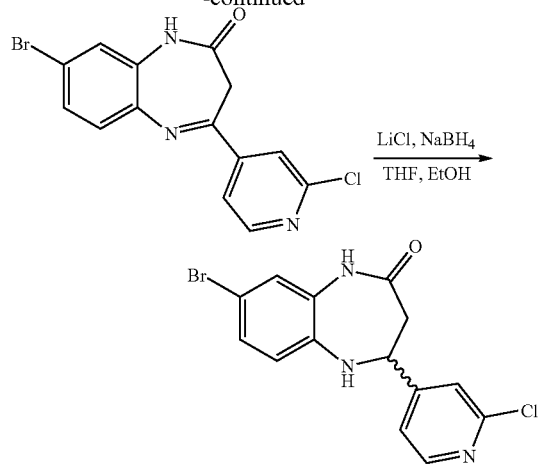

Step 1: Tert-Butyl (4-bromo-2-nitrophenyl)carbamate

To a stirred solution of 4-bromo-2-nitroaniline (10 g, 46.08 mmol) in THF (300 mL) was added DIPEA (24.1 mL, 138.24 mmol) followed by Boc-anhydride (10.6 mL, 46.1 mmol) at −10° C. under inert atmosphere. After being stirred for 10 min at −10° C.; DMAP (28.1 g, 23.01 mmol) was added portion wise to the above solution and continued stirring for further 15 min at −10° C. Then Boc-anhydride (20.1 mL, 92.2 mmol) was added again to the reaction mixture at −10° C. and stirred for 10 min. The resulting reaction mixture was allowed to warm to RT and stirred for 15 min; progress of the reaction was monitored by TLC. The reaction mixture was then cooled to 0° C.; diluted with water and extracted with EtOAc. The combined organic extracts were washed with citric acid, dried over anhydrous Na$_2$SO$_4$ and concentrated under reduced pressure to afford tert-butyl (4-bromo-2-nitrophenyl)carbamate (15.4 g, 96%) as a yellow solid. This was used in the next step without further purification. $^1$H NMR (500 MHz, CDCl$_3$): δ 8.27-8.17 (m, 1H), 7.78-7.74 (m, 1H), 7.28-7.18 (m, 1H), 1.4 (s, 9H). MS (ESI): m/z 318 [M+1]$^+$.

Step 2: Synthesis of tert-Butyl (2-amino-4-bromophenyl)carbamate

To a stirred solution of tert-butyl (4-bromo-2-nitrophenyl)carbamate (1.0 g, 3.15 mmol) in acetic acid (8 mL) was added Fe-powder (0.53 g, 9.46 mmol) at RT under inert atmosphere and resulting reaction mixture was stirred for 30 min at reflux temperature; progress of the reaction was monitored by TLC. The reaction mixture was allowed to cool to RT, filtered through a pad of celite and the filtrate was concentrated under reduced pressure to obtain the crude product. The crude material was purified by silica gel column chromatography to afford tert-butyl (2-amino-4-bromophenyl)carbamate (0.11 g, 12%) as a pale yellow solid. $^1$H NMR (400 MHz, CDCl$_3$): δ 7.14 (d, J=8.4 Hz, 1H), 6.91-6.87 (m, 2H), 6.09 (bs, 1H), 3.78 (bs, 2H), 1.50 (s, 9H). Mass: m/z 288 [M+1]$^+$ Step 3: tert-Butyl (4-bromo-2-(3-(2-chloropyridin-4-yl)-3-oxopropanamido)phenyl)carbamate A mixture of tert-butyl (2-amino-4-bromophenyl)carbamate (0.3 g, 1.04 mmol) and methyl 3-(2-chloropyridin-4-yl)-

3-oxopropanoate (compound I) (0.268 g, 1.25 mmol) in toluene (15 mL) was stirred for 48 h at reflux temperature; progress of the reaction was monitored by TLC. The reaction mixture was allowed to cool to RT; the reaction mixture was concentrated under reduced pressure to obtain the crude product. The crude material was purified by silica gel column chromatography to afford tert-butyl (4-bromo-2-(3-(2-chloropyridin-4-yl)-3-oxopropanamido)phenyl)carbamate as a mixture with its enolic form (0.2 g, 41%) as a solid. $^1$H NMR (400 MHz, DMSO-$d_6$): δ 13.96 (bs, 1H), 9.74-9.73 (m, 1H), 8.72-8.67 (m, 1H), 8.58-8.53 (m, 1H), 7.87-7.86 (m, 1H), 7.73-7.66 (m, 2H), 7.56-7.49 (m, 1H), 7.36-7.31 (m, 1H), 6.33 (s, 1H), 4.27 (s, 1H), 1.47 (s, 9H). LCMS: m/z 468.3 [M+1]$^+$ at 3.94 RT.

Step 4: 8-Bromo-4-(2-chloropyridin-4-yl)-1H-benzo[b][1,4]diazepin-2(3H)-one

A solution of tert-butyl (4-bromo-2-(3-(2-chloropyridin-4-yl)-3-oxopropanamido)phenyl)carbamate (0.2 g, 0.43 mmol) in 4M HCl in 1,4-dioxane (2.5 mL) was stirred at RT for 36 h. After consumption of the starting material (by TLC), the reaction mixture was poured into water, basified with saturated NaHCO$_3$ solution and extracted with EtOAc. The combined organic extracts were dried over anhydrous Na$_2$SO$_4$ and concentrated under reduced pressure to obtain the crude product. The crude material was purified by silica gel column chromatography to afford 8-bromo-4-(2-chloropyridin-4-yl)-1H-benzo[b][1,4]diazepin-2(3H)-one (0.12 g, 81%) as a solid. $^1$H NMR (400 MHz, DMSO-$d_6$): δ 10.77 (bs, 1H), 8.60 (d, J=5.2 Hz, 1H), 8.01 (s, 1H), 7.96-7.95 (m, 1H), 7.43-7.39 (m, 3H), 3.59 (s, 2H). LCMS: m/z 348 [M−1] at 3.60 RT. HPLC: 99.6%.

Step 5: 8-Bromo-4-(2-chloropyridin-4-yl)-4,5-dihydro-1H-benzo[b][1,4]diazepin-2(3H)-one (Racemate)

To a stirred solution of LiCl (27 mg, 0.64 mmol) in EtOH (1 mL) was added NaBH$_4$ (25 mg, 0.64 mmol) at 0° C. under inert atmosphere. After being stirred for 30 min at RT; a solution of 8-bromo-4-(2-chloropyridin-4-yl)-1H-benzo[b][1,4]diazepin-2(3H)-one (75 mg, 0.21 mmol) in THF (1 mL) at 0° C. was added drop wise to the reaction mixture and stirring was continued for another 16 h at RT. After consumption of the starting material (by TLC), the reaction mixture was quenched with water (10 mL) and extracted with CH$_2$Cl$_2$ (2×100 mL). The combined organic extracts were dried over anhydrous Na$_2$SO$_4$ and concentrated under reduced pressure. The obtained crude material was purified by silica gel column chromatography [eluent: 35% EtOAc/Hexane] to afford the racemic chloropyridine (25 mg, 33.3%) as an off-white solid. $^1$H NMR (400 MHz, DMSO-$d_6$): δ 9.64 (bs, 1H), 8.37 (d, J=5.2 Hz, 1H), 7.52 (s, 1H), 7.44 (d, J=3.6 Hz, 1H), 7.12-7.09 (m, 1H), 7.04-7.03 (m, 1H), 6.87 (d, J=8.8 Hz, 1H), 6.21-6.20 (m, 1H), 5.04-5.02 (m, 1H), 2.84-2.80 (m, 1H), 2.70-2.64 (m, 1H). MS (ESI): m/z 350.1 [M]$^+$. HPLC: 96.1%.

Example 159A: (−)-8-Bromo-4-(2-chloropyridin-4-yl)-4,5-dihydro-1H-benzo[b][1,4]diazepin-2(3H)-one (Enantiomer A); and Example 159B: (+)-8-Bromo-4-(2-chloropyridin-4-yl)-4,5-dihydro-1H-benzo[b][1,4]diazepin-2(3H)-one (Enantiomer B)

Chiral preparative HPLC of Enantiomers: The enantiomers of Example 159 (25 mg, 0.07 mmol) were separated by normal-phase preparative high performance liquid chromatography (Chiralpak IC, 250×4.6 mm, 5μ; using (A) 0.1% DEA in n-hexane—(B) ethanol A:B: (70:30) as a mobile phase; Flow rate: 1.0 mL/min) to obtain enantiomer A (6.4 mg) and enantiomer B (7.4 mg).

Analytical data for Enantiomer A: $^1$H NMR (400 MHz, DMSO-$d_6$): δ 9.64 (bs, 1H), 8.37 (d, J=5.2 Hz, 1H), 7.52 (s, 1H), 7.44 (d, J=3.6 Hz, 1H), 7.12-7.09 (m, 1H), 7.04-7.03 (m, 1H), 6.87 (d, J=8.8 Hz, 1H), 6.21-6.20 (m, 1H), 5.04-5.02 (m, 1H), 2.84-2.80 (m, 1H), 2.70-2.64 (m, 1H). Chiral HPLC: 100% R$_t$=14.75 min (Chiralpak IC, 250×4.6 mm, 5μ; using (A) 0.1% DEA in n-hexane—(B) ethanol A:B: (70:30) as a mobile phase; Flow rate: 1.0 mL/min). MS (ESI): m/z 350.1 [M]$^+$. HPLC: 99.8%. Optical rotation [α]$_D^{25}$: −10.64° (c 0.1, acetone).

Analytical data for Enantiomer B: $^1$H NMR (400 MHz, DMSO-$d_6$): δ 9.64 (bs, 1H), 8.37 (d, J=5.2 Hz, 1H), 7.52 (s, 1H), 7.44 (d, J=3.6 Hz, 1H), 7.12-7.09 (m, 1H), 7.04-7.03 (m, 1H), 6.87 (d, J=8.8 Hz, 1H), 6.21-6.20 (m, 1H), 5.04-5.02 (m, 1H), 2.84-2.80 (m, 1H), 2.70-2.64 (m, 1H). Chiral HPLC: 100% R$_t$=9.50 min (Chiralpak IC, 250×4.6 mm, 5μ; using (A) 0.1% DEA in n-hexane—(B) ethanol A:B: (70:30) as a mobile phase; Flow rate: 1.0 mL/min). MS (ESI): m/z 350.1 [M]$^+$. HPLC: 99.8%. Optical rotation [α]$_D^{25}$: +21.44° (c 0.1, acetone).

Example 160: 2-(2-Cyanopyridin-4-yl)-4-oxo-2,3,4,5-tetrahydro-1-benzo[b][1,4]diazepine-7-carboxylic Acid (Racemate)

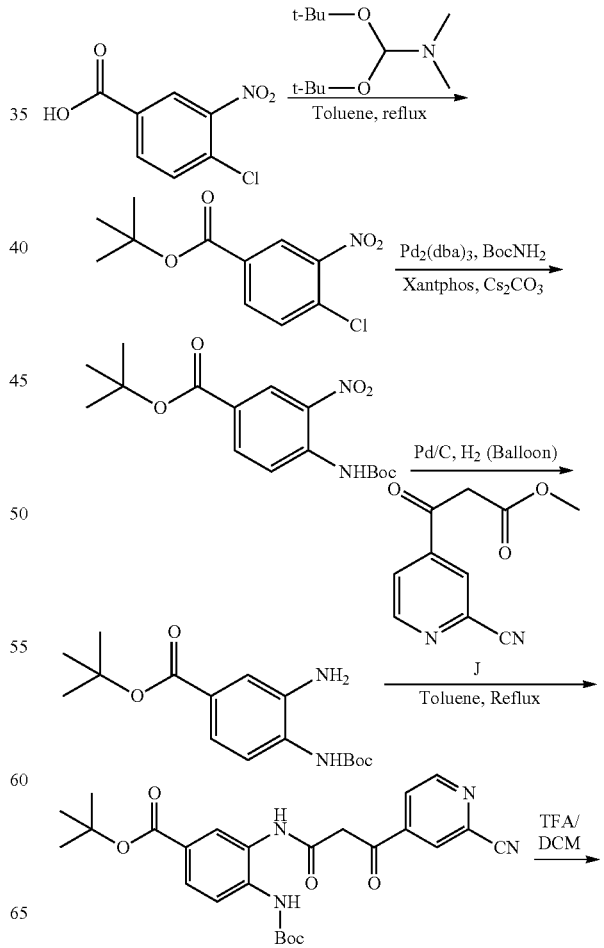

-continued

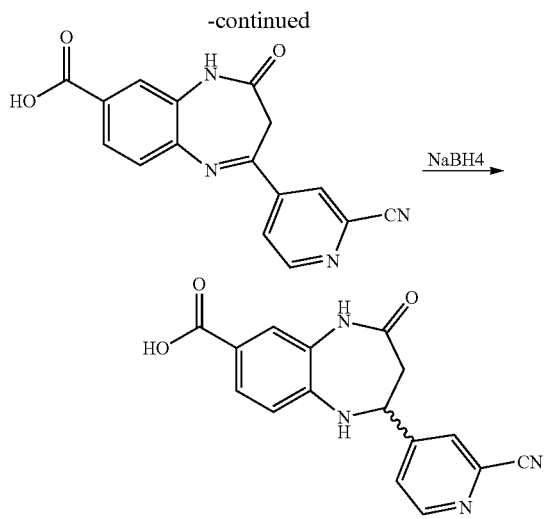

Step 1: tert-Butyl 4-chloro-3-nitrobenzoate

To a solution of 4-chloro-3-nitrobenzoic acid (5 g, 24.8 mmol) in toluene (100 mL) was added 1,1-di-tert-butoxy-N,N-dimethylmethanamine (20 mL) dropwise over 30 mins. The mixture was heated at reflux for 1 h. After completion of the reaction, the mixture was cooled down. The mixture washed with water (100 mL), saturated $NaHCO_3$ (100 mL) and brine (100 mL). The organic layer was dried over $Na_2SO_4$, concentrated and purified by column separation to give the desired product, tert-butyl 4-chloro-3-nitrobenzoate (4.6 g, yield: 71.8%).

Step 2: tert-Butyl 4-(tert-butoxycarbonylamino)-3-nitrobenzoate

To the solution of tert-butyl 4-chloro-3-nitrobenzoate (4.5 g, 17.5 mmol) in Dioxane (100 mL) was added $NH_2Boc$ (8.2 g, 70.0 mmol), $Pd_2(dba)_3$ (1.4 g, 1.75 mmol), X-phos (833 mg, 1.75 mmol) and $Cs_2CO_3$ (11.4 mg, 35.0 mmol). The mixture was heated under an atmosphere of $N_2$ at 80° C. for 5 hrs. After removal of the solvent, the residue was extracted with $EtOAc/H_2O$ (200 mL). The organic layer was dried over $Na_2SO_4$, concentrated and purified by column separation to give tert-butyl 4-(tert-butoxycarbonylamino)-3-nitrobenzoate (2.3 g, yield: 39.0%).

Step 3: tert-Butyl 3-amino-4-(tert-butoxycarbonylamino)benzoate

To the solution of tert-butyl 4-(tert-butoxycarbonylamino)-3-nitrobenzoate (2.0 g, 6.47 mmol) in MeOH (130 mL) was added Pd/C (400 mg). The mixture was stirred under an atmosphere of $H_2$ (50 Psi) at 25° C. for 12 h. After completion of the reaction, the mixture was filtered and dried to give tert-butyl 3-amino-4-(tert-butoxycarbonylamino)benzoate (1.8 g, yield: 90.0%). $^1H$ NMR (400 MHz, DMSO-$d_6$): δ 8.46 (s, 1H), 7.46 (d, J=8.4 Hz, 1H), 7.25 (d, J=2.0 Hz, 1H), 7.08-7.10 (m, 1H), 5.10 (s, 2H), 1.51 (s, 9H), 1.47 (s, 9H). LC/MS: 253.1.

Step 4: tert-Butyl 4-(tert-butoxycarbonylamino)-3-(3-(2-cyanopyridin-4-yl)-3-oxopropanamido)benzoate To the solution of compound J (170 mg, 0.83 mmol) in toluene (10 mL) was added tert-butyl 3-amino-4-(tert-butoxycarbonylamino)benzoate (281 mg, 0.91 mmol). The mixture was heated at reflux for 16 hrs. The solvent was removed to give tert-butyl 4-(tert-butoxycarbonylamino)-3-(3-(2-cyanopyridin-4-yl)-3-oxopropanamido)benzoate (200 mg) which was used directly to the next step without further purification.

Step 5: 4-(2-Cyanopyridin-4-yl)-2-oxo-2,3-dihydro-1H-benzo[b][1,4]diazepine-8-carboxylic Acid To the solution of tert-butyl 4-(tert-butoxycarbonylamino)-3-(3-(2-cyanopyridin-4-yl)-3-oxopropanamido)benzoate (180 mg, 0.37 mmol) in DCM (10 mL) was added TFA (2 mL). The mixture was stirred at room temperature for 2 h. After removal of the solvent, the residue was washed with MeOH (10 mL) to give the crude product which was purified by Prep-HPLC to give 4-(2-cyanopyridin-4-yl)-2-oxo-2,3-dihydro-1H-benzo[b][1,4]diazepine-8-carboxylic acid (50 mg, 44%). $^1H$ NMR (400 MHz, DMSO-$d_6$): δ 10.86 (s, 1H), 8.96 (d, J=4.8 Hz, 1H), 8.58 (s, 1H), 8.30 (d, J=5.2 Hz, 1H), 7.85 (s, 1H), 7.79 (d, J=8.4 Hz, 1H), 7.54 (d, J=8.4 Hz, 1H), 3.66 (s, 2H). LC/MS: 307.0 (M+1).

Step 6: 2-(2-Cyanopyridin-4-yl)-4-oxo-2,3,4,5-tetrahydro-1H-benzo[b][1,4]diazepine-7-carboxylic Acid (Racemate)

To the solution of 4-(2-cyanopyridin-4-yl)-2-oxo-2,3-dihydro-1H-benzo[b][1,4]diazepine-8-carboxylic acid (150 mg, 0.49 mmol) in MeOH (5 mL) was added $NaBH_4$ (72 mg, 1.96 mmol) at 0° C. The mixture was stirred at 25° C. for 5 h. After removal of the solvent, the residue was purified by HPLC to give the title compound as a solid (40 mg, 26%). $^1H$ NMR (400 MHz, DMSO-$d_6$): δ 9.66 (s, 1H), 8.74 (d, J=5.2 Hz, 1H), 8.05 (s, 1H), 7.77 (d, J=5.2 Hz, 1H), 7.53 (s, 1H), 7.51 (s, 1H), 6.93 (d, J=8.8 Hz, 1H), 6.84 (d, J=4.8 Hz, 1H), 5.19-5.15 (m, 1H), 2.98-2.78 (m, 3H). LC/MS: 309.1 (M+1).

Example 161: 2-(3-Cyanophenyl)-4-oxo-2,3,4,5-tetrahydro-1H-benzo[b][1,4]diazepine-7-carboxylic Acid (Racemate)

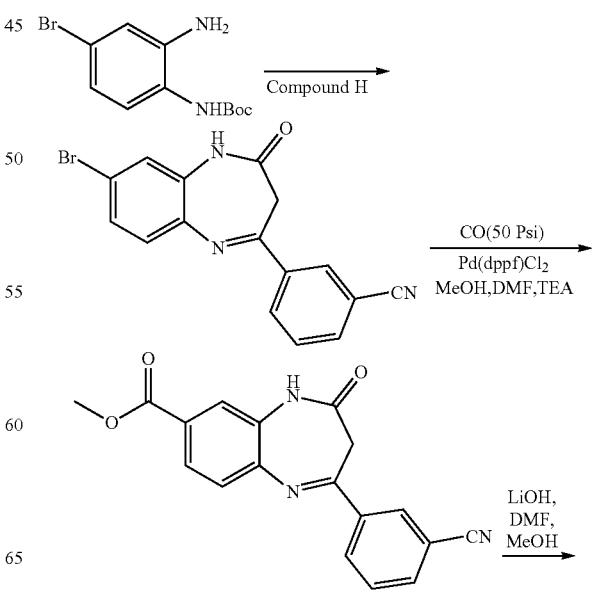

223

-continued

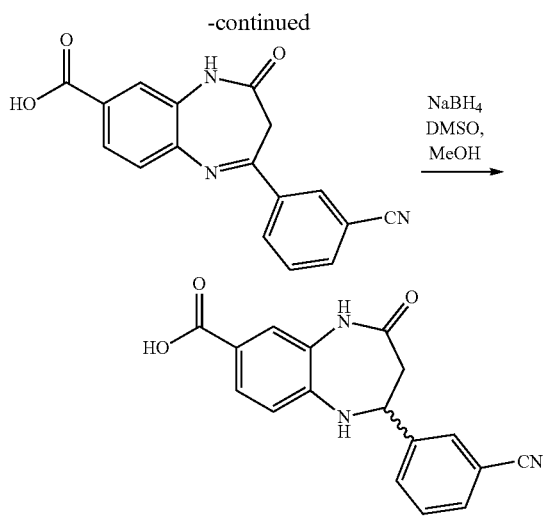

Step 1: 3-(8-Bromo-2-oxo-2,3-dihydro-1H-benzo[b][1,4]diazepin-4-yl)benzonitrile

To the solution of tert-butyl 2-amino-4-bromophenylcarbamate (1.2 g, 3.5 mmol) in DMF (15 mL) and MeOH (5 mL) was added Pd(dppf)Cl$_2$ (127 mg, 0.18 mmol) and TEA (5 mL). The mixture was heated at 80° C. under the atmosphere of CO (50 Psi) for 24 hrs. After removal of the solvent, the residue was extracted by EtOAc/H$_2$O (200 mL). The organic layer was dried over Na$_2$SO$_4$, concentrated and purified by HPLC using formic acid to give 3-(8-bromo-2-oxo-2,3-dihydro-1H-benzo[b][1,4]diazepin-4-yl)benzonitrile (600 mg, yield: 53.6%). $^1$H NMR (400 MHz, DMSO-d$_6$): δ 8.50 (s, 1H), 8.39 (d, J=8.4 Hz, 1H), 8.06 (d, J=7.6 Hz, 1H), 7.85 (s, 1H), 7.75-7.80 (m, 2H), 7.55 (d, J=8.8 Hz, 1H), 3.88 (s, 3H), 3.64 (s, 2H). LC/MS: 319.9 (M+1).

Step 2: Methyl 4-(3-cyanophenyl)-2-oxo-2,3-dihydro-1H-benzo[b][1,4]diazepine-8-carboxylate To the solution of 3-(8-bromo-2-oxo-2,3-dihydro-1H-benzo[b][1,4]diazepin-4-yl)benzonitrile (100 mg, 0.31 mmol) in DMF/MeOH (1:1, 5 mL) was added LiOH (30 mg, 1.24 mmol) in H$_2$O (1 mL). The mixture was stirred at 50° C. for 4 h. After removal of the solvent, the residue was purified by HPLC using formic acid to give methyl 4-(3-cyanophenyl)-2-oxo-2,3-dihydro-1H-benzo[b][1,4]diazepine-8-carboxylate (29 mg, yield: 26.4%). $^1$H NMR (400 MHz, DMSO-d$_6$): δ 10.78 (s, 1H), 8.49 (s, 1H), 8.40 (d, J=8.4 Hz, 1H), 8.06 (d, J=7.6 Hz, 1H), 7.82 (s, 1H), 7.75-7.79 (m, 2H), 7.51 (d, J=8.4 Hz, 1H), 3.63 (s, 2H). LC/MS: 305.0 (M+1).

Step 3: 2-(3-Cyanophenyl)-4-oxo-2,3,4,5-tetrahydro-1H-benzo[b][1,4]diazepine-7-carboxylic Acid (Racemate)

Methyl 4-(3-cyanophenyl)-2-oxo-2,3-dihydro-1H-benzo[b][1,4]diazepine-8-carboxylate was reduced using NaBH$_4$ in DMSO and MeOH using the procedure described for Example 160, Step 6 to give the title compound. $^1$H NMR (400 MHz, DMSO-d$_6$) δ 12.4 (br s, 1H), 9.65 (s, 1H), 7.83 (s, 1H), 7.74 (m, 2H), 7.58 (m, 1H), 7.49 (m, 2H), 6.92 (d, 1H), 6.82 (d, 1H), 5.11 (m, 1H), 2.83 (m, 2H). LC/MS: 308.1 (M+1).

224

Example 162: Benzyl (2-(3-(2,6-dimethylpyridin-4-yl) phenyl)-4-oxo-2,3,4,5-tetrahydro-1H-benzo[b][1,4]diazepin-7-yl)carbamate (Racemate)

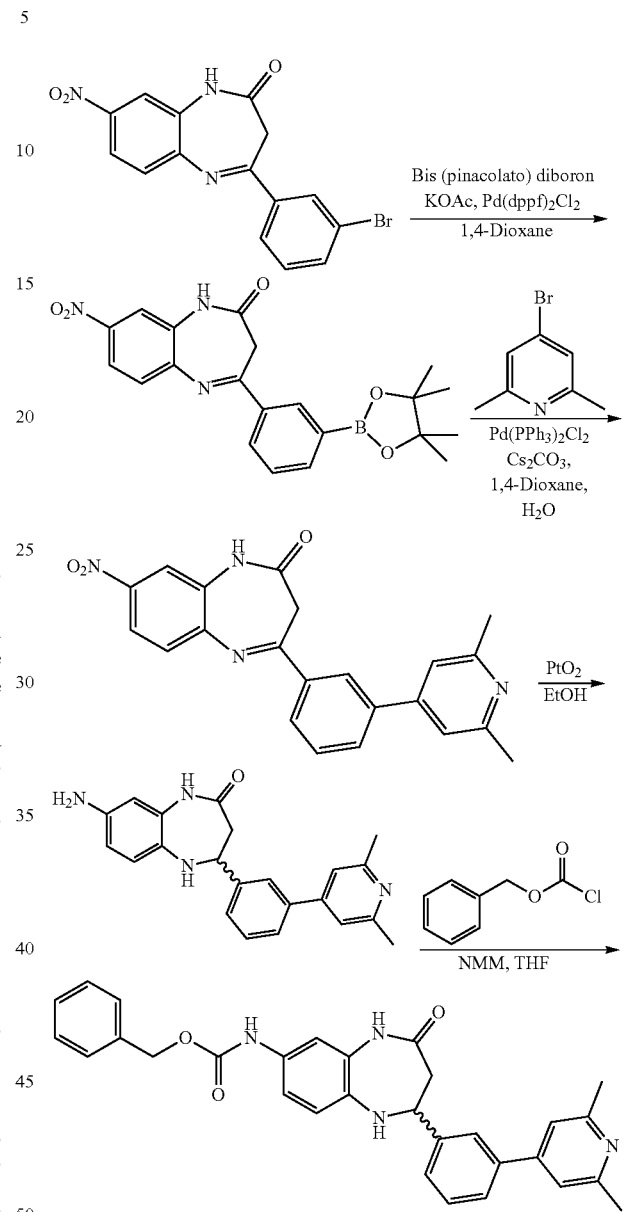

Step 1: 8-Nitro-4-(3-(4,4,5,5-tetramethyl-1,3,2-dioxaborolan-2-yl) phenyl)-1H-benzo[b][1,4]diazepin-2(3H)-one To a stirred solution of 4-(3-bromophenyl)-8-nitro-1H-benzo[b][1,4]diazepin-2(3H)-one (1 g, 2.77 mmol) in 1,4-dioxane (25 mL) under inert atmosphere were added fused potassium acetate (817.8 mg, 8.33 mmol), and bis (pinacolato) diboron (775.9 mg, 3.05 mmol) and purged with argon for 10 min. Then Pd(dppf)$_2$Cl$_2$ (203.2 mg, 0.27 mmol) was added and again degassed for another 15 min; heated to 100° C. and stirred for 3 h. The progress of the reaction was monitored by TLC. After completion of the reaction, the reaction mixture was diluted with water (20 mL) and extracted with EtOAc (2×25 mL). The combined organic extracts were washed with water (20 mL), dried over Sodium sulfate, filtered and concentrated under reduced pressure to obtain the crude product. The crude product was purified by silica gel column chromatography [Eluent: 25% EtOAc/Hexanes] to afford 8-nitro-4-(3-(4,4,5,5-tetramethyl-1,3,2-dioxaborolan-2-yl)phenyl)-1H-benzo[b][1,4]diazepin-2(3H)-one (700 mg, 62%) as a pale yellow solid. $^1$H NMR (500 MHz, DMSO-$d_6$): δ 10.94 (s, 1H), 8.37 (s, 1H), 8.24 (d, J=8.5 Hz, 1H), 8.11 (s, 1H), 8.06-8.04 (m, 1H), 7.88 (d, J=7.0 Hz, 1H), 7.89-7.75 (m, 1H), 7.61-7.59 (m, 1H), 3.65 (s, 2H), 1.17 (s, 12H).

Step 2: 4-(3-(2,6-Dimethylpyridin-4-yl) phenyl)-8-nitro-1H-benzo [b][1,4]diazepin-2 (3H)-one To a stirred solution of 8-nitro-4-(3-(4,4,5,5-tetramethyl-1,3,2-dioxaborolan-2-yl)phenyl)-1H-benzo[b][1,4]diazepin-2(3H)-one (950 mg, 2.33 mmol) in 1,4-dioxane:$H_2O$ (3:0.1, 15.5 mL) under inert atmosphere were added cesium carbonate (2.28 g, 7.01 mmol) and 4-bromo-2,6-dimethylpyridine (478.7 mg, 2.57 mmol) and purged with argon for 10 min. Then Pd(PPh$_3$)$_2$Cl$_2$ (164.2 mg, 0.23 mmol) was added and again degassed for another 15 min; heated to 100° C. and stirred for 12 h. The progress of the reaction was monitored by TLC. After completion of the reaction, the reaction mixture was diluted with water (25 mL) and extracted with EtOAc (2×25 mL). The combined organic extracts were washed with water (20 mL), dried over Sodium sulfate, filtered and concentrated under reduced pressure to obtain the crude product. The crude product was purified by silica gel column chromatography [Eluent: 40% EtOAc/Hexanes] to afford 4-(3-(2,6-dimethylpyridin-4-yl)phenyl)-8-nitro-1H-benzo[b][1,4]diazepin-2(3H)-one (440 mg, 49%) as an off-white solid. $^1$H NMR (400 MHz, DMSO $d_6$): δ 10.95 (s, 1H), 8.40 (s, 1H), 8.18 (d, J=7.6 Hz, 1H), 8.12-8.11 (m, 1H), 8.08-8.05 (m, 1H), 7.85 (d, J=8.0 Hz, 1H), 7.72-7.66 (m, 2H), 7.46 (s, 2H), 3.77 (s, 2H), 2.50 (s, 6H).

Step 3: 8-Amino-4-(3-(2,6-dimethylpyridin-4-yl) phenyl)-4,5-dihydro-1H-benzo [b][1,4]diazepin-2 (3H)-one To a stirred solution of 4-(3-(2,6-dimethylpyridin-4-yl) phenyl)-8-nitro-1H-benzo[b][1,4]diazepin-2(3H)-one (100 mg, 0.25 mmol) in EtOH (10 mL) under inert atmosphere was added platinum (IV) oxide (60 mg) at RT under $H_2$ atmosphere (balloon pressure) and stirred for 18 h. The progress of the reaction was monitored by TLC. After completion of the reaction, the reaction mixture was filtered under vacuum. The filtrate was concentrated under reduced pressure to obtain the crude 8-amino-4-(3-(2,6-dimethylpyridin-4-yl)phenyl)-4,5-dihydro-1H-benzo[b][1,4]diazepin-2(3H)-one (100 mg) as an off-white solid. $^1$H NMR (500 MHz, DMSO $d_6$): δ 9.39 (s, 1H), 7.79 (s, 1H), 7.70-7.69 (m, 1H), 7.43-7.40 (m, 2H), 7.35-7.33 (m, 3H), 6.68 (d, J=8.0 Hz, 1H), 6.29-6.28 (m, 1H), 6.32-6.22 (m, 1H), 4.88-4.86 (m, 2H), 4.66-4.62 (m, 2H), 2.63-2.67 (m, 1H), 2.42 (s, 6H).

Step 4: Benzyl (2-(3-(2,6-dimethylpyridin-4-yl) phenyl)-4-oxo-2,3,4,5-tetrahydro-1H-benzo[b][1,4] diazepin-7-yl)carbamate (Racemate)

To a stirred solution of 8-amino-4-(3-(2,6-dimethylpyridin-4-yl)phenyl)-4,5-dihydro-1H-benzo[b][1,4]diazepin-2(3H)-one (100 mg, 0.27 mmol) in dry THF (7 mL) under inert atmosphere were added N-methyl morpholine (56.4 mg, 0.55 mmol) and Benzyl chloro formate (56.9 mg, 0.33 mmol) at 0° C. The reaction mixture was warmed to RT and stirred for 1 h. The progress of the reaction was monitored by TLC. After completion of the reaction, the reaction mixture was diluted with water (15 mL) and extracted with EtOAc (2×20 mL). The combined organic extracts were washed with water (15 mL), dried over Sodium sulfate, filtered and concentrated under reduced pressure to obtain the crude product. The crude product was purified by silica gel column chromatography [Eluent: 3% MeOH/$CH_2Cl_2$] to afford the title compound (racemate) (40 mg, 29%) as an off-white solid.

Example 162A: Benzyl (2-(3-(2,6-dimethylpyridin-4-yl) phenyl)-4-oxo-2,3,4,5-tetrahydro-1H-benzo[b] [1,4]diazepin-7-yl)carbamate (Enantiomer A); and
Example 162B: Benzyl (2-(3-(2,6-dimethylpyridin-4-yl) phenyl)-4-oxo-2,3,4,5-tetrahydro-1H-benzo[b] [1,4]diazepin-7-yl)carbamate (Enantiomer B)

Chiral preparative HPLC of enantiomers: The enantiomers of Example 162 (40 mg, 0.08 mmol) were separated by normal-phase preparative high performance liquid chromatography (Chiralpak IA, 250×4.0 mm, 5 µm); (A) n-hexane (B) DCM:MeOH (80:20) (A:B: 55:45); Flow rate: 1.0 mL/min) to obtain enantiomer A (15 mg) and enantiomer B (15 mg) as off-white solids.

Analytical data for enantiomer A: $^1$H NMR (500 MHz, CDCl$_3$): δ 7.60 (s, 1H), 7.55 (d, J=7.0 Hz, 1H), 7.47-7.33 (m, 7H), 7.31 (s, 1H), 7.18-7.16 (m, 2H), 7.14 (s, 1H), 6.99 (d, J=7.0 Hz, 1H), 6.71 (d, J=8.5 Hz, 1H), 6.61 (br s, 1H), 5.20 (s, 2H), 5.08-5.05 (m, 1H), 3.72 (br s, 1H), 2.88-2.85 (m, 2H), 2.58 (s, 6H). Chiral HPLC: 100% R$_t$=24.19 min (Chiralpak IA, 250×4.0 mm, 5 µm); mobile phase (A) n-Hexane (B) DCM:Methanol (80:20) (A:B: 55:45); flow Rate: 1.0 mL/min) MS (ESI): m/z 493 [M+1]$^+$ HPLC: 99.7%

Analytical data for enantiomer B: $^1$H NMR (500 MHz, CDCl$_3$): δ 7.60 (s, 1H), 7.55 (d, J=8.0 Hz, 1H), 7.47-7.34 (m, 7H), 7.29 (s, 1H), 7.18-7.16 (m, 2H), 7.14 (s, 1H), 6.99 (d, J=8.5 Hz, 1H), 6.81 (d, J=8.5 Hz, 1H), 6.61 (br s, 1H), 5.20 (s, 2H), 5.08-5.05 (m, 1H), 3.72 (br s, 1H), 2.85-2.79 (m, 2H), 2.58 (s, 6H). Chiral HPLC: 99.89% R$_t$=29.87 min (Chiralpak IA, 250×4.0 mm, 5 µm); mobile phase (A) n-Hexane (B) DCM:Methanol (80:20) (A:B: 55:45); flow Rate: 1.0 mL/min) MS (ESI): m/z 493 [M+1]$^+$ HPLC: 99.9%.

Example 163: Phenyl (2-(3-(2,6-dimethylpyridin-4-yl) phenyl)-4-oxo-2,3,4,5-tetrahydro-1H-benzo[b][1, 4]diazepin-7-yl)carbamate (Racamate)

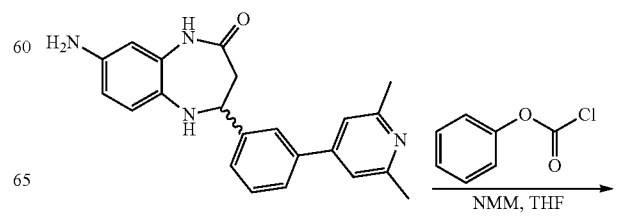

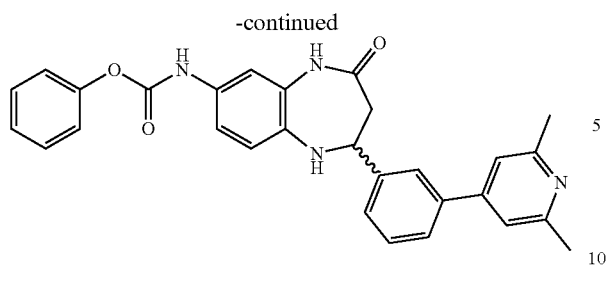

To a stirred solution of 8-amino-4-(3-(2,6-dimethylpyridin-4-yl)phenyl)-4,5-dihydro-1H-benzo[b][1,4]diazepin-2(3H)-one (100 mg, 0.27 mmol) in dry THF (5 mL) under inert atmosphere were added N-methyl morpholine (56.4 mg, 0.55 mmol) and phenyl chloroformate (52.4 mg, 0.33 mmol) at 0° C. The reaction mixture was warmed to RT and stirred for 1 h. The progress of the reaction was monitored by TLC. After completion of the reaction, the reaction mixture was diluted with water (20 mL) and extracted with EtOAc (2×20 mL). The combined organic extracts were washed with water (15 mL), dried over sodium sulfate, filtered and concentrated under reduced pressure to obtain the crude product. The crude product was purified by silica gel column chromatography [Eluent: 3% MeOH/DCM] to afford the title compound (40 mg, 30%) as pale-yellow solid.

Example 163A: Phenyl (2-(3-(2,6-dimethylpyridin-4-yl) phenyl)-4-oxo-2,3,4,5-tetrahydro-1H-benzo[b][1,4]diazepin-7-yl)carbamate Enantiomer A; and
Example 163B: Phenyl (2-(3-(2,6-dimethylpyridin-4-yl) phenyl)-4-oxo-2,3,4,5-tetrahydro-1H-benzo[b][1,4]diazepin-7-yl)carbamate Enantiomer B Chiral preparative HPLC of Enantiomers: The enantiomers of Example 163 (40 mg, 0.08 mmol) were separated by normal-phase preparative high performance liquid chromatography (Chiralpak IA, 250×4.6 mm, 5µ); (A) n-hexane (B) DCM:MeOH (80:20) (A:B: 50:50); Flow rate: 1.0 mL/min) to obtain enantiomer A (10 mg) and enantiomer B (10 mg) as yellow color solids.

Analytical data for enantiomer A: $^1$H NMR (400 MHz, CDCl$_3$): δ 7.61 (s, 1H), 7.57-7.55 (m, 1H), 7.48-7.38 (m, 5H), 7.32 (br s, 1H), 7.19 (d, J=7.6 Hz, 2H), 7.15 (s, 1H), 7.09-7.07 (m, 2H), 6.88-6.84 (m, 2H), 5.10-5.06 (m, 1H), 3.76 (br s, 1H), 2.90-2.80 (m, 2H), 2.59 (s, 6H). Chiral HPLC: 100% R$_t$=16.76 min (Chiralpak IA, 250×4.6 mm, 5µ); mobile phase (A) n-Hexane (B) DCM:Methanol (80:20) (A:B: 50:50); flow Rate: 1.0 mL/min) MS (ESI): m/z 479 [M+1]$^+$ HPLC: 99.4%

Analytical data for enantiomer B: $^1$H NMR (400 MHz, CDCl$_3$): δ 7.61 (s, 2H), 7.56-7.48 (m, 1H), 7.46-7.39 (m, 4H), 7.37 (br s, 1H), 7.24-7.19 (m, 3H), 7.18 (d, J=8.0 Hz, 1H), 7.17 (s, 1H), 7.11 (d, J=8.4 Hz, 1H), 6.98 (br s, 1H), 6.85 (d, J=8.4 Hz, 1H), 5.10-5.06 (m, 1H), 3.77 (br s, 1H), 2.90-2.87 (m, 2H), 2.58 (s, 6H). Chiral HPLC: 99.95% R$_t$=23.50 min (Chiralpak IA, 250×4.6 mm, 5µ); mobile phase (A) n-Hexane (B) DCM:Methanol (80:20) (A:B: 50:50); flow Rate: 1.0 mL/min) MS (ESI): m/z 479 [M+1]$^+$ HPLC: 99.5%.

Example 164: 7-Methyl-4-(3-(pyrimidin-2-yloxy)phenyl)-8-(trifluoromethyl)-4,5-dihydro-1H-benzo[b][1,4]diazepin-2(3H)-one (Racemate)

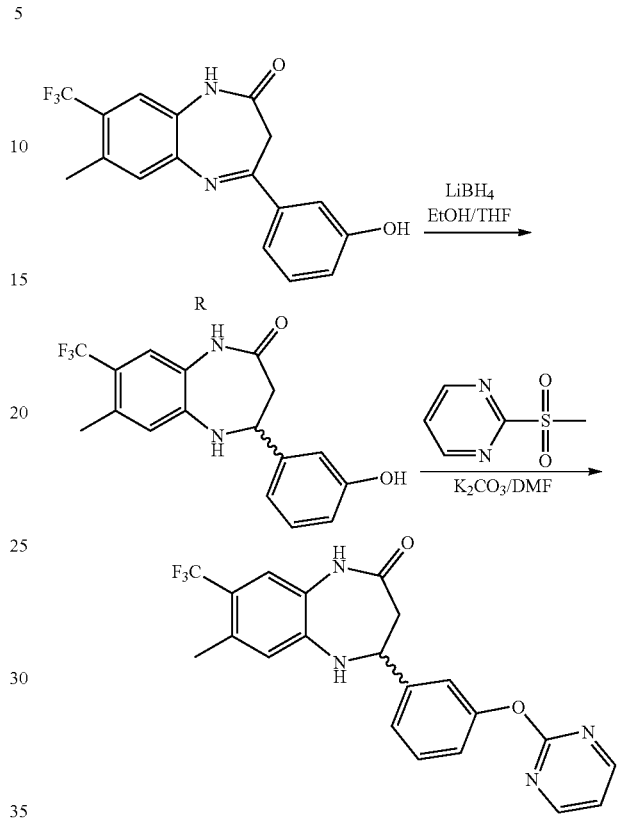

Step 1: 4-(3-Hydroxyphenyl)-7-methyl-8-(trifluoromethyl)-4,5-dihydro-1H-benzo[b][1,4]diazepin-2(3H)-one To a stirred solution of lithium chloride (253.8 mg, 5.98 mmol) in EtOH (40 mL) under inert atmosphere was added sodium borohydride (226.5 mg, 5.98 mmol) at 0° C. After being stirred for 30 min; a solution of compound R (400 mg, 1.19 mmol) in dry THF (40 mL) was added drop wise to the reaction mixture and stirring was continued for 48 h at RT. The progress of the reaction was monitored by TLC, after completion of the reaction volatiles were removed and then the reaction mixture was diluted with water (25 mL) and extracted with CH$_2$Cl$_2$ (3×20 mL). The combined organic extracts were washed with water (20 mL), dried over sodium sulfate, filtered and concentrated under reduced pressure to obtain the crude product. The crude product was purified by silica gel column chromatography [Eluent: 30% EtOAc/Hexanes] to afford 4-(3-hydroxyphenyl)-7-methyl-8-(trifluoromethyl)-4,5-dihydro-1H-benzo[b][1,4]diazepin-2(3H)-one (190 mg, 42%) as an off-white solid. $^1$H NMR (400 MHz, DMSO-d$_6$): δ 9.52 (s, 1H), 7.19 (s, 1H), 7.11 (t, J=5.0 Hz, 1H), 6.81 (s, 1H), 6.75-6.72 (m, 2H), 6.64 (d, J=8.0 Hz, 1H), 6.58-6.56 (m, 1H), 4.81-4.79 (m, 1H), 2.80-2.79 (m, 1H), 2.70-2.69 (m, 1H), 2.15 (s, 3H). MS (ESI): m/z 414 [M+1]$^+$ HPLC: 96.0%.

Step 2: 7-Methyl-4-(3-(pyrimidin-2-yloxy)phenyl)-8-(trifluoromethyl)-4,5-dihydro-1H-benzo[b][1,4]diazepin-2(3H)-one (Racemate)

To a stirred solution of 4-(3-hydroxyphenyl)-7-methyl-8-(trifluoromethyl)-4,5-dihydro-1H-benzo[b][1,4]diazepin-2(3H)-one (120 mg, 0.35 mmol) in DMF (20 mL) under inert atmosphere were added potassium carbonate (49.3 mg, 0.35 mmol) and 2-(methylsulfonyl) pyrimidine (56.4 mg, 0.35 mmol) at 0° C. The reaction mixture was warmed to RT and stirred for 48 h. The progress of the reaction was monitored by TLC. After completion of the reaction, the reaction mixture was diluted with water (20 mL) and extracted with EtOAc (2×20 mL). The combined organic extracts were washed with water (20 mL), dried over sodium sulfate, filtered and concentrated under reduced pressure to obtain the crude product. The crude product was purified by silica gel column chromatography [Eluent: 50% EtOAc/Hexanes] to afford the title compound (racemate) (30 mg, 20%) as an off-white solid.

Example 164A: 7-Methyl-4-(3-(pyrimidin-2-yloxy)phenyl)-8-(trifluoromethyl)-4,5-dihydro-1H-benzo[b][1,4]diazepin-2(3H)-one Enantiomer A; and
Example 164B: 7-Methyl-4-(3-(pyrimidin-2-yloxy)phenyl)-8-(trifluoromethyl)-4,5-dihydro-1H-benzo[b][1,4]diazepin-2(3H)-one Enantiomer B Chiral preparative HPLC of Enantiomers: The enantiomers of Example 164 (70 mg, 0.07 mmol) were separated by normal-phase preparative high performance liquid chromatography (Chiralpak IA, 250×4.6 mm, 5µ); (A) n-hexane (B) DCM:MeOH (50:50) (A:B: 85:15); Flow rate: 1.0 mL/min) to obtain enantiomer A (6 mg) enantiomer B (8 mg) as off-white solids.

Analytical data for enantiomer A: $^1$H NMR (400 MHz, DMSO-$d_6$): δ 9.57 (s, 1H), 8.64-8.62 (m, 2H), 7.38 (t, J=8.0 Hz, 1H), 7.27-7.25 (m, 2H), 7.16 (d, J=9.0 Hz, 1H), 7.10 (d, J=7.0 Hz, 1H), 6.83 (s, 1H), 6.68-6.67 (m, 1H), 5.00-4.98 (m, 1H), 2.85-2.73 (m, 2H), 2.22 (s, 3H). Chiral HPLC: 100% $R_t$=20.18 min (Chiralpak IA, 250×4.6 mm, 5µ); mobile phase (A) n-Hexane (B) DCM:Methanol (50:50) (A:B: 85:15); flow Rate: 1.0 mL/min) MS (ESI): m/z 415 [M+1]$^+$ HPLC: 99.0%.

Analytical data for enantiomer B: $^1$H NMR (400 MHz, DMSO-$d_6$): δ 9.57 (s, 1H), 8.64-8.62 (m, 2H), 7.40 (t, J=7.6 Hz, 1H), 7.27-7.25 (m, 2H), 7.16 (d, J=9.0 Hz, 2H), 7.09 (d, J=8.4 Hz, 1H), 6.83 (s, 1H), 6.68-6.67 (m, 1H), 4.99-4.98 (m, 1H), 2.85-2.77 (m, 2H), 2.26 (s, 3H). Chiral HPLC: 88.76% $R_t$=22.74 min (Chiralpak IA, 250×4.6 mm, 5µ); mobile phase (A) n-Hexane (B) DCM:Methanol (50:50) (A:B: 85:15); flow Rate: 1.0 mL/min) MS (ESI): m/z 415 [M+1]$^+$ HPLC: 97.8%.

Example 165: 7-Methyl-4-(3-(pyridin-2-yloxy)phenyl)-8-(trifluoromethyl)-4,5-dihydro-1H-benzo[b][1,4]diazepin-2(3H)-one (Racemate)

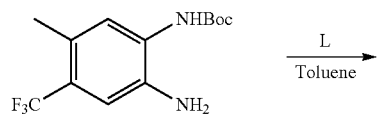

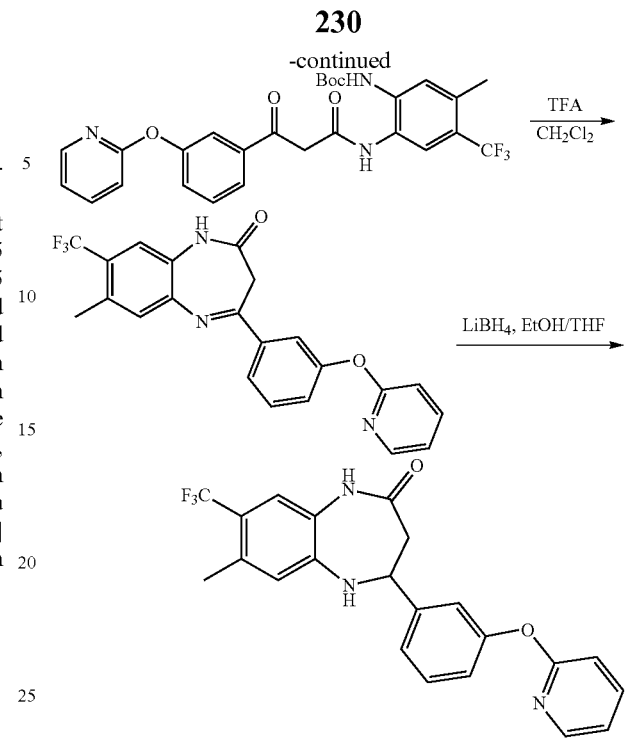

Step 1: tert-Butyl (5-methyl-2-(3-oxo-3-(3-(pyridin-2-yloxy)phenyl)propanamido)-4-(trifluoro methyl)phenyl)carbamate To a stirred solution of the compound from tert-butyl 2-amino-5-methyl-4-(trifluoromethyl)phenylcarbamate (315 mg, 1.08 mmol) in toluene (10 mL) under inert atmosphere was added intermediate L (310 mg, 1.08 mmol) at RT; heated to 120° C. and stirred for 12 h. The progress of the reaction was monitored by TLC. After completion of the reaction, the volatiles were evaporated under reduced pressure to obtain the crude product. The crude product was triturated with diethyl ether (2×10 mL) to afford tert-butyl (5-methyl-2-(3-oxo-3-(3-(pyridin-2-yloxy)phenyl)propanamido)-4-(trifluoro methyl)phenyl)carbamate (290 mg, 50%) as colorless liquid. $^1$H NMR (500 MHz, DMSO-$d_6$): δ 9.84 (s, 1H), 9.73 (s, 1H), 8.67-8.66 (m, 1H), 8.13-8.12 (m, 1H), 7.88-7.86 (m, 2H), 7.81-7.80 (m, 1H), 7.61 (d, J=8.5 Hz, 1H), 7.46 (d, J=8.0 Hz, 1H), 7.37-7.27 (m, 1H), 7.16-7.09 (m, 1H), 7.06 (d, J=8.0 Hz, 1H), 4.20-4.13 (m, 2H), 2.38 (s, 3H), 1.48 (s, 9H).

Step 2: 7-Methyl-4-(3-(pyridin-2-yloxy)phenyl)-8-(trifluoromethyl)-1H-benzo[b][1,4]diazepin-2(3H)-one To a stirred solution of tert-butyl (5-methyl-2-(3-oxo-3-(3-(pyridin-2-yloxy)phenyl)propanamido)-4-(trifluoro methyl)phenyl)carbamate (26 mg, 0.049 mmol) in CH$_2$Cl$_2$ (2 mL) under inert atmosphere was added TFA (0.1 mL) at 0° C.; warmed to RT and stirred for 6 h. The progress of the reaction was monitored by TLC. After completion of the reaction, the reaction mixture was quenched with water (10 mL) and extracted with CH$_2$Cl$_2$ (3×10 mL). The combined organic extracts were washed with water (10 mL), dried over sodium sulfate, filtered and concentrated under reduced pressure to obtain the crude product. The crude product was triturated with diethyl ether (2×4 mL) to afford 7-methyl- 4-(3-(pyridin-2-yloxy)phenyl)-8-(trifluoromethyl)-1H-benzo[b][1,4]diazepin-2(3H)-one (13 mg, 65%) as an off-white solid. $^1$H NMR (500 MHz, DMSO-d$_6$): δ 10.68 (s, 1H), 8.15-8.14 (m, 1H), 7.92-7.87 (m, 2H), 7.80 (s, 1H), 7.59 (t, J=8.0 Hz, 1H), 7.49 (s, 1H), 7.44 (s, 1H), 7.34 (t, J=10.0 Hz, 1H), 7.16-7.10 (m, 2H), 3.56 (s, 2H), 2.43 (s, 3H). MS (ESI): m/z 412 [M+1]$^+$ HPLC: 96.1%.

Step 3: 7-Methyl-4-(3-(pyridin-2-yloxy)phenyl)-8-(trifluoromethyl)-4,5-dihydro-1H-benzo[b][1,4]diazepin-2(3H)-one (Racemate)

To a stirred solution of lithium chloride (46.4 mg, 1.09 mmol) in EtOH (5 mL) under inert atmosphere was added sodium borohydride (41.3 mg, 1.09 mmol) at 0° C. After being stirred for 1 h; a solution of 7-methyl-4-(3-(pyridin-2-yloxy)phenyl)-8-(trifluoromethyl)-1H-benzo[b][1,4]diazepin-2(3H)-one (150 mg, 0.36 mmol) in dry THF (10 mL) was added drop wise to the reaction mixture and stirring was continued for 6 h at RT. The progress of the reaction was monitored by TLC. After completion of the reaction, the reaction mixture was diluted with water (15 mL) and extracted with EtOAc (2×15 mL). The combined organic extracts were washed with water (15 mL), dried over sodium sulfate, filtered and concentrated under reduced pressure to obtain the crude product. The crude product was purified by silica gel column chromatography [Eluent: 25% EtOAc/Hexanes] to afford 3 (racemate; 43 mg, 29%) as an off-white solid.

Example 165A: 7-Methyl-4-(3-(pyridin-2-yloxy)phenyl)-8-(trifluoromethyl)-4,5-dihydro-1H-benzo[b][1,4]diazepin-2(3H)-one Enantiomer A; and
Example 165B: 7-Methyl-4-(3-(pyridin-2-yloxy)phenyl)-8-(trifluoromethyl)-4,5-dihydro-1H-benzo[b][1,4]diazepin-2(3H)-one Enantiomer B Chiral preparative HPLC of Enantiomers: The enantiomers of Example 165 (43 mg, 0.10 mmol) were separated by normal-phase preparative high performance liquid chromatography (Chiralpak IC, 250×4.6 mm, 5 μm); (A) n-Hexane:THF (80:20); Flow rate: 1.0 mL/min) to obtain enantiomer A (10 mg) and enantiomer B (12 mg) as off-white solids.

Analytical data for enantiomer A: $^1$H NMR (500 MHz, DMSO-d$_6$): δ 9.56 (s, 1H), 8.15 (s, 1H), 7.83 (t, J=7.0 Hz, 1H), 7.38 (t, J=8.0 Hz, 1H), 7.21 (d, J=7.5 Hz, 1H), 7.13 (t, J=8.0 Hz, 3H), 7.02-6.97 (m, 1H), 6.81 (s, 1H), 6.66 (d, J=3.5 Hz, 1H), 5.00-4.97 (m, 1H), 2.83-2.73 (m, 2H), 2.25 (s, 3H). Chiral HPLC: 97.9% R$_t$=22.34 min (Chiralpak IC, 250×4.6 mm, 5 μm); mobile phase (A) n-Hexane:THF (80:20); flow Rate: 1.0 mL/min) MS (ESI): m/z 414 [M+1]$^+$ HPLC: 96.1%

Analytical data for enantiomer B: $^1$H NMR (500 MHz, DMSO-d$_6$): δ 9.56 (s, 1H), 8.15 (d, J=4.0 Hz, 1H), 7.83 (t, J=7.0 Hz, 1H), 7.38 (t, J=7.5 Hz, 1H), 7.21 (d, J=7.5 Hz, 1H), 7.13 (t, J=9.0 Hz, 2H), 7.02-6.97 (m, 2H), 6.81 (s, 1H), 6.66 (s, 1H), 5.03-4.98 (m, 1H), 3.75-3.71 (br s, 1H), 2.83-2.73 (m, 2H), 2.25 (s, 3H). Chiral HPLC: 99.29% R$_t$=28.68 min (Chiralpak IC, 250×4.6 mm, 5 μm); mobile phase (A) n-Hexane:THF (80:20); flow Rate: 1.0 mL/min) MS (ESI): m/z 414 [M+1]$^+$ HPLC: 95.96%.

Example 166: 7-Methyl-4-(3-(pyrimidin-2-ylthio)phenyl)-8-(trifluoromethyl)-4,5-dihydro-1H-benzo[b][1,4]diazepin-2(3H)-one (Racemate)

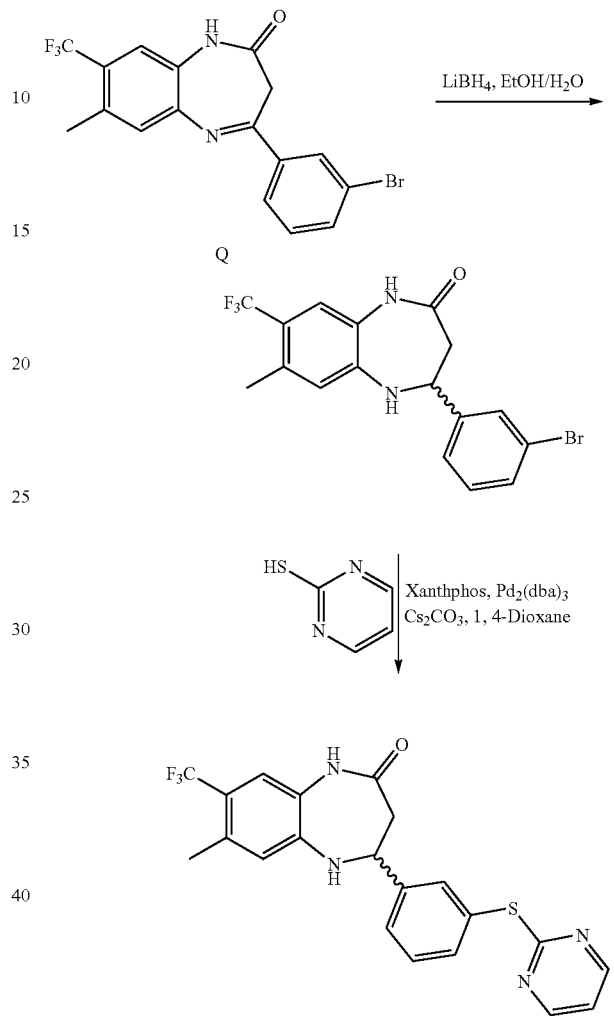

Step 1: 4-(3-Bromophenyl)-7-methyl-8-(trifluoromethyl)-4,5-dihydro-1H-benzo[b][1,4]diazepin-2(3H)-one To a stirred solution of lithium chloride (32.0 mg, 0.75 mmol) in EtOH (4 mL) under inert atmosphere was added sodium borohydride (9.5 mg, 0.25 mmol) at 0° C. After being stirred for 1 h; a solution of compound Q (100 mg, 0.25 mmol) in dry THF (4 mL) was added drop wise to the reaction mixture and stirring was continued for 12 h at RT. The progress of the reaction was monitored by TLC. After completion of the reaction volatiles were removed, the reaction mixture was diluted with water (30 mL) and extracted with EtOAc (2×20 mL). The combined organic extracts were washed with water (20 mL), dried over sodium sulfate, filtered and concentrated under reduced pressure to obtain the crude product. The crude product was purified by silica gel column chromatography [Eluent: 30% EtOAc/Hexanes] to afford 4-(3-bromophenyl)-7-methyl-8-(trifluoromethyl)-4,5-dihydro-1H-benzo[b][1,4]diazepin-2(3H)- one (60 mg, 60%) as an off white solid. $^1$H NMR (500 MHz, DMSO-$d_6$): δ 9.56 (s, 1H), 7.56 (s, 1H), 7.45 (d, J=7.5 Hz, 1H), 7.37 (d, J=8.0 Hz, 1H), 7.30 (t, J=7.5 Hz, 1H), 7.14 (s, 1H), 6.82 (s, 1H), 6.68-6.66 (m, 1H), 5.00-4.97 (m, 1H), 2.80-2.77 (m, 2H), 2.27 (s, 3H).

Step 2: 7-Methyl-4-(3-(pyrimidin-2-ylthio)phenyl)-8-(trifluoromethyl)-4,5-dihydro-1H-benzo[b][1,4]diazepin-2(3H)-one (Racemate)

To a stirred solution of 4-(3-bromophenyl)-7-methyl-8-(trifluoromethyl)-4,5-dihydro-1H-benzo[b][1,4]diazepin-2(3H)-one (390 mg, 0.97 mmol) in 1,4-dioxane (20 mL) under inert atmosphere were added pyrimidine-2-thiol (109.7 mg, 0.97 mmol), cesium carbonate (573.2 mg, 1.76 mmol), xanthphos (25.3 mg, 0.04 mmol) at RT and purged with argon for 30 min. Then Pd$_2$(dba)$_3$ (35.8 mg, 0.04 mmol) was added and again purged for another 15 min; heated to 100° C. and stirred for 36 h. The progress of the reaction was monitored by TLC. After completion of the reaction, the volatiles were evaporated under reduced pressure to obtain the crude product. The crude product was purified by silica gel column chromatography [Eluent: 60% EtOAc/Hexanes] to afford the title compound (310 mg, 74%) as a pale yellow solid.

Example 166A: 7-Methyl-4-(3-(pyrimidin-2-ylthio) phenyl)-8-(trifluoromethyl)-4,5-dihydro-1H-benzo [b][1,4]diazepin-2(3H)-one Enantiomer A; and Example 166B: 7-Methyl-4-(3-(pyrimidin-2-ylthio) phenyl)-8-(trifluoromethyl)-4,5-dihydro-1H-benzo [b][1,4]diazepin-2(3H)-one Enantiomer B Chiral preparative HPLC of enantiomers: The enantiomers of Example 166 (310 mg, 0.72 mmol) were separated by normal-phase preparative high performance liquid chromatography (Chiralpak IC, 250×4.6 mm, 5μ); (A) 0.1% DEA in n-hexane (B) Ethanol:THF (50:50) (A:B: 85:15); Flow rate: 1.0 mL/min) to obtain enantiomer A (15 mg) and enantiomer B (15 mg) as pale-yellow solids.

Analytical data for enantiomer A: $^1$H NMR (400 MHz, DMSO-$d_6$): δ 9.57 (s, 1H), 8.59-8.57 (m, 2H), 7.59 (s, 1H), 7.51-7.49 (m, 3H), 7.23 (t, J=4.8 Hz, 1H), 7.16 (s, 1H), 6.83 (s, 1H), 6.68-6.69 (m, 1H), 5.02-5.00 (m, 1H), 2.86-2.83 (m, 2H), 2.26 (s, 3H). Chiral HPLC: 97.8% R$_t$=12.20 min (Chiralpak IC, 250×4.6 mm, 5μ); mobile phase (A) 0.1% DEA in n-Hexane (B) Ethanol:THF (50:50) (A:B: 85:15); flow Rate: 1.0 mL/min) MS (ESI): m/z 431 [M+1]$^+$ HPLC: 97.5%.

Analytical data for enantiomer B: $^1$H NMR (400 MHz, DMSO-$d_6$): δ 9.57 (s, 1H), 8.59-8.57 (m, 2H), 7.59 (s, 1H), 7.51-7.49 (m, 3H), 7.23 (t, J=4.8 Hz, 1H), 7.16 (s, 1H), 6.83 (s, 1H), 6.68-6.69 (m, 1H), 5.02-5.00 (m, 1H), 2.86-2.83 (m, 2H), 2.26 (s, 3H). Chiral HPLC: 96.7% R$_t$=14.38 min (Chiralpak IC, 250×4.6 mm, 5μ); mobile phase (A) 0.1% DEA in n-Hexane (B) Ethanol:THF (50:50) (A:B: 85:15); flow Rate: 1.0 mL/min) MS (ESI): m/z 431 [M+1]$^+$ HPLC: 94.0%.

Example 167: 4-(3-(1H-Indol-1-yl)phenyl)-7-methyl-8-(trifluoromethyl)-4,5-dihydro-1H-benzo[b][1,4]diazepin-2(3H)-one (Racemate)

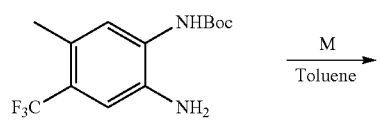

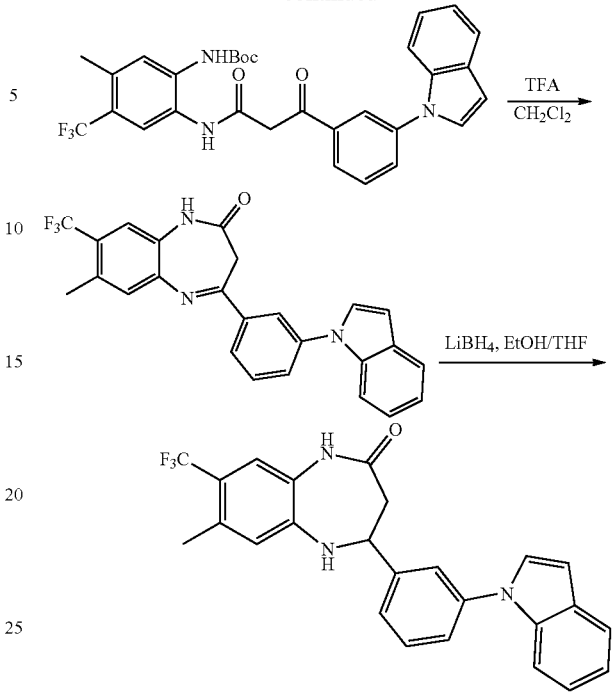

Step 1: tert-Butyl (2-(3-(3-(1H-indol-1-yl)phenyl)-3-oxopropanamido)-5-methyl-4-(trifluoromethyl) phenyl)carbamate To a stirred solution of tert-butyl 2-amino-5-methyl-4-(trifluoromethyl)phenylcarbamate (500 mg, 1.72 mmol) in toluene (10 mL) under inert atmosphere was added intermediate M (529.8 mg, 1.72 mmol) at RT; heated to 110° C. and stirred for 15 h. The progress of the reaction was monitored by TLC. After completion of the reaction, the volatiles were removed under reduced pressure to obtain the crude product. The crude product was purified by silica gel column chromatography [Eluent: 30% EtOAc/Hexanes] to afford tert-butyl (2-(3-(3-(1H-indol-1-yl)phenyl)-3-oxopropanamido)-5-methyl-4-(trifluoromethyl)phenyl)carbamate (270 mg, 28%) as a pale yellow solid. $^1$H NMR (500 MHz, DMSO-$d_6$): δ 9.79 (s, 1H), 8.71 (s, 1H), 8.19 (s, 1H), 8.03-8.02 (m, 2H), 7.76-7.65 (m, 3H), 7.63-7.60 (m, 1H), 7.17-7.16 (m, 2H), 6.76-6.74 (m, 1H), 4.34-4.31 (m, 2H), 2.40 (s, 3H), 1.43 (s, 9H).

Step 2: 4-(3-(1H-Indol-1-yl)phenyl)-7-methyl-8-(trifluoromethyl)-1H-benzo[b][1,4]diazepin-2(3H)-one To a stirred solution of tert-butyl (2-(3-(3-(1H-indol-1-yl)phenyl)-3-oxopropanamido)-5-methyl-4-(trifluoromethyl) phenyl)carbamate (220 mg, 0.39 mmol) in CH$_2$Cl$_2$ (40 mL) under inert atmosphere was added TFA (12 mL) at 0° C. The reaction mixture was allowed to warm to RT and stirred for 12 h. The progress of the reaction was monitored by TLC. After completion of the reaction, the reaction mixture was quenched with aq. NaHCO$_3$ solution (25 mL) and extracted with CH$_2$Cl$_2$ (3×20 mL). The combined organic extracts were washed with water (20 mL), dried over sodium sulfate, filtered and concentrated under reduced pressure to obtain the crude product. The crude product was purified by silica gel column chromatography [Eluent: 20% EtOAc/Hexanes] to afford 4-(3-(1H-indol-1-yl)phenyl)-7-methyl-8-(trifluoromethyl)-1H-benzo[b][1,4]diazepin-2(3H)-one (110 mg, 64%) as a pale yellow solid. ¹H NMR (400 MHz, DMSO-d₆): δ 10.73 (s, 1H), 8.24 (s, 1H), 8.10 (d, J=8.0 Hz, 1H), 7.84-7.74 (m, 4H), 7.69 (d, J=7.6 Hz, 1H), 7.60 (d, J=8.4 Hz, 1H), 7.51 (d, J=9.6 Hz, 1H), 7.21-7.16 (m, 1H), 6.76-6.75 (m, 1H), 3.67.3.65 (m, 2H), 2.50 (s, 3H). MS (ESI): m/z 434 [M+1]⁺ HPLC: 91.1%.

Step 3: 4-(3-(1H-Indol-1-yl)phenyl)-7-methyl-8-(trifluoromethyl)-4,5-dihydro-1H-benzo[b][1,4]diazepin-2(3H)-one (Racemate)

To a stirred solution of lithium chloride (32.3 mg, 0.76 mmol) in EtOH (10 mL) under inert atmosphere was added sodium borohydride (28.8 mg, 0.76 mmol) at 0° C. After being stirred for 30 min; a solution of 4-(3-(1H-indol-1-yl)phenyl)-7-methyl-8-(trifluoromethyl)-1H-benzo[b][1,4]diazepin-2(3H)-one (110 mg, 0.25 mmol) in dry THF (10 mL) was added drop wise to the reaction mixture and stirring was continued for 6 h at RT. The progress of the reaction was monitored by TLC. After completion of the reaction, the reaction mixture was diluted with water (10 mL) and extracted with EtOAc (2×10 mL). The combined organic extracts were washed with water (10 mL), dried over sodium sulfate, filtered and concentrated under reduced pressure to obtain the crude product. The crude product was purified by silica gel column chromatography [Eluent: 20% EtOAc/Hexanes] to afford the title compound (racemate; 100 mg, 91%) as a pale yellow solid.

Example 167A: 4-(3-(1H-Indol-1-yl)phenyl)-7-methyl-8-(trifluoromethyl)-4,5-dihydro-1H-benzo[b][1,4]diazepin-2(3H)-one Enantiomer A; and Example 167B: 4-(3-(1H-Indol-1-yl)phenyl)-7-methyl-8-(trifluoromethyl)-4,5-dihydro-1H-benzo[b][1,4]diazepin-2(3H)-one Enantiomer B Chiral preparative HPLC of Enantiomers: The enantiomers of Example 167 (100 mg, 0.22 mmol) were separated by normal-phase preparative high performance liquid chromatography (Chiralpak IA, 250×4.6 mm, 5µ); (A) 0.1% DEA in n-hexane (B) DCM:MeOH (80:20) (A:B: 70:30); Flow rate: 1.0 mL/min) to obtain enantiomer A (15 mg) and enantiomer B (15 mg) as pale yellow solids.

Analytical data for enantiomer A: ¹H NMR (400 MHz, DMSO-d₆): δ 9.63 (s, 1H), 7.65-7.53 (m, 5H), 7.46 (d, J=9.0 Hz, 1H), 7.38 (d, J=8.0 Hz, 1H), 7.19-7.10 (m, 3H), 6.87 (s, 1H), 6.77-6.75 (m, 1H), 6.70-6.68 (m, 1H), 5.10-5.09 (m, 1H), 2.95-2.90 (m, 1H), 2.85-2.81 (m, 1H), 2.26 (s, 3H). Chiral HPLC: 99.93% R$_t$=7.57 min (Chiralpak IA, 250×4.6 mm, 5µ); mobile phase (A) 0.1% DEA in n-Hexane (B) DCM:Methanol (80:20) (A:B: 70:30); flow Rate: 1.0 mL/min) MS (ESI): m/z 436 [M+1]⁺ HPLC: 90.7%

Analytical data for enantiomer B: ¹H NMR (400 MHz, DMSO-d₆): δ 9.63 (s, 1H), 7.65-7.53 (m, 5H), 7.46 (d, J=9.0 Hz, 1H), 7.38 (d, J=8.0 Hz, 1H), 7.19-7.10 (m, 3H), 6.87 (s, 1H), 6.77-6.75 (m, 1H), 6.70-6.68 (m, 1H), 5.10-5.09 (m, 1H), 2.95-2.90 (m, 1H), 2.85-2.81 (m, 1H), 2.26 (s, 3H). Chiral HPLC: 99.9% R$_t$=10.69 min (Chiralpak IA, 250×4.6 mm, 5µ); mobile phase (A) 0.1% DEA in n-Hexane (B) DCM:Methanol (80:20) (A:B: 70:30); flow Rate: 1.0 mL/min) MS (ESI): m/z 436 [M+1]⁺ HPLC: 91.4%

Example 168: 3-(8-Methyl-4-oxo-7-(trifluoromethyl)-2,3,4,5-tetrahydro-1H-benzo[b][1,4]diazepin-2-yl)benzamide

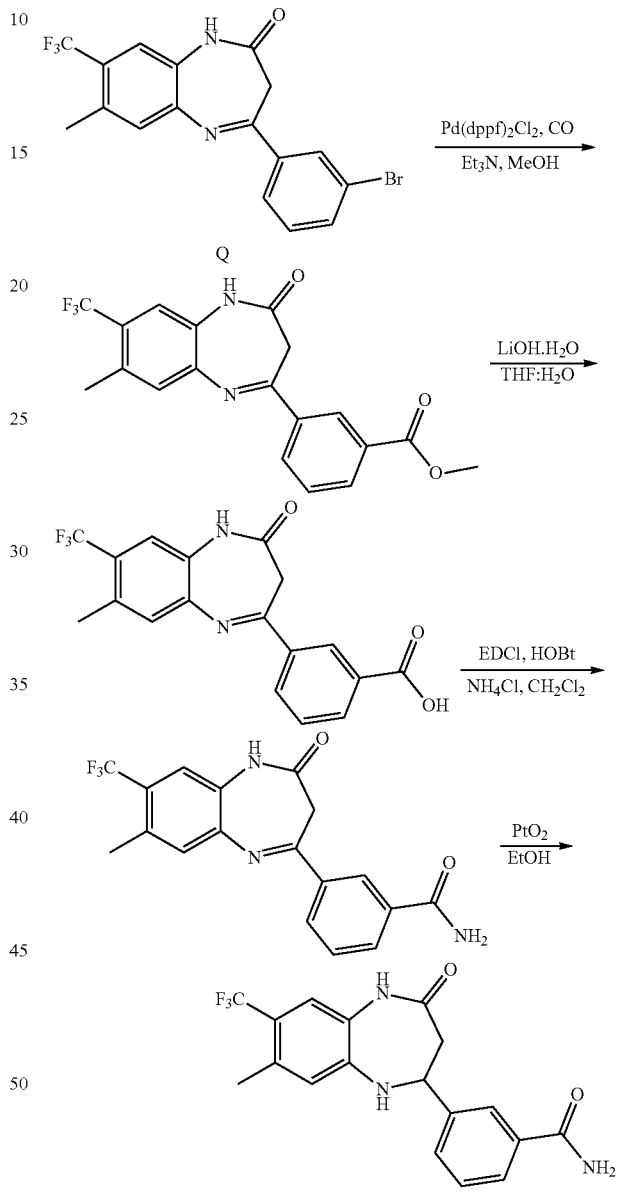

Step 1: Methyl 3-(7-methyl-2-oxo-8-(trifluoromethyl)-2,3-dihydro-1H-benzo[b][1,4]diazepin-4-yl)benzoate To a stirred solution of compound Q (500 mg, 1.25 mmol) in MeOH:ACN (4:1) (20 mL) under inert atmosphere was added triethylamine (0.04 mL, 3.14 mmol) and purged for 20 min. The reaction mixture was charged into steel bomb and was added Pd(dppf)₂Cl₂ (184.3 mg, 0.25 mmol); heated at 80° C. under CO atmosphere (80 Psi) for 3 days. The progress of the reaction was monitored by TLC. After completion of the reaction, the volatiles were evaporated under reduced pressure to obtain the crude product. The crude product was purified by silica gel column chromatography [Eluent: 25% EtOAc/Hexanes] to afford methyl 3-(7-methyl-2-oxo-8-(trifluoromethyl)-2,3-dihydro-1H-benzo[b][1,4]diazepin-4-yl)benzoate (320 mg, 68%) as an off-white solid. $^1$H NMR (400 MHz, DMSO-$d_6$): δ 10.72 (s, 1H), 8.65 (s, 1H), 8.34 (d, J=8.4 Hz, 1H), 8.15 (d, J=8.0 Hz, 1H), 7.72 (t, J=8.0 Hz, 1H), 7.52 (s, 2H), 3.91 (s, 3H), 3.62 (s, 2H), 2.50 (s, 3H).

Step 2: 3-(7-Methyl-2-oxo-8-(trifluoromethyl)-2,3-dihydro-1H-benzo[b][1,4]diazepin-4-yl)benzoic Acid To a stirred solution of methyl 3-(7-methyl-2-oxo-8-(trifluoromethyl)-2,3-dihydro-1H-benzo[b][1,4]diazepin-4-yl)benzoate (125 mg, 0.33 mmol) in THF:H$_2$O (5:1; 6 mL) was added lithium hydroxide monohydrate (69.8 mg, 1.66 mmol) at RT and stirred for 12 h. The progress of the reaction was monitored by TLC, after completion of the reaction; the reaction mixture was acidified with saturated citric acid solution (pH-4) and extracted with EtOAc (2×20 mL). The combined organic extracts were washed with water (20 mL), dried over sodium sulfate, filtered and concentrated under reduced pressure to obtain the crude product. The crude product was triturated with diethyl ether (2×3 mL) to afford 3-(7-methyl-2-oxo-8-(trifluoromethyl)-2,3-dihydro-1H-benzo[b][1,4]diazepin-4-yl)benzoic acid (110 mg, 92%) as an off-white solid. $^1$H NMR (400 MHz, DMSO $d_6$): δ 10.70 (s, 1H), 8.6 (s, 1H), 8.32-8.28 (m, 1H), 8.18-8.14 (m, 1H), 7.62-7.61 (m, 2H), 7.58 (s, 1H), 3.65 (s, 3H), 2.45 (s, 3H). MS (ESI): m/z 361 [M−1] HPLC: 94.4%.

Step 3: 3-(7-Methyl-2-oxo-8-(trifluoromethyl)-2,3-dihydro-1H-benzo[b][1,4]diazepin-4-yl)benzamide To a stirred solution of 3-(7-methyl-2-oxo-8-(trifluoromethyl)-2,3-dihydro-1H-benzo[b][1,4]diazepin-4-yl)benzoic acid (5 mg, 0.01 mmol) in CH$_2$Cl$_2$ (3 mL) under inert atmosphere were added DIPEA (17.8 mg, 0.13 mmol), HOBt (9.3 mg, 0.06 mmol), EDCI.HCl (13.2 mg, 0.06 mmol) and ammonium chloride (7.4 mg, 0.01 mmol) at RT and stirred for 15 h. The progress of the reaction was monitored by TLC. After completion of the reaction, the reaction mixture was diluted with water (10 mL) and extracted with EtOAc (2×5 mL). The combined organic extracts were washed with water (5 mL), dried over sodium sulfate, filtered and concentrated under reduced pressure to obtain the crude product. The crude product was purified by silica gel column chromatography [Eluent: 50% EtOAc/Hexanes] to afford 3-(7-methyl-2-oxo-8-(trifluoromethyl)-2,3-dihydro-1H-benzo[b][1,4]diazepin-4-yl)benzamide (3 mg, 60%) as a pale yellow solid. $^1$H NMR (400 MHz, DMSO $d_6$): δ 10.69 (s, 1H), 8.56 (s, 1H), 8.21 (d, J=8.4 Hz, 1H), 8.17 (s, 1H), 8.06 (d, J=8.0 Hz, 1H), 7.63 (t, J=7.6 Hz, 1H), 7.51-7.50 (m, 3H), 3.64 (s, 2H), 2.46 (s, 3H). MS (ESI): m/z 362 [M+1]$^+$ HPLC: 99.6%.

Step 4: 3-(8-Methyl-4-oxo-7-(trifluoromethyl)-2,3,4,5-tetrahydro-1H-benzo[b][1,4]diazepin-2-yl)benzamide To a stirred solution of 3-(7-methyl-2-oxo-8-(trifluoromethyl)-2,3-dihydro-1H-benzo[b][1,4]diazepin-4-yl)benzamide (60 mg, 0.16 mmol) in EtOH (12 mL) was added platinum (IV)oxide (24 mg) at RT and stirred under H$_2$ atmosphere (balloon pressure) for 2 h. The progress of the reaction was monitored by TLC. After completion of the reaction, the reaction mixture was filtered under vacuum. The filtrate was concentrated under reduced pressure to obtain the crude product. The crude product was purified by silica gel column chromatography [Eluent: 3% MeOH/DCM] to afford the title compound (50 mg, 83%) as an off-white solid.

Example 168A: 3-(8-Methyl-4-oxo-7-(trifluoromethyl)-2,3,4,5-tetrahydro-1H-benzo[b][1,4]diazepin-2-yl)benzamide Enantiomer A; and Example 168B: 3-(8-Methyl-4-oxo-7-(trifluoromethyl)-2,3,4,5-tetrahydro-1H-benzo[b][1,4]diazepin-2-yl)benzamide Enantiomer B Chiral preparative HPLC of Enantiomers: The enantiomers of Example 168 (50 mg, 0.13 mmol) were separated by normal-phase preparative high performance liquid chromatography (Chiralpak IC, 250×4.6 mm, 5µ); (A) n-hexane (B) DCM:MeOH (80:20) (A:B: 65:35); Flow rate: 1.0 mL/min) to obtain enantiomer A (15 mg) and enantiomer B (15 mg) as off-white solids.

Analytical data for enantiomer A: $^1$H NMR (400 MHz, DMSO-$d_6$): δ 9.56 (s, 1H), 7.94 (s, 1H), 7.89 (s, 1H), 7.76 (d, J=7.6 Hz, 1H), 7.51 (d, J=8.0 Hz, 1H), 7.41 (t, J=7.6 Hz, 1H), 7.34 (s, 1H), 7.17 (s, 1H), 6.85 (s, 1H), 6.64-6.63 (m, 1H), 5.02-5.00 (m, 1H), 2.86-2.73 (m, 2H), 2.28 (s, 3H). Chiral HPLC: 99.5% R$_t$=19.72 min (Chiralpak IC, 250×4.6 mm, 5µ); mobile phase (A) n-Hexane (B) DCM:Methanol (80:20) (A:B: 65:35); flow Rate: 1.0 mL/min) MS (ESI): m/z 364 [M+1]$^+$ HPLC: 98.8%

Analytical data for enantiomer B: $^1$H NMR (400 MHz, DMSO-$d_6$): δ 9.56 (s, 1H), 7.94 (s, 1H), 7.89 (s, 1H), 7.76 (d, J=7.5 Hz, 1H), 7.51 (d, J=7.5 Hz, 1H), 7.41 (t, J=7.5 Hz, 1H) 7.34 (s, 1H), 7.16 (s, 1H), 6.85 (s, 1H), 6.64 (s, 1H), 5.03-4.99 (m, 1H), 2.85-2.81 (m, 1H), 2.76-2.74 (m, 1H), 2.28 (s, 3H). Chiral HPLC: 97.9% R$_t$=21.69 min (Chiralpak IC, 250×4.6 mm, 5µ); mobile phase (A) n-Hexane (B) DCM:Methanol (80:20) (A:B: 65:35); flow Rate: 1.0 mL/min) MS (ESI): m/z 364 [M+1]$^+$ HPLC: 99.8%.

Example 169: 3-(8-Methyl-7-(trifluoromethyl)-2,3,4,5-tetrahydro-1H-benzo[b][1,4]diazepin-2-yl)benzoic Acid

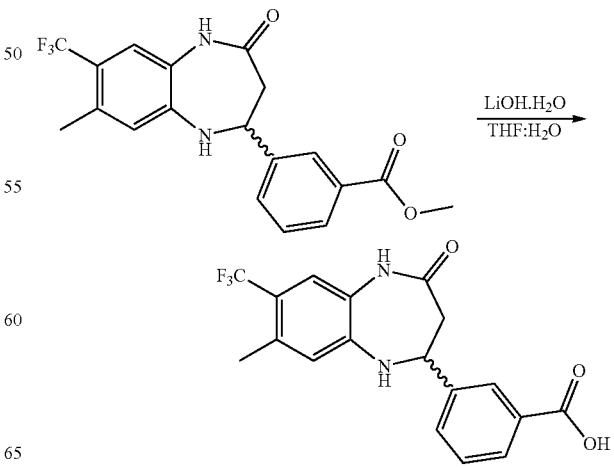

To a stirred solution of methyl 3-(8-methyl-4-oxo-7-(trifluoromethyl)-2,3,4,5-tetrahydro-1H-benzo[b][1,4]diazepin-2-yl)benzoate (Example 151) (150 mg, 0.39 mmol) in THF:H₂O (5:1; 6 mL) was added lithium hydroxide monohydrate (83.1 mg, 0.19 mmol) at RT and stirred for 12 h. The progress of the reaction was monitored by TLC. After completion of the reaction, the reaction mixture was acidified with saturated citric acid solution (pH-4) and extracted with EtOAc (2×30 mL). The combined organic extracts were washed with water (25 mL), dried over sodium sulfate, filtered and concentrated under reduced pressure to obtain the crude product. The crude material was triturated with n-pentane (2×5 mL) to afford the title compound (140 mg, 97%) as a pale yellow solid. ¹H NMR (400 MHz, DMSO-$d_6$): δ 12.93 (br s, 1H), 9.56 (s, 1H), 7.97 (s, 1H), 7.84-7.82 (m, 1H), 7.61 (d, J=8.0 Hz, 1H), 7.46 (t, J=7.6 Hz, 1H), 6.84 (s, 1H), 6.78 (s, 1H), 6.72-6.71 (m, 1H), 5.09-5.07 (m, 1H), 2.81-2.80 (m, 2H), 2.28 (s, 3H). MS (ESI): m/z 365 [M+1]⁺. HPLC: 91.14%.

Example 170: 3-(8-Methyl-4-oxo-7-(trifluoromethyl)-2,3,4,5-tetrahydro-1H-benzo[b][1,4]diazepin-2-yl)-N-(prop-2-yn-1-yl)benzamide (Racemate)

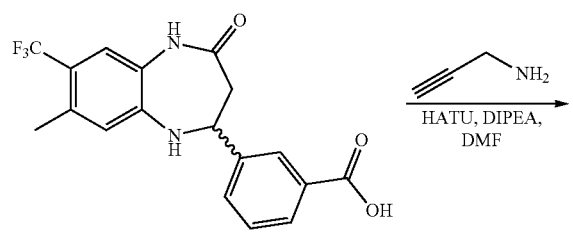

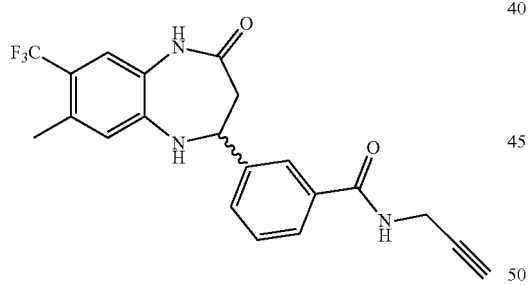

To a stirred solution 3-(8-methyl-7-(trifluoromethyl)-2,3,4,5-tetrahydro-1H-benzo[b][1,4]diazepin-2-yl)benzoic acid (Example 169) (25 mg, 0.06 mmol) in DMF (2 mL) under inert atmosphere were added DIPEA (44.3 mg, 0.34 mmol), HATU (40.1 mg, 0.10 mmol) and propargyl amine (5.6 mg, 0.10 mmol) at RT and stirred for 3 h. The progress of the reaction was monitored by TLC. After completion of the reaction, the reaction mixture was diluted with water (15 mL) and extracted with EtOAc (2×20 mL). The combined organic extracts were washed with brine solution (15 mL), dried over sodium sulfate, filtered and concentrated under reduced pressure to obtain the crude product. The crude product was purified by silica gel column chromatography [Eluent: 30% EtOAc/Hexanes] to afford the title compound (20 mg, 73%) as an off-white solid.

Example 170A: 3-(8-Methyl-4-oxo-7-(trifluoromethyl)-2,3,4,5-tetrahydro-1H-benzo[b][1,4]diazepin-2-yl)-N-(prop-2-yn-1-yl)benzamide Enantiomer A; and Example 170B: 3-(8-Methyl-4-oxo-7-(trifluoromethyl)-2,3,4,5-tetrahydro-1H-benzo[b][1,4]diazepin-2-yl)-N-(prop-2-yn-1-yl)benzamide Enantiomer B Chiral preparative HPLC of Enantiomers: The enantiomers of Example 170 (20 mg, 0.04 mmol) were separated by normal-phase preparative high performance liquid chromatography (Chiralpak IC, 250×4.6 mm, 5μ); (A) 0.1% DEA in n-hexane (B) DCM:MeOH (80:20) (A:B: 80:20); Flow rate: 1.0 mL/min) to obtain enantiomer A (30 mg) and enantiomer B (30 mg) as off white solids.

Analytical data for enantiomer A: ¹H NMR (400 MHz, DMSO-$d_6$): δ 9.57 (s, 1H), 8.90 (t, J=5.6 Hz, 1H), 7.88 (s, 1H), 7.74 (d, J=7.2 Hz, 1H), 7.54 (d, J=7.6 Hz, 1H), 7.44 (t, J=8.0 Hz, 1H), 7.17 (s, 1H), 6.86 (s, 1H), 6.65-6.64 (m, 1H), 5.03-4.99 (m, 1H), 4.05-4.03 (m, 2H), 3.10 (s, 1H), 2.84-2.80 (m, 1H), 2.50 (s, 3H). Chiral HPLC: 99.4% $R_t$=29.97 min (Chiralpak IC, 250×4.6 mm, 5μ); mobile phase (A) 0.1% DEA in n-Hexane (B) DCM:Methanol (80:20) (A:B: 80:20); flow Rate: 1.0 mL/min) MS (ESI): m/z 402 [M+1]⁺ HPLC: 99.4%

Analytical data for enantiomer B: ¹H NMR (400 MHz, DMSO-$d_6$): δ 9.57 (s, 1H), 8.90 (t, J=5.6 Hz, 1H), 7.88 (s, 1H), 7.74 (d, J=8.0 Hz, 1H), 7.54 (d, J=8.0 Hz, 1H), 7.44 (t, J=8.0 Hz, 1H), 7.16 (s, 1H), 6.86 (s, 1H), 6.65-6.64 (m, 1H), 5.02-4.99 (m, 1H), 4.05-4.03 (m, 2H), 3.10 (s, 1H), 2.86-2.80 (m, 1H), 2.28 (s, 3H). Chiral HPLC: 99.3% $R_t$=32.54 min (Chiralpak IC, 250×4.6 mm, 5μ); mobile phase (A) 0.1% DEA in n-Hexane (B) DCM:Methanol (80:20) (A:B: 80:20); flow Rate: 1.0 mL/min) MS (ESI): m/z 402 [M+1]⁺ HPLC: 99.6%

Example 171: Benzyl (3-(3-(8-methyl-4-oxo-7-(trifluoromethyl)-2,3,4,5-tetrahydro-1H-benzo[b][1,4]diazepin-2-yl)phenyl)propyl)carbamate

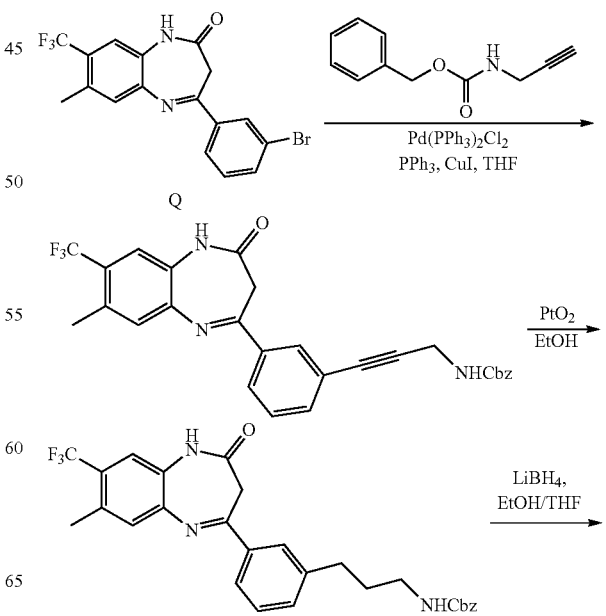

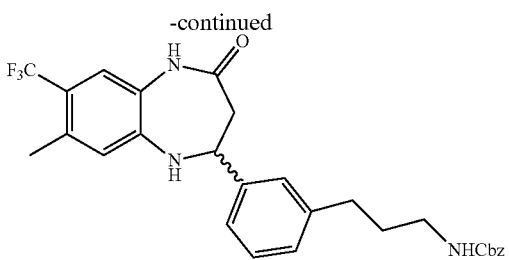

Step 1: Benzyl (3-(3-(7-methyl-2-oxo-8-(trifluoromethyl)-2,3-dihydro-1H-benzo[b][1,4]diazepin-4-yl)phenyl)prop-2-yn-1-yl)carbamate To a stirred solution of compound Q (160 mg, 0.40 mmol) in THF (10 mL) under inert atmosphere were added compound benzyl prop-2-yn-1-ylcarbamate (152 mg, 0.80 mmol), copper iodide (1.5 mg, 0.008 mmol), triphenyl phosphine (5.2 mg, 0.002 mmol) and triethyl amine (183 mg, 1.81 mmol) at RT and purged under argon for 30 min. Then Pd(PPh$_3$)$_2$Cl$_2$ (14 mg, 0.002 mmol) was added to the reaction mass and again purged for another 10 min. The reaction mixture was heated to 60° C. and stirred for 24 h. The progress of the reaction was monitored by TLC. After completion of the reaction, the reaction mixture was diluted with water (20 mL) and extracted with ethyl acetate (2×20 mL). The combined organic extracts were washed with water (15 mL), dried over sodium sulfate, filtered and concentrated under reduced pressure to obtain the crude product. The crude product was purified by silica gel column chromatography [Eluent: 20% EtOAc/Hexanes] to afford benzyl (3-(3-(7-methyl-2-oxo-8-(trifluoromethyl)-2,3-dihydro-1H-benzo[b][1,4]diazepin-4-yl)phenyl)prop-2-yn-1-yl)carbamate (60 mg, 30%) as a pale yellow solid. $^1$H NMR (400 MHz, DMSO-d$_6$): δ 10.71 (s, 1H), 8.08-8.06 (m, 2H), 7.86-7.84 (m, 1H), 7.64-7.61 (m, 5H), 7.58-7.48 (m, 2H), 7.37-7.31 (m, 2H), 5.07 (s, 2H), 4.11-4.10 (m, 2H), 3.57 (s, 2H), 2.50 (s, 3H).

Step 2: Benzyl (3-(3-(7-methyl-2-oxo-8-(trifluoromethyl)-2,3-dihydro-1H-benzo[b][1,4]diazepin-4-yl)phenyl)propyl)carbamate To a stirred solution of benzyl (3-(3-(7-methyl-2-oxo-8-(trifluoromethyl)-2,3-dihydro-1H-benzo[b][1,4]diazepin-4-yl)phenyl)prop-2-yn-1-yl)carbamate (60 mg, 0.11 mmol) in EtOH (10 mL) was added platinum (IV) oxide (15 mg) and stirred at RT under H$_2$ atmosphere (balloon pressure) for 3 h. The progress of the reaction was monitored by TLC. After completion of the reaction, the reaction mixture was filtered under vacuum. The filtrate was concentrated under reduced pressure to obtain the crude product. The crude product was purified by silica gel column chromatography [Eluent: 30% EtOAc/Hexanes] to afford benzyl (3-(3-(7-methyl-2-oxo-8-(trifluoromethyl)-2,3-dihydro-1H-benzo[b][1,4]diazepin-4-yl)phenyl)propyl)carbamate (20 mg, 33%) as pale yellow solid. $^1$H NMR (400 MHz, DMSO-d$_6$): δ 10.66 (s, 1H), 7.93-7.88 (m, 2H), 7.55-7.43 (m, 4H), 7.38-7.31 (m, 6H), 5.02 (s, 2H), 3.57 (s, 2H), 3.07-3.02 (m, 2H), 2.69-2.65 (m, 2H), 2.50-2.45 (m, 3H), 1.78-1.71 (m, 2H).

Step 3: Benzyl (3-(3-(8-methyl-4-oxo-7-(trifluoromethyl)-2,3,4,5-tetrahydro-1H-benzo[b][1,4]diazepin-2-yl)phenyl)propyl)carbamate To a stirred solution of lithium chloride (8.3 mg, 1.95 mmol) in EtOH (5 mL) under inert atmosphere was added sodium borohydride (7.4 mg, 1.95 mmol) at RT. After being stirred for 1 h; a solution of benzyl (3-(3-(7-methyl-2-oxo-8-(trifluoromethyl)-2,3-dihydro-1H-benzo[b][1,4]diazepin-4-yl)phenyl)propyl)carbamate (20 mg, 0.39 mmol) in dry THF (5 mL) was added drop wise to the reaction mixture and stirring was continued for 24 h. The progress of the reaction was monitored by TLC. After completion of the reaction, the reaction mixture was diluted with water (10 mL) and extracted with EtOAc (2×15 mL). The combined organic extracts were washed with water (10 mL), dried over sodium sulfate, filtered and concentrated under reduced pressure to obtain the crude product. The crude product was purified by silica gel column chromatography [Eluent: 30% EtOAc/Hexanes] to afford the title compound (4 mg, 20%) as a pale yellow solid. $^1$H NMR (400 MHz, CD$_3$OD-d$_4$): δ 7.33-7.19 (m, 9H), 6.12-6.10 (m, 1H), 6.83 (s, 1H), 5.05 (s, 2H), 4.97-4.95 (m, 1H), 3.12-3.09 (m, 2H), 2.90-2.86 (m, 1H), 2.88-2.78 (m, 1H), 2.64-2.61 (m, 2H), 2.34-2.33 (m, 3H), 1.83-1.77 (m, 2H). MS (ESI): m/z 512 [M+1]$^+$ HPLC: 94.1%.

Example 172: 7-Methyl-8-(trifluoromethyl)-4-(3-(3-(trifluoromethyl)phenoxy)phenyl)-4,5-dihydro-1H-benzo[b][1,4]diazepin-2(3H)-one

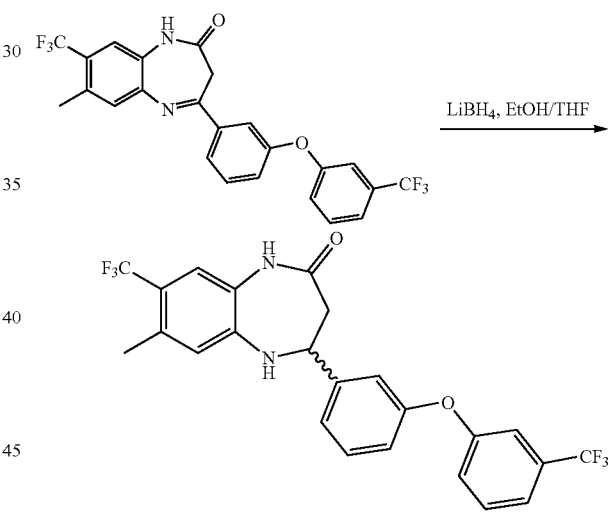

To a stirred solution of lithium chloride (26.6 mg, 0.62 mmol) in EtOH (10 mL) under inert atmosphere was added sodium borohydride (23.7 mg, 0.62 mmol) at RT. After being stirred for 1 h, a solution of 7-methyl-8-(trifluoromethyl)-4-(3-(3-(trifluoromethyl)phenoxy)phenyl)-1H-benzo[b][1,4]diazepin-2(3H)-one (Example 147) (100 mg, 0.20 mmol) in dry THF (10 mL) was added drop wise to the reaction mixture and stirring was continued for 12 h. The progress of the reaction was monitored by TLC. After completion of the reaction volatiles were removed, the reaction mixture was diluted with water (20 mL) and extracted with EtOAc (2×25 mL). The combined organic extracts were washed with water (20 mL), dried over sodium sulfate, filtered and concentrated under reduced pressure to obtain the crude product. The crude product was purified by silica gel column chromatography [Eluent: 30% EtOAc/Hexanes] to afford the title compound (60 mg, 60%) as a pale yellow solid.

Example 172A: 7-Methyl-8-(trifluoromethyl)-4-(3-(3-(trifluoromethyl)phenoxy)phenyl)-4,5-dihydro-1H-benzo[b][1,4]diazepin-2(3H)-one Enantiomer A; and Example 172B: 7-Methyl-8-(trifluoromethyl)-4-(3-(3-(trifluoromethyl)phenoxy)phenyl)-4,5-dihydro-1H-benzo[b][1,4]diazepin-2(3H)-one Enantiomer B Chiral preparative HPLC of Enantiomers: The enantiomers of Example 172 (60 mg, 0.12 mmol) were separated by normal-phase preparative high performance liquid chromatography (Chiralpak IA, 250×4.6 mm, 5μ); (A) 0.1% DEA in n-hexane (B) DCM:MeOH (80:20) (A:B: 88:12); Flow rate: 1.0 mL/min) to obtain enatiomer A (15 mg) and enatiomer B (15 mg) as pale yellow solids.

Analytical data for enatiomer A: $^1$H NMR (400 MHz, DMSO-$d_6$): δ 9.55 (s, 1H), 7.62-7.58 (m, 1H), 7.46 (d, J=7.6 Hz, 1H), 7.41 (t, J=8.0 Hz, 1H), 7.29-7.21 (m, 3H), 7.13 (d, J=8.8 Hz, 2H), 7.00-6.97 (m, 1H), 6.78 (s, 1H), 6.67-6.66 (m, 1H), 5.01-4.99 (m, 1H), 2.80-2.70 (m, 2H), 2.24 (s, 3H). Chiral HPLC: 99.9% $R_t$=18.80 min (Chiralpak IA, 250×4.6 mm, 5μ); mobile phase (A) 0.1% DEA in n-Hexane (B) DCM:MeOH (80:20) (A:B: 88:12); flow Rate: 1.0 mL/min) MS (ESI): m/z 481 [M+1]$^+$ HPLC: 99.3%.

Analytical data for enatiomer B: $^1$H NMR (400 MHz, DMSO-$d_6$): δ 9.55 (s, 1H), 7.62-7.58 (m, 1H), 7.46 (d, J=8.0 Hz, 1H), 7.41 (t, J=8.0 Hz, 1H), 7.29-7.21 (m, 3H), 7.14-7.12 (m, 2H), 7.00-6.97 (m, 1H), 6.79 (s, 1H), 6.67-6.66 (m, 1H), 5.02-4.98 (m, 1H), 2.80-2.73 (m, 2H), 2.24 (s, 3H). Chiral HPLC: 99.9% $R_t$=25.70 min (Chiralpak IA, 250×4.6 mm, 5μ); mobile phase (A) 0.1% DEA in n-Hexane (B) DCM:MeOH (80:20) (A:B: 88:12); flow Rate: 1.0 mL/min) MS (ESI): m/z 481 [M+1]$^+$ HPLC: 98.5%.

Example 173: 4-(3-(3-Bromophenoxy)phenyl)-7-methyl-8-(trifluoromethyl)-4,5-dihydro-1H-benzo[b][1,4]diazepin-2(3H)-one

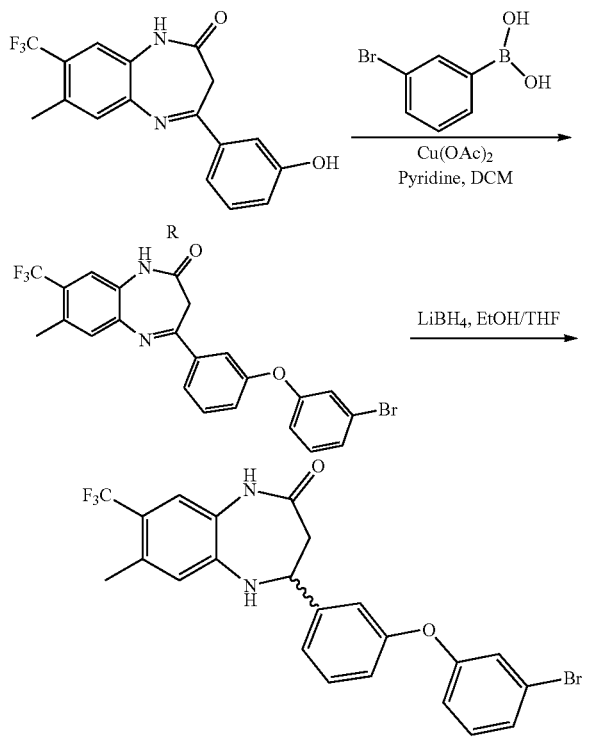

Step 1: 4-(3-(3-Bromophenoxy)phenyl)-7-methyl-8-(trifluoromethyl)-1H-benzo[b][1,4]diazepin-2(3H)-one To a stirred solution of molecular sieves (1.5 g) in CH$_2$Cl$_2$ (20 mL) under inert atmosphere were added compound R (150 mg, 0.44 mmol), (3-bromophenyl) boronic acid (135.2 mg, 0.67 mmol), copper acetate (134.4 mg, 0.67 mmol) and pyridine (177.3 mg 2.24 mmol) at RT and stirred under O$_2$ atmosphere for 12 h. The progress of the reaction was monitored by TLC. After completion of the reaction, the reaction mixture was filtered under vacuum and the filtrate was concentrated under reduced pressure to obtain the crude product. The crude product was purified by silica gel column chromatography [Eluent: 8% EtOAc/Hexanes] to afford 4-(3-(3-bromophenoxy)phenyl)-7-methyl-8-(trifluoromethyl)-1H-benzo[b][1,4]diazepin-2(3H)-one (100 mg, 46%) as a pale-yellow solid. $^1$H NMR (400 MHz, DMSO-$d_6$): δ 10.69 (s, 1H), 7.89 (d, J=8.8 Hz, 1H), 7.75-7.55 (m, 1H), 7.61 (t, J=8.0 Hz, 1H), 7.50 (s, 1H), 7.45 (s, 1H), 7.38-7.36 (m, 2H), 7.30-7.28 (m, 2H), 7.08-7.05 (m, 1H), 3.58-3.56 (m, 2H), 2.50 (s, 3H). MS (ESI): m/z 490 [M+2]$^+$ HPLC: 98.6%.

Step 2: 4-(3-(3-Bromophenoxy)phenyl)-7-methyl-8-(trifluoromethyl)-4,5-dihydro-1H-benzo[b][1,4]diazepin-2(3H)-one To a stirred solution of lithium chloride (26 mg, 0.61 mmol) in EtOH (5 mL) under inert atmosphere was added sodium borohydride (23.1 mg, 0.61 mmol) at RT. After being stirred for 1 h; a solution of 4-(3-(3-bromophenoxy)phenyl)-7-methyl-8-(trifluoromethyl)-1H-benzo[b][1,4]diazepin-2(3H)-one (100 mg, 0.20 mmol) in ethanol (10 mL) was added drop wise to the reaction mixture and stirring was continued for 12 h. The progress of the reaction was monitored by TLC. After completion of the reaction, the volatiles were evaporated under reduced pressure and the residue was diluted with water (25 mL) and extracted with EtOAc (2×20 mL). The combined organic extracts were washed with water (20 mL), dried over sodium sulfate, filtered and concentrated under reduced pressure to obtain the crude product. The crude product was purified by silica gel column chromatography [Eluent: 30% EtOAc/Hexanes] to afford the title compound (75 mg, 75%) as a pale yellow solid.

Example 173A: 4-(3-(3-Bromophenoxy)phenyl)-7-methyl-8-(trifluoromethyl)-4,5-dihydro-1H-benzo[b][1,4]diazepin-2(3H)-one Enantiomer A; and Example 173B: 4-(3-(3-Bromophenoxy)phenyl)-7-methyl-8-(trifluoromethyl)-4,5-dihydro-1H-benzo[b][1,4]diazepin-2(3H)-one Enantiomer B Chiral preparative HPLC of Enantiomers: The enantiomers of Example 173 (75 mg, 0.15 mmol) were separated by normal-phase preparative high performance liquid chromatography (Chiralpak IA, 250×4.6 mm, 5μ); (A) 0.1% DEA in n-hexane (B) DCM:MeOH (80:20) (A:B: 85:15); Flow rate: 1.0 mL/min) to obtain enantiomer A (25 mg) and enantiomer B (25 mg) as pale yellow solids.

Analytical data for enantiomer A: $^1$H NMR (400 MHz, DMSO-$d_6$): δ 9.55 (s, 1H), 7.40 (t, J=8.0 Hz, 1H), 7.34-7.31 (m, 2H), 7.20 (d, J=7.6 Hz, 1H), 7.16 (d, J=6.4 Hz, 1H), 7.10 (s, 1H), 6.99-6.98 (m, 1H), 6.80 (s, 1H), 6.65-6.64 (m, 1H), 5.00-4.98 (m, 1H), 2.79-2.75 (m, 2H), 2.25 (s, 3H). Chiral HPLC: 100% $R_t$=18.08 min (Chiralpak IA, 250×4.6 mm, 5μ); mobile phase (A) 0.1% DEA in n-Hexane (B) DCM: MeOH (80:20) (A:B: 85:15); flow Rate: 1.0 mL/min) MS (ESI): m/z 491 [M]+ HPLC: 98.6%.

Analytical data for enantiomer B: $^1$H NMR (400 MHz, DMSO-$d_6$): δ 9.56 (s, 1H), 7.40 (t, J=8.0 Hz, 1H), 7.34-7.29 (m, 2H), 7.22-7.18 (m, 4H), 7.16 (d, J=7.6 Hz, 1H), 7.10 (s, 1H), 6.79 (s, 1H), 6.66-6.65 (m, 1H), 5.00-4.98 (m, 1H), 2.79-2.75 (m, 2H), 2.25 (s, 3H). Chiral HPLC: 99.9% $R_t$=24.98 min (Chiralpak IA, 250×4.6 mm, 5μ); mobile phase (A) 0.1% DEA in n-Hexane (B) DCM; MeOH (80:20) (A:B: 85:15); flow Rate: 1.0 mL/min) MS (ESI): m/z 491 [M]+ HPLC: 97.1%.

Example 174: 4-(3-(3,5-Difluorophenoxy)phenyl)-7-methyl-8-(trifluoromethyl)-4,5-dihydro-1H-benzo[b][1,4]diazepin-2(3H)-one

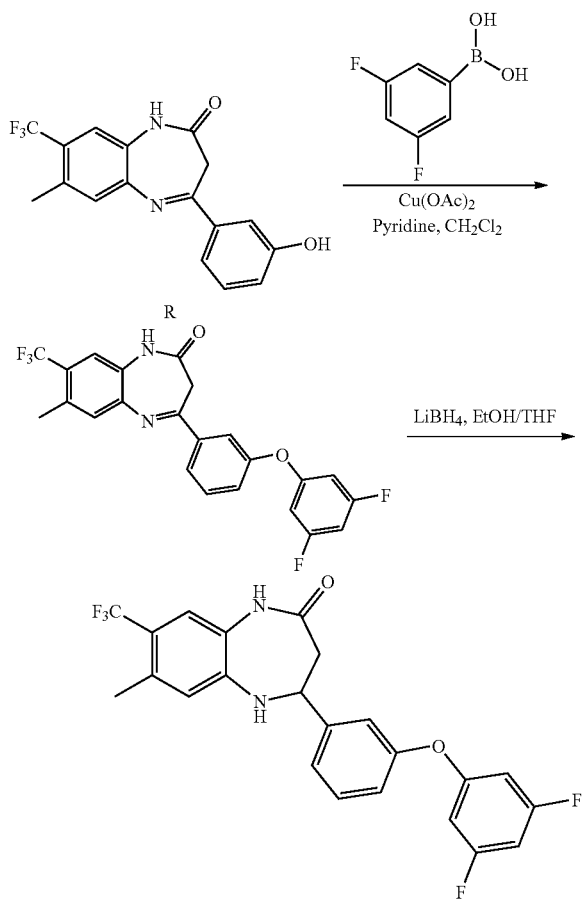

Step 1: 4-(3-(3,5-Difluorophenoxy)phenyl)-7-methyl-8-(trifluoromethyl)-1H-benzo[b][1,4]diazepin-2(3H)-one To a stirred solution of molecular sieves (2 g) in DCM (20 mL) under inert atmosphere were added compound R (200 mg, 0.59 mmol), (3,5-difluorophenyl) boronic acid (141.9 mg, 0.89 mmol), copper acetate (179.2 mg, 0.89 mmol) and pyridine (236.5 mg, 2.99 mmol) at RT and stirred under $O_2$ atmosphere for 15 h. The progress of the reaction was monitored by TLC. After completion of the reaction, the reaction mixture was filtered under vacuum and the filtrate was concentrated under reduced pressure to obtain the crude product. The crude product was purified by silica gel column chromatography [Eluent: 7% EtOAc/Hexanes] to afford 4-(3-(3,5-difluorophenoxy)phenyl)-7-methyl-8-(trifluoromethyl)-1H-benzo[b][1,4]diazepin-2(3H)-one (125 mg, 45%) as pale-yellow solid. $^1$H NMR (400 MHz, DMSO-$d_6$): δ 10.70 (s, 1H), 7.94 (d, J=8.0 Hz, 1H), 7.80 (s, 1H), 7.62 (t, J=8.4 Hz, 1H), 7.51-7.49 (m, 2H), 7.36 (d, J=8.0 Hz, 1H), 7.06-7.04 (m, 1H), 6.80 (d, J=7.5 Hz, 2H), 3.60 (s, 2H), 2.50 (s, 3H). MS (ESI): m/z 447 [M+1]+ HPLC: 90.0%.

Step 2: 4-(3-(3,5-Difluorophenoxy)phenyl)-7-methyl-8-(trifluoromethyl)-4,5-dihydro-1H-benzo[b][1,4]diazepin-2(3H)-one To a stirred solution of lithium chloride (31.3 mg, 0.73 mmol) in EtOH (10 mL) under inert atmosphere was added sodium borohydride (27.9 mg, 0.73 mmol) at RT. After being stirred for 1 h; a solution of 4-(3-(3,5-difluorophenoxy)phenyl)-7-methyl-8-(trifluoromethyl)-1H-benzo[b][1,4]diazepin-2(3H)-one (110 mg, 0.24 mmol) in dry THF (8 mL) was added drop wise to the reaction mixture and stirring was continued for 12 h. The progress of the reaction was monitored by TLC. After completion of the reaction, the reaction mixture was diluted with water (30 mL) and extracted with EtOAc (2×20 mL). The combined organic extracts were washed with water (20 mL), dried over sodium sulfate, filtered and concentrated under reduced pressure to obtain the crude product. The crude product was purified by silica gel column chromatography [Eluent: 25% EtOAc/Hexanes] to afford the title compound (90 mg, 82%) as a pale yellow solid.

Example 174A: 4-(3-(3,5-Difluorophenoxy)phenyl)-7-methyl-8-(trifluoromethyl)-4,5-dihydro-1H-benzo[b][1,4]diazepin-2(3H)-one Enantiomer A; and
Example 174B: 4-(3-(3,5-Difluorophenoxy)phenyl)-7-methyl-8-(trifluoromethyl)-4,5-dihydro-1H-benzo[b][1,4]diazepin-2(3H)-one Enantiomer B Chiral preparative HPLC of Enantiomers: The enantiomers of Example 174 (90 mg, 0.20 mmol) were separated by normal-phase preparative high performance liquid chromatography (Chiralpak IA, 250×4.6 mm, 5μ); (A) 0.1% DEA in n-hexane (B) DCM:MeOH (80:20) (A:B: 85:15); Flow rate: 1.0 mL/min) to obtain enantiomer A (20 mg) and enantiomer B (20 mg) as pale yellow solids.

Analytical data for enantiomer A: $^1$H NMR (400 MHz, DMSO-$d_6$): δ 9.56 (s, 1H), 7.42 (t, J=8.0 Hz, 1H), 7.25 (d, J=7.6 Hz, 1H), 7.15 (s, 2H), 7.04-6.94 (m, 2H), 6.80 (s, 1H), 6.70-6.66 (m, 3H), 5.03-5.00 (m, 1H), 2.84-2.74 (m, 2H), 2.25 (s, 3H). Chiral HPLC: 99.8% $R_t$=15.64 min (Chiralpak IA, 250×4.6 mm, 5μ); mobile phase (A) 0.1% DEA in n-Hexane (B) DCM:MeOH (80:20) (A:B: 85:15); flow Rate: 1.0 mL/min) MS (ESI): m/z 449 [M+1]+ HPLC: 98.8%.

Analytical data for enantiomer B: $^1$H NMR (400 MHz, DMSO-$d_6$): δ 9.56 (s, 1H), 7.42 (t, J=8.0 Hz, 1H), 7.25 (d, J=7.6 Hz, 1H), 7.15 (s, 2H), 7.04-6.94 (m, 2H), 6.80 (s, 1H), 6.70-6.66 (m, 3H), 5.02-5.00 (m, 1H), 2.91-2.73 (m, 2H), 2.25 (s, 3H). Chiral HPLC: 99.6% $R_t$=20.19 min (Chiralpak IA, 250×4.6 mm, 5μ); mobile phase (A) 0.1% DEA in n-Hexane (B) DCM:MeOH (80:20) (A:B: 85:15); flow Rate: 1.0 mL/min) MS (ESI): m/z 449 [M+1]+ HPLC: 99.6%.

Example 175: 4-(3-Ethynylphenyl)-7-methyl-8-(trifluoromethyl)-4,5-dihydro-1H-benzo[b][1,4]diazepin-2(3H)-one

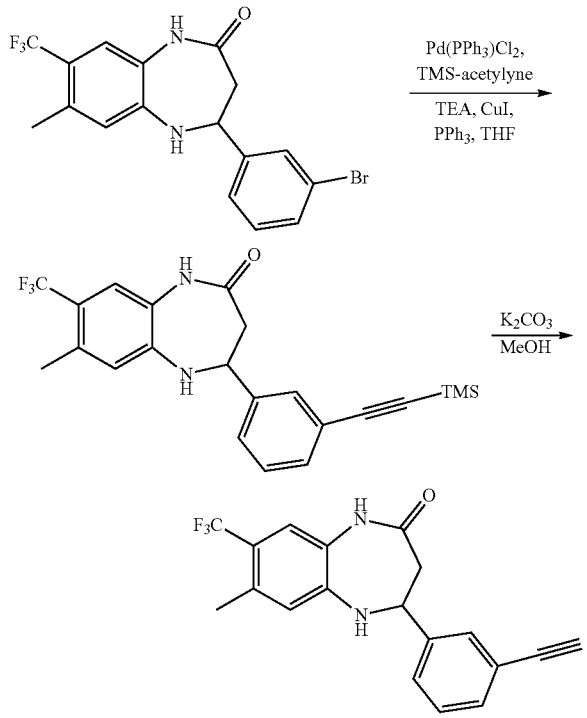

Step 1: 7-methyl-8-(trifluoromethyl)-4-(3-((trimethylsilyl)ethynyl)phenyl)-4,5-dihydro-1H-benzo[b][1,4]diazepin-2(3H)-one To a stirred solution of 4-(3-bromophenyl)-7-methyl-8-(trifluoromethyl)-4,5-dihydro-1H-benzo[b][1,4]diazepin-2(3H)-one (Example 166, Step 1) (204 mg, 0.51 mmol) in THF (3 mL) under inert atmosphere were added TMS acetylene (100 mg, 1.02 mmol), copper iodide (1.9 mg, 0.01 mmol), triphenyl phosphine (6.7 mg, 0.02 mmol) and triethyl amine (232.2 mg, 2.29 mmol) at RT and purged with argon for 30 min. Then Pd(PPh$_3$)Cl$_2$ (17.9 mg, 0.02 mmol) was added to the reaction mixture and again purged for another 10 min; heated to 60° C. and stirred for 48 h. The progress of the reaction was monitored by TLC. After completion of the reaction, the reaction mixture was diluted with 5% citric acid solution (10 mL) and extracted with EtOAc (2×30 mL). The combined organic extracts were washed with water (20 mL), dried over sodium sulfate, filtered and concentrated under reduced pressure to obtain the crude product. The crude product was purified by silica gel column chromatography [Eluent: 5% EtOAc/Hexanes] to afford 7-methyl-8-(trifluoromethyl)-4-(3-((trimethylsilyl)ethynyl)phenyl)-4,5-dihydro-1H-benzo[b][1,4]diazepin-2(3H)-one (130 mg, 61%) as an off-white solid. $^1$H NMR (500 MHz, DMSO-d$_6$): δ 9.54 (s, 1H), 7.45 (s, 1H), 7.38-7.37 (m, 1H), 7.34-7.33 (m, 2H), 7.14 (s, 1H), 6.82 (s, 1H), 6.65-6.64 (m, 1H), 4.99-4.97 (m, 1H), 2.79-2.78 (m, 2H), 2.36 (s, 3H), 0.02 (s, 9H).

Step 2: 4-(3-Ethynylphenyl)-7-methyl-8-(trifluoromethyl)-4,5-dihydro-1H-benzo[b][1,4]diazepin-2(3H)-one (Racemic)

To a stirred solution of compound 7-methyl-8-(trifluoromethyl)-4-(3-((trimethylsilyl)ethynyl)phenyl)-4,5-dihydro-1H-benzo[b][1,4]diazepin-2(3H)-one (130 mg, 0.31 mmol) in MeOH (10 mL) under inert atmosphere was added potassium carbonate (86.2 mg, 0.62 mmol) at 0° C. The reaction mixture was warmed to RT and stirred for 30 min. The progress of the reaction was monitored by TLC. After completion of the reaction, the reaction mixture was diluted with water (20 mL) and extracted with EtOAc (2×20 mL). The combined organic extracts were washed with water (20 mL), dried over sodium sulfate, filtered and concentrated under reduced pressure to obtain the crude product. The crude product was purified by silica gel column chromatography [Eluent: 30% EtOAc/Hexanes] to afford the title compound (70 mg, 65%) as an off-white solid.

Example 175A: 4-(3-Ethynylphenyl)-7-methyl-8-(trifluoromethyl)-4,5-dihydro-1H-benzo[b][1,4]diazepin-2(3H)-one Enantiomer A; and Example 175B: 4-(3-Ethynylphenyl)-7-methyl-8-(trifluoromethyl)-4,5-dihydro-1H-benzo[b][1,4]diazepin-2(3H)-one Enantiomer B Chiral preparative HPLC of Enantiomers: The enantiomers of Example 175 (70 mg, 0.20 mmol) were separated by normal-phase preparative high performance liquid chromatography (Chiralpak IA, 250×4.6 mm, 5µ); (A) 0.1% DEA in n-hexane (B) DCM:MeOH (80:20) (A:B: 80:20; Flow rate: 1.0 mL/min) to obtain enantiomer A (30 mg) and enantiomer B (30 mg) as off-white solids.

Analytical data for enantiomer A: $^1$H NMR (500 MHz, DMSO-d$_6$): δ 9.55 (s, 1H), 7.46 (br s, 1H), 7.38-7.34 (m, 3H), 7.14 (s, 1H), 6.82 (s, 1H), 6.67-6.64 (m, 1H), 5.08-5.03 (m, 1H), 4.15 (s, 1H), 2.83-2.75 (m, 2H), 2.26 (s, 3H). Chiral HPLC: 100% R$_t$=11.94 min (Chiralpak IA, 250×4.6 mm, 5µ); mobile phase (A) 0.1% DEA in n-Hexane (B) DCM:Methanol (80:20) (A:B: 80:20); flow Rate: 1.0 mL/min) MS (ESI): m/z 345 [M+1]$^+$ HPLC: 97.4%

Analytical data for enantiomer B: $^1$H NMR (500 MHz, DMSO-d$_6$): δ 9.55 (s, 1H), 7.46 (br s, 1H), 7.38-7.34 (m, 3H), 7.14 (s, 1H), 6.82 (s, 1H), 6.67-6.64 (m, 1H), 5.01-4.98 (m, 1H), 4.19 (s, 1H), 2.81-2.76 (m, 2H), 2.26 (s, 3H). Chiral HPLC: 99.7% R$_t$=15.27 min (Chiralpak IA, 250×4.6 mm, 5µ); mobile phase (A) 0.1% DEA in n-Hexane (B) DCM:Methanol (80:20) (A:B: 80:20); flow Rate: 1.0 mL/min) MS (ESI): m/z 345 [M+1]$^+$ HPLC: 95.7%

Example 176: 4-(3-Benzylphenyl)-7-methyl-8-(trifluoromethyl)-4,5-dihydro-1H-benzo[b][1,4]diazepin-2(3H)-one (Racemate)

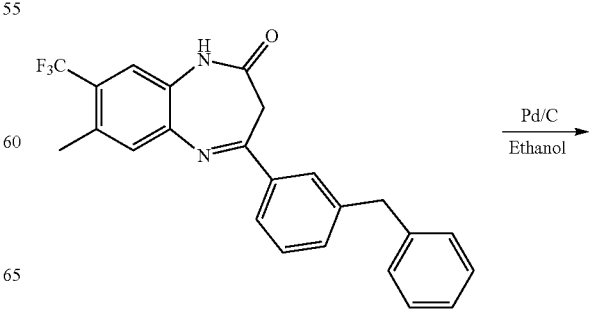

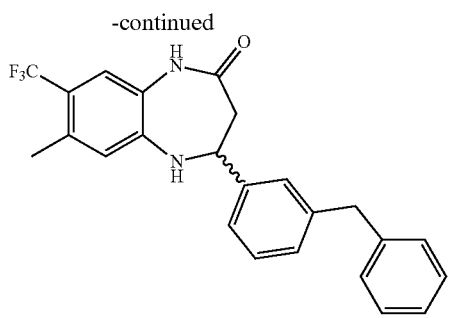

To a stirred solution of 4-(3-benzylphenyl)-8-(trifluoromethyl)-1H-benzo[b][1,4]diazepin-2-(3H)-one (Example 142) (50 mg, 0.12 mmol) in EtOH (10 mL) under inert atmosphere was added Pd/C (10 mg) at RT and stirred under $H_2$ atmosphere (balloon pressure) for 4 h. The progress of the reaction was monitored by TLC. After completion of the reaction, the reaction mixture was filtered under vacuum. The filtrate was diluted with water (20 mL) and extracted with EtOAc (2×15 mL). The combined organic extracts were washed with water (20 mL), dried over sodium sulfate, filtered and concentrated under reduced pressure to afford the title compound (40 mg, 80%) as pale yellow solid.

Example 176A: 4-(3-Benzylphenyl)-7-methyl-8-(trifluoromethyl)-4,5-dihydro-1H-benzo[b][1,4]diazepin-2(3H)-one Enantiomer; and Example 176B: 4-(3-Benzylphenyl)-7-methyl-8-(trifluoromethyl)-4,5-dihydro-1H-benzo[b][1,4]diazepin-2(3H)-one Enantiomer B Chiral preparative HPLC of Enantiomers: The enantiomers of Example 176 (40 mg, 0.09 mmol) were separated by normal-phase preparative high performance liquid chromatography (Chiralpak IA, 250×4.6 mm, 5 μm); (A) 0.1% DEA in n-hexane (B) DCM:MeOH (80:20) (A:B: 75:25; Flow rate: 1.0 mL/min) to obtain enatiomer (5 mg) and enatiomer B (15 mg) as off-white solids.

Analytical data for enatiomer A: $^1$H NMR (400 MHz, DMSO-$d_6$): δ 9.56 (s, 1H), 7.36-7.10 (m, 9H), 6.81 (s, 1H), 6.55-6.54 (m, 1H), 4.91-4.89 (m, 1H), 4.14-4.12 (m, 1H), 3.92 (s, 2H), 2.81-2.76 (m, 1H), 2.68-2.64 (m, 1H), 2.26 (s, 3H). Chiral HPLC: 100% $R_t$=8.13 min (Chiralpak IA, 250× 4.6 mm, 5μ); mobile phase (A) 0.1% DEA in n-Hexane (B) DCM:Methanol (80:20) (A:B: 75:25); flow Rate: 1.0 mL/min) MS (ESI): m/z 411 [M+1]$^+$ HPLC: 91.8%

Analytical data for enatiomer B: $^1$H NMR (400 MHz, DMSO-$d_6$): δ 9.56 (s, 1H), 7.28-7.10 (m, 9H), 6.81 (s, 1H), 6.55-6.54 (m, 1H), 4.91-4.89 (m, 1H), 4.14-4.12 (m, 1H), 3.92 (s, 2H), 2.81-2.76 (m, 1H), 2.68-2.64 (m, 1H), 2.26 (s, 3H). Chiral HPLC: 99.9% $R_t$=12.30 min (Chiralpak IA, 250×4.6 mm, 5μ); mobile phase (A) 0.1% DEA in n-Hexane (B) DCM:Methanol (80:20) (A:B: 75:25); flow Rate: 1.0 mL/min) MS (ESI): m/z 411 [M+1]$^+$ HPLC: 93.6%.

Example 177: 7-Methyl-4-(3-phenoxyphenyl)-8-(trifluoromethyl)-4,5-dihydro-1H-benzo[b][1,4]diazepin-2(3H)-one

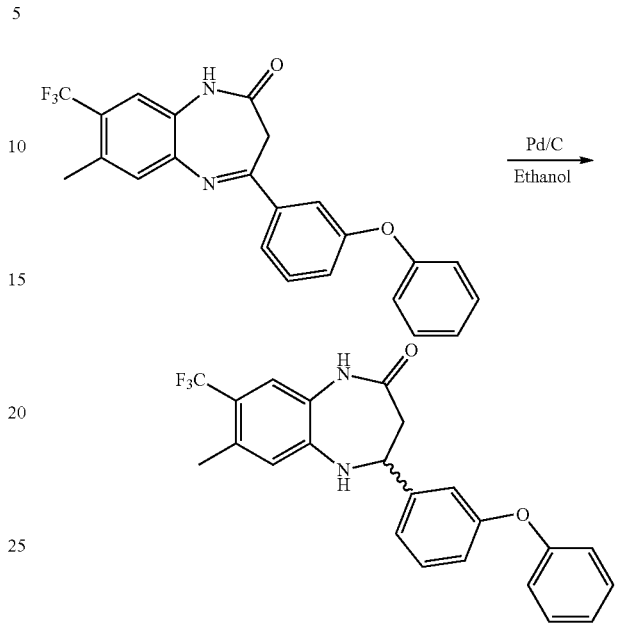

To a stirred solution of 7-methyl-4-(3-phenoxyphenyl)-8-(trifluoromethyl)-1H-benzo[b][1,4]diazepin-2(3H)-one (50 mg, 0.12 mmol) in EtOH (10 mL) under inert atmosphere was added Pd/C (15 mg) at RT and stirred at RT under $H_2$ atmosphere (balloon pressure) for 1 h. The progress of the reaction was monitored by TLC. After completion of the reaction, the reaction mixture was filtered under vacuum. The filtrate was concentrated under reduced pressure to obtain the crude product. The crude product was purified by silica gel column chromatography [Eluent: 20% EtOAc/Hexanes] to afford 3 (racemate, 45 mg, 90%) as pale yellow solid.

Example 177A: 7-Methyl-4-(3-phenoxyphenyl)-8-(trifluoromethyl)-4,5-dihydro-1H-benzo[b][1,4]diazepin-2(3H)-one Enantiomer A; and Example 177B: 7-Methyl-4-(3-phenoxyphenyl)-8-(trifluoromethyl)-4,5-dihydro-1H-benzo[b][1,4]diazepin-2(3H)-one Enantiomer B Chiral preparative HPLC of Enantiomers: The enantiomers of Example 177 (45 mg, 0.10 mmol) were separated by normal-phase preparative high performance liquid chromatography (Chiralpak IA, 250×4.6 mm, 5μ); (A) 0.1% DEA in n-hexane (B) DCM:MeOH (80:20) (A:B: 75:25; Flow rate: 1.0 mL/min) to obtain enantiomer A (15 mg) enantiomer B (15 mg) as pale yellow solids.

Analytical data for enantiomer A: $^1$H NMR (500 MHz, DMSO-$d_6$): δ 9.54 (s, 1H), 7.35 (d, J=8.0 Hz, 3H), 7.13-7.09 (m, 3H), 7.04 (br s, 1H), 6.97 (d, J=7.5 Hz, 2H), 6.85-6.90 (m, 1H), 6.77 (s, 1H), 6.62 (d, J=3.5 Hz, 1H), 4.98-4.95 (m, 1H), 2.77-2.71 (m, 2H), 2.23 (s, 3H). Chiral HPLC: 100% $R_t$=8.22 min (Chiralpak IA, 250×4.6 mm, 5μ); mobile phase (A) 0.1% DEA in n-Hexane (B) DCM:Methanol (80:20) (A:B: 75:25); flow Rate: 1.0 mL/min) MS (ESI): m/z 413 [M+1]$^+$ HPLC: 99.6%

Analytical data for enantiomer B: $^1$H NMR (500 MHz, DMSO-$d_6$): δ 9.54 (s, 1H), 7.35 (d, J=8.0 Hz, 3H), 7.13-7.09

(m, 3H), 7.04 (br s, 1H), 6.97 (d, J=7.5 Hz, 2H), 6.85-6.90 (m, 1H), 6.77 (s, 1H), 6.62 (d, J=3.5 Hz, 1H), 4.98-4.95 (m, 1H), 2.77-2.71 (m, 2H), 2.24 (s, 3H). Chiral HPLC: 99.9% $R_t$=11.68 min (Chiralpak IA, 250×4.6 mm, 5µ); mobile phase (A) 0.1% DEA in n-Hexane (B) DCM:Methanol (80:20) (A:B: 75:25); flow Rate: 1.0 mL/min) MS (ESI): m/z 413 [M+1]$^+$ HPLC: 99.7%

Example 178: 4-(3-(Benzyloxy)phenyl)-7-methyl-8-(trifluoromethyl)-4,5-dihydro-1H-benzo[b][1,4]diazepin-2(3H)-one (Racemate)

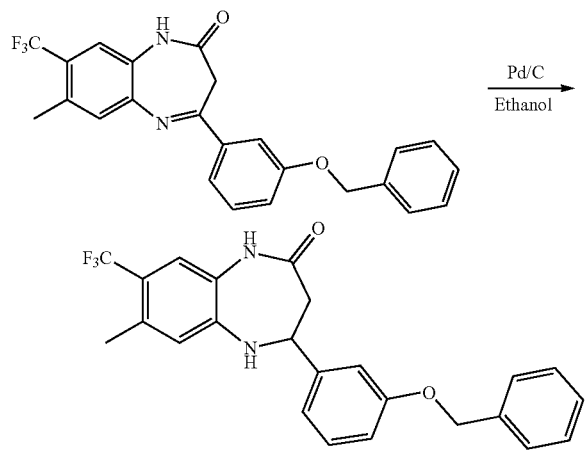

To a stirred solution of 4-(3-(benzyloxy)phenyl)-7-methyl-8-(trifluoromethyl)-1H-benzo[b][1,4]diazepin-2 (3H)-one (Example 144) (120 mg, 0.28 mmol) in EtOH (10 mL) under inert atmosphere was added Pd/C (30 mg) at RT and stirred under H$_2$ atmosphere (balloon pressure) for 2 h. The progress of the reaction was monitored by TLC. After completion of the reaction, the reaction mixture was filtered under vacuum. The filtrate was concentrated under reduced pressure. The obtained crude product was purified by silica gel column chromatography [Eluent: 18% EtOAc/Hexanes] to afford the title compound (90 mg, 75%) as an off-white solid.

Example 178A: 4-(3-(Benzyloxy)phenyl)-7-methyl-8-(trifluoromethyl)-4,5-dihydro-1H-benzo[b][1,4] diazepin-2(3H)-one Enantiomer A; and Example 178B: 4-(3-(Benzyloxy)phenyl)-7-methyl-8-(trifluoromethyl)-4,5-dihydro-1H-benzo[b][1,4]diazepin-2 (3H)-one Enantiomer B Chiral preparative HPLC of Enantiomers: The enantiomers of Example 178 (90 mg, 0.21 mmol) were separated by normal-phase preparative high performance liquid chromatography (Chiralpak IA, 250×4.6 mm, 5µ); (A) 0.1% DEA in n-hexane (B) DCM:MeOH (80:20) (A:B: 75:25; Flow rate: 1.0 mL/min) to obtain enantiomer A (30 mg) and enantiomer B (30 mg) as off-white solids.

Analytical data for enantiomer A: $^1$H NMR (500 MHz, DMSO-d$_6$): δ 9.55 (s, 1H), 7.41 (d, J=7.5 Hz, 2H), 7.36 (t, J=7.5 Hz, 2H), 7.32 (d, J=10 Hz, 1H), 7.24 (t, J=7.5 Hz, 1H), 7.15 (s, 1H), 7.00 (s, 1H), 6.92 (d, J=8.5 Hz, 2H), 6.83 (s, 1H), 6.79-6.58 (m, 1H), 5.06 (s, 1H), 4.90 (t, J=4.0 Hz, 1H), 2.82-2.77 (m, 1H), 2.70-2.67 (m, 1H), 2.26 (s, 3H). Chiral HPLC: 100% $R_t$=12.76 min (Chiralpak IA, 250×4.6 mm, 5µ); mobile phase (A) 0.1% DEA in n-Hexane (B) DCM: Methanol (80:20) (A:B: 75:25); flow Rate: 1.0 mL/min) MS (ESI): m/z 427 [M+1]$^+$ HPLC: 95.1%.

Analytical data for enantiomer B: $^1$H NMR (500 MHz, DMSO-d$_6$): δ 9.55 (s, 1H), 7.41 (d, J=7.5 Hz, 2H), 7.36 (t, J=7.5 Hz, 2H), 7.32 (d, J=10 Hz, 1H), 7.24 (t, J=7.5 Hz, 1H), 7.15 (s, 1H), 7.00 (s, 1H), 6.92 (d, J=8.5 Hz, 2H), 6.83 (s, 1H), 6.79-6.58 (m, 1H), 5.06 (s, 1H), 4.90 (t, J=4.0 Hz, 1H), 2.82-2.78 (m, 1H), 2.70-2.67 (m, 1H), 2.26 (s, 3H). Chiral HPLC: 99.9% $R_t$=20.52 min (Chiralpak IA, 250×4.6 mm, 5µ); mobile phase (A) 0.1% DEA in n-Hexane (B) DCM: Methanol (80:20) (A:B: 75:25); flow Rate: 1.0 mL/min) MS (ESI): m/z 427 [M+1]$^+$ HPLC: 99.3%.

Example 179: 8-Bromo-4-(3-(pyridin-3-yl)phenyl)-1,3-dihydro-2H-benzo[b][1,4]diazepin-2-one

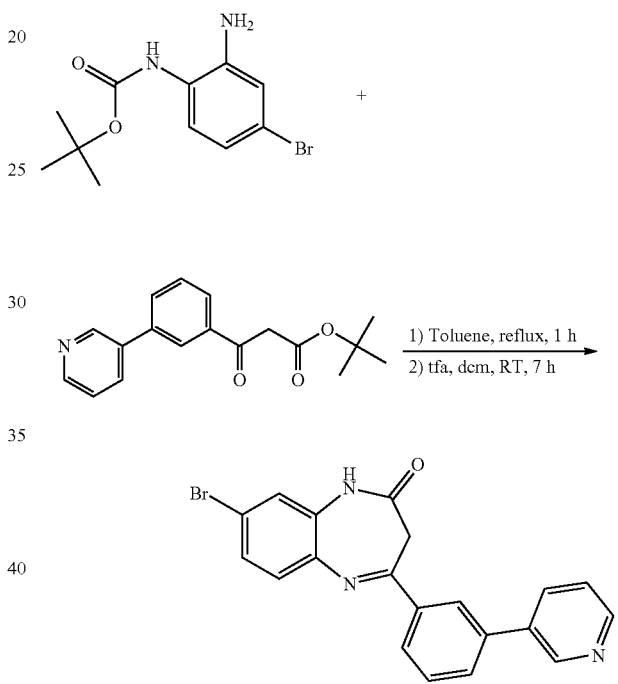

tert-Butyl (2-amino-4-bromophenyl)carbamate (0.861 g, 3 mmol) and tert-butyl 3-oxo-3-(3-(pyridin-3-yl)phenyl) propanoate (0.981 g, 3.3 mmol) were dissolved in toluene (5 mL) and heated at reflux for 1 h. The reaction mixture was cooled and excess solvent was removed under reduced pressure. Hexanes was added to the reaction mixture and the precipitated compound was filtered and dried. The crude intermediate was taken in DCM and TFA (3.42 g, 30 mmol) was added dropwise to it at 0° C. The resulting reaction mixture was stirred at rt for 7 h. The crude mixture was washed with sodium bicarbonate and the aqueous layer extracted with DCM. The combined organic layer washed with water, brine and dried over Na$_2$SO$_4$. Evaporation of the solvent followed by column chromatography using hexanes: ethyl acetate (1:1) yielded the title compound as a pale yellow solid (0.600 g, 51%). $^1$H NMR (400 MHz, DMSO-d$_6$): δ 10.69 (s, 1H), 8.96 (d, J=2.3 Hz, 1H), 8.61 (d, J=6.0 Hz, 1H), 8.33 (s, 1H), 8.16-8.09 (m, 2H), 7.66 (t, J=7.8 Hz, 1H), 7.48-7.42 (m, 1H), 7.39-7.38 (m, 3H), 3.64 (s, 2H). HRMS (ESI) m/z calcd for C$_{20}$H$_{14}$BrN$_3$O [M+H]$^+$: 392.0320. Found: 392.0397.

Example 180: 4-(8-Fluoro-2-oxo-2,3-dihydro-1H-benzo[b][1,4]diazepin-4-yl)picolinonitrile

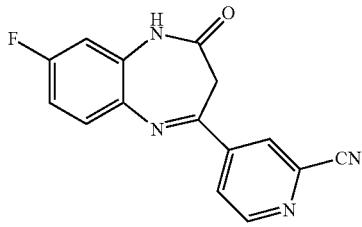 [SMILES: N#Cc1cc(C2=Nc3ccc(F)cc3NC(=O)C2)ccn1]

The title compound was prepared as a yellow solid (0.186 g, 66%) from the appropriate starting materials using a similar procedure as described in Example 179. $^1$H NMR (400 MHz, DMSO-d$_6$): δ 10.74 (s, 1H), 8.91 (d, J=5.0 Hz, 1H), 8.55 (s, 1H), 8.26-8.24 (m, 1H), 7.30-7.23 (m, 3H), 3.62 (s, 2H). LCMS ESI m/z: 281.00 [M+H]$^+$. HRMS (ESI) m/z calcd for C$_{15}$H$_9$FN$_4$O [M+H]$^+$: 281.0762. Found: 281.0834.

Examples 181-201 were synthesized from the appropriate tert-butyl (2-amino-phenyl)carbamate (1 mmol) and tert-butyl 3-oxo-phenylpropanoate (1.1 mmol) and TFA (10 mmol) according to the general procedure described in Example 179.

Example 181: 4-(8-Chloro-2-oxo-2,3-dihydro-1H-benzo[b][1,4]diazepin-4-yl)picolinonitrile

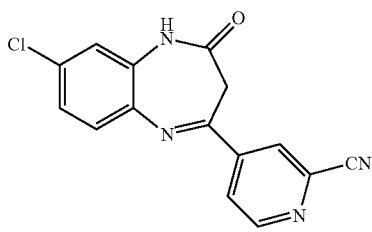 [SMILES: N#Cc1cc(C2=Nc3ccc(Cl)cc3NC(=O)C2)ccn1]

Yellow solid (0.184 g, 62%). LCMS ESI m/z: 297.00 [M+H]$^+$. HRMS (ESI) m/z calcd for C$_{15}$H$_9$ClN$_4$O [M+H]$^+$ 297.0467, found 297.0538.

Example 182: 4-(8-Bromo-2-oxo-2,3-dihydro-1H-benzo[b][1,4]diazepin-4-yl)picolinonitrile

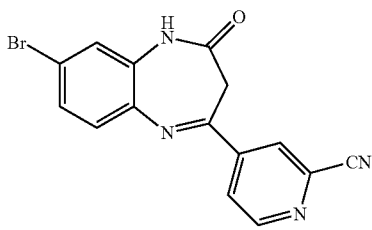

Yellow solid (0.267 g, 78%), $^1$H NMR (400 MHz, DMSO-d$_6$) δ 10.77 (s, 1H), 8.89 (d, J=5.0 Hz, 1H), 8.51 (s, 1H), 8.24 (dd, J=1.0 Hz, 5.0 Hz, 1H), 7.41-7.36 (m, 3H), 3.61 (s, 2H). LCMS ESI m/z: 341.00 [M+H]$^+$.

Example 183: 4-(8-Iodo-2-oxo-2,3-dihydro-1H-benzo[b][1,4]diazepin-4-yl)picolinonitrile

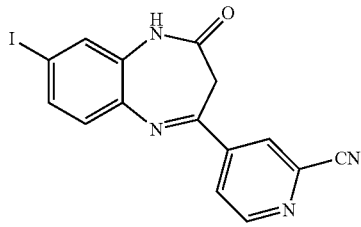 [SMILES: N#Cc1cc(C2=Nc3ccc(I)cc3NC(=O)C2)ccn1]

White solid (0.352 g, 90%), mp: 253-255° C. $^1$H NMR (400 MHz, DMSO-d$_6$): δ 10.74 (s, 1H), 8.92 (d, J=5.0 Hz, 1H), 8.54 (s, 1H), 8.25-8.23 (m, 1H), 7.58-7.56 (m, 2H), 7.24 (d, J=8.2 Hz, 1H), 3.62 (s, 2H). LCMS ESI m/z: 389.00[M+H]$^+$.

Example 184: 4-(2-Oxo-8-(trifluoromethyl)-2,3-dihydro-1H-benzo[b][1,4]diazepin-4-yl)picolinonitrile

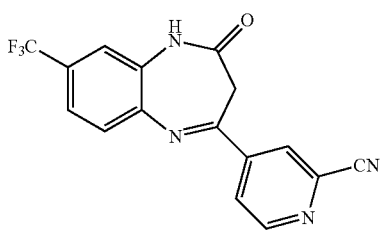 [SMILES: N#Cc1cc(C2=Nc3ccc(C(F)(F)F)cc3NC(=O)C2)ccn1]

Yellow solid (0.261 g, 79%). $^1$H NMR (400 MHz, DMSO-d$_6$) δ 10.93 (s, 1H), 8.95 (d, J=5.5 Hz, 1H), 8.53 (s, 1H), 8.26-8.24 (m, 1H), 7.64-7.53 (m, 3H), 3.71 (s, 2H). LCMS ESI m/z: 332.00 [M+H]$^+$.

Example 185: 4-(8-((4-Fluorophenyl)ethynyl)-2-oxo-2,3-dihydro-1H-benzo[b][1,4]diazepin-4-yl)picolinonitrile

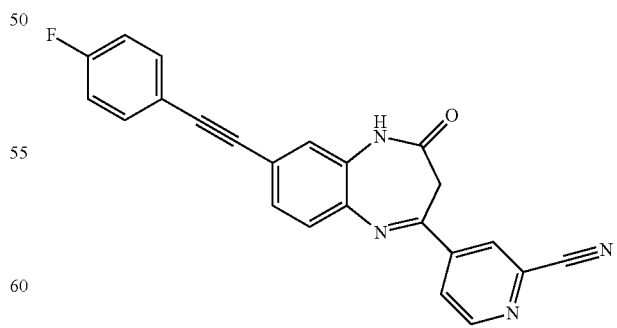

Yellow solid (0.258 g, 68%). $^1$H NMR (400 MHz, DMSO-d$_6$): δ 10.83 (s, 1H), 8.92 (d, J=5.0 Hz, 1H), 8.56 (s, 1H), 8.26-8.25 (m, 1H), 7.65-7.61 (m, 2H), 7.50-7.25 (m, 5H), 3.64 (s, 2H). LCMS ESI m/z: 381.00 [M+H]$^+$.

Example 186: 8-(4-Chlorophenyl)-4-(2-chloropyridin-4-yl)-1,3-dihydro-2H-benzo[b][1,4]diazepin-2-one

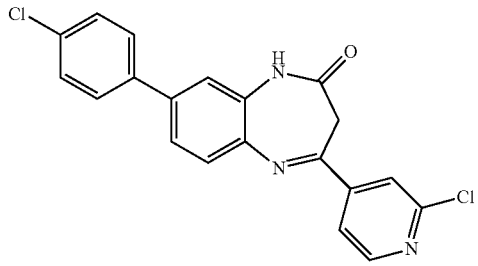 [SMILES: O=C1CC(c2ccnc(Cl)c2)=Nc2ccc(-c3ccc(Cl)cc3)cc2N1]

Yellow solid (0.210 g, 55%). (¹H NMR (400 MHz, DMSO-d₆): δ 10.75 (s, 1H), 8.58 (d, J=5.0 Hz, 1H), 8.02-7.96 (m, 2H), 7.73-7.68 (m, 2H), 7.59-7.52 (m, 4H), 7.48-7.46 (m, 1H), 3.60 (s, 2H). LCMS (ESI) m/z: 382.00 [M+H]⁺.

Example 187: 4-(2-Chloropyridin-4-yl)-8-(2-fluorophenyl)-1,3-dihydro-2H-benzo[b][1,4]diazepin-2-one

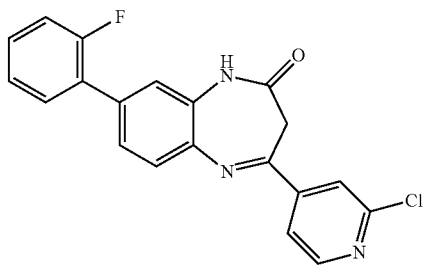 [SMILES: O=C1CC(c2ccnc(Cl)c2)=Nc2ccc(-c3ccccc3F)cc2N1]

Yellow solid (0.172 g, 47%). ¹H NMR (400 MHz, DMSO-d₆) δ 10.89 (s, 1H), 8.61-8.57 (m, 2H), 8.04-7.97 (m, 2H), 7.57-7.32 (m, 6H), 3.62 (s, 2H). LCMS (ESI) m/z: 366.00 [M+H]⁺.

Example 188: 4-(2-Chloropyridin-4-yl)-8-(2-fluoropyridin-3-yl)-1,3-dihydro-2H-benzo[b][1,4]diazepin-2-one

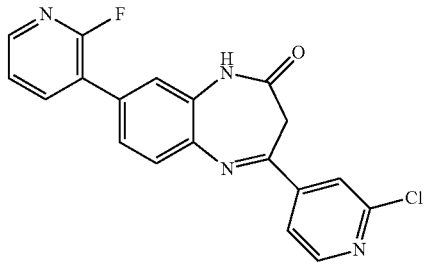 [SMILES: O=C1CC(c2ccnc(Cl)c2)=Nc2ccc(-c3cccnc3F)cc2N1]

Yellow solid (0.139 g, 38%). ¹H NMR (400 MHz, DMSO-d₆) δ 10.85 (s, 1H), 8.60-8.58 (m, 1H), 8.27-8.26 (m, 1H), 8.19-8.11 (m, 1H), 8.02-7.92 (m, 2H), 7.61-7.47 (m, 4H), 3.62 (s, 2H). LCMS (ESI) m/z: 367.00 [M+H]⁺.

Example 189: 4-(2-Chloropyridin-4-yl)-8-(trifluoromethyl)-1,3-dihydro-2H-benzo[b][1,4]diazepin-2-one

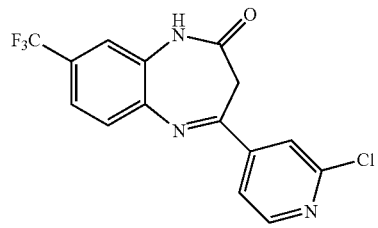

White solid (0.271 g, 68%). ¹H NMR (400 MHz, DMSO-d₆) δ 9.56 (s, 1H), 8.56 (d, J=5.0 Hz, 1H), 8.01 (d, J=1.0 Hz, 1H), 7.87-7.85 (m, 1H), 7.65-7.62 (m, 1H), 7.56-7.55 (m, 1H), 7.46 (s, 1H), 3.57 (s, 2H). LCMS (ESI) m/z: 340.00 [M+H]⁺.

Example 190: 4-(2-Chloropyridin-4-yl)-8-(3,5-difluorophenyl)-1,3-dihydro-2H-benzo[b][1,4]diazepin-2-one

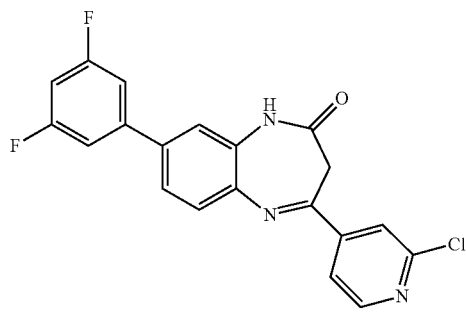 [SMILES: O=C1CC(c2ccnc(Cl)c2)=Nc2ccc(-c3cc(F)cc(F)c3)cc2N1]

Yellow solid (0.161 g, 42%). ¹H NMR (400 MHz, DMSO-d₆) δ 10.76 (s, 1H), 8.60 (d, J=5.0 Hz, 1H), 8.13 (s, 1H), 7.98 (d, J=8.0 Hz, 1H), 7.63-7.58 (m, 1H), 7.57-7.55 (m, 2H), 7.44-7.42 (m, 2H), 7.31-7.28 (m, 1H), 3.62 (s, 2H). LCMS (ESI) m/z: 384.00 [M+H]⁺.

Example 191: 4-(2-Bromopyridin-4-yl)-8-(trifluoromethyl)-1,3-dihydro-2H-benzo[b][1,4]diazepin-2-one

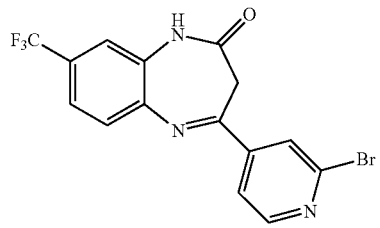 [SMILES: O=C1CC(c2ccnc(Br)c2)=Nc2ccc(C(F)(F)F)cc2N1]

Yellow solid (0.260 g, 68%). ¹H NMR (400 MHz, DMSO-d₆) 10.91 (s, 1H), 8.56 (d, J=5.0 Hz, 1H), 7.98 (s, 1H), 7.98 (d, J=8.0 Hz, 1H), 7.67-7.65 (m, 2H), 7.20-7.10 (m, 1H), 3.62 (s, 2H). LCMS (ESI) m/z: 384.00 [M+H]⁺.

Example 192: 4-(2-Chloropyridin-4-yl)-8-(4-ethoxyphenyl)-1,3-dihydro-2H-benzo[b][1,4]diazepin-2-one

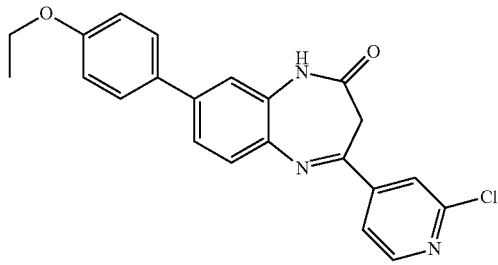 [SMILES: CCOc1ccc(-c2ccc3c(c2)NC(=O)CC(c2ccnc(Cl)c2)=N3)cc1]

Yellow solid (0.207 g, 53%). $^1$H NMR (400 MHz, DMSO-$d_6$) δ 8.52 (d, J=5.9 Hz, 1H), 8.32 (s, 1H), 8.02-8.01 (m, 1H), 7.87-7.86 (m, 1H), 7.56-7.53 (m, 4H), 7.24 (d, J=1.8 Hz, 1H), 7.01 (d, J=8.7 Hz, 2H), 4.11 (q, J=7.3 Hz, 2H), 3.57 (s, 2H), 1.44 (t, J=7.3 Hz, 3H). LCMS (ESI) m/z: 392.00 [M+H]$^+$.

Example 193: 4-(2-Chloropyridin-4-yl)-8-(m-tolyl)-1,3-dihydro-2H-benzo[b][1,4]diazepin-2-one

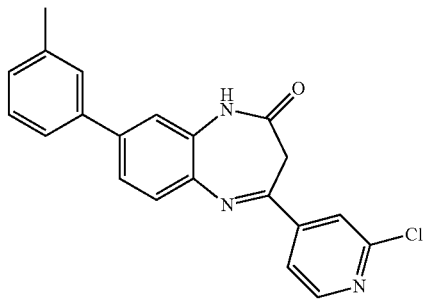 [SMILES: Cc1cccc(-c2ccc3c(c2)NC(=O)CC(c2ccnc(Cl)c2)=N3)c1]

Yellow solid (0.199 g, 55%). $^1$H NMR (400 MHz, DMSO-$d_6$) δ 8.80 (s, 1H), 8.52 (d, J=5.0 Hz, 1H), 8.01 (d, J=1.8 Hz, 1H), 7.86-7.85 (m, 1H), 7.58-7.53 (m, 2H), 7.43-7.22 (m, 5H), 3.56 (s, 2H), 2.45 (s, 3H). LCMS (ESI) m/z: 362.00 [M+H]$^+$.

Example 194: 8-(2,4-Bis(trifluoromethyl)phenyl)-4-(2-bromopyridin-4-yl)-1,3-dihydro-2H-benzo[b][1,4]diazepin-2-one

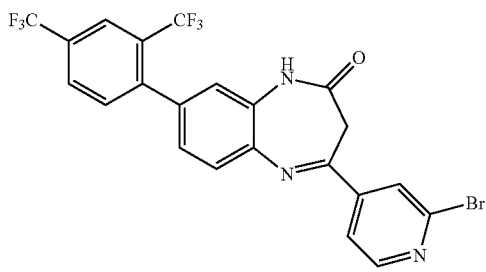 [SMILES: O=C1CC(c2ccnc(Br)c2)=Nc2ccc(-c3ccc(C(F)(F)F)cc3C(F)(F)F)cc2N1]

Yellow solid (0.311 g, 59%). $^1$H NMR (400 MHz, DMSO-$d_6$) δ 10.88 (s, 1H), 8.62 (d, J=5.0 Hz, 1H), 8.17 (s, 2H), 8.05 (s, 1H), 8.00-7.99 (m, 1H), 7.72 (d, J=8.2 Hz, 1H), 7.56 (d, J=8.2 Hz, 1H), 7.29-7.26 (m, 1H), 7.20-7.19 (m, 1H), 3.62 (s, 2H). LCMS (ESI) m/z: 528.00 [M+H]$^+$.

Example 195: 4-(2-Chloropyridin-4-yl)-8-(3,4-dimethoxyphenyl)-1,3-dihydro-2H-benzo[b][1,4]diazepin-2-one

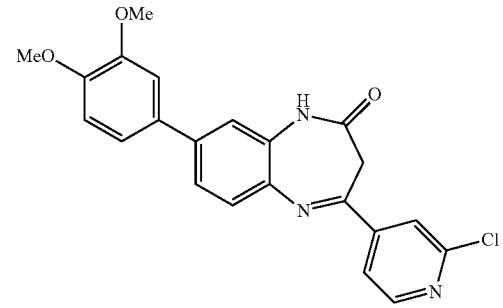 [SMILES: COc1ccc(-c2ccc3c(c2)NC(=O)CC(c2ccnc(Cl)c2)=N3)cc1OC]

Yellow solid (0.200 g, 49%). $^1$H NMR (400 MHz, DMSO-$d_6$) δ 10.70 (s, 1H), 8.58 (d, J=5.5 Hz, 1H), 8.01 (s, 1H), 7.96 (d, J=5.0 Hz, 1H), 7.58-7.56 (m, 1H), 7.51-7.47 (m, 2H), 7.23-7.20 (m, 2H), 7.05 (d, J=8.2 Hz, 1H), 3.85 (s, 3H), 3.79 (s, 3H), 3.58 (s, 2H). LCMS (ESI) m/z: 408.00 [M+H]$^+$.

Example 196: 8-(4-Chloro-2-methylphenyl)-4-(2-chloropyridin-4-yl)-1,3-dihydro-2H-benzo[b][1,4]diazepin-2-one

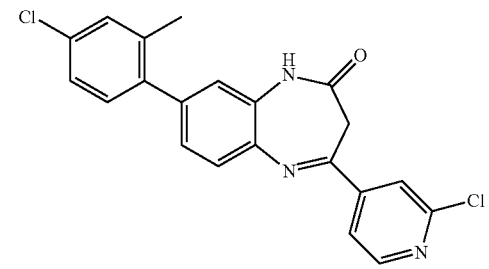 [SMILES: Cc1cc(Cl)ccc1-c1ccc2c(c1)NC(=O)CC(c1ccnc(Cl)c1)=N2]

Yellow solid (0.130 g, 33%). $^1$H NMR (400 MHz, DMSO-$d_6$) δ 10.77 (s, 1H), 8.60 (d, J=5.5 Hz, 1H), 8.04 (s, 1H), 7.98 (d, J=5.5 Hz, 1H), 7.52 (d, J=8.2 Hz, 1H), 7.43-7.42 (m, 1H), 7.35-7.33 (m, 1H), 7.26-7.24 (m, 2H), 7.17-7.16 (m, 1H), 3.61 (s, 2H), 2.23 (s, 3H). LCMS (ESI) m/z: 397.00 [M+H]$^+$.

Example 197: 4-(2-Chloropyridin-4-yl)-8-phenyl-1,3-dihydro-2H-benzo[b][1,4]diazepin-2-one

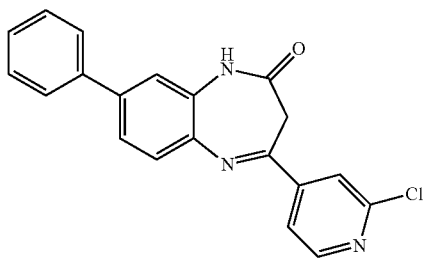 [SMILES: O=C1CC(c2ccnc(Cl)c2)=Nc2ccc(-c3ccccc3)cc2N1]

Yellow solid (0.174 g, 50%). ¹H NMR (400 MHz, DMSO-d₆) δ 10.77 (s, 1H), 8.57 (d, J=5.5 Hz, 1H), 8.02 (s, 1H), 7.97 (d, J=5.5 Hz, 1H), 7.67-7.64 (m, 2H), 7.58-7.56 (m, 2H), 7.53 (s, 1H), 7.40-7.37 (m, 3H), 3.59 (s, 2H). LCMS (ESI) m/z: 348.00 [M+H]⁺.

Example 198: 4-(2-Phenylpyridin-4-yl)-8-(trifluoromethyl)-1,3-dihydro-2H-benzo[b][1,4]diazepin-2-one

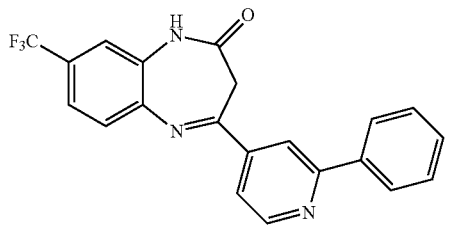 [SMILES: O=C1CC(c2ccnc(-c3ccccc3)c2)=Nc2ccc(C(F)(F)F)cc2N1]

Yellow solid (0.263 g, 69%). ¹H NMR (400 MHz, DMSO-d₆) δ 10.89 (s, 1H), 8.58 (d, J=5.5 Hz, 1H), 8.45 (s, 1H), 8.16 (d, J=6.9 Hz, 2H), 7.93-7.92 (m, 1H), 7.69-7.67 (m, 1H), 7.59-7.45 (m, 5H), 3.73 (s, 2H). LCMS (ESI) m/z: 382.00 [M+H]⁺.

Example 199: 8-(6-Bromopyridin-3-yl)-4-(2-chloropyridin-4-yl)-1,3-dihydro-2H-benzo[b][1,4]diazepin-2-one

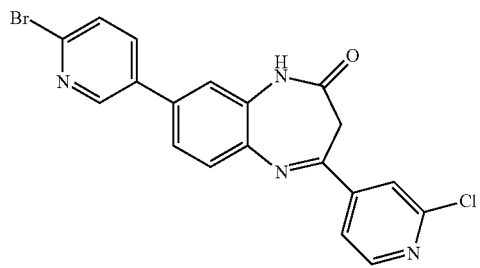 [SMILES: O=C1CC(c2ccnc(Cl)c2)=Nc2ccc(-c3ccc(Br)nc3)cc2N1]

Yellow solid (0.204 g, 48%). ¹H NMR (400 MHz, DMSO-d₆) δ 10.81 (s, 1H), 8.78 (s, 1H), 8.62-8.58 (m, 2H), 8.06-8.04 (m, 1H), 7.99 (d, J=5.5 Hz, 1H), 7.79-7.77 (m, 2H), 7.67-7.65 (m, 1H), 7.60-7.53 (m, 1H), 3.62 (s, 2H). LCMS (ESI) m/z: 427.00 [M+H]⁺.

Example 200: 4-(2-(2-Fluorophenyl)pyridin-4-yl)-8-(trifluoromethyl)-1,3-dihydro-2H-benzo[b][1,4]diazepin-2-one

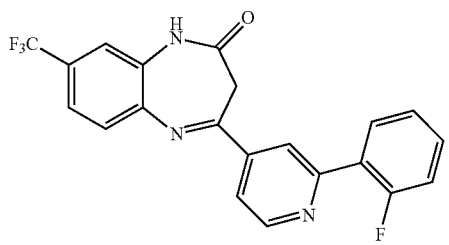 [SMILES: O=C1CC(c2ccnc(-c3ccccc3F)c2)=Nc2ccc(C(F)(F)F)cc2N1]

White solid (0.223 g, 56%). ¹H NMR (DMSO-d₆): δ 8.89 (d, J=5.5 Hz, 1H), 8.68 (s, 1H), 8.44 (s, 1H), 8.02-7.98 (m, 1H), 7.92-7.89 (m, 1H), 7.66 (d, J=8.2 Hz, 1H), 7.56-7.54 (m, 1H), 7.42-7.39 (m, 4H), 3.63 (s, 2H). LCMS (ESI) m/z: 400.00 [M+H]⁺.

Example 201: 4-(2-Chloropyridin-4-yl)-8-(2-fluoro-4-(trifluoromethyl)phenyl)-1,3-dihydro-2H-benzo[b][1,4]diazepin-2-one

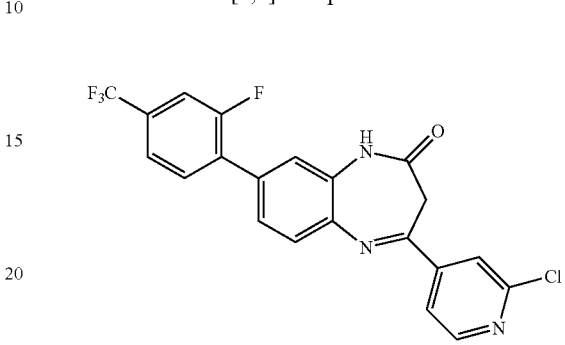

Yellow solid (0.290 g, 67%). ¹H NMR (DMSO-d₆): δ 10.88 (s, 1H), 8.60 (d, J=5.0 Hz, 1H), 8.04 (s, 1H), 7.78 (dd, J=1.0 Hz, 5.0 Hz, 1H), 7.82-7.70 (m, 3H), 7.60-7.45 (m, 3H), 3.63 (s, 2H). LCMS (ESI) m/z: 434.00 [M+H]⁺.

Example 202: 7-Methyl-4-(3-phenylethynyl-phenyl)-8-trifluoromethyl-1,3-dihydro-benzo[b][1,4]diazepin-2-one

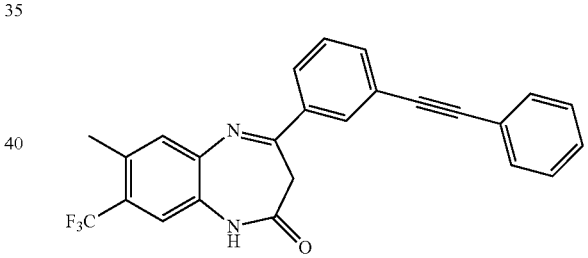

To a solution of 4-(3-bromo-phenyl)-7-methyl-8-trifluoromethyl-1,3-dihydro-benzo[b][1,4]diazepin-2-one (100 mg, 0.25 mmol) in THF (10 mL) and iPr₂NH (10 mL) was added CuI (9.5 mg, 0.05 mmol) and Pd(dppf)Cl₂ (20 mg, 0.025 mmol) under N₂ and the mixture was stirred for 10 min. Ethynyl-benzene (510 mg, 5.0 mmol) was added to the above solution, and the reaction mixture was stirred at 80° C. overnight. The reaction was quenched with water and the mixture was concentrated to remove most MeOH. The aqueous phase was extracted with EtOAc (30 mL×3). The extracts were dried over Na₂SO₄, concentrated and purified by silica gel chromatography (from PE to PE/EA=20/1-5/1), further purified by prep-HPLC to give 10 mg of 7-methyl-4-(3-phenylethynyl-phenyl)-8-trifluoromethyl-1,3-dihydro-benzo[b][1,4]diazepin-2-one (yield: 10%) as a yellow solid. ¹H NMR (DMSO-d₆, 400 HMz): δ 10.75 (1H, brs), 8.25 (1H, s), 8.14-8.10 (1H, m), 7.79-7.75 (1H, m), 7.68-7.42 (8H, m), 3.62 (2H, s), 2.42 (3H, s). MS: m/z 419.2 (M+H⁺).

Example 203: 4-[3-(3-Hydroxy-prop-1-ynyl)-phenyl]-7-methyl-8-trifluoromethyl-1,3-dihydro-benzo[b][1,4]diazepin-2-one

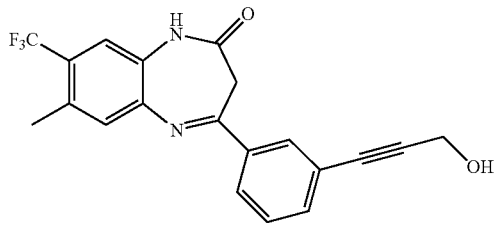 [SMILES: Cc1cc2c(cc1C(F)(F)F)NC(=O)CC(c1cccc(C#CCO)c1)=N2]

To a solution of prop-2-yn-1-ol (300 mg, 5.36 mmol) and TBSCl (893 mg, 5.95 mmol) in DCM (4 mL) was added TEA (0.85 mL, 5.95 mmol). Then the mixture was stirred at rt for 2 h. The mixture was concentrated under reduced pressure. The reaction was quenched with 5 mL of water. The mixture was extracted with EtOAc (20 mL×2). The extracts were washed with brine and dried over $Na_2SO_4$. The solution was concentrated to afford 500 mg of tert-butyl-dimethyl-prop-2-ynyloxy-silane (yield: 55%) as yellow oil, which was used for next step without further purification. To a mixture of 4-(3-bromo-phenyl)-7-methyl-8-trifluoromethyl-1,3-dihydro-benzo[b][1,4]diazepin-2-one (180 mg, 0.455 mmol), Pd(dppf)$Cl_2$ (35 mg, 0.0455 mmol), CuI (8 mg, 0.0455 mmol) in a flask under $N_2$ was added tert-butyl-dimethyl-prop-2-ynyloxy-silane (155 mg, 0.909 mmol) in TEA (5 mL) and THF (5 mL). Then the mixture was stirred at 80° C. overnight. The mixture was concentrated under reduced pressure. The residue was diluted with 5 mL of water. The mixture was extracted with EtOAc (20 mL×2). The extracts were washed with brine, dried over $Na_2SO_4$ and concentrated to dryness. The residue was purified by prep-HPLC to afford 30 mg of 4-{3-[3-(tert-butyl-dimethyl-silanyloxy)-prop-1-ynyl]-phenyl}-7-methyl-8-trifluoromethyl-1,3-dihydro-benzo[b][1,4]diazepin-2-one (yield: 16%) as white solid. MS: m/z 486.9 (M+H$^+$). To a solution of 4-{3-[3-(tert-butyl-dimethyl-silanyloxy)-prop-1-ynyl]-phenyl}-7-methyl-8-trifluoromethyl-1,3-dihydro-benzo[b][1,4]diazepin-2-one (30 mg, 0.0617 mmol) in THF was added TBAF (17 mg, 0.0679 mmol) at room temperature. The mixture was stirred at rt for 12 h. The mixture was concentrated under reduced pressure and residue was treated with aq. $NH_4Cl$. The mixture was extracted with EtOAc (10 mL×2). The extracts were washed with brine and dried over $Na_2SO_4$. The solution was concentrated to dryness and the residue was purified by prep-HPLC to afford 15 mg of 4-[3-(3-hydroxy-prop-1-ynyl)-phenyl]-7-methyl-8-trifluoromethyl-1,3-dihydro-benzo[b][1,4]diazepin-2-one (yield: 65%) as a white solid. $^1$H NMR (CDCl$_3$, 400 MHz): δ 8.19 (1H, s), 8.06 (1H, d), 7.93 (1H, brs), 7.57 (1H, d), 7.45 (1H, t), 7.41 (1H, s), 7.33 (1H, s), 4.53 (2H, s), 3.57 (2H, s), 2.52 (3H, s). MS: m/z 373.2 (M+H$^+$).

PHARMACEUTICAL COMPOSITION EXAMPLES

Example A1: Parenteral Composition

To prepare a parenteral pharmaceutical composition suitable for administration by injection, 100 mg of a water-soluble salt of a compound of Formula (I), (Ia), (Ib), (Ic), (II), (IIa), (IIb), (IIc), (III), (IIIa), (IIIb), (IV), (IVa), or (IVb), or pharmaceutically acceptable salt, N-oxide, racemate or stereoisomer thereof, is dissolved in 2% HPMC, 1% Tween 80 in DI water, pH 2.2 with MSA, q.s. to at least 20 mg/mL. The mixture is incorporated into a dosage unit form suitable for administration by injection.

Example A2: Oral Composition

To prepare a pharmaceutical composition for oral delivery, 100 mg of a compound of Formula (I), (Ia), (Ib), (Ic), (II), (IIa), (IIb), (IIc), (III), (IIIa), (IIIb), (IV), (IVa), or (IVb), or pharmaceutically acceptable salt, N-oxide, racemate or stereoisomer thereof, is mixed with 750 mg of starch. The mixture is incorporated into an oral dosage unit for, such as a hard gelatin capsule, which is suitable for oral administration.

BIOLOGY EXAMPLES

Example B1: mGlu$_2$ and mGlu$_3$ In Vitro GIRK Thallium Flux Assays

Human Embryonic Kidney (HEK-293) cell lines co-expressing rat mGlu receptors 2, 3, 4, 6, 7 or 8 and G protein-coupled inwardly-rectifying potassium (GIRK) channels_ENREF_54 were grown in Growth Media containing 45% DMEM, 45% F-12, 10% FBS, 20 mM HEPES, 2 mM L-glutamine, antibiotic/antimycotic, non-essential amino acids, 700 μg/ml G418, and 0.6 μg/ml puromycin at 37° C. in the presence of 5% $CO_2$. All cell culture reagents were purchased from Invitrogen Corp. (Carlsbad, Calif.) unless otherwise noted. Compound activity at the group II (mGlu$_2$ and mGlu$_3$) mGlus was assessed using thallium flux through GIRK channels. Briefly, cells were plated into 384-well, black-walled, clear-bottomed poly-D-lysine-coated plates at a density of 15,000 cells/20 μL/well in DMEM containing 10% dialyzed FBS, 20 mM HEPES, and 100 units/mL penicillin/streptomycin (assay media). Plated cells were incubated overnight at 37° C. in the presence of 5% $CO_2$. The following day, the medium was exchanged from the cells to assay buffer [Hanks' balanced salt solution (Invitrogen) containing 20 mM HEPES, pH 7.3] using an ELX405 microplate washer (BioTek), leaving 20 μL/well, followed by the addition of 20 μL/well FluoZin2-AM (330 nM final concentration) indicator dye (Invitrogen; prepared as a stock in DMSO and mixed in a 1:1 ratio with Pluronic acid F-127) in assay buffer. Cells were incubated for 1 h at room temperature, and the dye exchanged to assay buffer using an ELX405, leaving 20 μL/well. Test compounds were diluted to 2 times their final desired concentration in assay buffer (0.3% DMSO final concentration). Agonists were diluted in thallium buffer [125 mM sodium bicarbonate (added fresh the morning of the experiment), 1 mM magnesium sulfate, 1.8 mM calcium sulfate, 5 mM glucose, 12 mM thallium sulfate, and 10 mM HEPES, pH 7.3] at 5 times the final concentration to be assayed. Cell plates and compound plates were loaded onto a kinetic imaging plate reader (FDSS 6000 or 7000; Hamamatsu Corporation, Bridgewater, N.J.). Appropriate baseline readings were taken (10 images at 1 Hz; excitation, 470±20 nm; emission, 540±30 nm) and test compounds were added in a 20 μL volume and incubated for either 2.5 min or 60 min as indicated before the addition of 10 μL of thallium buffer with or without agonist. After the addition of agonist, data were collected for approximately an additional 2.5 min. Data were analyzed using Excel (Microsoft Corp, Redmond, Wash.). The slope of the fluorescence increase beginning 5 s after thallium/ agonist addition and ending 15 s after thallium/agonist addition was calculated, corrected to vehicle and maximal agonist control slope values, and plotted in using either XLfit (ID Business Solutions Ltd) or Prism software (Graph-Pad Software, San Diego, Calif.) to generate concentration-response curves. Potencies were calculated from fits using a four-point parameter logistic equation. For concentration-response curve experiments, compounds were serially diluted 1:3 into 10 point concentration response curves and were transferred to daughter plates using an Echo acoustic plate reformatter (Labcyte, Sunnyvale, Calif.). Test compounds were applied and followed by $EC_{80}$ concentrations of glutamate.

Representative in vitro biochemical data selectivity data is presented in Table 1.

TABLE 1

In vitro potency against mGlu2 or mGlu3 receptors in thallium flux assays for NAMs.

| Ex. | mGlu2 $EC_{50}$ (μM) (2.5 min) | mGlu2 $EC_{50}$ (μM) (60 min) | mGlu3 $EC_{50}$ (μM) (2.5 min) | mGlu2 $EC_{50}$ (μM) (60 min) |
|---|---|---|---|---|
| 1 | 0.33 | 0.48 | 1.21 | >10 |
| 2 | >30 | >10 | >30 | >10 |
| 3 | >30 | >10 | >10 | >10 |
| 4 | 2.26 | 2.50 | >10 | >10 |
| 5 | 1.35 | 0.85 | 3.11 | 2.55 |
| 6 | >10 | >10 | >10 | >10 |
| 7 | 2.40 | >10 | >10 | >30 |
| 8 | >10 | 1.92 | >10 | >10 |
| 9 | 0.64 | 0.35 | >10 | >30 |
| 10 | >10 | >10 | >10 | >10 |
| 11 | 1.59 | 3.40 | >30 | >30 |
| 12 | 1.73 | 2.14 | 1.77 | 2.86 |
| 13 | >10 | >10 | >10 | >30 |
| 14 | >30 | >10 | >30 | >10 |
| 15 | 1.50 | 0.93 | >10 | >10 |
| 16 | 2.57 | 1.93 | 3.32 | >10 |
| 17 | >30 | >30 | >30 | >10 |
| 18 | >10 | >30 | >10 | >30 |
| 19 | 3.67 | 1.55 | >10 | >10 |
| 20 | >30 | >10 | >30 | >10 |
| 21 | >10 | >10 | >10 | >10 |
| 22 | >30 | >10 | >30 | >10 |
| 23 | 1.81 | 1.35 | >10 | >10 |
| 24 | 0.57 | 0.80 | 0.79 | 1.33 |
| 25 | >10 | >10 | >10 | >10 |
| 26 | >30 | >30 | >10 | >10 |
| 27 | >10 | >30 | >30 | >30 |
| 28 | 0.42 | 0.20 | >10 | >10 |
| 29 | 2.58 | 1.10 | 4.02 | >10 |
| 30 | >10 | >10 | >30 | >30 |
| 31 | 1.23 | 0.67 | 3.09 | >10 |
| 32 | >10 | 4.98 | >30 | >10 |
| 33 | 4.83 | >10 | >10 | >10 |
| 34 | >10 | 0.28 | >10 | >10 |
| 35 | 3.83 | 0.27 | >10 | 0.83 |
| 36 | 3.47 | >10 | >10 | >10 |
| 37 | 2.98 | 1.72 | >10 | >10 |
| 38 | 0.10 | 0.05 | 0.52 | 0.46 |
| 39 | 0.32 | 0.05 | 2.28 | 0.45 |
| 40 | 0.40 | 0.10 | 2.78 | 0.59 |
| 41 | 0.89 | 0.11 | >10 | >10 |
| 42 | 3.63 | 3.71 | >10 | >10 |
| 43 | 0.17 | 0.11 | 3.43 | 1.23 |
| 44 | 0.68 | 0.18 | >10 | >10 |
| 45 | >10 | >10 | >10 | >10 |
| 46 | >10 | >10 | >30 | >10 |
| 47 | >10 | >10 | >30 | >30 |
| 48 | 1.33 | 0.79 | >10 | >10 |
| 49 | >10 | >30 | >10 | >10 |
| 49A | >10 | >10 | 1.36 | 0.89 |
| 50 | 0.59 | 1.48 | >10 | >10 |
| 51 | >10 | >10 | 5.80 | 1.87 |
| 52 | >10 | >10 | 3.11 | 1.51 |
| 53 | >10 | 3.67 | 4.29 | 1.68 |
| 54 | >10 | 2.71 | 3.90 | 1.40 |
| 55 | >10 | 6.58 | 2.96 | 0.46 |
| 56 | 3.22 | >10 | >10 | 1.16 |
| 57 | >10 | >10 | >10 | 2.32 |
| 58 | >10 | >10 | 5.56 | 0.85 |
| 59 | >10 | 3.78 | >10 | 2.63 |
| 60 | >10 | >10 | 5.30 | 1.97 |
| 61 | >30 | >30 | >10 | >10 |
| 62 | >10 | >30 | 0.21 | >30 |
| 63 | >10 | >10 | 4.45 | 2.29 |
| 64 | >10 | >30 | >10 | >10 |
| 65 | >10 | >30 | >30 | >30 |
| 66 | >10 | >10 | >10 | >10 |
| 67 | >10 | >10 | >10 | 2.63 |
| 68 | >10 | >30 | >10 | >30 |
| 69 | 0.95 | 0.11 | 1.07 | 0.34 |
| 70 | 1.26 | 0.20 | 1.58 | 1.09 |
| 71 | >10 | >10 | >10 | >10 |
| 72 | >10 | >10 | >10 | >10 |
| 73 | 0.82 | 0.17 | 1.18 | 0.78 |
| 74 | 6.76 | >10 | 6.52 | >10 |
| 75 | 1.27 | 0.50 | >10 | 1.35 |
| 76 | 1.53 | 0.09 | 1.61 | 0.52 |
| 77 | 0.96 | 0.29 | 1.59 | 1.70 |
| 78 | 3.49 | 1.18 | 6.32 | 1.95 |
| 79 | 0.83 | 0.09 | 0.89 | 0.62 |
| 80 | 0.78 | 0.13 | 2.40 | 1.59 |
| 81 | 3.78 | 0.44 | 2.13 | 0.25 |
| 82 | 1.42 | 0.49 | 1.32 | 0.53 |
| 83 | 2.95 | 1.23 | >10 | 6.25 |
| 84 | 2.79 | ND | 4.91 | ND |
| 85 | >30 | >10 | >30 | >10 |
| 86 | 0.80 | 0.04 | 0.92 | 0.12 |
| 87 | 1.07 | 0.06 | 1.00 | 0.25 |
| 87A | 1.12 | 0.24 | 1.26 | 0.40 |
| 88 | 0.68 | 0.34 | 1.13 | 0.55 |
| 89 | 1.24 | 0.14 | 2.25 | 0.25 |
| 90 | 3.68 | 2.49 | >10 | >10 |
| 91 | 1.52 | 0.28 | >10 | >10 |
| 92 | 2.79 | 0.40 | 3.37 | 0.73 |
| 93 | >10 | 1.60 | >10 | 2.31 |
| 94 | 0.15 | 0.14 | 0.28 | 0.27 |
| 95 | >10 | ND | >10 | ND |
| 96 | 5.38 | 1.08 | 6.11 | 1.52 |
| 97 | 1.07 | 0.36 | 2.21 | 1.71 |
| 98 | 2.87 | 0.35 | 2.47 | 1.23 |
| 99 | >10 | 1.30 | 2.83 | 1.48 |
| 100 | 1.21 | 0.16 | 2.21 | 1.24 |
| 101 | >10 | 0.95 | >10 | 1.39 |
| 102 | 3.33 | 0.88 | 3.12 | 1.48 |
| 103 | 4.69 | 0.99 | 4.54 | 1.41 |
| 104 | 1.44 | 0.24 | 1.90 | 0.53 |
| 105 | >10 | 3.19 | >10 | >10 |
| 106 | 1.19 | 1.42 | 5.06 | 6.39 |
| 107 | 4.53 | 0.42 | >10 | 1.12 |
| 108 | 1.50 | 0.15 | 1.49 | 0.68 |
| 109 | 1.34 | 0.297 | 2.13 | 0.63 |
| 110 | 4.08 | 0.65 | 5.34 | 1.51 |
| 111 | >10 | >10 | >10 | >10 |
| 112 | 3.19 | 0.75 | 3.14 | 1.61 |
| 113 | 0.40 | 0.23 | 1.15 | 0.45 |
| 114 | 0.40 | 0.15 | 1.36 | 0.14 |
| 115 | 0.28 | 0.12 | 0.96 | 0.45 |
| 116 | 2.11 | 0.27 | 8.58 | >10 |
| 117 | 0.08 | 0.07 | 0.28 | 0.46 |
| 118 | 0.26 | 1.01 | 1.38 | 4.82 |
| 119 | 0.05 | 0.06 | 0.35 | 0.54 |
| 120 | 1.43 | 0.35 | 1.41 | 0.56 |
| 121 | 0.35 | 0.31 | 2.21 | 1.56 |
| 122 | 0.15 | 0.07 | 0.53 | 0.08 |
| 123 | 0.75 | 0.43 | 2.39 | 1.46 |
| 124 | ND | 1.29 | ND | 2.60 |

TABLE 1-continued

In vitro potency against mGlu2 or mGlu3 receptors
in thallium flux assays for NAMs.

| Ex. | mGlu2 EC$_{50}$ (μM) (2.5 min) | mGlu2 EC$_{50}$ (μM) (60 min) | mGlu3 EC$_{50}$ (μM) (2.5 min) | mGlu2 EC$_{50}$ (μM) (60 min) |
|---|---|---|---|---|
| 125 | >10 | >10 | >30 | >10 |
| 126 | >30 | >10 | >30 | >10 |
| 127 | 5.33 | >10 | 3.90 | 3.14 |
| 128 | >30 | >30 | >30 | >10 |
| 129 | >10 | 3.25 | >10 | 6.48 |
| 130 | >30 | >10 | >30 | >10 |
| 131 | >10 | 3.36 | >10 | 3.44 |
| 132 | >10 | 7.10 | 5.26 | 2.93 |
| 133 | ND | 0.73 | ND | 0.33 |
| 134 | ND | >10 | ND | >10 |
| 135 | ND | >10 | ND | 2.45 |
| 136 | 0.88 | 0.04 | 0.81 | 0.12 |
| 137 | 0.45 | 0.06 | 0.30 | 0.06 |
| 138 | ND | >10 | ND | 4.15 |
| 139 | ND | ND | ND | ND |
| 140 | ND | ND | ND | ND |
| 141 | ND | >10 | ND | >10 |
| 142 | 3.22 | 1.04 | 2.97 | 0.96 |
| 143 | 2.21 | 1.19 | 2.62 | 1.93 |
| 144 | >10 | 2.36 | 2.93 | 0.74 |
| 145 | >10 | >10 | >10 | 1.65 |
| 146 | >10 | >10 | >10 | 1.10 |
| 147 | ND | ND | ND | ND |
| 148 | ND | ND | ND | ND |
| 149 | 0.42 | 0.02 | 0.37 | 0.15 |
| 150 | 2.79 | 0.42 | 1.52 | 0.70 |
| 151 | ND | >10 | ND | >10 |
| 152 | ND | 3.26 | ND | 3.39 |
| 153 | ND | ND | ND | ND |
| 154 | >10 | 4.43 | >10 | >10 |
| 155B | ND | >10 | ND | >10 |
| 156 | >10 | 3.70 | >10 | >10 |
| 157 | ND | >10 | ND | >10 |
| 158 | ND | >10 | ND | >10 |
| 159 | ND | ND | ND | ND |
| 160 | ND | >30 | ND | >30 |
| 161 | ND | >30 | ND | >30 |
| 162 | >10 | 5.36 | >10 | 5.81 |
| 163 | >10 | >10 | >10 | >10 |
| 164 | >10 | 1.56 | 5.57 | 2.89 |
| 165 | 4.37 | 1.47 | 3.47 | 1.90 |
| 166B | 8.47 | 1.23 | 4.53 | 1.59 |
| 167B | ND | >10 | ND | >10 |
| 168A | ND | >10 | ND | >10 |
| 169 | ND | ND | ND | ND |
| 170B | ND | 3.68 | ND | >10 |
| 171 | ND | ND | ND | ND |
| 172B | ND | >10 | ND | >10 |
| 173B | ND | >10 | ND | 3.25 |
| 174B | ND | >10 | ND | 4.97 |
| 175B | ND | 4.47 | ND | 4.53 |
| 176 | ND | ND | ND | ND |
| 177 | >10 | >10 | >10 | >10 |
| 178 | ND | >10 | ND | >10 |
| 179 | 2.74 | 0.02 | 1.37 | 0.10 |
| 180 | 0.88 | 0.31 | 0.86 | 2.92 |
| 181 | >10 | ND | >10 | ND |
| 182 | 0.04 | 0.04 | 0.04 | 0.05 |
| 183 | 0.11 | 0.03 | 0.07 | 0.16 |
| 184 | 0.49 | 0.07 | 0.41 | 0.39 |
| 185 | >10 | ND | 1.45 | ND |
| 186 | 2.42 | 1.01 | 1.36 | 2.25 |
| 187 | 0.98 | ND | 0.71 | ND |
| 188 | >10 | ND | 1.70 | ND |
| 189 | 0.29 | 0.08 | 0.28 | 0.42 |
| 190 | >10 | ND | >10 | ND |
| 191 | 0.25 | 0.08 | 0.18 | 0.39 |
| 192 | >10 | ND | >10 | ND |
| 193 | >10 | 0.95 | >10 | 2.16 |
| 194 | >10 | 3.47 | >10 | >10 |
| 195 | 3.83 | 2.62 | 1.39 | 2.24 |
| 196 | 3.59 | 0.60 | 2.94 | 1.13 |
| 197 | >10 | ND | >10 | ND |
| 198 | >10 | 0.26 | 0.46 | 0.55 |
| 199 | 1.70 | 4.27 | 1.82 | >10 |
| 200 | >10 | 0.22 | 0.75 | 0.40 |
| 201 | >10 | 0.52 | 1.61 | 1.58 |
| 202 | >10 | >10 | >10 | >10 |
| 203 | 0.65 | 0.02 | 0.39 | 0.32 |

ND = Not Determined.

Example B2: Microsomal Stability In Vitro Assay

Pooled rat liver microsomes (BD Biosciences, #452701) were preincubated with test compounds at 37.5° C. for 5 min in the absence of NADPH. The reaction was initiated by addition of NADPH and incubated under the same conditions. The final incubation concentrations were 4 μM test compound, 2 mM NADPH, and 1 mg/mL (total protein) liver microsomes in phosphate-buffered saline (PBS) at pH 7.4. One aliquot (100 μL) of the incubation mixture was withdrawn at 15 min time points and combined immediately with 100 μL of ACN/MeOH. After mixing, the sample was centrifuged at approximately 13000 rpm for 12 min. The supernatant was filtered and transferred into an autosampler vial and the amount of test compound was quantified using a Shimadzu LCMS 2010EV mass spectrometer. The change of the AUC (area under the curve) of the parent compound as a function of time was used as a measure of microsomal stability. Test compounds were run in duplicate with a positive control.

Representative microsomal stability data is presented in Table 2.

Example B3: Plasma Stability In Vitro Assay

A 20 μL aliquot of a 10 mM solution in DMSO of the test compound was added to 2.0 mL of heparinized rat plasma (Lampire, P1-150N) to obtain a 100 μM final solution. The mixture was incubated for 1 h at 37.5° C. Aliquots of 100 μL were taken at 15 min intervals and diluted with 100 μL of MeOH/ACN. After mixing, the sample was centrifuged at approximately 13000 rpm for 12 min. The supernatant was filtered and transferred into an autosampler vial and the amount of test compound was quantified using the Shimadzu LCMS-2010EV system. The change of the AUC of the parent compound in function of time was used as a measure of plasma stability.

Representative plasma stability data is presented in Table 2.

TABLE 2

Plasma and microsomal stability data for representative NAMs.

| Example | Plasma Stability* | Microsomal Stability* |
|---|---|---|
| 184 | 100 | 97 |
| 179 | 100 | 30 |
| 149 | 97 | 91 |
| 136 | 99 | 90 |
| 137 | 66 | 68 |
| 86 | 100 | 100 |

TABLE 2-continued

Plasma and microsomal stability data for representative NAMs.

| Example | Plasma Stability* | Microsomal Stability* |
|---|---|---|
| 79 | 86 | 82 |
| 76 | 100 | 95 |
| 87 | 97 | 92 |
| 89 | 100 | 82 |
| 122 | 83 | 83 |
| 114 | 93 | 66 |
| 1 | 93 | 3 |
| 9 | 98 | 4 |
| 38 | 65 | 2 |
| 43 | 95 | 66 |

*Percent Remaining @ 1 hour

Example B4: Forced Swim Test (FST)

Male Wistar rats (Charles River, Hollister, Calif.), weighing 175-225 g (Charles River, Portage, Ind.) used for the forced swim test study were housed in pairs with food and water available ad libitum, except during testing, in a temperature and humidity controlled vivarium (21° C.). Rats were maintained on a 12-hour reverse light-dark cycle with lights on at 6 pm. All experimental procedures occurred during the dark cycle, were approved by the Institutional Animal Care and Use Committee of the Scripps Research Institute, and were in accordance with the Association for the Assessment and Accreditation of Laboratory Animal Care (AAALAC) guidelines. Animals were allowed to habituate to their new environment for at least 1 week before the start of any procedure, during which time they were handled at least twice.

After the habituation swim and 24 hours prior to the test swim, rats were administered one of three doses of a mGlu$_{2/3}$ NAM, with doses and pretreatment time based on maximal brain penetration as determined by PK studies for each compound. Blood and brain tissue were collected immediately after the FST and the PK properties of each compound were analyzed together with FST behavior. The modified forced swim test was carried out as described previously in Cryan et al., 2003. Briefly, rats were taken from the vivarium and immediately placed individually for 15 min in Pyrex cylinders (21×46 cm; Fisher Scientific, Tustin, Calif.), which were filled with water to a depth of 30 cm. The testing room was bright, and two bright (60-watt) lamps provided extra illumination above the cylinders. The rats were removed 15 min later, dried, and placed in their home cage. Twenty-four hours after their first exposure, the animals were again placed in the swim apparatus for 5 min, and behaviors were monitored from above by video camera for subsequent analysis. The rater of the behavioral patterns was blind with respect to the experimental conditions being scored. A time sampling technique was employed whereby the predominant behavior in each 5-sec period of the 300-sec test was recorded. Climbing behavior consisted of upward-directed movements of the forepaws along the side of the swim chamber. Swimming behavior was defined as movement (usually horizontal) throughout the swim chamber, which also included crossing into another quadrant. Immobility was assigned when no additional activity was observed other than that required to keep the rat's head above water.

Compounds 182 and 191 displayed antidepressant activity by decreasing immobility and increasing swimming in the Forced Swim Test (FTR) data as presented in FIG. 1.

Representative in vitro biochemical data selectivity data is presented in Table 3.

TABLE 3

PK data for representative NAMs.

| Example | Brain (μM) | Plasma (μM) |
|---|---|---|
| 191 | 1.43 ± 0.46 | 0.28 ± 0.06 |
| 182 | 0.28 ± 0.10 | 0.16 ± 0.03 |
| 73 | 0.14 ± 0.09 | 9.01 ± 2.23 |
| 94 | 0.49 ± 0.06 | 15.90 ± 0.95 |
| 43 | 0.21 ± 0.04 | 4.69 ± 0.78 |
| 49 | 0.50 ± 0.05 | 19.20 ± 2.10 |

What is claimed is:

1. A compound, or a pharmaceutically acceptable salt thereof, having the structure of Formula (III):

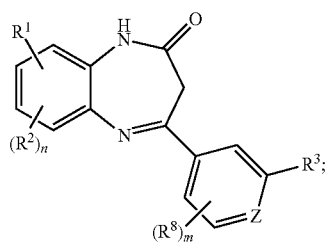

Formula (III)

wherein:
Z is =N— or =C(H)—;
R$^1$ is halogen, —OR$^5$, —NO$_2$, —CN, substituted or unsubstituted C$_1$-C$_6$alkyl, substituted or unsubstituted C$_1$-C$_6$fluoroalkyl, substituted or unsubstituted aryl, substituted or unsubstituted heteroaryl, or —CO$_2$R$^6$;
each R$^2$ is independently halogen, —OR$^5$, NO$_2$, substituted or unsubstituted C$_1$-C$_6$alkyl, or substituted or unsubstituted C$_1$-C$_6$fluoroalkyl;
R$^3$ is —X—R$^4$;
X is —O—, —S—, —S(O)$_2$—, —N(R$^7$)—, or —C≡C—;
R$^4$ is substituted or unsubstituted C$_3$-C$_6$cycloalkyl, substituted or unsubstituted aryl, or substituted or unsubstituted heteroaryl;
each R$^5$ is independently hydrogen, or substituted or unsubstituted C$_1$-C$_6$alkyl;
R$^6$ is hydrogen or substituted or unsubstituted C$_1$-C$_6$alkyl;
R$^7$ is hydrogen or substituted or unsubstituted C$_1$-C$_6$alkyl;
each R$^8$ is independently halogen or substituted or unsubstituted C$_1$-C$_6$alkyl;
n is 1, 2, or 3; and
m is 0, 1, or 2.

2. The compound of claim 1, or a pharmaceutically acceptable salt thereof, having the structure of Formula (IIIa) or Formula (IIIb):

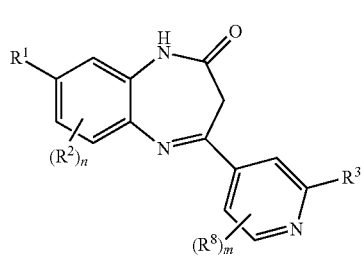

Formula (IIIa)

Formula (IIIb)

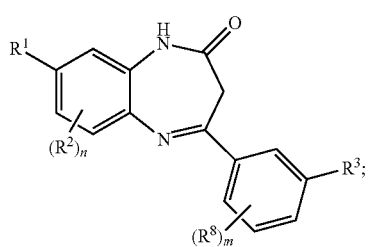

wherein R³ is —X—R⁴; and R⁴ is substituted or unsubstituted aryl or substituted or unsubstituted heteroaryl.

3. The compound of claim 1, or a pharmaceutically acceptable salt thereof, wherein X is —O—.

4. The compound of claim 1, or a pharmaceutically acceptable salt thereof, wherein R⁴ is substituted or unsubstituted heteroaryl.

5. The compound of claim 1, or a pharmaceutically acceptable salt thereof, wherein n is 1 and R² is halogen or —CH₃.

6. The compound of claim 1, or a pharmaceutically acceptable salt thereof, wherein R¹ is —CF₃.

7. The compound of claim 1, or a pharmaceutically acceptable salt thereof, wherein m is 0.

8. The compound of claim 1, or a pharmaceutically acceptable salt thereof having the structure:

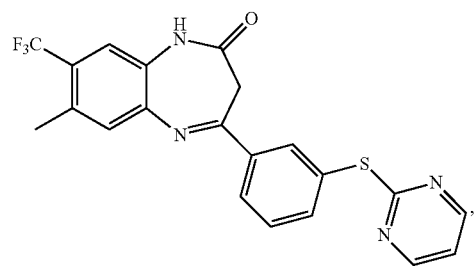

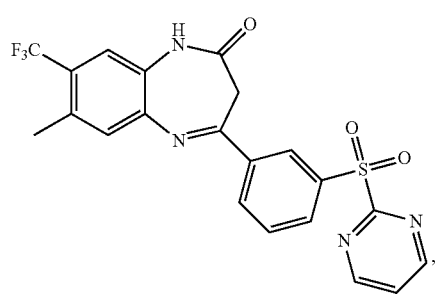

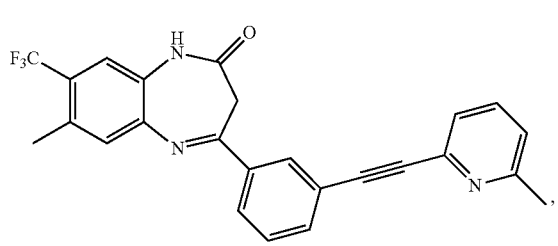

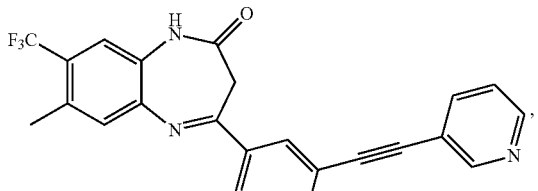

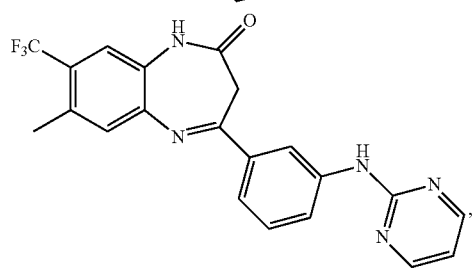

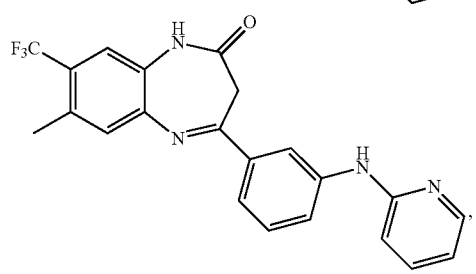

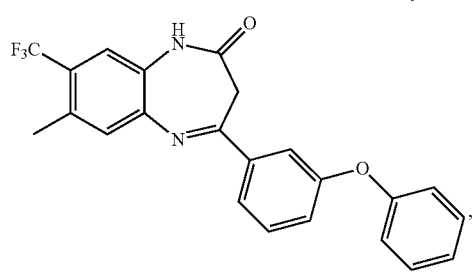

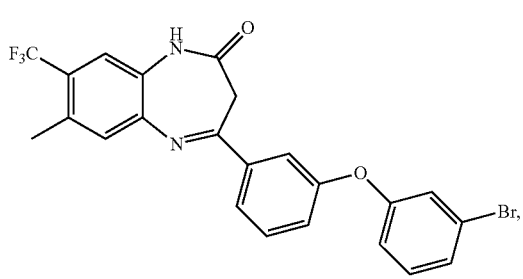

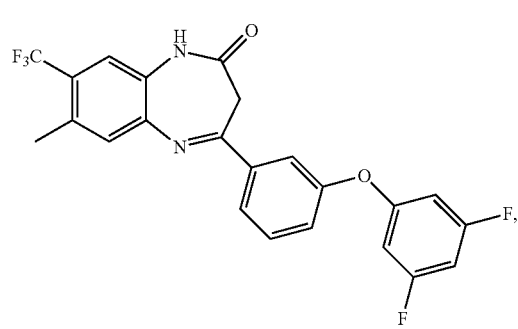

-continued

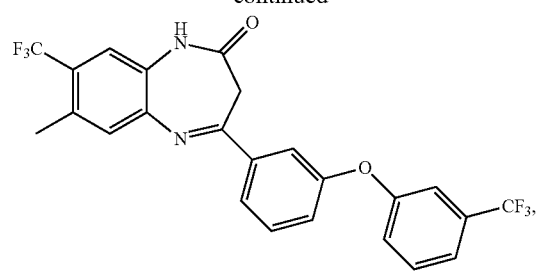

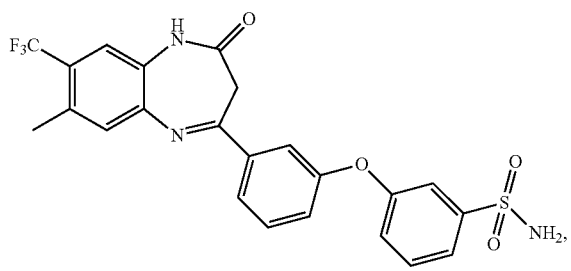

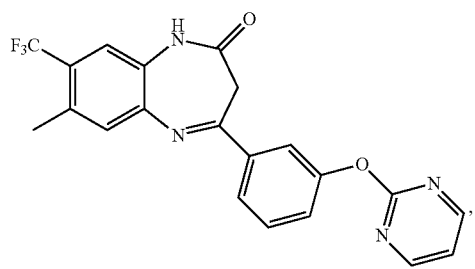

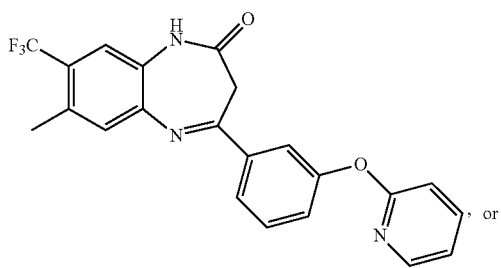

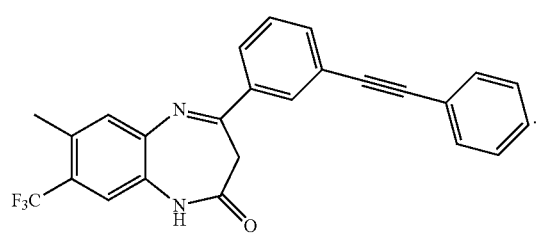

9. A pharmaceutical composition comprising a compound of claim 1, or a pharmaceutically acceptable salt, and at least one pharmaceutically acceptable excipient.

10. A method of treating a central nervous disorder (CNS), the method comprising the step of administering to a subject in need thereof, an effective amount of a compound of claim 1, thereby treating the disorder.

11. A compound, or a pharmaceutically acceptable salt thereof, having the structure of Formula (IV):

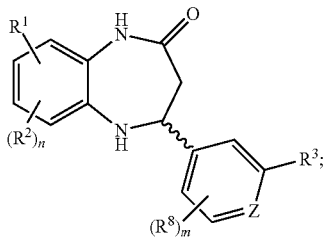

Formula (IV)

wherein:

Z is =N— or =C(H)—;

$R^1$ is halogen, —$OR^5$, —$NO_2$, —CN, substituted or unsubstituted $C_1$-$C_6$alkyl, substituted or unsubstituted $C_1$-$C_6$fluoroalkyl, substituted or unsubstituted aryl, substituted or unsubstituted heteroaryl, or —$CO_2R^6$;

$R^2$ is halogen, —$OR^5$, $NO_2$, substituted or unsubstituted $C_1$-$C_6$alkyl, or substituted or unsubstituted $C_1$-$C_6$fluoroalkyl;

$R^3$ is halogen, substituted or unsubstituted $C_1$-$C_6$alkyl, substituted or unsubstituted $C_1$-$C_6$fluoroalkyl, substituted or unsubstituted $C_3$-$C_6$cycloalkyl, substituted or unsubstituted $C_2$-$C_7$heterocycloalkyl, substituted or unsubstituted aryl, unsubstituted heteroaryl, —C(O)$NR^9R^{10}$, or —X—$R^4$;

X is —O—, —S—, —$S(O)_2$—, —$N(R^7)$—, or —C≡C—;

$R^4$ is substituted or unsubstituted $C_1$-$C_6$alkyl, substituted or unsubstituted $C_3$-$C_6$cycloalkyl, substituted or unsubstituted aryl, or substituted or unsubstituted heteroaryl;

each $R^5$ is independently hydrogen or substituted or unsubstituted $C_1$-$C_6$alkyl;

$R^6$ is hydrogen or substituted or unsubstituted $C_1$-$C_6$alkyl;

$R^7$ is hydrogen or substituted or unsubstituted $C_1$-$C_6$alkyl;

$R^8$ is halogen or substituted or unsubstituted $C_1$-$C_6$alkyl;

$R^9$ and $R^{10}$ are independently hydrogen or substituted or unsubstituted $C_1$-$C_6$alkyl;

n is 0, 1, 2, or 3; and m is 0, 1, or 2.

12. The compound of claim 11, or a pharmaceutically acceptable salt thereof, having the structure of Formula (IVa) or Formula (IVb):

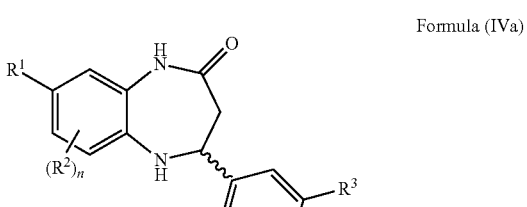

Formula (IVa)

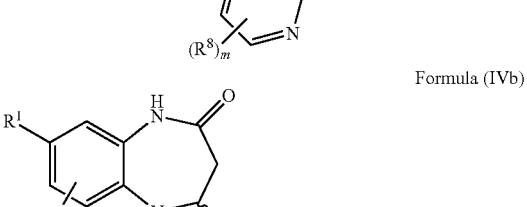

Formula (IVb)

wherein R³ is halogen, unsubstituted heteroaryl, or —X—R⁴; and R⁴ is substituted or unsubstituted aryl, or substituted or unsubstituted heteroaryl.

13. The compound of claim 11, or a pharmaceutically acceptable salt thereof, wherein X is —O—.

14. The compound of claim 11, or a pharmaceutically acceptable salt thereof, wherein R⁴ is substituted or unsubstituted heteroaryl.

15. The compound of claim 11, or a pharmaceutically acceptable salt thereof, wherein n is 1 and R² is halogen or —CH₃.

16. The compound of claim 11, or a pharmaceutically acceptable salt thereof, wherein R¹ is —CF₃.

17. The compound of claim 11, or a pharmaceutically acceptable salt thereof, wherein m is 0.

18. The compound of claim 11, or a pharmaceutically acceptable salt thereof having the structure:

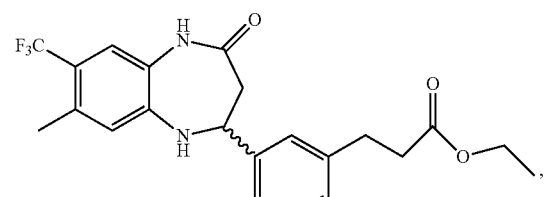

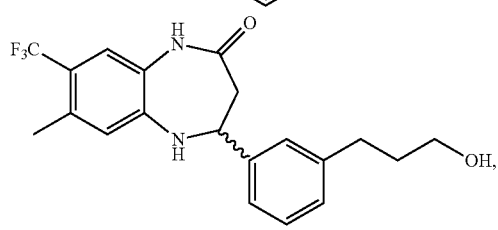

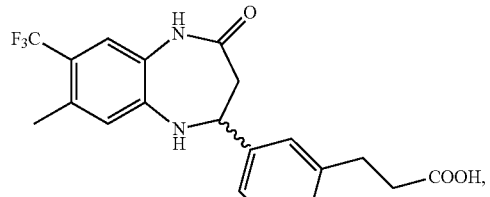

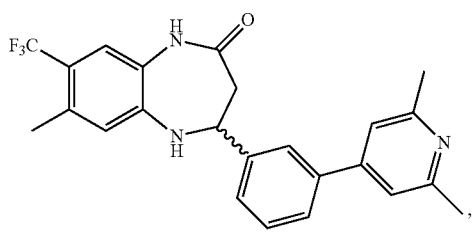

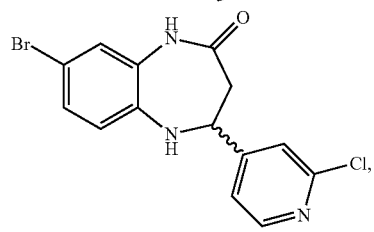

-continued

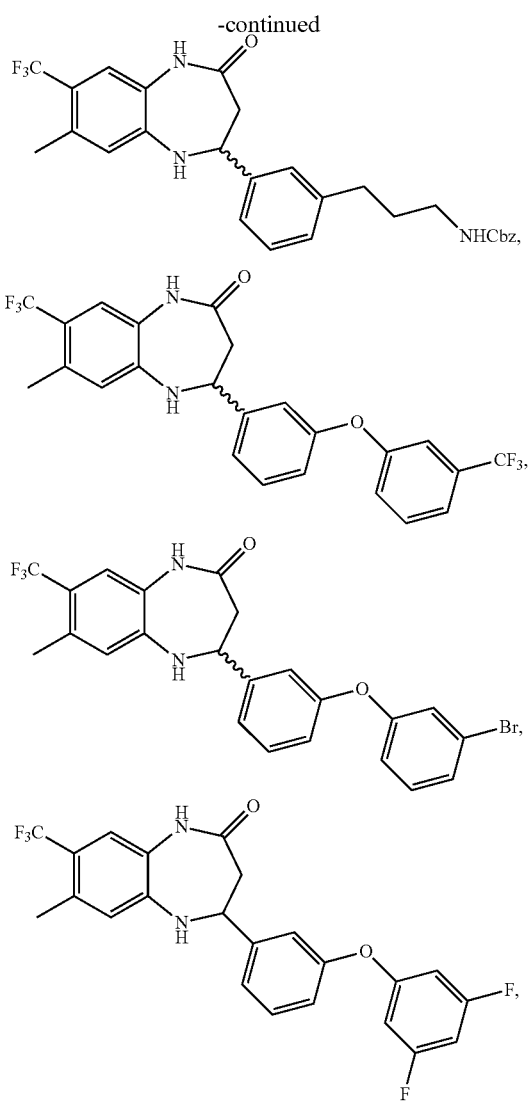
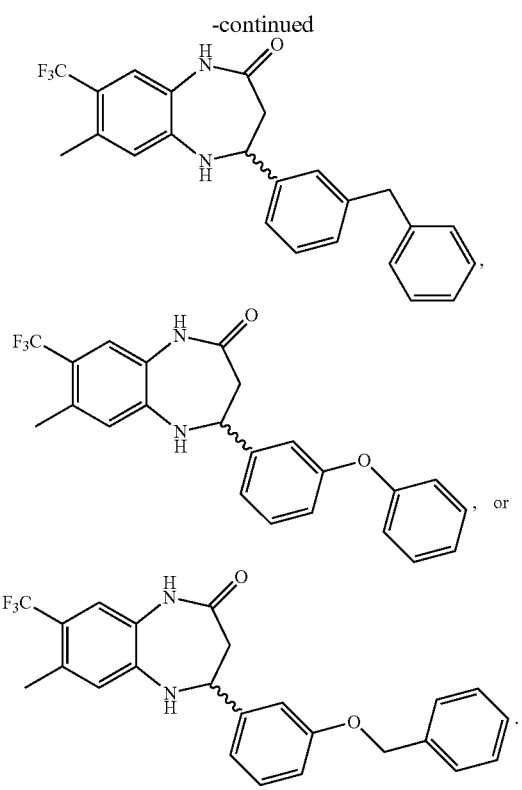

19. A pharmaceutical composition comprising a compound of claim 11, or a pharmaceutically acceptable salt, and at least one pharmaceutically acceptable excipient.

20. A method of treating a central nervous disorder (CNS), the method comprising the step of administering to a subject in need thereof, an effective amount of the compound of claim 11, thereby treating the disorder.

* * * * *